(12) United States Patent
Aftab et al.

(10) Patent No.: US 8,642,584 B2
(45) Date of Patent: *Feb. 4, 2014

(54) METHOD OF USING PI3K AND MEK MODULATORS

(75) Inventors: Dana T. Aftab, San Rafael, CA (US); A. Douglas Laird, San Mateo, CA (US); Peter Lamb, Oakland, CA (US); Jean-Francois A. Martini, Redwood City, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,649

(22) Filed: Aug. 7, 2012

(65) Prior Publication Data

US 2012/0302545 A1    Nov. 29, 2012

Related U.S. Application Data

(63) Continuation of application No. 12/373,257, filed as application No. PCT/US2007/018057 on Aug. 16, 2007, now abandoned.

(60) Provisional application No. 60/838,307, filed on Aug. 16, 2006.

(51) Int. Cl.
| | |
|---|---|
| *A61K 31/498* | (2006.01) |
| *A61K 31/4985* | (2006.01) |
| *A61K 31/551* | (2006.01) |
| *A61K 31/5377* | (2006.01) |
| *A61P 35/00* | (2006.01) |
| *A61P 35/02* | (2006.01) |

(52) U.S. Cl.
USPC ............ 514/210.18; 514/249; 514/210.21; 514/218; 514/234.8

(58) Field of Classification Search
None
See application file for complete search history.

(56) References Cited

U.S. PATENT DOCUMENTS

| | | | |
|---|---|---|---|
| 7,803,839 B2 | 9/2010 | Aay et al. | |
| 7,915,250 B2 | 3/2011 | Aay et al. | |
| 7,989,622 B2* | 8/2011 | Bajjalieh et al. | 544/356 |
| 7,999,006 B2* | 8/2011 | Lamb | 514/477 |
| 8,044,062 B2 | 10/2011 | Baik et al. | |
| 8,101,622 B2 | 1/2012 | Baik et al. | |
| 8,481,001 B2 | 7/2013 | Lamb et al. | |
| 8,513,266 B2 | 8/2013 | Lamb et al. | |
| 2004/0009993 A1 | 1/2004 | Angiolini et al. | |
| 2009/0062274 A1 | 3/2009 | Baik et al. | |
| 2010/0075947 A1 | 3/2010 | Aftab et al. | |
| 2010/0087456 A1 | 4/2010 | Baik et al. | |
| 2010/0150827 A1 | 6/2010 | Buhr et al. | |
| 2010/0209340 A1 | 8/2010 | Buhr et al. | |
| 2011/0207712 A1 | 8/2011 | Bajjalieh et al. | |
| 2011/0237608 A1 | 9/2011 | Baik et al. | |
| 2012/0302545 A1 | 11/2012 | Aftab et al. | |
| 2013/0172371 A1 | 7/2013 | Aftab et al. | |

FOREIGN PATENT DOCUMENTS

| | | |
|---|---|---|
| WO | 9833798 | 8/1998 |
| WO | 2005105801 | 11/2005 |
| WO | 2006/044453 | 4/2006 |
| WO | 2006/045514 | 5/2006 |
| WO | 2007-023186 | 3/2007 |
| WO | 2007/044515 | 4/2007 |
| WO | 2007/044813 | 4/2007 |
| WO | 2007044698 | 4/2007 |
| WO | 2007044729 | 4/2007 |

OTHER PUBLICATIONS

Morissette et al. In Advanced Drug Delivery Review's 56 (2004) 275-300.
Shelton. J. G. et al., "Effects of the RAF/MEK/ERK and PI3K/AKT signet transduction pathways on the abrogation of cytokine-dependence and prevention of apoptosis in hematopoietic cells.", Oncogene, 2003, 22(16), 2478-2492.
Tsao in Journal of Investigative Dermatology 122:337-341, 2004.
International Search Report for PCT/US2007/018057, mailed May 28, 2008.
U.S. Appl. No. 13/694,772, filed Jan. 3, 2013, not published.
U.S. Appl. No. 13/809,002, filed Jan. 8, 2013, not published.

* cited by examiner

*Primary Examiner* — Dennis Heyer
(74) *Attorney, Agent, or Firm* — Honigman Miller Schwartz and Cohn LLP; Heidi M. Berven; Jonathan P. O'Brien

(57) ABSTRACT

The invention provides methods of treating cancer with a combination of compounds which inhibit kinases, more specifically MEK and PI3K.

2 Claims, No Drawings

METHOD OF USING PI3K AND MEK MODULATORS

CROSS REFERENCE TO RELATED APPLICATIONS

This application is a continuation of U.S. Ser. No. 12/373,257, filed Jan. 9, 2009, which is a 371 application of PCT/US2007/018057, filed Aug. 16, 2007, and claims benefit under 35 U.S.C. §119(e) to U.S. Ser. No. 60/838,307, filed Aug. 16, 2006, which is hereby incorporated by reference in its entirety for all purposes.

BACKGROUND OF THE INVENTION

1. Field of the Invention

This invention relates to methods of treating cancer with a combination of compounds that modulate protein kinase enzymatic activities and the resultant modulation of cellular activities (such as proliferation, differentiation, programmed cell death, migration, chemoinvasion and metabolism). In particular, this invention relates to a compound that inhibits mitogen activated protein kinase (MEK) used in combination with a compound that inhibits phosphatidylinositol 3-kinase (PI3K) signaling pathways.

2. State of the Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular. They are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. In addition, there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene*, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive target for small-molecule modulation, with respect to antiangiogenic and antiproliferative activity is MEK. The MEK-ERK signal transduction cascade is a conserved pathway which regulates cell growth, proliferation, differentiation, and apoptosis in response to growth factors, cytokines, and hormones. This pathway operates downstream of Ras which is often upregulated or mutated in human tumors. It has been demonstrated that MEK is a critical effector of Ras function. A large portion of human cancers, including 80% pancreatic, 50% colorectal, and 40% lung cancers, harbor activating Ras mutations. It has been shown that inhibition of the ERK pathway, and in particular inhibition of MEK kinase activity, results in antimetastatic and anti-angiogenic effects largely due to a reduction of cell-cell contact and motility as well as downregulation of vascular endothelial growth factor (VEGF) expression. Furthermore, expression of dominant negative MEK, or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention.

Accordingly, the identification of small-molecule compounds that specifically inhibit, regulate and/or modulate the signal transduction of kinases, particularly MEK, is desirable as a means to treat or prevent disease states associated with cancer and is an object of this invention.

Phosphatidylinositol 3-kinase (PI3Kα), a dual specificity protein kinase, is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer, cervical cancer, breast cancer, colorectal cancer, and glioblastomas, among others. The tumor suppressor PTEN inhibits cell growth through multiple mechanisms. PTEN can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

Thus, an object of this invention is the identification of small-molecule compounds that specifically inhibit, regulate and/or modulate the signal transduction of kinases, particularly phosphatidylinositol 3-kinase, in order to treat, prevent, and/or inhibit diseases and conditions associated with cancers.

Combination therapy has been commonly utilized to overcome drug resistance. Clinical trials of dasatinib or nilotinib (AMN-107) in combination with the current standard CML therapy, ie., imatinib (Gleevec®), are ongoing (ClinicalTrials.gov). Dasatinib in combination with Gleevec® has shown improved efficacy against various Abl mutants except for T315I in preclinical studies (O'Hare T, Walters D K, Stoffregen E P, et al., "Combined Abl inhibitor therapy for minimizing drug resistance in chronic myeloid leukemia: Src/Abl inhibitors are compatible with imatinib", *Clin Cancer Res.* 11, 6987-6993 (2005)). Recently, specific mutations in B-RAF have been shown to confer reduced sensitivity to treatment of cells and tumors with compounds that inhibit MEK (Solit et al. *Nature* online, pgs 1-5 Nov. 6, 2005). Combination therapys treating multiple kinases pathways should eliminate this reduced sensitivity.

SUMMARY OF THE INVENTION

This invention provides a method of using an MEK inhibitor of Formula I, Ia, Ic, Id, II, III, IV, or V in combination with a PI3K inhibitor of Formula VI, VIa, VIb, or VII, or in combination with a PI3K inhibitor of Formula VIII, VIIIa, VIIIb, IX, X, XI or XI for the treatment of hyperproliferative disorders, such as cancers.

In one embodiment, in section I an MEK inhibitor of Formula I is as follows:

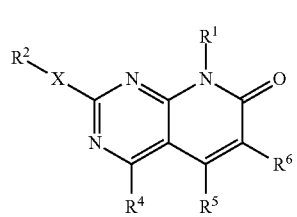

and optionally a pharmaceutically acceptable salt or solvate thereof, wherein the A ring, X, $R^1$, $R^2$, $R^4$, $R^5$, $R^6$, and $R^7$ are as defined below in Section I.

In one embodiment, in section II a PI3K inhibitor of Formula VI is as follows:

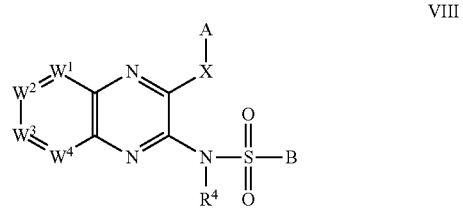

and optionally a pharmaceutically acceptable salt hydrate or solvate thereof, wherein X, $R^1$, $R^2$, $R^4$, $R^5$, and $R^6$ are as defined below in Section II.

In one embodiment, in section III a PI3K inhibitor of Formula VIII is as follows:

VIII and optionally a pharmaceutically acceptable salt hydrate or solvate thereof, wherein $W^1$, $W^2$, $W^3$, $W^4$, A, X, $R^4$, and B are as defined in Section III.

The invention encompasses using the MEK inhibitor disclosed in Section I in combination with the PI3K inhibitor of section II or section III to treat a hyperproliferative diseases and disorders and in particular cancers comprising administering to a patient a compound of Formula I, Ia, Ic, Id, II, III, IV, or V, with a compound of the Formula VI, VIa, VIb, or VII, or a compound of the Formula VIII, VIIIa, VIIIb, IX, X, or XI, or a pharmaceutical composition thereof.

The foregoing merely summarizes certain embodiments of the invention and is not intended to be limiting in nature. These embodiments and other embodiments and embodiments are described more fully below. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

DETAILED DESCRIPTION OF THE INVENTION

The following applies to all three sections.

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—OCH$_2$—" is meant to mean not only "—OCH$_2$—" as drawn, but also "—CH$_2$O—.

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deforrnians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethyl amine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.).

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular IRK, IGF1R, c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an embodiment of the invention.

As well, one of ordinary skill in the art would appreciate that such suitable x-ray quality crystals can be used as part of a method of identifying a candidate agent capable of binding to and modulating the activity of kinases. Such methods may be characterized by the following embodiments: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Embodiments a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following embodiments: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required.

Ophthalmic Formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

General Synthetic Section

The compounds of the invention, or their pharmaceutically acceptable salts, may have asymmetric carbon atoms or quaternized nitrogen atoms in their structure.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

Abbreviations and their Definitions

The following abbreviations and terms have the indicated meanings throughout:

| Abbreviation | Meaning |
| --- | --- |
| Ac | acetyl |
| br | broad |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DIPEA | N,N-diisopropylethylamine |
| DMF | N-N-dimethylformamide |
| DMSO | dimethyl sulfoxide |
| EI | Electron Impact ionization |
| Et | Ethyl |
| g | gram(s) |
| GC | gas chromatography |
| h or hr | hour(s) |
| HOAc | acetic acid |
| HOBt | Hydroxybenzotriazole |
| HPLC | high pressure liquid chromatography |
| L | liter(s) |
| M | molar or molarity |
| m | Multiplet |
| Me | Methyl |
| mesyl | Methanesulfonyl |
| mg | milligram(s) |
| MHz | megahertz (frequency) |
| Min | minute(s) |
| mL | milliliter(s) |
| mM | Millimolar |
| mmol | millimole(s) |
| mol | mole(s) |
| MS | mass spectral analysis |

-continued

| Abbreviation | Meaning |
| --- | --- |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | Phenyl |
| PhOH | Phenol |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| q | Quartet |
| RT | Room temperature |
| Sat'd | Saturated |
| s | Singlet |
| s- | Secondary |
| t- | Tertiary |
| t or tr | Triplet |
| TBDMS | t-butyldimethylsilyl |
| TES | Triethylsilyl |
| TFA | trifluoroacetic acid |
| THF | Tetrahydrofuran |
| TMOF | trimethyl orthoformate |
| TMS | trimethylsilyl |
| tosyl | p-toluenesulfonyl |
| Trt | triphenylmethyl |
| uL | microliter(s) |
| uM | Micromole(s) or micromolar |

Section I

As noted above, this invention relates to compounds of Formula I and which inhibit MEK.

In one embodiment, in section I the invention provides a compound of Formula I below:

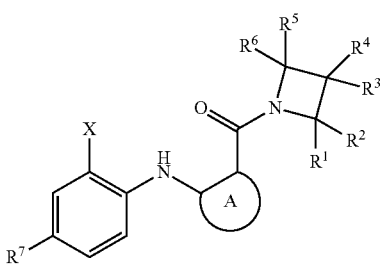

I and optionally a pharmaceutically acceptable salt or solvate thereof, wherein the A ring represents an arylene or heteroarylene group and the A ring is optionally substituted with one, two, three or four groups selected from $R^{10}$, $R^{12}$, $R^{14}$, and $R^{16}$ where $R^{10}$, $R^{12}$, $R^{14}$, and $R^{16}$ are independently hydrogen, lower alkanyl, lower alkenyl, lower alkynyl, halo, haloalkoxy, hydroxy, lower alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ or —NR$^8$C(O)R$^{8'}$;

X is lower alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^8$, —NR$^8$C(O)OR$^{8'}$, —NR$^8$C(O)NR$^8$R$^{8''}$, —NR$^8$C(O)OR$^{8'}$, or —NR$^8$C(O)R$^{8'}$; or $R^1$, $R^2$, $R^3$, $R^4$, $R^5$ and $R^6$ are independently lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NHS(O)$_2$R$^8$, —CN, —S(O)$_m$R$^8$, —C(O)R$^8$, —C(O)OR$^8$,
—C(O)NR$^8$R$^{8'}$, —NR$^8$C(O)NR$^8$R$^{8''}$, —NR$^8$C(O)OR$^{8'}$, and —NR$^8$C(O)R$^{8'}$, or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or lower alkyl; and $R^8$, $R^{8'}$ and $R^{8''}$ are independently hydrogen, hydroxy, alkoxy, substituted alkoxy, lower alkanyl, haloalkyl, lower alkenyl, lower alkynyl, aryl, cycloalkyl, heteroaryl, or heterocycloalkyl; where the lower alkanyl, lower alkenyl, lower alkynyl, aryl, cycloalkyl, heteroaryl, and heterocycloalkyl are independently optionally substituted with one, two three, four, or five groups independently selected from lower alkanyl, halo, hydroxy, hydroxyalkyl, lower alkoxy, substituted alkoxy, alkoxyalkyl, haloalkyl, carboxy, carboxy ester, nitro, cyano, —S(O)$_n$R$^{31}$ (where n is 0, 1, or 2 and $R^{31}$ is alkyl, substituted alkyl, optionally substituted aryl, optionally substituted heterocycloalkyl, or optionally substituted heteroaryl), —NR$^{34}$SO$_2$R$^{34a}$ (where $R^{34}$ is hydrogen or lower alkyl and $R^{34a}$ is lower alkyl, lower alkenyl, optionally substituted aryl, optionally substituted heterocycloalkyl, optionally substituted cycloalkyl, or optionally substituted heteroaryl),
—SO$_2$NR$^{35}$R$^{35a}$ (where $R^{35}$ is hydrogen or alkyl and $R^{35a}$ is lower alkyl, lower alkenyl, optionally substituted aryl, optionally substituted heterocycloalkyl, optionally substituted cycloalkyl, or optionally substituted heteroaryl), optionally substituted cycloalkyl, optionally substituted heterocycloalkyl, optionally substituted aryl, optionally substituted arylalkyl, aryloxy, arylalkyloxy, optionally substituted heteroaryl, —NHC(O)R$^{32}$ (where $R^{32}$ is lower alkanyl, lower alkenyl, alkoxy, or cycloalkyl) and —NR$^{30}$R$^{30'}$ (where $R^{30}$ and $R^{30'}$ are independently hydrogen, lower alkyl, or hydroxyalkyl), and —C(O) NHR$^{33}$ (where $R^{33}$ is lower alkanyl, lower alkenyl, lower alkynyl, or cycloalkyl).

In one embodiment, in section I the invention provides a compound of Formula Ia below:

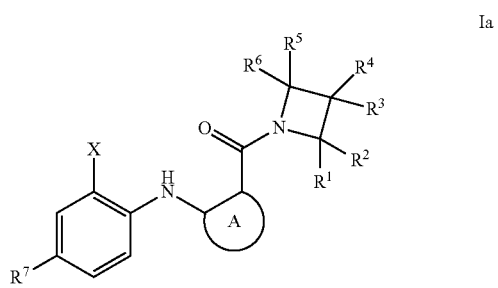

Ia and optionally as a pharmaceutically acceptable salt or solvate thereof, wherein the A ring represents an arylene or heteroarylene group and the A ring is optionally substituted with one, two, three or four groups selected from $R^{10}$, $R^{14}$, and $R^{16}$ where $R^{10}$, $R^{12}$, $R^{14}$, and $R^{16}$ are independently hydrogen, lower alkanyl, lower alkenyl, lower alkynyl, halo, haloalkoxy, hydroxy, lower alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ or —NR$^8$C(O)R$^{8'}$;

X is lower alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^{8'}$R$^{8''}$, —NR$^8$C(O)OR$^{8'}$, —NR$^8$C(O)R$^{8'}$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NHS(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$, and —NR$^8$C(O)R$^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or lower alkyl;

$R^8$, $R^{8'}$ and $R^{8''}$ are independently hydrogen, hydroxy, alkoxy, substituted alkoxy, lower alkanyl, haloalkyl, lower alkenyl, lower alkynyl, aryl, cycloalkyl, heteroaryl, or heterocycloalkyl; where the lower alkanyl, lower alkenyl, lower alkynyl, aryl, cycloalkyl, heteroaryl, and heterocycloalkyl are independently optionally substituted with one, two three, four, or five groups independently selected from lower alkanyl, halo, hydroxy, hydroxyalkyl, lower alkoxy, substituted alkoxy, alkoxyalkyl, haloalkyl, carboxy, carboxy ester, nitro, cyano, —S(O)$_n$R$^{31}$ (where n is 0, 1, or 2 and $R^{31}$ is alkyl, substituted alkyl, optionally substituted aryl, optionally substituted heterocycloalkyl, or optionally substituted heteroaryl), —NR$^{34}$SO$_2$R$^{34a}$ (where $R^{34}$ is hydrogen or lower alkyl and $R^{34a}$ is lower alkyl, lower alkenyl, optionally substituted aryl, optionally substituted heterocycloalkyl, optionally substituted cycloalkyl, or optionally substituted heteroaryl),
—SO$_2$NR$^{35}$R$^{35a}$ (where $R^{35}$ is hydrogen or alkyl and $R^{35a}$ is lower alkyl, lower alkenyl, optionally substituted aryl, optionally substituted heterocycloalkyl, optionally substituted cycloalkyl, or optionally substituted heteroaryl), optionally substituted cycloalkyl, optionally substituted heterocycloalkyl, optionally substituted aryl, optionally substituted arylalkyl, aryloxy, arylalkyloxy, optionally substituted heteroaryl, —NHC(O)R$^{32}$ (where $R^{32}$ is lower alkanyl, lower alkenyl, alkoxy, or cycloalkyl) and —NR$^{30}$R$^{30'}$ (where $R^{30}$ and $R^{30'}$ are independently hydrogen, lower alkyl, or hydroxyalkyl), and —C(O)NHR$^{33}$ (where $R^{33}$ is lower alkanyl, lower alkenyl, lower alkynyl, or cycloalkyl); and $R^9$ is lower alkanyl, lower alkenyl, lower alkynyl, aryl, cycloalkyl, heteroaryl, or heterocycloalkyl; where the lower alkanyl, lower alkenyl, lower alkynyl, aryl, cycloalkyl, heteroaryl, and heterocycloalkyl are independently optionally substituted with one, two, three, four, or five groups selected from lower alkanyl, halo, hydroxy, haloalkoxy, haloalkyl, amino, alkylamino, and dialkylamino.

In another embodiment, the invention provides a compound of Formula I or Ia where $R^7$ is halo and all other groups are as defined for a Compound of Formula I or Ia, respectively. In another embodiment, $R^7$ is iodo or bromo. In another embodiment, $R^7$ is iodo. In another embodiment, the compound is that where $R^7$ is iodo or bromo; the A ring is phenylene optionally substituted with one, two, three, or four groups selected from $R^{10}$, $R^{12}$, $R^{14}$, and $R^{16}$; and all other groups are as defined for a Compound of Formula I or Ia, respectively.

In another embodiment, the invention provides a compound of Formula I or Ia where X is halo and all other groups are as defined for a Compound of Formula I or Ia, respectively. In another embodiment, X is fluoro or chloro. In another embodiment, X is fluoro. In yet another embodiment, the compound is that where X is fluoro or chloro; the A ring is phenylene optionally substituted with one, two, three, or four groups selected from $R^{10}$, $R^{12}$, $R^{14}$, and $R^{16}$; and all other groups are as defined for a Compound of Formula I or Ia, respectively.

In another embodiment, the invention provides a compound of Formula I or Ia where $R^1$, $R^2$, $R^5$, and $R^6$ are hydrogen and all other groups are as defined for a Compound of Formula I or Ia, respectively. In another embodiment, $R^1$, $R^2$, $R^5$, and $R^6$ are hydrogen; the A ring is phenylene optionally substituted with one, two, three, or four groups selected from $R^{10}$, $R^{12}$, $R^{14}$, and $R^{16}$; and all other groups are as defined for a Compound of Formula I or Ia, respectively.

In another embodiment, the invention provides a compound of Formula I or Ia where the A ring is a phenylene ring optionally substituted with one, two, three, or four groups selected from $R^{10}$, $R^{12}$, $R^{14}$, and $R^{16}$ where $R^{10}$, $R^{12}$, $R^{14}$, $R^{16}$, and all groups are as defined for a Compound of Formula I or Ia, respectively.

In another embodiment, the invention provides a compound of Formula I or Ia where $R^7$ and X are halo and all other groups are as defined for a Compound of Formula I or Ia, respectively. In another embodiment, $R^7$ is iodo and X is fluoro.

In yet another embodiment (A1), the compound of Formula I or Ia is that where $R^7$ and X are halo; the A ring is phenylene optionally substituted with one, two, three, or four groups selected from $R^{10}$, $R^{12}$, $R^{14}$, and $R^{16}$; and all other groups are as defined for a Compound of Formula I or Ia, respectively. In another embodiment, $R^7$ is iodo and X is fluoro; the A ring is phenylene optionally substituted with one, two, three, or four groups selected from $R^{10}$, $R^{12}$, $R^{14}$, and $R^{16}$; and all other groups are as defined for a Compound of Formula I or Ia, respectively.

In another embodiment (A2), the invention provides a Compound of Formula I or Ia where the A ring is phenylene; $R^{14}$ and $R^{16}$ are hydrogen; $R^{10}$ and $R^{12}$ are independently hydrogen or halo; and all other groups are as defined for a Compound of Formula I or Ia, respectively In another embodiment, $R^{10}$ and $R^{12}$ are independently hydrogen or fluoro. In another embodiment, $R^{10}$ is 3-fluoro and $R^{12}$ is hydrogen. In another embodiment, $R^{10}$ and $R^{12}$ are fluoro. In another embodiment, $R^{10}$ and $R^{12}$ are 3-fluoro and 4-fluoro, 4-fluoro and 5-fluoro, or 4-fluoro and 6-fluoro.

In another embodiment of the invention (A3), the compound of Formula I or Ia is that where $R^1$, $R^2$, $R^5$ and $R^6$ are hydrogen; the A ring is phenylene optionally substituted with one, two, three, or four groups selected from $R^{10}$, $R^{12}$, $R^{14}$, $R^{16}$; and all other groups are as defined for a Compound of Formula I or Ia, respectively.

In another embodiment (A4), the invention provides a Compound of Formula Ia where the A ring is phenylene optionally substituted with one, two, three, or four groups selected from $R^{10}$, $R^{12}$, $R^{14}$, and $R^{16}$; X, $R^7$, $R^{10}$, $R^{12}$, $R^{14}$, and $R^{16}$ are as defined for a Compound of Formula Ia; and
one of $R^1$, $R^2$, $R^3$, $R^4$, $R^5$, and $R^6$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are independently optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted aryl alkyl, optionally substituted heteroaryl, —$OR^8$, —$NR^8R^{8'}$, —$NHS(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; and the others of $R^1$, $R^2$, $R^3$, $R^4$, $R^5$, and $R^6$ are as defined for a Compound of Formula Ia; or
one of $R^1$ and $R^2$ together with the carbon to which they are attached, $R^3$ and $R^4$ together with the carbon to which they are attached, and $R^5$ and $R^6$ together with the carbon to which they are attached forms C(O) or C(=NOH); the others of $R^1$, $R^2$, $R^3$, $R^4$, $R^5$, and $R^6$ are as defined for a Compound of Formula Ia; and
all other groups are as defined in Formula Ia.

In another embodiment (A5), the invention provides a Compound of Formula Ia where the A ring is phenylene optionally substituted with one, two, three, or four groups selected from $R^{10}$, $R^{12}$, $R^{14}$, and $R^{16}$; X, $R^7$, $R^{10}$, $R^{12}$, $R^{14}$, and $R^{16}$ are as defined for a Compound of Formula Ia; and
$R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are independently optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NHS(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; and $R^4$ is as defined in Formula Ia; or
$R^3$ and $R^4$ together with the carbon to which they are attached form C(O) or C(=NOH); and all other groups are as defined in Formula Ia.

Another embodiment of embodiment A5 is that where $R^1$, $R^2$, $R^5$ and $R^6$ are hydrogen.

In another embodiment (A6), the Compound id of Formula Ia where the A ring is phenylene optionally substituted with one, two, three, or four groups selected from $R^{10}$, $R^{12}$, $R^{14}$, and $R^{16}$; X, $R^7$, $R^{10}$, $R^{12}$, $R^{14}$, and $R^{16}$ are as defined for a Compound of Formula Ia; and $R^3$ and $R^4$ are independently halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^8$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are independently optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; or
$R^3$ and $R^4$ together with the carbon to which they are attached form C(O) or C(=NOH); and all other groups are as defined in Formula Ia.

Another embodiment of embodiment A6 is that where $R^1$, $R^2$, $R^5$ and $R^6$ are hydrogen.

In another embodiment (A7), the invention provides a Compound of Formula Ia where the A ring is phenylene optionally substituted with $R^{10}$, $R^{12}$, $R^{14}$, and $R^{16}$ where $R^{14}$ and $R^{16}$ are hydrogen and where $R^{10}$ and $R^{12}$ are independently hydrogen or halo; X and $R^7$ are halo; $R^1$, $R^2$, $R^5$ and $R^6$ are hydrogen; and
$R^3$ is hydrogen and $R^4$ is —$NR^8R^{8'}$ (where $R^8$ is hydrogen, hydroxy, lower alkanyl, alkoxy, aryl, cycloalkyl, heteroaryl, or heterocycloalkyl and $R^{8'}$ is hydroxy, alkoxy, aryl, cycloalkyl, heteroaryl, or heterocycloalkyl), —NHS$(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, lower alkenyl, and lower alkynyl; where the lower alkenyl and lower alkynyl are optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NHS(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; or
$R^3$ and $R^4$ together with the carbon to which they are attached form C(O) or C(=NOH);
m, $R^{8''}$, and $R^9$ are as defined for a Compound of Formula Ia; and unless otherwise specified in this embodiment, $R^8$ and $R^{8'}$, and all other groups, are as defined in the Summary of the Invention for a Compound of Formula Ia.

In another embodiment of the Invention (A8), the invention provides a Compound of Formula I or Ia where the A ring is phenylene optionally substituted with one, two, three, or four groups selected from $R^{10}$, $R^{12}$, $R^{14}$, and $R^{16}$; $R^3$ is hydrogen, halo, hydroxy, alkoxy, or amino; and all other groups are as defined in Formula I or Ia, respectively. In another embodiment, $R^3$ is hydrogen, fluoro, hydroxy, methoxy, or amino. In yet another embodiment, $R^3$ is hydrogen or hydroxy. In another embodiment, $R^3$ is hydroxy.

In another embodiment of embodiment A8, X and $R^7$ are halo; A is phenylene optionally substituted with $R^{10}$, $R^{12}$, $R^{14}$, and $R^{16}$ where $R^{14}$ and $R^{16}$ are hydrogen and where $R^{10}$ and $R^{12}$ are independently hydrogen or halo; $R^1$, $R^2$, $R^5$ and $R^6$ are hydrogen; and $R^4$ is as defined in Formula I or Ia, respectively.

In another embodiment of the Invention (A9), the invention provides a Compound of Formula Ia where the A ring is phenylene optionally substituted with one, two, three, or four groups selected from $R^{10}$, $R^{12}$, $R^{14}$, and $R^{16}$; $R^1$, $R^2$, $R^5$ and $R^6$ are hydrogen; $R^3$ is hydrogen, halo, hydroxy, alkoxy, or amino; and $R^4$ is heterocycloalkyl, heteroaryl, or alkyl substituted with —NR$^8$R$^{8'}$ where $R^8$ and $R^{8'}$ and all other groups are as defined in Formula Ia.

Another embodiment of embodiment A9 is that where $R^4$ is alkyl substituted with —NR$^8$R$^{8'}$ where $R^8$ and $R^{8'}$ and all other groups are as defined in Formula Ia. In another embodiment, the compound is of Formula I(c) or I(d):

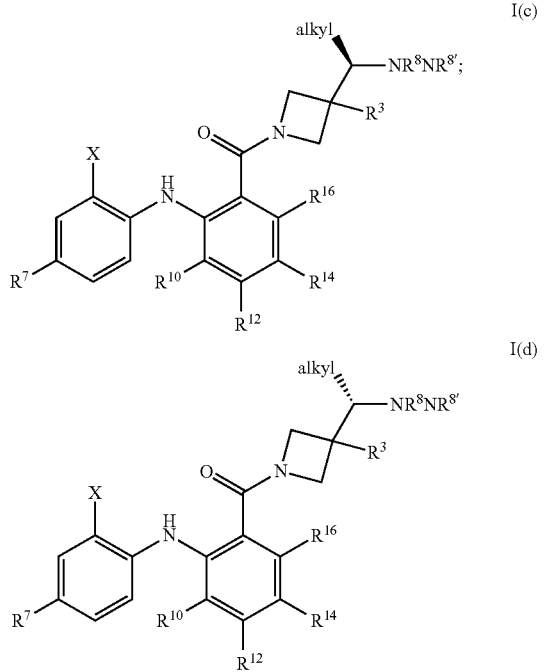

where $R^3$ is as defined in A9; X, $R^7$, $R^8$, $R^{8'}$, $R^{10}$, $R^{12}$, $R^{14}$, and $R^{16}$ are as defined in Formula Ia.

Another embodiment of embodiment A9 is that where $R^4$ is heterocycloalkyl.

In another embodiment of embodiment A9, the compound is that where X and $R^7$ are halo; A is phenylene optionally substituted with $R^{10}$, $R^{12}$, $R^{14}$, and $R^{16}$ where $R^{14}$ and $R^{16}$ are hydrogen and where $R^{10}$ and $R^{12}$ are independently hydrogen or halo; $R^3$ is hydroxy; and $R^4$ is alkyl substituted with —NR$^8$R$^{8'}$ or $R^4$ is heterocycloalkyl optionally substituted with one, two, or three groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NHS(O)$_2$R$^9$,
—CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; and where m, $R^3$, $R^8$, $R^{8'}$, $R^{8''}$, and $R^9$ are as defined in Formula Ia.

In another embodiment of the Invention (A10), the invention provides a Compound of Formula Ia where the A ring is phenylene optionally substituted with one, two, three, or four groups selected from $R^{10}$, $R^{12}$, $R^{14}$, and $R^{16}$;

$R^4$ is
a) hydrogen;
b) lower alkanyl;
c) lower alkanyl substituted with one or two —OR$^8$ where $R^8$ is hydrogen, aryl, or lower alkanyl where the lower alkanyl in $R^8$ is substituted with one or two hydroxy;
d) lower alkanyl substituted with one, two, or three halo;
e) lower alkanyl substituted with nitro;
f) lower alkanyl substituted with —S(O)$_m$R$^9$ (where m is 0 and $R^9$ is aryl);
g) lower alkanyl substituted with optionally substituted heterocycloalkyl;
h) lower alkenyl;
i) —NR$^8$R$^{8'}$ (where $R^8$ and $R^{8'}$ are independently hydrogen; lower alkanyl; lower alkenyl; lower alkanyl substituted with one or two hydroxy; lower alkanyl substituted with one or two —NR$^{30}$R$^{30'}$ where $R^{30}$ and $R^{30'}$ are independently hydrogen, alkyl, or hydroxyalkyl; lower alkanyl substituted with optionally substituted heteroaryl; or lower alkanyl substituted with optionally substituted cycloalkyl);
j) —C(O)NR$^8$R$^{8'}$ (where $R^8$ is hydrogen, lower alkanyl, or lower alkenyl; and $R^{8'}$ is hydrogen; hydroxy; lower alkanyl; lower alkenyl; lower alkanyl substituted with one or two hydroxy; lower alkanyl substituted with optionally substituted heterocycloalkyl; lower alkanyl substituted with —NR$^{30}$R$^{30'}$ where $R^{30}$ and $R^{30'}$ are independently hydrogen, alkyl, or hydroxyalkyl; or alkoxy);
k) —NR$^8$C(O)OR$^{8'}$ (where $R^8$ and $R^{8'}$ are independently hydrogen, lower alkanyl, or lower alkenyl);
l) lower alkanyl substituted with —NR$^8$R$^{8'}$ (where $R^8$ is hydrogen, lower alkanyl, lower alkenyl, lower alkynyl, or lower alkanyl substituted with one or two hydroxy; and $R^{8'}$ is hydrogen; hydroxy; alkoxy; lower alkanyl; lower alkenyl; lower alkynyl; alkoxy; lower alkanyl substituted with one or two hydroxy; lower alkanyl substituted with one or two alkoxy; lower alkanyl substituted with —NR$^{30}$R$^{30'}$ where $R^{30}$ and $R^{30'}$ are independently hydrogen, lower alkanyl, or hydroxyalkyl; lower alkanyl substituted with one or two hydroxy and one or two —NR$^{30}$R$^{30'}$ where $R^{30}$ and $R^{30'}$ are independently hydrogen, lower alkanyl, or hydroxyalkyl; lower alkanyl substituted with one, two, three, four, or five halo; lower alkanyl substituted with optionally substituted cycloalkyl; lower alkanyl substituted with optionally substituted aryl; lower alkanyl substituted with one or two hydroxy and one optionally substituted aryl; lower alkanyl substituted with optionally substituted heterocycloalkyl; lower alkanyl substituted with optionally substituted heteroaryl; heteroaryl; aryl; aryl substituted with one or two hydroxy; aryl substituted with one or two alkoxy; aryl substituted with one or two halo; aryl substituted with one or two —NR$^{32}$C(O)R$^{32a}$ where $R^{32}$ is hydrogen or lower alkanyl and $R^{32a}$ is lower alkanyl, lower alkenyl, alkoxy, or cycloalkyl; aryl substituted with —NR$^{34}$SO$_2$R$^{34a}$ where $R^{34}$ is hydrogen or lower alkanyl and $R^{34a}$ is lower alkanyl, lower alkenyl, cycloalkyl, aryl, heteroaryl, or heterocycloalkyl; cycloalkyl; cycloalkyl substituted with one or two hydroxy; cycloalkyl substituted with one or two hydroxy and one or two hydroxyalkyl; cycloalkyl substituted with one or two alkoxy; cycloalkyl substituted with carboxy; cycloalkyl substituted with —C(O)NR$^{33}$R$^{33a}$ where $R^{33}$ is hydrogen or lower alkanyl and $R^{33a}$ is lower alkanyl, lower alkenyl, lower alkynyl, or cycloalkyl; lower alkanyl substituted with —C(O)NR$^{33}$R$^{33a}$ where $R^{33}$ is hydrogen or lower alkanyl and $R^{33a}$ is lower alkanyl, lower alkenyl, lower alkynyl, or cycloalkyl; cycloalkyl substituted with optionally substituted cycloalkyl; heterocycloalkyl; heterocycloalkyl substituted with lower alkanyl; heterocycloalkyl substituted with alkoxycarbonyl; heterocycloalkyl substituted with optionally substituted arylalkyl; heterocycloalkyl substituted with one or two hydroxy; heterocycloalkyl substituted with one or two alkoxy; heterocycloalkyl substituted with one or two hydroxyalkyl; heterocycloalkyl substituted with one or two hydroxy, one or two alkoxy, and one or two hydroxyalkyl; lower alkanyl substituted with optionally substituted aryloxy; lower alkanyl substituted with —S(O)$_n$R$^{31}$ where n is 0 and R$^{31}$ is lower alkanyl; lower alkanyl substituted with carboxy; lower alkanyl substituted with alkoxycarbonyl; or lower alkanyl substituted with —NR$^{32}$C(O)R$^{32a}$ where R$^{32}$ is hydrogen or lower alkanyl and R$^{32a}$ is lower alkanyl, lower alkenyl, alkoxy, or cycloalkyl);

m) —NR$^8$C(O)R$^{8'}$ (where R$^8$ is hydrogen, lower alkanyl, or lower alkenyl; and R$^{8'}$ is hydrogen; lower alkanyl; lower alkanyl substituted with one or two hydroxy; lower alkanyl substituted with optionally substituted heterocycloalkyl; lower alkanyl substituted with —NR$^{30}$R$^{30'}$ where R$^{30}$ and R$^{30'}$ are independently hydrogen, lower alkanyl, hydroxyalkyl, or lower alkenyl);

n) cycloalkyl;

o) cycloalkyl substituted with —NR$^8$R$^{8'}$ where R$^8$ and R$^{8'}$ are independently hydrogen, lower alkanyl, or lower alkenyl;

p) heterocycloalkyl;

q) heterocycloalkyl substituted with —NR$^8$R$^{8'}$ where R$^8$ and R$^{8'}$ are independently hydrogen, lower alkanyl, or lower alkenyl;

r) heterocycloalkyl substituted with one or two lower alkanyl;

s) heterocylcloalkyl substituted with —C(O)OR$^8$ where R$^8$ is lower alkanyl or lower alkenyl;

t) lower alkanyl substituted with —NR$^8$C(O)R$^{8'}$ (where R$^8$ is hydrogen, lower alkanyl, or lower alkenyl and R$^{8'}$ is lower alkanyl; lower alkenyl; or lower alkanyl substituted with alkoxy, aryl, and one, two, or three halo);

u) heteroaryl;

v) heteroaryl substituted with —NR$^8$R$^{8'}$ where R$^8$ and R$^{8'}$ are independently hydrogen, lower alkanyl, or lower alkenyl; lower alkanyl substituted with optionally substituted heteroaryl;

w) lower alkanyl substituted with —NR$^8$S(O)$_2$R$^9$ where R$^8$ is hydrogen, lower alkanyl, or lower alkenyl and R$^9$ is lower alkanyl or lower alkenyl;

x) lower alkanyl substituted with —NR$^8$C(O)OR$^{8'}$ where R$^8$ and R$^{8'}$ are independently hydrogen, lower alkanyl, or lower alkenyl;

y) lower alkanyl substituted with one aryl and one —NR$^8$R$^{8'}$ where R$^8$ and R$^{8'}$ are independently hydrogen, lower alkanyl, or lower alkenyl; or z) lower alkanyl substituted with one or two —OR$^8$ (where R$^8$ is hydrogen) and one or two —NR$^8$R$^{8'}$ where R$^8$ and R$^{8'}$ are independently hydrogen, lower alkanyl, or lower alkenyl; and all other groups are as defined for a Compound of Formula Ia.

Another embodiment of embodiment A10 is that wherein X and R$^7$ are halo; A is phenylene optionally substituted with R$^{10}$, R$^{12}$, R$^{14}$, and R$^{16}$ where R$^{14}$ and R$^{16}$ are hydrogen and where R$^{10}$ and R$^{12}$ are independently hydrogen or halo; R$^1$, R$^2$, R$^5$ and R$^6$ are hydrogen; and R$^3$ is hydrogen, halo, hydroxy, alkoxy, or amino.

Another embodiment of embodiment A10 is that where R$^3$ is hydrogen and R$^4$ is
 a) hydrogen;
 b) —NR$^8$R$^{8'}$ (where R$^8$ and R$^{8'}$ are independently hydrogen; lower alkanyl; lower alkenyl; lower alkanyl substituted with one or two hydroxy; lower alkanyl substituted with one or two —NR$^{30}$R$^{30'}$ where R$^{30}$ and R$^{30'}$ are independently hydrogen, lower alkanyl, or hydroxyalkyl; lower alkanyl substituted with optionally substituted heteroaryl; or lower alkanyl substituted with optionally substituted cycloalkyl);
 c) —C(O)NR$^8$R$^{8'}$ (where R$^8$ is hydrogen, lower alkanyl, or lower alkenyl; and R$^{8'}$ is hydrogen; hydroxy; lower alkanyl; lower alkenyl; lower alkanyl substituted with one or two hydroxy; lower alkanyl substituted with heterocycloalkyl; lower alkanyl substituted with —NR$^{30}$R$^{30'}$ where R$^{30}$ and R$^{30'}$ are independently hydrogen, lower alkanyl, or hydroxyalkyl; alkoxy; or substituted alkoxy);
 d) —NR$^8$C(O)OR$^{8'}$ (where R$^8$ and R$^{8'}$ are independently hydrogen, lower alkanyl, or lower alkenyl);
 e) —NR$^8$C(O)R$^{8'}$ (where R$^8$ is hydrogen, lower alkanyl, or lower alkenyl; and R$^{8'}$ is hydrogen; lower alkanyl; lower alkanyl substituted with one or two hydroxy; lower alkanyl substituted with optionally substituted heterocycloalkyl; lower alkanyl substituted with —NR$^{30}$R$^{30'}$ where R$^{30}$ and R$^{30'}$ are independently hydrogen, lower alkanyl, hydroxyalkyl, or lower alkenyl);
 f) lower alkanyl;
 g) lower alkanyl substituted with one or two —OR$^8$ (where R$^8$ is hydrogen);
 h) lower alkanyl substituted with —NR$^8$R$^{8'}$ (where R$^8$ is hydrogen, lower alkanyl, lower alkenyl, lower alkynyl, or lower alkanyl substituted with one or two hydroxy; and R$^{8'}$ is hydrogen; lower alkanyl; lower alkenyl; lower alkynyl; lower alkanyl substituted with one or two hydroxy; heterocycloalkyl substituted with lower alkanyl; or lower alkanyl substituted with —NR$^{30}$R$^{30'}$ where R$^{30}$ and R$^{30'}$ are independently hydrogen, lower alkanyl, or hydroxyalkyl);
 i) heterocycloalkyl; or
 j) heterocycloalkyl substituted with —NR$^8$R$^{8'}$ (where R$^8$ and R$^{8'}$ are independently hydrogen, lower alkanyl, or lower alkenyl).

Another embodiment of embodiment A10 is that where R$^3$ is alkoxy and R$^4$ is lower alkanyl substituted with —NR$^8$R$^{8'}$ (where R$^8$ and R$^{8'}$ are independently hydrogen, lower alkanyl, or lower alkenyl). In another embodiment, R$^3$ is methoxy and R$^4$ is lower alkanyl substituted with —NR$^8$R$^{8'}$ (where R$^8$ and R$^{8'}$ are independently hydrogen, lower alkanyl, or lower alkenyl).

Another embodiment of embodiment A10 is that where R$^3$ is halo and R$^4$ is lower alkanyl substituted with —NR$^8$R$^{8'}$ (where R$^8$ and R$^{8'}$ are independently hydrogen, lower alkanyl, or lower alkenyl). In another embodiment, R$^3$ is fluoro and R$^4$ is lower alkanyl substituted with —NR$^8$R$^{8'}$ (where R$^8$ and R$^{8'}$ are independently hydrogen, lower alkanyl, or lower alkenyl).

Another embodiment of embodiment A10 is that where R$^3$ is amino and R$^4$ is lower alkanyl substituted with —NR$^8$R$^{8'}$ (where R$^8$ and R$^{8'}$ are independently hydrogen, lower alkanyl, or lower alkenyl).

Another embodiment of embodiment A10 is that where R$^3$ is hydroxy and R$^4$ is
 a) hydrogen;
 b) lower alkanyl;
 c) lower alkenyl;
 d) lower alkanyl substituted with one or two —OR$^8$ where R$^8$ is hydrogen, aryl, or lower alkanyl where the lower alkanyl in R$^8$ is substituted with one or two hydroxy;
 e) lower alkanyl substituted with one, two, or three halo;

f) lower alkanyl substituted with nitro;
g) lower alkanyl substituted with —S(O)$_m$R$^9$ (where m is 0 and R$^9$ is aryl);
h) lower alkanyl substituted with optionally substituted heterocycloalkyl;
i) lower alkanyl substituted with —NR$^8$R$^{8'}$ (where R$^8$ is hydrogen, lower alkanyl, lower alkenyl, lower alkynyl, or lower alkanyl substituted with one or two hydroxy; and R$^{8'}$ is hydrogen; hydroxy; alkoxy; lower alkanyl; lower alkenyl; lower alkynyl; alkoxy; substituted alkoxy; lower alkanyl substituted with one or two hydroxy; lower alkanyl substituted with —NR$^{30}$R$^{30'}$ where R$^{30}$ and R$^{30'}$ are independently hydrogen, lower alkanyl, or hydroxyalkyl; lower alkanyl substituted with one or two hydroxy and one or two —NR$^{30}$R$^{30'}$ where R$^{30}$ and R$^{30'}$ are independently hydrogen, lower alkanyl, or hydroxyalkyl; heterocycloalkyl substituted with lower alkanyl, alkoxycarbonyl, or optionally substituted arylalkyl; lower alkanyl substituted with one, two, three, four, or five halo; lower alkanyl substituted with optionally substituted cycloalkyl; lower alkanyl substituted with optionally substituted aryl; lower alkanyl substituted with one or two hydroxy and one optionally substituted aryl; lower alkanyl substituted with optionally substituted heterocycloalkyl; lower alkanyl substituted with optionally substituted heteroaryl; heteroaryl; aryl; aryl substituted with one or two hydroxy; aryl substituted with one or two alkoxy; aryl substituted with one or two halo; aryl substituted with one or two —NR$^{32}$C(O)R$^{32a}$ where R$^{32}$ is hydrogen or lower alkanyl and R$^{32a}$ is lower alkanyl, lower alkenyl, alkoxy, or cycloalkyl; aryl substituted with —NR$^{34}$SO$_2$R$^{34a}$ where R$^{34}$ is hydrogen or lower alkanyl and R$^{34a}$ is lower alkanyl, lower alkenyl, cycloalkyl, aryl, heteroaryl, or heterocycloalkyl; cycloalkyl; cycloalkyl substituted with one or two hydroxy; cycloalkyl substituted with one or two hydroxy and one or two hydroxyalkyl; cycloalkyl substituted with one or two alkoxy; cycloalkyl substituted with carboxy; cycloalkyl substituted with —C(O)NR$^{33}$R$^{33a}$ where R$^{33}$ is hydrogen or alkyl and R$^{33a}$ is lower alkanyl, lower alkenyl, lower alkynyl, or cycloalkyl; cycloalkyl substituted with optionally substituted cycloalkyl; heterocycloalkyl; heterocycloalkyl substituted with one or two hydroxy; heterocycloalkyl substituted with one or two alkoxy; heterocycloalkyl substituted with one or two hydroxyalkyl; heterocycloalkyl substituted with one or two hydroxy, one or two alkoxy, and one or two hydroxyalkyl; lower alkanyl substituted with —C(O)NR$^{33}$R$^{33a}$ where R$^{33}$ is hydrogen or alkyl and R$^{33a}$ is lower alkanyl, lower alkenyl, lower alkynyl, or cycloalkyl; lower alkanyl substituted with optionally substituted aryloxy; lower alkanyl substituted with —S(O)$_n$R$^{31}$ where n is 0 and R$^{31}$ is lower alkanyl; lower alkanyl substituted with carboxy; lower alkanyl substituted with alkoxycarbonyl; or lower alkanyl substituted with —NR$^{32}$C(O)R$^{32a}$ where R$^{32}$ is hydrogen or lower alkanyl and R$^{32a}$ is lower alkanyl, lower alkenyl, alkoxy, or cycloalkyl);
j) heterocycloalkyl;
k) —C(O)NR$^8$R$^{8'}$ (where R$^8$ is hydrogen, lower alkanyl, or lower alkenyl; and R$^{8'}$ is hydrogen; lower alkanyl; lower alkenyl; or substituted with one or two hydroxy);
l) lower alkanyl substituted with —NR$^8$C(O)R$^{8'}$ (where R$^8$ is hydrogen, lower alkanyl, or lower alkenyl and R$^{8'}$ is lower alkanyl; lower alkenyl; or lower alkanyl substituted with alkoxy, aryl, and one, two, or three halo);
m) cycloalkyl;
n) cycloalkyl substituted with —NR$^8$R$^{8'}$ where R$^8$ and R$^{8'}$ are independently hydrogen, lower alkanyl, or lower alkenyl;
o) cycloalkyl substituted with —C(O)NR$^{33}$R$^{33a}$ where R$^{33}$ is hydrogen or lower alkanyl and R$^{33a}$ is lower alkanyl, lower alkenyl, lower alkynyl, or cycloalkyl;
p) heterocycloalkyl;
q) heterocycloalkyl substituted with one or two lower alkanyl;
r) heterocylcloalkyl substituted with —C(O)OR$^8$ where R$^8$ is lower alkanyl or lower alkenyl;
s) heteroaryl;
t) heteroaryl optionally substituted with —NR$^8$R$^{8'}$ where R$^8$ and R$^{8'}$ are independently hydrogen, lower alkanyl, or lower alkenyl;
u) lower alkanyl substituted with optionally substituted heteroaryl;
v) lower alkanyl substituted with —NR$^8$S(O)$_2$R$^9$ where R$^8$ is hydrogen, lower alkanyl, or lower alkenyl and R$^9$ is lower alkanyl or lower alkenyl;
w) lower alkanyl substituted with —NR$^8$C(O)OR$^{8'}$ where R$^8$ and R$^{8'}$ are independently hydrogen, lower alkanyl, or lower alkenyl;
x) lower alkanyl substituted with one aryl and one —NR$^8$R$^{8'}$ where R$^8$ and R$^{8'}$ are independently hydrogen, lower alkanyl, or lower alkenyl; or
y) lower alkanyl substituted with one or two —OR$^8$ (where R$^8$ is hydrogen) and one or two —NR$^8$R$^{8'}$ where R$^8$ and R$^{8'}$ are independently hydrogen, lower alkanyl, or lower alkenyl.

Another embodiment of the Invention (A11) provides a compound of Formula I or Ia where the A ring is phenylene optionally substituted with R$^{10}$, R$^{12}$, R$^{14}$, and R$^{16}$; R$^3$ and R$^4$ together with the carbon to which they are attached form C(O) or C(=NOH); and all other groups are as defined for a Compound of Formula I or Ia, respectively. In another embodiment, X and R$^7$ are halo; A is phenylene optionally substituted with R$^{10}$, R$^{12}$, R$^{14}$, and R$^{16}$ where R$^{14}$ and R$^{16}$ are hydrogen and where R$^{10}$ and R$^{12}$ are independently hydrogen or halo; R$^1$, R$^2$, R$^5$ and R$^6$ are hydrogen; and R$^3$ and R$^4$ together with the carbon to which they are attached form C(O) or C(=NOH).

Another embodiment of the Invention (A12) provides a Compound of Formula I or Ia where the A ring is phenylene optionally substituted with R$^{10}$, R$^{12}$, R$^{14}$, and R$^{16}$ where R$^{14}$ and R$^{16}$ are hydrogen and where R$^{10}$ and R$^{12}$ are independently hydrogen or halo; X and R$^7$ are halo; and R$^1$, R$^2$, R$^4$, R$^5$ and R$^6$ are hydrogen; and all other groups are as defined in Formula I or Ia, respectively.

Another embodiment of the Invention (A14) provides a Compound of Formula I or Ia where the A ring is phenylene optionally substituted with R$^{10}$, R$^{12}$, R$^{14}$, and R$^{16}$; R$^1$ is hydrogen; and R$^2$ is alkyl substituted with —NR$^8$R$^{8'}$; where R$^8$ and R$^{8'}$ and all other groups are as defined in Formula I or Ia, respectively.

Another embodiment of the Invention (A15) provides a Compound Formula I or Ia where the A ring is phenylene optionally substituted with R$^{10}$, R$^{12}$, R$^{14}$, and R$^{16}$; R$^7$ is iodo or bromo; X is fluoro or chloro; R$^1$, R$^2$, R$^5$, and R$^6$ are hydrogen; and R$^{10}$, R$^{12}$, R$^{14}$, and R$^{16}$ are independently hydrogen or fluoro; and all other groups are as defined in Formula I or Ia, respectively. In another embodiment, R$^{10}$ is 3-fluoro and R$^{12}$, R$^{14}$, and R$^{16}$ are hydrogen or halo; R$^{10}$ is 3-fluoro, R$^{12}$ is 4-fluoro, and R$^{14}$ and R$^{16}$ are hydrogen; R$^{10}$ is 4-fluoro, R$^{12}$ is 5-fluoro, and R$^{14}$ and R$^{16}$ are hydrogen; R$^{10}$ is 4-fluoro, R$^{12}$ is 6-fluoro, and R$^{14}$ and R$^{16}$ are hydrogen; or R$^{12}$ is 4-fluoro and R$^{10}$, R$^{14}$, and R$^{16}$ are hydrogen.

In another embodiment, the invention is a compound of Formula I or Ia where the A ring is phenylene optionally substituted with $R^{10}$, $R^{12}$, $R^{14}$, and $R^{16}$; $R^3$ is hydroxy and $R^4$ is heterocycloalkyl, lower alkanyl, or heteroaryl, where the lower alkanyl is optionally substituted with —$NR^{8'}$ (where $R^8$ is hydrogen or lower alkanyl and $R^{8'}$ is hydrogen, lower alkanyl, or cycloalkyl where the cycloalkyl is optionally substituted with groups independently selected from hydroxy and lower alkanyl) and the heteroaryl is optionally substituted with lower alkanyl; and all other groups are as defined in Formula I or Ia, respectively. In another embodiment, $R^3$ is hydroxy and $R^4$ is heterocycloalkyl or lower alkanyl, where the lower alkanyl is optionally substituted with —$NR^8R^{8'}$ (where $R^8$ is hydrogen or lower alkanyl and $R^{8'}$ is hydrogen, lower alkanyl, or cycloalkyl where the cycloalkyl is optionally substituted with groups independently selected from hydroxy and lower alkanyl).

Another embodiment of the invention is a compound of Formula II:

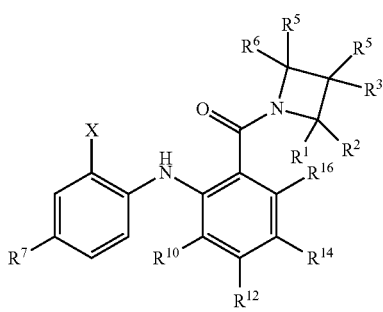

II and optionally as a pharmaceutically acceptable salt or solvate thereof, wherein X, $R^1$, $R^2$, $R^3$, $R^4$, $R^5$, $R^6$, and $R^7$ are as defined above for Formula I, and $R^{10}$, $R^{12}$, $R^{14}$ and $R^{16}$ are independently selected from hydrogen, lower alkanyl, lower alkenyl, lower alkynyl, halo, haloalkoxy, hydroxy, lower alkoxy, amino, alkylamino, dialkylamino, haloalkyl, —NHS$(O)_2R^8$, —CN, —C(O)$R^8$, —C(O)O$R^8$, —C(O)N$R^8R^{8'}$ and —$NR^8C(O)R^{8'}$.

In another embodiment of Formula II, $R^7$ and X are halo and $R^{10}$, $R^{12}$, $R^{14}$ and $R^{16}$ are independently selected from hydrogen and halo.

Another embodiment of the invention is a Compound of Formula III:

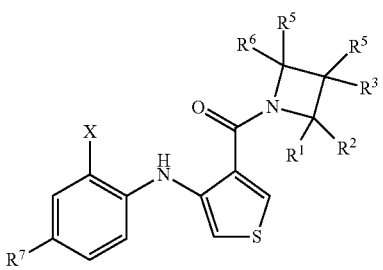

III and optionally as a pharmaceutically acceptable salt or solvate thereof, wherein X, $R^1$, $R^2$, $R^3$, $R^4$, $R^5$, $R^6$, and $R^7$ are as defined above for a Compound of Formula I.

In another embodiment of Formula III, X and $R^7$ are halo. In another embodiment, X is fluoro or chloro and $R^7$ is iodo or bromo.

In another embodiment of Formula III, $R^3$ is halo, nitro, —$NR^8R^{8'}$, —O$R^8$, —NHS$(O)_2R^8$, —CN, —S$(O)_mR^8$, —S$(O)_2NR^8R^{8'}$, —C(O)$R^8$, —C(O)O$R^8$, —C(O)N$R^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are independently optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —O$R^8$, —$NR^8R^{8'}$, —$NR^8S(O)_2R^9$, —CN, —S$(O)_mR^9$, —C(O)$R^8$, —C(O)O$R^8$, —C(O)N$R^8R^{8'}$, —$NR^8C(O)NR^{8'}R^{8''}$, —$NR^8C(O)OR^{8'}$ and —$NR^8C(O)R^{8'}$ and $R^4$ is as defined in Formula III; or $R^3$ and $R^4$ together with the carbon to which they are attached form C(O) or C(=NOH); and all other groups are as defined in Formula III. More specifically, $R^1$, $R^2$, $R^5$ and $R^6$ are hydrogen; and X and $R^7$ are halo.

In another embodiment of Formula III, $R^3$ and $R^4$ are independently halo, nitro, —$NR^8R^{8'}$, —O$R^8$, —NH S$(O)_2R^8$, —CN, —S$(O)_mR^8$, —S$(O)_2NR^8R^{8'}$, —C(O)$R^8$, —C(O)O$R^8$, —C(O)N$R^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, lower alkanyl, lower alkenyl, lower alkynyl, cycloalkyl, heteroaryl, or heterocycloalkyl; where the lower alkanyl, lower alkenyl, lower alkynyl, cycloalkyl, heteroaryl, and heterocycloalkyl are independently optionally substituted with one, two, three, four, five, six or seven groups independently selected from halo, lower alkanyl, haloalkyl, nitro, optionally substituted cycloalkyl, optionally substituted heterocycloalkyl, optionally substituted aryl, optionally substituted arylalkyl, optionally substituted heteroaryl, —O$R^8$, —$NR^8R^{8'}$, —$NR^8S(O)_2R^9$, —CN, —S$(O)_mR^9$, —C(O)$R^8$, —C(O)O$R^8$, —C(O)N$R^8R^{8'}$, —$NR^8C(O)NR^{8'}R^{8''}$, —$NR^8C(O)OR^{8'}$ and —$NR^8C(O)R^{8'}$; or $R^3$ and $R^4$ together with the carbon to which they are attached form C(O) or C(=NOH); and all other groups are as defined in Formula III. In another embodiment, $R^1$, $R^2$, $R^5$ and $R^6$ are hydrogen; and X and $R^7$ are halo.

In another embodiment of the invention (B5), the invention provides a Compound of Formula I where the A ring is thiendiyl and X, $R^1$, $R^2$, $R^3$, $R^4$, $R^5$, $R^6$, $R^7$, $R^{10}$, and $R^{12}$ are as defined in Formula I. In another embodiment, the A ring is thien-3,4-diyl; $R^{10}$ and $R^{12}$ are hydrogen; X and $R^7$ are halo; and $R^1$, $R^2$, $R^5$, and $R^6$ are hydrogen. In another embodiment, X is fluoro or chloro; $R^7$ is iodo or bromo; $R^3$ is hydrogen or hydroxy; and $R^4$ is —$NR^8R^{8'}$ (where $R^8$ and $R^{8'}$ are independently hydrogen or lower alkanyl), heterocycloalkyl, heteroaryl (optionally substituted with lower alkanyl), or lower alkanyl where the lower alkanyl is optionally substituted with —$NR^8R^{8'}$ (where $R^8$ is hydrogen or lower alkanyl and $R^{8'}$ is hydrogen, lower alkanyl, or cycloalkyl where the cycloalkyl is optionally substituted with one or two groups independently selected from hydroxy and lower alkanyl).

Another embodiment of the invention is a compound of Formula IV:

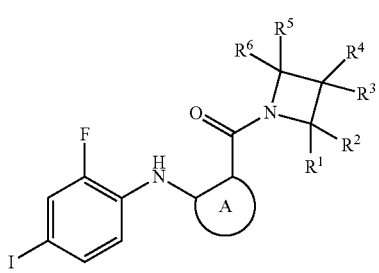

IV and optionally as a pharmaceutically acceptable salt or solvate thereof, wherein the A ring, $R^1$, $R^2$, $R^3$, $R^4$, $R^5$, and $R^6$ are as defined above for Formula I.

Another embodiment of the invention is a compound of Formula V:

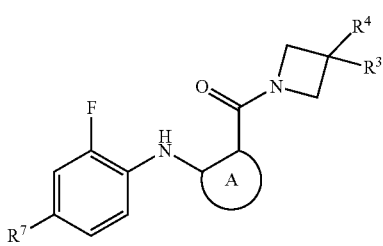

and optionally as a pharmaceutically acceptable salt or solvate thereof, wherein the A ring, $R^3$, $R^4$, and $R^7$ are as defined above for Formula I.

Another embodiment of the Invention (E) is directed to a Compound of Formula Ia where the A ring is phenylene optionally substituted with one or two groups selected from $R^{10}$, $R^{12}$, $R^{14}$, and $R^{16}$ where $R^{10}$, $R^{12}$, $R^{14}$ and $R^{16}$ are independently hydrogen or halo;

X is halo;

$R^1$, $R^2$, $R^5$ and $R^6$ are hydrogen;

$R^3$ is hydrogen, halo, hydroxy, alkoxy, or amino;

$R^4$ is hydrogen, halo, $-NR^8R^{8'}$, $-C(O)OR^8$, $-C(O)NR^8R^{8'}$, $-NR^8C(O)OR^{8'}$, $-NR^8C(O)R^{8'}$, lower alkanyl, lower alkenyl, cycloalkyl, heterocycloalkyl, or heteroaryl; where the $R^4$ lower alkanyl is optionally substituted with one, two, or three groups independently selected from $-OR^8$, halo, nitro, $-S(O)_mR^9$, optionally substituted heterocycloalkyl, $-NR^8R^{8'}$, $-NR^8C(O)R^{8'}$, $-NR^8S(O)_2R^9$, $-NR^8C(O)OR^{8'}$, and aryl; where the $R^4$ cycloalkyl is optionally substituted with one or two groups selected from $-OR^8$ and $-NR^8R^{8'}$; where the $R^4$ heterocycloalkyl is optionally substituted with one or two groups independently selected from lower alkanyl and $-C(O)OR^8$; and where the $R^4$ heteroaryl is optionally substituted with $-NR^8R^{8'}$; or $R^3$ and $R^4$ together with the carbon to which they are attached form C(O) or C(=NOH);

m is 1 or 2;

$R^7$ is halo;

$R^8$ and $R^{8'}$ are independently selected from hydrogen, hydroxy, lower alkanyl, lower alkenyl, lower alkynyl, aryl, heterocycloalkyl, heteroaryl, and cycloalkyl;

where the $R^8$ and $R^{8'}$ alkyl are independently optionally substituted with one, two, or three groups independently selected from hydroxy, $-NR^{30}R^{30'}$ (where $R^{30}$ and $R^{30'}$ are independently hydrogen, lower alkanyl, or hydroxyalkyl), optionally substituted heteroaryl, optionally substituted cycloalkyl), alkoxy, substituted alkoxy, optionally substituted cycloalkyl, optionally substituted aryl, optionally substituted heterocycloalkyl, optionally substituted heteroaryl, $-C(O)NR^{33}R^{33a}$ (where $R^{33}$ is hydrogen or alkyl and $R^{33a}$ is lower alkanyl, lower alkenyl, lower alkynyl, or cycloalkyl), optionally substituted aryloxy, $-S(O)_nR^{31}$ (where n is 0 and $R^{31}$ is alkyl), carboxy, alkoxycarbonyl, and $-NR^{32}C(O)R^{32a}$ (where $R^{32}$ is hydrogen or alkyl and $R^{32a}$ is lower alkanyl, lower alkenyl, alkoxy, or cycloalkyl); or where the lower alkanyl is optionally substituted with one, two, three, four, or five halo;

where the $R^8$ and $R^{8'}$ heteroaryl are independently optionally substituted with one or two groups independently selected from amino and lower alkanyl;

where the $R^8$ and $R^{8'}$ heterocycloalkyl are independently optionally substituted with one, two, or three groups independently selected from lower alkanyl, alkoxycarbonyl, optionally substituted arylalkyl, hydroxy, alkoxy, and hydroxyalkyl;

where the $R^8$ and $R^{8'}$ aryl are independently optionally substituted with one or two groups independently selected from hydroxy, alkoxy, halo, $-NR^{32}C(O)R^{32a}$ (where $R^{32}$ is hydrogen or lower alkanyl and $R^{32a}$ is lower alkanyl, lower alkenyl, alkoxy, or cycloalkyl), and $-NR^{34}SO_2R^{34a}$ (where $R^{34}$ is hydrogen or alkyl and $R^{34a}$ is lower alkanyl, lower alkenyl, cycloalkyl, aryl, heteroaryl, or heterocycloalkyl); and where the $R^8$ and $R^{8'}$ cycloalkyl are independently optionally substituted with one, two, or three groups independently selected from hydroxy, hydroxyalkyl, alkoxy, carboxy, $-C(O)NR^{33}R^{33a}$ (where $R^{33}$ is hydrogen or alkyl and $R^{33a}$ is lower alkanyl, lower alkenyl, lower alkynyl, or cycloalkyl), and optionally substituted cycloalkyl; and $R^9$ is lower alkanyl or aryl.

Another embodiment of Embodiment (E) is directed to a Compound of Formula Ia where $R^3$ is hydrogen, halo, hydroxy, or alkoxy;

$R^4$ is hydrogen, halo, $-NR^8R^{8'}$, $-NHS(O)_2R^8$, $-C(O)OR^8$, $-C(O)NR^8R^{8'}$, $-NR^8C(O)OR^{8'}$, $-NR^8C(O)R^{8'}$, lower alkanyl, lower alkenyl, or heterocycloalkyl; where the $R^4$ lower alkanyl is optionally substituted with one, two, or three groups independently selected from $-OR^8$, halo, optionally substituted heterocycloalkyl, and $-NR^8R^{8'}$; and where the $R^4$ heterocycloalkyl is optionally substituted with one or two groups independently selected from lower alkanyl and $-C(O)OR^8$; or $R^3$ and $R^4$ together with the carbon to which they are attached form C(O) or C(=NOH);

m is 1 or 2;

$R^7$ is halo;

$R^8$ and $R^{8'}$ are independently selected from hydrogen, hydroxy, lower alkanyl, and lower alkenyl; where the $R^8$ and $R^{8'}$ lower alkanyl are independently optionally substituted with one, two, or three groups independently selected from halo, hydroxy, and $-NR^{30}R^{30'}$ (where $R^{30}$ and $R^{30'}$ are independently hydrogen, lower alkanyl, or hydroxyalkyl); and all other groups are as defined in Embodiment E.

Another embodiment (F) of the Invention is a Compound of Formula Ia where the A ring is phenylene optionally substituted with one or two groups selected from $R^{10}$, $R^{12}$, $R^{14}$, and $R^{16}$ where $R^{10}$, $R^{12}$, $R^{14}$ and $R^{16}$ are independently hydrogen or halo;

X is halo;

$R^1$, $R^2$, $R^5$ and $R^6$ are hydrogen;

$R^3$ is hydrogen, halo, hydroxy, or alkoxy;

$R^4$ is $-NR^8R^{8'}$, $-NHS(O)_2R^8$, $-C(O)OR^8$, $-C(O)NR^8R^{8'}$, $-NR^8C(O)OR^{8'}$, $-NR^8C(O)R^{8'}$, lower alkanyl, lower alkenyl, or heterocycloalkyl; where the $R^4$ lower alkanyl is optionally substituted with one, two, or three groups independently selected from $-OR^8$, halo, optionally substituted heterocycloalkyl, and $-NR^8R^{8'}$; and where the $R^4$ heterocycloalkyl is optionally substituted with one or two groups independently selected from lower alkanyl and $-C(O)OR^8$; or $R^3$ and $R^4$ together with the carbon to which they are attached form C(O) or C(=NOH); and $R^8$ and $R^{8'}$ are independently selected from hydrogen, hydroxy, lower alkanyl, and lower alkenyl; where the $R^8$ and $R^{8'}$ lower alkanyl are independently optionally substituted with one, two, or three groups independently selected from halo, hydroxy, and —$NR^{30}R^{30'}$ (where $R^{30}$ and $R^{30'}$ are independently hydrogen, lower alkanyl, or hydroxyalkyl).

Another embodiment (G) of the Invention is directed to a Compound of Formula Ia where the A ring is thien-3,4-diyl optionally substituted with one, two, or three groups independently selected from $R^{10}$, $R^{12}$, $R^{14}$, and $R^{16}$ where $R^{10}$, $R^{12}$, $R^{14}$ and $R^{16}$ are independently hydrogen, lower alkanyl, halo, or amino;

X is halo;

$R^1$, $R^2$, $R^5$ and $R^6$ are hydrogen;

$R^3$ is hydrogen or hydroxy;

$R^4$ is —$OR^8$, —$NR^8R^{8'}$, heterocycloalkyl, heteroaryl, or lower alkanyl; where the lower alkanyl is optionally substituted with —$NR^8R^{8'}$ and where the heteroaryl is optionally substituted with lower alkanyl;

$R^7$ is halo;

$R^8$ is hydrogen or lower alkanyl; and $R^{8'}$ is hydrogen, lower alkanyl, or cycloalkyl; where the cycloalkyl is optionally substituted with one or two groups independently selected from hydroxy and lower alkanyl.

Another embodiment of the Invention (H) is directed to a Compound of Formula Ia where the A ring is thien-3,4-diyl;

X is halo;

$R^1$, $R^2$, $R^5$ and $R^6$ are hydrogen;

$R^3$ is hydrogen or hydroxy;

$R^4$ is —$OR^8$, —$NR^8R^{8'}$, heterocycloalkyl, or lower alkanyl; where the lower alkanyl is optionally substituted with —$NR^8R^{8'}$;

$R^7$ is halo;

$R^8$ is hydrogen or lower alkanyl;

$R^{8'}$ is hydrogen or lower alkanyl; and all other groups are as defined in Embodiment E.

Another embodiment of the invention is a pharmaceutical composition comprising a compound according to any of Formulas I, Ia, Ic, Id, II, III, IV, and V or a compound as depicted in Table 1, and a pharmaceutically acceptable carrier. In another embodiment, the Compound is according to Formula Ia, according to Formula V, or according to Embodiment G.

Section I Definitions

As used in this section, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, and "---" means a single bond and optionally a double bond. When chemical structures are depicted or described, unless explicitly stated otherwise, all carbons are assumed to have hydrogen substitution to conform to a valence of four. Sometimes a particular atom in a structure is described in textual Formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

"Alkyl" or "lower alkyl" means a ($C_1$-$C_{20}$) linear, branched, or cyclic hydrocarbon group and combinations thereof, inclusively. For example, "$C_8$ alkyl" refers to an n-octyl, iso-octyl, cyclohexylethyl, isobutenyl, and but-2-ynyl groups and the like. Examples of lower alkyl groups include methyl, ethyl, propyl, isopropyl, butyl, s-butyl, t-butyl, isobutyl, pentyl, hexyl and the like. Exemplary alkyl groups are those of $C_{20}$ or below.

In this application, alkyl includes alkanyl, alkenyl, alkynyl, and cycloalkyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"Alkanyl" means a linear saturated monovalent hydrocarbon radical of one to twenty carbon atoms or a branched saturated monovalent hydrocarbon radical of three to 20 carbon atoms, e.g., methyl, ethyl, propyl, 2-propyl, butyl (including all isomeric forms), or pentyl (including all isomeric forms), and the like. "Lower alkanyl" means alkanyl having one to six carbons atoms.

The term "cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Optionally substituted cycloalkyl" means a cycloalkyl radical, as defined herein, that is optionally substituted with one, two, three, or four groups independently selected from $C_1$-$C_6$ alkanyl, $C_1$-$C_6$ alkoxy, halo, haloalkyl, haloalkoxy, oxo, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl di($C_1$-$C_6$)alkylamino($C_1$-$C_6$) alkyl, carboxy, carboxy ester, cycloalkyl, hydroxyalkyl, —C(O)NR'R" (where R' is hydrogen, alkyl, hydroxy, or alkoxy and R" is hydrogen, alkyl, aryl, or heterocyclyl), optionally substituted heterocycloalkyl, optionally substituted heteroaryl, —NR'C(O)R" (where R' is hydrogen or alkyl and R" is alkyl, aryl, or heterocyclyl), and —NHS(O)$_2$R' (where R' is alkyl, aryl, or heterocyclyl).

"Alkenyl" means a straight or branched hydrocarbon radical having from 2 to 20 carbon atoms and at least one double bond and includes ethenyl, propenyl, 1-but-3-enyl, 1-pent-3-enyl, 1-hex-5-enyl and the like. "Lower alkenyl" is alkenyl having 2-6 carbon atoms.

"Alkynyl" means a straight or branched hydrocarbon radical having from 2 to 20 carbon atoms and at least one triple bond and includes ethynyl, propynyl, butynyl, pentyn-2-yl and the like. "Lower alkynyl" is alkynyl having 2-6 carbon atoms.

"Alkylene" means a straight or branched divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" means a straight or branched, divalent group consisting solely of carbon and hydrogen atoms, having from two to ten carbon atoms, and containing at least one double bond. Representative examples include ethylidene, propylidene, n-butylidene, and the like.

"Alkylidyne" means a straight or branched chain divalent group consisting solely of carbon and hydrogen atoms having from two to ten carbon atoms, and containing at least one triple bond, for example, propylid-2-ynyl, n-butylid-1-ynyl, and the like.

"Alkoxy" or "alkoxyl" means —O-alkyl, where the alkyl group includes from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" means an —OR radical where R is substituted alkyl as defined herein. Representative examples include groups such as —OCH$_2$CH$_2$OCH$_3$, and glycol ethers such as polyethyleneglycol and —O(CH$_2$CH$_2$O)$_x$CH$_3$, (where x is an integer of between two and twenty, preferable, between two and ten, and more preferably, between two and five). Another exemplary substituted alkoxy group is hydroxyalkoxy or —OCH$_2$(CH$_2$)$_y$OH (where y is an integer of between one and ten, in another example y is an integer of between one and four).

"Alkoxyalkyl" means a lower alkyl group, as defined herein, substituted with at least one, preferably one, two, or three, alkoxy groups as defined herein. Representative examples include methoxymethyl and the like.

"Alkoxycarbonylamino" means a —NR'C(O)OR" group where R' is hydrogen, alkyl, hydroxy, or alkoxy and R" is alkyl.

"Alkylcarbonyloxy" means an —OC(O)R group where R is alkyl, as defined herein.

"Acyl" means a —C(O)R radical where R is alkyl (i.e., one to ten carbon atoms of a straight, branched, or cyclic configuration, and is saturated or unsaturated) or R is optionally substituted aryl or optionally substituted heteroaryl. One or more carbons in the R residue may be replaced by nitrogen, oxygen or sulfur. Examples include acetyl, benzoyl, propionyl, isobutyryl, t-butoxycarbonyl, benzyloxycarbonyl, and pyridinylcarbonyl, and the like. Lower-acyl refers to groups containing one to six carbons.

"Acylamino" means a —NRR' group where R is acyl, as defined herein, and R' is hydrogen or alkyl.

"Alkylamino" means a —NHR radical where R is alkyl as defined herein, or an N-oxide derivative, or a protected derivative thereof, e.g., methylamino, ethylamino, n-, isopropylamino, n-, iso-, tert-butylamino, or methylamino-N-oxide, and the like.

"Alkylaminoalkyl" means an alkyl group substituted with one or two alkylamino groups, as defined herein.

"Alkylaminocarbonyl" means a —C(O)NHR radical where R is lkyl, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Optionally substituted aryl" means an aryl group, as defined herein, which is optionally substituted with one, two, three, four, of five groups selected from halo, haloalkyl, haloalkoxy, hydroxy, lower alkanyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), and —NHS(O)$_2$R' (where R' is alkyl, aryl, or heteroaryl).

"Arylalkyl" means a residue in which an aryl moiety is attached to a parent structure via one of an alkylene, alkylidene, or alkylidyne group. Examples include benzyl, phenethyl, phenylvinyl, phenylallyl and the like. "Lower arylalkyl" refers to an arylalkyl where the "alkyl" portion of the group has one to six carbons; this can also be referred to as C$_{1-6}$ arylalkyl.

"Optionally substituted arylalkyl means an alkyl group substituted with one or two optionally substituted aryl group(s) as defined herein. In addition the alkyl group may itself be substituted as described under "substituted alkyl".

"Arylalkyloxy" means an —OR group where R is arylalkyl, as defined herein.

"Carboxy ester" means a —C(O)OR group where R is lower alkanyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Dialkylamino" means a —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminocarbonyl" means a —C(O)NRR' group where R and R' are alkyl.

"Exo-alkenyl" refers to a double bond that emanates from an annular carbon, and is not within the ring system.

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" means a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention may themselves have spiro rings attached thereto via a single ring atom of the fused-polycyclic.

"Haloaloxy" means an —OR' group where R' is haloalkyl as defined herein, e.g., trifluoromethoxy or 2,2,2-trifluoroethoxy, and the like.

"Halogen" or "halo" means fluoro, chloro, bromo or iodo.

"Haloalkyl" and "haloaryl" mean an alkyl and an aryl group, respectively, that are substituted with one or more halogens, preferably one to five halo atoms. Thus, "dihaloaryl," "dihaloalkyl," and "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" means a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems. The terms "heterocycloalkyl" and "heteroaryl" are groups that are encompassed by the broader term "heterocyclyl." The nitrogen, phosphorus, carbon and sulfur atoms in the heterocyclyl group may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Optionally substituted heterocyclyl" means a heterocyclyl group, as defined herein, optionally substituted with one, two, three, four, or five groups selected from halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), amino, alkylamino, dialkylamino, and —NHS(O)$_2$R' (where R' is alkyl, aryl, or heteroaryl).

"Heteroalicyclic" and "heterocycloalkyl" mean a non-aromatic heterocyclyl group, as defined herein. A "heteroalicyclic" or "heterocycloalkyl" may be fully saturated or may contain unsaturation, but is not aromatic. "Heteroalicyclic" or "heterocycloalkyl" may be monocyclic or bicyclic (including fused, bridged, and spiro ring systems).

"Optionally substituted heteroalicyclic" and "optionally substituted heterocycloalkyl" mean, respectively, a heteroalicyclic and heterocycloalkyl ring, each as defined herein, optionally substituted with one, two, three, four, or five groups selected from halo, haloalkyl, haloalkoxy, hydroxy, oxo, lower alkanyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), amino, alkylamino, dialkylamino, and —NHS(O)$_2$R' (where R' is alkyl, aryl, or heteroaryl).

"Heteroaryl" means a 5- to 12-membered, monocyclic aromatic heterocyclyl (where heterocyclyl is defined herein) or bicyclic heterocyclyl ring system (where at least one of the rings in the bicyclic system is aromatic) where the monocyclic ring and at least one of the rings in the bicyclic ring system contains one, two, three, four, or five heteroatom(s) selected from nitrogen, oxygen, phosphorous, and sulfur. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

"Optionally substituted heteroaryl" means a heteroaryl group, as defined herein, optionally substituted with one, two, three, four, or five groups selected from halo, haloalkyl, haloalkoxy, lower alkanyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), and —NHS(O)$_2$R' (where R' is alkyl, aryl, or heteroaryl).

"Optionally substituted heterocyclylalkyl" means an alkyl group substituted with an optionally substituted heterocyclyl group, as defined herein. Examples include (4-methylpiperazin-1-yl)methyl, (morpholin-4-yl)methyl, (pyridin-4-yl)methyl, 2-(oxazolin-2-yl)ethyl, 4-(4-methylpiperazin-1-yl)-2-butenyl, and the like. In addition, the alkyl portion of a heterocyclylalkyl group may be substituted as described in the definition for "substituted". "Lower heterocyclylalkyl" means a heterocyclylalkyl where the "alkyl" portion of the group has one to six carbons. "Heteroalicyclylalkyl" or "lower heterocycloalkylalkyl" means a heterocyclylalkyl where the heterocyclyl portion of the group is non-aromatic; and "heteroarylalkyl" means a heterocyclylalkyl where the heterocyclyl portion of the group contains an aromatic ring. Such terms may be described in more than one way, for example, "lower heterocyclylalkyl" and "heterocyclyl C$_{1-6}$alkyl" are equivalent terms. Additionally, for simplicity, the number of annular atoms (including heteroatoms) in a heterocycle may be denoted as "C$_x$-C$_y$" (as in "C$_x$-C$_y$-heterocyclyl" and "C$_x$-C$_y$-heteroaryl" (and the like)), where x and y are integers. So, for example, C$_5$-C$_{14}$-heterocyclyl refers to a 5 to 14 membered ring system having at least one heteroatom and not a ring system containing 5 to 14 annular carbon atoms.

Preferred heterocyclyls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Hydroxyalkyl" means an alkanyl, alkenyl, or alkynyl radical, as defined herein, substituted with at least one, preferably one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxy butyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, or 1-(hydroxymethyl)-2-hydroxyethyl, and the like.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-13}$ alkyl," both the "$C_{1-8}$ alkyl" portion and the "aryl" portion of the molecule may or may not be substituted. A list of exemplary optional substitutions is presented below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spiro", "Spirocyclyl" or "spiro ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

"Substituted" alkyl, alkylene, alkylidene, and alkylidyne refer respectively to alkyl, alkylene, alkylidene, and alkylidyne where one or more (for example up to about five, in another example, up to about three) hydrogen atoms are replaced by a substituent independently selected from halo, optionally substituted aryl, hydroxy, alkoxy, optionally substituted heterocyclyl, alkylenedioxy, amino, alkylamino, dialkylamino), amidino, aryloxy, arylalkyloxy, carboxy, carboxy ester, alkylcarbonyloxy, carbamyl, alkylaminocarbonyl, dialkylaminocarbonyl, benzyloxycarbonylamino (CBZ-amino), cyano, acyl, nitro, $S(O)_{n1}R'$ (where n1 is 0, 1, or 2 and R' is alkyl, substituted alkyl, optionally substituted aryl, optionally substituted heterocycloalkyl, or optionally substituted heteroaryl), oxo, acylamino, and sulfonamido.

Table 1 depicts a representative example of the compounds of Section I.

TABLE 1

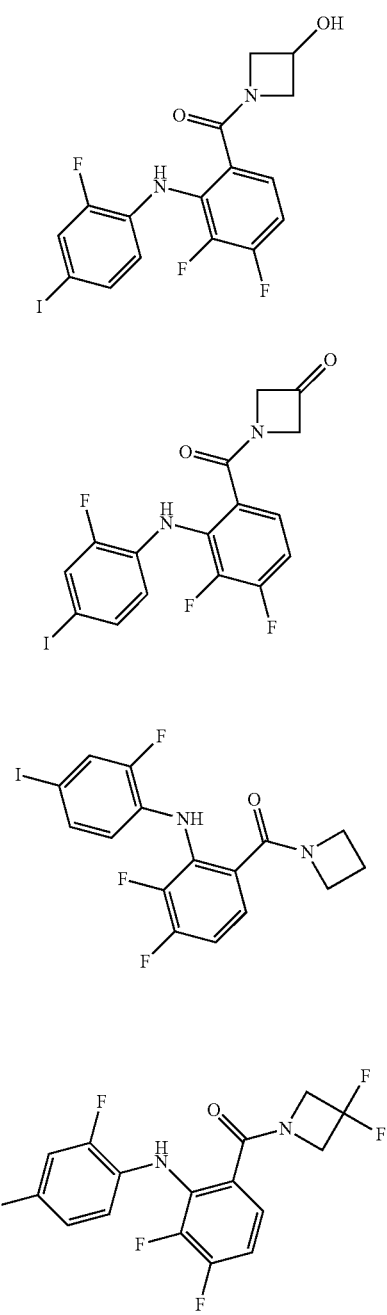

TABLE 1-continued
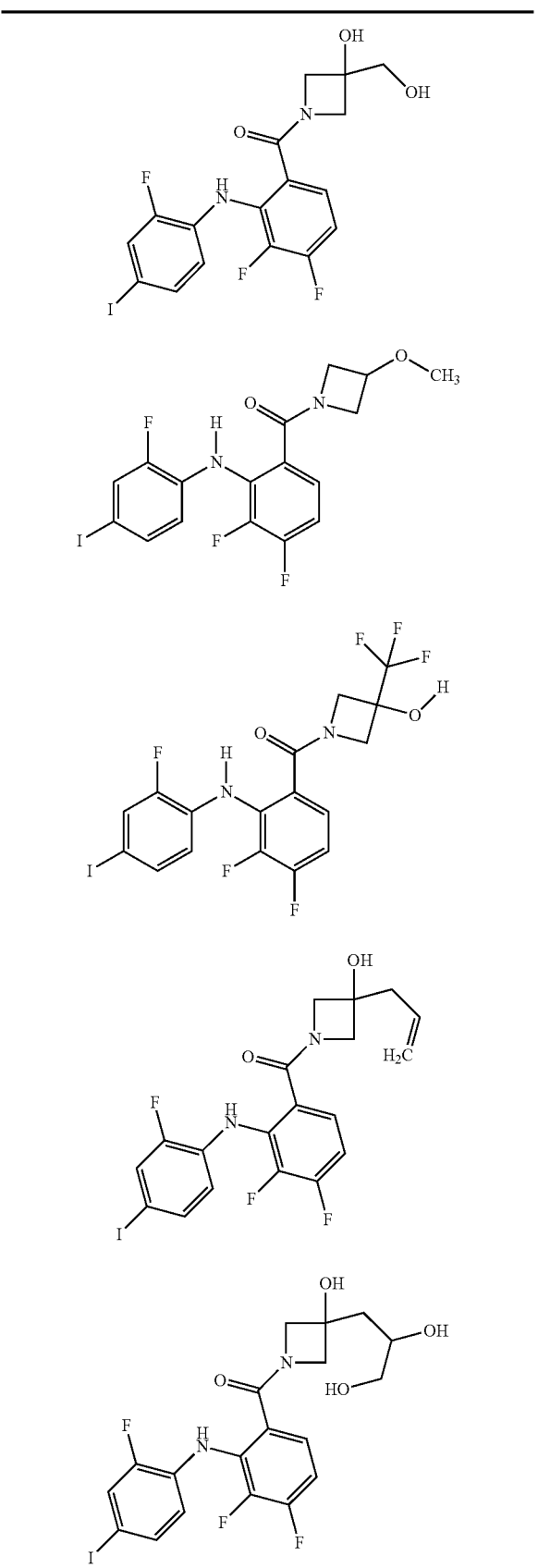
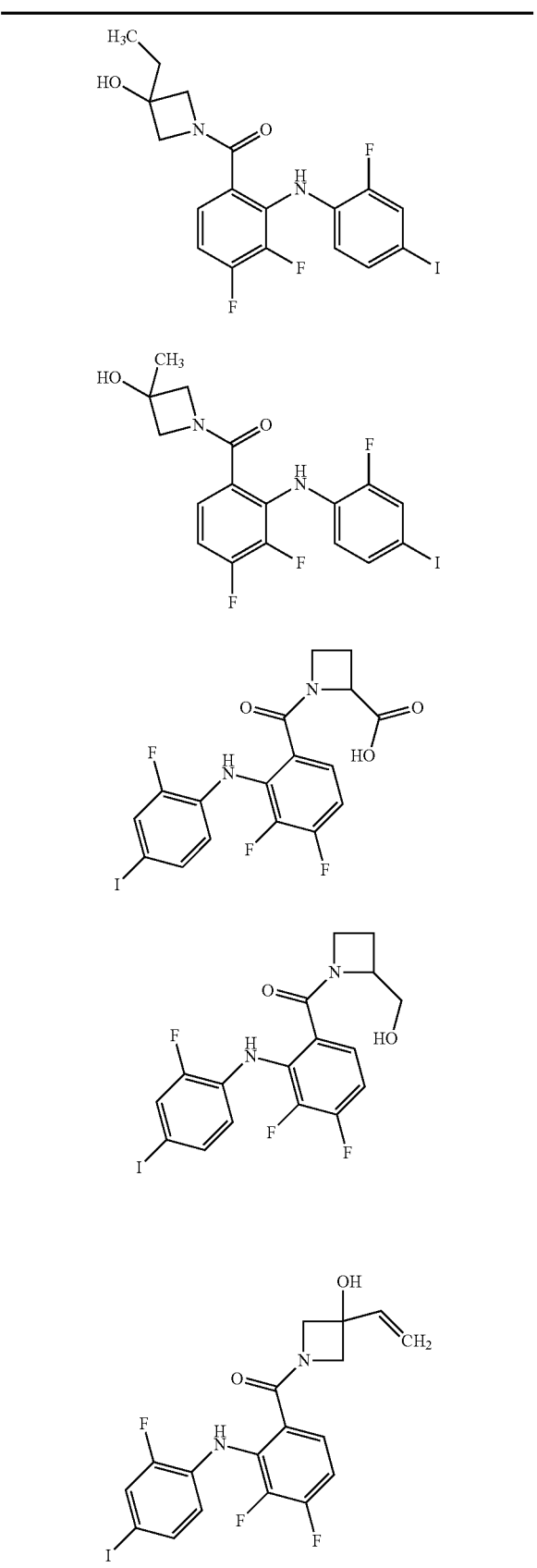

TABLE 1-continued
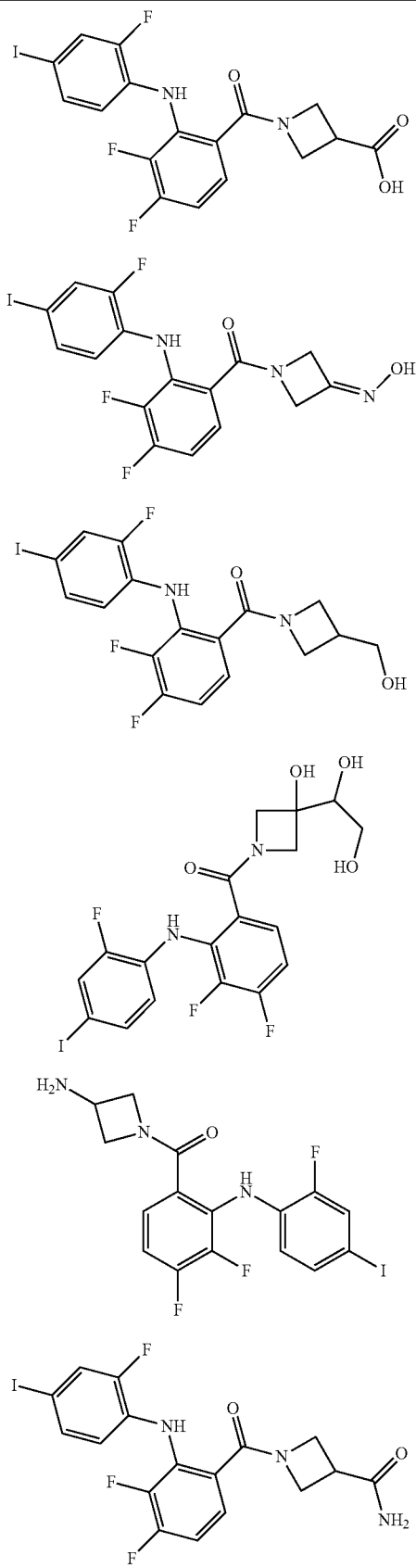
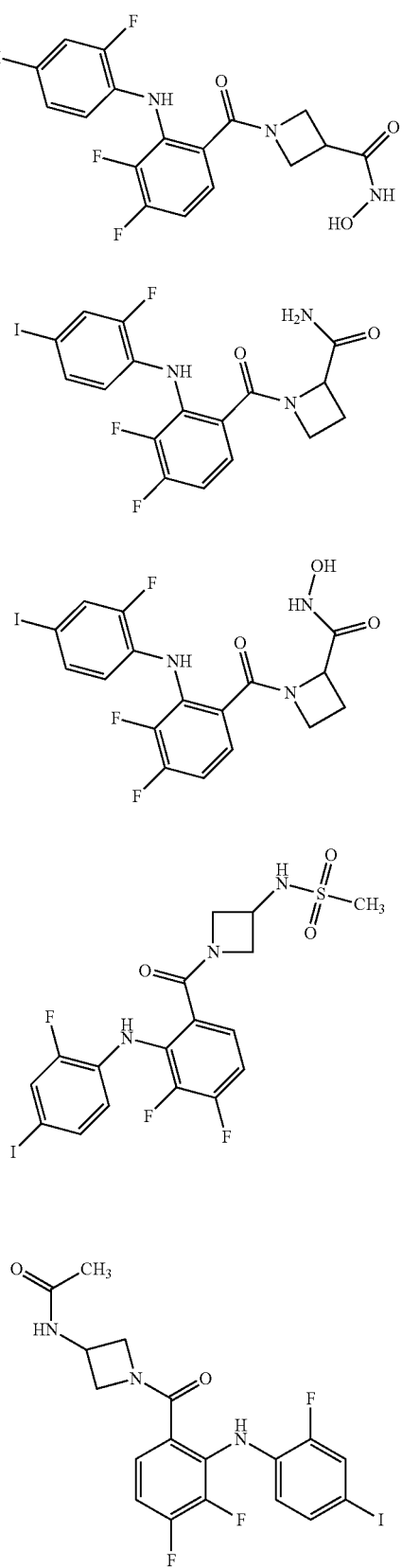

TABLE 1-continued
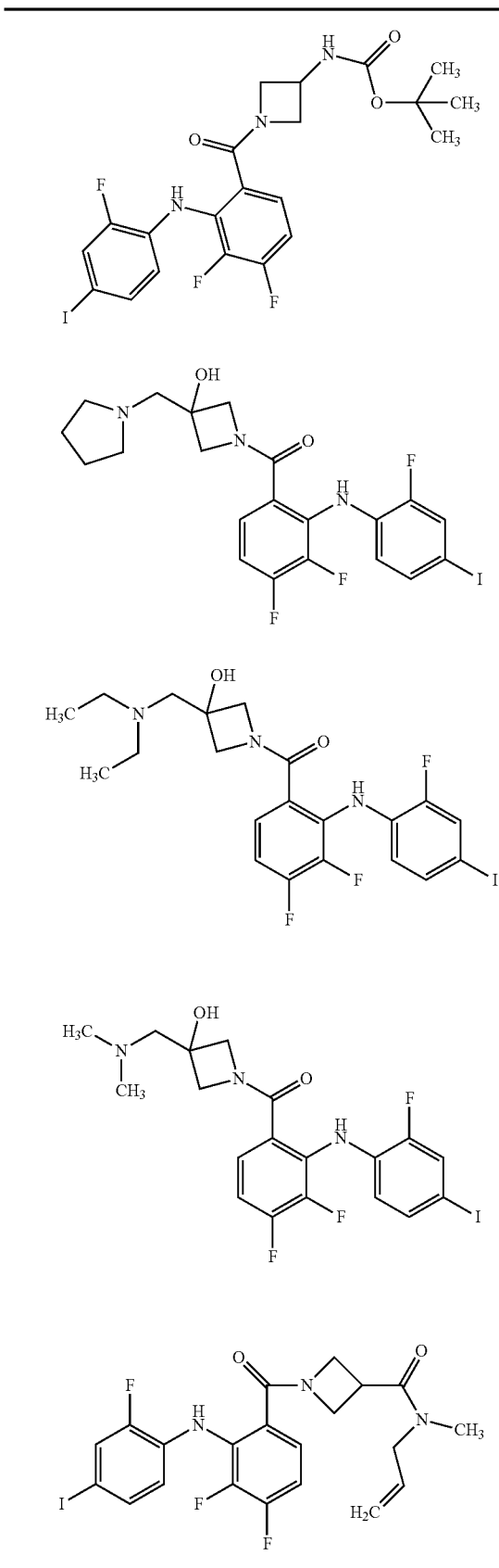
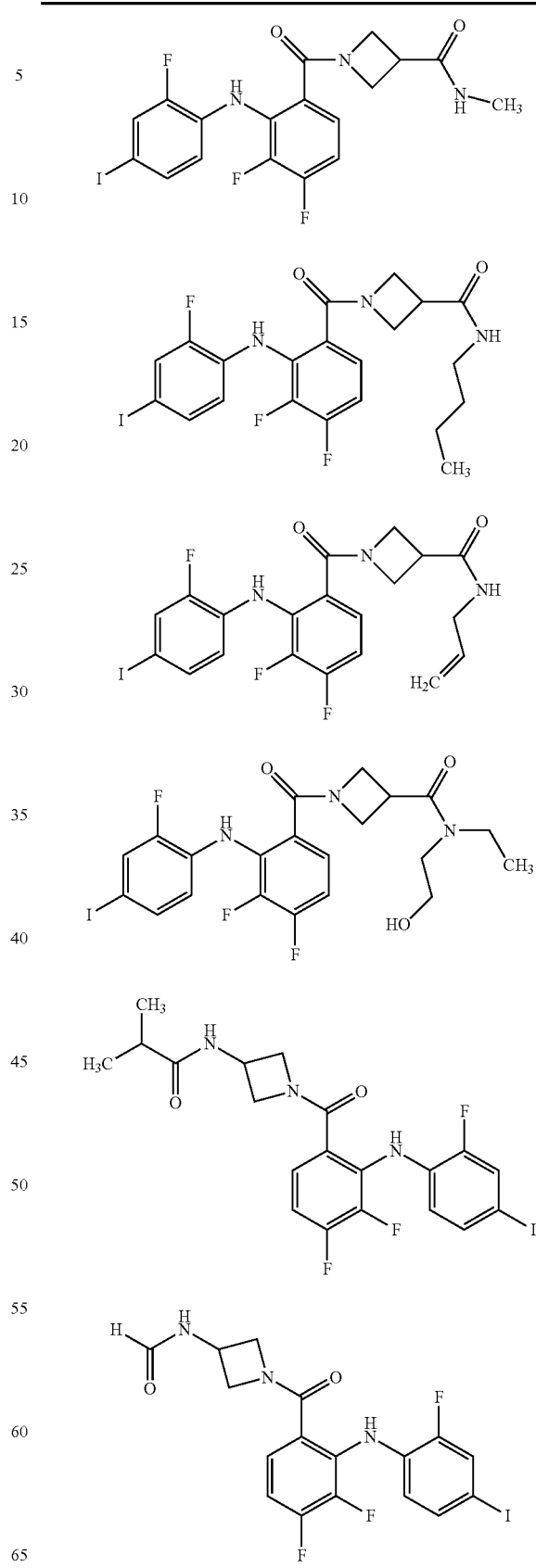

TABLE 1-continued
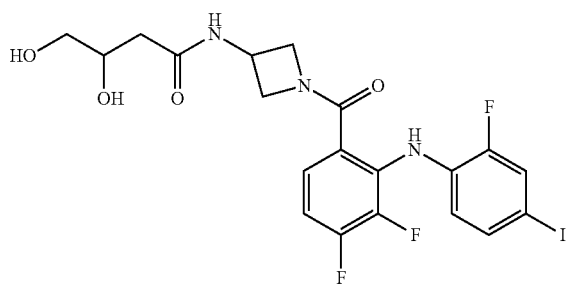 [SMILES: O=C(CC(O)CO)NC1CN(C(=O)c2ccc(F)c(F)c2Nc2ccc(I)cc2F)C1]
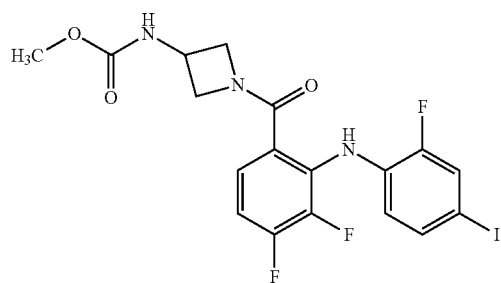 [SMILES: COC(=O)NC1CN(C(=O)c2ccc(F)c(F)c2Nc2ccc(I)cc2F)C1]
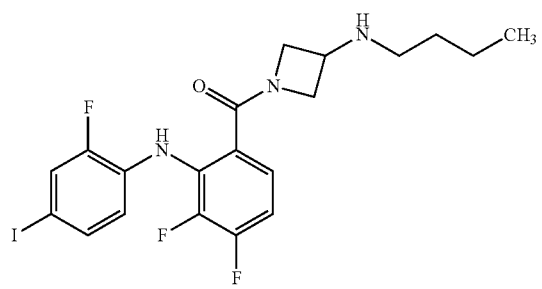 [SMILES: CCCCNC1CN(C(=O)c2ccc(F)c(F)c2Nc2ccc(I)cc2F)C1]
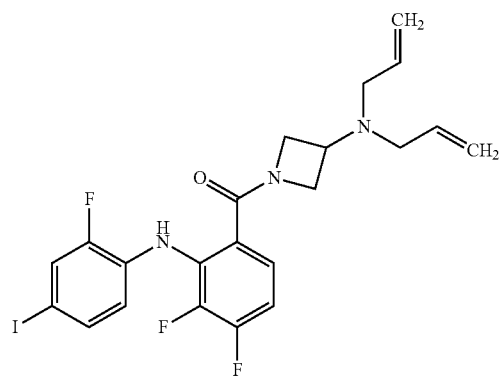 [SMILES: C=CCN(CC=C)C1CN(C(=O)c2ccc(F)c(F)c2Nc2ccc(I)cc2F)C1]
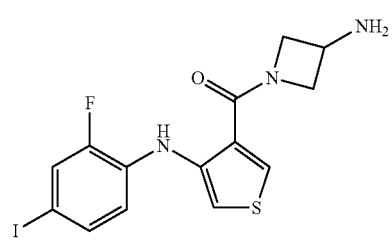 [SMILES: NC1CN(C(=O)c2cscc2Nc2ccc(I)cc2F)C1]
TABLE 1-continued
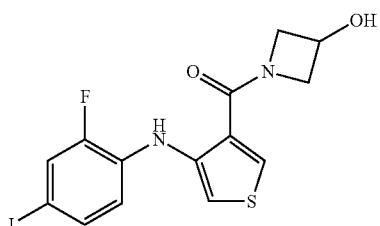
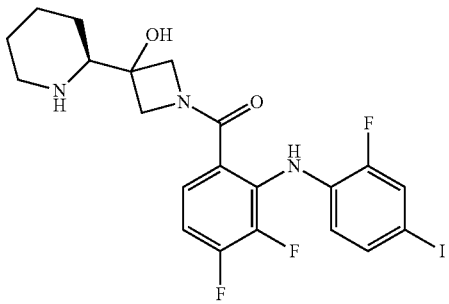 [SMILES: O=C(c1ccc(F)c(F)c1Nc1ccc(I)cc1F)N1CC(O)([C@@H]2CCCCN2)C1]
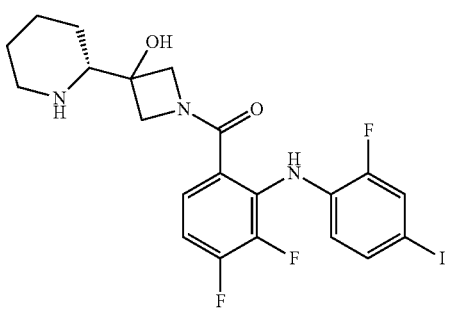 [SMILES: O=C(c1ccc(F)c(F)c1Nc1ccc(I)cc1F)N1CC(O)([C@H]2CCCCN2)C1]
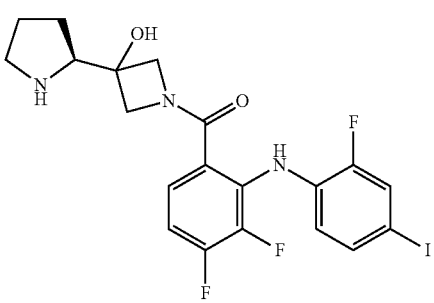 [SMILES: O=C(c1ccc(F)c(F)c1Nc1ccc(I)cc1F)N1CC(O)([C@@H]2CCCN2)C1]
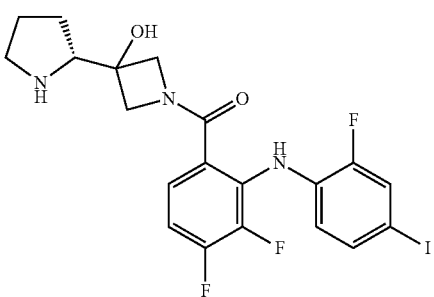 [SMILES: O=C(c1ccc(F)c(F)c1Nc1ccc(I)cc1F)N1CC(O)([C@H]2CCCN2)C1]

TABLE 1-continued

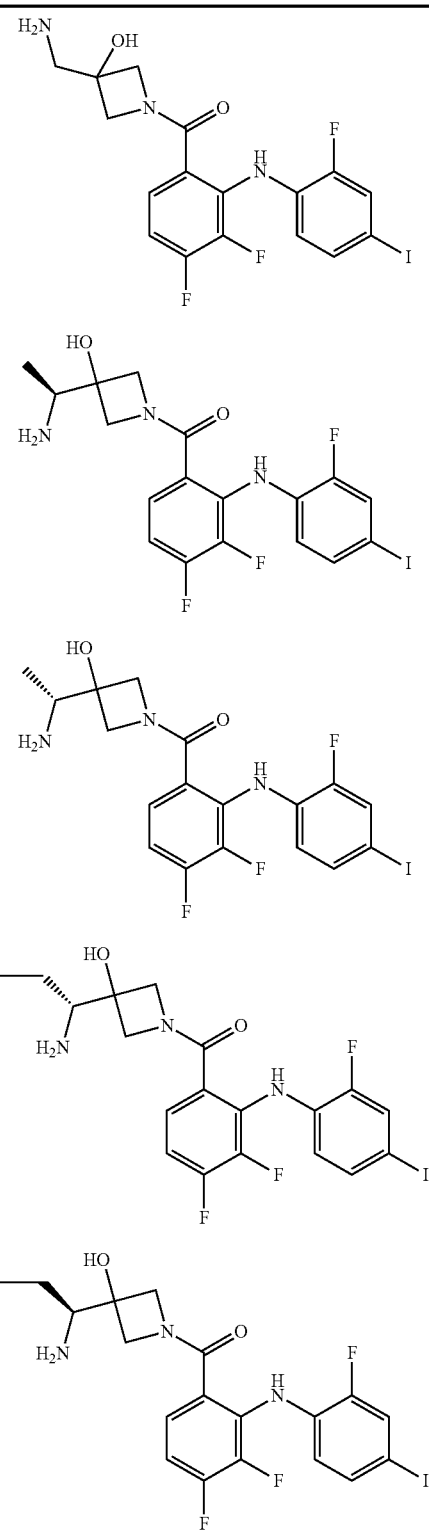

As use in one embodiment of the invention, the MEK inhibitor is selected from the compounds in Table I having a MEK-binding affinity of about 4 μM or less. In another embodiment, the MEK inhibitor is selected from the compounds in Table I having a MEK-binding affinity of about 3 μM or less. In another embodiment, the MEK inhibitor is selected from the compounds in Table I having a MEK-binding affinity of about 2 μM or less. In another embodiment, the MEK inhibitor is selected from the compounds in Table I having a MEK-binding affinity of about 1.6 μM or less. In another embodiment, the MEK inhibitor is selected from the compounds in Table I having a MEK-binding affinity of about 1 μM or less. In another embodiment, the MEK inhibitor is selected from the compounds in Table I having a MEK-binding affinity of about 0.7 μM or less. In another embodiment, the MEK inhibitor is selected from the compounds in Table I having a MEK-binding affinity of about 0.3 μM or less. In another embodiment, the MEK inhibitor is selected from the compounds in Table I having a MEK-binding affinity of about 0.2 μM or less. In another embodiment, the MEK inhibitor is selected from the compounds in Table I having a MEK-binding affinity of about 0.1 μM or less.

EXPERIMENTAL

Preparation of Compounds

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] or [M+Na] ion (positive mode) or [M−1] ion (negative mode). $^1$H-NMR data for compounds was taken with a Varian AS400 Spectrometer (400 MHz, available from Varian GmbH, Darmstadt, Germany).

Starting materials and intermediates used to prepare a compound of the invention are either commercially available or can be prepared by one of ordinary skill in the art.

Example 1

1-({3,4-Difluoro-2-[(2-fluoro-4-iodophenyl)-amino]phenyl}carbonyl)azetidin-3-ol 3,4-Difluoro-2-[(2-fluoro-4-iodophenyl)amino]benzoic acid (2.1 g, 5.3 mmol) was taken into DMF (10 mL) followed by addition of PyBOP (2.6 g, 5.3 mmol) and the mixture was allowed to stir at room temperature over 15 minutes. Azetidin-3-ol hydrochloride (870 mg, 8.0 mmol) and DIPEA (1.85 mL, 11.2 mmol) was then added and the mixture was allowed to stir an additional hour at room temperature. The mixture was then partitioned with ethyl acetate and 0.5 M aqueous sodium hydroxide solution. The organic layer was then washed with water (3×) then brine and dried over anhydrous sodium sulfate. Filtration and concentration followed by silica gel flash chromatography using ethyl acetate:hexanes (5:1) eluent afforded 1-({3,4-difluoro-2-[(2-fluoro-4-iodophenyl)amino]phenyl}carbonyl)azetidin-3-ol (2.09 g, 87% yield) as a colorless amorphous solid. 1H NMR (400 MHz, CDCl$_3$): 8.47 (s, 1H), 7.39 (dd, 1H), 7.32 (d, 1H), 7.13-7.09 (m, 1H), 6.84-638 (m, 1H), 6.63-6.57 (m, 1H), 4.74-4.67 (m, 1H), 4.43-4.39 (m, 2H), 4.20-3.96 (br d, 2H), 2.50 (d, 1H).

Example 2

4-(2-Fluoro-4-iodo-phenylamino)-thiophene-3-carboxylic acid

A solution of methyl-4-oxo-tetrahydro-thiophene-3-carboxylate (5.75 g, 35.9 mmol) and 2-fluoro-4-iodo-aniline (9.4 g, 40.9 mmol) were heated to reflux in a mixture of ethanol (25 mL) and acetic acid (0.3 mL) for 18 hours. The solution was cooled to room temperature, filtered and the solid product dried in vacuo to provide methyl-4-(2-fluoro-4-iodo-phenylamino)-2,3-dihydro-thiophene-3-carboxylate (5.70 g, 42% yield). MS (EI) for $C_{12}H_{11}FINO_2S$: 380 (MH$^+$).

A mixture of methyl-4-(2-fluoro-4-iodo-phenylamino)-2,3-dihydro-thiophene-3-carboxylate (5.7 g, 15.0 mmol) and chloranil (5.7 g, 15.0 mmol) in toluene (50 mL) was heated to reflux for 2 hours. The solution was cooled to room temperature and the solvent was evaporated. The resulting dark brown solid was recrystallized from methanol to provide methyl 4-(2-fluoro-4-iodo-phenylamino)-thiophene-3-carboxylate (2.8 g, 49.5% yield). MS (EI) for $C_{12}H_9FINO_2S$: 378 (MH$^+$).

Methyl 4-(2-Fluoro-4-iodo-phenylamino)-thiophene-3-carboxylate (270 mg, 0.72 mmol) was dissolved in a mixture of tetrahydrofuran:methanol (6:1, 3 mL) and a solution of lithium hydroxide (0.1 g, 4.2 mmol) in 1 mL of water was added. The solution was stirred at room temperature for 18 hours and the solvent was concentrated. The residue was dissolved in 5 mL of water and the solution was acidified to pH 1 with 1N HCl. The resulting solid was filtered and dried in vacuo to provide 210 mg (79% yield) of 4-(2-fluoro-4-iodo-phenylamino)-thiophene-3-carboxylic acid. MS (EI) for $C_{11}H_7FINO_2S$: 364 (MH$^+$).

Example 3

Using the same or analogous synthetic techniques described in examples 1 and 2 and substituting with alternative reagents, the following compounds of the invention were prepared:

a) 1-({3,4-difluoro-2-[(2-fluoro-4-iodophenyl)amino]phenyl}carbonyl)azetidin-3-ol: MS (EI) for $C_{16}H_{12}F_3IN_2O_2$: 449 (MH$^+$).
b) 1-({3,4-difluoro-2-[(2-fluoro-4-iodophenyl)amino]phenyl}carbonyl)azetidin-3-one: MS (EI) for $C_{16}H_{10}F_3IN_2O_2$: 447 (MH$^+$).
c) 6-(azetidin-1-ylcarbonyl)-2,3-difluoro-N-(2-fluoro-4-iodophenyl)aniline: MS (EI) for $C_{16}H_{12}F_3IN_2O$: 433 (MH$^+$).
d) 6-[(3,3-difluoroazetidin-1-yl)carbonyl]-2,3-difluoro-N-(2-fluoro-4-iodophenyl)aniline: MS (EI) for $C_{16}H_{10}F_5IN_2O_3$: 469 (MH$^+$).
e) 1-({3,4-difluoro-2-[(2-fluoro-4-iodophenyl)amino]phenyl}carbonyl)-3-(hydroxymethyl)azetidin-3-ol: MS (EI) for $C_{17}H_{14}F_3IN_2O_3$: 479 (MH$^+$).
f) 2,3-difluoro-N-(2-fluoro-4-iodophenyl)-6-{[3-(methyloxy)azetidin-1-yl]carbonyl}aniline: MS (EI) for $C_{17}H_{14}F_3IN_2O_2$: 463 (MH$^+$).
g) 1-({3,4-difluoro-2-[(2-fluoro-4-iodophenyl)amino]phenyl}carbonyl)-3-(trifluoromethyl)azetidin-3-ol: MS (EI) for $C_{17}H_{11}F_6IN_2O_2$: 517 (MH$^+$).
h) 1-({3,4-difluoro-2-[(2-fluoro-4-iodophenyl)amino]phenyl}carbonyl)-3-prop-2-en-1-ylazetidin-3-ol: MS (EI) for $C_{19}H_{16}F_3IN_2O_2$: 489 (MH$^+$).
i) 3-[1-({3,4-difluoro-2-[(2-fluoro-4-iodophenyl)amino]phenyl}carbonyl)-3-hydroxyazetidin-3-yl]propane-1,2-diol: MS (EI) for $C_{19}H_{18}F_3IN_2O_4$: 523 (MH$^+$).
j) 1-({3,4-difluoro-2-[(2-fluoro-4-iodophenyl)amino]phenyl}carbonyl)-3-ethylazetidin-3-ol: MS (EI) for $C_{18}H_{16}F_3IN_2O_2$: 477 (MH$^+$).
k) 1-({3,4-difluoro-2-[(2-fluoro-4-iodophenyl)amino]phenyl}carbonyl)-3-methylazetidin-3-ol: MS (EI) for $C_{17}H_{14}F_3IN_2O_2$: 463 (MH$^+$).
l) 1-({3,4-difluoro-2-[(2-fluoro-4-iodophenyl)amino]phenyl}carbonyl)azetidine-2-carboxylic acid: MS (EI) for $C_{17}H_{12}F_3IN_2O_3$: 477 (MH$^+$).
m) [1-({3,4-difluoro-2-[(2-fluoro-4-iodophenyl)amino]phenyl}carbonyl)azetidin-2-yl]methanol: MS (EI) for $C_{17}H_{14}F_3IN_2O_2$: 463 (MH$^+$).
n) 1-({3,4-difluoro-2-[(2-fluoro-4-iodophenyl)amino]phenyl}carbonyl)-3-ethenylazetidin-3-ol: MS (EI) for $C_{18}H_{14}F_3IN_2O_2$: 475 (MH$^+$).
o) 1-({3,4-difluoro-2-[(2-fluoro-4-iodophenyl)amino]phenyl}carbonyl)azetidine-3-carboxylic acid: MS (EI) for $C_{17}H_{12}F_3IN_2O_3$: 477 (MH$^+$).
p) 1-({3,4-difluoro-2-[(2-fluoro-4-iodophenyl)amino]phenyl}carbonyl)azetidin-3-one oxime: MS (EI) for $C_{16}H_{11}F_3IN_3O_2$: 462 (MH$^+$).
q) [1-({3,4-difluoro-2-[(2-fluoro-4-iodophenyl)amino]phenyl}carbonyl)azetidin-3-yl]methanol: MS (EI) for $C_{17}H_{14}F_3IN_2O_2$: 463 (MH$^+$).
r) 1-[1-({3,4-difluoro-2-[(2-fluoro-4-iodophenyl)amino]phenyl}carbonyl)-3-hydroxyazetidin-3-yl]ethane-1,2-diol: MS (EI) for $C_{18}H_{16}F_3IN_2O_4$: 509 (MH$^+$).
s) 1-({3,4-difluoro-2-[(2-fluoro-4-iodophenyl)amino]phenyl}carbonyl)azetidin-3-amine: MS (EI) for $C_{16}H_{13}F_3IN_3O$: 448 (MH$^+$).
t) 1-({3,4-difluoro-2-[(2-fluoro-4-iodophenyl)amino]phenyl}carbonyl)azetidine-3-carboxamide: MS (EI) for $C_{17}H_{13}F_3IN_3O_2$: 476 (MH$^+$).
u) 1-({3,4-difluoro-2-[(2-fluoro-4-iodophenyl)amino]phenyl}carbonyl)-N-hydroxyazetidine-3-carboxamide: MS (EI) for $C_{17}H_{13}F_3IN_3O_3$: 492 (MH$^+$).
v) 1-({3,4-difluoro-2-[(2-fluoro-4-iodophenyl)amino]phenyl}carbonyl)azetidine-2-carboxamide: MS (EI) for $C_{17}H_{13}F_3IN_3O_2$: 476 (MH$^+$).
w) 1-({3,4-difluoro-2-[(2-fluoro-4-iodophenyl)amino]phenyl}carbonyl)-N-hydroxyazetidine-2-carboxamide: MS (EI) for $C_{17}H_{13}F_3IN_3O_3$: 492 (MH$^+$).
x) N-[1-({3,4-difluoro-2-[(2-fluoro-4-iodophenyl)amino]phenyl}carbonyl)azetidin-3-yl]methanesulfonamide: MS (EI) for $C_{17}H_{15}F_3IN_3O_3S$: 526 (MH$^+$).
y) N-[1-({3,4-difluoro-2-[(2-fluoro-4-iodophenyl)amino]phenyl}carbonyl)azetidin-3-yl]acetamide: MS (EI) for $C_{18}H_{15}F_3IN_3O_2$: 490 (MH$^+$).
z) 1,1-dimethylethyl [1-({3,4-difluoro-2-[(2-fluoro-4-iodophenyl)amino]phenyl}carbonyl)azetidin-3-yl]carbamate: MS (EI) for $C_{21}H_{21}F_3IN_3O_3$: 548 (MH$^+$).
aa) 1-({3,4-difluoro-2-[(2-fluoro-4-iodophenyl)amino]phenyl}carbonyl)-3-(pyrrolidin-1-ylmethyl)azetidin-3-ol: MS (EI) for $C_{21}H_{21}F_3IN_3O_2$: 532 (MH$^+$).
bb) 3-[(diethylamino)methyl]-1-({3,4-difluoro-2-[(2-fluoro-4-iodophenyl)amino]phenyl}carbonyl)azetidin-3-ol: MS (EI) for $C_{21},H_{23}F_3IN_3O_2$: 534 (MH$^+$).
cc) 1-({3,4-difluoro-2-[(2-fluoro-4-iodophenyl)amino]phenyl}carbonyl)-3-[(dimethylamino)methyl]azetidin-3-ol: MS (EI) for $C_{19}H_{19}F_3IN_3O_2$: 506 (MH$^+$).
dd) 1-({3,4-difluoro-2-[(2-fluoro-4-iodophenyl)amino]phenyl}carbonyl)-N-methyl-N-prop-2-en-1-ylazetidine-3-carboxamide: MS (EI) for $C_{21}H_{19}F_3IN_3O_2$: 530 (MH$^+$).
ee) 1-({3,4-difluoro-2-[(2-fluoro-4-iodophenyl)amino]phenyl}carbonyl)-N-methylazetidine-3-carboxamide: MS (EI) for $C_{18}H_{15}F_3IN_3O_2$: 490 (MH$^+$).
ff) N-butyl-1-({3,4-difluoro-2-[(2-fluoro-4-iodophenyl)amino]phenyl}carbonyl)azetidine-3-carboxamide: MS (EI) for $C_{21}H_{21}F_3IN_3O_2$: 532 (MH$^+$).
gg) 1-({3,4-difluoro-2-[(2-fluoro-4-iodophenyl)amino]phenyl}carbonyl)-N-prop-2-en-1-ylazetidine-3-carboxamide: MS (EI) for $C_{20}H_{17}F_3IN_3O_2$: 516 (MH$^+$).
hh) 1-({3,4-difluoro-2-[(2-fluoro-4-iodophenyl)amino]phenyl}carbonyl)-N-ethyl-N-(2-hydroxyethyl)azetidine-3-carboxamide: MS (EI) for $C_{21}H_{21}F_3IN_3O_3$: 548 (MH$^+$).

ii) N-[1-({3,4-difluoro-2-[(2-fluoro-4-iodophenyl)amino]phenyl}carbonyl)azetidin-3-yl]-2-methylpropanamide: MS (EI) for $C_{20}H_{19}F_3IN_3O_2$: 518 (MH$^+$).

jj) N-[1-({3,4-difluoro-2-[(2-fluoro-4-iodophenyl)amino]phenyl}carbonyl)azetidin-3-yl]formamide: MS (EI) for $C_{17}H_{13}F_3IN_3O_2$: 476 (MH$^+$).

kk) N-[1-({3,4-difluoro-2-[(2-fluoro-4-iodophenyl)amino]phenyl}carbonyl)azetidin-3-yl]-3,4-dihydroxybutanamide: MS (EI) for $C_{20}H_{19}F_3IN_3O_4$: 550 (MH$^+$).

ll) methyl [1-({3,4-difluoro-2-[(2-fluoro-4-iodophenyl)amino]phenyl}carbonyl)azetidin-3-yl]carbamate: MS (EI) for $C_{18}H_{15}F_3IN_3O_3$: 550 (MH$^+$).

mm) N-butyl-1-({3,4-difluoro-2-[(2-fluoro-4-iodophenyl)amino]phenyl}carbonyl)azetidin-3-amine: MS (EI) for $C_{20}H_{21}F_3IN_3O$: 504 (MH$^+$).

nn) 1-({3,4-difluoro-2-[(2-fluoro-4-iodophenyl)amino]phenyl}carbonyl)-N,N-diprop-2-en-1-ylazetidin-3-amine: MS (EI) for $C_{22}H_{21}F_3IN_3O$: 528 (MH$^+$).

oo) 1-({4-[(2-fluoro-4-iodophenyl)amino]-3-thienyl}carbonyl)azetidin-3-amine: MS (EI) for $C_{14}H_{13}FIN_3OS$: 418 (MH$^+$).

pp) 1-({4-[(2-fluoro-4-iodophenyl)amino]-3-thienyl}carbonyl)azetidin-3-ol: MS (EI) for $C_{14}H_{12}FIN_2O_2S$: 419 (MH$^+$).

qq) 1-({3,4-difluoro-2-[(2-fluoro-4-iodophenyl)amino]phenyl}carbonyl)-3-[(2S)-piperidin-2-yl]azetidin-3-ol: MS (EI) for $C_{21}H_{21}F_3IN_3O_2$: 532 (MH$^+$).

rr). 1-({3,4-difluoro-2-[(2-fluoro-4-iodophenyl)amino]phenyl}carbonyl)-3-[(2R)-piperidin-2-yl]azetidin-3-ol: MS (EI) for $C_{21}H_{21}F_3IN_3O_2$: 532 (MH$^+$).

ss) 1-({3,4-difluoro-2-[(2-fluoro-4-iodophenyl)amino]phenyl}carbonyl)-3-[2-pyrrolidin-2-yl]azetidin-3-ol: MS (EI) for $C_{20}H_{19}F_3IN_3O_2$: 518 (MH$^+$).

tt). 3-(aminomethyl)-1-({3,4-difluoro-2-[(2-fluoro-4-iodophenyl)amino]phenyl}carbonyl)azetidin-3-ol: MS (EI) for $C_{17}H_{15}F_3IN_3O_2$: 478 (MH$^+$).

uu) 3-[1-aminoethyl]-1-({3,4-difluoro-2-[(2-fluoro-4-iodophenyl)amino]phenyl}carbonyl)azetidin-3-ol: MS (EI) for $C_{18}H_{17}F_3IN_3O_2$: 492 (MH$^+$).

vv) 3-[1-aminopropyl]-1-({3,4-difluoro-2-[(2-fluoro-4-iodophenyl)amino]phenyl}carbonyl)azetidin-3-ol: MS (EI) for $C_{19}H_{19}F_3IN_3O_2$: 506 (MH$^+$).

Assay

For a biochemical measurement of MEK1 inhibitory activity, compounds of the invention were screened in a triple coupled cRaf-MEK-ERK2 assay using ALPHASCREEN (Registered Trademark of Perkin Elmer) technology (Perkin Elmer). The compound of the invention, 0.5 µL of 100% DMSO stock solution, is diluted into an assay buffer composed of 20 mM Tris (pH=7.5), 10 mM magnesium chloride, 0.03% CHAPS and 1 mM DTT. Subsequently, 10 µl of substrate mixture is added composed of unactive MEK1 (3 nM), ATP (50 µM), unactive ERK2 (4 nM), biotinylated MBP peptide (b-FFKNIVTPRTPPPSQGK, 1 µM) and antiphospho MBP peptide (0.5 nM). The mixture is then gently shaken for 30 minutes at room temperature followed by addition of active cRaf (5 µL at 0.5 nM) to initiate reaction. The mixture is then shaken for 100 minutes at room temperature then quenched by addition of 10 µL of a mixture of 5 µg/mL streptavidin donor beads and 5 µg/mL protein A acceptor beads in detection buffer (75 mM Hepes pH=7.5, 300 mM sodium chloride, 120 mM EDTA, 0.3% BSA and 0.03% Tween), followed by incubation overnight and signal detection on an ALPHAQuest® (Registered Trademark of Perkin Elmer) plate reader (Perkin Elmer).

Section II

In one embodiment, in section II the invention provides compounds that are useful as inhibitors of PI3K that have the Formula VI:

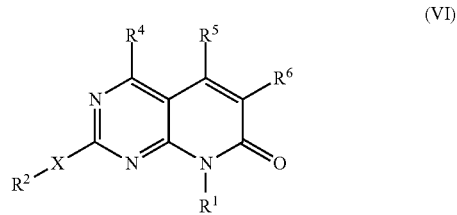

(VI)

and optionally as a pharmaceutically acceptable salt or hydrate thereof, wherein $R^1$ is hydrogen, optionally substituted $C_1$-$C_6$ alkyl, optionally substituted $C_3$-$C_7$ cycloalkyl, optionally substituted aryl, optionally substituted heterocyclyl, optionally substituted heterocyclylalkyl, optionally substituted heteroaryl or optionally substituted heteroarylalkyl;

X is —NR$^3$—;

$R^2$ is hydrogen, optionally substituted $C_1$-$C_6$ alkyl, optionally substituted $C_3$-$C_7$ cycloalkyl, optionally substituted aryl, optionally substituted aryl-$C_{1-6}$ alkyl, optionally substituted heterocyclyl, optionally substituted heterocyclyl alkyl, optionally substituted heterocyclyl-aryl- or optionally substituted heteroaryl; $R^2$ is optionally further substituted with 1, 2, 3, or 4 $R^8$ groups;

$R^3$ is hydrogen;

$R_4$ is hydrogen or optionally substituted $C_1$-$C_6$ alkyl, optionally substituted $C_1$-$C_6$ alkoxy, $C_1$-$C_6$ alkoxyalkyl, aminoalkyl, optionally substituted $C_3$-$C_7$ cycloalkyl, optionally substituted aryl, or optionally substituted heteroaryl;

$R^5$ is hydrogen or optionally substituted $C_1$-$C_6$ alkyl;

$R^6$ is hydrogen, halo, haloalkyl, haloalkoxy, —NR$^3$—, optionally substituted $C_1$-$C_6$ alkyl, optionally substituted $C_1$-$C_6$ alkoxy, $C_1$-$C_6$ alkoxyalkyl, acyl, aminoalkyl, optionally substituted $C_3$-$C_7$ cycloalkyl, optionally substituted aryl, optionally substituted aryl-$C_{1-6}$ alkyl, optionally substituted heterocyclyl, or optionally substituted heteroaryl; substitutable $R^6$ groups are optionally further substituted with 1, 2, 3, or 4 $R^9$ groups;

$R^8$ at each occurrence is independently hydroxy, halo, haloalkyl, haloalkoxy, optionally substituted $C_1$-$C_6$ alkyl, optionally substituted $C_1$-$C_6$ alkoxy, $C_1$-$C_6$ alkoxyalkyl, $C_1$-$C_6$ alkoxyalkylaminoalkyl, $C_1$-$C_6$ alkylcarboxyheterocyclyl, —O—$C_1$-$C_6$alkylheterocyclyl, aminoalkyl, optionally substituted $C_3$-$C_7$ cycloalkyl, optionally substituted aryl, optionally substituted aryl $C_1$-$C_6$ alkyl, optionally substituted heteroalicyclic, optionally substituted heteroalicyclicalkyl, optionally substituted heteroaryl or optionally substituted heteroarylalkyl; and $R^9$ at each occurrence is independently halo, haloalkyl, haloalkoxy, optionally substituted $C_1$-$C_6$ alkyl, optionally substituted $C_1$-$C_6$ alkoxy, $C_1$-$C_6$ alkoxyalkyl, $C_1$-$C_6$ carboxyalkyl, alkoxycarbonyl, aminoalkyl, optionally substituted $C_3$-$C_7$ cycloalkyl, optionally substituted aryl, optionally substituted aryl $C_1$-$C_6$ alkyl, optionally substituted aryloxy, optionally substituted heterocyclyl, or optionally substituted heteroaryl.

In one embodiment, the invention provides a PI3K inhibitor of formula VIa:

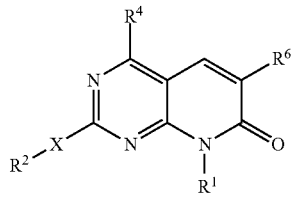

(VIa)

and optionally as a pharmaceutically acceptable salt or hydrate thereof, wherein $R^1$ is hydrogen, optionally substituted $C_1$-$C_6$ alkyl, optionally substituted $C_3$-$C_7$ cycloalkyl, optionally substituted aryl, optionally substituted heteroalicyclic, optionally substituted heteroalicyclicalkyl, optionally substituted heteroaryl or optionally substituted heteroarylalkyl;

X is —$NR^3$—;

$R^2$ is hydrogen, optionally substituted $C_1$-$C_6$ alkyl, $C_3$-$C_7$ cycloalkyl, aryl, aryl-$C_{1-6}$ alkyl, heteroalicyclic, heterocyclylalkyl, heterocyclyl-aryl- or heteroaryl; where the cycloalkyl, aryl, aryl-$C_{1-6}$ alkyl, heteroalicyclic, heterocyclylalkyl, heterocyclyl-aryl-, and heteroaryl groups in $R^2$ are optionally substituted with 1, 2, 3, or 4 $R^8$ groups;

$R^3$ is hydrogen;

$R^4$ is optionally substituted $C_1$-$C_6$ alkyl;

$R^6$ is hydrogen, acyl, phenyl, heteroalicyclic, or heteroaryl; where the phenyl, heteroalicyclic, and heteroaryl in $R^6$ are optionally substituted with 1, 2, 3, or 4 $R^9$ groups;

$R^8$ at each occurrence is independently hydroxy, halo, haloalkyl, $C_1$-$C_6$ alkyl, optionally substituted $C_1$-$C_6$ alkoxy, $C_1$-$C_6$ alkoxyalkyl, $C_1$-$C_6$ alkoxyalkylaminoalkyl, $C_1$-$C_6$ alkylcarboxyheterocyclyl, —O—$C_1$-$C_6$alkylheterocyclyl, aminoalkyl, optionally substituted $C_3$-$C_7$ cycloalkyl, optionally substituted aryl, optionally substituted aryl $C_1$-$C_6$ alkyl, optionally substituted heteroalicyclic, optionally substituted heteroalicyclicalkyl, optionally substituted heteroaryl or optionally substituted heteroarylalkyl; and $R^9$ at each occurrence is independently halo, haloalkyl, haloalkoxy, $C_1$-$C_6$ alkyl, $C_1$-$C_6$ alkoxy, $C_1$-$C_6$ alkoxyalkyl, $C_1$-$C_6$ carboxyalkyl, alkoxycarbonyl, aminoalkyl, optionally substituted $C_3$-$C_7$ cycloalkyl, optionally substituted aryl, optionally substituted aryl $C_1$-$C_6$ alkyl, optionally substituted aryloxy, optionally substituted heteroalicyclic, or optionally substituted heteroaryl.

In one embodiment, the invention provides a PI3K inhibitor of formula VIb:

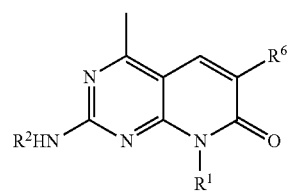

(VIb)

and optionally a pharmaceutically acceptable salt or solvate thereof, wherein $R^1$ is hydrogen, optionally substituted $C_1$-$C_6$ alkyl, optionally substituted $C_3$-$C_7$ cycloalkyl, optionally substituted aryl, optionally substituted heteroalicyclic, optionally substituted heteroalicyclicalkyl, optionally substituted heteroaryl or optionally substituted heteroarylalkyl;

$R^6$ is phenyl, acyl, or heteroaryl wherein the phenyl and heteroaryl are optionally substituted with 1, 2, 3, or 4 $R^9$ groups; and $R^9$ at each occurrence is independently halo, haloalkyl, haloalkoxy, $C_1$-$C_6$ alkyl, $C_1$-$C_6$ alkoxy, $C_1$-$C_6$ alkoxyalkyl, $C_1$-$C_6$ carboxyalkyl, alkoxycarbonyl, aminoalkyl, optionally substituted $C_3$-$C_7$ cycloalkyl, optionally substituted aryl, optionally substituted aryl $C_1$-$C_6$ alkyl, aryloxy, optionally substituted heteroalicyclic, or optionally substituted heteroaryl.

In another embodiment (A), the invention provides a compound of Formula VIa where $R^1$ is hydrogen, $C_1$-$C_6$ optionally substituted alkyl, optionally substituted $C_3$-$C_7$ cycloalkyl, optionally substituted cycloalkylalkyl, optionally substituted aryl, optionally substituted heteroalicyclic, optionally substituted heteroalicyclicalkyl, optionally substituted heteroaryl or optionally substituted heteroarylalkyl; and all other groups are as defined in Formula VIa. In another embodiment, $R^1$ is hydrogen, optionally substituted alkyl, optionally substituted cycloalkyl, or optionally substituted heteroalicyclicalkyl. In yet another embodiment, $R^1$ is hydrogen, alkyl, alkyl substituted with one or two hydroxy, alkyl substituted with alkoxy, alkyl substituted with aryl, $C_3$-$C_7$ cycloalkyl, or heteroalicyclicalkyl. In yet another embodiment, $R^1$ is hydrogen, methyl, ethyl, propyl, isopropyl, 2-hydroxypropyl, 3-hydroxypropyl, 2-ethoxyethyl, 3-methoxypropyl, 3-ethoxypropyl, 3-isopropoxypropyl, cyclopropyl, cyclobutyl, cyclopentyl, cyclohexyl, benzyl, or 2-piperidin-1-ylethyl. In yet another embodiment, $R^1$ is ethyl, isopropyl, cyclopentyl, or cyclohexyl. In yet another embodiment, $R^1$ is ethyl.

In another embodiment (B), the invention provides a compound of Formula VIa where $R^2$ is hydrogen or optionally substituted $C_1$-$C_6$ alkyl; and all other groups are as defined in Formula VIa. In another embodiment, $R^2$ is hydrogen or alkyl where the alkyl is optionally substituted with one, two, or three amino, alkylamino, dialkylamino, or halo. In another embodiment, $R^2$ is hydrogen, methyl, ethyl, propyl, isopropyl, tert-butyl, 3-aminopropyl, 3-(N-methylamino)-propyl, or 3-(N,N-dimethylamino)-propyl. In another embodiment, $R^2$ is hydrogen or ethyl. In another embodiment, $R^2$ is hydrogen.

In another embodiment, the invention provides a compound of Formula VIa or VIb where $R^2$ is hydrogen and all other groups are as defined for Formula VIa or VIb, respectively.

In another embodiment, the invention provides a compound of Formula VIa or VIb where $R^2$ is optionally substituted $C_1$-$C_6$ alkyl; and all other groups are as defined in Formula VIa or VIb, respectively. In another embodiment, $R^2$ is alkyl where the alkyl is optionally substituted with one, two, or three amino, alkylamino, dialkylamino, or halo. In another embodiment, $R^2$ is methyl, ethyl, propyl, isopropyl, tert-butyl, 3-aminopropyl, 3-(N-methylamino)-propyl, or 3-(N,N-dimethylamino)-propyl. In another embodiment, $R^2$ is ethyl.

In another embodiment (C), the invention is directed to a Compound of Formula VIa where $R^4$ is optionally substituted $C_1$-$C_6$ alkyl; and all other groups are as defined in Formula VIa. In another embodiment, $R^4$ is methyl or ethyl. In another embodiment, $R^4$ is methyl.

Another embodiment (D), the invention is directed to a Compound of Formula VIa or VIb where $R^2$ is hydrogen or optionally substituted $C_1$-$C_6$ alkyl and $R^6$ is acyl; and all other groups are as defined in Formula VIa or VIb, respectively. In another embodiment, $R^6$ is alkylcarbonyl. In another embodiment, $R^6$ is acetyl.

Another embodiment (E), the invention is directed to a Compound of Formula VIa or VIb where $R^2$ is hydrogen or optionally substituted $C_1$-$C_6$ alkyl and $R^6$ is phenyl optionally substituted with 1, 2, 3, or 4 $R^9$ groups; and all other groups are as defined in Formula VIa or VIb, respectively. In another embodiment, $R^6$ is phenyl optionally substituted with one or two $R^9$ groups; and $R^9$ at each instance is independently selected from aryl, halo, alkoxy, aryloxy, alkoxycarbonyl, alkyl, and haloalkyl. In another embodiment, $R^6$ is phenyl optionally substituted with one or two $R^9$ groups; and each $R^9$ at each instance is independently selected from phenyl, fluoro, chloro, methoxy, phenyloxy, methyl, methoxycarbonyl, and trifluoromethyl. In another embodiment, $R^6$ is phenyl, phenyl substituted with phenyl, fluorophenyl, difluorophenyl, chlorophenyl, dichlorophenyl, phenyl substituted with chloro and fluoro, methoxyphenyl, dimethoxyphenyl, phenyloxyphenyl, or trifluoromethylphenyl. Yet even more specifically, $R^6$ is phenyl, 2-phenyl-phenyl, 3-phenyl-phenyl, 4-phenyl-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3-chloro-4-fluoro-phenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 4-phenyloxyphenyl, 2-trifluoromethylphenyl, or 3-trifluoromethylphenyl.

Another embodiment, the invention is directed to a Compound of Formula VIa or VIb where $R^6$ is phenyl substituted with 1, 2, 3, or 4 $R^9$ groups; and all other groups are as defined in Formula VIa or VIb, respectively.

Another embodiment, the invention is directed to a Compound of Formula VIa or VIb where $R^6$ is heteroaryl optionally substituted with 1, 2, 3, 4, or 5 $R^9$ groups; and all other groups are as defined in Formula VIa or VIb, respectively.

In another embodiment (G), the invention is directed to a Compound of Formula VIa or VIb where $R^2$ is hydrogen or optionally substituted $C_1$-$C_6$ alkyl and $R^6$ is heteroaryl optionally substituted with 1, 2, 3, 4, or 5 $R^9$ groups; and all other groups are as defined in Formula VIa or VIb, respectively.

In another embodiment (G1), the invention is directed to a Compound of Formula VIa or VIb where $R^2$ is hydrogen or ethyl and $R^6$ is a 6-membered heteroaryl optionally substituted with one or two $R^9$; and all other groups are as defined in Formula VIa or VIb, respectively. In another embodiment, $R^6$ is pyridinyl, pyrazinyl, pyrimidinyl, or pyridazinyl each of which is optionally substituted with one $R^9$ where $R^9$ at each instance is halo. In another embodiment, $R^6$ is pyridin-2-yl, pyridin-3-yl, pyridin-4-yl, 3-fluoropyridin-4-yl, pyrazin-2-yl, pyrazin-3-yl, pyrimidin-2-yl, pyrimidin-4-yl, pyrimidin-5-yl, pyridazin-3-yl, or pyridazin-4-yl, each of which is optionally substituted with one or two $R^9$.

In another embodiment (G2), the invention is directed to a Compound of Formula VIa or VIb where $R^2$ is hydrogen or ethyl and $R^6$ is pyrazinyl, pyrimidinyl, or pyridazinyl each of which is optionally substituted with one $R^9$ where $R^9$ at each instance is halo; and all other groups are as defined in Formula VIa or VIb, respectively. In another embodiment, $R^6$ is pyrazin-2-yl, pyrazin-3-yl, pyrimidin-2-yl, pyrimidin-4-yl, pyrimidin-5-yl, pyridazin-3-yl, or pyridazin-4-yl.

In another embodiment (G3), the invention is directed to a Compound of Formula VIa or VIb where $R^2$ is hydrogen or ethyl and $R^6$ is 5-membered heteroaryl optionally substituted with one or two $R^9$; and all other groups are as defined in Formula VIa or VIb, respectively. In another embodiment $R^6$ is pyrazolyl, imidazolyl, thienyl, thiazolyl, oxazolyl, isoxazolyl, oxadiazolyl, furanyl, pyrrolyl, triazolyl, or tetrazolyl, each of which is optionally substituted with one $R^9$ where $R^9$ at each instance is alkyl, arylalkyl, cyano, aryl, alkoxycarbonyl, or halo. In another embodiment $R^6$ is pyrazolyl, thienyl, thiazolyl, oxazolyl, furanyl, or pyrrolyl, each of which is optionally substituted with one $R^9$ where $R^9$ at each instance is alkyl, alkoxycarbonyl, or halo. In another embodiment, $R^6$ is pyrazol-1-yl, pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, furan-3-yl, pyrrol-1-yl, pyrrol-2-yl, or pyrrol-3-yl; each of which is optionally substituted with one $R^9$ where $R^9$ at each instance, is methyl, N-tert-butoxycarbonyl, or chloro. In another embodiment, $R^6$ is pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, furan-3-yl, pyrrol-2-yl, or pyrrol-3-yl; each of which is optionally substituted with one $R^9$ where $R^9$, when present, is methyl, N-tert-butoxycarbonyl, or chloro.

In another embodiment (G4), the invention is directed to a Compound of Formula VIa or VIb where $R^2$ is hydrogen or ethyl and $R^6$ is thien-2-yl, thien-3-yl, pyrrol-2-yl, furan-2-yl, furan-3-yl, pyrazol-3-yl, pyrazol-4-yl, pyrazol-5-yl, thiazol-2-yl, thiazol-5-yl, isoxazol-4-yl, imidazol-5-yl, triazol-5-yl, or tetrazol-5-yl, each of which is optionally substituted with one $R^9$ where $R^9$, when present, is methyl, N-tert-butoxycarbonyl, or chloro; and all other groups are as defined in Formula VIa or VIb, respectively.

In another embodiment (G5), the invention is directed to a Compound of Formula VIa or VIb where $R^2$ is hydrogen or ethyl and $R^6$ is indolyl optionally substituted with 1, 2, 3, or 4 $R^9$ groups; and all other groups are as defined in Formula VIa or VIb, respectively. In another embodiment $R^6$ is indol-2-yl, indol-3-yl, indol-4-yl, indol-5-yl, indol-6-yl, or indol-7-yl; each of which is optionally substituted with 1, 2, 3, or 4 $R^9$ groups. In another embodiment, $R^6$ is indol-6-yl.

In another embodiment of the Invention (H), the invention is directed to a Compound of Formula VIa where $R^1$ is hydrogen, optionally substituted $C_1$-$C_6$ alkyl, optionally substituted $C_3$-$C_7$ cycloalkyl, or optionally substituted heteroalicyclicalkyl; $R^2$ is hydrogen or $C_1$-$C_6$ alkyl optionally substituted with amino, alkylamino, dialkylamino, or halo; $R^4$ is alkyl; $R^6$ is phenyl or heteroaryl wherein the phenyl and heteroaryl are optionally substituted with one, two, or three $R^9$ groups; and each $R^9$, when present, is independently alkyl, arylalkyl, cyano, aryl, alkoxycarbonyl, or halo.

In another embodiment of the Invention (J), the invention is directed to a Compound of Formula VIa where $R^2$ is hydrogen or ethyl, $R^4$ is methyl, and $R^6$ is pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, furan-3-yl, pyrrol-2-yl, or pyrrol-3-yl; each of which is optionally substituted with 1, 2, 3, 4, or 5 $R^9$ groups; and all other groups are as defined in Formula VIa.

In another embodiment of the Invention (K), the invention is directed to a Compound of Formula VIa where $R^1$ is alkyl or cycloalkyl; $R^4$ is methyl; and $R^6$ is heteroaryl optionally substituted with one or two $R^9$ groups; and all other groups are as defined in Formula VIa. In another embodiment, each $R^9$, when present, is independently alkyl, alkoxycarbonyl, or halo. In another embodiment, $R^6$ is pyrazol-3-yl, pyrazol-4- yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, furan-3-yl, pyrrol-2-yl, or pyrrol-3-yl; each of which is optionally substituted with one $R^9$ where $R^9$, when present, is methyl or N-tert-butoxycarbonyl.

In another embodiment (K1) of embodiment K, the invention is directed to a Compound of Formula VIa where $R^2$ is hydrogen; and all other groups are as defined in Embodiment K.

In another embodiment (K2) of embodiment K, the invention is directed to a Compound of Formula VIa where $R^2$ is methyl or ethyl; and all other groups are as defined in Embodiment K.

In another embodiment (L), the invention is directed to a Compound of Formula VIa where $R^1$ is alkyl or cycloalkyl; $R^4$ is methyl; and $R^6$ is phenyl optionally substituted with one or two $R^9$ groups; and all other groups are as defined in Formula VIa. In another embodiment, each $R^9$, when present, is independently halo, alkoxy, or haloalkyl.

In another embodiment (M), the invention is directed to a Compound of Formula VIa where $R^1$ is alkyl or cycloalkyl; $R^4$ is methyl; and $R^2$ is hydrogen; and all other groups are as defined in Formula VIa.

In another embodiment (N), the invention is directed to a Compound of Formula VIa where $R^1$ is alkyl or cycloalkyl; $R^4$ is methyl; and $R^2$ is optionally substituted alkyl; and all other groups are as defined in Formula VIa.

In another embodiment, the invention is directed to a Compound of Formula VII;

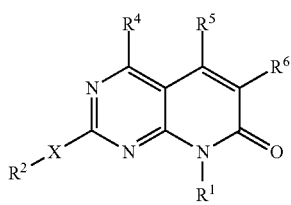

VII $R^1$ is hydrogen, optionally substituted $C_1$-$C_6$ alkyl, optionally substituted $C_3$-$C_7$ cycloalkyl, optionally substituted aryl, optionally substituted heteroalicyclic, optionally substituted heteroalicyclicalkyl, optionally substituted heteroaryl or optionally substituted heteroarylalkyl;
X is —$NR^3$—;
$R^3$ is hydrogen;
$R^4$ is optionally substituted $C_1$-$C_6$ alkyl;
$R^5$ is hydrogen;
$R^6$ is acyl and $R^2$ is heterocyclyl-aryl- optionally substituted with 1, 2, 3, or 4 $R^8$ groups; or
$R^6$ is halo and $R^2$ is optionally substituted $C_1$-$C_6$ alkyl, $C_3$-$C_7$ cycloalkyl, phenyl, aryl-$C_{1-6}$ alkyl, heteroalicyclicalkyl, or heterocyclyl-aryl-; where the $C_3$-$C_7$ cycloalkyl, phenyl, phenyl, aryl-$C_{1-6}$alkyl, heteroalicyclicalkyl, and heterocyclyl-aryl- groups in $R^2$ are optionally substituted with 1, 2, 3, or 4 $R^8$ groups; or
$R^6$ is phenyl optionally substituted with 1, 2, or 3 halo; and $R^2$ is phenyl or heterocyclyl-aryl-; where the phenyl and heterocyclyl-aryl- groups in $R^2$ are optionally substituted with 1, 2, 3, or 4 $R^8$ groups; or
$R^6$ is heteroaryl optionally substituted with 1, 2, or 3 halo; and $R^2$ is heterocyclyl-aryl-optionally substituted with 1, 2, 3, 4, or 5 $R^8$ groups;
each $R^8$ at each instance is independently hydroxy, halo, $C_1$-$C_6$ alkyl, haloalkyl, optionally substituted $C_1$-$C_6$ alkoxy, $C_1$-$C_6$ alkoxyalkyl, $C_1$-$C_6$ alkoxycarbonyl, $C_1$-$C_6$ alkoxyalkylaminoalkyl, —O—$C_1$-$C_6$alkylheterocyclyl, aminoalkyl, optionally substituted $C_3$-$C_7$ cycloalkyl, optionally substituted aryl, optionally substituted aryl $C_1$-$C_6$ alkyl, optionally substituted heteroalicyclic, optionally substituted heteroalicyclalkyl, optionally substituted heteroaryl or optionally substituted heteroarylalkyl.

In another embodiment (A), the invention is directed to a Compound of Formula VII where $R^1$ is hydrogen, optionally substituted $C_1$-$C_6$ alkyl, optionally substituted $C_3$-$C_7$ cycloalkyl, optionally substituted aryl, optionally substituted heteroalicyclic, optionally substituted heteroalicyclicalkyl, optionally substituted heteroaryl or optionally substituted heteroarylalkyl; and all other groups are as defined in Formula VII. In another embodiment, $R^1$ is hydrogen, optionally substituted $C_1$-$C_6$ alkyl, or optionally substituted $C_3$-$C_7$ cycloalkyl. In another embodiment, $R^1$ is $C_1$-$C_6$ alkyl or $C_3$-$C_7$ cycloalkyl. In another embodiment, $R^1$ is methyl, ethyl, propyl, isopropyl, cyclopropyl, cyclobutyl, cyclopentyl, or cyclohexyl. In another embodiment, $R^1$ is ethyl, isopropyl, or cyclopentyl.

In another embodiment (B), the invention is directed to a Compound of Formula VII where $R^4$ is optionally substituted $C_1$-$C_6$ alkyl; and all other groups are as defined in Formula VII. In another embodiment, $R^4$ is methyl or ethyl. In another embodiment, $R^4$ is methyl.

In another embodiment (C), the invention is directed to a Compound of Formula VII where $R^6$ is acyl and $R^2$ is heterocyclyl-aryl- optionally substituted with 1, 2, 3, or 4 $R^8$ groups; and all other groups are as defined in Formula VII. In another embodiment, $R^6$ is alkylcarbonyl. In another embodiment, $R^6$ is acetyl.

In another embodiment of embodiment C, the invention is directed to a Compound of Formula VII where $R^6$ is acyl and $R^2$ is heteroalicyclic-phenyl- optionally substituted with 1, 2, 3, or 4 $R^8$ groups; and all other groups are as defined in Formula VII. In another embodiment, $R^8$, when $R^8$ is present, is $C_1$-$C_6$ alkyl, $C_1$-$C_6$ alkoxycarbonyl, or aryl $C_1$-$C_6$ alkyl. In another embodiment, $R^2$ is piperazinyl-phenyl- where the piperazinyl is optionally substituted with one $R^8$ where $R^8$, when present, is methyl, ethyl, isopropyl, ten-butoxycarbonyl, or benzyl. In another embodiment, $R^2$ is piperazinyl-phenyl- where the piperazinyl is optionally substituted with $C_1$-$C_6$ alkyl.

In another embodiment (E), the invention is directed to a Compound of Formula VII where $R^6$ is phenyl optionally substituted with 1, 2, 3, or 4 $R^9$ groups; and $R^2$ is phenyl or heterocyclyl-aryl-; where the phenyl and heterocyclyl-aryl- groups in $R^2$ are optionally substituted with 1, 2, 3, or 4 $R^8$ groups; and all other groups are as defined in Formula VII. In another embodiment, $R^6$ is phenyl, phenyl substituted with one or two halo. In another embodiment, $R^6$ is phenyl, fluorophenyl, difluorophenyl, chlorophenyl, or dichlorophenyl. In another embodiment, $R^6$ is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, or 3,5-difluorophenyl.

In another embodiment (E1) of Embodiment E, the invention is directed to a Compound of Formula VII where $R^2$ is phenyl or heteroalicyclic-phenyl-; where the phenyl and heteroalicyclic-phenyl- groups in $R^2$ are optionally substituted with 1, 2, 3, or 4 $R^8$ groups; and all other groups are as defined in Embodiment E.

In another embodiment of embodiment E1, the invention is directed to a Compound of Formula VII where $R^2$ is phenyl or heteroalicyclic-phenyl-; where the phenyl and heteroalicyclic-phenyl- groups in $R^2$ are optionally substituted with one or two $R^8$ where each $R^8$, when present, is independently hydroxy, $C_1$-$C_6$ alkyl, optionally substituted $C_1$-$C_6$ alkoxy, alkoxycarbonyl, or —O—$C_1$-$C_6$alkylheteroalicyclic; and all other groups are as defined in Embodiment E1.

In another embodiment of embodiment E1, $R^2$ is phenyl or phenyl substituted with one or two $R^8$ where each $R^8$, when $R^8$ is present, is independently hydroxy, —O—$C_1$-$C_6$alkylheteroalicyclic, or $C_1$-$C_6$ alkoxy where the $C_1$-$C_6$ alkoxy is optionally substituted with amino, alkylamino or dialkylamino; and all other groups are as defined in Embodiment E1. In another embodiment, $R^2$ is phenyl, hydroxyphenyl, [(2-aminoethyl)-oxy]-phenyl, [(2-alkylamino-ethyl)-oxy]-phenyl, [(2-dialkylamino-ethyl)-oxy]-phenyl, (morpholinylalkyloxy)-phenyl, (piperidinylalkyloxy)-phenyl, (piperazinylalkyloxy)-phenyl, (N-alkyl-piperazinylalkyloxy)-phenyl, or (N-benzylpiperazinylalkyloxy)-phenyl. In another embodiment, $R^2$ is hydroxyphenyl, [(2-aminoethyl)-oxy]-phenyl, [(2-alkylamino-ethyl)-oxy]-phenyl, [(2-dialkylamino-ethyl)-oxy]-phenyl, (morpholinylalkyloxy)-phenyl, (piperidinylalkyloxy)-phenyl, (piperazinylalkyloxy)-phenyl, (N-alkyl-piperazinylalkyloxy)-phenyl, or (N-benzylpiperazinylalkyloxy)-phenyl. In another embodiment, 2-hydroxyphenyl, 3-hydroxyphenyl, 4-hydroxyphenyl, 4-[(2-dimethylamino-ethyl)-oxy]-phenyl, 4-[2-(morpholin-4-yl)-ethyloxy]-phenyl, 4-[2-(piperidinyl)-ethyloxy]-phenyl, 4-[2-(piperazin-4-yl)-ethyloxy]-phenyl, 4-[2-(N-methyl-piperazin-4-yl)-ethyloxy]-phenyl, or 4-[2-(N-ethyl-piperazin-4-yl)-ethyloxy]-phenyl.

In another embodiment of embodiment E1, $R^2$ is piperazinyl-phenyl- where the piperazinyl is optionally substituted with one $R^8$ where $R^8$, when present, is alkyl; and all other groups are as defined in Embodiment E1. In another embodiment, $R^2$ is morpholinylphenyl, piperazinylphenyl, or (N-alkyl-piperazinyl)-phenyl. In another embodiment, $R^2$ is 4-morpholin-4-ylphenyl, 4-piperazin-4-ylphenyl, 4-(N-methyl-piperazin-4-yl)-phenyl, or 4-(N-ethyl-piperazin-4-yl)-phenyl.

In another embodiment (F), the invention is directed to a Compound of Formula VII where $R^6$ is heteroaryl optionally substituted with 1, 2, or 3 halo; and $R^2$ is heterocyclyl-aryl- optionally substituted with 1, 2, 3, 4, or 5 $R^8$ groups.

In another embodiment (F1) of embodiment F, the invention is directed to a Compound of Formula VII where $R^6$ is a 5-membered heteroaryl optionally substituted with one or two halo; $R^2$ is heteroalicyclic-phenyl- where the heteroalicyclic and phenyl portions of $R^2$ are independently optionally substituted with one $R^8$ where $R^8$, when $R^8$ is present is $C_1$-$C_6$ alkyl or aryl $C_1$-$C_6$ alkyl; and all other groups are as defined in embodiment F.

In another embodiment (F2) of embodiment F, the invention is directed to a Compound of Formula VII where $R^6$ is pyrazolyl, thienyl, thiazolyl, oxazolyl, furanyl, or pyrrolyl, each of which is optionally substituted with one or two halo. In another embodiment, $R^6$ is pyrazol-1-yl, pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, or furan-3-yl; each of which is optionally substituted with one chloro. In another embodiment, $R^6$ is pyrazol-3-yl, pyrazol-4-yl, pyrazol-5-yl, thien-2-yl, thiazol-2-yl, thiazol-4-yl, thiazol-5-yl, oxazol-2-yl, oxazol-4-yl, oxazol-5-yl, furan-2-yl, or furan-3-yl.

In another embodiment (G), the invention is directed to a Compound of Formula VII where $R^6$ is halo and $R^2$ is optionally substituted $C_1$-$C_6$ alkyl, $C_3$-$C_7$ cycloalkyl, phenyl, aryl-$C_{1-6}$ alkyl, heteroalicyclicalkyl, or heterocyclyl-aryl-; where the $C_3$-$C_7$ cycloalkyl, phenyl, phenyl, aryl-$C_{1-6}$ alkyl, heteroalicyclicalkyl, and heterocyclyl-aryl- groups in $R^2$ are optionally substituted with 1, 2, 3, or 4 $R^8$ groups. In another embodiment, $R^6$ is bromo and $R^2$ is $C_3$-$C_7$ cycloalkyl, $C_1$-$C_6$ alkyl optionally substituted with heteroalicyclic, dialkylamino, phenyl substituted with one or two halo, or heteroalicyclic-phenyl-; where the heteroalicyclic-phenyl- is optionally substituted with one or two $R^8$ selected from $C_1$-$C_6$ alkyl and phenyl-$C_{1-6}$alkyl. In another embodiment, $R^2$ is cyclopentyl, cyclohexyl, 2-(morpholinyl)-ethyl, 3-(morpholinyl)-propyl, 3-(dimethylamino)-propyl, 2-fluorophenyl, 3-fluorophenyl, 4-fluorophenyl, 4-[4-methyl-piperazinyl]-phenyl, 4-[4-ethyl-piperazinyl]-phenyl, 4-[4-benzyl-piperazinyl]-phenyl, or 4-(morpholinyl)-phenyl.

In another embodiment (H), the invention is directed to a Compound of Formula VII where $R^1$ is $C_1$-$C_6$ alkyl or $C_3$-$C_7$ cycloalkyl; $R^4$ is methyl; and $R^6$ is heteroaryl. In another embodiment, $R^6$ is pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, or furan-3-yl.

In another embodiment (J), the invention is directed to a Compound of Formula VII where $R^1$ is $C_1$-$C_6$ alkyl or $C_3$-$C_7$ cycloalkyl; $R^4$ is methyl; $R^5$ is hydrogen and $R^6$ is phenyl optionally substituted with 1, 2, or 3 halo.

In another embodiment (M), the invention is directed to a Compound of Formula VII where $R^6$ is pyrazol-3-yl, pyrazol-4-yl, pyrazol-5-yl, thien-2-yl, thien-3-yl, thiazol-2-yl, thiazol-4-yl, thiazol-5-yl, oxazol-2-yl, oxazol-4-yl, oxazol-5-yl, furan-2-yl, or furan-3-yl.

Another aspect of the invention is a pharmaceutical composition comprising a compound of formula VI, VIa, VIb or VII, or a pharmaceutically acceptable salt or solvate thereof, in combination with a compound of formula I, Ia, Ic, Id, II, III, IV, or V and a pharmaceutically acceptable carrier.

Another aspect of the invention is a method of inhibiting the in vivo activity of PI3Kα, and MEK the method comprising administering to a subject an effective PI3Kα-inhibiting amount of a compound of formula VI, VIa, VIb or VII, or a pharmaceutically acceptable salt or solvate thereof, in combination with a compound of formula I, Ia, Ic, Id, II, III, IV, or V or a pharmaceutical composition thereof.

Another aspect of the invention is a method of treating diseases or disorders associated with uncontrolled, abnormal, and/or unwanted cellular activities effected directly or indirectly by PI3Kα and MEK, the method comprising administering to a mammal (preferably human) in need thereof a therapeutically effective amount of a compound of any of formula VI, VIa, VIb or VII, or a pharmaceutically acceptable salt or solvate thereof, in combination with a compound of formula I, Ia, Ic, Id, II, III, IV, or V or a pharmaceutical composition thereof. In another embodiment, the MEK Compound is of Formula Ia and the PI3K Compound is of Formula VIa. In another embodiment, the MEK Compound is of Formula Ia and the PI3K Compound is of Formula VIb. In another embodiment, the MEK Compound is of Formula V and the PI3K Compound is of Formula VIa or VIb. In another embodiment, the MEK Compound is of Section I, Embodiment G and the PI3K Compound is of a compound from Section II, Formula VIa or VIb, Embodiment E. In another embodiment, the MEK Compound is of Section I, Embodiment G and the PI3K Compound is of a compound of Section II, Formula VIa or VIb, Embodiment G or G3. In another embodiment, the MEK Compound is of Formula Ia and the PI3K Compound is of Formula VII. In another embodiment, the MEK Compound is of Formula V and the PI3K Com pound is of Formula VII. In another embodiment, the MEK Compound is of Section I, Embodiment G and the PI3K Compound is of a compound from Section II, Formula VII, Embodiment E. In another embodiment, the MEK Compound is of Section I, Embodiment G and the PI3K Compound is of a compound of Section II, Formula VI, Embodiment F1 or F2. In another embodiment, the MEK Compound is of Section I, Table 1 and the PI3K Compound is of Formula VI, VIa, VIb or VII.

Another aspect of the invention is a method of inhibiting proliferative activity in a cell, the method comprising administering to a cell or a plurality of cells an effective amount of a compound of formula VI, VIa, VIb or VII, or a pharmaceutically acceptable salt or solvate thereof, in combination with a compound of formula I, Ia, Ic, Id, II, III, IV, or V or pharmaceutical composition thereof.

A further aspect of the invention is a method of treating malignancies such as melanoma, ovarian cancer, cervical cancer, breast cancer, colorectal cancer, and glioblastomas, among others, in a patient in need of such treatment, by administering a compound or salt of formula VI, VIa, VIb or VII, or a pharmaceutically acceptable salt or solvate thereof, in combination with a compound of formula I, Ia, Ic, Id, II, III, IV, or V or a pharmaceutical composition thereof.

Section II Definitions

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, "----" means a single or double bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "⁓" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

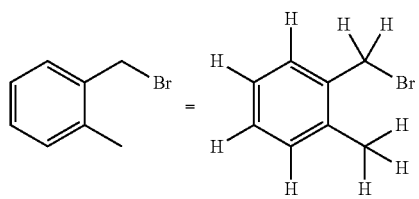

If a group "R" is depicted as "floating" on a ring system, as for example in the formula:

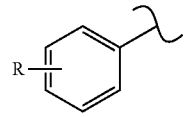

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

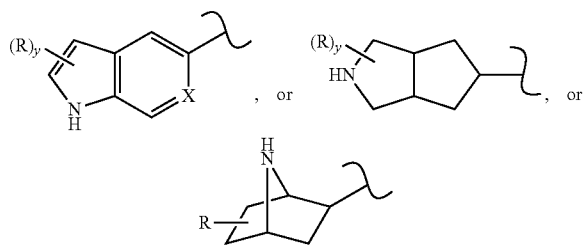

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

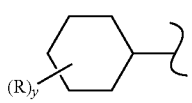

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

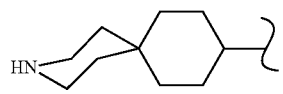

"Alkyl" is intended to include linear or branched hydrocarbon structures and combinations thereof, inclusively. For example, "$C_8$ alkyl" may refer to an n-octyl, iso-ctyl, and the like. Lower alkyl refers to alkyl groups of from one to six carbon atoms. Examples of lower alkyl groups include methyl, ethyl, propyl, isopropyl, butyl, s-butyl, t-utyl, isobutyl, pentyl, and the like. Higher alkyl refers to alkyl groups containing more that eight carbon atoms. A "$C_0$" alkyl (as in "$C_0$-$C_6$-alkyl") is a covalent bond. Exemplary alkyl groups are those of $C_{20}$ or below. In this application, alkyl refers to alkanyl, alkenyl, and alkynyl residues (and combinations thereof); it is intended to include vinyl, ally, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, 1-butyl, isobutenyl and but-2-ynyl groups; and for example, "propyl" or "$C_3$ alkyl" each include n-propyl, propenyl, and isopropyl.

"Cycloalkyl" means a cyclic hydrocarbon groups of from three to thirteen carbon atoms. Examples of cycloalkyl groups include c-propyl, c-butyl, c-pentyl, norbornyl, adamantyl and the like.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Optionally substituted alkoxy" refers to the group —OR where R is optionally substituted alkyl, as defined herein. One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"Acyloxy" means an —OR group where R is acyl as defined herein.

"Acylamino" means an —NHR group where R is acyl as defined herein.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent substituents. As univalent substituents, the aforementioned ring examples are named, phenyl, naphthyl, indanyl, tetralinyl, and fluorenyl.

"Arylalkyl" refers to a residue in which an aryl moiety is attached to a parent structure via one of an alkylene, alkylidene, or alkylidyne group. Examples include benzyl, phenethyl, phenylvinyl, phenylallyl and the like. Both the aryl and the corresponding alkylene, alkylidene, or alkylidyne group portion of an arylalkyl group may be optionally substituted. "Lower arylalkyl" refers to an arylalkyl where the "alkyl" portion of the group has one to six carbons; this can also be referred to as $C_{1-6}$ arylalkyl.

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Halogen" or "halo" refers to fluorine, chlorine, bromine or iodine.

"Haloalkyl" and "haloaryl" refer generically to alkyl and aryl groups that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl. Haloalkyl includes, for instance, mono- to per-halo$C_1$-$C_6$ alkyl.

"Heteroatom" refers to O, S, N, or P.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —$S(O)_{0-2}$—, refers to —S— (sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl group. A heteroalicyclic may contain unsaturation, but is not aromatic.

"Heteroalicyclicalkyl" refers specifically to an alkyl group substituted with one or two non-aromatic heterocyclyl group. The heteroalicyclic ring portion of this group may contain unsaturation, but is not aromatic.

"Heteroaryl" refers specifically to an aromatic heterocyclyl group.

"Heterocyclylalkyl" refers to a residue in which a heterocyclyl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms. Additionally, for simplicity, the number of annular atoms (including heteroatoms) in a heterocycle may be denoted as "$C_x$-$C_y$," (as in "$C_x$-$C_y$-heterocyclyl" and "$C_x$-$C_y$-heteroaryl" (and the like)), where x and y are integers. So, for example, $C_5$-$C_{14}$-heterocyclyl refers to a 5 to 14 membered ring system having at least one heteroatom and not a ring system containing 5 to 14 annular carbon atoms.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Heterocyclyl-aryl-" means an aryl group substituted with at least one, specifically 1 or 2 heterocyclyl, as defined herein. "Optionally substituted heterocyclyl-aryl-" means that either or both the aryl and the heterocyclyl can be substituted as defined in "substituted."

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," optional substitution may occur on both the "$C_{1-8}$ alkyl" portion and the "aryl" portion of the molecule may or may not be substituted. A list of exemplary optional substitutions is presented below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

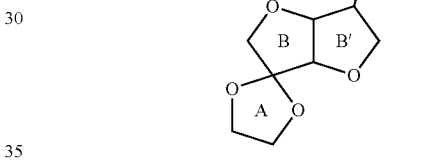

"Substituted" alkyl, cycloalkyl, aryl, and heterocyclyl (including heteroalicyclic and heteroaryl), refer respectively to alkyl, aryl, and heterocyclyl, where one or more (for example up to about five, in another example, up to about three) hydrogen atoms are replaced by a substituent. The substituent(s) on alkyl, aryl, heteroaryl, and heterocyclyl (including when any of these groups are part of another group, such as the alkyl portion of alkoxy, or the aryl portion of aryloxy) include, for instance, one or more groups selected from alkylenedioxy (for example methylenedioxy), aryloxy (for example, phenoxy), carboxy, acyloxy, acylamino, benzyloxycarbonylamino, acyl, carbamyl, oxo, hydroxy, halo, nitro, cyano, —O—$C_1$-$C_6$ alkyl, haloalkyl, $C_1$-$C_6$ alkyl, cycloalkyl, —C(O)O—$C_1$-$C_6$ alkyl, —O—$C_1$-$C_6$ alkyl-aryl, —$C_1$-$C_6$ alkyl-aryl, —O—$C_1$-$C_6$ alkyl-O—$C_1$-$C_6$ alkyl, —N($R^a$)($R^b$), ($R^a$)($R^b$)N—$C_1$-$C_6$ alkyl-, —O—$C_1$-$C_6$ alkyl-N($R^a$)($R^b$), —O—$C_1$-$C_6$ alkyl-heterocyclyl, $C_0$-$C_6$ alkyl-heterocyclyl, $C_0$-$C_6$ alkyl-aryl, $C_0$-$C_6$ alkyl-heteroaryl, —C(O)N($R^a$)—$C_1$-$C_6$-alkyl-N($R^a$)($R^b$), sulfanyl, sulfinyl, sulfonyl, aryl, heteroaryl, heterocyclyl, arylalkyl-, heteroarylalkyl-, and heterocyclylalkyl, where $R^a$ and $R^b$ are independently hydrogen or alkyl, or $R^a$ and $R^b$ together with the nitrogen to which they are attached form a heterocyclyl group. Examples of heterocyclyl groups formed by $R^a$ and $R^b$ include morpholinyl and piperazinyl. Each substituent of a substituted group is optionally substituted, but these optional substituents themselves are not further substituted. Thus, an optionally substituted moiety is one that may or may not have one or more substituents, and each of the substituents may or may not have one or more substituents. But, the substituents of the substituents may not be substituted.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O₂)—H, —S(O₂)-(optionally substituted alkyl), —S(O₂)-optionally substituted aryl), —S(O₂)-(optionally substituted heterocyclyl), —S(O₂)— (optionally substituted alkoxy), —S(O₂)-optionally substituted aryloxy), and —S(O₂)-(optionally substituted heterocyclyloxy).

Preparation of Compounds

The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Specific examples of methods of preparation can be found in the art. For examples, see M. Barvian et al. J. Med. Chem. 2000, 43, 4606-4616; S. N. VanderWei et al. J. Med. Chem. 2005, 48, 2371-2387; P. L. Toogood et al. J. Med. Chem. 2005, 48, 2388-2406; J. Kasparec et al. Tetrahedron Letters 2003, 44, 4567-4570; and references cited therein. See also U.S. Pre-grant publication US2004/0009993 A1 (M. Angiolini et al.), which is incorporated herein by reference, and references cited therein.

The following examples illustrate but do not limit the invention. All references cited herein are incorporated by reference in their entirety.

EXAMPLES

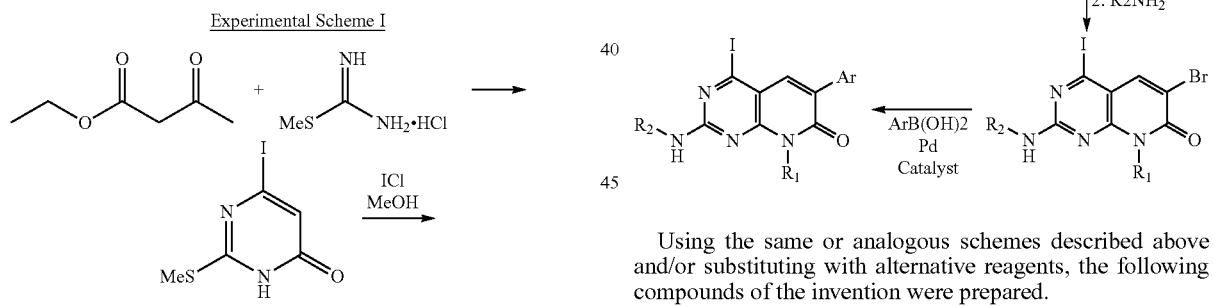

Experimental Scheme I

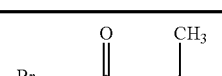

Using the same or analogous schemes described above and/or substituting with alternative reagents, the following compounds of the invention were prepared.

Illustrative compounds of Section II are shown in Table I.

TABLE 1

Section II

| Example | Structure | Name |
|---|---|---|
| 1 | (structure shown) | 6-bromo-8-ethyl-4-methyl-2-(methylamino)pyrido[2,3-d]pyrimidin-7(8H)-one |

TABLE 1-continued
Section II
| Example | Structure | Name |
|---|---|---|
| 2 | 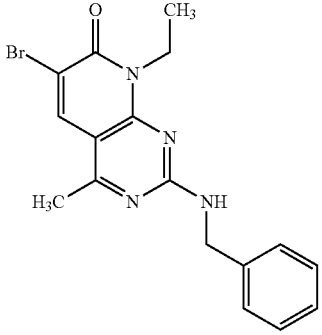 [SMILES: CCn1c(=O)c(Br)cc2c(C)nc(NCc3ccccc3)nc21] | 6-bromo-8-ethyl-4-methyl-2-[(phenylmethyl)amino]pyrido[2,3-d]pyrimidin-7(8H)-one |
| 3 | 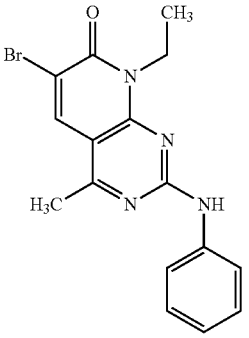 [SMILES: CCn1c(=O)c(Br)cc2c(C)nc(Nc3ccccc3)nc21] | 6-bromo-8-ethyl-4-methyl-2-(phenylamino)pyrido[2,3-d]pyrimidin-7(8H)-one |
| 4 | 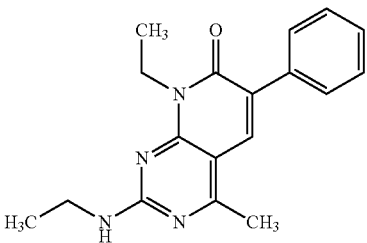 | 8-ethyl-2-(ethylamino)-4-methyl-6-phenylpyrido[2,3-d]pyrimidin-7(8H)-one |
| 5 | 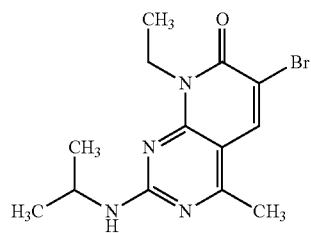 | 6-bromo-8-ethyl-4-methyl-2-[(1-methylethyl)amino]pyrido[2,3-d]pyrimidin-7(8H)-one |
| 6 | 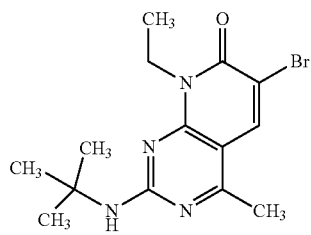 [SMILES: CCn1c(=O)c(Br)cc2c(C)nc(NC(C)(C)C)nc21] | 6-bromo-2-[(1,1-dimethylethyl)amino]-8-ethyl-4-methylpyrido[2,3-d]pyrimidin-7(8H)-one |

TABLE 1-continued

Section II

| Example | Structure | Name |
|---|---|---|
| 7 | 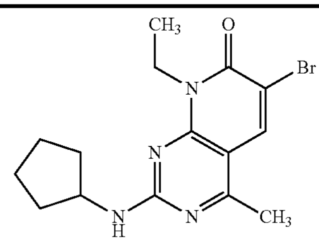 | 6-bromo-2-(cyclopentylamino)-8-ethyl-4-methylpyrido[2,3-d]pyrimidin-7(8H)-one |
| 8 | 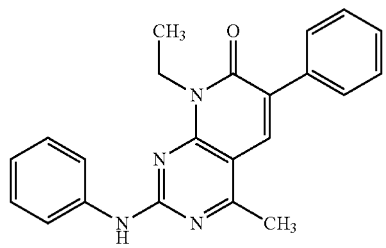 [SMILES: CCn1c(=O)c(-c2ccccc2)cc2c(C)nc(Nc3ccccc3)nc21] | 8-ethyl-4-methyl-6-phenyl-2-(phenylamino)pyrido[2,3-d]pyrimidin-7(8H)-one |
| 9 | 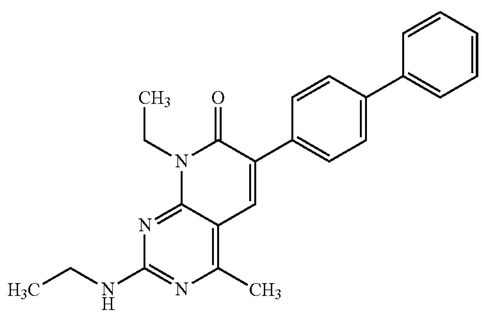 [SMILES: CCNc1nc(C)c2cc(-c3ccc(-c4ccccc4)cc3)c(=O)n(CC)c2n1] | 6-biphenyl-4-yl-8-ethyl-2-(ethylamino)-4-methylpyrido[2,3-d]pyrimidin-7(8H)-one |
| 10 | 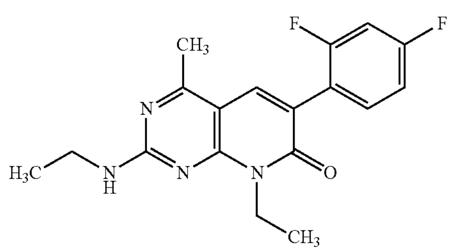 [SMILES: CCNc1nc(C)c2cc(-c3ccc(F)cc3F)c(=O)n(CC)c2n1] | 6-(2,4-difluorophenyl)-8-ethyl-2-(ethylamino)-4-methylpyrido[2,3-d]pyrimidin-7(8H)-one |
| 11 | 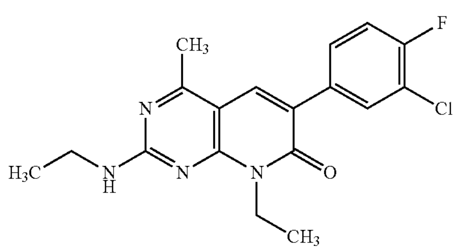 | 6-(3-chloro-4-fluorophenyl)-8-ethyl-2-(ethylamino)-4-methylpyrido[2,3-d]pyrimidin-7(8H)-one |
| 12 | 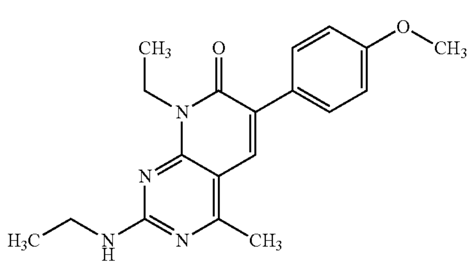 [SMILES: CCNc1nc(C)c2cc(-c3ccc(OC)cc3)c(=O)n(CC)c2n1] | 8-ethyl-2-(ethylamino)-4-methyl-6-[4-(methyloxy)phenyl]pyrido[2,3-d]pyrimidin-7(8H)-one |

TABLE 1-continued

Section II

| Example | Structure | Name |
|---|---|---|
| 13 | 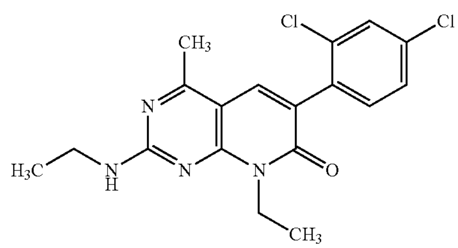 [SMILES: CCNc1nc(C)c2cc(-c3ccc(Cl)cc3Cl)c(=O)n(CC)c2n1] | 6-(2,4-dichlorophenyl)-8-ethyl-2-(ethylamino)-4-methylpyrido[2,3-d]pyrimidin-7(8H)-one |
| 14 | 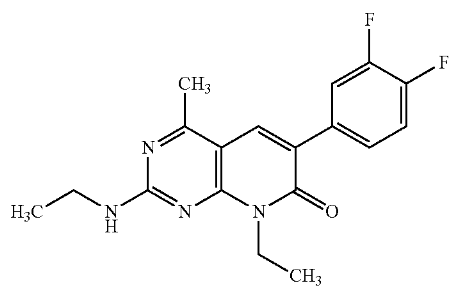 [SMILES: CCNc1nc(C)c2cc(-c3ccc(F)c(F)c3)c(=O)n(CC)c2n1] | 6-(3,4-difluorophenyl)-8-ethyl-2-(ethylalmino)-4-methylpyrido[2,3-d]pyrimidin-7(8H)-one |
| 15 | 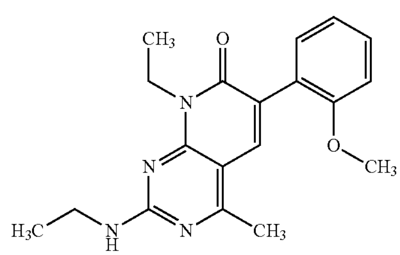 [SMILES: CCNc1nc(C)c2cc(-c3ccccc3OC)c(=O)n(CC)c2n1] | 8-ethyl-2-(ethylamino)-4-methyl-6-[2-(methyloxy)phenyl]pyrido[2,3-d]pyrimidin-7(8H)-one |
| 16 | 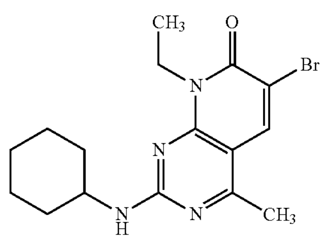 [SMILES: CCn1c(=O)c(Br)cc2c(C)nc(NC3CCCCC3)nc21] | 6-bromo-2-(cyclohexylamino)-8-ethyl-4-methylpyrido[2,3-d]pyrimidin-7(8H)-one |
| 17 | 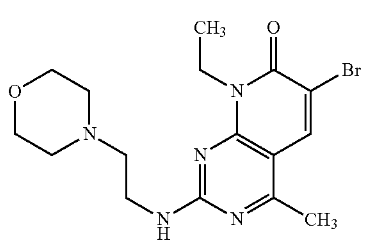 [SMILES: CCn1c(=O)c(Br)cc2c(C)nc(NCCN3CCOCC3)nc21] | 6-bromo-8-ethyl-4-methyl-2-[(2-morpholin-4-ylethyl)amino]pyrido[2,3-d]pyrimidin-7(8H)-one |

TABLE 1-continued

Section II

| Example | Structure | Name |
|---|---|---|
| 18 | 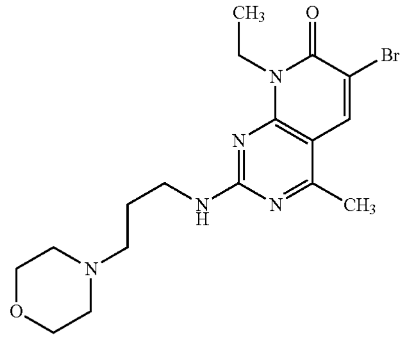 [SMILES: CCn1c(=O)c(Br)cc2c(C)nc(NCCCN3CCOCC3)nc21] | 6-bromo-8-ethyl-4-methyl-2-[(3-mopholin-2-ylpropyl)amino]pyrido[2,3-d]pyrimidin-7(8H)-one |
| 19 | 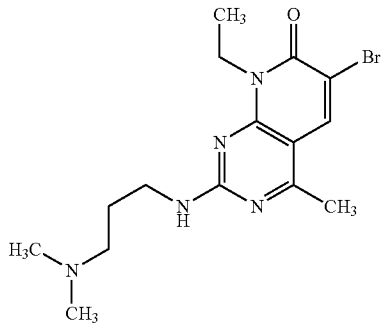 [SMILES: CCn1c(=O)c(Br)cc2c(C)nc(NCCCN(C)C)nc21] | 6-bromo-2-{[3-(dimethylamino)propyl]amino}-8-ethyl-4-methylpyrido[2,3-d]pyrimidin-7(8H)-one |
| 20 | 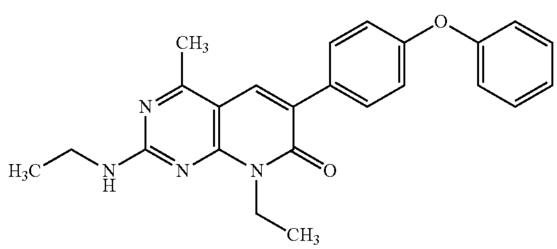 [SMILES: CCNc1nc(C)c2cc(-c3ccc(Oc4ccccc4)cc3)c(=O)n(CC)c2n1] | 8-ethyl-2-(ethylamino)-4-methyl-6-[4-(phenyloxy)phenyl]pyrido[2,3-d]pyrimidin-7(8H)-one |
| 21 | 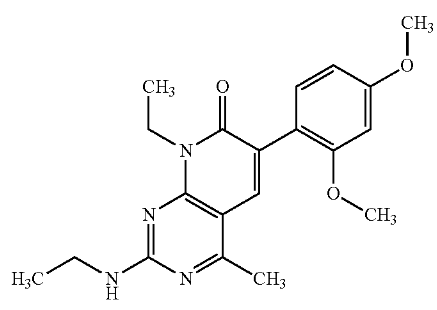 [SMILES: CCNc1nc(C)c2cc(-c3ccc(OC)cc3OC)c(=O)n(CC)c2n1] | 6-[2,4-bis(methyloxy)phenyl]-8-ethyl-2-(ethylamino)-4-methylpyrido[2,3-d]pyrimidin-7(8H)-one |
| 22 | 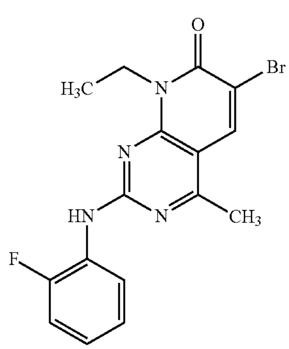 [SMILES: CCn1c(=O)c(Br)cc2c(C)nc(Nc3ccccc3F)nc21] | 6-bromo-8-ethyl-2-[(2-fluorophenyl)amino]-4-methylpyrido[2,3-d]pyrimidin-7(8H)-one |

TABLE 1-continued

Section II

| Example | Structure | Name |
|---|---|---|
| 23 | 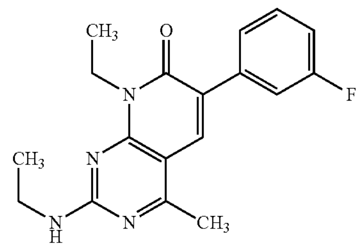 [SMILES: CCNc1nc(C)c2cc(-c3cccc(F)c3)c(=O)n(CC)c2n1] | 8-ethyl-2-(ethylamino)-6-(3-fluorophenyl)-4-methylpyrido[2,3-d]pyrimidin-7(8H)-one |
| 24 | 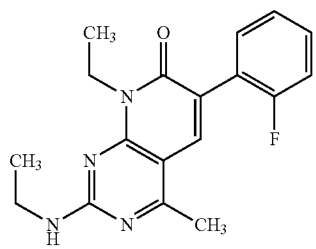 [SMILES: CCNc1nc(C)c2cc(-c3ccccc3F)c(=O)n(CC)c2n1] | 8-ethyl-2-(ethylamino)-6-(2-fluorophenyl)-4-methylpyrido[2,3-d]pyrimidin-7(8H)-one |
| 25 | 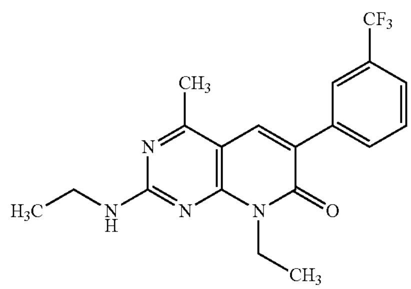 | 8-ethyl-2-(ethylamino)-4-methyl-6-[3-(trifluoromethyl)phenyl]pyrido[2,3-d]pyrimidin-7(8H)-one |
| 26 | 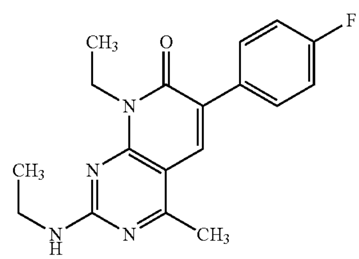 [SMILES: CCNc1nc(C)c2cc(-c3ccc(F)cc3)c(=O)n(CC)c2n1] | 8-ethyl-2-(ethylamino)-6-(4-fluorophenyl)-4-methylpyrido[2,3-d]pyrimidin-7(8H)-one |
| 27 | 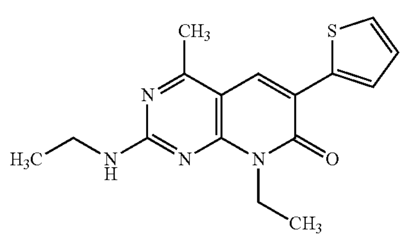 [SMILES: CCNc1nc(C)c2cc(-c3cccs3)c(=O)n(CC)c2n1] | 8-ethyl-2-(ethylamino)-4-methyl-6-(2-thienyl)pyrido[2,3-d]pyrimidin-7(8H)-one |
| 28 | 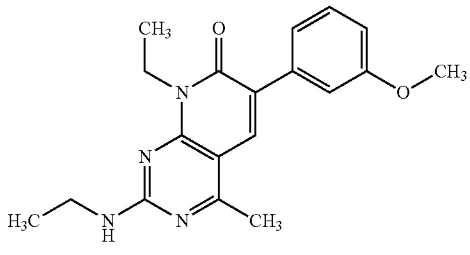 [SMILES: CCNc1nc(C)c2cc(-c3cccc(OC)c3)c(=O)n(CC)c2n1] | 8-ethyl-2-(ethylamino)-4-methyl-6-[3-(methyloxy)phenyl]pyrido[2,3-d]pyrimidin-7(8H)-one |

TABLE 1-continued

Section II

| Example | Structure | Name |
|---|---|---|
| 29 | 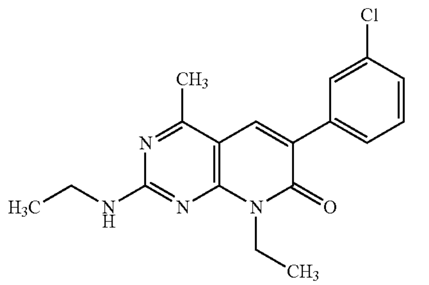 [SMILES: CCNc1nc(C)c2cc(-c3cccc(Cl)c3)c(=O)n(CC)c2n1] | 6-(3-chlorophenyl)-8-ethyl-2-(ethylamino)-4-methylpyrido[2,3-d]pyrimidin-7(8H)-one |
| 30 | 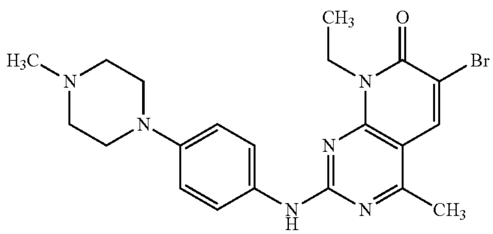 [SMILES: CCn1c(=O)c(Br)cc2c(C)nc(Nc3ccc(N4CCN(C)CC4)cc3)nc21] | 6-bromo-8-ethyl-4-methyl-2-{[4-(4-methylpiperazin-1-yl)phenyl]amino}pyrido[2,3-d]pyrimidin-7(8H)-one |
| 31 | 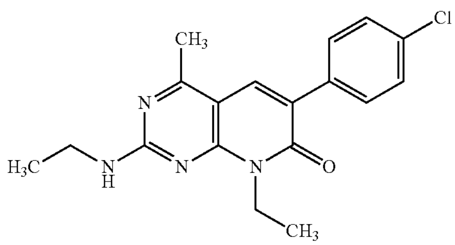 [SMILES: CCNc1nc(C)c2cc(-c3ccc(Cl)cc3)c(=O)n(CC)c2n1] | 6-(4-chlorophenyl)-8-ethyl-2-(ethylamino)-4-methylpyrido[2,3-d]pyrimidin-7(8H)-one |
| 32 | 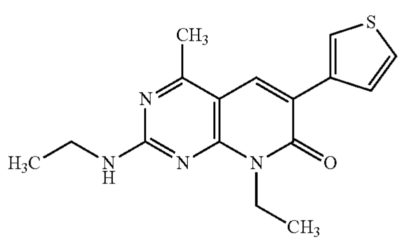 | 8-ethyl-2-(ethylamino)-4-methyl-6-(3-thienyl)pyrido[2,3-d]pyrimidin-7(8H)-one |
| 33 | 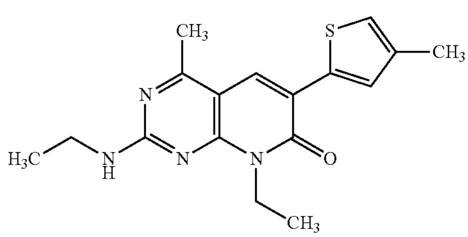 [SMILES: CCNc1nc(C)c2cc(-c3cc(C)cs3)c(=O)n(CC)c2n1] | 8-ethyl-2-(ethylamino)-4-methyl-6-(4-methyl-2-thienyl)pyrido[2,3-d]pyrimidin-7(8H)-one |
| 34 | 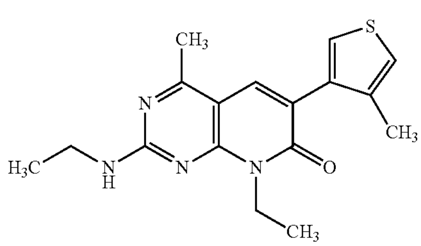 [SMILES: CCNc1nc(C)c2cc(-c3cscc3C)c(=O)n(CC)c2n1] | 8-ethyl-2-(ethylamino)-4-methyl-6-(4-methyl-3-thienyl)pyrido[2,3-d]pyrimidin-7(8H)-one |

TABLE 1-continued

Section II

| Example | Structure | Name |
|---|---|---|
| 35 | 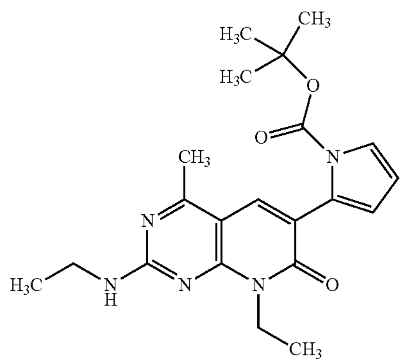 [SMILES: CCNc1nc(C)c2cc(-c3cccn3C(=O)OC(C)(C)C)c(=O)n(CC)c2n1] | 1,1-dimethylethyl 2-[8-ethyl-2-(ethylamino)-4-methyl-7-oxo-7,8-dihydropyrido[2,3-d]pyrimidin-6-yl]-1H-pyrrole-1-carboxylate |
| 36 | 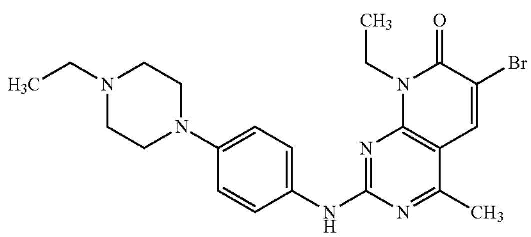 [SMILES: CCN1CCN(c2ccc(Nc3nc(C)c4cc(Br)c(=O)n(CC)c4n3)cc2)CC1] | 6-bromo-8-ethyl-2-{[4-(4-ethylpiperazin-1-yl)phenyl]amino}-4-methylpyrido[2,3-d]pyrimidin-7(8H)-one |
| 37 | 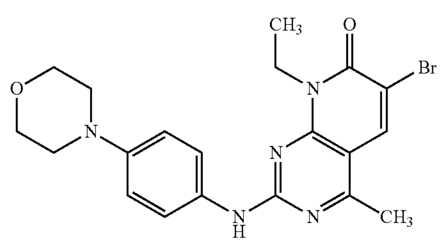 [SMILES: CCn1c(=O)c(Br)cc2c(C)nc(Nc3ccc(N4CCOCC4)cc3)nc21] | 6-bromo-8-ethyl-4-methyl-2-[(4-morpholin-4-ylphenyl)amino]pyrido[2,3-d]pyrimidin-7(8H)-one |
| 38 | 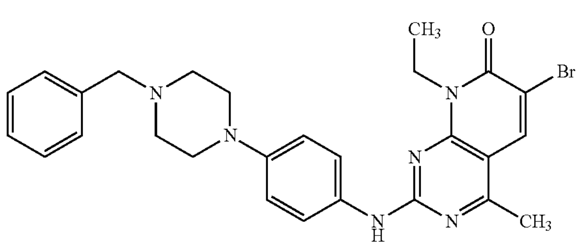 [SMILES: CCn1c(=O)c(Br)cc2c(C)nc(Nc3ccc(N4CCN(Cc5ccccc5)CC4)cc3)nc21] | 6-bromo-8-ethyl-4-methyl-2-({4-[4-(phenylmethyl)piperazin-1-yl]phenyl}amino)pyrido[2,3-d]pyrimidin-7(8H)-one |
| 39 | 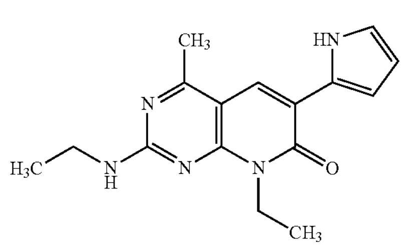 [SMILES: CCNc1nc(C)c2cc(-c3ccc[nH]3)c(=O)n(CC)c2n1] | 8-ethyl-2-(ethylamino)-4-methyl-6-(1H-pyrrol-2-yl)pyrido[2,3-d]pyrimidin-7(8H)-one |

TABLE 1-continued

Section II

| Example | Structure | Name |
|---|---|---|
| 40 | 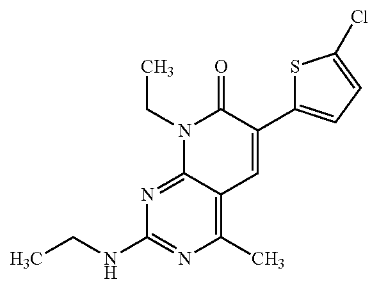 [SMILES: CCNc1nc(C)c2cc(-c3ccc(Cl)s3)c(=O)n(CC)c2n1] | 6-(5-chloro-2-thienyl)-8-ethyl-2-(ethylamino)-4-methylpyrido[2,3-d]pyrimidin-7(8H)-one |
| 41 | 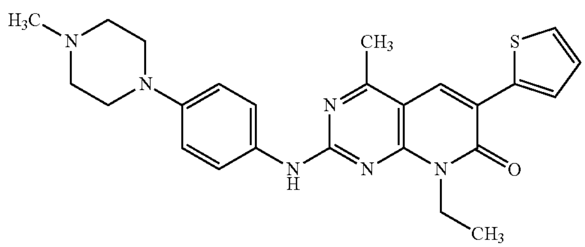 [SMILES: CCn1c(=O)c(-c2cccs2)cc2c(C)nc(Nc3ccc(N4CCN(C)CC4)cc3)nc21] | 8-ethyl-4-methyl-2-{[4-(4-methylpiperazin-1-yl)phenyl]amino}-6-(2-thienyl)pyrido[2,3-d]pyrimidin-7(8H)-one |
| 42 | 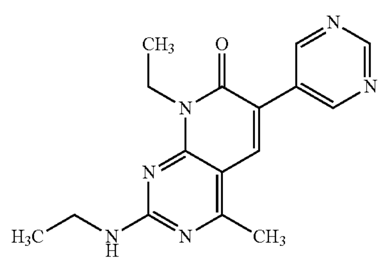 [SMILES: CCNc1nc(C)c2cc(-c3cncnc3)c(=O)n(CC)c2n1] | 8-ethyl-2-(ethylamino)-4-methyl-6-pyrimidin-5-ylpyrido[2,3-d]pyrimidin-7(8H)-one |
| 43 | 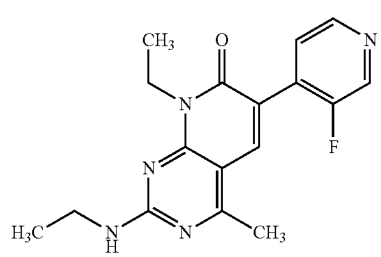 [SMILES: CCNc1nc(C)c2cc(-c3ccncc3F)c(=O)n(CC)c2n1] | 8-ethyl-2-(ethylamino)-6-(3-fluoropyridin-4-yl)-4-methylpyrido[2,3-d]pyrimidin-7(8H)-one |
| 44 | 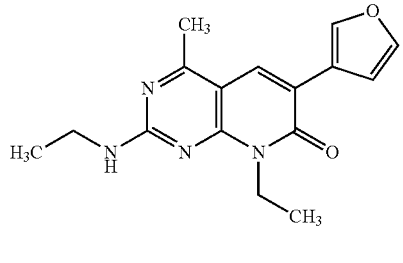 [SMILES: CCNc1nc(C)c2cc(-c3ccoc3)c(=O)n(CC)c2n1] | 8-ethyl-2-(ethylamino)-6-furan-3-yl-4-methylpyrido[2,3-d]pyrimidin-7(8H)-one |

TABLE 1-continued

Section II

| Example | Structure | Name |
|---|---|---|
| 45 | 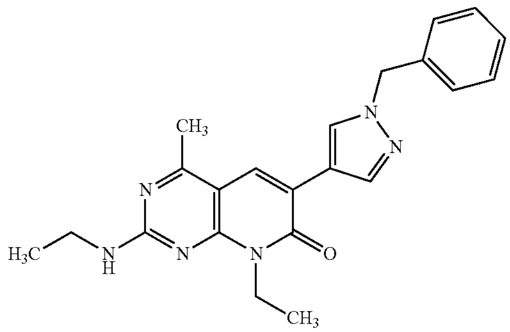 [SMILES: CCNc1nc(C)c2cc(-c3cnn(Cc4ccccc4)c3)c(=O)n(CC)c2n1] | 8-ethyl-2-(ethylamino)-4-methyl-6-[1-(phenylmethyl)-1H-pyrazol-4-yl]pyrido[2,3-d]pyrimidin-7(8H)-one |
| 46 | 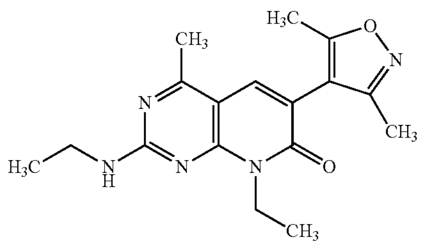 [SMILES: CCNc1nc(C)c2cc(-c3c(C)noc3C)c(=O)n(CC)c2n1] | 6-(3,5-dimethylisoxazol-4-yl)-8-ethyl-2-(ethylamino)-4-methylpyrido[2,3-d]pyrimidin-7(8H)-one |
| 47 | 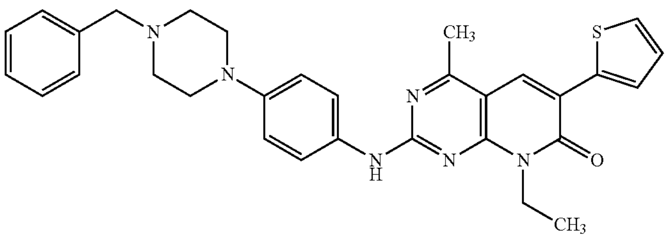 [SMILES: CCn1c(=O)c(-c2cccs2)cc2c(C)nc(Nc3ccc(N4CCN(Cc5ccccc5)CC4)cc3)nc21] | 8-ethyl-4-methyl-2-({4-[4-(phenylmethyl)piperazin-1-yl]phenyl}amino)-6-(2-thienyl)pyrido[2,3-d]pyrimidin-7(8H)-one |
| 48 | 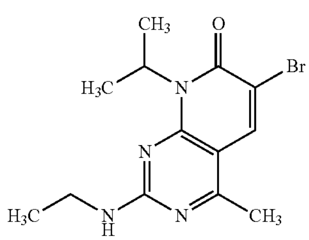 [SMILES: CCNc1nc(C)c2cc(Br)c(=O)n(C(C)C)c2n1] | 6-bromo-2-(ethylamino)-4-methyl-8-(1-methylethyl)pyrido[2,3-d]pyrimidin-7(8H)-one |
| 49 | 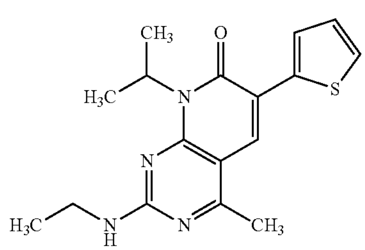 [SMILES: CCNc1nc(C)c2cc(-c3cccs3)c(=O)n(C(C)C)c2n1] | 2-(ethylamino)-4-methyl-8-(1-methylethyl)-6-(2-thienyl)pyrido[2,3-d]pyrimidin-7(8H)-one |
| 50 | 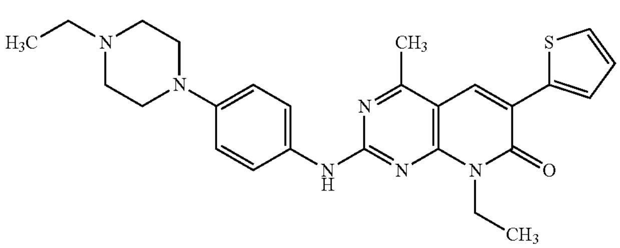 [SMILES: CCN1CCN(c2ccc(Nc3nc(C)c4cc(-c5cccs5)c(=O)n(CC)c4n3)cc2)CC1] | 8-ethyl-2-{[4-(4-ethylpiperazin-1-yl)phenyl]amino}-4-methyl-6-(2-thienyl)pyrido[2,3-d]pyrimidin-7(8H)-one |

TABLE 1-continued

Section II

| Example | Structure | Name |
|---|---|---|
| 51 | 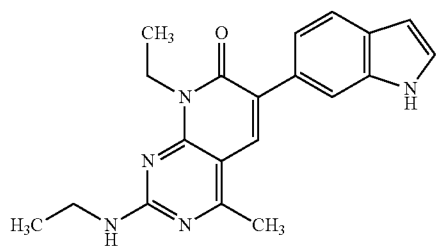 [SMILES: CCNc1nc(C)c2cc(-c3ccc4cc[nH]c4c3)c(=O)n(CC)c2n1] | 8-ethyl-2-(ethylamino)-6-(1H-indol-6-yl)-4-methylpyrido[2,3-d]pyrimidin-7(8H)-one |
| 52 | 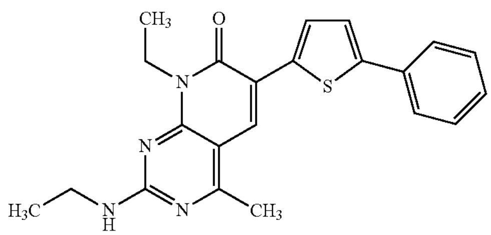 [SMILES: CCNc1nc(C)c2cc(-c3ccc(-c4ccccc4)s3)c(=O)n(CC)c2n1] | 8-ethyl-2-(ethylamino)-4-methyl-6-(5-phenyl-2-thienyl)pyrido[2,3-d]pyrimidin-7(8H)-one |
| 53 | 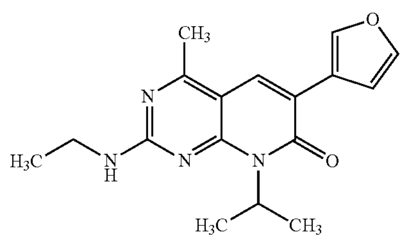 [SMILES: CCNc1nc(C)c2cc(-c3ccoc3)c(=O)n(C(C)C)c2n1] | 2-(ethylamino)-6-furan-3-yl-4-methyl-8-(1-methylethyl)pyrido[2,3-d]pyrimidin-7(8H)-one |
| 54 | 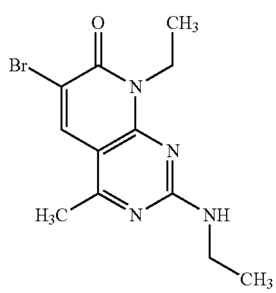 [SMILES: CCNc1nc(C)c2cc(Br)c(=O)n(CC)c2n1] | 6-bromo-8-ethyl-2-(ethylamino)-4-methylpyrido[2,3-d]pyrimidin-7(8H)-one |
| 55 | 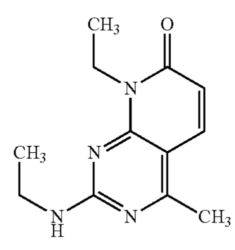 [SMILES: CCNc1nc(C)c2ccc(=O)n(CC)c2n1] | 8-ethyl-2-(ethylamino)-4-methylpyrido[2,3-d]pyrimidin-7(8H)-one |
| 56 | 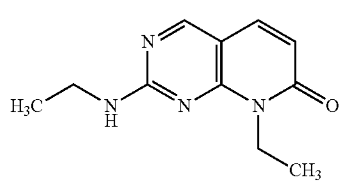 [SMILES: CCNc1ncc2ccc(=O)n(CC)c2n1] | 8-ethyl-2-(ethylamino)pyrido[2,3-d]pyrimidin-7(8H)-one |

TABLE 1-continued

Section II

| Example | Structure | Name |
|---|---|---|
| 57 | 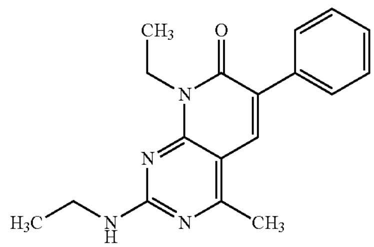 [SMILES: CCNc1nc(C)c2cc(-c3ccccc3)c(=O)n(CC)c2n1] | 8-ethyl-2-(ethylamino)-4-methyl-6-phenylpyrido[2,3-d]pyrimidin-7(8H)-one |
| 58 | 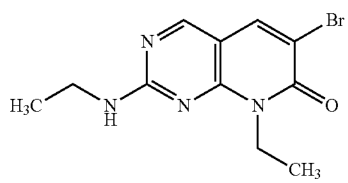 | 6-bromo-8-ethyl-2-(ethylamino)pyrido[2,3-d]pyrimidin-7(8H)-one |
| 59 | 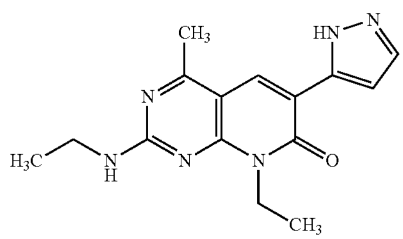 [SMILES: CCNc1nc(C)c2cc(-c3ccn[nH]3)c(=O)n(CC)c2n1] | 8-ethyl-2-(ethylamino)-4-methyl-6-(1H-pyrazol-5-yl)pyrido[2,3-d]pyrimidin-7(8H)-one |
| 60 | 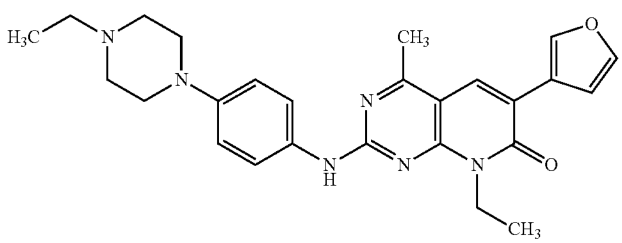 [SMILES: CCN1CCN(c2ccc(Nc3nc(C)c4cc(-c5ccoc5)c(=O)n(CC)c4n3)cc2)CC1] | 8-ethyl-2-{[4-(4-ethylpiperazin-1-yl)phenyl]amino}-6-furan-3-yl-4-methylpyrido[2,3-d]pyrimidin-7(8H)-one |
| 61 | 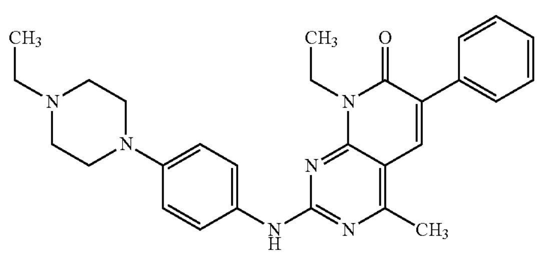 [SMILES: CCN1CCN(c2ccc(Nc3nc(C)c4cc(-c5ccccc5)c(=O)n(CC)c4n3)cc2)CC1] | 8-ethyl-2-{[4-(4-ethylpiperazin-1-yl)phenyl]amino}-4-methyl-6-phenylpyrido[2,3-d]pyrimidin-7(8H)-one |
| 62 | 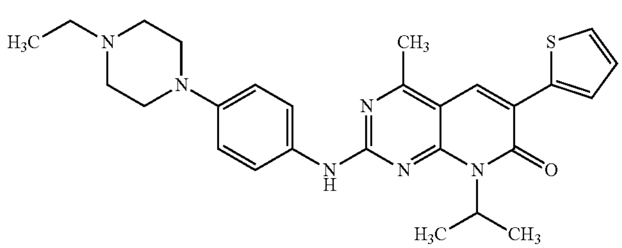 [SMILES: CCN1CCN(c2ccc(Nc3nc(C)c4cc(-c5cccs5)c(=O)n(C(C)C)c4n3)cc2)CC1] | 2-{[4-(4-ethylpiperazin-1-yl)phenyl]amino}-4-methyl-8-(1-methylethyl)-6-(2-thienyl)pyrido[2,3-d]pyrimidin-7(8H)-one |

TABLE 1-continued

Section II

| Example | Structure | Name |
| --- | --- | --- |
| 63 | 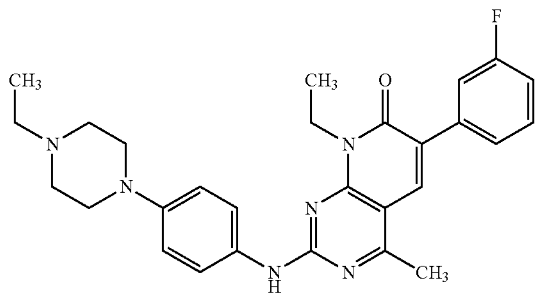 [SMILES: CCN1CCN(c2ccc(Nc3nc(C)c4cc(-c5cccc(F)c5)c(=O)n(CC)c4n3)cc2)CC1] | 8-ethyl-2-{[4-(4-ethylpiperazin-1-yl)phenyl]amino}-6-(3-fluorophenyl)-4-methylpyrido[2,3-d]pyrimidin-7(8H)-one |
| 64 | 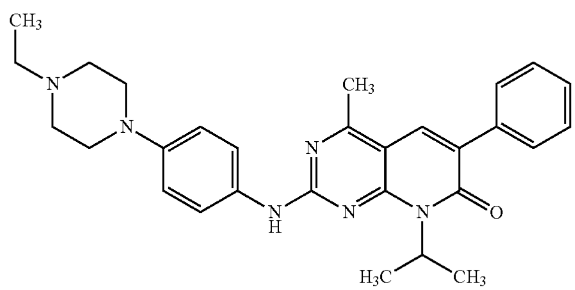 [SMILES: CCN1CCN(c2ccc(Nc3nc(C)c4cc(-c5ccccc5)c(=O)n(C(C)C)c4n3)cc2)CC1] | 2-{[4-(4-ethylpiperazin-1-yl)phenyl]amino}-4-methyl-8-(1-methylethyl)-6-phenylpyrido[2,3-d]pyrimidin-7(8H)-one |
| 65 | 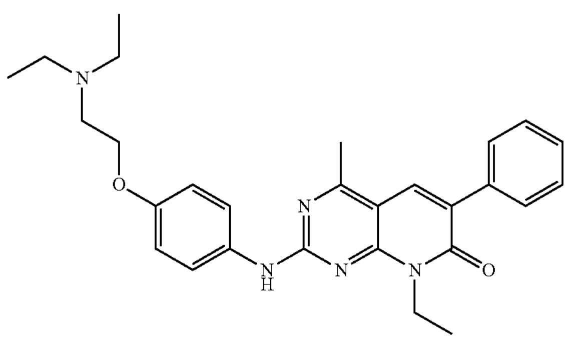 [SMILES: CCN(CC)CCOc1ccc(Nc2nc(C)c3cc(-c4ccccc4)c(=O)n(CC)c3n2)cc1] | 2-[(4-{[2-(diethylamino)ethyl]oxy}phenyl)amino]-8-ethyl-4-methyl-6-phenylpyrido[2,3-d]pyrimidin-7(8H)-one |
| 66 | 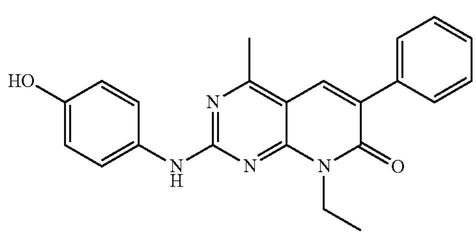 [SMILES: CCn1c(=O)c(-c2ccccc2)cc2c(C)nc(Nc3ccc(O)cc3)nc21] | 8-ethyl-2-[(4-hydroxyphenyl)amino]-4-methyl-6-phenylpyrido[2,3-d]pyrimidin-7(8H)-one |
| 67 | 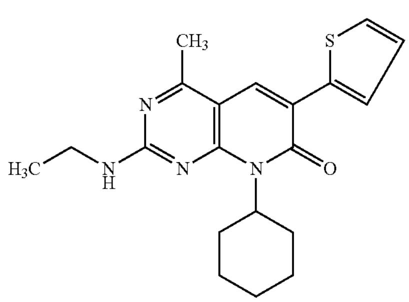 [SMILES: CCNc1nc(C)c2cc(-c3cccs3)c(=O)n(C3CCCCC3)c2n1] | 8-cyclohexyl-2-(ethylamino)-4-methyl-6-(2-thienyl)pyrido[2,3-d]pyrimidin-7(8H)-one |

TABLE 1-continued

Section II

| Example | Structure | Name |
|---|---|---|
| 68 | 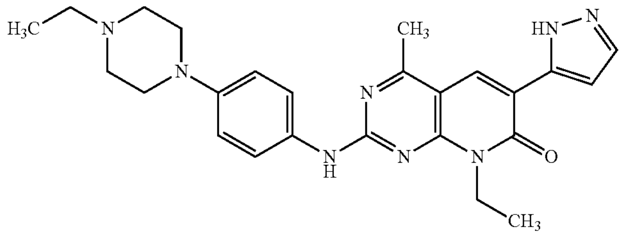 [SMILES: CCN1CCN(c2ccc(Nc3nc(C)c4cc(-c5ccn[nH]5)c(=O)n(CC)c4n3)cc2)CC1] | 8-ethyl-2-{[4-(4-ethylpiperazin-1-yl)phenyl]amino}-4-methyl-6-(1H-pyrazol-5-yl)pyrido[2,3-d]pyrimidin-7(8H)-one |
| 69 | 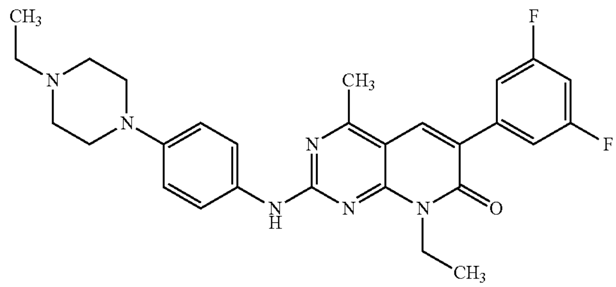 [SMILES: CCN1CCN(c2ccc(Nc3nc(C)c4cc(-c5cc(F)cc(F)c5)c(=O)n(CC)c4n3)cc2)CC1] | 6-(3,5-difluorophenyl)-8-ethyl-2-{[4-(4-ethylpiperazin-1-yl)phenyl]amino}-4-methylpyrido[2,3-d]pyrimidin-7(8H)-one |
| 70 | 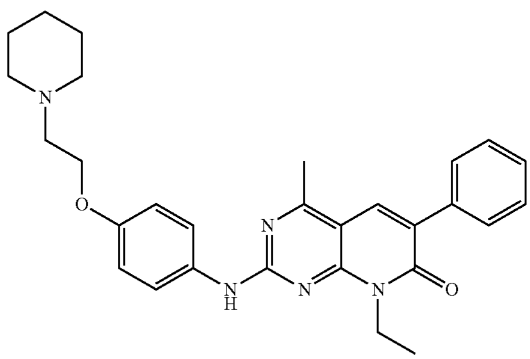 [SMILES: CCn1c(=O)c(-c2ccccc2)cc2c(C)nc(Nc3ccc(OCCN4CCCCC4)cc3)nc21] | 8-ethyl-4-methyl-6-phenyl-2-({4-[(2-piperidin-1-ylethyl)oxy]phenyl}amino)pyrido[2,3-d]pyrimidin-7(8H)-one |
| 71 | 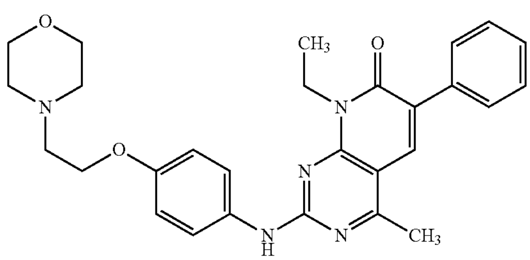 [SMILES: CCn1c(=O)c(-c2ccccc2)cc2c(C)nc(Nc3ccc(OCCN4CCOCC4)cc3)nc21] | 8-ethyl-4-methyl-2-({4-[(2-morpholin-4-ylethyl)oxy]phenyl}amino)-6-phenylpyrido[2,3-d]pyrimidin-7(8H)-one |
| 72 | 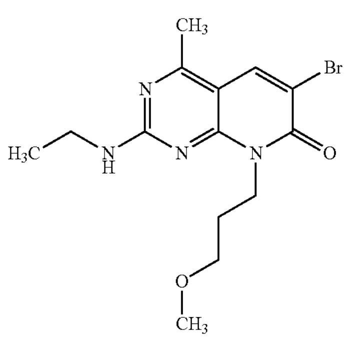 [SMILES: CCNc1nc(C)c2cc(Br)c(=O)n(CCCOC)c2n1] | 6-bromo-2-(ethylamino)-4-methyl-8-[3-(methyloxy)propyl]pyrido[2,3-d]pyrimidin-7(8H)-one |

TABLE 1-continued
Section II
| Example | Structure | Name |
|---|---|---|
| 73 | 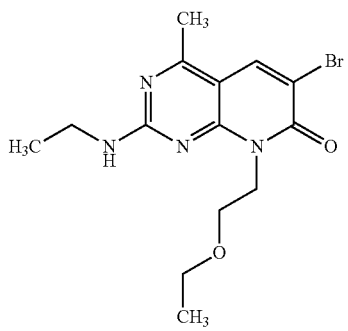 [SMILES: CCNc1nc(C)c2cc(Br)c(=O)n(CCOCC)c2n1] | 6-bromo-2-(ethylamino)-8-[2-(ethyloxy)ethyl]-4-methylpyrido[2,3-d]pyrimidin-7(8H)-one |
| 74 | 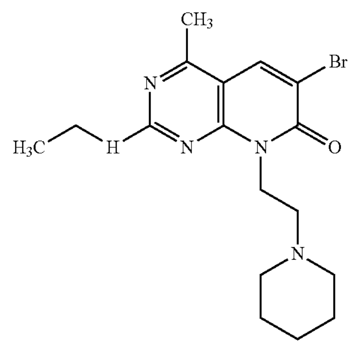 | 6-bromo-2-(ethylamino)-4-methyl-8-(2-piperidin-1-ylethyl)pyrido[2,3-d]pyrimidin-7(8H)-one |
| 75 | 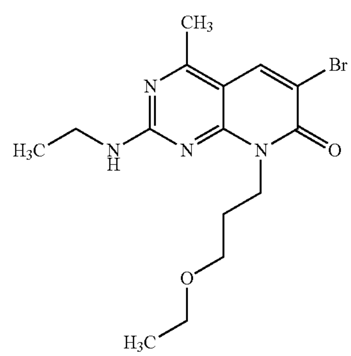 [SMILES: CCNc1nc(C)c2cc(Br)c(=O)n(CCCOCC)c2n1] | 6-bromo-2-(ethylamino)-8-[3-(ethyloxy)propyl]-4-methylpyrido[2,3-d]pyrimidin-7(8H)-one |
| 76 | 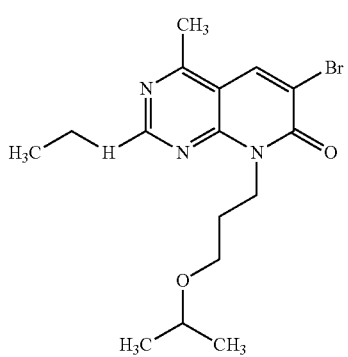 | 6-bromo-2-(ethylamino)-4-methyl-8-{3-[(1-methylethyl)oxy]propyl}pyrido[2,3-d]pyrimidin-7(8H)-one |

TABLE 1-continued

Section II

| Example | Structure | Name |
|---|---|---|
| 77 | 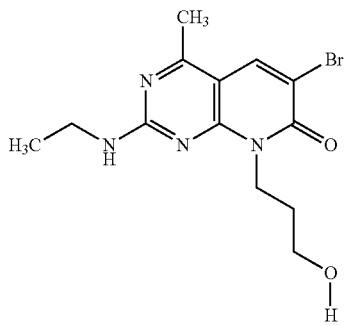 [SMILES: CCNc1nc(C)c2cc(Br)c(=O)n(CCCO)c2n1] | 6-bromo-2-(ethylamino)-8-(3-hydroxypropyl)-4-methylpyrido[2,3-d]pyrimidin-7(8H)-one |
| 78 | 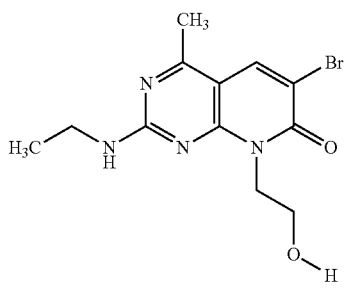 [SMILES: CCNc1nc(C)c2cc(Br)c(=O)n(CCO)c2n1] | 6-bromo-2-(ethylamino)-8-(2-hydroxyethyl)-4-methylpyrido[2,3-d]pyrimidin-7(8H)-one |
| 79 | 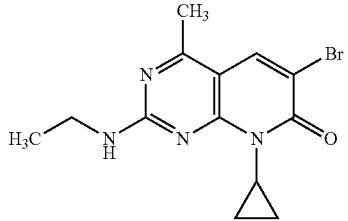 [SMILES: CCNc1nc(C)c2cc(Br)c(=O)n(C3CC3)c2n1] | 6-bromo-8-cyclopropyl-2-(ethylamino)-4-methylpyrido[2,3-d]pyrimidin-7(8H)-one |
| 80 | 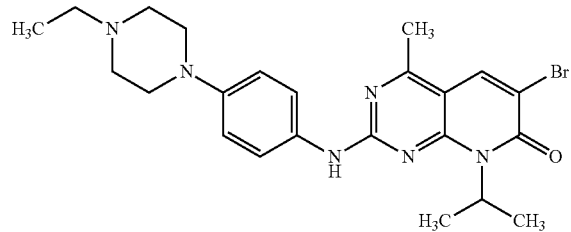 [SMILES: CCN1CCN(c2ccc(Nc3nc(C)c4cc(Br)c(=O)n(C(C)C)c4n3)cc2)CC1] | 6-bromo-2-{[4-(4-ethylpiperazin-1-yl)phenyl]amino}-4-methyl-8-(1-methylethyl)pyrido[2,3-d]pyrimidin-7(8H)-one |
| 81 | 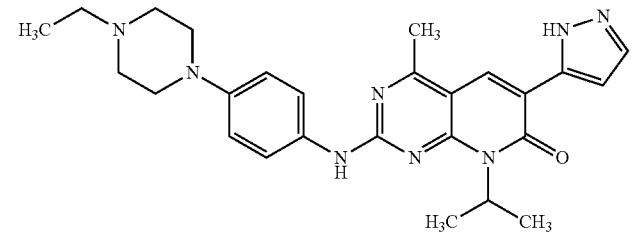 [SMILES: CCN1CCN(c2ccc(Nc3nc(C)c4cc(-c5ccn[nH]5)c(=O)n(C(C)C)c4n3)cc2)CC1] | 2-{[4-(4-ethylpiperazin-1-yl)phenyl]amino}-4-methyl-8-(1-methylethyl)-6-(1H-pyrazol-5-yl)pyrido[2,3-d]pyrimidin-7(8H)-one |
| 82 | 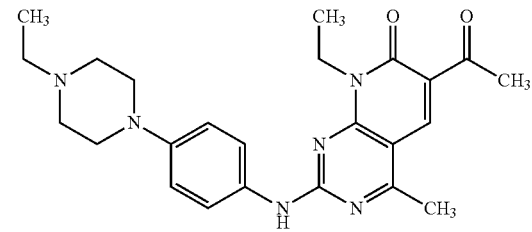 [SMILES: CCN1CCN(c2ccc(Nc3nc(C)c4cc(C(C)=O)c(=O)n(CC)c4n3)cc2)CC1] | 6-acetyl-8-ethyl-2-{[4-(4-ethylpiperazin-1-yl)phenyl]amino}-4-methylpyrido[2,3-d]pyrimidin-7(8H)-one |

TABLE 1-continued

Section II

| Example | Structure | Name |
|---|---|---|
| 83 | 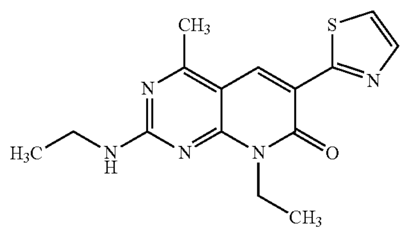 [SMILES: CCNc1nc(C)c2cc(-c3nccs3)c(=O)n(CC)c2n1] | 8-ethyl-2-(ethylamino)-4-methyl-6-(1,3-thiazol-2-yl)pyrido[2,3-d]pyrimidin-7(8H)-one |
| 84 | 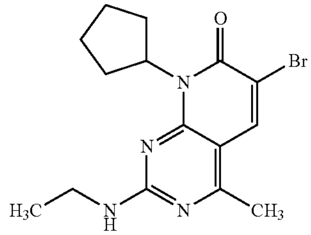 [SMILES: CCNc1nc(C)c2cc(Br)c(=O)n(C3CCCC3)c2n1] | 6-bromo-8-cyclopentyl-2-(ethylamino)-4-methylpyrido[2,3-d]pyrimidin-7(8H)-one |
| 85 | 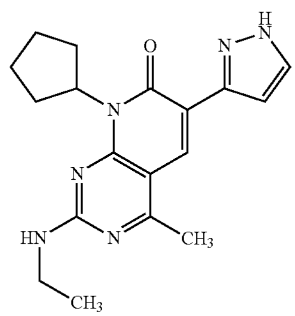 [SMILES: CCNc1nc(C)c2cc(-c3cc[nH]n3)c(=O)n(C3CCCC3)c2n1] | 8-cyclopentyl-2-(ethylamino)-4-methyl-6-(1H-pyrazol-3-yl)pyrido[2,3-d]pyrimidin-7(8H)-one |
| 86 | 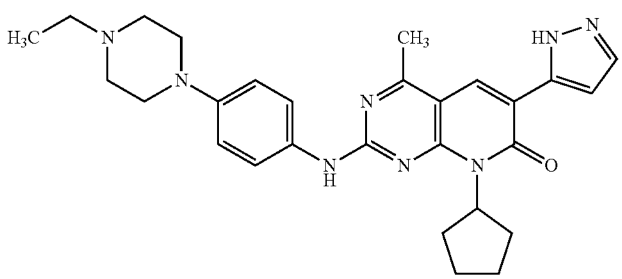 [SMILES: CCN1CCN(c2ccc(Nc3nc(C)c4cc(-c5ccn[nH]5)c(=O)n(C5CCCC5)c4n3)cc2)CC1] | cyclopentyl-2-{[4-(4-ethylpiperazin-1-yl)phenyl]amino}-4-methyl-6-(1H-pyrazol-5-yl)pyrido[2,3-d]pyrimidin-7(8H)-one |
| 87 | 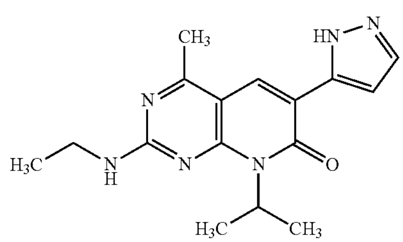 [SMILES: CCNc1nc(C)c2cc(-c3ccn[nH]3)c(=O)n(C(C)C)c2n1] | 2-(ethylamino)-4-methyl-8-(1-methylethyl)-6-(1H-pyrazol-5-yl)pyrido[2,3-d]pyrimidin-7(8H)-one |
| 88 | 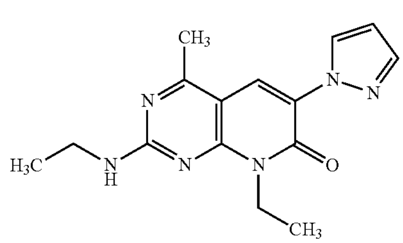 [SMILES: CCNc1nc(C)c2cc(-n3cccn3)c(=O)n(CC)c2n1] | 8-ethyl-2-(ethylamino)-4-methyl-6-(1H-pyrazol-1-yl)pyrido[2,3-d]pyrimidin-7(8H)-one |

TABLE 1-continued

Section II

| Example | Structure | Name |
|---|---|---|
| 89 | 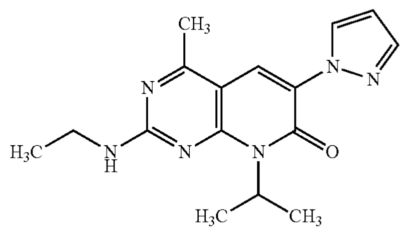 [SMILES: CCNc1nc(C)c2cc(-n3cccn3)c(=O)n(C(C)C)c2n1] | 2-(ethylamino)-4-methyl-8-(1-methylethyl)-6-(1H-pyrazol-1-yl)pyrido[2,3-d]pyrimidin-7(8H)-one |
| 90 | 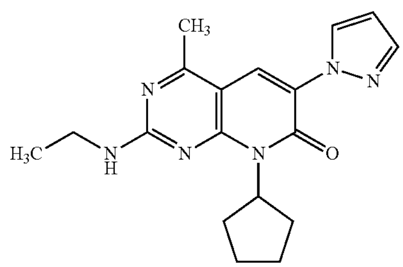 [SMILES: CCNc1nc(C)c2cc(-n3cccn3)c(=O)n(C3CCCC3)c2n1] | 8-cyclopentyl-2-(ethylamino)-4-methyl-6-(1H-pyrazol-1-yl)pyrido[2,3-d]pyrimidin-7(8H)-one |
| 91 | 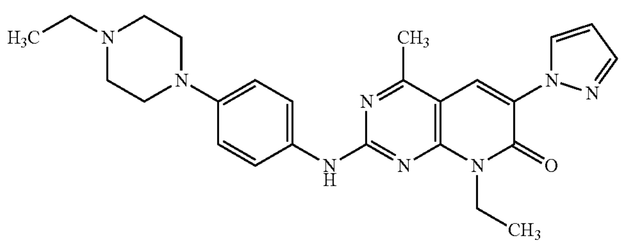 [SMILES: CCN1CCN(c2ccc(Nc3nc(C)c4cc(-n5cccn5)c(=O)n(CC)c4n3)cc2)CC1] | 8-ethyl-2-{[4-(4-ethylpiperazin-1-yl)phenyl]amino}-4-methyl-6-(1H-pyrazol-1-yl)pyrido[2,3-d]pyrimidin-7(8H)-one |
| 92 | 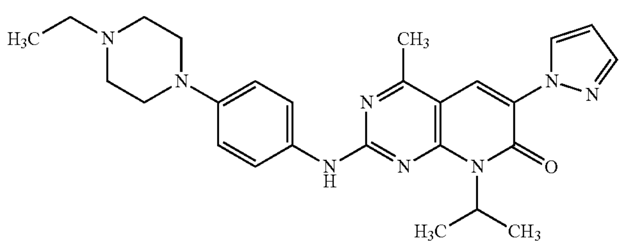 [SMILES: CCN1CCN(c2ccc(Nc3nc(C)c4cc(-n5cccn5)c(=O)n(C(C)C)c4n3)cc2)CC1] | 2-{[4-(4-ethylpiperazin-1-yl)phenyl]amino}-4-methyl-8-(1-methylethyl)-6-(1H-pyrazol-1-yl)pyrido[2,3-d]pyrimidin-7(8H)-one |
| 93 | 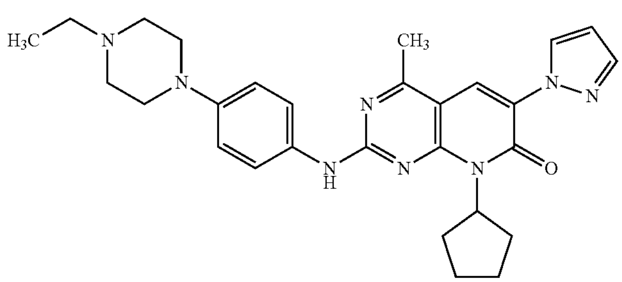 [SMILES: CCN1CCN(c2ccc(Nc3nc(C)c4cc(-n5cccn5)c(=O)n(C5CCCC5)c4n3)cc2)CC1] | 8-cyclopentyl-2-n[4-(4-ethylpiperazin-1-yl)phenyl]amino}-4-methyl-6-(1H-pyrazol-1-yl)pyrido[2,3-d]pyrimidin-7(8H)-one |

In one embodiment of the invention, the PI3K inhibitor is selected from the compounds in Table I having a PI3K-binding affinity of about 9 μM or less. In another embodiment, the PI3K inhibitor is selected from the compounds in Table I having a PI3K-binding affinity of about 5 μM or less. In another embodiment, the PI3K inhibitor is selected from the compounds in Table I having a PI3K-binding affinity of about 3 μM or less. In another embodiment, the PI3K inhibitor is selected from the compounds in Table I having a PI3K-binding affinity of about 1.5 μM or less. In another embodiment, the PI3K inhibitor is selected from the compounds in Table I having a PI3K-binding affinity of about 1 μM or less. In another embodiment, the PI3K inhibitor is selected from the compounds in Table I having a PI3K-binding affinity of about 0.6 μM or less. In another embodiment, the PI3K inhibitor is selected from the compounds in Table I having a PI3K-binding affinity of about 0.3 μM or less. In another embodiment, the PI3K inhibitor is selected from the compounds in Table I having a PI3K-binding affinity of about 0.2 μM or less. In another embodiment, the PI3K inhibitor is selected from the compounds in Table I having a PI3K-binding affinity of about 0.1 μM or less. In another embodiment, the PI3K inhibitor is selected from the compounds in Table I having a PI3K-binding affinity of about 0.04 μM or less. In another embodiment, the PI3K inhibitor is selected from the compounds in Table I having a PI3K-binding affinity of about 0.020 μM or less.

In Vitro Enzymatic Assay Description for Sections II and III:

PI3Kalpha Luciferase-Coupled Chemiluminescence Assay Protocol

PI3Kalpha activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume. The standard assay concentrations for enzyme, ATP, and substrate are 1.1 nm, 1 μM, and 7.5 μM, respectively. The reaction mixture was incubated at ambient temperature for 2 h. Following the kinase reaction, a 10 μL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references. In this assay, preferred compounds of the invention exhibit an $IC_{50}$ of less than 50 micromolar. More preferred compounds of the invention exhibit an $IC_{50}$ of less than 1 micromolar. Even more preferred compounds of the invention exhibit an $IC_{50}$ of less than 500 nanomolar. Still more preferred compounds of the invention exhibit an IC50 of less than 250 nanomolar.

Cell Assay Descriptions:

Phospho AKT Assay

PC3 cells were seeded on 6-well plates at 150,000 cells/well. Cells were cultured for 3 days, then treated with compounds in serum-free medium for 3 hr. EGF (100 ng/ml) was added for the last 10 min. Cells were lysed in TENN buffer. Phospho T308 Akt and total Akt were quantified by ELISA performed according to the Biosource assay protocol. The readings of phospho Akt were normalized to total Akt readings.

Phospho S6 Assay

PC3 cells were seeded on 96-well plates at 8,000 cells/well. For each experiment, cells were seeded and treated in duplicated plates: one plate for phospho S6 CellELISA, and one plate for total S6 CellELISA. Cells were cultured on the plates for 3 days, then treated with compounds in serum-free medium for 3 hr in triplicate. Cells were fixed with 4% formaldehyde, quenched with 0.6% $H_2O_2$, blocked with 5% BSA, incubated with either phospho S6 antibody or total S6 antibody overnight, incubated with goat-anti-rabbit-IgG-HRP for 1 hr, and developed in chemiluminescent substrate.

PIP3 Assay

MCF-7 cells grown in 10-cm dishes were starved for 3 hours in DMEM, and then treated with compounds for 20 minutes. In the last 2 minutes of the incubation with the compounds, EGF (100 ng/ml) was added to stimulate the production of PIP3. The medium was aspirated and the cells were scraped with 10% trichloroacetic acid. The lipids were extracted from the pellet after the cell lysates were centrifuged. PIP3 in the cellular lipid extraction was quantified with the AlphaScreen assay in which Grp1-PH is used as the PIP3 specific probe. The amount of cellular PIP3 was calculated from the standard curve of $diC_8$ PI (3,4,5) P3.

Section III

In one embodiment, in section III the invention provides a compound of Formula VIII:

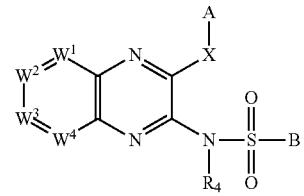

VIII or a pharmaceutically acceptable salt or solvate thereof, wherein $W^1$, $W^2$, $W^3$, and $W^4$ are —C($R_1$)— or one or two of $W^1$, $W^2$, $W^3$, and $W^4$ are independently —N— and the remaining are —C($R_1$)—;

X is —N($R_5$)—;

A is aryl, arylalkyl, —S(O)$_2$-aryl, heteroaryl, cycloalkyl, heterocycloalkyl, halo, haloalkyl, haloalkoxy, $C_1$-$C_6$-alkyl, $C_1$-$C_6$-alkoxy, or —$C_1$-$C_6$-alkyl-N($R_7$)$R_{7a}$, where each of the aryl, heteroaryl, cycloalkyl, heterocycloalkyl, and alkyl groups, each either alone or as part of another group within A, is independently optionally substituted with $(R_2)_{n1}$;

B is aryl, heteroaryl, $C_1$-$C_6$-alkyl, —$C_1$-$C_6$-alkylaryl, or —$C_1$-$C_6$-alkylheteroaryl, wherein each of the aryl, heteroaryl and alkyl groups are independently optionally substituted with $(R_3)_{n2}$;

n1 and n2 are independently 0 or an integer from 1 to 5;

each $R_1$ is independently hydrogen, $C_1$-$C_6$-alkyl, haloalkyl, $C_1$-$C_6$-alkoxy, haloalkoxy, —NO$_2$, halo, hydroxy, hydroxyalkyl, —CN, cyanoalkyl, or —$C_0$-$C_6$ alkyl-N($R_{10}$)$R_{10a}$ where $R_{10}$ and $R_{10a}$ are independently hydrogen, —$C_1$-$C_6$-alkyl, —OH, —O—$C_1$-$C_6$ alkyl, haloalkyl, or haloalkoxy;

each $R_2$ (when $R_2$ is present) is independently selected from —$C_1$-$C_6$-alkanyl, —$C_1$-$C_6$-alkenyl, —$C_2$-$C_6$-alkenyl-C(O)OR$_6$, —OR$_6$, —N($R_7$)C(O)R$_6$, —N($R_7$)C(O)—$C_0$-$C_6$-alkyl-N($R_{7b}$)$R_{7a}$, —OC(O)—$C_0$-$C_6$-alkyl-N($R_7$)$R_{7a}$, —N($R_7$)C(O)—$C_1$-$C_6$-alkylC(O)OR$_6$, —$C_0$-$C_6$-alkyl-C(O)R$_6$, —S(O)$_2$N($R_7$)$R_{7a}$, —C(O)OR$_6$, —CH(R$_6$)$_2$—C(O)OR$_6$, —S(O)$_2$R$_6$, cycloalkyl, heterocycloalkyl, heteroaryl, —C(O)N($R_7$)—$C_1$-$C_6$-alkyl-OR$_6$, —$C_0$-$C_6$-alkyl-C(O)N($R_7$)—$C_1$-$C_6$-alkyl-C(O)OR$_6$, —$C_0$-$C_6$-alkyl-C(O)N($R_7$)$R_{7a}$, aryl, arylalkyl, —S—($C_1$-$C_6$-alkyl), halo, oxo, —NO$_2$, —S—CN, —CN, and —$C_0$-$C_6$-alkyl-N($R_7$)$R_{7a}$, wherein each of the alkyl, alkoxy, aryl, cycloalkyl, heterocycloalkyl, and heteroaryl groups, either alone or as part of another group within $R_2$, is independently optionally substituted with 1, 2, 3, 4, or 5 groups selected from $C_1$-$C_6$-alkyl, halo, haloalkyl, haloalkoxy, oxo, —NO$_2$, —CN, —OH, —N($R_8$)$R_{8a}$, $C_1$-$C_6$-alkoxy, and —C(O)OR$_9$;

each $R_3$ (when $R_3$ is present) is independently NO$_2$, halo, —CN, $C_1$-$C_6$-alkanyl, $C_2$-$C_6$-alkenyl, $C_2$-$C_6$-alkynyl, $C_1$-$C_6$-alkoxy, $C_3$-$C_6$-cycloalkyl, $C_0$-$C_6$-alkyl-heterocycloalkyl, —$C_0$-$C_6$-alkyl-N($R_7$)C(O)—$C_0$-$C_6$-alkyl-N($R_{7b}$)$R_{7a}$, —$C_0$-$C_6$-alkyl-N($R_7$)C(O)—$C_0$-$C_6$-alkyl-N($R_{7b}$)C(O)$R_{7a}$, —$C_0$-$C_6$ alkyl-C(O)—$C_0$-$C_6$-alkyl-N($R_7$)$R_{7a}$, —$C_0$-$C_6$-alkyl-C(O)N($R_7$)—$C_0$-$C_6$-alkyl-N($R_{7b}$)$R_{7a}$, —$C_0$-$C_6$-alkyl-C(O)N($R_7$)—$C_1$-$C_6$alkylC(O)OR$_{7a}$, —$C_0$-$C_6$-alkyl-N($R_7$)C(O)—$C_0$-$C_6$-alkyl-($R_{7b}$)—$C_0$-$C_6$-alkyl-N($R_7$)—$C_0$-$C_6$-alkyl-N($R_{7b}$)$R_{7a}$, —$C_0$-$C_6$-alkyl-N (R$_7$)C(O)—C$_0$-C$_6$-alkyl-N(R$_{7b}$)—C$_0$-C$_6$-alkyl-N(R$_{7c}$) (R$_{7a}$), —C$_0$-C$_6$-alkyl-N(R$_7$)C(O)O—C$_0$-C$_6$-alkyl-N(R$_{7b}$) R$_{7a}$, —C$_0$-C$_6$-alkyl-N(R$_7$)C(O)O—C$_0$-C$_6$-alkyl-aryl, —C$_0$-C$_6$-alkyl-C(O)N(R$_7$)—C$_0$-C$_6$-alkyl-N(R$_{7b}$)R$_{7a}$, —C$_0$-C$_6$-alkyl-N(R$_7$)—C$_0$-C$_6$-alkyl-C(=N(R$_{7b}$)(R$_{7a}$)) (NR$_{7c}$R$_{7d}$), —C$_0$-C$_6$-alkyl-aryl, —C$_0$-C$_6$-alkyl-heteroaryl, —C$_0$-C$_6$-alkyl-heterocycloalkyl, —O—C$_1$-C$_6$-alkyl-N(R$_7$)R$_{7a}$, —C$_0$-C$_6$-alkyl-OR$_6$, —C$_0$-C$_6$ alkyl-C(O) OR$_6$, —C$_0$-C$_6$-alkyl-N(R$_7$)R$_{7a}$, —C$_0$-C$_6$-alkyl-C(O) NR$_7$R$_{7a}$, —C$_0$-C$_6$-alkyl-C(O)—R$_7$, —SR$_7$, —S(O)$_2$R$_7$, —S(O)$_3$R$_7$, —S(O)R$_7$, —S(O)$_2$N(R$_7$)—C$_0$-C$_6$-alkyl-N (R$_{7b}$)R$_{7a}$, —S-heteroaryl, —S-aryl, —S-heterocycloalkyl, —C$_0$-C$_6$-alkyl-N(R$_7$)-aryl, —C$_0$-C$_6$-alkyl-N(R$_7$)-heteroaryl, —C$_0$-C$_6$-alkyl-N(R$_7$)-heterocycloalkyl, —C$_0$-C$_6$-alkyl-C(O)N(R$_7$)—C$_0$-C$_6$-alkyl-cycloalkyl, —C$_0$-C$_6$-alkyl-C(O)N(R$_7$)—C$_0$-C$_6$-alkyl-aryl, —C$_0$-C$_6$-alkyl-C(O)N(R$_7$)—C$_0$-C$_6$-alkyl-heteroaryl, —C$_0$-C$_6$-alkyl-C(O) N(R$_7$)—C$_0$-C$_6$-alkyl-heterocycloalkyl, —C$_0$-C$_6$-alkyl-N (R$_7$)C(O)—C$_0$-C$_6$-alkyl-cycloalkyl, —C$_0$-C$_6$-alkyl-N(R$_7$) C(O)—C$_0$-C$_6$-alkyl-aryl, —C$_0$-C$_6$-alkyl-N(R$_7$)C(O)—C$_0$-C$_6$-alkyl-heteroaryl, —C$_0$-C$_6$-alkyl-N(R$_7$)C(O)—C$_0$-C$_6$-alkyl-heterocycloalkyl, —C$_0$-C$_6$-alkyl-N(R$_7$)C(O)—C$_0$-C$_6$-alkyl-heterocycloalkyl-aryl, —N(R$_7$)C(O)OR$_6$, or —N(R$_7$)—C(O)—R$_{7a}$, wherein each of the alkyl, alkanyl, alkenyl, cycloalkyl, aryl, alkoxy, heterocycloalkyl, and heteroaryl groups, either alone or as part of another group within R$_3$, is independently optionally substituted with 1, 2, 3, 4, or 5 groups selected from C$_1$-C$_6$-alkanyl, C$_1$-C$_6$-alkenyl, —C$_0$-C$_6$-alkyl-OR$_9$, cycloalkyl, halo, haloalkyl, haloalkoxy, —C(O)R$_9$, —NO$_2$, —CN, oxo, —C$_0$-C$_6$-alkyl-N(R$_8$)R$_{8a}$, —C$_0$-C$_6$-alkyl-heterocycloalkyl, —C$_0$-C$_6$-alkyl-aryl, —C$_0$-C$_6$-alkyl-heteroaryl, —C(O)OR$_9$, and hydroxyalkyl;

R$_4$ is hydrogen, aryl, —C$_0$-C$_6$-alkyl-N(R$_7$)R$_{7a}$, C$_1$-C$_6$-alkoxy, or C$_1$-C$_6$ alkyl, wherein each of the alkyl and aryl groups, either alone or as part of another group in R$_4$, is independently optionally substituted with 1, 2, 3, 4, or 5 groups selected from C$_1$-C$_6$-alkyl, halo, haloalkyl, haloalkoxy, —NO$_2$, —CN, —OH, —N(R$_8$)R$_{8a}$, C$_1$-C$_6$-alkoxy, and —C(O)OR$_6$;

R$_5$ is hydrogen, —C$_1$-C$_6$-alkyl-N(R$_7$)R$_{7a}$, C$_1$-C$_6$-alkoxy, C$_1$-C$_6$-alkyl, or aryl, wherein each of the alkyl and aryl is optionally substituted with 1, 2, 3, 4, or 5 groups selected from C$_1$-C$_6$-alkyl, halo, haloalkyl, haloalkoxy, —NO$_2$, —CN, —OH, —N(R$_8$)R$_{8a}$, C$_1$-C$_6$-alkoxy, or —C(O)OR$_6$; or R$_6$ and R$_9$ are independently hydrogen, —OH, C$_1$-C$_6$-alkyl, aryl, arylalkyl, cycloalkyl, cycloalkylalkyl, heterocycloalkyl, heterocycloalkylalkyl, heteroaryl, heteroarylalkyl, or aryl, each C$_1$-C$_6$ alkyl, aryl, cycloalkyl, heterocycloalkyl, and heteroaryl, either alone or as part of another group within R$_6$ and R$_9$, is independently optionally substituted with 1, 2, 3, 4, or 5 groups independently selected from —NH$_2$, —OH, C$_1$-C$_6$-alkoxy, C$_1$-C$_6$-alkyl, and halo; and R$_7$, R$_{7a}$, R$_{7b}$, R$_{7c}$, R$_{7d}$, R$_8$, and R$_{8a}$ are independently hydrogen, —C$_1$-C$_6$-alkanyl, —C$_1$-C$_6$-alkenyl, —OH, —O—C$_1$-C$_6$ alkanyl, —O—C$_1$-C$_6$ alkenyl, —O—C$_0$-C$_6$-alkyl-aryl, —C$_0$-C$_6$-alkyl-C(O)OR$_6$, —C$_0$-C$_6$-alkyl-C(O)R$_6$, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within R$_7$, R$_{7a}$, R$_{7b}$, R$_{7c}$, and R$_{7d}$, is independently optionally substituted with 1, 2, 3, 4, or 5 groups selected from —NH$_2$, alkylamino, dialkylamino, —S—C$_1$-C$_6$-alkyl, —CN, —OH, —NO$_2$, oxo, C$_1$-C$_6$-alkoxy, C$_1$-C$_6$-alkyl, halo, aryl, and heteroaryl optionally substituted with one or two C$_1$-C$_6$-alkyl.

In one embodiment, in section III the invention provides a compound of Formula VIIIa:

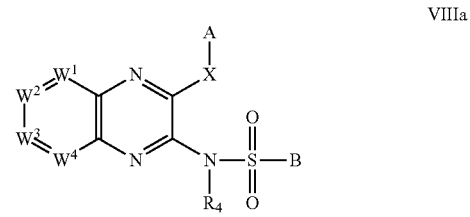

VIIIa or a pharmaceutically acceptable salt or solvate thereof, wherein

W$^1$, W$^2$, W$^3$, and W$^4$ are —C(R$_1$)— or W$^2$ and W$^3$ are —C(R$_1$)— and one of W$^1$ and W$^4$ is —N— and the other is —C(R$_1$)—;

X is —N(R$_5$)—;

A is aryl, heteroaryl, or heterocycloalkyl where the aryl, heteroaryl, and heterocycloalkyl are optionally substituted with (R$_2$)$_{n1}$; or B is aryl, —C$_1$-C$_6$ alkylaryl, heteroaryl, or heterocycloalkyl, where the aryl, C$_1$-C$_6$-alkyl, heteroaryl, and heterocycloalkyl are independently optionally substituted with (R$_3$)$_{n2}$;

n1 is 0, 1, 2, or 3;

n2 is or an integer from 1 to 5;

each R$_1$ is independently hydrogen, C$_1$-C$_6$-alkyl, haloalkyl, C$_1$-C$_6$-alkoxy, haloalkoxy, or —NO$_2$;

each R$_2$ (when R$_2$ is present) is independently —C$_1$-C$_6$-alkanyl, —C$_1$-C$_6$-alkenyl, —OR$_6$, —N(R$_7$)—C(O)—R$_6$, —N(R$_7$)—C(O)—C$_0$-C$_6$ alkyl-N(R$_{7b}$)R$_{7a}$, —OC(O)—C$_0$-C$_6$ alkyl-N(R$_7$)R$_{7a}$, —C$_0$-C$_6$alkyl-C(O)R$_6$, heterocycloalkyl, aryl, halo, —NO$_2$, or —C$_0$-C$_6$-alkyl-N(R$_7$)R$_{7a}$, wherein each alkyl, aryl, and heterocycloalkyl groups, each either alone or as part of another group within R$_2$, is independently optionally substituted with one, two, three, four, or five groups selected from C$_1$-C$_6$-alkyl, C$_1$-C$_6$-alkoxy, halo, haloalkyl, and haloalkoxy;

each R$_3$ (when R$_3$ is present) is independently hydroxy, —NO$_2$, halo, —CN, C$_1$-C$_6$-alkanyl, C$_2$-C$_6$-alkenyl, C$_1$-C$_6$ alkoxy, —C$_0$-C$_6$alkyl-N(R$_7$)C(O)—C$_0$-C$_6$-alkyl-N(R$_{7b}$) R$_{7a}$, —C$_0$-C$_6$-alkyl-N(R$_7$)C(O)—C$_0$-C$_6$-alkyl-N(R$_{7b}$)C (O)R$_{7a}$, —C$_0$-C$_6$ alkyl-C(O)N(R$_7$)—C$_0$-C$_6$-alkyl-N(R$_7$) R$_{7a}$, —C$_0$-C$_6$-alkyl-C(O)N(R$_7$)—C$_1$-C$_6$-alkyl-C(O) OR$_{7a}$, —C$_0$-C$_6$-alkyl-N(R$_7$)—C(O)—C$_0$-C$_6$-alkyl-(R$_7$), —C$_0$-C$_6$-alkyl-N(R$_7$)—C$_0$-C$_6$-alkyl-N(R$_7$)R$_{7a}$, —C$_0$-C$_6$-alkyl-N(R$_7$)C(O)—C$_0$-C$_6$-alkyl-N(R$_{7b}$)—C$_0$-C$_6$-alkyl-N (R$_{7c}$)R$_{7a}$, —C$_0$-C$_6$-alkyl-N(R$_7$)C(O)O—C$_0$-C$_6$-alkyl-N (R$_{7b}$)R$_{7a}$, —C$_0$-C$_6$-alkyl-N(R$_7$)—C$_0$-C$_6$alkyl-C(=N (R$_{7b}$)(R$_{7a}$))(NR$_{7c}$R$_{7d}$), —C$_0$-C$_6$-alkyl-heteroaryl, —C$_0$-C$_6$-alkyl-OR$_6$, —C$_0$-C$_6$-alkyl-C(O)OR$_6$, —C$_0$-C$_6$-alkyl-N(R$_7$)R$_{7a}$, —C$_0$-C$_6$-alkyl-C(O)—NR$_7$R$_{7a}$, —C$_0$-C$_6$-alkyl-C(O)—R$_7$, —S(O)$_2$R$_7$, —SO$_2$N(R$_7$)—C$_0$-C$_6$-alkyl-N(R$_7$)R$_{7a}$, —C$_0$-C$_6$-alkyl-C(O)-heterocycloalkyl (dupe of C(O)R7), —C$_0$-C$_6$-alkyl-C(O)N(R$_7$)—C$_0$-C$_6$-alkyl-heterocycloalkyl, —C$_0$-C$_6$-alkyl-N(R$_7$)C(O)—C$_0$-C$_6$-alkyl-cycloalkyl, —C$_0$-C$_6$-alkyl-N(R$_7$)—C(O)—C$_0$-C$_6$-alkyl-aryl, —C$_0$-C$_6$-alkyl-N(R$_7$)—C(O)—C$_0$-C$_6$-alkyl-heteroaryl, —C$_0$-C$_6$-alkyl-N(R$_7$)C(O)—C$_0$-C$_6$-alkyl-heterocycloalkyl, —C$_0$-C$_6$-alkyl-N(R$_7$)C(O)—C$_0$-C$_6$-alkyl-heterocycloalkyl-aryl, or —N(R$_7$)C(O)R$_{7a}$, wherein each of the alkyl, alkanyl, alkenyl, cycloalkyl, aryl, alkoxy, heterocycloalkyl, and heteroaryl groups, either alone or as part of another group within $R_3$, is independently optionally substituted with 1, 2, 3, 4, or 5 groups selected from $C_1$-$C_6$-alkanyl, $C_1$-$C_6$ alkenyl, cycloalkyl, halo, —C(O)—$R_6$, oxo, hydroxy, —$C_0$-$C_6$-alkyl-N($R_8$)$R_{8a}$, —$C_0$-$C_6$-alkyl-heterocycloalkyl, —$C_0$-$C_6$-alkyl-aryl, —$C_0$-$C_6$-alkyl-heteroaryl, —C(O)O$R_6$, and hydroxyalkyl;

$R_4$ is hydrogen;
$R_5$ is hydrogen;
$R_6$ and $R_9$ are independently hydrogen, $C_1$-$C_6$-alkyl, aryl, arylalkyl, or cycloalkyl, where each of the —$C_1$-$C_6$-alkyl, aryl, arylalkyl, and cycloalkyl, is independently optionally substituted with 1, 2, 3, 4, or 5 groups selected from $C_1$-$C_6$-alkoxy, $C_1$-$C_6$-alkyl, and halo; and
$R_7$, $R_{7a}$ $R_{7b}$, $R_{7c}$, and $R_{7d}$ are independently hydrogen, —$C_1$-$C_6$-alkanyl, —$C_1$-$C_6$-alkenyl, —OH, —O—$C_1$-$C_6$ alkanyl, —O—$C_1$-$C_6$ alkenyl, —O—$C_0$-$C_6$-alkyl-aryl, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within $R_7$, $R_{7a}$ $R_{7b}$, $R_{7c}$, and $R_{7d}$, is independently optionally substituted with 1, 2, 3, 4, or 5 —NH$_2$, alkylamino, dialkylamino, —S—$C_1$-$C_6$-alkyl, —CN, hydroxy, oxo, $C_1$-$C_6$ alkoxy, $C_1$-$C_6$ alkyl, or halo.

In another embodiment (A1), the invention provides a compound of Formula VIIIa where X is —N($R_5$)—, $R_5$ is hydrogen, and all other groups are as defined above for a compound of Formula VIIIa.

In another embodiment (A2), the invention provides a compound of Formula VIIIa where A is aryl or heteroaryl where the aryl and the heteroaryl are optionally substituted with $(R_2)_{n1}$ where n1 is 1, 2, 3, 4, or 5; B is aryl or heteroaryl where the aryl and the heteroaryl are optionally substituted with $(R_3)_{n2}$ where n2 is 1, 2, 3, 4, or 5; and all other groups are as defined above for a compound of Formula VIIIa.

In another embodiment (A3), the invention provides a compound of Formula VIIIa where $W^1$, $W^2$, $W^3$, and $W^4$ are —C($R_1$)— where each $R_1$ is independently hydrogen, $C_1$-$C_6$ alkyl, $C_1$-$C_6$ alkoxy, or nitro; and all other groups are as defined in the Summary of the Invention. In another embodiment, $W^1$ and $W^4$ are —CH— and $W^2$ and $W^3$ are —C($R_1$)— where each $R_1$ is independently hydrogen, $C_1$-$C_6$ alkyl, $C_1$-$C_6$ alkoxy, or nitro. In another embodiment, $W^1$ and $W^4$ are —CH— and $W^2$ and $W^3$ are —C($R_1$)— where each $R_1$ is independently hydrogen, methyl, methoxy, or nitro. In another embodiment, $W^1$, $W^2$, $W^3$, and $W^4$ are —CH—.

In another embodiment, the invention provides a compound of Formula VIIIb:

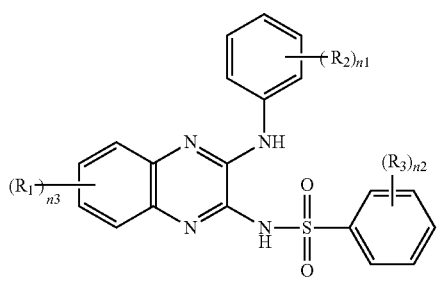

VIIIb or a pharmaceutically acceptable salt or solvate thereof, wherein
n1 is one or two; and n2 is one or two; n3 is 0, 1, or two;
each $R_1$ is independently hydrogen, $C_1$-$C_6$-alkyl, haloalkyl, $C_1$-$C_6$-alkoxy, haloalkoxy, —NO$_2$, halo, hydroxy, hydroxyalkyl, —CN, cyanoalkyl, or —$C_0$-$C_6$ alkyl-N($R_{10}$)$R_{10a}$ where $R_{10}$ and $R_{10a}$ are independently hydrogen, —$C_1$-$C_6$-alkyl, —OH, —O—$C_1$-$C_6$ alkyl, haloalkyl, or haloalkoxy;
each $R_2$ (when $R_2$ is present) is independently $C_1$-$C_6$-alkanyl, $C_1$-$C_6$-alkenyl, —O$R_6$, —N($R_7$)—C(O)—$R_6$, —N($R_7$)—C(O)—$C_0$-$C_6$ alkyl-N($R_{7b}$)$R_{7a}$, —OC(O)—$C_0$-$C_6$ alkyl-N($R_7$)$R_{7a}$, —$C_0$-$C_6$alkyl-C(O)$R_6$, heterocycloalkyl, aryl, halo, —NO$_2$, or —$C_0$-$C_6$-alkyl-N($R_7$)$R_{7a}$, wherein each alkyl, aryl, and heterocycloalkyl groups, each either alone or as part of another group within $R_2$, is independently optionally substituted with one, two, three, four, or five groups selected from $C_1$-$C_6$-alkyl, $C_1$-$C_6$-alkoxy, halo, haloalkyl, and haloalkoxy;
each $R_3$ (when $R_3$ is present) is independently hydroxy, —NO$_2$, halo, —CN, $C_1$-$C_6$-alkanyl, $C_2$-$C_6$-alkenyl, $C_1$-$C_6$ alkoxy, —$C_0$-$C_6$ alkyl-N($R_7$)C(O)—$C_0$-$C_6$-alkyl-N($R_{7b}$)$R_{7a}$, —$C_0$-$C_6$-alkyl-N($R_7$)C(O)—$C_0$-$C_6$-alkyl-N($R_{7b}$)C(O)$R_{7a}$, —$C_0$-$C_6$ alkyl-C(O)N($R_7$)—$C_0$-$C_6$-alkyl-N($R_7$)$R_{7a}$, —$C_0$-$C_6$-alkyl-C(O)N($R_7$)—$C_1$-$C_6$-alkyl-C(O)OR$_{7a}$, —$C_0$-$C_6$-alkyl-N($R_7$)—C(O)—$C_0$-$C_6$-alkyl-(R$_7$), —$C_0$-$C_6$-alkyl-N($R_7$)—$C_0$-$C_6$-alkyl-N($R_7$)$R_{7a}$, —$C_0$-$C_6$-alkyl-N($R_7$)C(O)—$C_0$-$C_6$-alkyl-N($R_{7b}$)—$C_0$-$C_6$-alkyl-N($R_{7c}$)$R_{7a}$, —$C_0$-$C_6$-alkyl-N($R_7$)C(O)O—$C_0$-$C_6$-alkyl-N($R_{7b}$)$R_{7a}$, —$C_0$-$C_6$-alkyl-N($R_7$)—$C_0$-$C_6$alkyl-C(=N($R_{7b}$)($R_{7a}$))(NR$_{7c}$R$_{7d}$), —$C_0$-$C_6$-alkyl-heteroaryl, —$C_0$-$C_6$-alkyl-O$R_6$, —$C_0$-$C_6$-alkyl-C(O)O$R_6$, —$C_0$-$C_6$-alkyl-N($R_7$)$R_{7a}$, —$C_0$-$C_6$-alkyl-C(O)—NR$_7$R$_{7a}$, —$C_0$-$C_6$-alkyl-C(O)—$R_7$, —S(O)$_2$R$_7$, —SO$_2$N($R_7$)—$C_0$-$C_6$-alkyl-N($R_7$)$R_{7a}$, —$C_0$-$C_6$-alkyl-C(O)-heterocycloalkyl (dupe of C(O)$R_7$), —$C_0$-$C_6$-alkyl-C(O)N($R_7$)—$C_0$-$C_6$-alkyl-heterocycloalkyl, —$C_0$-$C_6$-alkyl-N($R_7$)C(O)—$C_0$-$C_6$-alkyl-cycloalkyl, —$C_0$-$C_6$-alkyl-N($R_7$)—C(O)—$C_0$-$C_6$-alkyl-aryl, —$C_0$-$C_6$-alkyl-N($R_7$)—C(O)—$C_0$-$C_6$-alkyl-heteroaryl, —$C_0$-$C_6$-alkyl-N($R_7$)C(O)—$C_0$-$C_6$-alkyl-heterocycloalkyl, —$C_0$-$C_6$-alkyl-N($R_7$)C(O)—$C_0$-$C_6$-alkyl-heterocycloalkyl-aryl, or —N($R_7$)C(O)$R_{7a}$, wherein each of the alkyl, alkanyl, alkenyl, cycloalkyl, aryl, alkoxy, heterocycloalkyl, and heteroaryl groups, either alone or as part of another group within $R_3$, is independently optionally substituted with 1, 2, 3, 4, or 5 groups selected from $C_1$-$C_6$-alkanyl, $C_1$-$C_6$alkenyl, cycloalkyl, halo, —C(O)—$R_6$, oxo, hydroxy, —$C_0$-$C_6$-alkyl-N($R_8$)$R_{8a}$, —$C_0$-$C_6$-alkyl-heterocycloalkyl, —$C_0$-$C_6$-alkyl-aryl, —$C_0$-$C_6$-alkyl-heteroaryl, —C(O)O$R_6$, and hydroxyalkyl;

$R_4$ is hydrogen;
$R_5$ is hydrogen;
$R_6$ is hydrogen, $C_1$-$C_6$-alkyl, aryl, arylalkyl, or cycloalkyl, where each of the —$C_1$-$C_6$-alkyl, aryl, arylalkyl, and cycloalkyl, is independently optionally substituted with 1, 2, 3, 4, or 5 groups selected from $C_1$-$C_6$-alkoxy, $C_1$-$C_6$-alkyl, and halo; and
$R_7$, $R_{7a}$ $R_{7b}$, $R_{7c}$, and $R_{7d}$ are independently hydrogen, —$C_1$-$C_6$-alkanyl, —$C_1$-$C_6$-alkenyl, —OH, —O—$C_1$-$C_6$ alkanyl, —O—$C_1$-$C_6$ alkenyl, —O—$C_0$-$C_6$-alkyl-aryl, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within $R_7$, $R_{7a}$ $R_{7b}$, $R_{7c}$, and $R_{7d}$, is independently optionally substituted with 1, 2, 3, 4, or 5 —NH$_2$, alkylamino, dialkylamino, —S—$C_1$-$C_6$-alkyl, —CN, hydroxy, oxo, $C_1$-$C_6$ alkoxy, $C_1$-$C_6$ alkyl, or halo.

In another embodiment (C), the invention provides a compound according to Embodiment B, wherein $R_1$ is hydrogen, —$NO_2$, $C_1$-$C_4$ alkoxy, or $C_1$-$C_3$ alkyl. In another embodiment, one or two $R_1$ are hydrogen, methoxy, or methyl and the remaining $R_1$ are hydrogen. In another embodiment, each $R^1$ is hydrogen.

In another embodiment (D), the invention provides a compound according to Embodiment B wherein n1 is 1 or 2 and each $R_2$ is independently halo, —$OR_6$ (where $R_6$ is hydrogen or alkyl), —$N(R_7)$—$C(O)$—$C_0$-$C_6$ alkyl-$N(R_{7b})R_{7a}$ (where $R_7$, $R_{7a}$, and $R_{7b}$ are independently hydrogen or $C_1$-$C_6$-alkanyl), or —$C_0$-$C_6$alkyl-$C(O)R_6$ (where $R_6$ is $C_1$-$C_6$-alkanyl). In another embodiment, each $R_2$ is independently chloro, bromo, fluoro, hydroxy, methoxy, —$N(H)C(O)$—$CH_2$—$N(CH_3)_2$, —$C(O)CH_3$, or methyl. In another embodiment, each $R_2$ is independently hydrogen, methoxy, or chloro.

In another embodiment (E), the invention provides a compound according to Embodiment B wherein n2 is 1 or 2 and each $R_3$ is independently $C_1$-$C_6$-alkanyl, $C_1$-$C_6$-alkenyl, halo, —$C_0$-$C_6$-alkyl-$N(R_7)C(O)$—$C_0$-$C_6$-alkyl-$N(R_{7b})R_{7a}$, —$C_0$-$C_6$-alkyl-$N(R_7)C(O)$—$C_0$-$C_6$-alkyl-$N(R_{7b})$—$C_0$-$C_6$-alkyl-$N(R_{7c})(R_{7a})$, —$C_0$-$C_6$-alkyl-$N(R_7)C(O)$—$C_0$-$C_6$-alkyl-$(R_{7a})$, —$C_0$-$C_6$-alkyl-$N(R_7)C(O)$—$C_0$-$C_6$-alkyl-heterocycloalkyl, —$C_0$-$C_6$-alkyl-$N(R_7)R_{7a}$, —$C_0$-$C_6$-alkyl-$N(R_7)C(O)$—$C_0$-$C_6$-alkyl-heteroaryl; where $R_7$, $R_{7a}$, $R_{7b}$, and $R_{7c}$ are independently hydrogen, $C_1$-$C_6$-alkanyl, $C_1$-$C_6$-alkoxy, cycloalkylalkyl, hydroxy, or heterocycloalkyl (optionally substituted with $C_1$-$C_6$-alkyl); and where the alkyl and heterocycloalkyl, either alone or as part of another group within $R_3$, are independently optionally substituted with 1, 2, or 3 groups, preferably 1 or 2, selected from hydroxy, halo, —$C_0$-$C_6$-alkyl-$N(R_8)R_{8a}$ (where $R_8$ and $R_{8a}$ are independently hydrogen or $C_1$-$C_6$-alkanyl), and —$C_0$-$C_6$-alkyl-heteroaryl.

In another embodiment of embodiment E, n2 is 1 and $R_3$ is $C_1$-$C_6$-alkanyl, halo, —$N(R_7)C(O)$—$C_1$-$C_6$-alkyl-$N(R_{7b})R_{7a}$, —$N(R_7)C(O)$—$C_0$-$C_6$-alkyl-$N(R_{7b})$—$C_1$-$C_6$-alkyl-$N(R_{7c})(R_{7a})$, —$N(R_7)C(O)$—$C_0$-$C_6$-alkyl-$(R_{7a})$, —$N(R_7)C(O)$—$C_0$-$C_6$-alkyl-heterocycloalkyl, —$N(R_7)R_{7a}$, or —$N(R_7)C(O)$—$C_1$-$C_6$-alkyl-heteroaryl; where $R_7$, $R_{7a}$, $R_{7b}$, and $R_{7c}$ are independently hydrogen, $C_1$-$C_6$-alkanyl, $C_1$-$C_6$-alkoxy, cycloalkylalkyl, hydroxy, or heterocycloalkyl (optionally substituted with $C_1$-$C_6$-alkyl); and where the alkyl either alone or as part of another group within $R_3$, is independently optionally substituted with 1, 2, or 3 groups, preferably 1, or 2, groups selected from hydroxy, halo, —$C_0$-$C_6$-alkyl-$N(R_8)R_{8a}$ (where $R_8$ and $R_{8a}$ are independently hydrogen or $C_1$-$C_6$-alkanyl), and —$C_1$-$C_6$-alkyl-heteroaryl.

In another embodiment of embodiment E, n2 is 1 and $R_3$ is methyl, chloro, —$NHC(O)CH_2NH(CH_3)$, —$NHC(O)CH_2NH(CH_2CH_3)$, —$NHC(O)CH(CH_3)NH_2$, —$NHC(O)C(CH_3)_2NH_2$, —$NHC(O)CH_2N(CH_3)_2$, —$NHC(O)CH_2N(CH_3)CH_2CH_2N(CH_3)_2$, —$NHC(O)CH(NH_2)CH_2CH_3$, —$NHC(O)CH_2N(CH_3)CH_2CH_2N(CH_3)_2$, —$NHC(O)CH(CH_3)NH(CH_3)$, —$NHC(O)CH_2NH_2$, —$NHC(O)CH_2NH(CH_3)$, —$NHC(O)CH_2N(CH_3)_2$, —$NHC(O)H$, —$NHC(O)CH_2$(azetidin-1-yl), —$NHC(O)$(pyrrolidin-2-yl), —$NHC(O)CH(NH_2)CH_2OH$, —$NHC(O)$(azetidin-4-yl), —$NHC(O)C(CH_3)_2NH(CH_3)$, —$NH_2$, —$NHC(O)CH_2NH(CH_2CH_2CH_3)$, —$NHC(O)CH_2CH_2NH_2$, —$NHOH$, —$NHC(O)$(piperidin-3-yl), —$NHC(O)$(4-methyl-1,4-diazepan-1-yl), —$NHC(O)CH(NH_2)(CH_2CH_3)$, —$NHC(O)CH_2NH(CH_2CH(OH)(CH_3))$, —$NHC(O)CH_2NHCH_2CH_2F$, —$NHC(O)CH_2NH(OCH_2CH(CH_3)_2)$, —$NHC(O)$(1-aminocycloprop-1-yl), —$NHC(O)CH_2NH(CH_2$cyclopropyl), —$NHC(O)CH_2$(3-(dimethylamino)-azetidin-1-yl), —$NHC(O)$(piperidin-2-yl), —$NHC(O)$(morpholin-4-yl), —$NHC(O)CH_2$(pyrrolidin-1-yl), —$NHC(O)CH$ ($NH_2$)$CH_2CH_2CH_2CH_2N(CH_3)_2$, —$NHC(O)CH_2N(CH_3)(CH_2CH_3)$, —$NHC(O)CH_2$(imidazol-5-yl), —$NHC(O)$(1-aminocyclopent-1-yl), —$NHC(O)CH_2NH(CH_2CH(CH_3)_2)$, —$NHC(O)$(N-(imidazol-4-ylmethyl)-azetidin-3-yl), —$NHC(O)$(N-ethyl-azetidin-3-yl), —$NHCH_2N(CH_3)CH_2CH_2N(CH_3)_2$, —$NHC(O)CH_2N(CH_3)$(N-methyl-pyrrolidin-3-yl), or —$NHC(O)CH_2N(CH_3)(CH_2CH_2N(CH_3)_2)$.

In another embodiment of embodiment E, n2 is 1 and $R_3$ is methyl, —$NHC(O)CH_2NH(CH_3)$, —$NHC(O)CH(CH_3)NH_2$, —$NHC(O)C(CH_3)_2NH_2$, —$NHC(O)CH_2N(CH_3)_2$, —$NHC(O)CH_2N(CH_3)CH_2CH_2N(CH_3)_2$, —$NHC(O)CH(NH_2)CH_2CH_3$, —$NHC(O)CH_2N(CH_3)CH_2CH_2N(CH_3)_2$, or —$NHC(O)CH(CH_3)NH(CH_3)$.

In another embodiment (F), the invention provides a compound of Formula VIIIb where n1 is two; $R^2$ is selected from —$OR_6$ (where $R^6$ is $C_1$-$C_6$-alkyl) and halo; n2 is 1; $R^3$ is —$C_0$-$C_6$ alkyl-$N(R_7)C(O)$—$C_0$-$C_6$-alkyl-$N(R_{7b})R_{7a}$ (where $R_7$, $R_{7a}$, and $R_{7b}$ are independently hydrogen or —$C_1$-$C_6$-alkanyl); and n3 is 0.

In one embodiment, in section III the invention provides a compound of Formula IX:

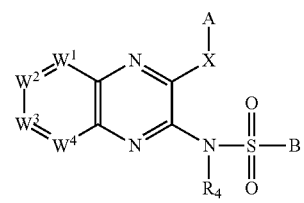

IX or a pharmaceutically acceptable salt thereof, wherein
$W^1$, $W^2$, $W^3$, and $W^4$ are —$C(R_1)$— or one or two of $W^1$, $W^2$, $W^3$, and $W^4$ are independently —N— and the remaining are —$C(R_1)$—;

X is a covalent bond, —$N(R_5)$—, —O—, —S—, or $C_1$-$C_6$ alkylene, wherein the alkylene is optionally substituted with 1, 2, 3, 4, or 5 groups selected from $C_1$-$C_6$ alkoxy, halo, haloalkoxy, —$NO_2$, —CN, —OH, —$N(R_7)R_{7a}$, and —$C(O)$—$OR_6$;

A is aryl, —$S(O)_2$-aryl, heteroaryl, cycloalkyl, heterocycloalkyl, halo, haloalkyl, haloalkoxy, $C_1$-$C_6$-alkyl, $C_1$-$C_6$-alkoxy, or —$C_1$-$C_6$-alkyl-$N(R_7)R_{7a}$, where each of the aryl, heteroaryl, cycloalkyl, heterocycloalkyl, alkyl and alkoxy groups, each either alone or as part of another group within A, are independently optionally substituted with $(R_2)_{n1}$;

B is aryl, heteroaryl, —$C_1$-$C_6$-alkylaryl, or —$C_1$-$C_6$-alkylheteroaryl, wherein each of the aryl, heteroaryl and alkyl groups are independently optionally substituted with $(R3)_{n2}$;

n1 and n2 are independently 0 or an integer from 1 to 5;

each $R_1$ is independently selected from hydrogen, $C_1$-$C_6$-alkoxy, $C_1$-$C_6$-alkyl, —$NO_2$, halo, —CN, and —$C_0$-$C_6$-alkyl-$N(R_7)R_{7a}$, wherein each of the alkyl and alkoxy groups is optionally substituted with 1, 2, 3, 4, or 5 groups selected from $C_1$-$C_6$-alkyl, $C_1$-$C_6$-alkoxy, halo, haloalkyl, haloalkoxy, —$NO_2$, —CN, hydroxy, —$N(R_8)R_{8a}$, and —$C(O)OR_6$;

each $R_2$ (when $R_2$ is present) is independently selected from $C_1$-$C_6$-alkanyl, $C_1$-$C_6$-alkenyl, $C_2$-$C_6$-alkenyl-$C(O)OR_6$, —$OR_6$, —$N(R_7)C(O)R_6$, —$N(R_7)C(O)$—$C_0$-$C_6$ alkyl-$N(R_{7b})R_{7a}$, —$OC(O)$—$C_0$-$C_6$ alkyl-$N(R_7)R_{7a}$, —$N(R_7)C(O)$—$C_1$-$C_6$ alkylC(O)$OR_6$, $C_0$-$C_6$-alkyl-$C(O)R_6$, oxo, dioxo, —$S(O)_2$—$N(R_7)R_{7a}$, —$C(O)OR_6$, —$CH(R_6)_2$—C (O)—OR$_6$, —S(O)$_2$R$_6$, cycloalkyl, heterocycloalkyl, heteroaryl, —C(O)N(R$_7$)—C$_1$-C$_6$-alkyl-OR$_6$, —C$_0$-C$_6$ alkyl-C(O)N(R$_7$)—C$_0$-C$_6$-alkyl-C(O)OR$_6$, —C$_0$-C$_6$-alkyl-C(O)N(R$_7$)R$_{7a}$, aryl, arylalkyl, —S—(C$_1$-C$_6$ alkyl), halo, oxo, —NO$_2$, —S—CN, —CN, and —C$_0$-C$_6$ alkyl-N(R$_7$)R$_{7a}$, wherein each of the alkyl (including, for example the alkyl within alkoxy), aryl, cycloalkyl, heterocycloalkyl, and heteroaryl groups, either alone or as part of another group within R$_2$, is independently optionally substituted with 1, 2, 3, 4, or 5 groups selected from C$_1$-C$_6$-alkyl, halo, haloalkyl, haloalkoxy, oxo, —NO$_2$, —CN, —OH, —N(R$_8$)R$_{8a}$, C$_1$-C$_6$-alkoxy, and —C(O)OR$_9$;

each R$_3$ (when R$_3$ is present) is independently oxo, —NO$_2$, halo, —CN, C$_1$-C$_6$-alkanyl, C$_2$-C$_6$-alkenyl, C$_2$-C$_6$-alkynyl, C$_1$-C$_6$-alkoxy, C$_3$-C$_6$-cycloalkyl, —C$_6$-C$_6$-alkyl-heterocycloalkyl, —C$_0$-C$_6$alkyl-N(R$_7$)C(O)—C$_0$-C$_6$-alkyl-N(R$_{7b}$)R$_{7a}$, —C$_0$-C$_6$ alkyl-N(R$_7$)C(O)—C$_0$-C$_6$-alkyl-N(R$_{7b}$)C(O)R$_7$, —C$_0$-C$_6$alkyl-C(O)—C$_0$-C$_6$-alkyl-N(R$_7$)R$_{7a}$, —C$_0$-C$_6$-alkyl-C(O)N(R$_7$)—C$_0$-C$_6$-alkyl-N(R$_{7b}$)R$_{7a}$, —C$_0$-C$_6$-alkyl-C(O)N(R$_7$)—C$_1$-C$_6$alkylC(O)OR$_{7a}$, —C$_0$-C$_6$ alkyl-N(R$_7$)C(O)—C$_0$-C$_6$-alkyl-(R$_{7a}$), —C$_0$-C$_6$ alkyl N(R$_7$)—C$_0$-C$_6$-alkyl-N(R$_{7b}$)R$_{7a}$, —C$_0$-C$_6$ alkyl-N(R$_7$)C(O)—C$_0$-C$_6$-alkyl-N(R$_{7b}$)—C$_0$-C$_6$ alkyl-N(R$_{7c}$)R$_{7a}$, —C$_0$-C$_6$-alkyl-N(R$_7$)C(O)O—C$_0$-C$_6$-alkyl-N(R$_{7b}$)R$_{7a}$, —C$_0$-C$_6$ alkyl-N(R$_7$)C(O)O—C$_0$-C$_6$-alkyl-aryl, —C$_0$-C$_6$ alkyl-C(O)N(R$_7$)—C$_0$-C$_6$-alkyl-N(R$_{7b}$)R$_{7a}$, —C$_0$-C$_6$ alkyl-N(R$_7$)—C$_0$-C$_6$ alkyl-C(=N(R$_{7b}$)(R$_{7a}$)(NR$_{7c}$R$_{7d}$), —C$_0$-C$_6$-alkyl-aryl, —C$_0$-C$_6$-alkyl-heteroaryl, —C$_0$-C$_6$ alkyl-heterocycloalkyl, —O—C$_0$-C$_6$ alkyl-N(R$_7$)R$_{7a}$, —C$_0$-C$_6$ alkyl-OR$_6$, —C$_0$-C$_6$ alkyl-C(O)OR$_6$, C$_0$-C$_6$-alkyl-N(R$_7$)R$_{7a}$, —C$_0$-C$_6$ alkyl-C(O)NR$_7$R$_{7a}$, —C$_0$-C$_6$ alkyl-C(O)—R$_7$, —SR$_7$, —S(O)$_2$R$_7$, —S(O)$_3$R$_7$, —S(O)R$_7$, —SO$_2$N(R$_7$)R$_{7a}$, —SO$_2$N(R$_7$)—C$_0$-C$_6$ alkyl-N(R$_{7b}$)R$_{7a}$, —S-heteroaryl, —S-aryl, —S-heterocycloalkyl, —C$_0$-C$_6$-alkyl-N(R$_7$)-aryl, —C$_0$-C$_6$-alkyl-N(R$_7$)-heteroaryl, —C$_0$-C$_6$-alkyl-N(R$_7$)-heterocycloalkyl, —C$_0$-C$_6$-alkyl-C(O)N(R$_7$)—C$_0$-C$_6$-alkyl-cycloalkyl, C$_0$-C$_6$-alkyl-C(O)N(R$_7$)—C$_0$-C$_6$-alkyl-aryl, C$_0$-C$_6$ alkyl-C(O)N(R$_7$)—C$_0$-C$_6$ alkyl-heteroaryl, C$_0$-C$_6$ alkyl-C(O)N(R$_7$)—C$_0$-C$_6$-alkyl-heterocycloalkyl, —C$_0$-C$_6$-alkyl-N(R$_7$)C(O)—C$_0$-C$_6$-alkyl-cycloalkyl, —C$_0$-C$_6$-alkyl-N(R$_7$)—C(O)—C$_0$-C$_6$-alkyl-aryl, C$_0$-C$_6$-alkyl-N(R$_7$)C(O)—C$_0$-C$_6$-alkyl-heteroaryl, —C$_0$-C$_6$-alkyl-N(R$_7$)C(O)—C$_0$-C$_6$-alkyl-heterocycloalkyl, C$_0$-C$_6$-alkyl-N(R$_7$)C(O)—C$_0$-C$_6$-alkyl-heterocycloalkyl-aryl, —N(R$_7$)C(O)OR$_6$, or —N(R$_7$)—C(O)—R$_{7a}$, wherein each of the alkyl, alkanyl, alkenyl, cycloalkyl, aryl, (including, for example the alkyl within alkoxy), heterocycloalkyl, and heteroaryl groups, either alone or as part of another group within R$_3$, is independently optionally substituted with 1, 2, 3, 4, or 5 groups selected from C$_1$-C$_6$-alkanyl, C$_1$-C$_6$-alkenyl, —C$_0$-C$_6$-alkyl-OR$_9$, cycloalkyl, halo, haloalkyl, haloalkoxy, —C(O)R$_9$, —NO$_2$, —CN, oxo, —C$_0$-C$_6$-alkyl-N(R$_8$)R$_{8a}$, —C$_0$-C$_6$-alkyl-heterocycloalkyl, —C$_0$-C$_6$-alkyl-aryl, —C$_0$-C$_6$-alkyl-heteroaryl, —C(O)OR$_9$, and hydroxyalkyl;

R$_4$ is hydrogen, aryl, —C$_0$-C$_6$-alkyl-N(R$_7$)R$_{7a}$, C$_1$-C$_6$-alkoxy, or C$_1$-C$_6$ alkyl, wherein each of the alkyl and aryl groups, either alone or as part of another group in R$_4$, is independently optionally substituted with 1, 2, 3, 4, or 5 groups selected from C$_1$-C$_6$-alkyl, halo, haloalkyl, haloalkoxy, —NO$_2$, —CN, —N(R$_8$)R$_{8a}$, C$_1$-C$_6$-alkoxy, and —C(O)OR$_6$;

R$_5$ is hydrogen, —C$_1$-C$_6$ alkyl-N(R$_7$)R$_{7a}$, C$_1$-C$_6$-alkoxy, C$_1$-C$_6$-alkyl, or aryl, wherein each of the alkyl and aryl is optionally substituted with 1, 2, 3, 4, or 5 groups selected from C$_1$-C$_6$-alkyl, halo, haloalkyl, haloalkoxy, —NO$_2$, —CN, —OH, —N(R$_8$)R$_{8a}$, C$_1$-C$_6$ alkoxy, or —C(O)OR$_6$;

R$_6$ and R$_9$ are independently hydrogen, —OH, C$_1$-C$_6$-alkyl, aryl, arylalkyl, cycloalkyl, cycloalkylalkyl, heterocycloalkyl, heterocycloalkylalkyl, heteroaryl, heteroarylalkyl, or aryl, each C$_1$-C$_6$ alkyl, aryl, cycloalkyl, heterocycloalkyl, and heteroaryl, either alone or as part of another group within R$_6$ and R$_9$, is independently optionally substituted with 1, 2, 3, 4, or 5 groups independently selected from —NH$_2$, —OH, C$_1$-C$_6$-alkoxy, C$_1$-C$_6$-alkyl, and halo; and R$_7$, R$_{7a}$ R$_{7b}$, R$_{7c}$, R$_{7d}$, R$_8$, and R$_{8a}$ are independently hydrogen, —C$_1$-C$_6$-alkanyl, —C$_1$-C$_6$-alkenyl, —OH, —O—C$_1$-C$_6$ alkanyl, —O—C$_1$-C$_6$ alkenyl, —O—C$_0$-C$_6$ alkyl-aryl, —C$_0$-C$_6$ alkyl-C(O)OR$_6$, —C$_0$-C$_6$ alkyl-C(O)R$_6$, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within R$_7$, R$_{7a}$ R$_{7b}$, R$_{7c}$, and R$_{7d}$, is independently optionally substituted with 1, 2, 3, 4, or 5 groups selected from —NH$_2$, —S—C$_1$-C$_6$ alkyl, —CN, —OH, —NO$_2$, C$_1$-C$_6$ alkoxy, C$_1$-C$_6$ alkyl, halo, aryl, and heteroaryl optionally substituted with one or two C$_1$-C$_6$ alkyl.

In another embodiment, the invention comprises a pharmaceutical composition comprising a PI3K inhibitor of Formula Formula VIII, VIIIa, VIIIb, or IX in combination with a compound of Formula I, Ia, Ic, Id, II, III, IV, or V and a pharmaceutically acceptable carrier, excipient, or diluent. In another embodiment, the compound is of Formula VIIIa or VIIIb.

In another embodiment, the invention provides a method of treating a disease or condition mediated by PI3K and MEK comprising administering to a patient a PI3K compound of Formula VIII, VIIIa, VIIIb, or IX in combination with a MEK compound of Formula I, Ia, Ic, Id, II, III, IV, or V. In another embodiment, the PI3K compound is of Formula VIIIa or VIIIb. In another embodiment, the MEK Compound is of Formula Ia and the PI3K Compound is of Formula VIIIa. In another embodiment, the MEK Compound is of Formula Ia and the PI3K Compound is of Formula VIIIb. In another embodiment, the MEK Compound is of Formula V and the PI3K Compound is of Formula VIIIb. In another embodiment, the MEK Compound is of Section I, Embodiment G and the PI3K Compound is of VIIIb. In another embodiment, the MEK Compound If of Section I, Table 1 and the PI3K compound is of Formula VIII, VIIIa, or VIIIb.

Another embodiment of the invention is directed to suitable x-ray quality crystals, and one of ordinary skill in the art would appreciate that they can be used as part of a method of identifying a candidate agent capable of binding to and modulating the activity of kinases. Such methods may be characterized by the following embodiments: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Embodiments a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following embodiments: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

Section III Definitions

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond, "- - - -" means a single or double bond. When a group is depicted removed from its parent Formula, the "∼∼" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

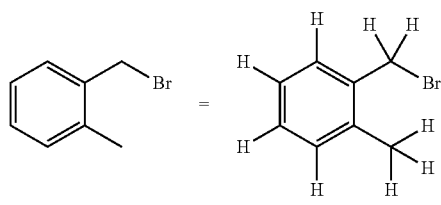

If a group "R" is depicted as "floating" on a ring system, as for example in the Formula:

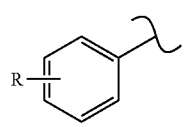

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the Formulae:

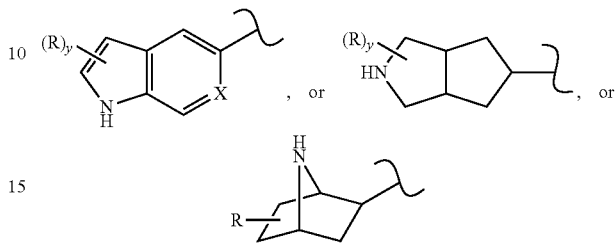

then, unless otherwise defined, a substituent "R" may reside on any atom of the fused ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "X" equals ═CH—) from one of the ring atoms, so long as a stable structure is formed. In the example depicted, the "R" group may reside on either the 5-membered or the 6-membered ring of the fused ring system. In the Formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the Formula:

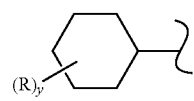

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the Formula:

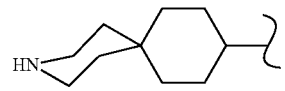

"Acyl" means a —C(O)R radical where R is alkyl (i.e., one to ten carbon atoms of a straight, branched, or cyclic configuration, and is saturated or unsaturated) or R is optionally substituted aryl or optionally substituted heteroaryl. One or more carbons in the R residue may be replaced by nitrogen, oxygen or sulfur. Examples include acetyl, benzoyl, propionyl, isobutyryl, t-butoxycarbonyl, benzyloxycarbonyl, and pyridinylcarbonyl, and the like. Lower-acyl refers to groups containing one to six carbons.

"Acylamino" means a —NRR' group where R is acyl, as defined herein, and R' is hydrogen or alkyl.

"Alkyl" means a ($C_1$-$C_{20}$) linear, branched, or cyclic hydrocarbon group (and combinations thereof, inclusively) and may be saturated or unsaturated. For example, "$C_6$ alkyl" may refer to an n-hexyl, iso-hexyl, cyclobutylethyl, and the like. "Lower alkyl" means an alkyl group of from one to six carbon atoms. Examples of lower alkyl groups include methyl, ethyl, propyl, isopropyl, butyl, s-butyl, t-butyl, isobutyl, pentyl, hexyl and the like. A "$C_0$" alkyl (as in "$C_0$-$C_6$-alkyl") is a covalent bond.

In this application, alkyl includes alkanyl, alkenyl, alkynyl, and cycloalkyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, "$C_4$ alkyl" is meant to include n-butyl, sec-butyl, isobutyl, t-butyl, cyclobutyl, isobutenyl and but-2-ynyl groups; and for example, "$C_3$ alkyl" each include n-propyl, propenyl, and isopropyl.

"Alkanyl" means a linear saturated monovalent hydrocarbon radical of one to twenty carbon atoms or a branched saturated monovalent hydrocarbon radical of three to 20 carbon atoms, e.g., methyl, ethyl, propyl, 2-propyl, butyl (including all isomeric forms), or pentyl (including all isomeric forms), and the like. "Lower alkanyl" means alkanyl having one to six carbons atoms.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Cycloalkylalkyl" means alkyl group substituted with one or two cycloalkyl group(s), as defined herein. Representative examples include cyclopropylmethyl and 2-cyclobutyl-ethyl, and the like.

"Optionally substituted cycloalkyl" means a cycloalkyl radical, as defined herein, that is optionally substituted with one, two, three, or four groups independently selected from $C_1$-$C_6$ alkanyl, $C_1$-$C_6$ alkoxy, halo, haloalkyl, haloalkoxy, oxo, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl di($C_1$-$C_6$)alkylamino($C_1$-$C_6$)alkyl, carboxy, carboxy ester, cycloalkyl, hydroxyalkyl, —C(O)NR'R" (where R' is hydrogen, alkyl, hydroxy, or alkoxy and R" is hydrogen, alkyl, aryl, or heterocyclyl), optionally substituted heterocycloalkyl, optionally substituted heteroaryl, —NR'C(O)R" (where R' is hydrogen or alkyl and R" is alkyl, aryl, or heterocyclyl), and —NHS(O)$_2$R' (where R' is alkyl, aryl, or heterocyclyl).

"Alkenyl" means a straight or branched hydrocarbon radical having from 2 to 20 carbon atoms and at least one double bond and includes ethenyl, propenyl, 1-but-3-enyl, 1-pent-3-enyl, 1-hex-5-enyl and the like. "Lower alkenyl" is alkenyl having 2-6 carbon atoms.

"Alkynyl" means a straight or branched hydrocarbon radical having from 2 to 20 carbon atoms and at least one triple bond and includes ethynyl, propynyl, butynyl, pentyn-2-yl and the like. "Lower alkynyl" is alkynyl having 2-6 carbon atoms.

"Alkylene" refers to straight or branched divalent hydrocarbon, containing no unsaturation and having from one to ten carbon atoms. Examples of alkylene include methylene (—CH$_2$—), ethylene (—CH$_2$CH$_2$—), propylene (—CH$_2$CH$_2$CH$_2$—), and dimethylpropylene (—CH$_2$C(CH$_3$)$_2$CH$_2$—), and the like.

"Alkylidyne" or "alkynylene" means a straight or branched divalent hydrocarbon having from two to ten carbon atoms, and containing at least one triple bond, for example, propylid-2-ynyl, n-butylid-1-ynyl, and the like.

"Alkoxy" or "alkoxyl" means —O-alkyl, where the alkyl group includes from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Alkylamino" means a —NHR radical where R is alkyl as defined herein, or an N-oxide derivative, or a protected derivative thereof, e.g., methylamino, ethylamino, n-, isopropylamino, n-, iso-, tert-butylamino, or methylamino-N-oxide, and the like.

"Alkylaminoalkyl" means an alkyl group substituted with one or two alkylamino groups, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Optionally substituted aryl" means an aryl group, as defined herein, which is optionally substituted with one, two, three, four, of five groups selected from halo, haloalkyl, haloalkoxy, hydroxy, lower alkanyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), and —NHS(O)$_2$R' (where R' is alkyl, aryl, or heteroaryl).

"Arylalkyl" means a residue in which an aryl moiety is attached to a parent structure via one of an alkylene, alkylidene, or alkylidyne group. Examples include benzyl, phenethyl, phenylvinyl, phenylallyl and the like. "Lower arylalkyl" refers to an arylalkyl where the "alkyl" portion of the group has one to six carbons; this can also be referred to as $C_{1-6}$ arylalkyl. When a group is referred to as "$C_1$-$C_6$ alkyl-aryl" or "$C_0$-$C_6$ alkyl-aryl", an aryl moiety is attached to a parent structure via an alkylene group. Examples include benzyl, phenethyl, and the like.

"Arylalkyloxy" means an —OR group where R is arylalkyl, as defined herein.

"Carboxy ester" means a —C(O)OR group where R is lower alkanyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Dialkylamino" means a —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloaloxy" means an —OR' group where R' is haloalkyl as defined herein, e.g., trifluoromethoxy or 2,2,2-trifluoroethoxy, and the like.

"Halogen" or "halo" means fluoro, chloro, bromo or iodo.

"Haloalkyl" and "haloaryl" mean an alkyl and an aryl group, respectively, that are substituted with one or more halogens, preferably one to five halo atoms. Thus, "dihaloaryl," "dihaloalkyl," and "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems. The terms "heterocycloalkyl" and "heteroaryl" are groups that are encompassed by the broader term "heterocyclyl." The nitrogen, phosphorus, carbon or sulfur atoms in the heterocyclyl group may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyi, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

"Optionally substituted heterocyclyl" means a heterocyclyl group, as defined herein, optionally substituted with one, two, three, four, or five groups selected from halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), amino, alkylamino, dialkylamino, and —NHS(O)$_2$R' (where R' is alkyl, aryl, or heteroaryl).

"Heteroalicyclic" and "heterocycloalkyl" mean a non-aromatic heterocyclyl group, as defined herein. A "heteroalicyclic" or "heterocycloalkyl" may be fully saturated or may contain unsaturation, but is not aromatic. "Heteroalicyclic" or "heterocycloalkyl" may be monocyclic or bicyclic (including fused, bridged, and spiro ring systems).

"Optionally substituted heteroalicyclic" and "optionally substituted heterocycloalkyl" mean, respectively, a heteroalicyclic and heterocycloalkyl ring, each as defined herein, optionally substituted with one, two, three, four, or five groups selected from halo, haloalkyl, haloalkoxy, hydroxy, oxo, lower alkanyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), amino, alkylamino, dialkylamino, and —NHS(O)$_2$R' (where R' is alkyl, aryl, or heteroaryl).

"Heteroaryl" means a 5- to 12-membered, monocyclic aromatic heterocyclyl (where heterocyclyl is defined herein) or bicyclic heterocyclyl ring system (where at least one of the rings in the bicyclic system is aromatic) where the monocyclic ring and at least one of the rings in the bicyclic ring system contains one, two, three, four, or five heteroatom(s) selected from nitrogen, oxygen, phosphorous, and sulfur. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

"Optionally substituted heteroaryl" means a heteroaryl group, as defined herein, optionally substituted with one, two, three, four, or five groups selected from halo, haloalkyl, haloalkoxy, lower alkanyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocloalkyl, heteroaryl, optionally substituted aryl, —C(O)NR'R" (where R' is hydrogen or alkyl and R" is hydrogen, alkyl, aryl, or heterocyclyl), —NR'C(O)R" (where R' is hydrogen or alkyl and R" is alkyl, aryl, or heterocyclyl), and —NHS(O)$_2$R' (where R' is alkyl, aryl, or heteroaryl).

"Optionally substituted heterocyclylalkyl" means an alkyl group substituted with an optionally substituted heterocyclyl group, as defined herein. Examples include (4-methylpiperazin-1-yl)methyl, (morpholin-4-yl)methyl, (pyridin-4-yl)methyl, 2-(oxazolin-2-yl)ethyl, 4-(4-methylpiperazin-1-yl)-2-butenyl, and the like. In addition, the alkyl portion of a heterocyclyl alkyl group may be substituted as described in the definition for "substituted". "Lower heterocyclylalkyl" means a heterocyclylalkyl where the "alkyl" portion of the group has one to six carbons. "Heteroalicyclylalkyl" or "lower heterocycloalkylalkyl" means a heterocyclylalkyl where the heterocyclyl portion of the group is non-aromatic; and "heteroarylalkyl" means a heterocyclylalkyl where the heterocyclyl portion of the group contains an aromatic ring. Such terms may be described in more than one way, for example, "lower heterocyclylalkyl" and "heterocyclyl $C_{1-6}$alkyl" are equivalent terms. Additionally, for simplicity, the number of annular atoms (including heteroatoms) in a heterocycle may be denoted as "$C_x$-$C_y$" (as in "$C_x$-$C_y$-heterocyclyl" and "$C_x$-$C_y$-heteroaryl" (and the like)), where x and y are integers. So, for example, $C_5$-$C_{14}$-heterocyclyl refers to a 5 to 14 membered ring system having at least one heteroatom and not a ring system containing 5 to 14 annular carbon atoms.

"Hydroxyalkyl" means an alkanyl, alkenyl, or alkynyl radical, as defined herein, substituted with at least one, preferably one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, or 1-(hydroxymethyl)-2-hydroxyethyl, and the like.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," both the "$C_{1-8}$ alkyl" portion and the "aryl" portion of the molecule may or may not be substituted. A list of exemplary optional substitutions is presented below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

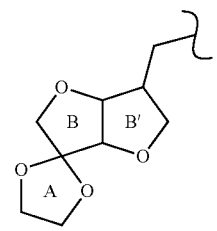

"Substituted" alkyl, alkylene, alkylidene, and alkylidyne refer respectively to alkyl, alkylene, alkylidene, and alkylidyne where one or more (for example up to about five, in another example, up to about three) hydrogen atoms are replaced by a substituent independently selected from halo, optionally substituted aryl, hydroxy, alkoxy, optionally substituted heterocyclyl, alkylenedioxy, amino, alkylamino, dialkylamino), amidino, aryloxy, arylalkyloxy, carboxy, carboxy ester, alkylcarbonyloxy, carbamyl, alkylaminocarbonyl, dialkylaminocarbonyl, benzyloxycarbonylamino (CBZ-amino), cyano, acyl, nitro, $S(O)_{n1}R'$ (where n1 is 0, 1, or 2 and R' is alkyl, substituted alkyl, optionally substituted aryl, optionally substituted heterocycloalkyl, or optionally substituted heteroaryl), oxo, acylamino, and sulfonamido.

"Sulfonamido" means a —$NRSO_2R'$ or —$SO_2NRR''$ group where R is hydrogen or lower alkyl, R' is lower alkanyl, lower alkenyl, optionally substituted aryl, optionally substituted heterocycloalkyl, optionally substituted cycloalkyl, or optionally substituted heteroaryl, and R'' is hydrogen or R'.

Representative compounds from Section III are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

TABLE 1

| Cpd. No. | Structure | IUPAC Name |
|---|---|---|
| 1 | 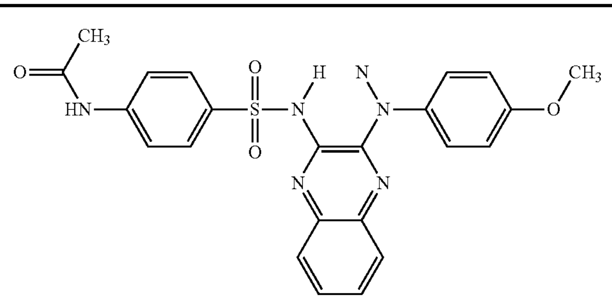 | N-(4-{[(3-{[4-(methyloxy)phenyl]amino-quinoxalin-2-yl)amino]sulfonyl}phenyl)acetamide |

TABLE 1-continued

| Cpd. No. | Structure | IUPAC Name |
|---|---|---|
| 2 | 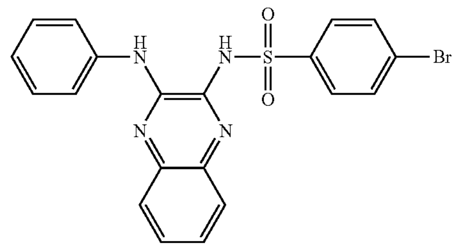 [SMILES: O=S(=O)(Nc1nc2ccccc2nc1Nc1ccccc1)c1ccc(Br)cc1] | 4-bromo-N-[3-(phenylamino)quinoxazlin-2-yl] benzene sulfonamide |
| 3 | 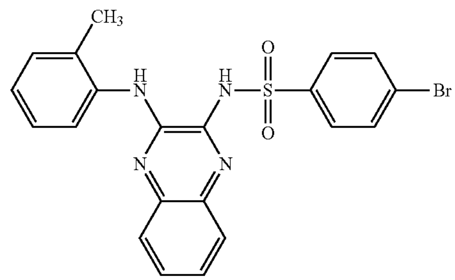 [SMILES: Cc1ccccc1Nc1nc2ccccc2nc1NS(=O)(=O)c1ccc(Br)cc1] | 4-bromo-N-{3-[(2-methylphenyl)amino]quinoxalin-2-yl}benzene sulfonamide |
| 4 | 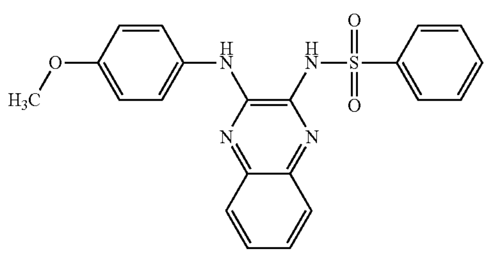 [SMILES: COc1ccc(Nc2nc3ccccc3nc2NS(=O)(=O)c2ccccc2)cc1] | N-(3-{[4-(methyloxy)phenyl]amino}quinoxalin-2-yl) benzene sulfonamide |
| 5 | 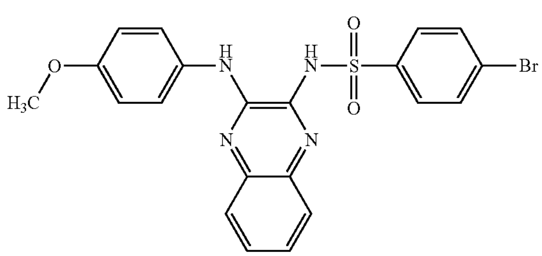 [SMILES: COc1ccc(Nc2nc3ccccc3nc2NS(=O)(=O)c2ccc(Br)cc2)cc1] | 4-bromo-N-(3-{[4-(methyloxy)phenyl]amino}quinoxalin-2-yl) benzenesulfonamide |
| 6 | 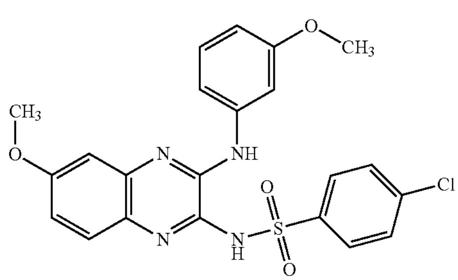 [SMILES: COc1cccc(Nc2nc3cc(OC)ccc3nc2NS(=O)(=O)c2ccc(Cl)cc2)c1] | 4-chloro-N-[6-(methyloxy)-3-{[3-(methyloxy)phenyl]amino}quinoxalin-2-yl]benzenesulfonamide |

TABLE 1-continued

| Cpd. No. | Structure | IUPAC Name |
|---|---|---|
| 7 | 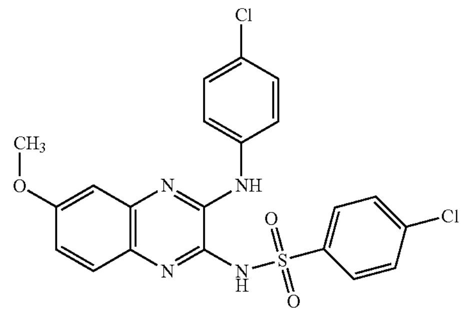 [SMILES: COc1ccc2nc(NS(=O)(=O)c3ccc(Cl)cc3)c(Nc3ccc(Cl)cc3)nc2c1] | 4-chloro-N-{3-[(4-chlorophenyl)amino]-6-(methyloxy)quinoxalin-2-yl}benzenesulfonamide |
| 8 | 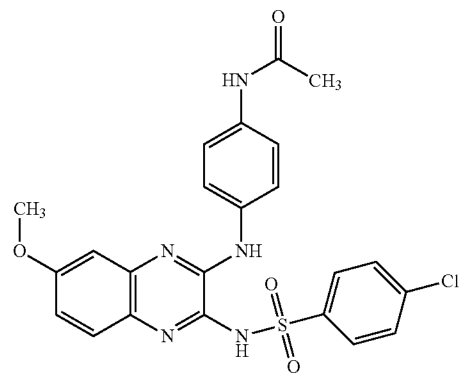 [SMILES: COc1ccc2nc(NS(=O)(=O)c3ccc(Cl)cc3)c(Nc3ccc(NC(C)=O)cc3)nc2c1] | N-(4-{[3-{[(4-chlorophenyl)sulfonyl)amino}-7-(methyloxy)quinoxalin-2-yl]amino}phenyl) acetamide |
| 9 | 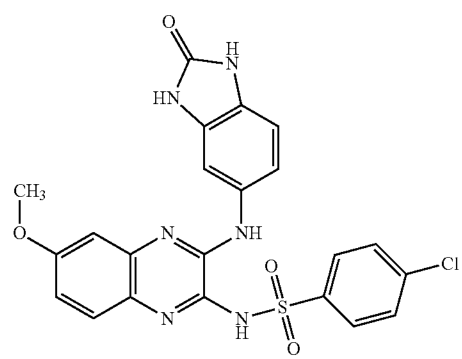 [SMILES: COc1ccc2nc(NS(=O)(=O)c3ccc(Cl)cc3)c(Nc3ccc4[nH]c(=O)[nH]c4c3)nc2c1] | 4-chloro-N-{6-(methyloxy)-3-[(2-oxo-2,3-dihydro-1H-benzimidazol-5-yl)amino]quinoxalin-2-yl}benzenesulfonamide |
| 10 | 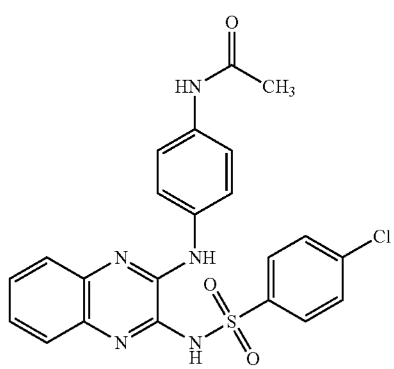 [SMILES: CC(=O)Nc1ccc(Nc2nc3ccccc3nc2NS(=O)(=O)c2ccc(Cl)cc2)cc1] | N-{4-[(3-{[(4-chlorophenyl)sulfonyl]amino}quinoxalin-2-yl)amino]phenyl}acetamide |

TABLE 1-continued

| Cpd. No. | Structure | IUPAC Name |
|---|---|---|
| 11 | 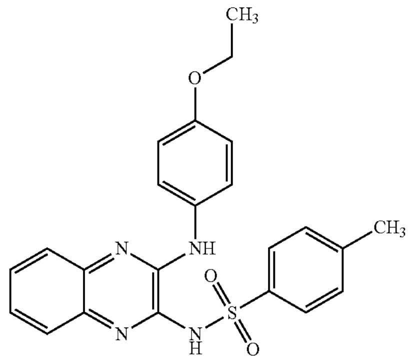 [SMILES: CCOc1ccc(Nc2nc3ccccc3nc2NS(=O)(=O)c2ccc(C)cc2)cc1] | N-(3-{[4-(ethyloxy)phenyl]amino}quinoxalin-2-yl)-4-methylbenzene sulfonamide |
| 12 | 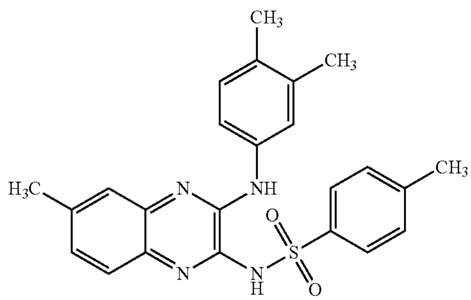 | N-{3-[(3,4-dimethylphenyl)amino]-6-methylquinoxalin-2-yl}-4-methylbenzene sulfonamide |
| 13 | 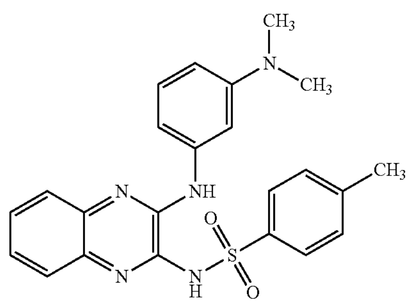 [SMILES: Cc1ccc(S(=O)(=O)Nc2nc3ccccc3nc2Nc2cccc(N(C)C)c2)cc1] | N-(3-{[3-(dimethylamino)phenyl]amino}quinoxalin-2-yl)-4-methylbenzene sulfonamide |
| 14 | 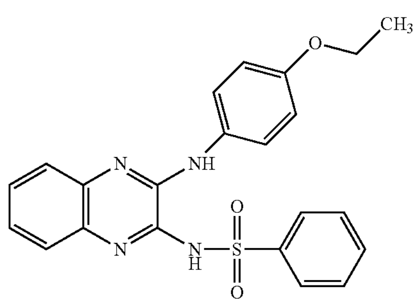 [SMILES: CCOc1ccc(Nc2nc3ccccc3nc2NS(=O)(=O)c2ccccc2)cc1] | N-(3-{[4-(ethyloxy)phenyl]amino}quinoxalin-2-yl)benzene sulfonamide |
| 15 | 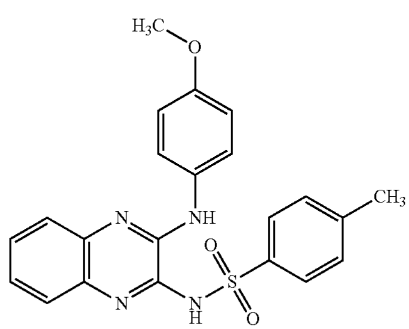 [SMILES: COc1ccc(Nc2nc3ccccc3nc2NS(=O)(=O)c2ccc(C)cc2)cc1] | 4-methyl-N-(3-{[4-(methyloxy)phenyl]amino}quinoxalin-2-yl) benzene sulfonamide |

TABLE 1-continued

| Cpd. No. | Structure | IUPAC Name |
|---|---|---|
| 16 | 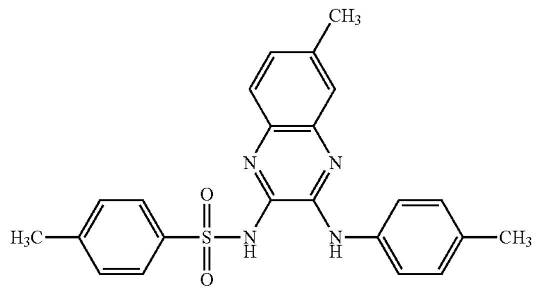 | 4-methyl-N-{6-methyl-3-[(4-methylphenyl)amino]quinoxalin-2-yl}benzene sulfonamide |
| 17 | 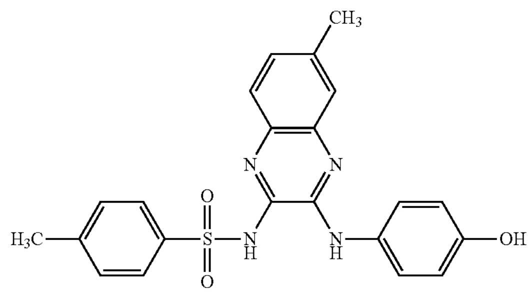 [SMILES: Cc1ccc(S(=O)(=O)Nc2nc3ccc(C)cc3nc2Nc2ccc(O)cc2)cc1] | N-{3-[(4-hydroxyphenyl)amino]-6-methylquinoxalin-2-yl}-4-methylbenzene sulfonamide |
| 18 | 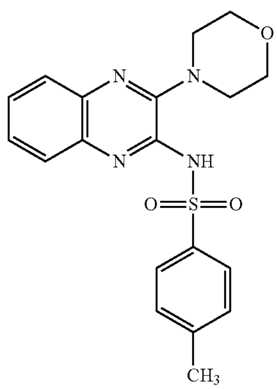 [SMILES: Cc1ccc(S(=O)(=O)Nc2nc3ccccc3nc2N2CCOCC2)cc1] | 4-methyl-N-(3-morpholin-4-ylquinoxalin-2-yl)benzenesulfonamide |
| 19 | 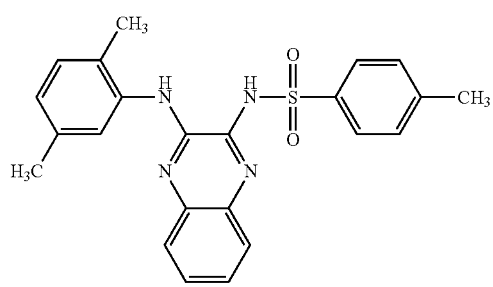 [SMILES: Cc1ccc(S(=O)(=O)Nc2nc3ccccc3nc2Nc2cc(C)ccc2C)cc1] | N-{3-[(2,5-dimethylphenyl)amino]quinoxalin-2-yl)-4-methylbenzenesulfonamide |
| 20 | 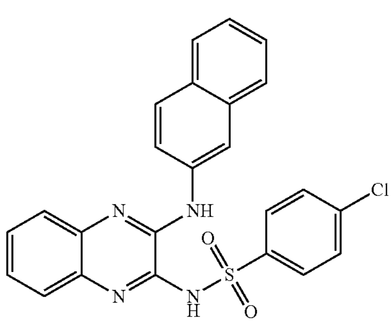 [SMILES: O=S(=O)(Nc1nc2ccccc2nc1Nc1ccc2ccccc2c1)c1ccc(Cl)cc1] | 4-chloro-N-[3-(naphthalen-2-ylamino)quinoxalin-2-yl]benzenesulfonamide |

TABLE 1-continued

| Cpd. No. | Structure | IUPAC Name |
|---|---|---|
| 21 | 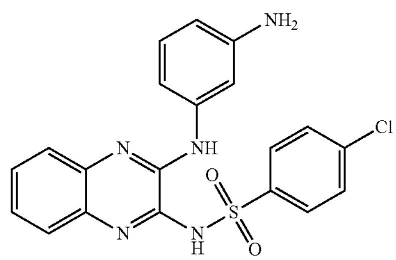 [SMILES: Nc1cccc(Nc2nc3ccccc3nc2NS(=O)(=O)c2ccc(Cl)cc2)c1] | N-{3-[(3-aminophenyl)amino]quinoxalin-2-yl}-4-chlorobenzenesulfonamide |
| 22 | 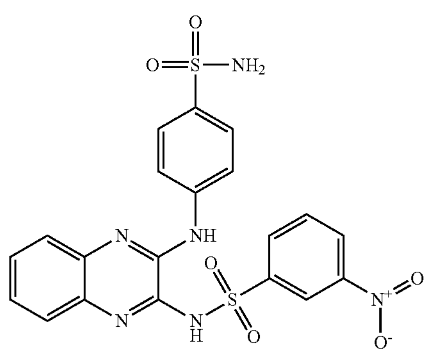 [SMILES: NS(=O)(=O)c1ccc(Nc2nc3ccccc3nc2NS(=O)(=O)c2cccc([N+](=O)[O-])c2)cc1] | N-(3-{[4-(aminosulfonyl)phenyl]amino}quinoxalin-2-yl)-3-nitrobenzenesulfonamide |
| 23 | 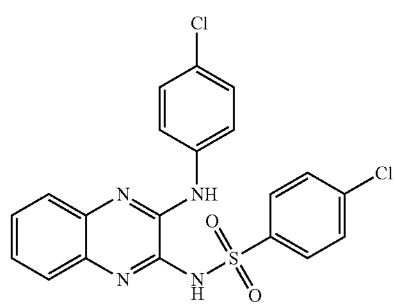 [SMILES: O=S(=O)(Nc1nc2ccccc2nc1Nc1ccc(Cl)cc1)c1ccc(Cl)cc1] | 4-chloro-N-{3-[(4-chlorophenyl)amino]quinoxalin-2-yl}benzenesulfonamide |
| 24 | 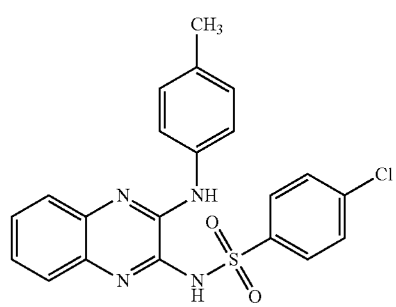 [SMILES: Cc1ccc(Nc2nc3ccccc3nc2NS(=O)(=O)c2ccc(Cl)cc2)cc1] | 4-chloro-N-{3-[(4-methylphenyl)amino]quinoxalin-2-yl}benzenesulfonamide |
| 25 | 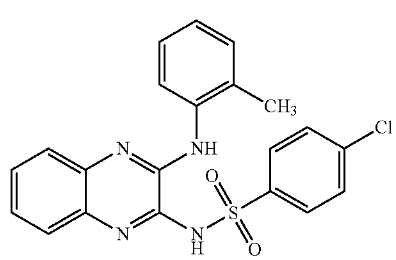 [SMILES: Cc1ccccc1Nc1nc2ccccc2nc1NS(=O)(=O)c1ccc(Cl)cc1] | 4-chloro-N-{3-[(2-methylphenyl)amino]quinoxalin-2-yl}benzenesulfonamide |

TABLE 1-continued
| Cpd. No. | Structure | IUPAC Name |
|---|---|---|
| 26 | 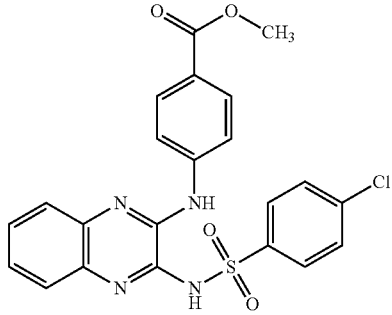 [SMILES: COC(=O)c1ccc(Nc2nc3ccccc3nc2NS(=O)(=O)c2ccc(Cl)cc2)cc1] | methyl 4-[(3-{[(4-chlorophenyl)sulfonyl]amino}quinoxalin-2-yl)amino]benzoate |
| 27 | 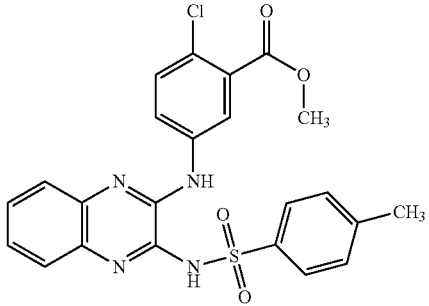 [SMILES: COC(=O)c1cc(Nc2nc3ccccc3nc2NS(=O)(=O)c2ccc(C)cc2)ccc1Cl] | methyl 2-chloro-5-[(3-{[(4-methylphenyl)sulfonyl]amino}quinoxalin-2-yl)amino]benzoate |
| 28 | 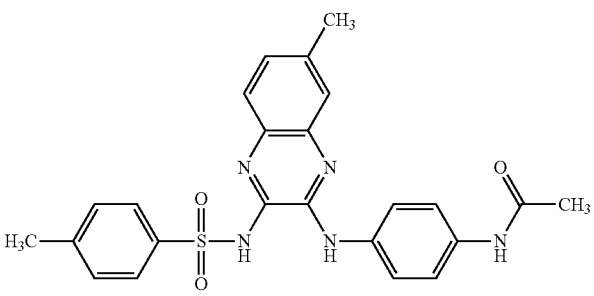 [SMILES: CC(=O)Nc1ccc(Nc2nc3cc(C)ccc3nc2NS(=O)(=O)c2ccc(C)cc2)cc1] | N-{4-[(7-methyl-3-{[(4-methylphenyl)sulfonyl]amino}quinoxalin-2-yl)amino]phenyl}acetamide |
| 29 | 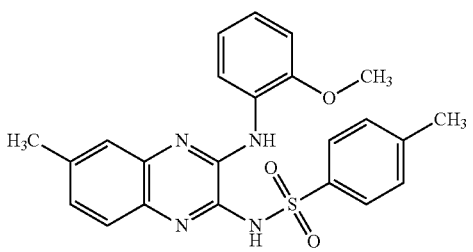 | 4-methyl-N-(6-methyl-3-{[2-(methyloxy)phenyl]amino}quinoxalin-2-yl)benzenesulfonamide |

TABLE 1-continued

| Cpd. No. | Structure | IUPAC Name |
|---|---|---|
| 30 | 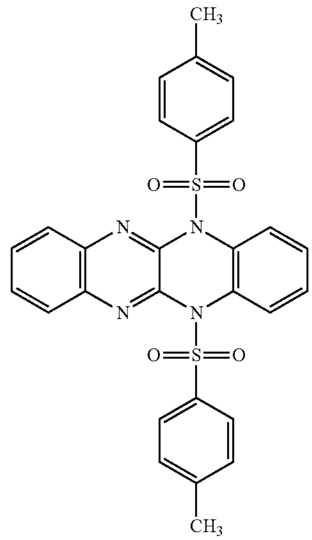 [SMILES: Cc1ccc(S(=O)(=O)N2c3ccccc3N(S(=O)(=O)c3ccc(C)cc3)c3nc4ccccc4nc32)cc1] | 5,12-bis[(4-methylphenyl)sulfonyl]-5,12-dihydroquinoxalino[2,3-d]quinoxaline |
| 31 | 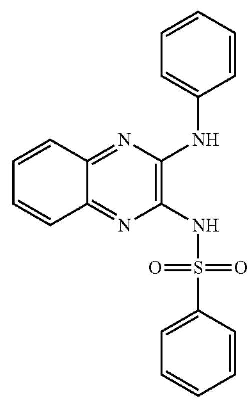 [SMILES: O=S(=O)(Nc1nc2ccccc2nc1Nc1ccccc1)c1ccccc1] | N-[3-(phenylamino)quinoxalin-2-yl]benzenesulfonamide |
| 32 | 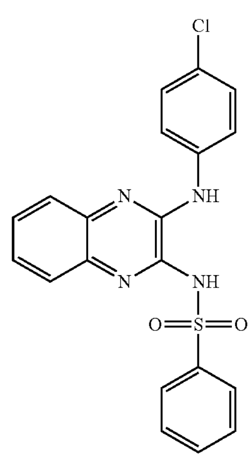 [SMILES: O=S(=O)(Nc1nc2ccccc2nc1Nc1ccc(Cl)cc1)c1ccccc1] | N-{3-[(4-chlorophenyl)amino]quinoxalin-2-yl}benzenesulfonamide |

TABLE 1-continued
| Cpd. No. | Structure | IUPAC Name |
|---|---|---|
| 33 | 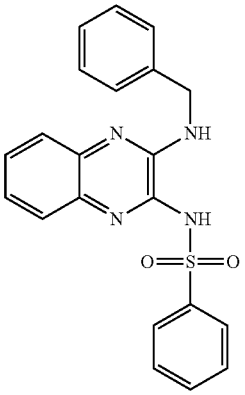 [SMILES: O=S(=O)(Nc1nc2ccccc2nc1NCc1ccccc1)c1ccccc1] | N-{3-[(phenylmethyl)amino]quinoxalin-2-yl}benzenesulfonamide |
| 34 | 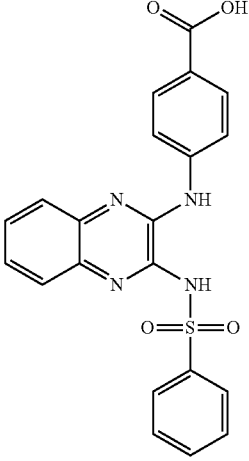 [SMILES: O=C(O)c1ccc(Nc2nc3ccccc3nc2NS(=O)(=O)c2ccccc2)cc1] | 4-({3-[(phenylsulfonyl)amino]quinoxalin-2-yl}amino)benzoic acid |
| 35 | 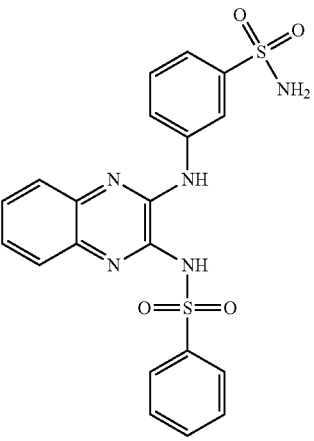 [SMILES: NS(=O)(=O)c1cccc(Nc2nc3ccccc3nc2NS(=O)(=O)c2ccccc2)c1] | 3-({3-[(phenylsulfonyl)amino]quinoxalin-2-yl}amino)benzenesulfonamide |

TABLE 1-continued
| Cpd. No. | Structure | IUPAC Name |
|---|---|---|
| 36 | 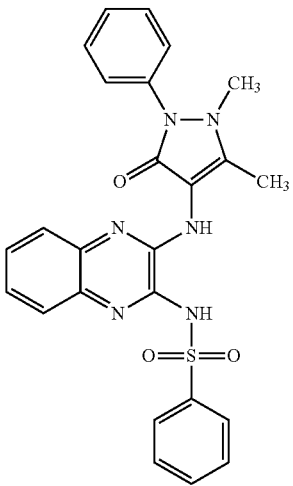 [SMILES: Cc1c(Nc2nc3ccccc3nc2NS(=O)(=O)c2ccccc2)c(=O)n(-c2ccccc2)n1C] | N-{3-[(1,5-dimethyl-3-oxo-2-phenyl-2,3-dihydro-1H-pyrazol-4-yl)amino]quinoxalin-2-yl}benzenesulfonamide |
| 37 | 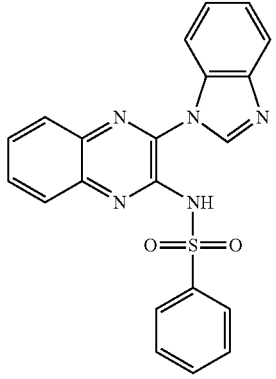 [SMILES: O=S(=O)(Nc1nc2ccccc2nc1-n1cnc2ccccc21)c1ccccc1] | N-[3-(1H-benzimidazol-1-yl)quinoxalin-2-yl]benzenesulfonamide |
| 38 | 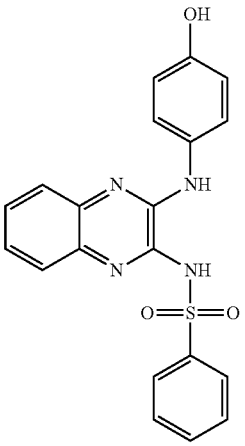 [SMILES: O=S(=O)(Nc1nc2ccccc2nc1Nc1ccc(O)cc1)c1ccccc1] | N-{3-[(4-hydroxyphenyl)amino]quinoxalin-2-yl}benzenesulfonamide |

TABLE 1-continued

| Cpd. No. | Structure | IUPAC Name |
|---|---|---|
| 39 | 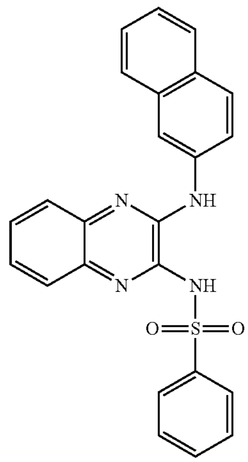 [SMILES: O=S(=O)(Nc1nc2ccccc2nc1Nc1ccc2ccccc2c1)c1ccccc1] | N-[3-(naphthalen-2-ylamino)quinoxalin-2-yl]benzenesulfonamide |
| 40 | 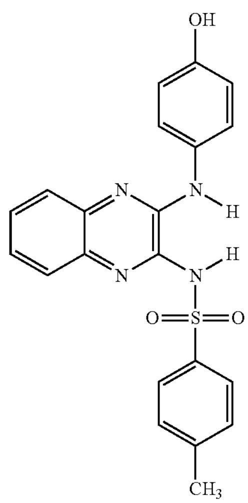 | N-{3-[(4-hydroxyphenyl)amino]quinoxalin-2-yl}-4-methylbenzenesulfonamide |
| 41 | 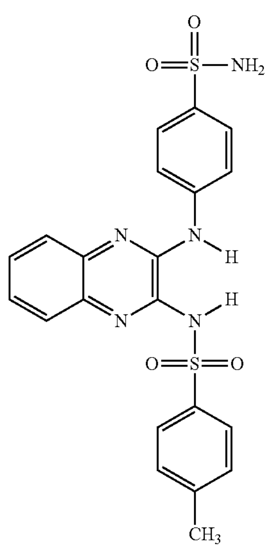 [SMILES: Cc1ccc(S(=O)(=O)Nc2nc3ccccc3nc2Nc2ccc(S(N)(=O)=O)cc2)cc1] | N-(3-{[4-(aminosulfonyl)phenyl]amino}quinoxalin-2-yl)-4-methylbenzenesulfonamide |

TABLE 1-continued
| Cpd. No. | Structure | IUPAC Name |
|---|---|---|
| 42 | 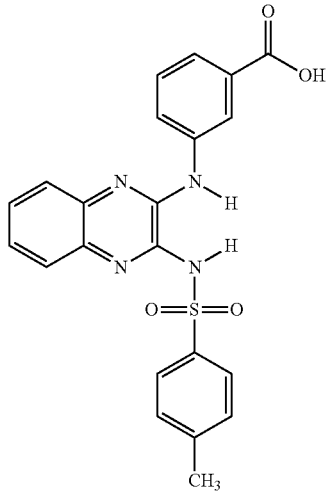 [SMILES: Cc1ccc(S(=O)(=O)Nc2nc3ccccc3nc2Nc2cccc(C(=O)O)c2)cc1] | 3-[(3-{[(4-methylphenyl)sulfonyl]amino}quinoxalin-2-yl)amino]benzoic acid |
| 43 | 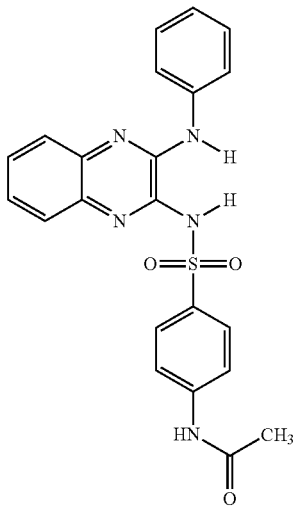 [SMILES: CC(=O)Nc1ccc(S(=O)(=O)Nc2nc3ccccc3nc2Nc2ccccc2)cc1] | N-[4-({[3-(phenylamino)quinoxalin-2-yl]amino}sulfonyl)phenyl]acetamide |
| 44 | 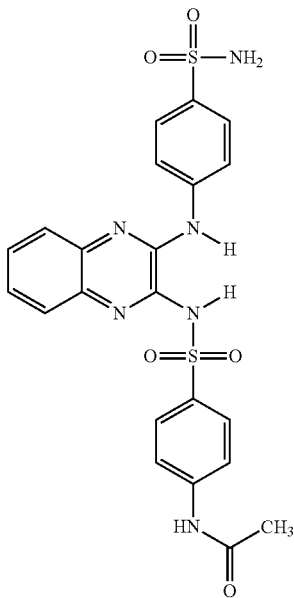 [SMILES: CC(=O)Nc1ccc(S(=O)(=O)Nc2nc3ccccc3nc2Nc2ccc(S(N)(=O)=O)cc2)cc1] | N-(4-{[(3-{[4-(aminosulfonyl)phenyl]amino}quinoxalin-2-yl)amino]sulfonyl}phenyl)acetamide |

TABLE 1-continued

| Cpd. No. | Structure | IUPAC Name |
|---|---|---|
| 45 | 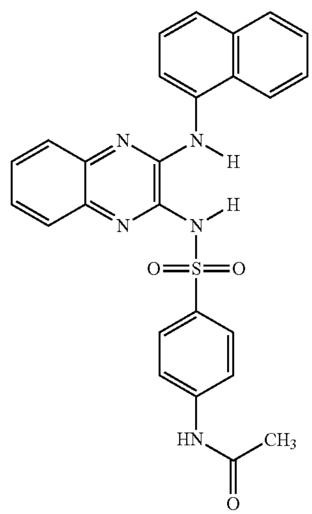 [SMILES: CC(=O)Nc1ccc(S(=O)(=O)Nc2nc3ccccc3nc2Nc2cccc3ccccc23)cc1] | N-[4-({[3-(naphthalen-1-ylamino)quinoxalin-2-yl]amino}sulfonyl)phenyl]acetamide |
| 46 | 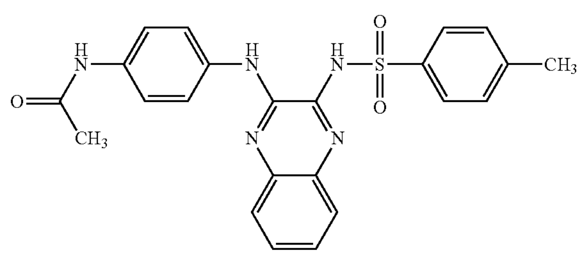 [SMILES: CC(=O)Nc1ccc(Nc2nc3ccccc3nc2NS(=O)(=O)c2ccc(C)cc2)cc1] | N-{4-[(3-{[(4-methylphenyl)sulfonyl]amino}quinoxalin-2-yl)amino]phenyl}acetamide |
| 47 | 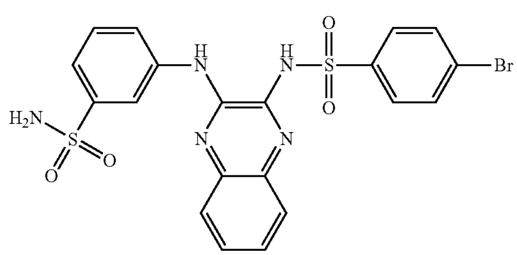 [SMILES: NS(=O)(=O)c1cccc(Nc2nc3ccccc3nc2NS(=O)(=O)c2ccc(Br)cc2)c1] | N-(3-{[3-(aminosulfonyl)phenyl]amino}quinoxalin-2-yl)-4-bromobenzenesulfonamide |
| 48 | 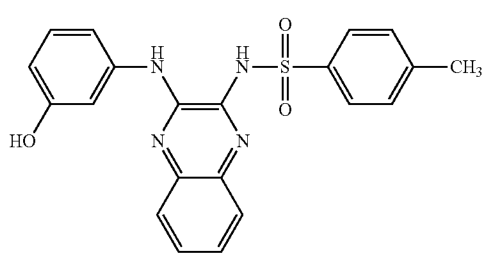 [SMILES: Cc1ccc(S(=O)(=O)Nc2nc3ccccc3nc2Nc2cccc(O)c2)cc1] | N-{3-[(3-hydroxyphenyl)amino]quinoxalin-2-yl}-4-methylbenzenesulfonamide |

TABLE 1-continued
| Cpd. No. | Structure | IUPAC Name |
|---|---|---|
| 49 | 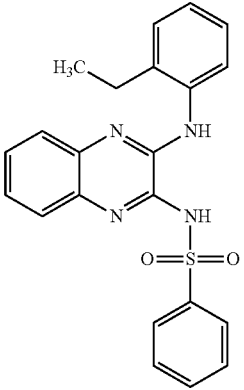 [SMILES: CCc1ccccc1Nc1nc2ccccc2nc1NS(=O)(=O)c1ccccc1] | N-{3-[(2-ethylphenyl)amino]quinoxalin-2-yl}benzenesulfonamide |
| 50 | 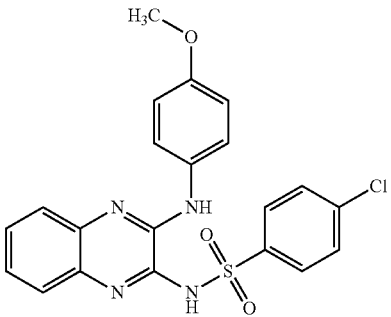 [SMILES: COc1ccc(Nc2nc3ccccc3nc2NS(=O)(=O)c2ccc(Cl)cc2)cc1] | 4-chloro-N-(3-{[4-(methyloxy)phenyl]amino}quinoxalin-2-yl)benzenesulfonamide |
| 51 | 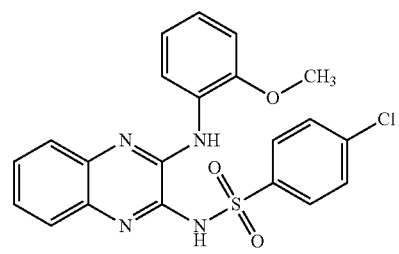 [SMILES: COc1ccccc1Nc1nc2ccccc2nc1NS(=O)(=O)c1ccc(Cl)cc1] | 4-chloro-N-(3-{[2-(methyloxy)phenyl]amino}quinoxalin-2-yl)benzenesulfonamide |
| 52 | 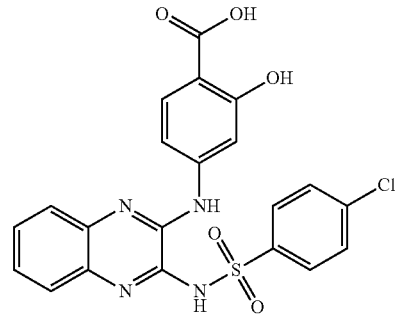 [SMILES: O=C(O)c1ccc(Nc2nc3ccccc3nc2NS(=O)(=O)c2ccc(Cl)cc2)cc1O] | 4-[(3-{[(4-chlorophenyl)sulfonyl]amino}quinoxalin-2-yl)amino]-2-hydroxybenzoic acid |

TABLE 1-continued

| Cpd. No. | Structure | IUPAC Name |
|---|---|---|
| 53 | 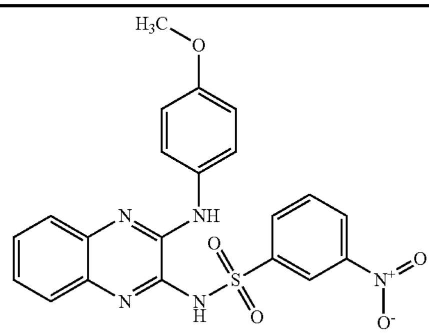 | N-(3-{[4-(methyloxy)phenyl]amino}quinoxalin-2-yl)-3-nitrobenzenesulfonamide |
| 54 | 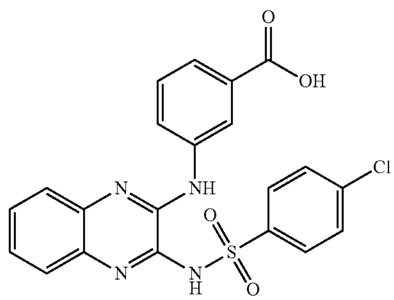 [SMILES: O=C(O)c1cccc(Nc2nc3ccccc3nc2NS(=O)(=O)c2ccc(Cl)cc2)c1] | 3-[(3-{[(4-chlorophenyl)sulfonyl]amino}quinoxalin-2-yl)amino]benzoic acid |
| 55 | 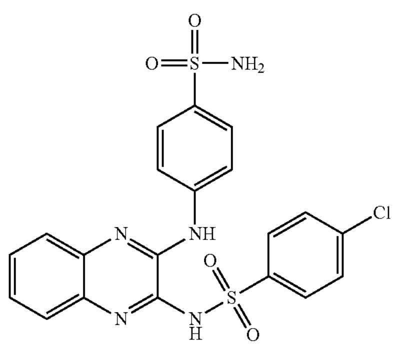 [SMILES: NS(=O)(=O)c1ccc(Nc2nc3ccccc3nc2NS(=O)(=O)c2ccc(Cl)cc2)cc1] | N-(3-{[4-(aminosulfonyl)phenyl]amino}quinoxalin-2-yl)-4-chlorobenzenesulfonamide |
| 56 | 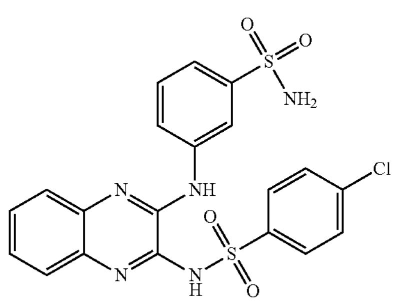 [SMILES: NS(=O)(=O)c1cccc(Nc2nc3ccccc3nc2NS(=O)(=O)c2ccc(Cl)cc2)c1] | N-(3-{[3-(aminosulfonyl)phenyl]amino}quinoxalin-2-yl)-4-chlorobenzenesulfonamide |
| 57 | 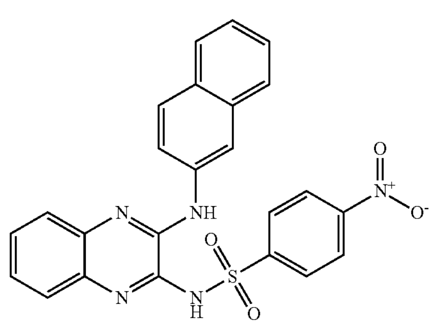 [SMILES: O=[N+]([O-])c1ccc(S(=O)(=O)Nc2nc3ccccc3nc2Nc2ccc3ccccc3c2)cc1] | N-[3-(naphthalen-2-ylamino)quinoxalin-2-yl]-4-nitrobenzenesulfonamide |

TABLE 1-continued
| Cpd. No. | Structure | IUPAC Name |
|---|---|---|
| 58 | 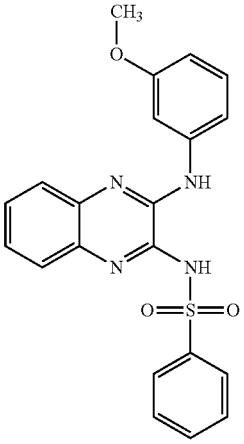 [SMILES: COc1cccc(Nc2nc3ccccc3nc2NS(=O)(=O)c2ccccc2)c1] | N-(3-{[3-(methyloxy)phenyl]amino}quinoxalin-2-yl)benzenesulfonamide |
| 59 | 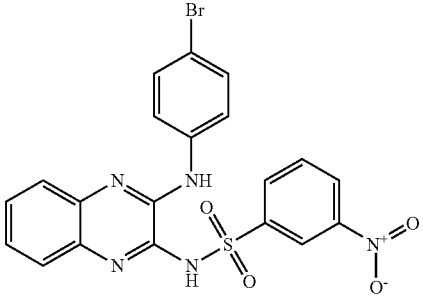 [SMILES: O=[N+]([O-])c1cccc(S(=O)(=O)Nc2nc3ccccc3nc2Nc2ccc(Br)cc2)c1] | N-{3-[(4-bromophenyl)amino]quinoxalin-2-yl}-3-nitrobenzenesulfonamide |
| 60 | 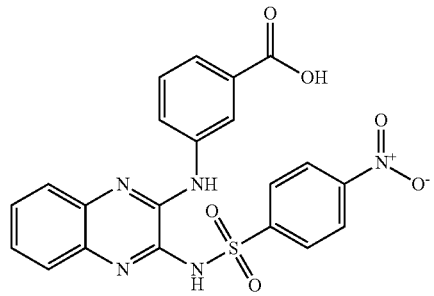 [SMILES: O=C(O)c1cccc(Nc2nc3ccccc3nc2NS(=O)(=O)c2ccc([N+](=O)[O-])cc2)c1] | 3-[(3-{[(4-nitrophenyl)sulfonyl]amino}quinoxalin-2-yl)amino]benzoic acid |
| 61 | 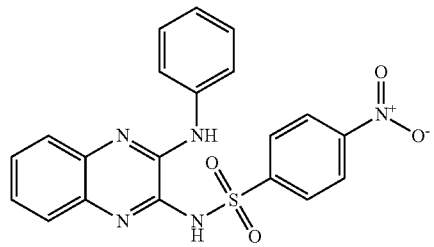 [SMILES: O=[N+]([O-])c1ccc(S(=O)(=O)Nc2nc3ccccc3nc2Nc2ccccc2)cc1] | 4-nitro-N-[3-(phenylamino)quinoxalin-2-yl]benzenesulfonamide |
| 62 | 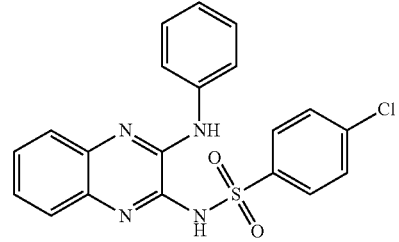 [SMILES: O=S(=O)(Nc1nc2ccccc2nc1Nc1ccccc1)c1ccc(Cl)cc1] | 4-chloro-N-[3-(phenylamino)quinoxalin-2-yl]benzenesulfonamide |

TABLE 1-continued

| Cpd. No. | Structure | IUPAC Name |
|---|---|---|
| 63 | 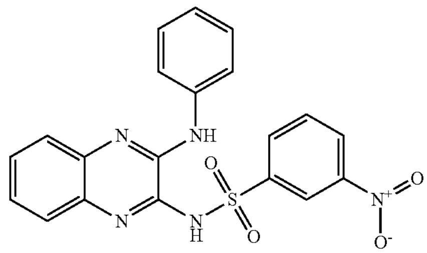 [SMILES: O=[N+]([O-])c1cccc(S(=O)(=O)Nc2nc3ccccc3nc2Nc2ccccc2)c1] | 3-nitro-N-[3-(phenylamino)quinoxalin-2-yl]benzenesulfonamide |
| 64 | 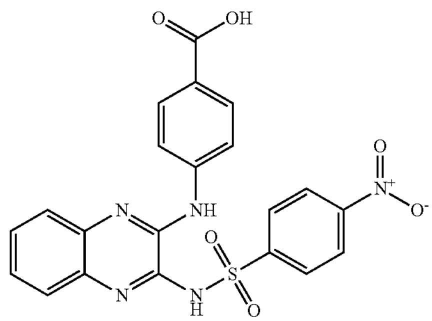 [SMILES: O=C(O)c1ccc(Nc2nc3ccccc3nc2NS(=O)(=O)c2ccc([N+](=O)[O-])cc2)cc1] | 4-[(3-{[(4-nitrophenyl)sulfonyl]amino}quinoxalin-2-yl)amino]benzoic acid |
| 65 | 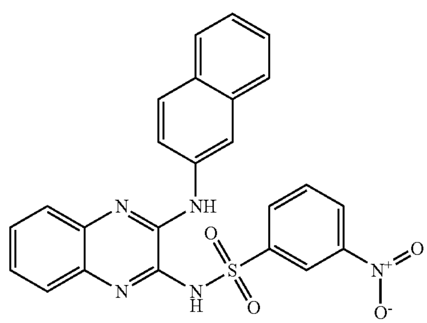 [SMILES: O=[N+]([O-])c1cccc(S(=O)(=O)Nc2nc3ccccc3nc2Nc2ccc3ccccc3c2)c1] | N-[3-(naphthalen-2-ylamino)quinoxalin-2-yl]-3-nitrobenzenesulfonamide |
| 66 | 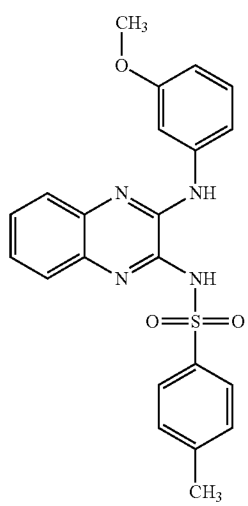 [SMILES: COc1cccc(Nc2nc3ccccc3nc2NS(=O)(=O)c2ccc(C)cc2)c1] | 4-methyl-N-(3-{[3-(methyloxy)phenyl]amino}quinoxalin-2-yl)benzenesulfonamide |

TABLE 1-continued
| Cpd. No. | Structure | IUPAC Name |
|---|---|---|
| 67 | 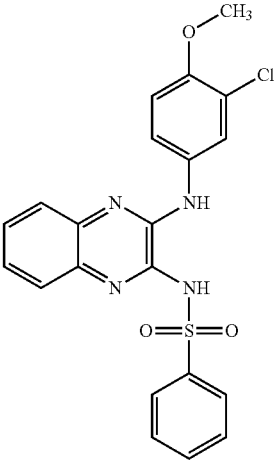 [SMILES: COc1ccc(Nc2nc3ccccc3nc2NS(=O)(=O)c2ccccc2)cc1Cl] | N-(3-{[3-chloro-4-(methyloxy)phenyl]amino}quinoxalin-2-yl)benzenesulfonamide |
| 68 | 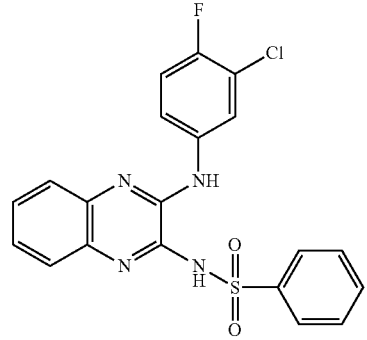 [SMILES: O=S(=O)(Nc1nc2ccccc2nc1Nc1ccc(F)c(Cl)c1)c1ccccc1] | N-{3-[(3-chloro-4-fluorophenyl)amino]quinoxalin-2-yl}benzenesulfonamide |
| 69 | 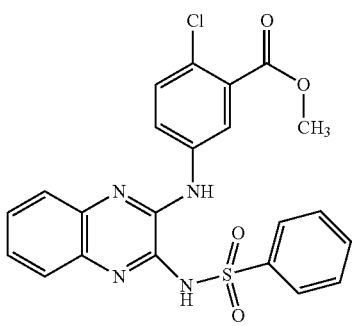 [SMILES: COC(=O)c1cc(Nc2nc3ccccc3nc2NS(=O)(=O)c2ccccc2)ccc1Cl] | methyl 2-chloro-5-({3-[(phenylsulfonyl)amino]quinoxalin-2-yl}amino)benzoate |
| 70 | 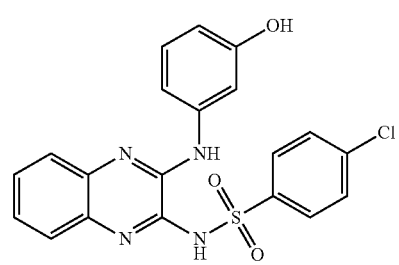 | 4-chloro-N-{3-[(3-hydroxyphenyl)amino]quinoxalin-2-yl)benzenesulfonamide |

TABLE 1-continued

| Cpd. No. | Structure | IUPAC Name |
|---|---|---|
| 71 | 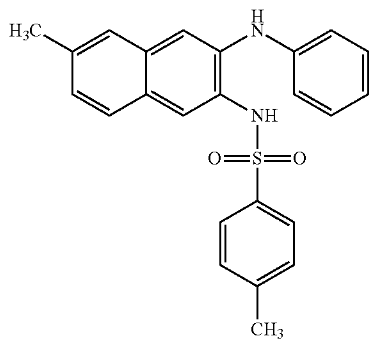 [SMILES: Cc1ccc(S(=O)(=O)Nc2cc3ccc(C)cc3cc2Nc2ccccc2)cc1] | 4-methyl-N-[6-methyl-3-(phenylamino)quinoxalin-2-yl]benzenesulfonamide |
| 72 | 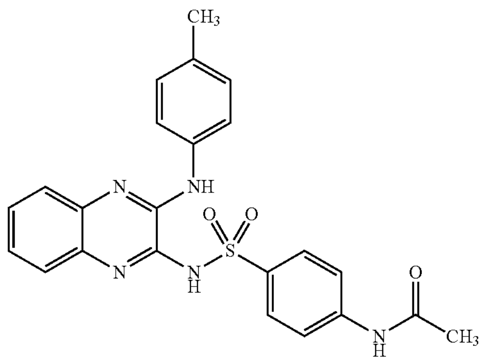 [SMILES: CC(=O)Nc1ccc(S(=O)(=O)Nc2nc3ccccc3nc2Nc2ccc(C)cc2)cc1] | N-{4-[({3-[(4-methylphenyl)amino]quinoxalin-2-yl}amino)sulfonyl]phenyl}acetamide |
| 73 | 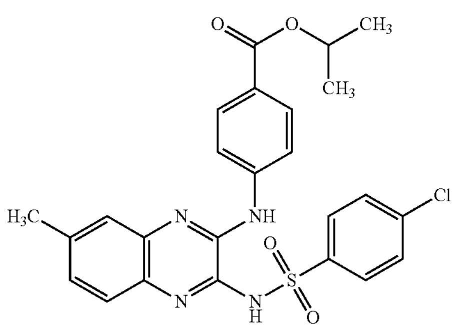 [SMILES: Cc1ccc2nc(NS(=O)(=O)c3ccc(Cl)cc3)c(Nc3ccc(C(=O)OC(C)C)cc3)nc2c1] | 1-methylethyl 4-[(3-{[(4-chlorophenyl)sulfonyl]amino}-7-methylquinoxalin-2-yl)amino]benzoate |
| 74 | 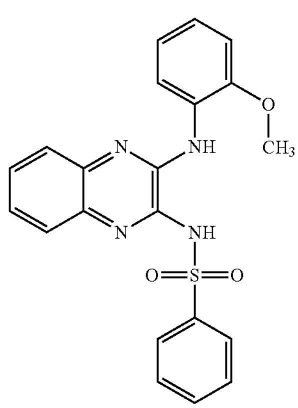 [SMILES: COc1ccccc1Nc1nc2ccccc2nc1NS(=O)(=O)c1ccccc1] | N-(3-{[2-(methyloxy)phenyl]amino}quinoxalin-2-yl)benzenesulfonamide |

TABLE 1-continued

| Cpd. No. | Structure | IUPAC Name |
|---|---|---|
| 75 | 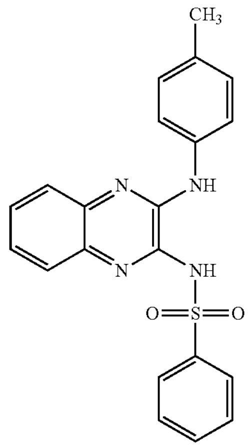 | N-{3-[(4-methylphenyl)amino]quinoxalin-2-yl)benzenesulfonamide |
| 76 | 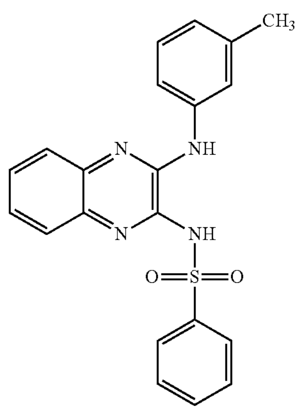 [SMILES: Cc1cccc(Nc2nc3ccccc3nc2NS(=O)(=O)c2ccccc2)c1] | N-{3-[(3-methylphenyl)amino]quinoxalin-2-yl}benzenesulfonamide |
| 77 | 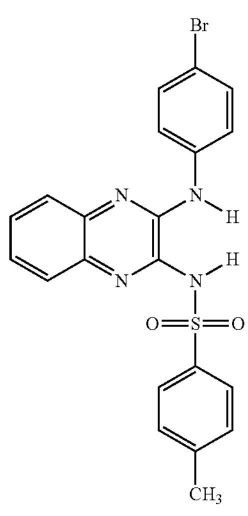 [SMILES: Cc1ccc(S(=O)(=O)Nc2nc3ccccc3nc2Nc2ccc(Br)cc2)cc1] | N-{3-[(4-bromophenyl)amino]quinoxalin-2-yl}-4-methylbenzenesulfonamide |

TABLE 1-continued

| Cpd. No. | Structure | IUPAC Name |
|---|---|---|
| 78 | 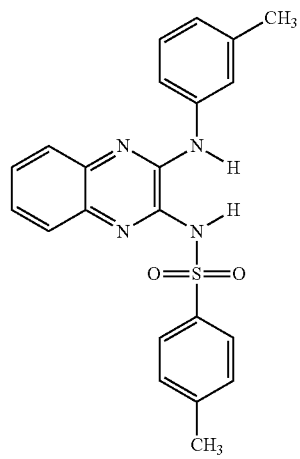 [SMILES: Cc1ccc(S(=O)(=O)Nc2nc3ccccc3nc2Nc2cccc(C)c2)cc1] | 4-methyl-N-{3-[(3-methylphenyl)amino]quinoxalin-2-yl}benzenesulfonamide |
| 79 | 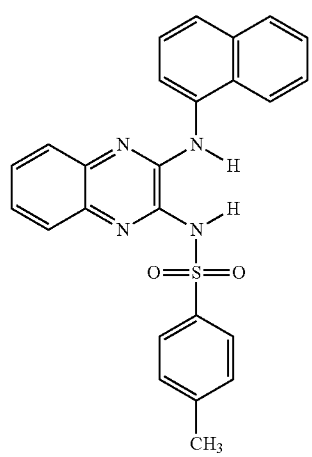 [SMILES: Cc1ccc(S(=O)(=O)Nc2nc3ccccc3nc2Nc2cccc3ccccc23)cc1] | 4-methyl-N-[3-(naphthalen-1-ylamino)quinoxalin-2-yl]benzenesulfonamide |
| 80 | 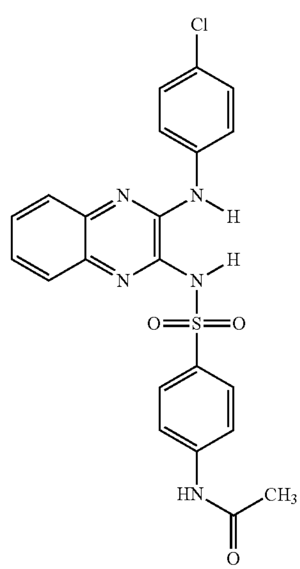 [SMILES: CC(=O)Nc1ccc(S(=O)(=O)Nc2nc3ccccc3nc2Nc2ccc(Cl)cc2)cc1] | N-{4-[({3-[(4-chlorophenyl)amino]quinoxalin-2-yl}amino)sulfonyl]phenyl}acetamide |

TABLE 1-continued

| Cpd. No. | Structure | IUPAC Name |
|---|---|---|
| 81 | 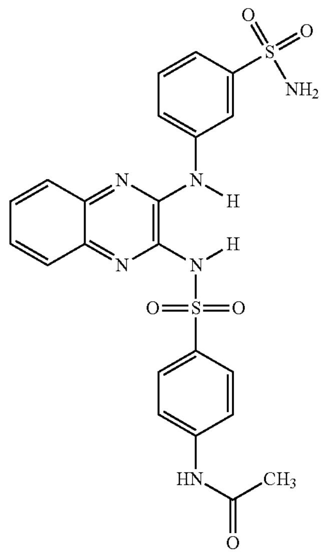 [SMILES: CC(=O)Nc1ccc(S(=O)(=O)Nc2nc3ccccc3nc2Nc2cccc(S(N)(=O)=O)c2)cc1] | N-(4-{[(3-{[3-(aminosulfonyl)phenyl]amino}quinoxalin-2-yl)amino]sulfonyl}phenyl)acetamide |
| 82 | 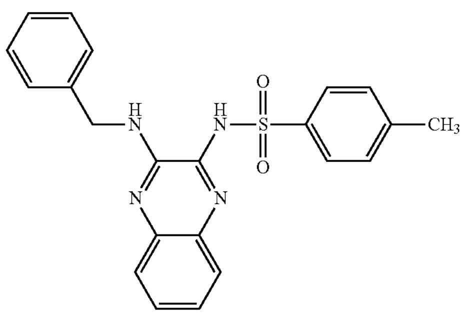 [SMILES: Cc1ccc(S(=O)(=O)Nc2nc3ccccc3nc2NCc2ccccc2)cc1] | 4-methyl-N-{3-[(phenylmethyl)amino]quinoxalin-2-yl}benzenesulfonamide |
| 83 | 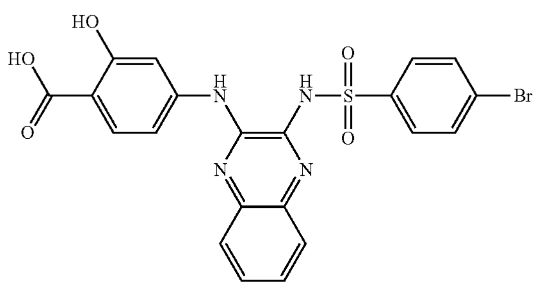 [SMILES: O=C(O)c1ccc(Nc2nc3ccccc3nc2NS(=O)(=O)c2ccc(Br)cc2)cc1O] | 4-[(3-{[(4-bromophenyl)sulfonyl]amino}quinoxalin-2-yl)amino]-2-hydroxybenzoic acid |
| 84 | 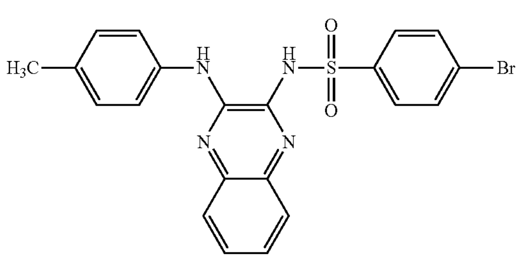 [SMILES: Cc1ccc(Nc2nc3ccccc3nc2NS(=O)(=O)c2ccc(Br)cc2)cc1] | 4-bromo-N-{3-[(4-methylphenyl)amino]quinoxalin-2-yl}benzenesulfonamide |

TABLE 1-continued

| Cpd. No. | Structure | IUPAC Name |
|---|---|---|
| 85 | 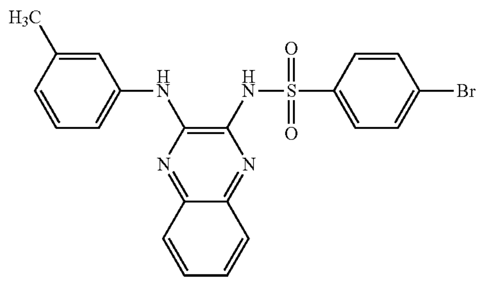 [SMILES: Cc1cccc(Nc2nc3ccccc3nc2NS(=O)(=O)c2ccc(Br)cc2)c1] | 4-bromo-N-{3-[(3-methylphenyl)amino]quinoxalin-2-yl}benzenesulfonamide |
| 86 | 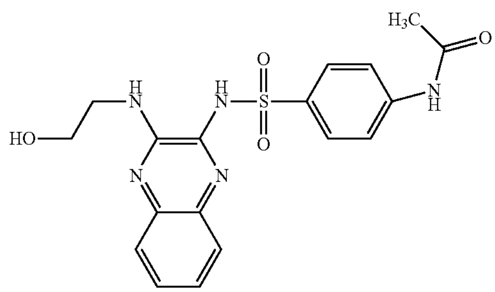 [SMILES: CC(=O)Nc1ccc(S(=O)(=O)Nc2nc3ccccc3nc2NCCO)cc1] | N-{4-[({3-[(2-hydroxyethyl)amino]quinoxalin-2-yl}amino)sulfonyl]phenyl}acetamide |
| 87 | 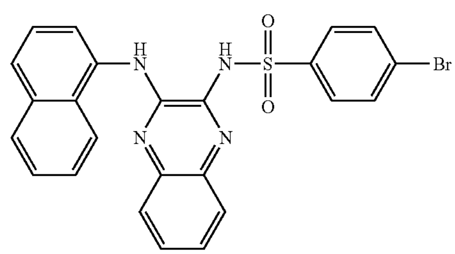 [SMILES: O=S(=O)(Nc1nc2ccccc2nc1Nc1cccc2ccccc12)c1ccc(Br)cc1] | 4-bromo-N-[3-(naphthalen-1-ylamino)quinoxalin-2-yl]benzenesulfonamide |
| 88 | 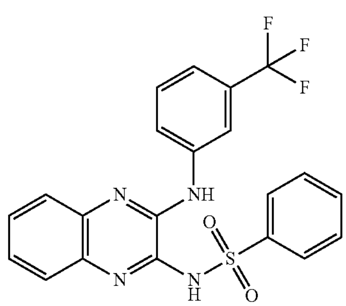 [SMILES: O=S(=O)(Nc1nc2ccccc2nc1Nc1cccc(C(F)(F)F)c1)c1ccccc1] | N-(3-{[3-(trifluoromethyl)phenyl]amino}quinoxalin-2-yl)benzenesulfonamide |
| 89 | 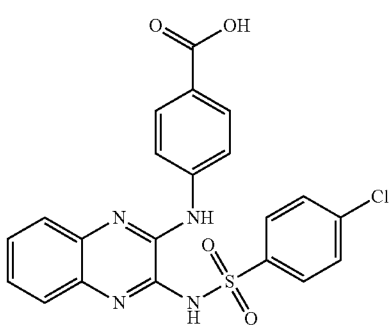 [SMILES: O=C(O)c1ccc(Nc2nc3ccccc3nc2NS(=O)(=O)c2ccc(Cl)cc2)cc1] | 4-[(3-{[(4-chlorophenyl)sulfonyl]amino}quinoxalin-2-yl)amino]benzoic acid |

TABLE 1-continued

| Cpd. No. | Structure | IUPAC Name |
|---|---|---|
| 90 | 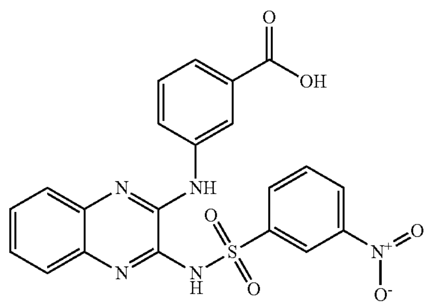 [SMILES: O=C(O)c1cccc(Nc2nc3ccccc3nc2NS(=O)(=O)c2cccc([N+](=O)[O-])c2)c1] | 3-[(3-{[(3-nitrophenyl)sulfonyl]amino}quinoxalin-2-yl)amino]benzoic acid |
| 91 | 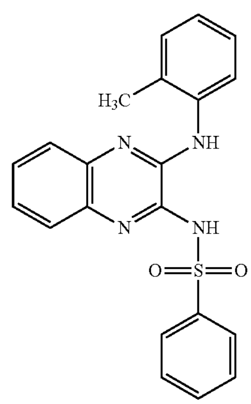 [SMILES: Cc1ccccc1Nc1nc2ccccc2nc1NS(=O)(=O)c1ccccc1] | N-{3-[(2-methylphenyl)amino]quinoxalin-2-yl}benzenesulfonamide |
| 92 | 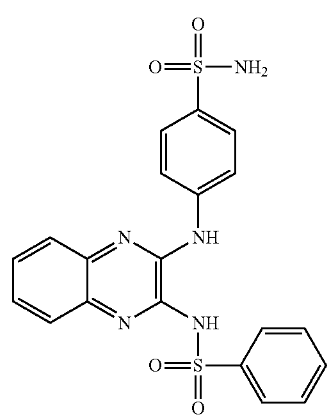 [SMILES: NS(=O)(=O)c1ccc(Nc2nc3ccccc3nc2NS(=O)(=O)c2ccccc2)cc1] | 4-({3-[(phenylsulfonyl)amino]quinoxalin-2-yl}amino)benzenesulfonamide |
| 93 | 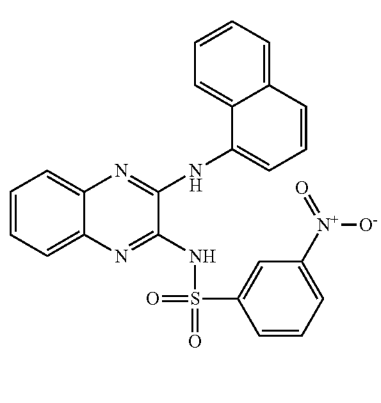 [SMILES: O=[N+]([O-])c1cccc(S(=O)(=O)Nc2nc3ccccc3nc2Nc2cccc3ccccc23)c1] | N-[3-(naphthalen-1-ylamino)quinoxalin-2-yl]-3-nitrobenzenesulfonamide |

TABLE 1-continued
| Cpd. No. | Structure | IUPAC Name |
|---|---|---|
| 94 | 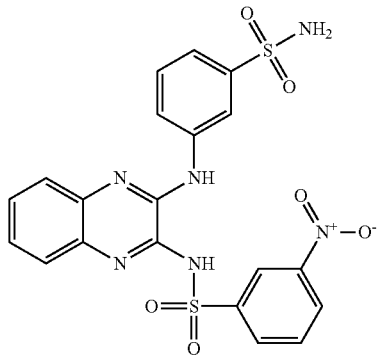 [SMILES: NS(=O)(=O)c1cccc(Nc2nc3ccccc3nc2NS(=O)(=O)c2cccc([N+](=O)[O-])c2)c1] | N-(3-{[3-(aminosulfonyl)phenyl]amino}quinoxalin-2-yl)-3-nitrobenzenesulfonamide |
| 95 | 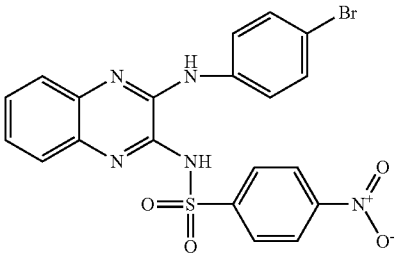 [SMILES: O=[N+]([O-])c1ccc(S(=O)(=O)Nc2nc3ccccc3nc2Nc2ccc(Br)cc2)cc1] | N-{3-[(4-bromophenyl)amino]quinoxalin-2-yl}-4-nitrobenzenesulfonamide |
| 96 | 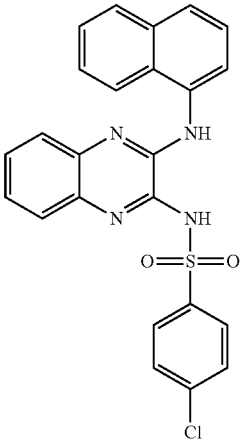 [SMILES: O=S(=O)(Nc1nc2ccccc2nc1Nc1cccc2ccccc12)c1ccc(Cl)cc1] | 4-chloro-N-[3-(naphthalen-1-ylamino)quinoxalin-2-yl]benzenesulfonamide |
| 97 | 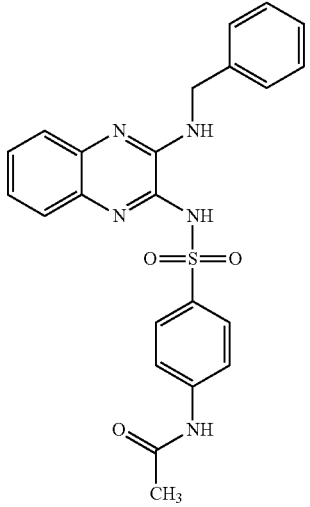 [SMILES: CC(=O)Nc1ccc(S(=O)(=O)Nc2nc3ccccc3nc2NCc2ccccc2)cc1] | N-{4-[({3-[(phenylmethyl)amino]quinoxalin-2-yl}amino)sulfonyl]phenyl}acetamide |

TABLE 1-continued
| Cpd. No. | Structure | IUPAC Name |
|---|---|---|
| 98 | 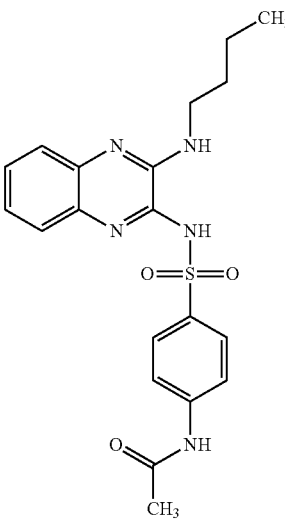 | N-[4-({[3-(butylamino)quinoxalin-2-yl]amino}sulfonyl)phenyl]acetamide |
| 99 | 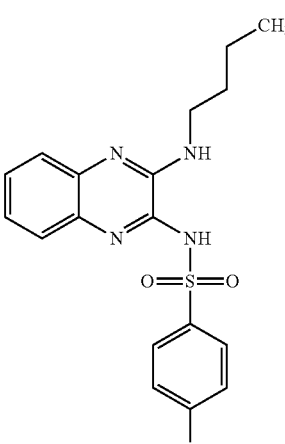 | N-[3-(butylamino)quinoxalin-2-yl]-4-methylbenzenesulfonamide |
| 100 | 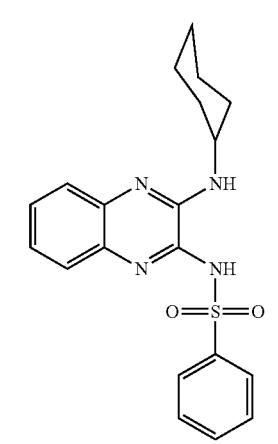 [SMILES: O=S(=O)(Nc1nc2ccccc2nc1NC1CCCCC1)c1ccccc1] | N-[3-(cyclohexylamino)quinoxalin-2-yl]benzenesulfonamide |

TABLE 1-continued

| Cpd. No. | Structure | IUPAC Name |
|---|---|---|
| 101 | 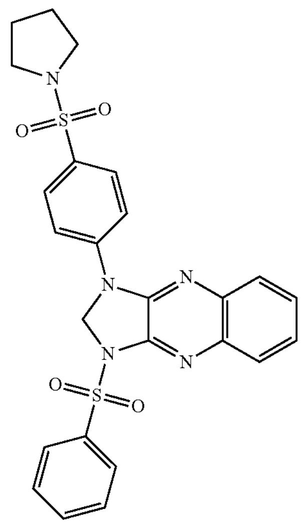 [SMILES: O=S(=O)(c1ccc(N2CN(S(=O)(=O)c3ccccc3)c3nc4ccccc4nc32)cc1)N1CCCC1] | 1-(phenylsulfonyl)-3-[4-(pyrrolidin-1-ylsulfonyl)phenyl]-2,3-dihydro-1H-imidazo[4,5-d]quinoxaline |
| 102 | 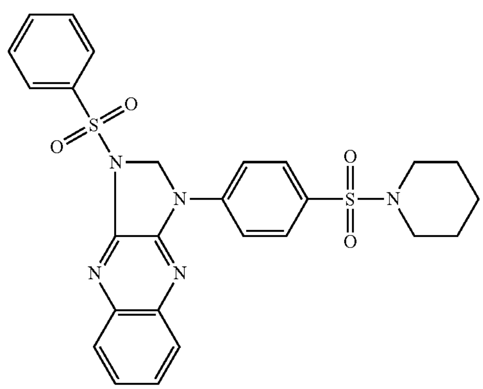 [SMILES: O=S(=O)(c1ccc(N2CN(S(=O)(=O)c3ccccc3)c3nc4ccccc4nc32)cc1)N1CCCCC1] | 1-(phenylsulfonyl)-3-[4-(piperidin-1-ylsulfonyl)phenyl]-2,3-dihydro-1H-imidazo[4,5-d]quinoxaline |
| 103 | 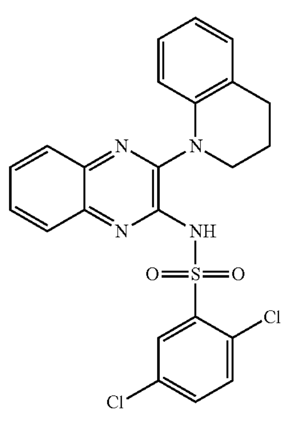 [SMILES: O=S(=O)(Nc1nc2ccccc2nc1N1CCCc2ccccc21)c1cc(Cl)ccc1Cl] | 2,5-dichloro-N-[3-(3,4-dihydroquinolin-1(2H)quinoxalin-2-yl]benzenesulfonamide |

TABLE 1-continued

| Cpd. No. | Structure | IUPAC Name |
|---|---|---|
| 104 | 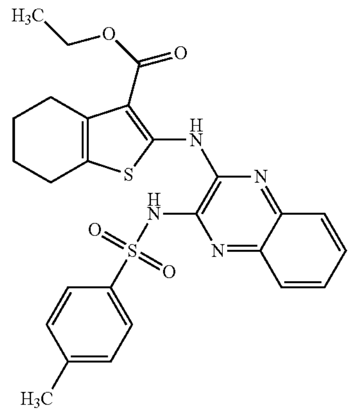 [SMILES: CCOC(=O)c1c(Nc2nc3ccccc3nc2NS(=O)(=O)c2ccc(C)cc2)sc2c1CCCC2] | ethyl 2-[(3-{[(4-methylphenyl)sulfonyl]amino}quinoxalin-2-yl)amino]-4,5,6,7-tetrahydro-1-benzothisophene-3-carboxylate |
| 105 | 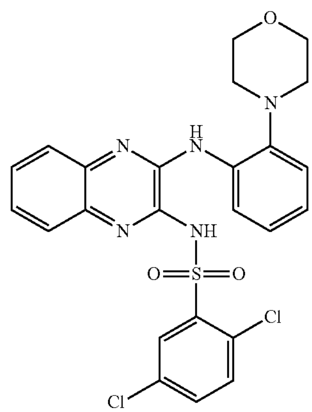 [SMILES: O=S(=O)(Nc1nc2ccccc2nc1Nc1ccccc1N1CCOCC1)c1cc(Cl)ccc1Cl] | 2,5-dichloro-N-{3-[(2-morpholin-4-ylphenyl)amino]quinoxalin-2-yl}benzenesulfonamide |
| 106 | 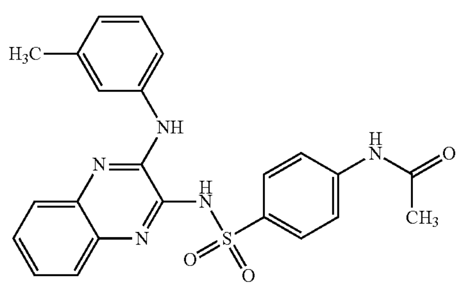 [SMILES: CC(=O)Nc1ccc(S(=O)(=O)Nc2nc3ccccc3nc2Nc2cccc(C)c2)cc1] | N-{4-[({3-[(3-methylphenyl)amino]quinoxalin-2-yl}amino)sulfonyl]phenyl}acetamide |
| 107 | 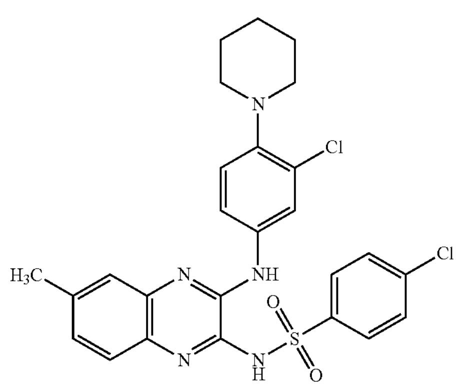 [SMILES: Cc1ccc2nc(NS(=O)(=O)c3ccc(Cl)cc3)c(Nc3ccc(N4CCCCC4)c(Cl)c3)nc2c1] | 4-chloro-N-{3-[(3-chloro-4-piperidin-1-ylphenyl)amino]-6-methylquinoxalin-2-yl}benzenesulfonamide |

TABLE 1-continued

| Cpd. No. | Structure | IUPAC Name |
|---|---|---|
| 108 | 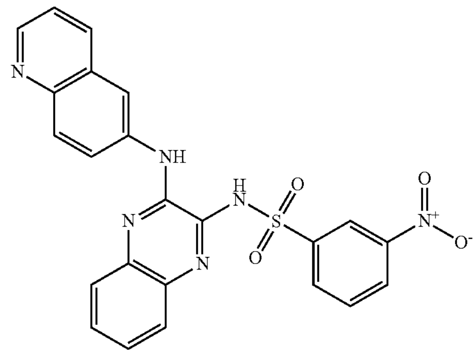 [SMILES: O=[N+]([O-])c1cccc(S(=O)(=O)Nc2nc3ccccc3nc2Nc2ccc3ncccc3c2)c1] | 3-nitro-N-[3-(quinolin-6-ylamino)quinoxalin-2-yl]benzenesulfonamide |
| 109 | 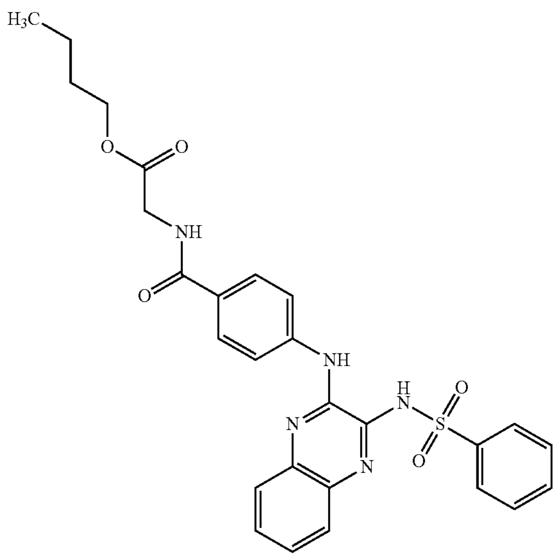 [SMILES: CCCCOC(=O)CNC(=O)c1ccc(Nc2nc3ccccc3nc2NS(=O)(=O)c2ccccc2)cc1] | butyl N-{[4-({3-[(phenylsulfonyl)amino]quinoxalin-2-yl}amino)phenyl]carbonyl}glycinate |
| 110 | 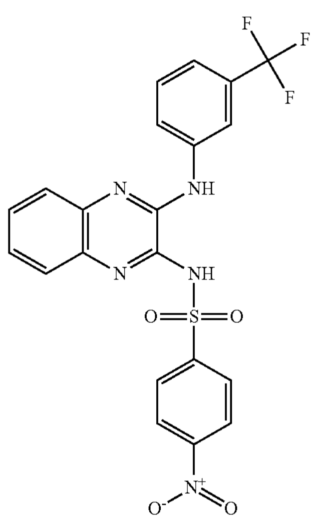 [SMILES: O=[N+]([O-])c1ccc(S(=O)(=O)Nc2nc3ccccc3nc2Nc2cccc(C(F)(F)F)c2)cc1] | 4-nitro-N-(3-{[3-(trifluoromethyl)phenyl]amino}quinoxalin-2-yl)benzenesulfonamide |

TABLE 1-continued

| Cpd. No. | Structure | IUPAC Name |
|---|---|---|
| 111 | 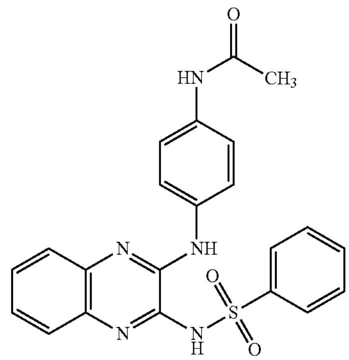 [SMILES: CC(=O)Nc1ccc(Nc2nc3ccccc3nc2NS(=O)(=O)c2ccccc2)cc1] | N-[4-({3-[(phenylsulfonyl)amino]quinoxalin-2-yl}amino)phenyl]acetamide |
| 112 | 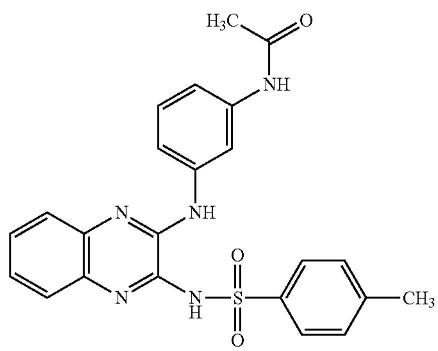 [SMILES: CC(=O)Nc1cccc(Nc2nc3ccccc3nc2NS(=O)(=O)c2ccc(C)cc2)c1] | N-{3-[(3-{[(4-methylphenyl)sulfonyl]amino}quinoxalin-2-yl)amino]phenyl}acetamide |
| 113 | 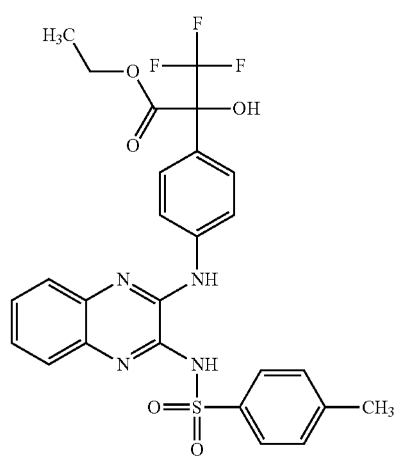 [SMILES: CCOC(=O)C(O)(c1ccc(Nc2nc3ccccc3nc2NS(=O)(=O)c2ccc(C)cc2)cc1)C(F)(F)F] | ethyl 3,3,3-trifluoro-2-hydroxy-2-{4-[(3-{[(4-methylphenyl)sulfonyl]amino}quinoxalin-2-yl)amino]phenyl}propanoate |
| 114 | 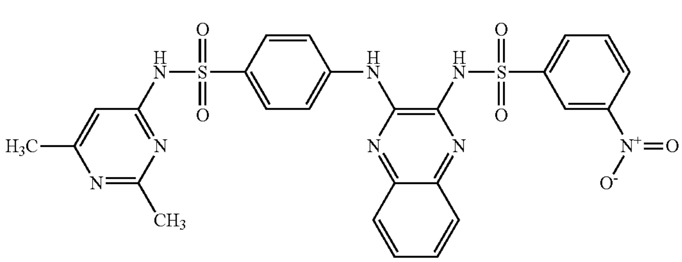 [SMILES: Cc1cc(NS(=O)(=O)c2ccc(Nc3nc4ccccc4nc3NS(=O)(=O)c3cccc([N+](=O)[O-])c3)cc2)nc(C)n1] | N-{3-[(4-{[(2,6-dimethylpyrimidin-4-yl)amino]sulfonyl}phenyl)amino]quinoxalin-2-yl}-3-nitrobenzenesulfonamide |

TABLE 1-continued

| Cpd. No. | Structure | IUPAC Name |
|---|---|---|
| 115 | 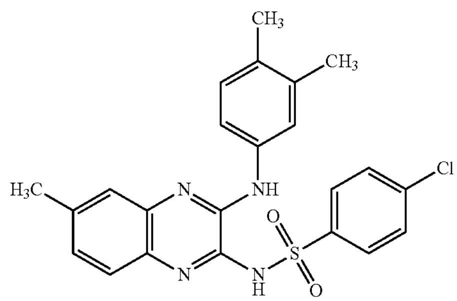 [SMILES: Cc1ccc2nc(NS(=O)(=O)c3ccc(Cl)cc3)c(Nc3ccc(C)c(C)c3)nc2c1] | 4-chloro-N-{3-[(3,4-dimethylphenyl)amino]-6-methylquinoxalin-2-yl}benzenesulfonamide |
| 116 | 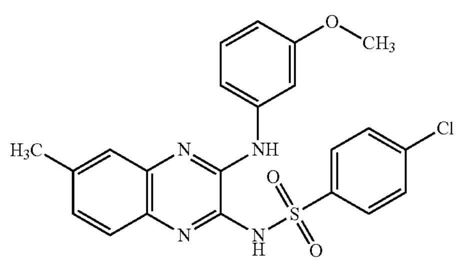 [SMILES: COc1cccc(Nc2nc3cc(C)ccc3nc2NS(=O)(=O)c2ccc(Cl)cc2)c1] | 4-chloro-N-(6-methyl-3-{[3-(methyloxy)phenyl]amino}quinoxalin-2-yl)benzenesulfonamide |
| 117 | 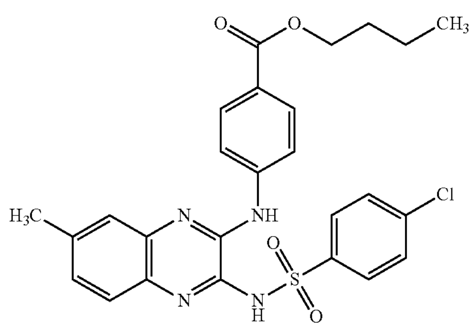 [SMILES: CCCCOC(=O)c1ccc(Nc2nc3cc(C)ccc3nc2NS(=O)(=O)c2ccc(Cl)cc2)cc1] | butyl 4-[(3-{[(4-chlorophenyl)sulfonyl]amino}-7-methylquinoxalin-2-yl)amino]benzoate |
| 118 | 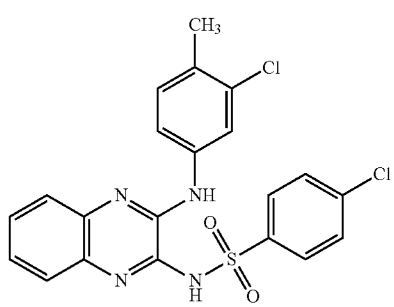 [SMILES: Cc1ccc(Nc2nc3ccccc3nc2NS(=O)(=O)c2ccc(Cl)cc2)cc1Cl] | 4-chloro-N-{3-[(3-chloro-4-methylphenyl)amino]quinoxalin-2-yl}benzenesulfonamide |
| 119 | 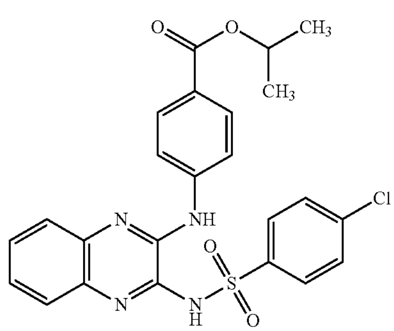 [SMILES: CC(C)OC(=O)c1ccc(Nc2nc3ccccc3nc2NS(=O)(=O)c2ccc(Cl)cc2)cc1] | 1-methylethyl 4-[(3-{[(4-chlorophenyl)sulfonyl]amino}quinoxalin-2-yl)amino]benzoate |

TABLE 1-continued

| Cpd. No. | Structure | IUPAC Name |
|---|---|---|
| 120 | 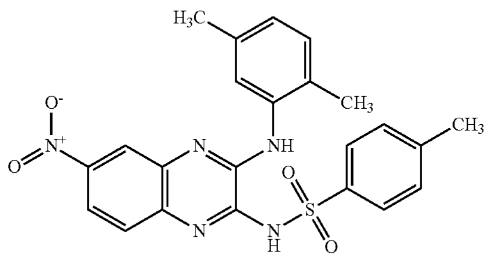 [SMILES: Cc1ccc(S(=O)(=O)Nc2nc3ccc([N+](=O)[O-])cc3nc2Nc2cc(C)ccc2C)cc1] | N-{3-[(2,5-dimethylphenyl)amino]-6-nitroquinoxalin-2-yl}-4-methylbenzenesulfonamide |
| 121 | 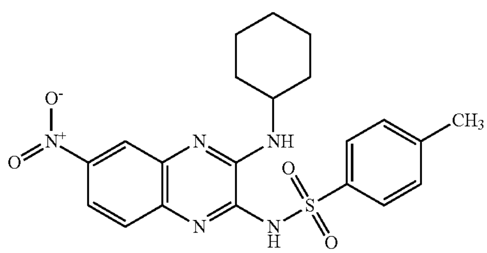 [SMILES: Cc1ccc(S(=O)(=O)Nc2nc3ccc([N+](=O)[O-])cc3nc2NC2CCCCC2)cc1] | N-[3-(6-cyclohexylamino)-6-nitroquinolin-2-yl]-4-methylbenzenesulfonamide |
| 122 | 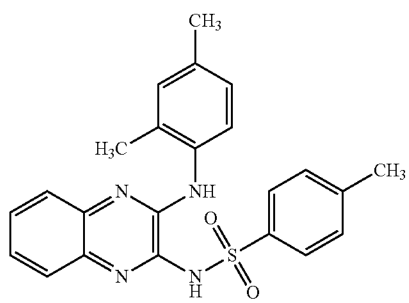 [SMILES: Cc1ccc(S(=O)(=O)Nc2nc3ccccc3nc2Nc2ccc(C)cc2C)cc1] | N-{3-[(2,4-dimethylphenyl)amino]quinoxalin-2-yl}-4-methylbenzenesulfonamide |
| 123 | 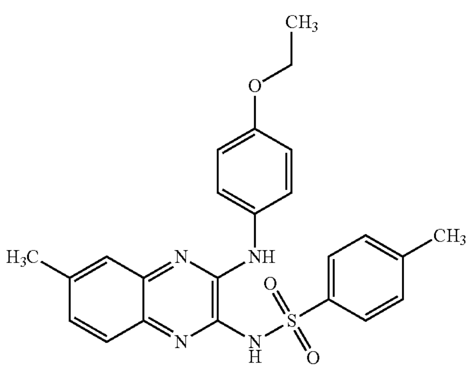 | N-(3-{[4-(ethyloxy)phenyl]amino}-6-methylquinoxalin-2-yl)-4-methylbenzenesulfonamide |
| 124 | 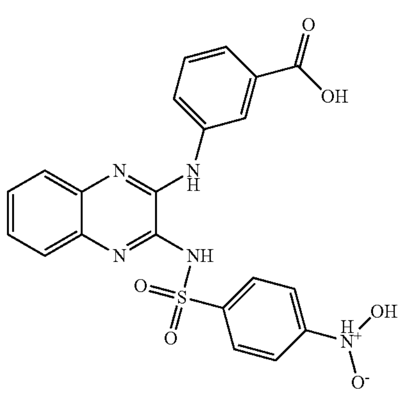 | 3-({3-[({4-[hydroxy(oxido)amino]phenyl}sulfonyl)amino]quinoxalin-2-yl}amino)benzoic acid |

TABLE 1-continued

| Cpd. No. | Structure | IUPAC Name |
|---|---|---|
| 125 | 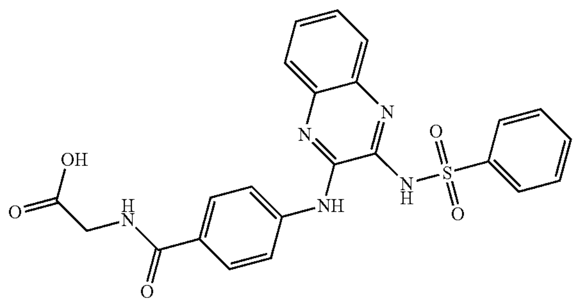 [SMILES: O=C(O)CNC(=O)c1ccc(Nc2nc3ccccc3nc2NS(=O)(=O)c2ccccc2)cc1] | N-{[4-({3-[(phenylsulfonyl)amino]quinoxalin-2-yl}amino)phenyl]carbonyl}glycine |
| 126 | 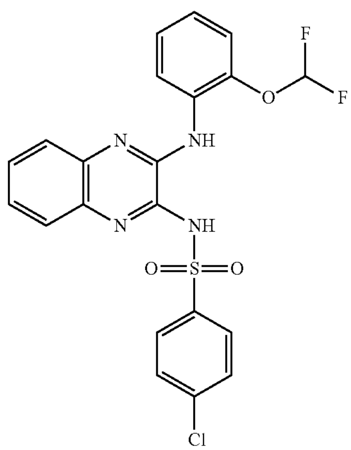 [SMILES: O=S(=O)(Nc1nc2ccccc2nc1Nc1ccccc1OC(F)F)c1ccc(Cl)cc1] | 4-chloro-N-[3-({2-[(difluoromethyl)oxy]phenyl}amino)quinoxalin-2-yl]benzenesulfonamide |
| 127 | 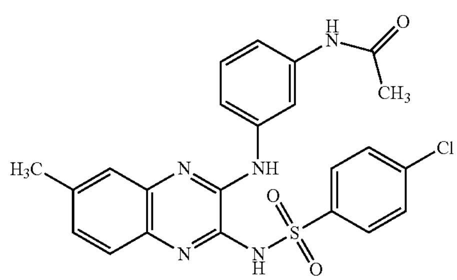 [SMILES: CC(=O)Nc1cccc(Nc2nc3cc(C)ccc3nc2NS(=O)(=O)c2ccc(Cl)cc2)c1] | N-{3-[(3-{[(4-chlorophenyl)sulfonyl]amino}-7-methylquinoxalin-2-yl)amino]phenyl}acetamide |
| 128 | 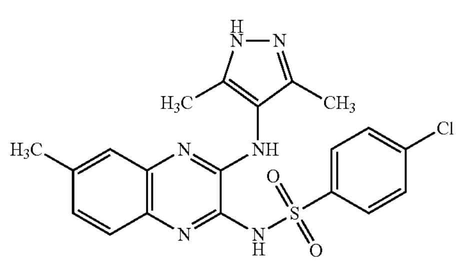 [SMILES: Cc1ccc2nc(NS(=O)(=O)c3ccc(Cl)cc3)c(Nc3c(C)n[nH]c3C)nc2c1] | 4-chloro-N-{3-[(3,5-dimethyl-1H-pyrazol-4-yl)amino]-6-methylquinoxalin-2-yl}benzenesulfonamide |

TABLE 1-continued
| Cpd. No. | Structure | IUPAC Name |
|---|---|---|
| 129 | 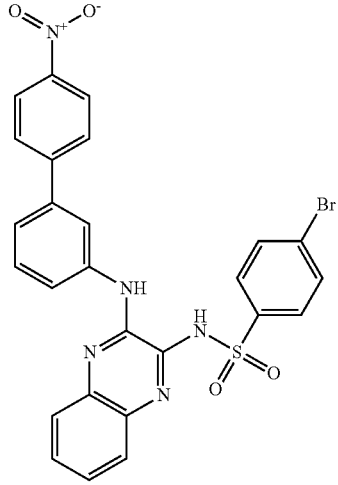 [SMILES: O=[N+]([O-])c1ccc(-c2cccc(Nc3nc4ccccc4nc3NS(=O)(=O)c3ccc(Br)cc3)c2)cc1] | 4-bromo-N-{3-[(4'-nitrobiphenyl-3-yl)amino]quinoxalin-2-yl}benzenesulfonamide |
| 130 | 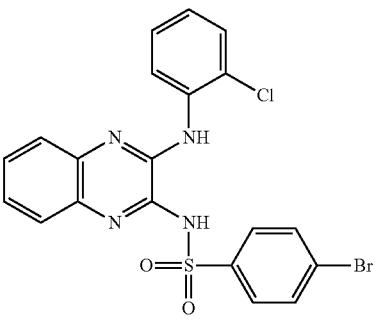 [SMILES: O=S(=O)(Nc1nc2ccccc2nc1Nc1ccccc1Cl)c1ccc(Br)cc1] | 4-bromo-N-{3-[(2-chlorophenyl)amino]quinoxalin-2-yl}benzenesulfonamide |
| 131 | 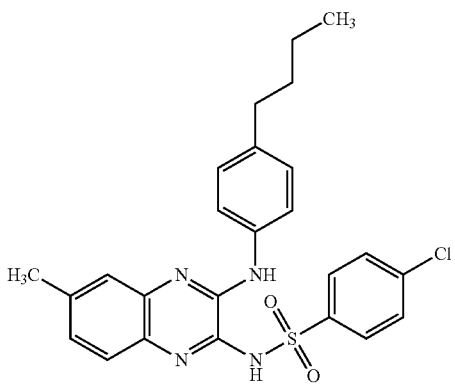 [SMILES: CCCCc1ccc(Nc2nc3cc(C)ccc3nc2NS(=O)(=O)c2ccc(Cl)cc2)cc1] | N-{3-[(4-butylphenyl)amino]-6-methylquinoxalin-2-yl}-4-chlorobenzenesulfonamide |
| 132 | 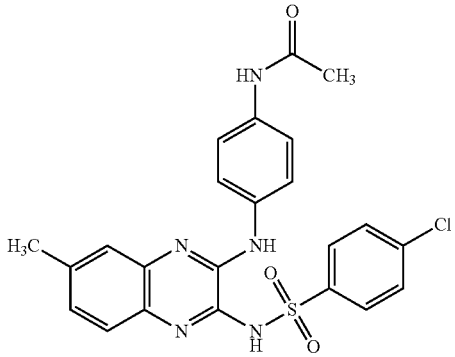 [SMILES: CC(=O)Nc1ccc(Nc2nc3cc(C)ccc3nc2NS(=O)(=O)c2ccc(Cl)cc2)cc1] | N-{4-[(3-{[(4-chlorophenyl)sulfonyl]amino}-7-methylquinoxalin-2-yl)amino]phenyl}acetamide |

TABLE 1-continued
| Cpd. No. | Structure | IUPAC Name |
|---|---|---|
| 133 | 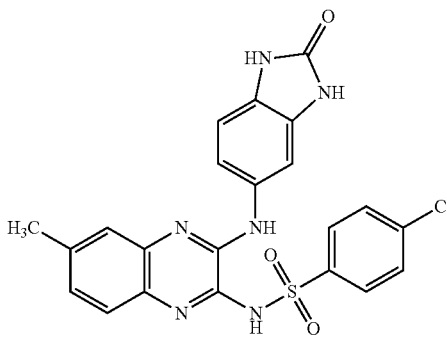 | 4-chloro-N-{6-methyl-3-[(2-oxo-2,3-dihydro-1H-benzimidazol-5-yl)amino]quinoxalin-2-yl}benzenesulfonamide |
| 134 | 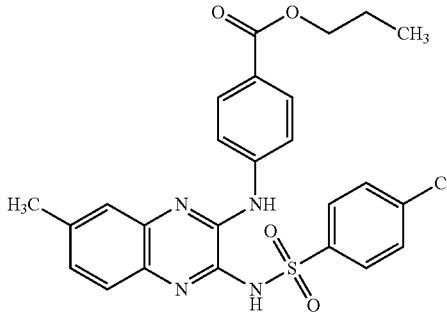 | propyl 4-[(3-{[(4-chlorophenyl)sulfonyl]amino}-7-methylquinoxalin-2-yl)amino]benzoate |
| 135 | 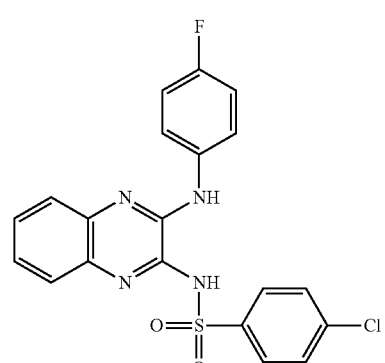 | 4-chloro-N-{3-[(4-fluorophenyl)amino]quinoxalin-2-yl}benzenesulfonamide |
| 136 | 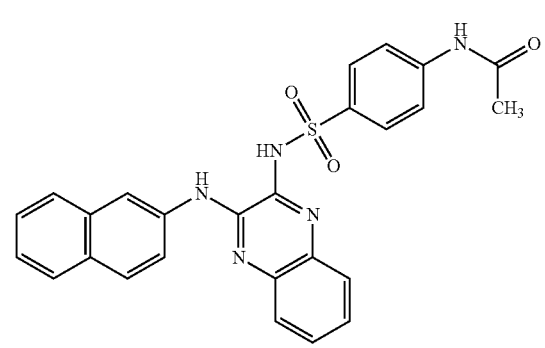 [SMILES: CC(=O)Nc1ccc(S(=O)(=O)Nc2nc3ccccc3nc2Nc2ccc3ccccc3c2)cc1] | N-[4-({[3-(naphthalen-2-ylamino)quinoxalin-2-yl]amino}sulfonyl)phenyl]acetamide |

| Cpd. No. | Structure | IUPAC Name |
|---|---|---|
| 137 | 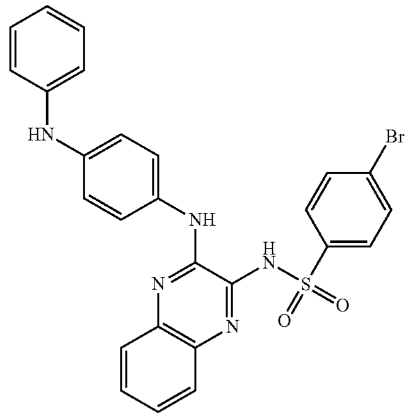 [SMILES: O=S(=O)(Nc1nc2ccccc2nc1Nc1ccc(Nc2ccccc2)cc1)c1ccc(Br)cc1] | 4-bromo-N-(3-{[4-(phenylamino)phenyl]amino}quinoxalin-2-yl)benzenesulfonamide |
| 138 | 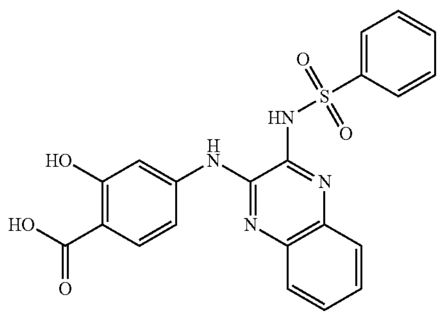 [SMILES: O=C(O)c1ccc(Nc2nc3ccccc3nc2NS(=O)(=O)c2ccccc2)cc1O] | 2-hydroxy-4-({3-[(phenylsulfonyl)amino]quinoxalin-2-yl}amino)benzoic acid |
| 139 | 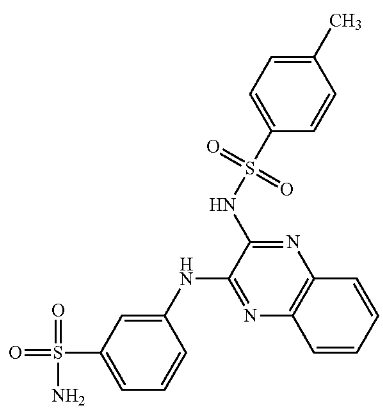 [SMILES: Cc1ccc(S(=O)(=O)Nc2nc3ccccc3nc2Nc2cccc(S(N)(=O)=O)c2)cc1] | N-(3-{[(3-nitrophenyl)sulfonyl]amino}quinoxalin-2-yl)amino]benzoic acid |
| 140 | 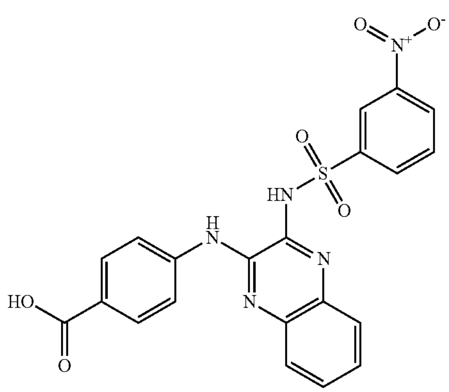 [SMILES: O=C(O)c1ccc(Nc2nc3ccccc3nc2NS(=O)(=O)c2cccc([N+](=O)[O-])c2)cc1] | 4-[(3-{[(3-nitrophenyl)sulfonyl]amino}quinoxalin-2-yl)amino]benzoic acid |

TABLE 1-continued

| Cpd. No. | Structure | IUPAC Name |
|---|---|---|
| 141 | 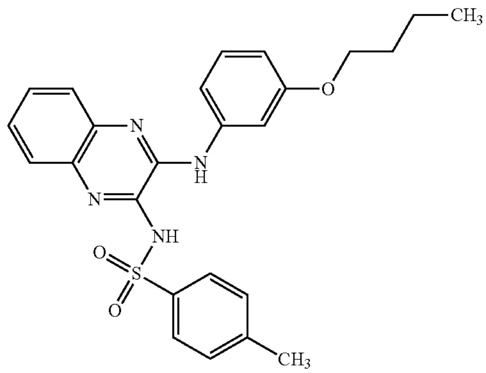 [SMILES: CCCCOc1cccc(Nc2nc3ccccc3nc2NS(=O)(=O)c2ccc(C)cc2)c1] | N-(3-{[3-(butyloxy)phenyl]amino}quinoxalin-2-yl)-4-methylbenzenesulfonamide |
| 142 | 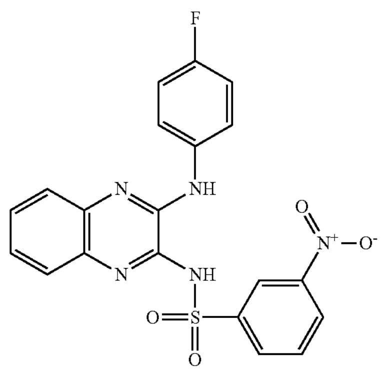 [SMILES: O=[N+]([O-])c1cccc(S(=O)(=O)Nc2nc3ccccc3nc2Nc2ccc(F)cc2)c1] | N-{3-[(4-fluorophenyl)amino]quinoxalin-2-yl}-3-nitrobenzenesulfonamide |
| 143 | 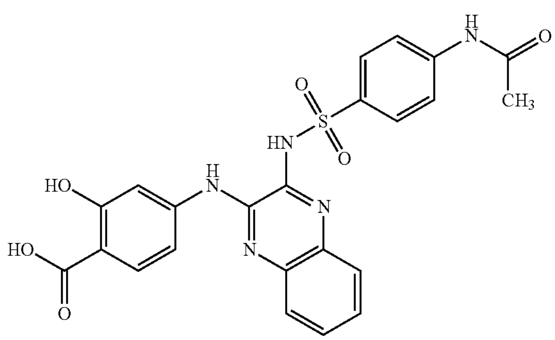 [SMILES: CC(=O)Nc1ccc(S(=O)(=O)Nc2nc3ccccc3nc2Nc2ccc(C(=O)O)c(O)c2)cc1] | 4-{[3-({[4-(acetylamino)phenyl]sulfonyl}amino)quinoxalin-2-yl]amino}-2-hydroxybenzoic acid |
| 144 | 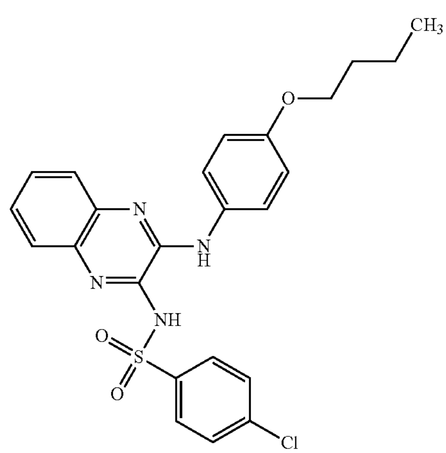 [SMILES: CCCCOc1ccc(Nc2nc3ccccc3nc2NS(=O)(=O)c2ccc(Cl)cc2)cc1] | N-(3-{[4-(butyloxy)phenyl]amino}quinoxalin-2-yl)-4-chlorobenzenesulfonamide |

TABLE 1-continued

| Cpd. No. | Structure | IUPAC Name |
|---|---|---|
| 145 | 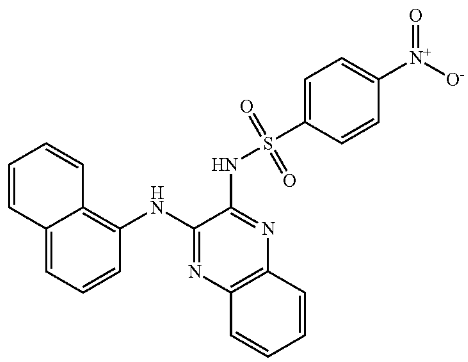 [SMILES: O=[N+]([O-])c1ccc(S(=O)(=O)Nc2nc3ccccc3nc2Nc2cccc3ccccc23)cc1] | N-[3-(naphthalen-1-ylamino)quinoxalin-2-yl]-4-nitrobenzenesulfonamide |
| 146 | 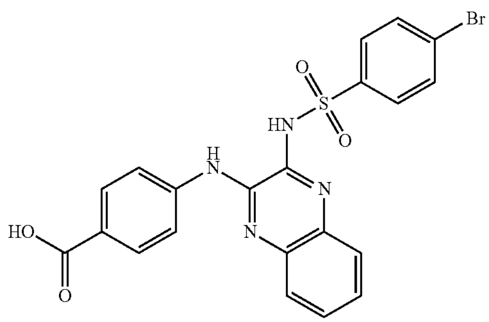 [SMILES: O=C(O)c1ccc(Nc2nc3ccccc3nc2NS(=O)(=O)c2ccc(Br)cc2)cc1] | 4-[(3-{[(4-bromophenyl)sulfonyl]amino}quinoxalin-2-yl)amino]benzoic acid |
| 147 | 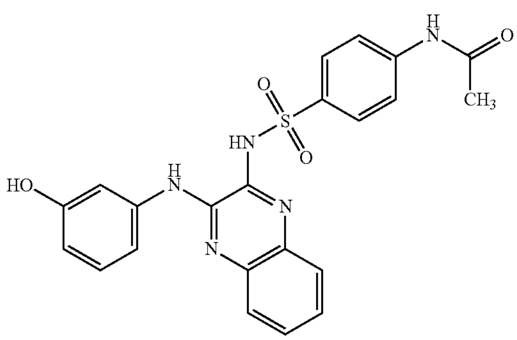 [SMILES: CC(=O)Nc1ccc(S(=O)(=O)Nc2nc3ccccc3nc2Nc2cccc(O)c2)cc1] | N-{4-[({3-[(3-hydroxyphenyl)amino]quinoxalin-2-yl}amino)sulfonyl]phenyl}acetamide |
| 148 | 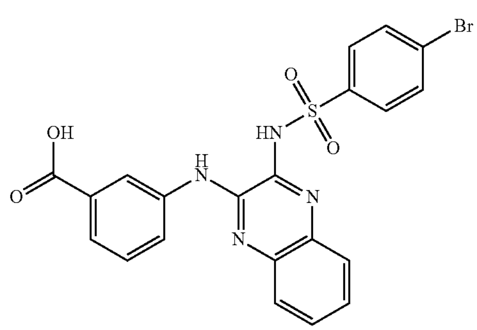 [SMILES: O=C(O)c1cccc(Nc2nc3ccccc3nc2NS(=O)(=O)c2ccc(Br)cc2)c1] | 3-[(3-{[(4-bomophenyl)sulfonyl]amino}quinoxalin-2-yl)amino]benzoic acid |

TABLE 1-continued

| Cpd. No. | Structure | IUPAC Name |
|---|---|---|
| 149 | 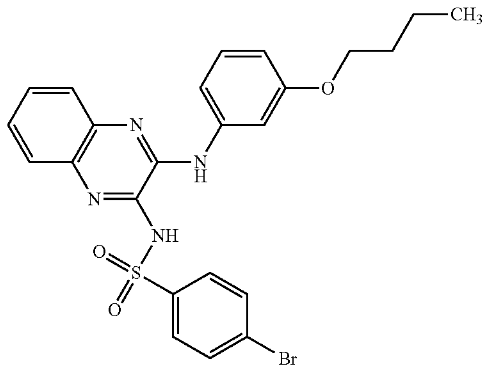 [SMILES: CCCCOc1cccc(Nc2nc3ccccc3nc2NS(=O)(=O)c2ccc(Br)cc2)c1] | 4-bromo-N-(3-{[3-(butyloxy)phenyl]amino}quinoxalin-2-yl)benzenesulfonamide |
| 150 | 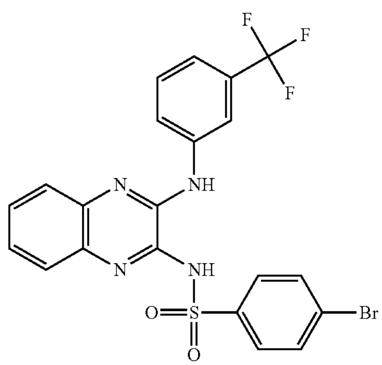 [SMILES: O=S(=O)(Nc1nc2ccccc2nc1Nc1cccc(C(F)(F)F)c1)c1ccc(Br)cc1] | 4-bromo-N-(3-{[3-(trifluoromethyl)phenyl]amino}quinoxalin-2-yl)benzenesulfonamide |
| 151 | 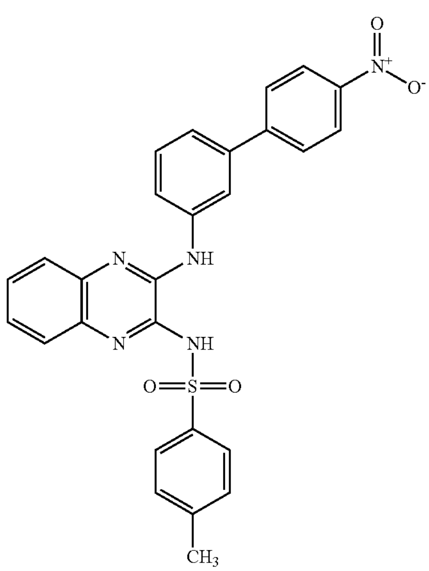 [SMILES: Cc1ccc(S(=O)(=O)Nc2nc3ccccc3nc2Nc2cccc(-c3ccc([N+](=O)[O-])cc3)c2)cc1] | 4-methyl-N-{3-[(4'-nitrobiphenyl-3-yl)amino]quinoxalin-2-yl}benzenesulfonamide |

TABLE 1-continued
| Cpd. No. | Structure | IUPAC Name |
|---|---|---|
| 152 | 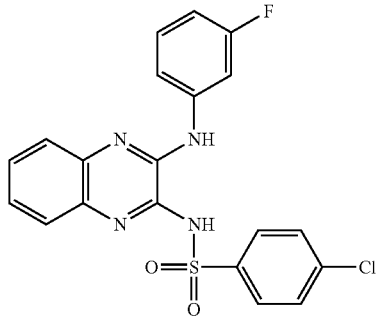 [SMILES: O=S(=O)(Nc1nc2ccccc2nc1Nc1cccc(F)c1)c1ccc(Cl)cc1] | 4-chloro-N-{3-[(3-fluorophenyl)amino]quinoxalin-2-yl}benzenesulfonamide |
| 153 | 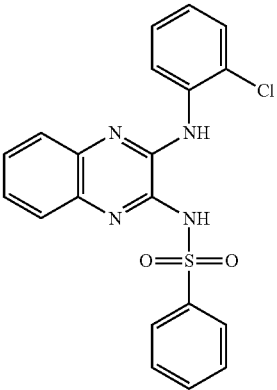 [SMILES: O=S(=O)(Nc1nc2ccccc2nc1Nc1ccccc1Cl)c1ccccc1] | N-{3-[(3-chlorophenyl)amino]quinoxalin-2-yl}benzenesulfonamide |
| 154 | 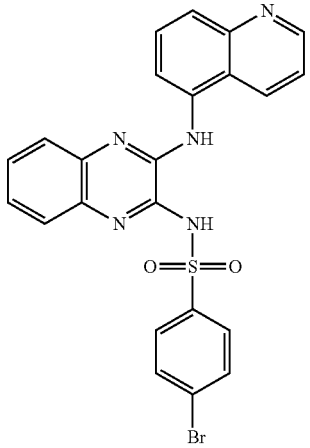 [SMILES: O=S(=O)(Nc1nc2ccccc2nc1Nc1cccc2ncccc12)c1ccc(Br)cc1] | 4-bromo-N-[3-(quinolin-5-ylamino)quinoxalin-2-yl]benzenesulfonamide |
| 155 | 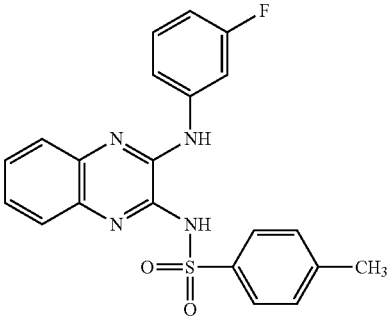 [SMILES: Cc1ccc(S(=O)(=O)Nc2nc3ccccc3nc2Nc2cccc(F)c2)cc1] | N-{3-[(3-fluorophenyl)amino]quinoxalin-2-yl}-4-methylbenzenesulfonamide |

TABLE 1-continued
| Cpd. No. | Structure | IUPAC Name |
|---|---|---|
| 156 | 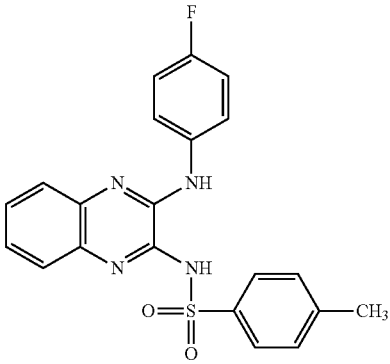 [SMILES: Cc1ccc(S(=O)(=O)Nc2nc3ccccc3nc2Nc2ccc(F)cc2)cc1] | N-{3-[(4-fluorophenyl)amino]quinoxalin-2-yl}-4-methylbenzenesulfonamide |
| 157 | 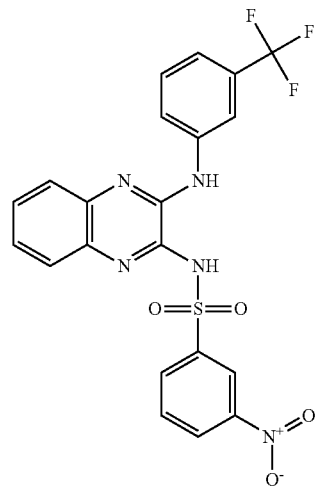 [SMILES: O=[N+]([O-])c1cccc(S(=O)(=O)Nc2nc3ccccc3nc2Nc2cccc(C(F)(F)F)c2)c1] | 3-nitro-N-(3-{[3-(trifluoromethyl)phenyl]amino}quinoxalin-2-yl)benzenesulfonamide |
| 158 | 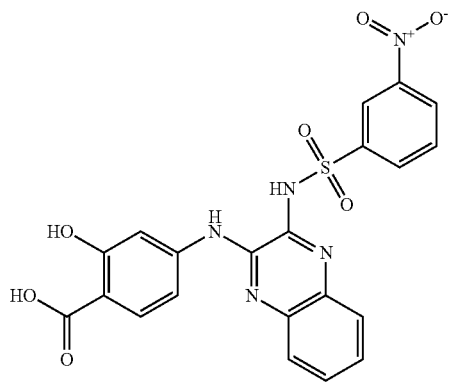 [SMILES: O=C(O)c1ccc(Nc2nc3ccccc3nc2NS(=O)(=O)c2cccc([N+](=O)[O-])c2)cc1O] | 2-hydroxy-4-[(3-{[(3-nitrophenyl)sulfonyl]amino}quinoxalin-2-yl)amino]benzoic acid |
| 159 | 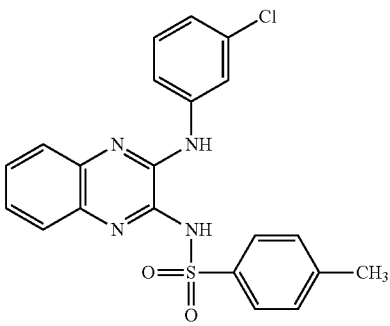 | N-{3-[(3-chlorophenyl)amino]quinoxalin-2-yl}-4-methylbenzenesulfonamide |

TABLE 1-continued

| Cpd. No. | Structure | IUPAC Name |
|---|---|---|
| 160 | 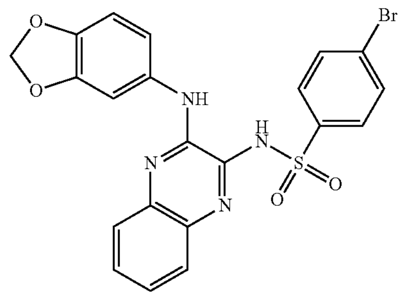 [SMILES: O=S(=O)(Nc1nc2ccccc2nc1Nc1ccc2c(c1)OCO2)c1ccc(Br)cc1] | N-[3-(1,3-benzodisoxol-5-ylamino)quinoxalin-2-yl]-4-bromobenzenesulfonamide |
| 161 | 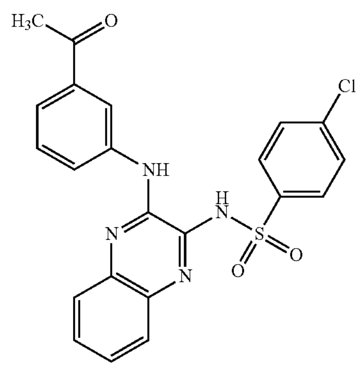 [SMILES: CC(=O)c1cccc(Nc2nc3ccccc3nc2NS(=O)(=O)c2ccc(Cl)cc2)c1] | N-{3-[(3-acetylphenyl)amino]quinoxalin-2-yl}-2-chlorobenzenesulfonamide |
| 162 | 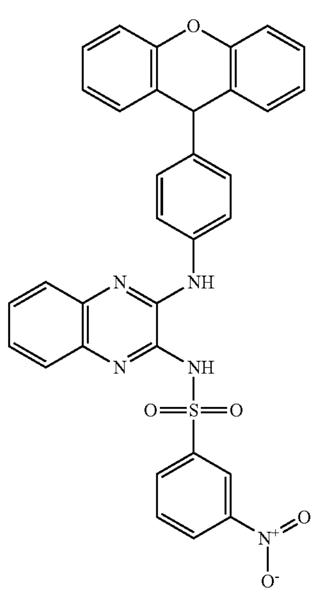 [SMILES: O=[N+]([O-])c1cccc(S(=O)(=O)Nc2nc3ccccc3nc2Nc2ccc(C3c4ccccc4Oc4ccccc43)cc2)c1] | 3-nitro-N-(3-{[4-(9H-xanthen-9-yl)phenyl]amino}quinoxalin-2-yl)benzenesulfonamide |

TABLE 1-continued

| Cpd. No. | Structure | IUPAC Name |
| --- | --- | --- |
| 163 | 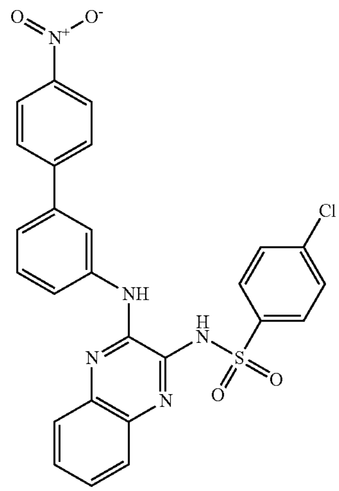 [SMILES: O=[N+]([O-])c1ccc(-c2cccc(Nc3nc4ccccc4nc3NS(=O)(=O)c3ccc(Cl)cc3)c2)cc1] | 4-chloro-N-{3-[(4'-nitrophenyl-3-yl)amino]quinoxalin-2-yl}benzenesulfonamide |
| 164 | 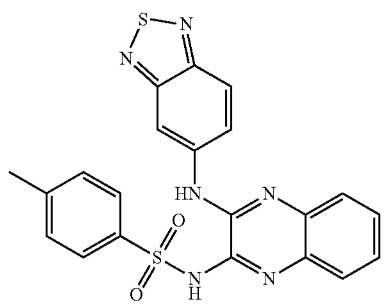 [SMILES: Cc1ccc(S(=O)(=O)Nc2nc3ccccc3nc2Nc2ccc3nsnc3c2)cc1] | N-[3-(2,1,3-benzothiadiazol-5-ylamino)quinoxalin-2-yl]-5-tolylsulfonamide |
| 165 | 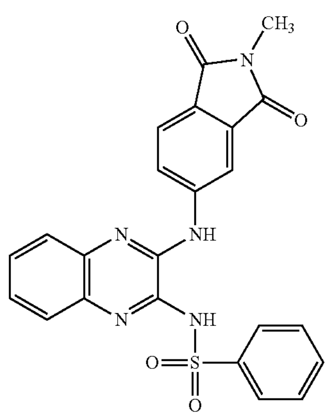 [SMILES: CN1C(=O)c2ccc(Nc3nc4ccccc4nc3NS(=O)(=O)c3ccccc3)cc2C1=O] | N-{3-[(2-methyl-1,3-disoxo-2,3-dihydro-1H-isoindol-5-yl)amino]quinoxalin-2-yl}benzenesulfonamide |
| 166 | 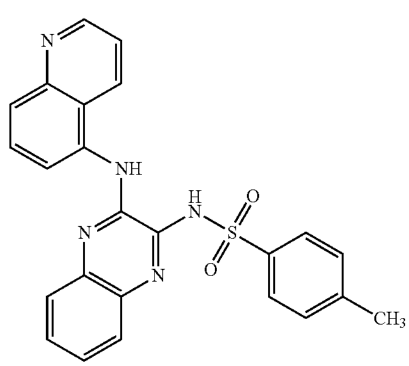 [SMILES: Cc1ccc(S(=O)(=O)Nc2nc3ccccc3nc2Nc2cccc3ncccc23)cc1] | 4-methyl-N-[3-(quinolin-5-ylamino)quinoxalin-2-yl]benzenesulfonamide |

TABLE 1-continued
| Cpd. No. | Structure | IUPAC Name |
|---|---|---|
| 167 | 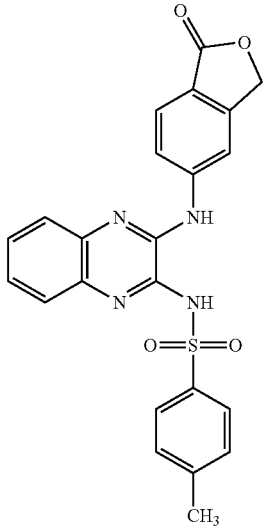 [SMILES: Cc1ccc(S(=O)(=O)Nc2nc3ccccc3nc2Nc2ccc3c(c2)COC3=O)cc1] | 4-methyl-N-{3-[(1-oxo-1,3-dihydro-2-benzofuran-5-yl)amino]quinoxalin-2-yl}benzenesulfonamide |
| 168 | 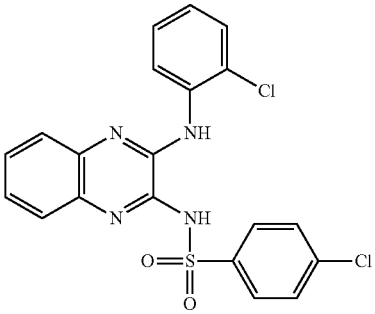 [SMILES: O=S(=O)(Nc1nc2ccccc2nc1Nc1ccccc1Cl)c1ccc(Cl)cc1] | 4-chloro-N-{3-[(2-chlorophenyl)amino]quinoxalin-2-yl}benzenesulfonamide |
| 169 | 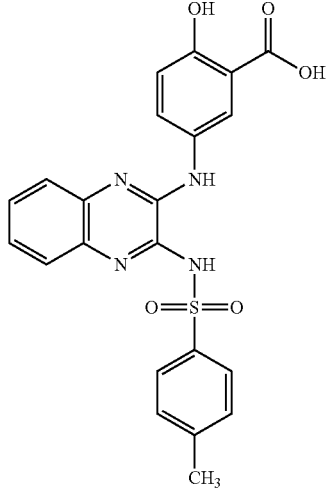 [SMILES: Cc1ccc(S(=O)(=O)Nc2nc3ccccc3nc2Nc2ccc(O)c(C(=O)O)c2)cc1] | 2-hydroxy-5-[(3-{[(4-methylphenyl)sulfonyl]amino}quinoxalin-2-yl)amino]benzoic acid |

TABLE 1-continued
| Cpd. No. | Structure | IUPAC Name |
|---|---|---|
| 170 | 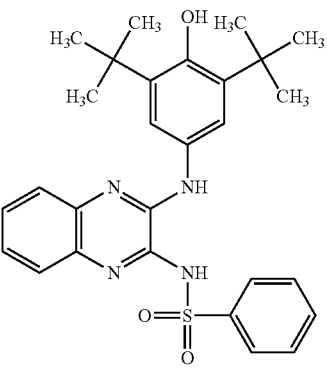 [SMILES: CC(C)(C)c1cc(Nc2nc3ccccc3nc2NS(=O)(=O)c2ccccc2)cc(C(C)(C)C)c1O] | N-(3-{[3,5-bis(1,1-dimethylethyl)-4-hydroxyphenyl]amino}quinoxalin-2-yl)benzenesulfonamide |
| 171 | 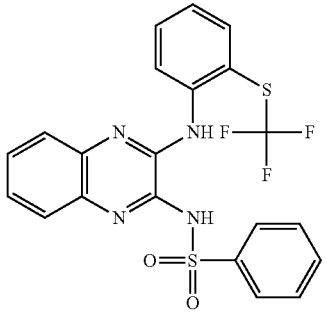 [SMILES: O=S(=O)(Nc1nc2ccccc2nc1Nc1ccccc1SC(F)(F)F)c1ccccc1] | N-[3-({2-[(trifluoromethyl)ethiso]phenyl}amino)quinoxalin-2-yl]benzenesulfonamide |
| 172 | 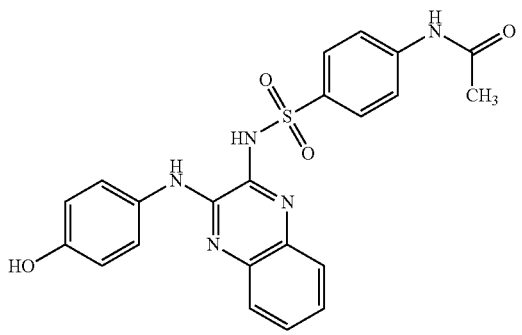 [SMILES: CC(=O)Nc1ccc(S(=O)(=O)Nc2nc3ccccc3nc2Nc2ccc(O)cc2)cc1] | N-{4-[({3-[(4-hydroxyphenyl)amino]quinoxalin-2-yl}amino)sulfonyl]phenyl}acetamide |
| 173 | 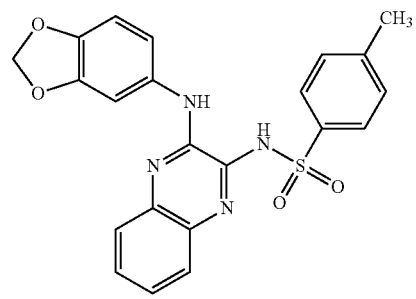 [SMILES: Cc1ccc(S(=O)(=O)Nc2nc3ccccc3nc2Nc2ccc3c(c2)OCO3)cc1] | N-[3-(1,3-benzodisoxol-5-ylamino)quinoxalin-2-yl]-4-methylbenzenesulfonamide |

TABLE 1-continued

| Cpd. No. | Structure | IUPAC Name |
|---|---|---|
| 174 | 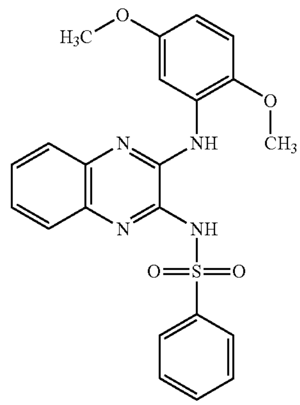 [SMILES: COc1ccc(OC)c(Nc2nc3ccccc3nc2NS(=O)(=O)c2ccccc2)c1] | N-(3-{[2,5-bis(methyloxy)phenyl]amino}quinoxalin-2-yl)benzenesulfonamide |
| 175 | 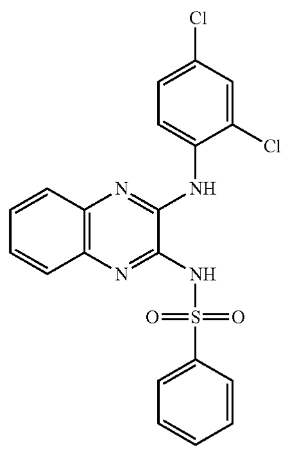 [SMILES: O=S(=O)(Nc1nc2ccccc2nc1Nc1ccc(Cl)cc1Cl)c1ccccc1] | N-{3-[(2,4-dichlorophenyl)amino]quinoxalin-2-yl}benzenesulfonamide |
| 176 | 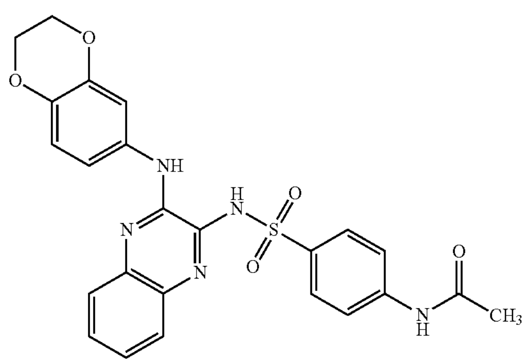 [SMILES: CC(=O)Nc1ccc(S(=O)(=O)Nc2nc3ccccc3nc2Nc2ccc3c(c2)OCCO3)cc1] | N-[4-({[3-(2,3-dihydro-1,4-benzodisoxin-6-ylamino)quinoxalin-2-yl]amino}sulfonyl)phenyl]acetamide |
| 177 | 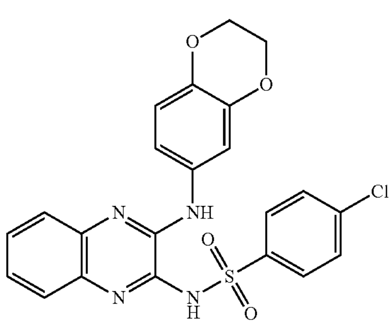 [SMILES: O=S(=O)(Nc1nc2ccccc2nc1Nc1ccc2c(c1)OCCO2)c1ccc(Cl)cc1] | 4-chloro-N-[3-(2,3-dihydro-1,4-benzodisoxin-6-ylamino)quinoxalin-2-yl]benzenesulfonamide |

TABLE 1-continued
| Cpd. No. | Structure | IUPAC Name |
|---|---|---|
| 178 | 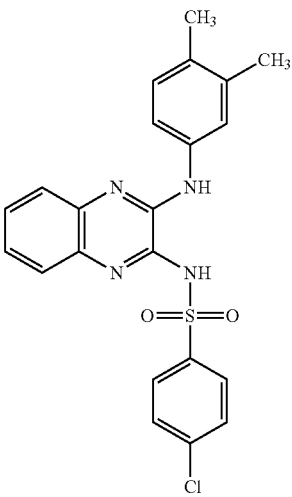 [SMILES: Cc1ccc(Nc2nc3ccccc3nc2NS(=O)(=O)c2ccc(Cl)cc2)cc1C] | 4-chloro-N-{3-[(3,4-dimethylphenyl)amino]quinoxalin-2-yl}benzenesulfonamide |
| 179 | 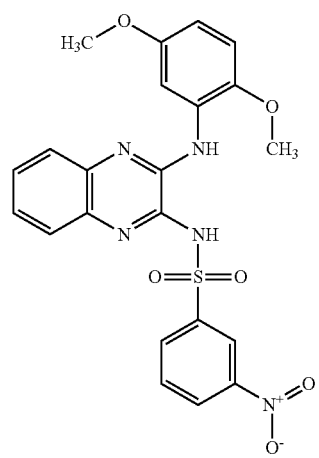 [SMILES: COc1ccc(OC)c(Nc2nc3ccccc3nc2NS(=O)(=O)c2cccc([N+](=O)[O-])c2)c1] | N-(3-{[2,5-bis(methyloxy)phenyl]amino}quinoxalin-2-yl)-3-nitrobenzenesulfonamide |
| 180 | 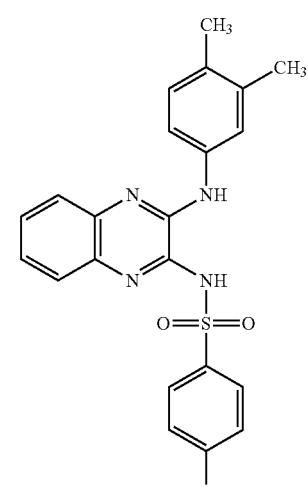 | 4-bromo-N-{3-[(3,4-dimethylphenyl)amino]quinoxalin-2-yl}benzenesulfonamide |

TABLE 1-continued

| Cpd. No. | Structure | IUPAC Name |
| --- | --- | --- |
| 181 | 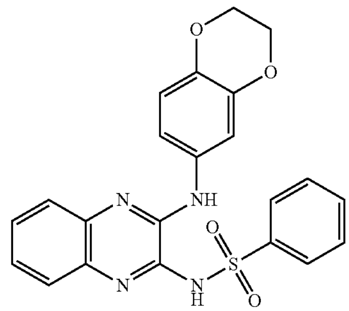 [SMILES: O=S(=O)(Nc1nc2ccccc2nc1Nc1ccc2c(c1)OCCO2)c1ccccc1] | N-[3-(2,3-dihydro-1,4-benzodisoxin-6-ylamino)quinoxalin-2-yl]benzenesulfonamide |
| 182 | 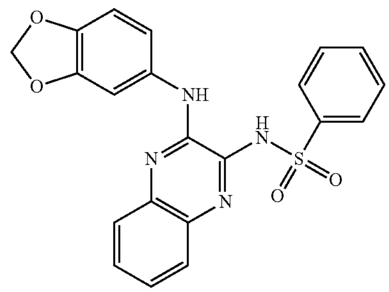 [SMILES: O=S(=O)(Nc1nc2ccccc2nc1Nc1ccc2c(c1)OCO2)c1ccccc1] | N-[3-(1,3-benzodisoxol-5-ylamino)quinoxalin-2-yl]benzenesulfonamide |
| 183 | 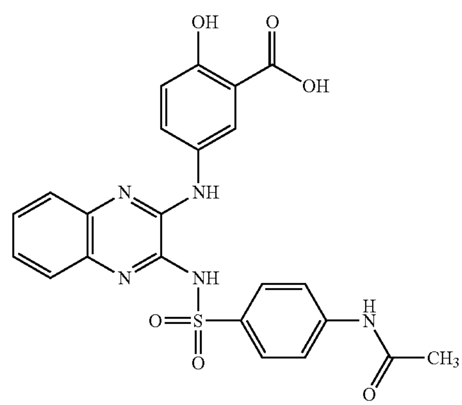 [SMILES: CC(=O)Nc1ccc(S(=O)(=O)Nc2nc3ccccc3nc2Nc2ccc(O)c(C(=O)O)c2)cc1] | 5-{[3-({[4-(acetylamino)phenyl]sulfonyl}amino)quinoxalin-2-yl]amino}-2-hydroxybenzoic acid |
| 184 | 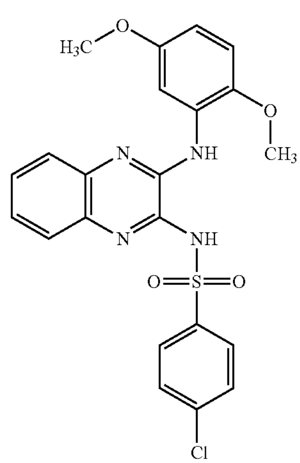 [SMILES: COc1ccc(OC)c(Nc2nc3ccccc3nc2NS(=O)(=O)c2ccc(Cl)cc2)c1] | N-(3-{[2,5-bis(methyloxy)phenyl]amino}quinoxalin-2-yl)-4-chlorobenzenesulfonamide |

TABLE 1-continued
| Cpd. No. | Structure | IUPAC Name |
|---|---|---|
| 185 | 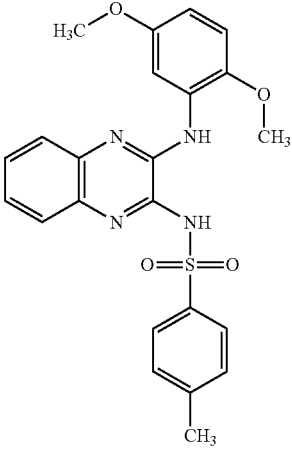 [SMILES: COc1ccc(OC)c(Nc2nc3ccccc3nc2NS(=O)(=O)c2ccc(C)cc2)c1] | N-(3-{[2,5-bis(methyloxy)phenyl]amino}quinoxalin-2-yl)-4-methylbenzenesulfonamide |
| 186 | 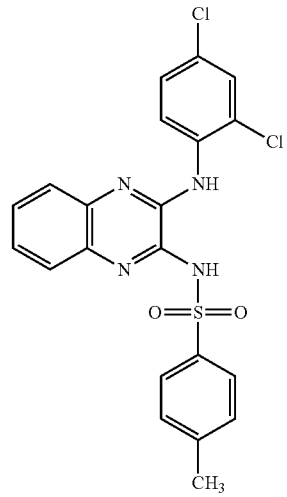 [SMILES: Cc1ccc(S(=O)(=O)Nc2nc3ccccc3nc2Nc2ccc(Cl)cc2Cl)cc1] | N-{3-[(2,4-dichlorophenyl)amino]quinoxalin-2-yl}-4-methylbenzenesulfonamide |
| 187 | 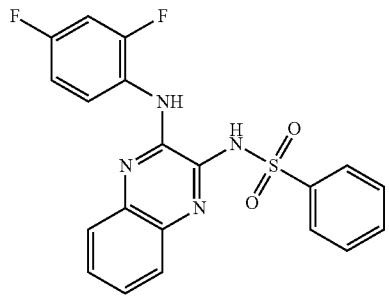 [SMILES: O=S(=O)(Nc1nc2ccccc2nc1Nc1ccc(F)cc1F)c1ccccc1] | N-{3-[(2,4-difluorophenyl)amino]quinoxalin-2-yl}benzenesulfonamide |

TABLE 1-continued

| Cpd. No. | Structure | IUPAC Name |
|---|---|---|
| 188 | 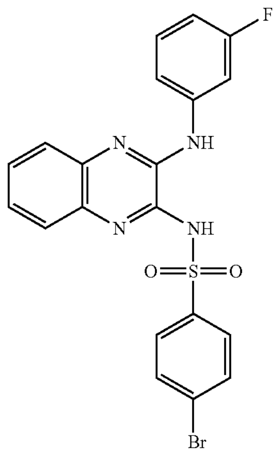 [SMILES: O=S(=O)(Nc1nc2ccccc2nc1Nc1cccc(F)c1)c1ccc(Br)cc1] | 4-bromo-N-{3-[(3-fluorophenyl)amino]quinoxalin-2-yl}benzenesulfonamide |
| 189 | 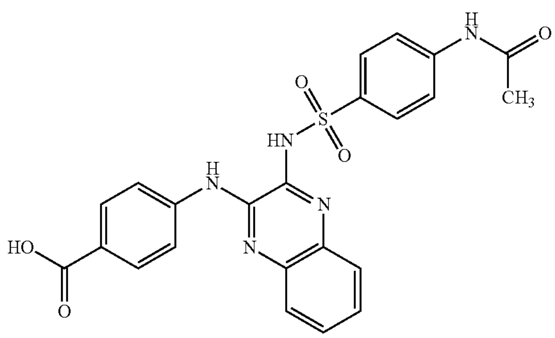 [SMILES: CC(=O)Nc1ccc(S(=O)(=O)Nc2nc3ccccc3nc2Nc2ccc(C(=O)O)cc2)cc1] | 4-{[3-({[4-(acetylamino)phenyl]sulfonyl}amino)quinoxalin-2-yl]amino}benzoic acid |
| 190 | 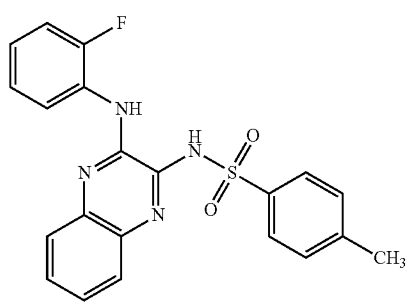 [SMILES: Cc1ccc(S(=O)(=O)Nc2nc3ccccc3nc2Nc2ccccc2F)cc1] | N-{3-[(2-fluorophenyl)amino]quinoxalin-2-yl}-4-methylbenzenesulfonamide |
| 191 | 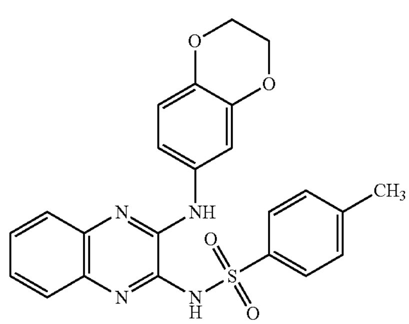 [SMILES: Cc1ccc(S(=O)(=O)Nc2nc3ccccc3nc2Nc2ccc3c(c2)OCCO3)cc1] | N-[3-(2,3-dihydro-1,4-benzodisoxin-6-ylamino)quinoxalin-2-yl]-4-methylbenzenesulfonamide |

TABLE 1-continued
| Cpd. No. | Structure | IUPAC Name |
|---|---|---|
| 192 | 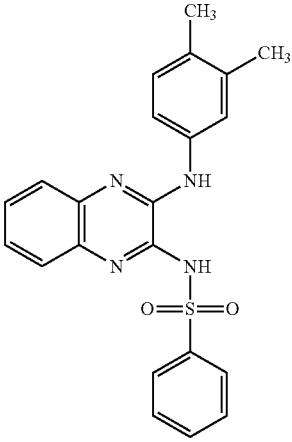 [SMILES: Cc1ccc(Nc2nc3ccccc3nc2NS(=O)(=O)c2ccccc2)cc1C] | N-{3-[(3,4-dimethylphenyl)amino]quinoxalin-2-yl}benzenesulfonamide |
| 193 | 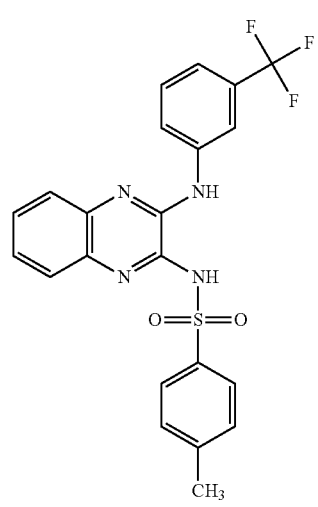 [SMILES: Cc1ccc(S(=O)(=O)Nc2nc3ccccc3nc2Nc2cccc(C(F)(F)F)c2)cc1] | 4-methyl-N-(3-{[3-(trifluoromethyl)phenyl]amino}quinoxalin-2-yl)benzenesulfonamide |
| 194 | 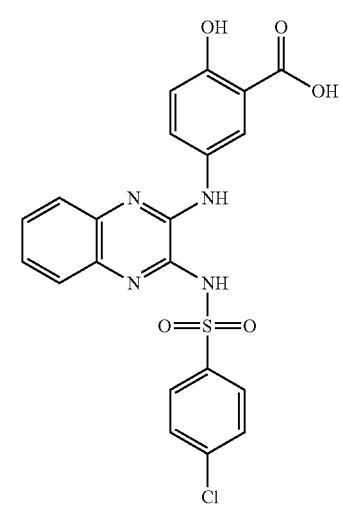 [SMILES: O=C(O)c1cc(Nc2nc3ccccc3nc2NS(=O)(=O)c2ccc(Cl)cc2)ccc1O] | 5-[(3-{[(4-chlorophenyl)sulfonyl]amino}quinoxalin-2-yl)amino]-2-hydroxybenzoic acid |

TABLE 1-continued

| Cpd. No. | Structure | IUPAC Name |
|---|---|---|
| 195 | 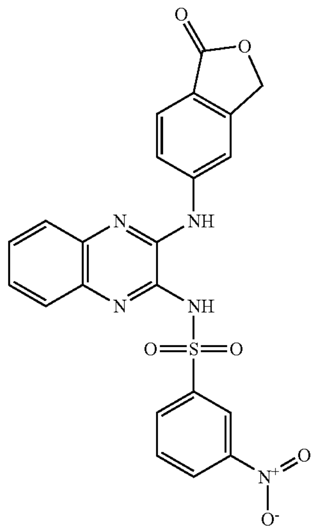 [SMILES: O=C1OCc2cc(Nc3nc4ccccc4nc3NS(=O)(=O)c3cccc([N+](=O)[O-])c3)ccc21] | 3-nitro-N-{3-[(1-oxo-1,3-dihydro-2-benzofuran-5-yl)amino]quinoxalin-2-yl}benzenesulfonamide |
| 196 | 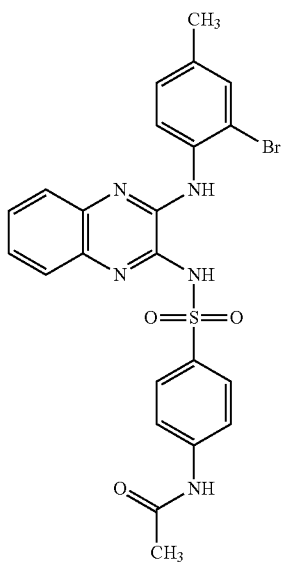 [SMILES: CC(=O)Nc1ccc(S(=O)(=O)Nc2nc3ccccc3nc2Nc2ccc(C)cc2Br)cc1] | N-{4-[({3-[(2-bromo-4-methylphenyl)amino]quinoxalin-2-yl}amino)sulfonyl]phenyl}acetamide |
| 197 | 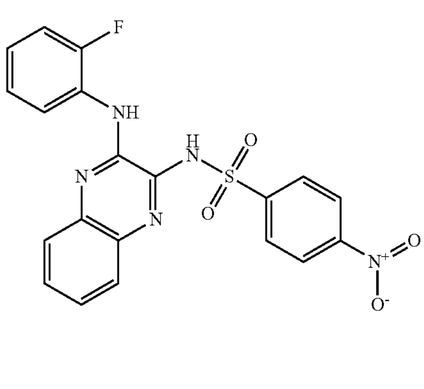 [SMILES: O=[N+]([O-])c1ccc(S(=O)(=O)Nc2nc3ccccc3nc2Nc2ccccc2F)cc1] | N-{3-[(2-fluorophenyl)amino]quinoxalin-2-yl}-4-nitrobenzenesulfonamide |

TABLE 1-continued
| Cpd. No. | Structure | IUPAC Name |
|---|---|---|
| 198 | 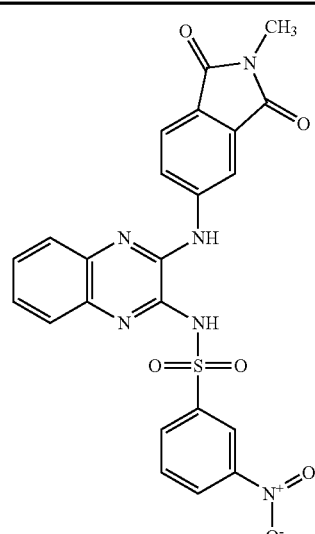 | N-{3-[(2-methyl-1,3-disoxo-2,3-dihydro-1H-isoindol-5-yl)amino]quinoxalin-2-yl}-3-nitrobenzenesulfonamide |
| 199 | 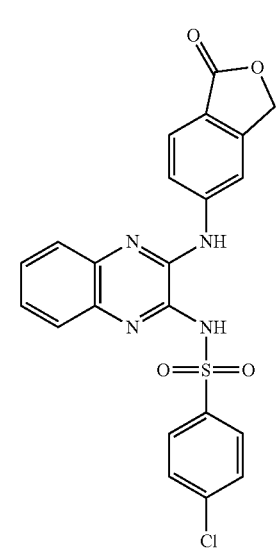 [SMILES: O=C1OCc2cc(Nc3nc4ccccc4nc3NS(=O)(=O)c3ccc(Cl)cc3)ccc21] | 4-chloro-N-{3-[(1-oxo-1,3-dihydro-2-benzofuran--yl)amino]quinoxalin-2-yl}benzenesulfonamide |
| 200 | 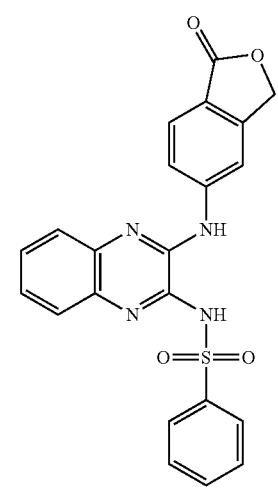 [SMILES: O=C1OCc2cc(Nc3nc4ccccc4nc3NS(=O)(=O)c3ccccc3)ccc21] | N-{3-[(1-oxo-1,3-dihydro-2-benzofuran-5-yl)amino]quinoxalin-2-yl}benzenesulfonamide |

TABLE 1-continued

| Cpd. No. | Structure | IUPAC Name |
|---|---|---|
| 201 | 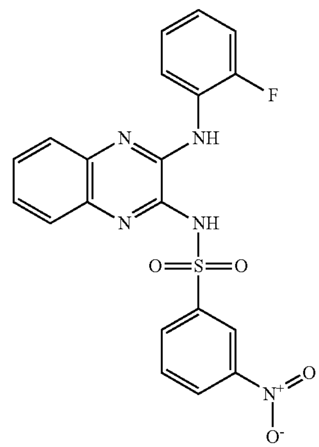 [SMILES: O=[N+]([O-])c1cccc(S(=O)(=O)Nc2nc3ccccc3nc2Nc2ccccc2F)c1] | N-{3-[(2-fluorophenyl)amino]quinoxalin-2-yl}-3-nitrobenzenesulfonamide |
| 202 | 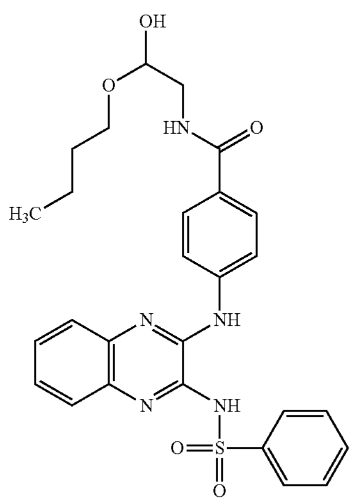 [SMILES: CCCCOC(O)CNC(=O)c1ccc(Nc2nc3ccccc3nc2NS(=O)(=O)c2ccccc2)cc1] | N-[2-(butyloxy)-2-hydroxyethyl]-4-({3-[(phenylsulfonyl)amino]quinoxalin-2-yl}amino)benzamide |
| 203 | 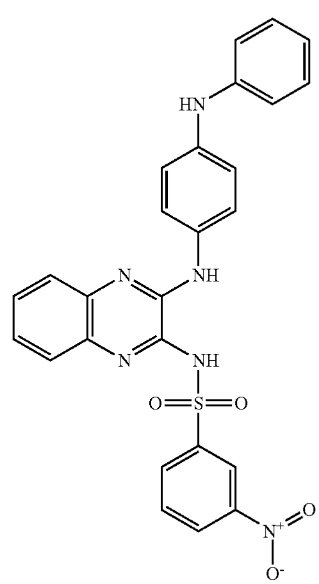 [SMILES: O=[N+]([O-])c1cccc(S(=O)(=O)Nc2nc3ccccc3nc2Nc2ccc(Nc3ccccc3)cc2)c1] | 3-nito-N-(3-{[4-(phenylamino)phenyl]amino}quinoxalin-2-yl)benzenesulfonamide |

TABLE 1-continued

| Cpd. No. | Structure | IUPAC Name |
|---|---|---|
| 204 | 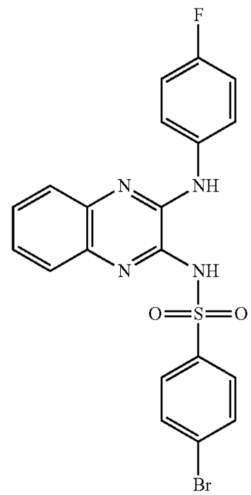 [SMILES: O=S(=O)(Nc1nc2ccccc2nc1Nc1ccc(F)cc1)c1ccc(Br)cc1] | 4-bromo-N-{3-[(4-fluorophenyl)amino]quinoxalin-2-yl}benzenesulfonamide |
| 205 | 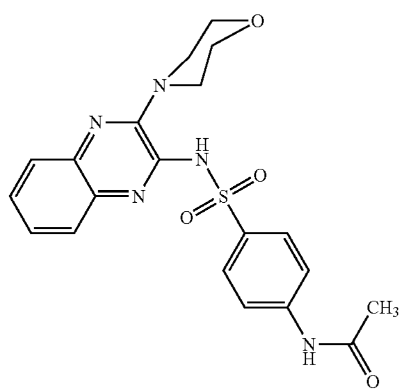 [SMILES: CC(=O)Nc1ccc(S(=O)(=O)Nc2nc3ccccc3nc2N2CCOCC2)cc1] | N-(4-{[(3-morpholin-4-ylquinoxalin-2-yl)amino]sulfonyl}phenyl)acetamide |
| 206 | 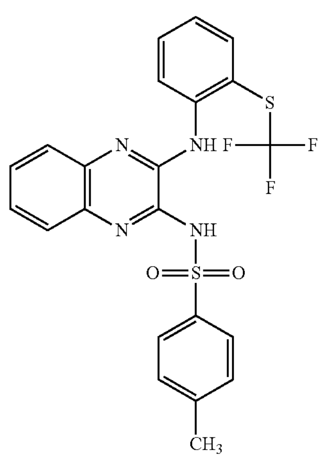 [SMILES: Cc1ccc(S(=O)(=O)Nc2nc3ccccc3nc2Nc2ccccc2SC(F)(F)F)cc1] | 4-methyl-N-[3-({2-[(trifluoromethyl)ethiso]phenyl}amino)quinoxalin-2-yl]benzenesulfonamide |

TABLE 1-continued

| Cpd. No. | Structure | IUPAC Name |
|---|---|---|
| 207 | 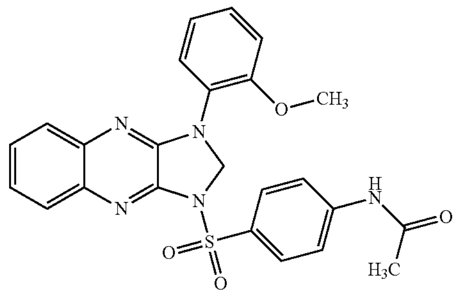 [SMILES: COc1ccccc1N1CN(S(=O)(=O)c2ccc(NC(C)=O)cc2)c2nc3ccccc3nc21] | N-[4-({3-[2-(methyloxy)phenyl]-2,3-dihydro-1H-imidazo[4,5-b]quinoxalin-1-yl}sulfonyl)phenyl]acetamide |
| 208 | 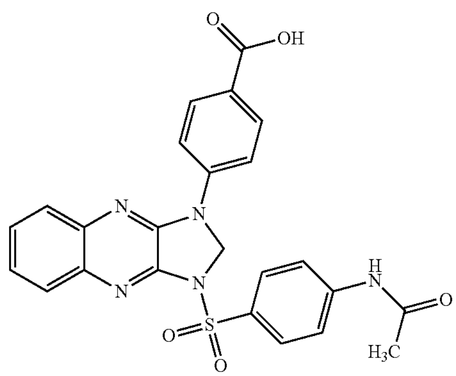 [SMILES: CC(=O)Nc1ccc(S(=O)(=O)N2CN(c3ccc(C(=O)O)cc3)c3nc4ccccc4nc32)cc1] | 4-(3-{[4-(acetylamino)phenyl]sulfonyl}-2,3-dihydro-1H-imidazo[4,5-b]quinoxalin-1-yl)benzoic acid |
| 209 | 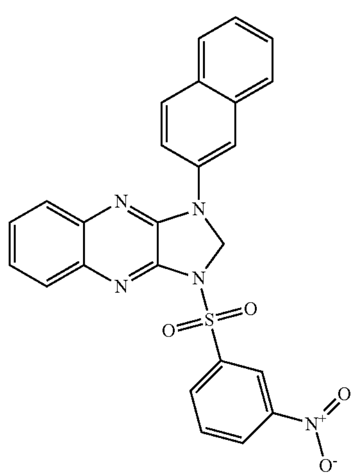 [SMILES: O=[N+]([O-])c1cccc(S(=O)(=O)N2CN(c3ccc4ccccc4c3)c3nc4ccccc4nc32)c1] | 1-naphthalen-2-yl-3-[(3-nitrophenyl)sulfonyl]-2,3-dihydro-1H-imidazo[4,5-b]quinoxaline |

TABLE 1-continued

| Cpd. No. | Structure | IUPAC Name |
|---|---|---|
| 210 | 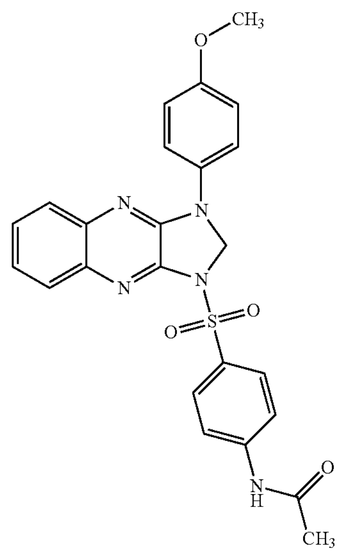 [SMILES: COc1ccc(N2CN(S(=O)(=O)c3ccc(NC(C)=O)cc3)c3nc4ccccc4nc32)cc1] | N-[4-({3-(methyloxy)phenyl]-2,3-dihydro-1H-imidazo[4,5-b]quinoxalin-1-yl}sulfonyl)phenyl]acetamide |
| 211 | 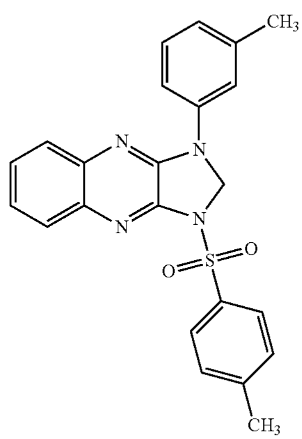 [SMILES: Cc1ccc(S(=O)(=O)N2CN(c3cccc(C)c3)c3nc4ccccc4nc32)cc1] | 1-(3-methylphenyl)-3-[(4-methylphenyl)sulfonyl]-2,3-dihydro-1H-imidazo[4,5-b]quinoxaline |
| 212 | 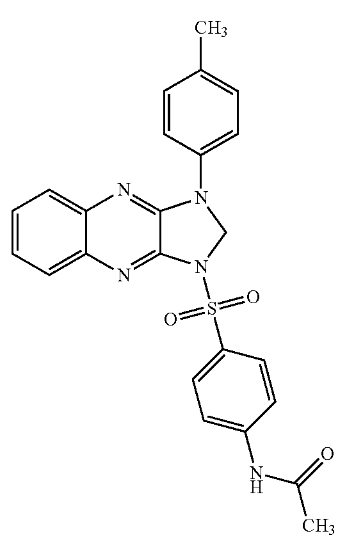 [SMILES: CC(=O)Nc1ccc(S(=O)(=O)N2CN(c3ccc(C)cc3)c3nc4ccccc4nc32)cc1] | N-(4-{[3-(4-methylphenyl)-2,3-dihydro-1H-imidazo[4,5-b]quinoxalin-1-yl]sulfonyl}phenyl)acetamide |

TABLE 1-continued

| Cpd. No. | Structure | IUPAC Name |
|---|---|---|
| 213 | 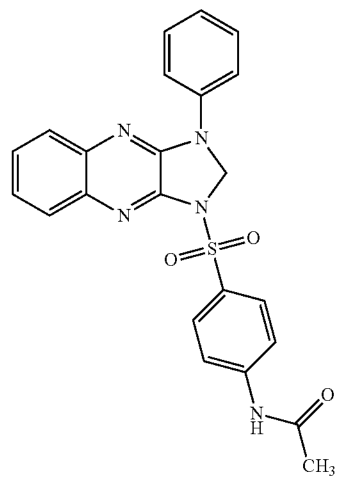 [SMILES: CC(=O)Nc1ccc(S(=O)(=O)N2CN(c3ccccc3)c3nc4ccccc4nc32)cc1] | N-{4-[(3-phenyl-2,3-dihydro-1H-imidazo[4,5-b]quinoxalin-1-yl)sulfonyl]phenyl}acetamide |
| 214 | 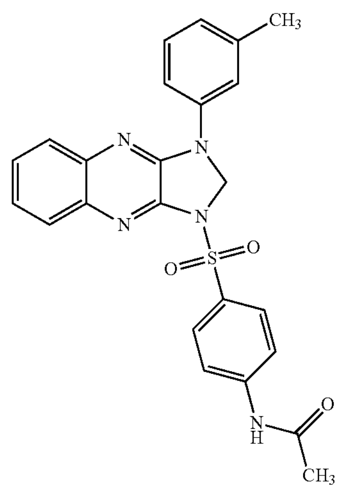 [SMILES: CC(=O)Nc1ccc(S(=O)(=O)N2CN(c3cccc(C)c3)c3nc4ccccc4nc32)cc1] | N-(4-{[3-(3-methylphenyl)-2,3-dihydro-1H-imidazo[4,5-b]quinoxalin-1-yl]sulfonyl}phenyl)acetamide |
| 215 | 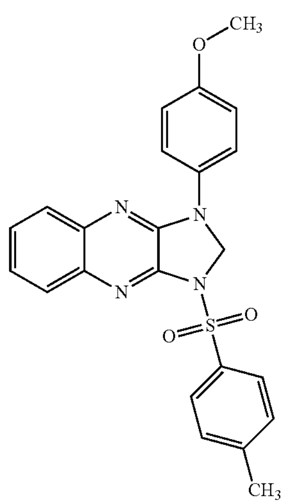 [SMILES: COc1ccc(N2CN(S(=O)(=O)c3ccc(C)cc3)c3nc4ccccc4nc32)cc1] | 1-[4-(methyloxy)phenyl]-3-[(4-methylphenyl)sulfonyl]-2,3-dihydro-1H-imidazo[4,5-b]quinoxaline |

TABLE 1-continued

| Cpd. No. | Structure | IUPAC Name |
|---|---|---|
| 216 | 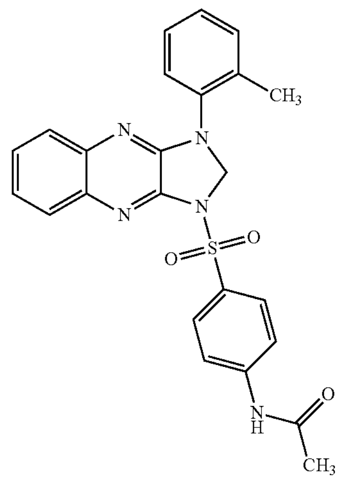 [SMILES: CC(=O)Nc1ccc(S(=O)(=O)N2CN(c3ccccc3C)c3nc4ccccc4nc32)cc1] | N-(4-{[3-(2-methylphenyl)-2,3-dihydro-1H-imidazo[4,5-b]quinoxalin-1-yl]sulfonyl}phenyl)acetamide |
| 217 | 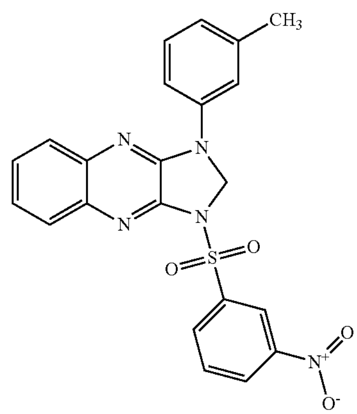 [SMILES: Cc1cccc(N2CN(S(=O)(=O)c3cccc([N+](=O)[O-])c3)c3nc4ccccc4nc32)c1] | 1-(3-methylphenyl)-3-[(3-nitrophenyl)sulfonyl]-2,3-dihydro-1H-imidazo[4,5-b]quinoxaline |
| 218 | 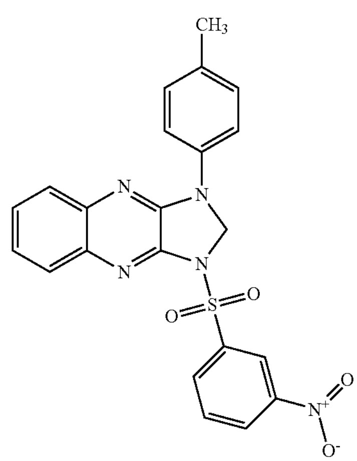 [SMILES: Cc1ccc(N2CN(S(=O)(=O)c3cccc([N+](=O)[O-])c3)c3nc4ccccc4nc32)cc1] | 1-(4-methylphenyl)-3-[(3-nitrophenyl)sulfonyl]-2,3-dihydro-1H-imidazo[4,5-b]quinoxaline |

TABLE 1-continued

| Cpd. No. | Structure | IUPAC Name |
|---|---|---|
| 219 | 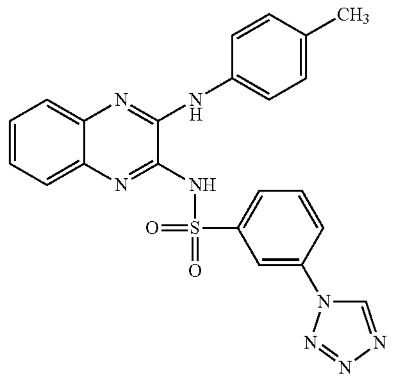 [SMILES: Cc1ccc(Nc2nc3ccccc3nc2NS(=O)(=O)c2cccc(-n3cnnn3)c2)cc1] | N-{3-[(4-methylphenyl)amino]quinoxalin-2-yl}-3-(1H-tetrazol-1-yl)benzenesulfonamide |
| 220 | 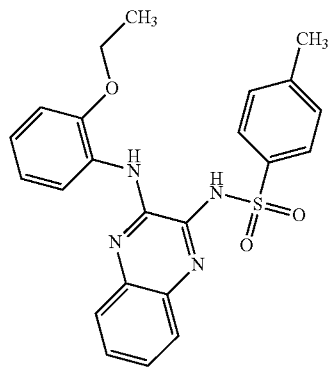 [SMILES: CCOc1ccccc1Nc1nc2ccccc2nc1NS(=O)(=O)c1ccc(C)cc1] | N-(3-{[2-(ethyloxy)phenyl]amino}quinoxalin-2-yl)-4-methylbenzenesulfonamide |
| 221 | 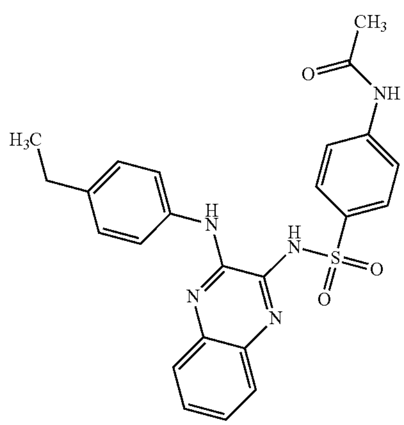 [SMILES: CCc1ccc(Nc2nc3ccccc3nc2NS(=O)(=O)c2ccc(NC(C)=O)cc2)cc1] | N-{4-[({3-[(4-ethylphenyl)amino]quinoxalin-2-yl}amino)sulfonyl]phenyl}acetamide |
| 222 | 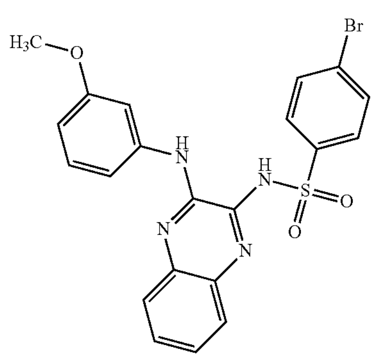 [SMILES: COc1cccc(Nc2nc3ccccc3nc2NS(=O)(=O)c2ccc(Br)cc2)c1] | 4-bromo-N-(3-{[3-(methyloxy)phenyl]amino}quinoxalin-2-yl)benzenesulfonamide |

TABLE 1-continued

| Cpd. No. | Structure | IUPAC Name |
|---|---|---|
| 223 | 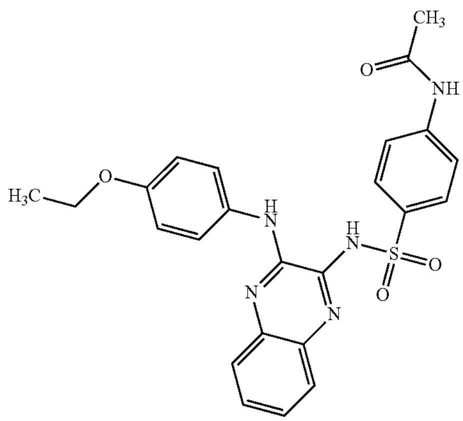 [SMILES: CCOc1ccc(Nc2nc3ccccc3nc2NS(=O)(=O)c2ccc(NC(C)=O)cc2)cc1] | N-(4-{[(3-{[4-(ethyloxy)phenyl]amino}quinoxalin-2-yl)amino]sulfonyl}phenyl)acetamide |
| 224 | 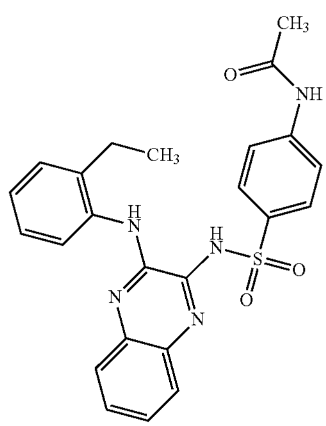 [SMILES: CCc1ccccc1Nc1nc2ccccc2nc1NS(=O)(=O)c1ccc(NC(C)=O)cc1] | N-{4-[({3-[(2-ethylphenyl)amino]quinoxalin-2-yl}amino)sulfonyl]phenyl}acetamide |
| 225 | 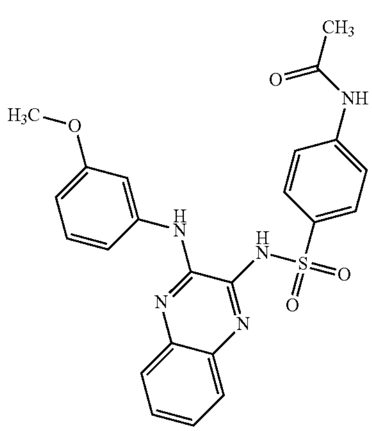 [SMILES: COc1cccc(Nc2nc3ccccc3nc2NS(=O)(=O)c2ccc(NC(C)=O)cc2)c1] | N-(4-{[(3-{[3-(methyloxy)phenyl]amino}quinoxalin-2-yl)amino]sulfonyl}phenyl)acetamide |

| Cpd. No. | Structure | IUPAC Name |
|---|---|---|
| 226 | 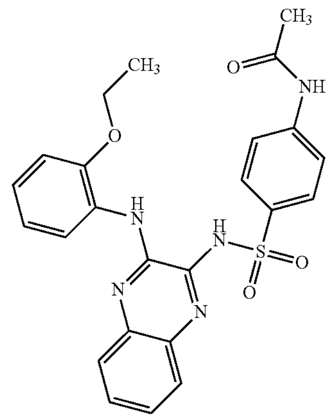 [SMILES: CCOc1ccccc1Nc1nc2ccccc2nc1NS(=O)(=O)c1ccc(NC(C)=O)cc1] | N-(4-{[(3-{[2-(ethyloxy)phenyl]amino}quinoxalin-2-yl)amino]sulfonyl}phenyl)acetamide |
| 227 | 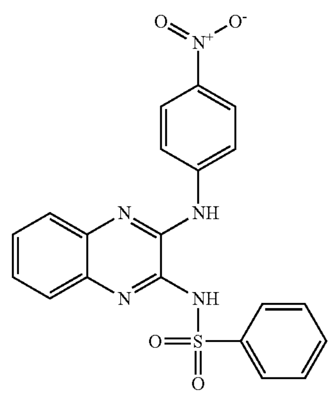 [SMILES: O=[N+]([O-])c1ccc(Nc2nc3ccccc3nc2NS(=O)(=O)c2ccccc2)cc1] | N-{3-[(4-nitrophenyl)amino]quinoxalin-2-yl}benzenesulfonamide |
| 228 | 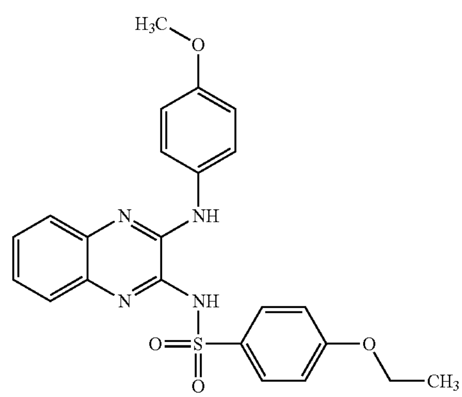 [SMILES: CCOc1ccc(S(=O)(=O)Nc2nc3ccccc3nc2Nc2ccc(OC)cc2)cc1] | 4-(ethyloxy)-N-(3-{[4-(methyloxy)phenyl]amino}quinoxalin-2-yl)benzenesulfonamide |
| 229 | 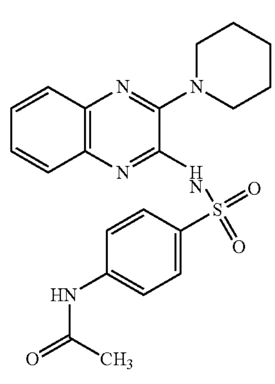 [SMILES: CC(=O)Nc1ccc(S(=O)(=O)Nc2nc3ccccc3nc2N2CCCCC2)cc1] | N-(4-{[(3-piperidin-1-ylquinoxalin-2-yl)amino]sulfonyl}phenyl)acetamide |

TABLE 1-continued

| Cpd. No. | Structure | IUPAC Name |
|---|---|---|
| 230 | 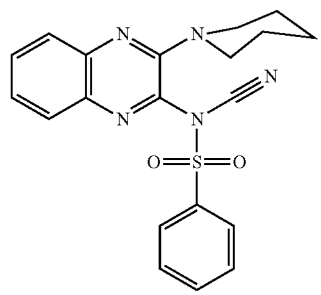 [SMILES: N#CN(c1nc2ccccc2nc1N1CCCCC1)S(=O)(=O)c1ccccc1] | N-cyano-N-(3-piperidin-1-ylquinoxalin-2-yl)benzenesulfonamide |
| 231 | 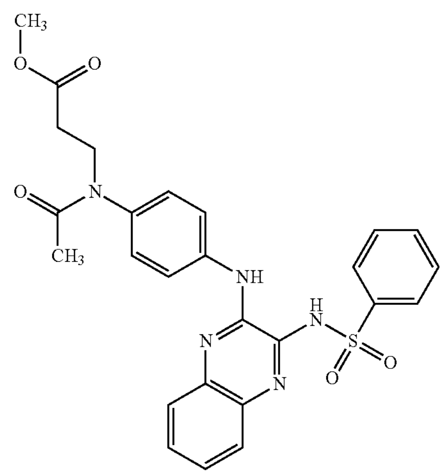 [SMILES: COC(=O)CCN(C(C)=O)c1ccc(Nc2nc3ccccc3nc2NS(=O)(=O)c2ccccc2)cc1] | methyl N-acetyl-N-[4-({3-[(phenylsulfonyl)amino]quinoxalin-2-yl}amino)phenyl]-beta-alaninate |
| 232 | 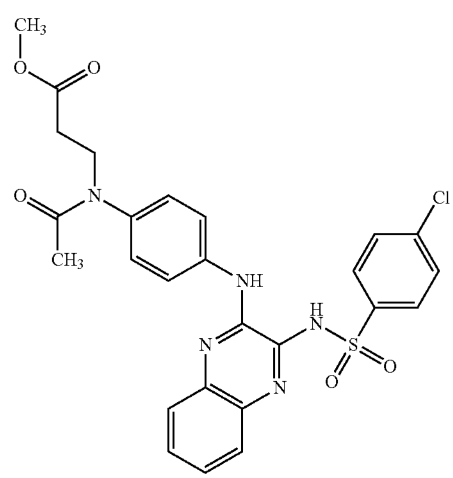 [SMILES: COC(=O)CCN(C(C)=O)c1ccc(Nc2nc3ccccc3nc2NS(=O)(=O)c2ccc(Cl)cc2)cc1] | methyl N-acetyl-N-{4-[(3-{[(4-chlorophenyl)sulfonyl]amino}quinoxalin-2-yl)amino]phenyl}-beta-alaninate |

TABLE 1-continued
| Cpd. No. | Structure | IUPAC Name |
|---|---|---|
| 233 | 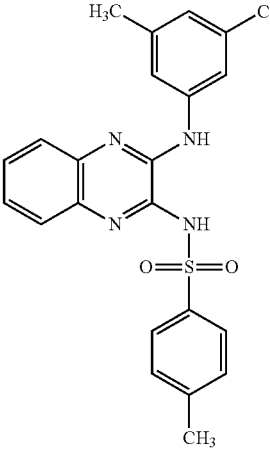 | N-{3-[(3-chloro-5-methylphenyl)amino]quinoxalin-2-yl}-4-methylbenzenesulfonamide |
| 234 | 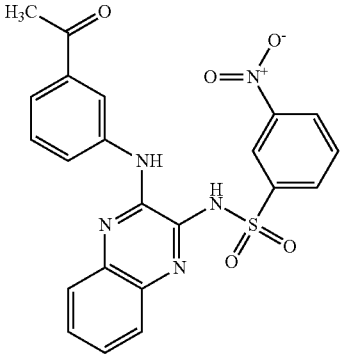 [SMILES: CC(=O)c1cccc(Nc2nc3ccccc3nc2NS(=O)(=O)c2cccc([N+](=O)[O-])c2)c1] | N-{3-[(3-acetylphenyl)amino]quinoxalin-2-yl}-3-nitrobenzenesulfonamide |
| 235 | 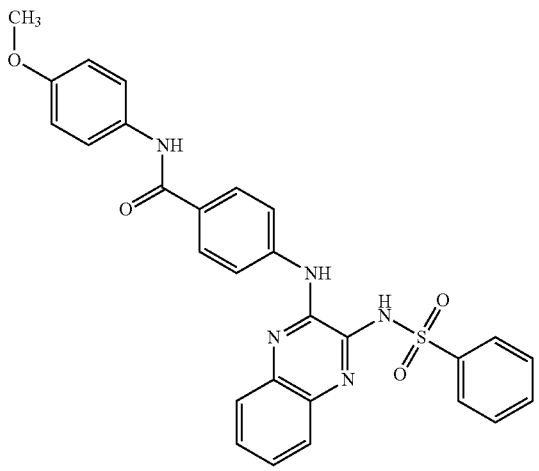 [SMILES: COc1ccc(NC(=O)c2ccc(Nc3nc4ccccc4nc3NS(=O)(=O)c3ccccc3)cc2)cc1] | N-[4-(methyloxy)phenyl]-4-({3-[(phenylsulfonyl)amino]quinoxalin-2-yl}amino)benzamide |

| Cpd. No. | Structure | IUPAC Name |
|---|---|---|
| 236 | 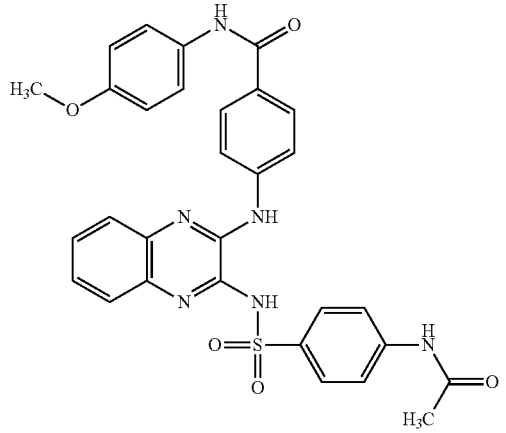 [SMILES: COc1ccc(NC(=O)c2ccc(Nc3nc4ccccc4nc3NS(=O)(=O)c3ccc(NC(C)=O)cc3)cc2)cc1] | 4-{[3-({[4-(acetylamino)phenyl]sulfonyl}amino)quinoxalin-2-yl]amino}-N-[4-(methyloxy)phenyl]benzamide |
| 237 | 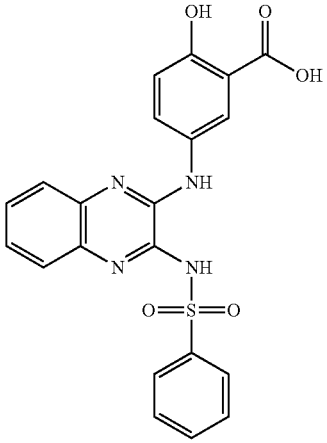 [SMILES: O=C(O)c1cc(Nc2nc3ccccc3nc2NS(=O)(=O)c2ccccc2)ccc1O] | 2-hydroxy-5-({3-[(phenylsulfonyl)amino]quinoxalin-2-yl}amino)benzoic acid |
| 238 | 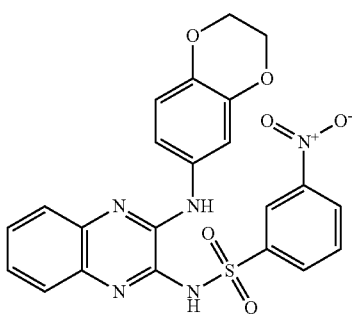 [SMILES: O=[N+]([O-])c1cccc(S(=O)(=O)Nc2nc3ccccc3nc2Nc2ccc3c(c2)OCCO3)c1] | N-[3-(2,3-dihydro-1,4-benzodisoxin-6-ylamino)quinoxalin-2-yl]-3-nitrobenzenesulfonamide |

TABLE 1-continued

| Cpd. No. | Structure | IUPAC Name |
|---|---|---|
| 239 | 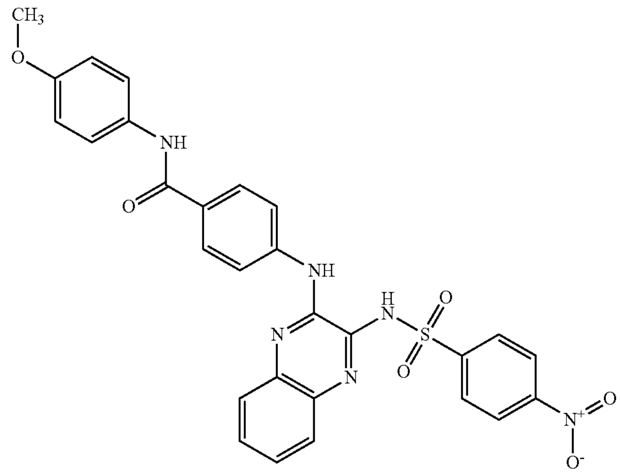 [SMILES: COc1ccc(NC(=O)c2ccc(Nc3nc4ccccc4nc3NS(=O)(=O)c3ccc([N+](=O)[O-])cc3)cc2)cc1] | N-[4-(methyloxy)phenyl]-4-[(3-{[(4-nitrophenyl)sulfonyl]amino}quinoxalin-2-yl)amino]benzamide |
| 240 | 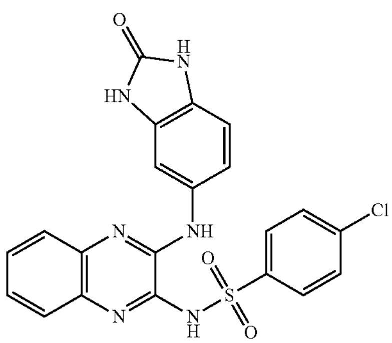 [SMILES: O=c1[nH]c2ccc(Nc3nc4ccccc4nc3NS(=O)(=O)c3ccc(Cl)cc3)cc2[nH]1] | 4-chloro-N-{3-[(2-oxo-2,3-dihydro-1H-benzimidazol-5-yl)amino]quinoxalin-2-yl}benzenesulfonamide |
| 241 | 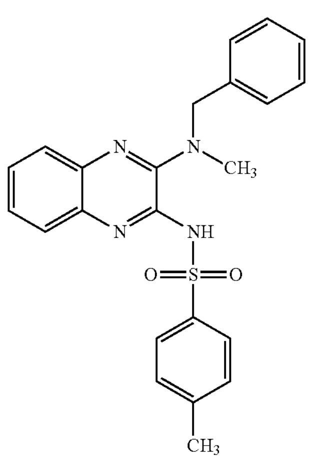 [SMILES: Cc1ccc(S(=O)(=O)Nc2nc3ccccc3nc2N(C)Cc2ccccc2)cc1] | 4-methyl-N-{3-[methyl(phenylmethyl)amino]quinoxalin-2-yl}benzenesulfonamide |

TABLE 1-continued

| Cpd. No. | Structure | IUPAC Name |
|---|---|---|
| 242 | 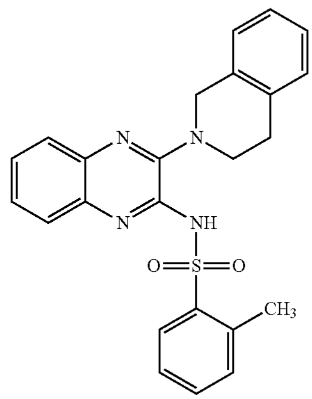 [SMILES: Cc1ccccc1S(=O)(=O)Nc1nc2ccccc2nc1N1CCc2ccccc2C1] | N-[3-(3,4-dihydroisoquinolin-2(1H)-yl)quinoxalin-2-yl]-2-methylbenzenesulfonamide |
| 243 | 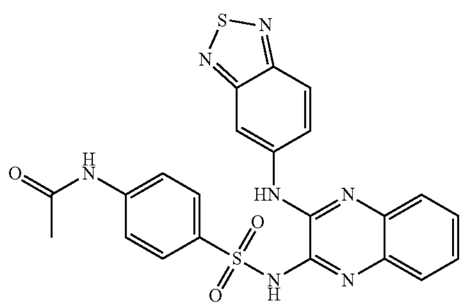 [SMILES: CC(=O)Nc1ccc(S(=O)(=O)Nc2nc3ccccc3nc2Nc2ccc3nsnc3c2)cc1] | N-[4-({[3-(2,1,3-benzothiadiazol-5-ylamino)quinoxalin-2-yl]amino}sulfonyl)phenyl]acetamide |
| 244 | 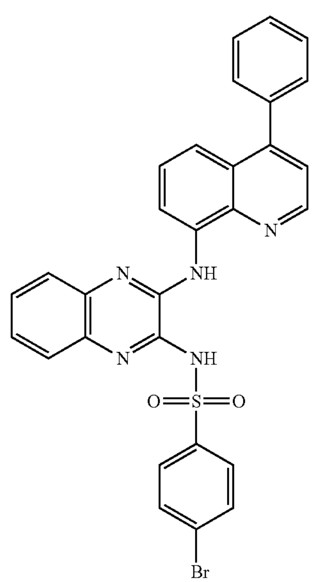 [SMILES: O=S(=O)(Nc1nc2ccccc2nc1Nc1cccc2c(-c3ccccc3)ccnc12)c1ccc(Br)cc1] | 4-bromo-N-{3-[(4-phenylquinolin-8-yl)amino]quinoxalin-2-yl}benzenesulfonamide |

TABLE 1-continued
| Cpd. No. | Structure | IUPAC Name |
|---|---|---|
| 245 | 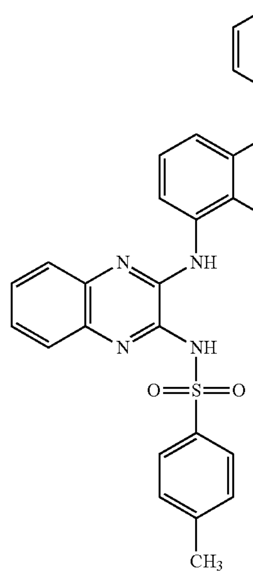 | 4-methyl-N-{3-[(4-phenylquinolin-8-yl)amino]quinoxalin-2-yl}benzenesulfonamide |
| 246 | 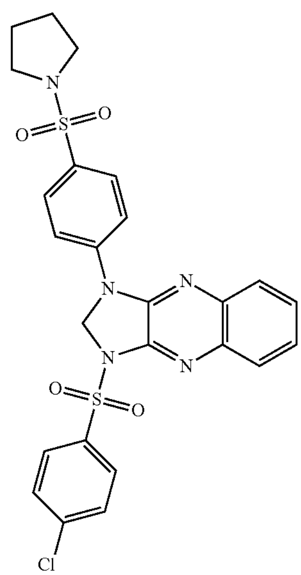 [SMILES: O=S(=O)(c1ccc(N2CN(S(=O)(=O)c3ccc(Cl)cc3)c3nc4ccccc4nc32)cc1)N1CCCC1] | 1-[(4-chlorophenyl)sulfonyl]-3-[4-(pyrrolidin-1-ylsulfonyl)phenyl]-2,3-dihydro-1H-imidazo[4,5-b]quinoxaline |
| 247 | 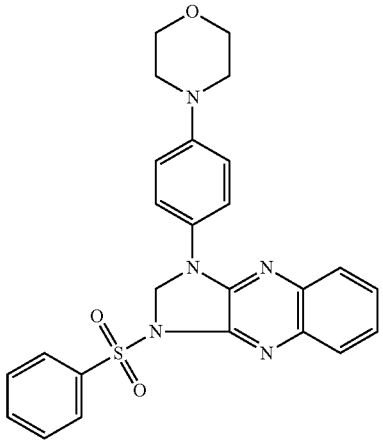 [SMILES: O=S(=O)(c1ccccc1)N1CN(c2ccc(N3CCOCC3)cc2)c2nc3ccccc3nc21] | 1-(4-morpholin-4-ylphenyl)-3-(phenylsulfonyl)-2,3-dihydro-1H-imidazo[4,5-b]quinoxaline |

TABLE 1-continued
| Cpd. No. | Structure | IUPAC Name |
|---|---|---|
| 248 | 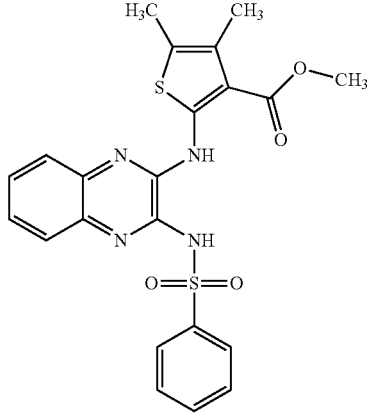 [SMILES: COC(=O)c1c(Nc2nc3ccccc3nc2NS(=O)(=O)c2ccccc2)sc(C)c1C] | methyl 4,5-dimethyl-2-({3-[(phenylsulfonyl)amino]quinoxalin-2-yl}amino)ethisophene-3-carboxylate |
| 249 | 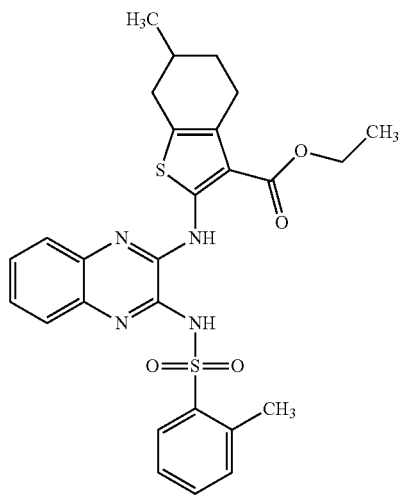 [SMILES: CCOC(=O)c1c(Nc2nc3ccccc3nc2NS(=O)(=O)c2ccccc2C)sc2c1CCC(C)C2] | ethyl 6-methyl-2-[(3-{[(2-methylphenyl)sulfonyl]amino}quinoxalin-2-yl)amino]-4,5,6,7-tetrahydro-1-benzothisophene-3-carboxylate |
| 250 | 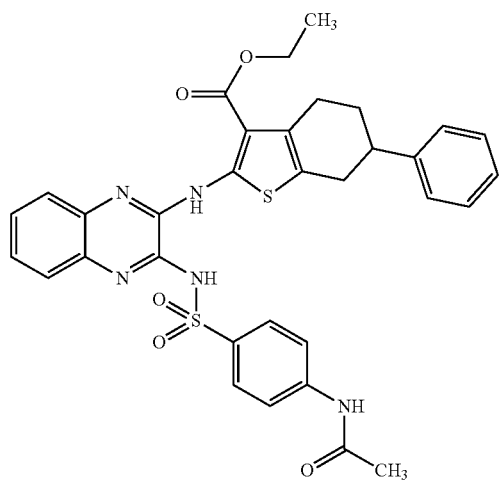 [SMILES: CCOC(=O)c1c(Nc2nc3ccccc3nc2NS(=O)(=O)c2ccc(NC(C)=O)cc2)sc2c1CCC(c1ccccc1)C2] | ethyl 2-{[3-({[4-(acetylamino)phenyl]sulfonyl}amino)quinoxalin-2-yl]amino}-6-phenyl-4,5,6,7-tetrahydro-1-benzothisophene-3-carboxylate |

| Cpd. No. | Structure | IUPAC Name |
|---|---|---|
| 251 | 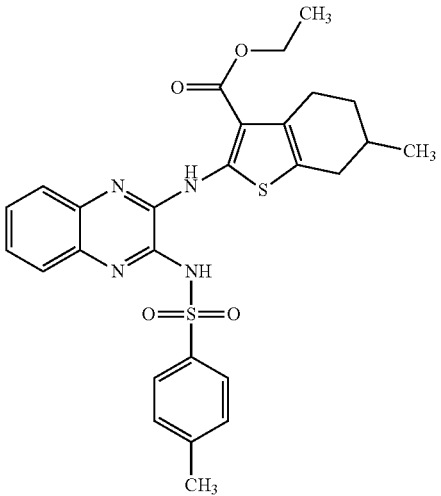 [SMILES: CCOC(=O)c1c(Nc2nc3ccccc3nc2NS(=O)(=O)c2ccc(C)cc2)sc2c1CCC(C)C2] | ethyl 6-methyl-2-[(3-{[(4-methylphenyl)sulfonyl]amino}quinoxalin-2-yl)amino]-4,5,6,7-ttrahydro-1-benzothisophene-3-carboxylate |
| 252 | 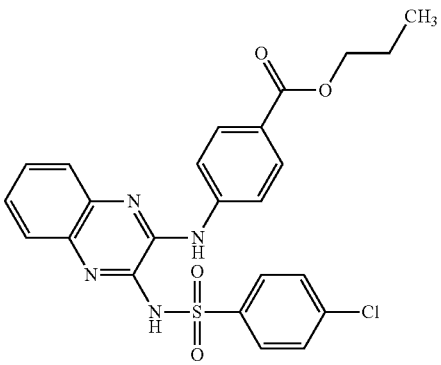 [SMILES: CCCOC(=O)c1ccc(Nc2nc3ccccc3nc2NS(=O)(=O)c2ccc(Cl)cc2)cc1] | propyl 4-[(3-{[(4-chlorophenyl)sulfonyl]amino}quinoxalin-2-yl)amino]benzoate |
| 253 | 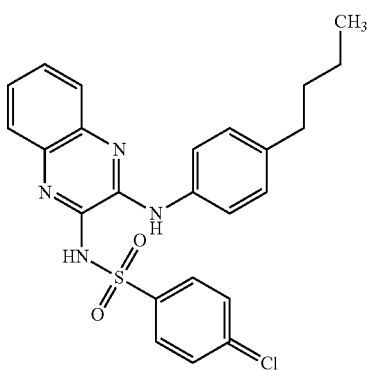 | N-{3-[(4-butylphenyl)amino]quinoxalin-2-yl}-4-chlorobenzenesulfonamide |

TABLE 1-continued

| Cpd. No. | Structure | IUPAC Name |
|---|---|---|
| 254 | 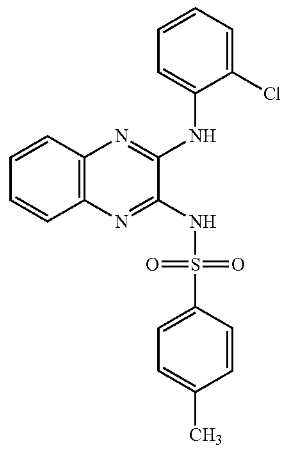 [SMILES: Cc1ccc(S(=O)(=O)Nc2nc3ccccc3nc2Nc2ccccc2Cl)cc1] | N-{3-[(2-chlorophenyl)amino]quinoxalin-2-yl}-4-methylbenzenesulfonamide |
| 255 | 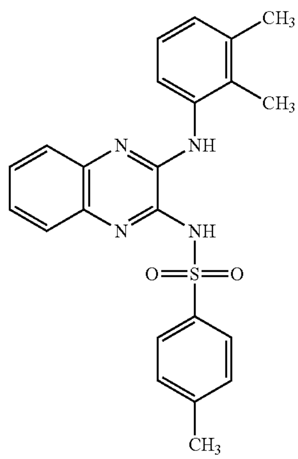 [SMILES: Cc1ccc(S(=O)(=O)Nc2nc3ccccc3nc2Nc2cccc(C)c2C)cc1] | N-{3-[(2,3-dimethylphenyl)amino]quinoxalin-2-yl}-4-methylbenzenesulfonamide |
| 256 | 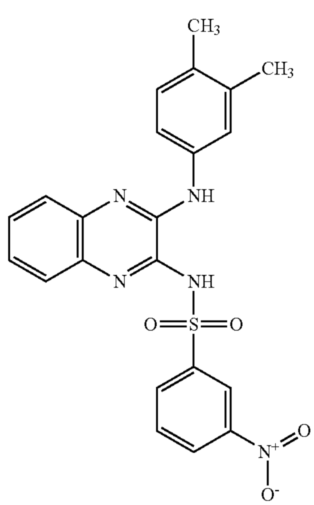 [SMILES: Cc1ccc(Nc2nc3ccccc3nc2NS(=O)(=O)c2cccc([N+](=O)[O-])c2)cc1C] | N-{3-[(3,4-dimethylphenyl)amino]quinoxalin-2-yl}-3-nitrobenzenesulfonamide |

TABLE 1-continued

| Cpd. No. | Structure | IUPAC Name |
|---|---|---|
| 257 | 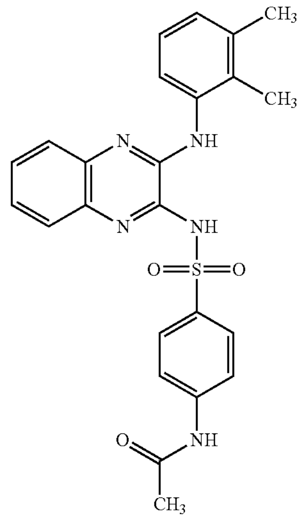 [SMILES: CC(=O)Nc1ccc(S(=O)(=O)Nc2nc3ccccc3nc2Nc2cccc(C)c2C)cc1] | N-{4-[({3-[(2,3-dimethylphenyl)amino]quinoxalin-2-yl}amino)sulfonyl]phenyl}acetamide |
| 258 | 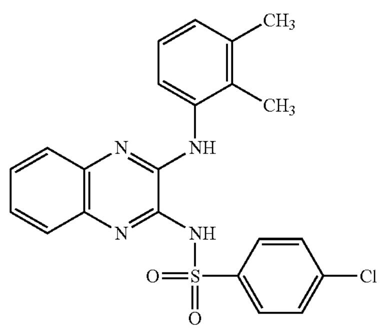 [SMILES: Cc1cccc(Nc2nc3ccccc3nc2NS(=O)(=O)c2ccc(Cl)cc2)c1C] | 4-chloro-N-{3-[(2,3-dimethylphenyl)amino]quinoxalin-2-yl}benzenesulfonamide |
| 259 | 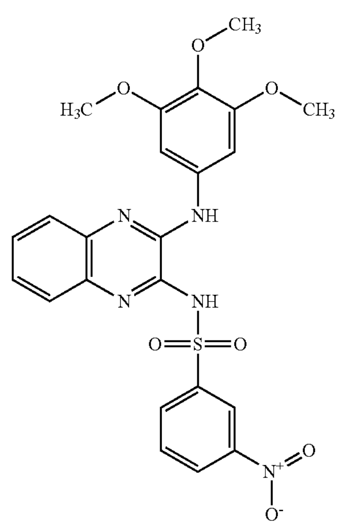 [SMILES: COc1cc(Nc2nc3ccccc3nc2NS(=O)(=O)c2cccc([N+](=O)[O-])c2)cc(OC)c1OC] | 3-nitro-N-(3-{[3m,4,5-tris(methyloxy)phenyl]amino}quinoxalin-2-yl)benzenesulfonamide |

TABLE 1-continued

| Cpd. No. | Structure | IUPAC Name |
|---|---|---|
| 260 | 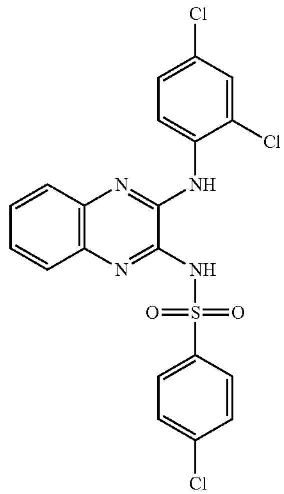 [SMILES: O=S(=O)(Nc1nc2ccccc2nc1Nc1ccc(Cl)cc1Cl)c1ccc(Cl)cc1] | 4-chloro-N-{3-[(2,4-dichlorophenyl)amino]quinoxalin-2-yl}benzenesulfonamide |
| 261 | 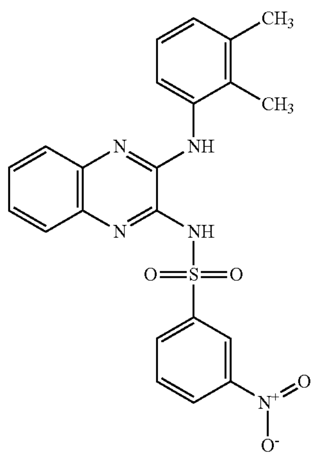 [SMILES: Cc1cccc(Nc2nc3ccccc3nc2NS(=O)(=O)c2cccc([N+](=O)[O-])c2)c1C] | N-{3-[(2,3-dimethylphenyl)amino]quinoxalin-2-yl}-3-nitrobenzenesulfonamide |
| 262 | 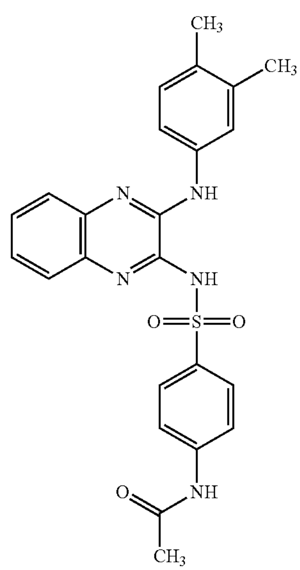 [SMILES: CC(=O)Nc1ccc(S(=O)(=O)Nc2nc3ccccc3nc2Nc2ccc(C)c(C)c2)cc1] | N-{4-[({3-[(3,4-dimethylphenyl)amino]quinoxalin-2-yl}amino)sulfonyl]phenyl}acetamide |

TABLE 1-continued

| Cpd. No. | Structure | IUPAC Name |
|---|---|---|
| 263 | 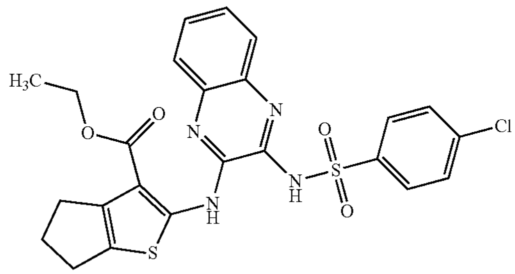 [SMILES: CCOC(=O)c1c(Nc2nc3ccccc3nc2NS(=O)(=O)c2ccc(Cl)cc2)sc2c1CCC2] | ethyl 2-[(3-{[(4-chlorophenyl)sulfonyl]amino}quinoxalin-2-yl)amino]-5,6-dihydro-4H-cyclopenta[b]thisophene-3-carboxylate |
| 264 | 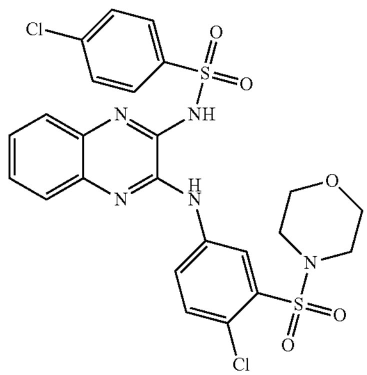 [SMILES: O=S(=O)(Nc1nc2ccccc2nc1Nc1ccc(Cl)c(S(=O)(=O)N2CCOCC2)c1)c1ccc(Cl)cc1] | 4-chloro-N-(3-{[4-chloro-3-(morpholin-4-ylsulfonyl)phenyl]amino}quinoxalin-2-yl)benzenesulfonamide |
| 265 | 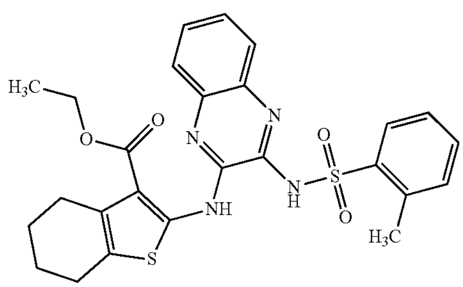 [SMILES: CCOC(=O)c1c(Nc2nc3ccccc3nc2NS(=O)(=O)c2ccccc2C)sc2c1CCCC2] | ethyl 2-[(3-{[(2-methylphenyl)sulfonyl]amino}quinoxalin-2-yl)amino]-4,5,6,7-tetrahydro-1-benzothisophene-3-carboxylate |
| 266 | 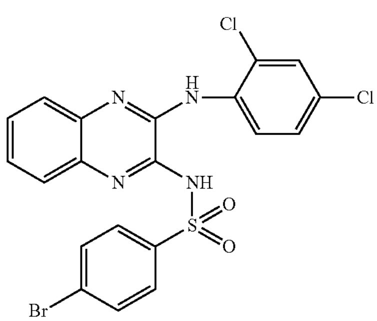 [SMILES: O=S(=O)(Nc1nc2ccccc2nc1Nc1ccc(Cl)cc1Cl)c1ccc(Br)cc1] | 4-bromo-N-{3-[(2,4-dichlorophenyl)amino]quinoxalin-2-yl}benzenesulfonamide |
| 267 | 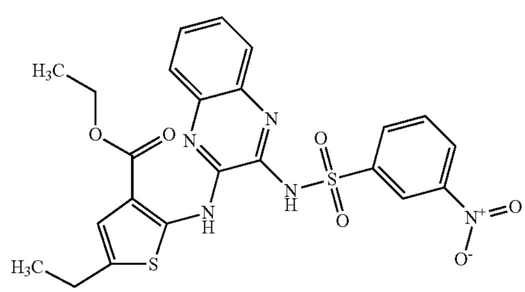 [SMILES: CCOC(=O)c1cc(CC)sc1Nc1nc2ccccc2nc1NS(=O)(=O)c1cccc([N+](=O)[O-])c1] | ethyl 5-ethyl-2-[(3-{[(3-nitrophenyl)sulfonyl]amino}quinoxalin-2-yl)amino]thisophene-3-carboxylate |

| Cpd. No. | Structure | IUPAC Name |
|---|---|---|
| 268 | 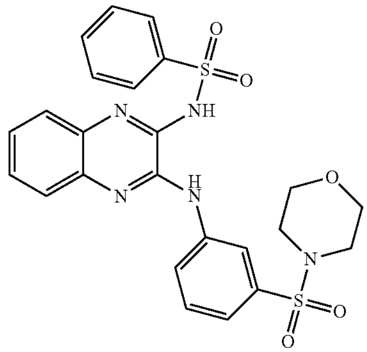 [SMILES: O=S(=O)(Nc1nc2ccccc2nc1Nc1cccc(S(=O)(=O)N2CCOCC2)c1)c1ccccc1] | N-(3-{[3-(mopholin-4-ylsulfonyl)phenyl]amino}quinoxalin-2-yl)benzenesulfonamide |
| 269 | 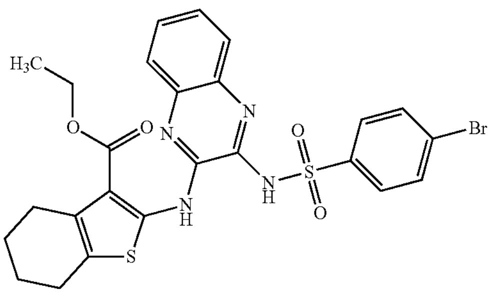 [SMILES: CCOC(=O)c1c(Nc2nc3ccccc3nc2NS(=O)(=O)c2ccc(Br)cc2)sc2c1CCCC2] | ethyl 2-[(3-{[(4-bromophenyl)sulfonyl]amino}quinoxalin-2-yl)amino]-4,5,6,7-tetrahydro-1-benzothisophene-3-carboxylate |
| 270 | 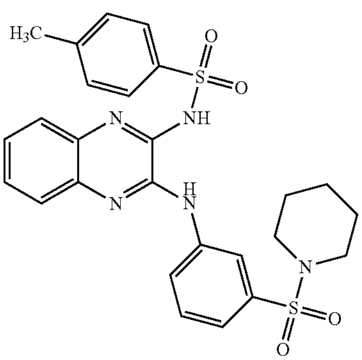 | 4-methyl-N-(3-{[3-(piperidin-1-ylsulfonyl)phenyl]amino}quinoxalin-2-yl)benzenesulfonamide |
| 271 | 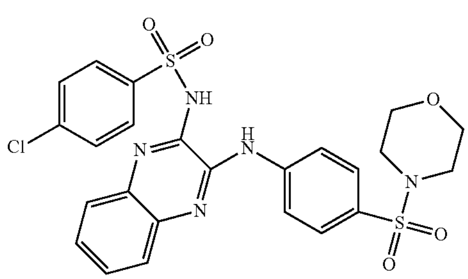 [SMILES: O=S(=O)(Nc1nc2ccccc2nc1Nc1ccc(S(=O)(=O)N2CCOCC2)cc1)c1ccc(Cl)cc1] | 4-chloro-N-(3-{[4-(morpholin-4-ylsulfonyl)phenyl]amino}quinoxalin-2-yl)benzenesulfonamide |

TABLE 1-continued

| Cpd. No. | Structure | IUPAC Name |
|---|---|---|
| 272 | 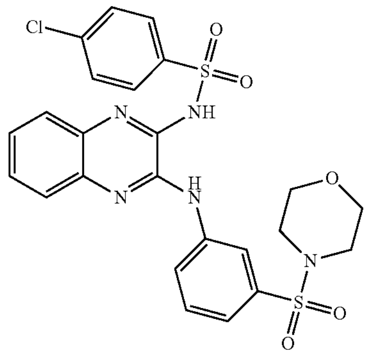 [SMILES: O=S(=O)(Nc1nc2ccccc2nc1Nc1cccc(S(=O)(=O)N2CCOCC2)c1)c1ccc(Cl)cc1] | 4-chloro-N-(3-{[3-morpholin-4-ylsulfonyl)phenyl]amino}quinoxalin-2-yl)benzenesulfonamide |
| 273 | 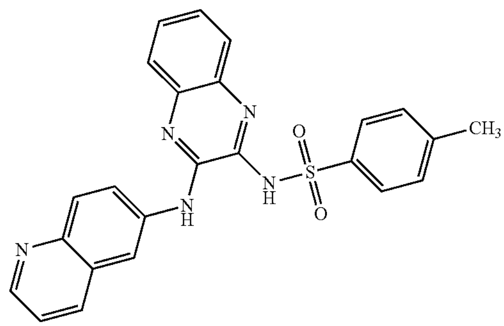 [SMILES: Cc1ccc(S(=O)(=O)Nc2nc3ccccc3nc2Nc2ccc3ncccc3c2)cc1] | 4-methyl-N-[3-(quinolin-6-ylamino)quinoxalin-2-yl]benzenesulfonamide |
| 274 | 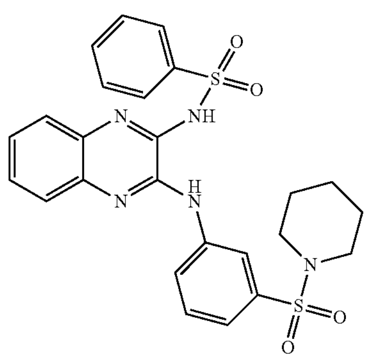 [SMILES: O=S(=O)(Nc1nc2ccccc2nc1Nc1cccc(S(=O)(=O)N2CCCCC2)c1)c1ccccc1] | N-(3-{[3-(piperidin-1-ylsulfonyl)phenyl]amino}quinoxalin-2-yl)benzenesulfonamide |
| 275 | 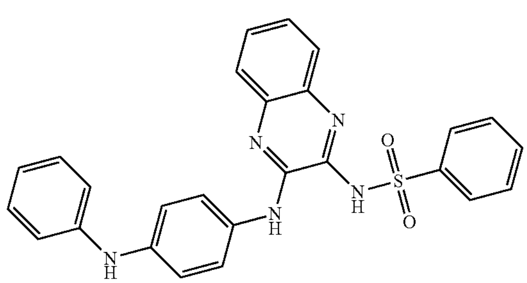 [SMILES: O=S(=O)(Nc1nc2ccccc2nc1Nc1ccc(Nc2ccccc2)cc1)c1ccccc1] | N-(3-{[4-(phenylamino)phenyl]amino}quinoxalin-2-yl)benzenesulfonamide |

TABLE 1-continued

| Cpd. No. | Structure | IUPAC Name |
|---|---|---|
| 276 | 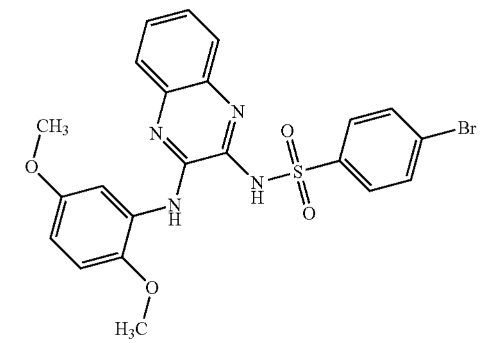 [SMILES: COc1ccc(OC)c(Nc2nc3ccccc3nc2NS(=O)(=O)c2ccc(Br)cc2)c1] | N-(3-{[2,5-bis(methyloxy)phenyl]amino}quinoxalin-2-yl)-4-bromobenzenesulfonamide |
| 277 | 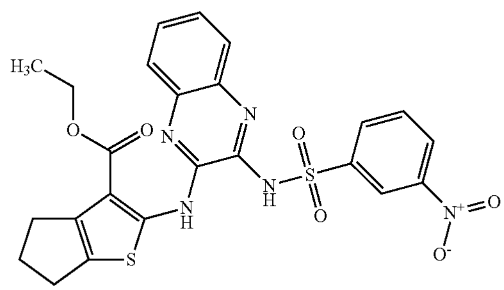 [SMILES: CCOC(=O)c1c(Nc2nc3ccccc3nc2NS(=O)(=O)c2cccc([N+](=O)[O-])c2)sc2c1CCC2] | ethyl 2-[(3-{[(3-nitrophenyl)sulfonyl]amino}quinoxalin-2-yl)amino]-5,6-dihydro-4H-cyclopenta[b]thisophene-3-carboxylate |
| 278 | 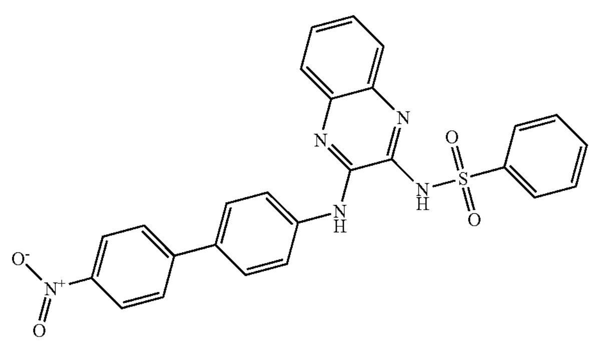 [SMILES: O=[N+]([O-])c1ccc(-c2ccc(Nc3nc4ccccc4nc3NS(=O)(=O)c3ccccc3)cc2)cc1] | N-{3-[(4'-nitrobiphenyl-4-yl)amino]quinoxalin-2-yl}benzenesulfonamide |
| 279 | 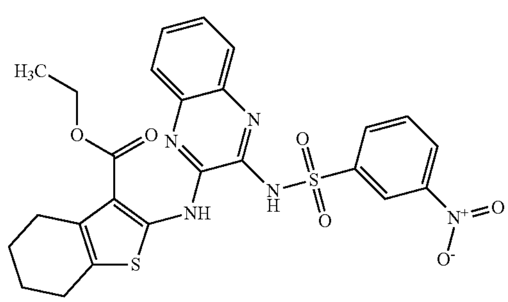 [SMILES: CCOC(=O)c1c(Nc2nc3ccccc3nc2NS(=O)(=O)c2cccc([N+](=O)[O-])c2)sc2c1CCCC2] | ethyl 2-[(3-{[(3-nitrophenyl)sulfonyl]amino}quinoxalin-2-yl)amino]-4,5,6,7-tetrahydro-1-benzothisophene-3-carboxylate |

TABLE 1-continued

| Cpd. No. | Structure | IUPAC Name |
|---|---|---|
| 280 | 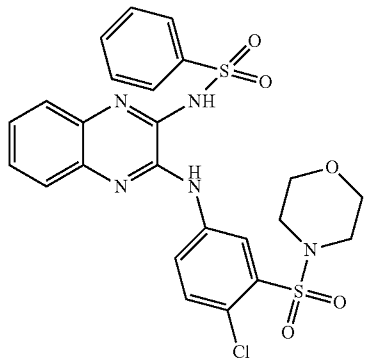 [SMILES: O=S(=O)(Nc1nc2ccccc2nc1Nc1ccc(Cl)c(S(=O)(=O)N2CCOCC2)c1)c1ccccc1] | N-(3-{[4-chloro-3-(morpholin-4-ylsulfonyl)phenyl]amino}quinoxalin-2-yl)benzenesulfonamide |
| 281 | 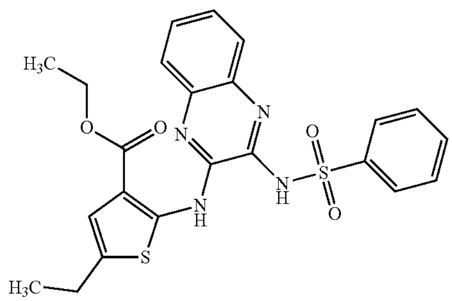 [SMILES: CCOC(=O)c1cc(CC)sc1Nc1nc2ccccc2nc1NS(=O)(=O)c1ccccc1] | ethyl 5-ethyl-2-({3-[(phenylsulfonyl)amino]quinoxalin-2-yl}amino)ethisophene-2-carboxylate |
| 282 | 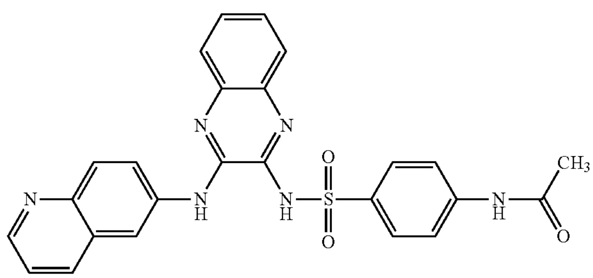 [SMILES: CC(=O)Nc1ccc(S(=O)(=O)Nc2nc3ccccc3nc2Nc2ccc3ncccc3c2)cc1] | N-[4-({[3-(quinolin-6-ylamino)quinoxalin-2-yl]amino}sulfonyl)phenyl]acetamide |
| 283 | 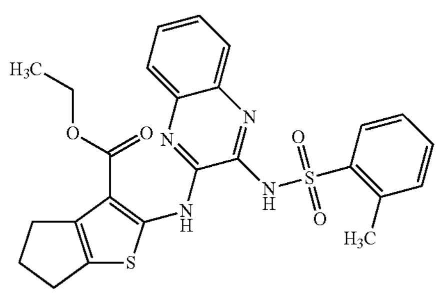 [SMILES: CCOC(=O)c1c(Nc2nc3ccccc3nc2NS(=O)(=O)c2ccccc2C)sc2c1CCC2] | ethyl 2-[(3-{[(2-methylphenyl)sulfonyl]amino}quinoxalin-2-yl)amino]-5,6-dihydro-4H-cyclopenta[b]thisophene-3-carboxylate |
| 284 | 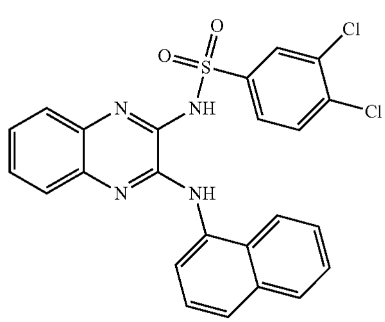 [SMILES: O=S(=O)(Nc1nc2ccccc2nc1Nc1cccc2ccccc12)c1ccc(Cl)c(Cl)c1] | 3,4-dichloro-N-[3-(naphthalen-1-ylamino)quinoxalin-2-yl]benzenesulfonamide |

TABLE 1-continued

| Cpd. No. | Structure | IUPAC Name |
|---|---|---|
| 285 | 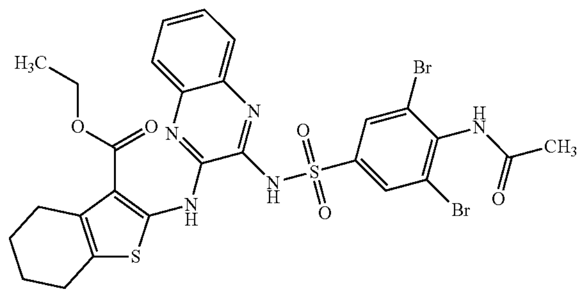 [SMILES: CCOC(=O)c1c(Nc2nc3ccccc3nc2NS(=O)(=O)c2cc(Br)c(NC(C)=O)c(Br)c2)sc2c1CCCC2] | ethyl 2-{[3-({[4-(acetylamino)-3,5-dibromophenyl]sulfonyl}amino)quinoxalin-2-yl]amino}-4,5,6,7-tetrahydro-1-benzothisophene-3-carboxylate |
| 286 | 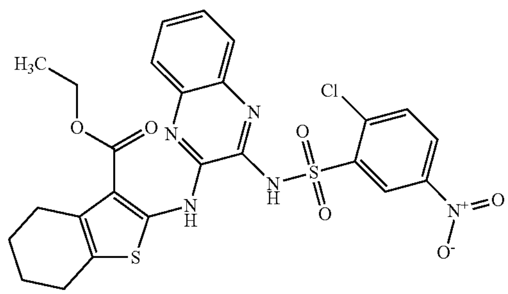 [SMILES: CCOC(=O)c1c(Nc2nc3ccccc3nc2NS(=O)(=O)c2cc([N+](=O)[O-])ccc2Cl)sc2c1CCCC2] | ethyl 2-[(3-{[(2-chloro-5-nitrophenyl)sulfonyl]amino}quinoxalin-2-yl)amino]-4,5,6,7-tetrahydro-1-benzothisophene-3-carboxylate |
| 287 | 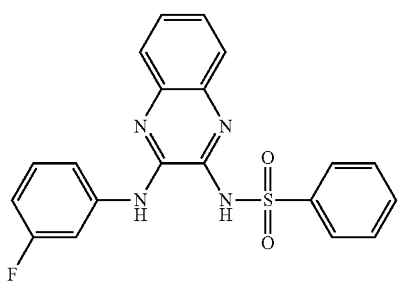 [SMILES: O=S(=O)(Nc1nc2ccccc2nc1Nc1cccc(F)c1)c1ccccc1] | N-{3-[(3-fluorophenyl)amino]quinoxalin-2-yl}benzenesulfonamide |
| 288 | 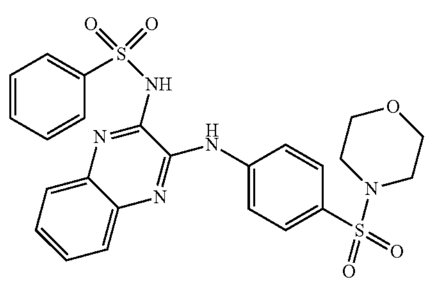 [SMILES: O=S(=O)(Nc1nc2ccccc2nc1Nc1ccc(S(=O)(=O)N2CCOCC2)cc1)c1ccccc1] | N-(3-{[4-(mopholin-4-ylsulfonyl)phenyl]amino}quinoxalin-2-yl)benzenesulfonamide |
| 289 | 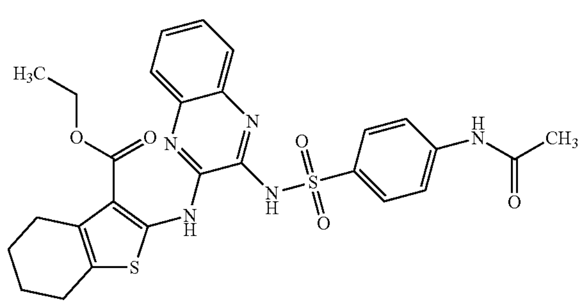 [SMILES: CCOC(=O)c1c(Nc2nc3ccccc3nc2NS(=O)(=O)c2ccc(NC(C)=O)cc2)sc2c1CCCC2] | ethyl 2-{[3-({[4-(acetylamino)phenyl]sulfonyl}amino)quinoxalin-2-yl]amino}-4,5,6,7-tetrahydro-1-benzothisophene-3-carboxylate |

TABLE 1-continued

| Cpd. No. | Structure | IUPAC Name |
|---|---|---|
| 290 | 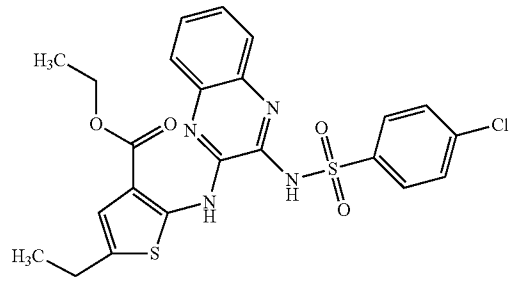 [SMILES: CCOC(=O)c1cc(CC)sc1Nc1nc2ccccc2nc1NS(=O)(=O)c1ccc(Cl)cc1] | ethyl 2-[(3-{[(4-chlorophenyl)sulfonyl]amino}quinoxalin-2-yl)amino]-5-ethylthisophene-3-carboxylate |
| 291 | 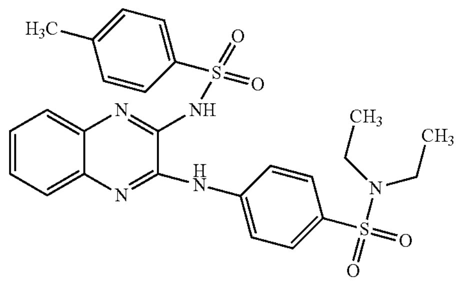 [SMILES: CCN(CC)S(=O)(=O)c1ccc(Nc2nc3ccccc3nc2NS(=O)(=O)c2ccc(C)cc2)cc1] | N,N-diethyl-3-[(3-{[(4-methylphenyl)sulfonyl]amino}quinoxalin-2-yl)amino]benzenesulfonamide |
| 292 | 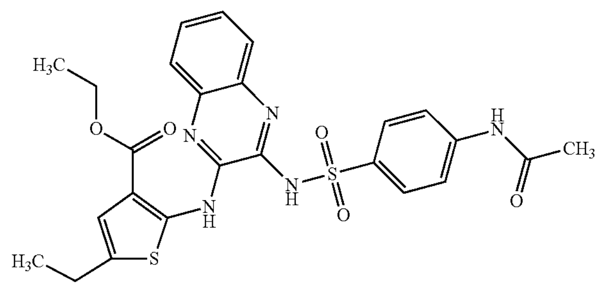 [SMILES: CCOC(=O)c1cc(CC)sc1Nc1nc2ccccc2nc1NS(=O)(=O)c1ccc(NC(C)=O)cc1] | ethyl 2-{[3-({[4-(acetylamino)phenyl]sulfonyl}amino)quinoxalin-2-yl]amino}-5-ethylthisophene-3-carboxylate |
| 293 | 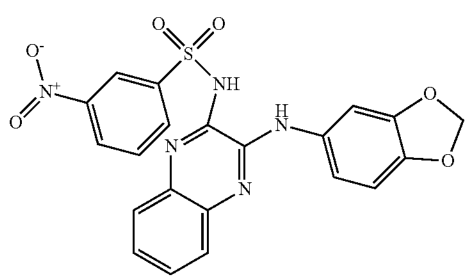 [SMILES: O=[N+]([O-])c1cccc(S(=O)(=O)Nc2nc3ccccc3nc2Nc2ccc3c(c2)OCO3)c1] | N-[3-(1,3-benzodisoxol-5-ylamino)quinoxalin-2-yl]-3-nitrobenzenesulfonamide |
| 294 | 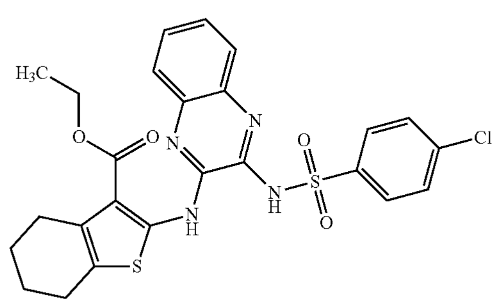 [SMILES: CCOC(=O)c1c(Nc2nc3ccccc3nc2NS(=O)(=O)c2ccc(Cl)cc2)sc2c1CCCC2] | ethyl 2-[(3-{[(4-chlorophenyl)sulfonyl]amino}quinoxalin-2-yl)amino]-4,5,6,7-tetrahydro-1-benzothisophene-3-carboxylate |

TABLE 1-continued

| Cpd. No. | Structure | IUPAC Name |
|---|---|---|
| 295 | 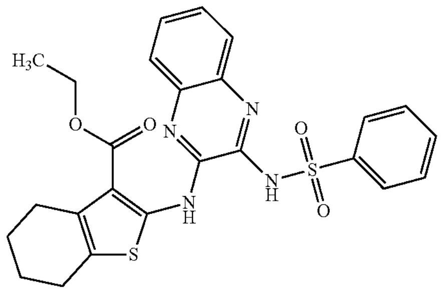 [SMILES: CCOC(=O)c1c(Nc2nc3ccccc3nc2NS(=O)(=O)c2ccccc2)sc2c1CCCC2] | ethyl 2-({3-[(phenylsulfonyl)amino]quinoxalin-2-yl}amino)-4,5,6,7-tetrahydro-1-benzothisophene-3-carboxylate |
| 296 | 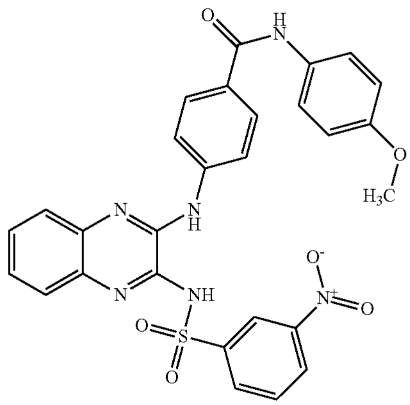 [SMILES: COc1ccc(NC(=O)c2ccc(Nc3nc4ccccc4nc3NS(=O)(=O)c3cccc([N+](=O)[O-])c3)cc2)cc1] | N-[4-(methyloxy)phenyl]-4-[(3-{[(3-nitrophenyl)sulfonyl]amino}quinoxalin-2-yl)amino]benzamide |
| 297 | 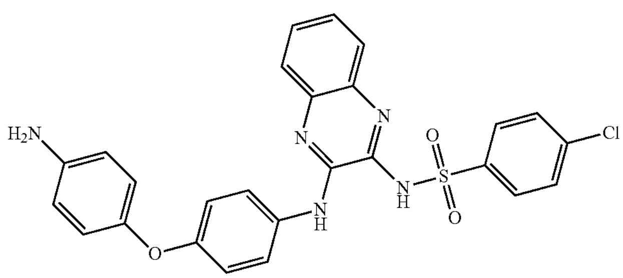 [SMILES: Nc1ccc(Oc2ccc(Nc3nc4ccccc4nc3NS(=O)(=O)c3ccc(Cl)cc3)cc2)cc1] | N-[3-({4-[(4-aminophenyl)oxy]phenyl}amino)quinoxalin-2-yl]-4-chlorobenzenesulfonamide |
| 298 | 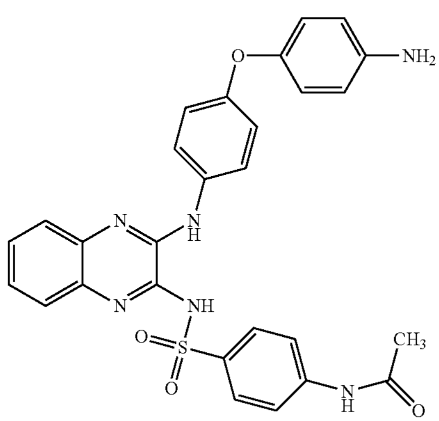 [SMILES: CC(=O)Nc1ccc(S(=O)(=O)Nc2nc3ccccc3nc2Nc2ccc(Oc3ccc(N)cc3)cc2)cc1] | N-[4-({[3-[(4-aminophenyl)oxy]phenyl}amino)quinoxalin-2-yl]amino}sulfonyl)phenyl]acetamide |

TABLE 1-continued

| Cpd. No. | Structure | IUPAC Name |
|---|---|---|
| 299 | 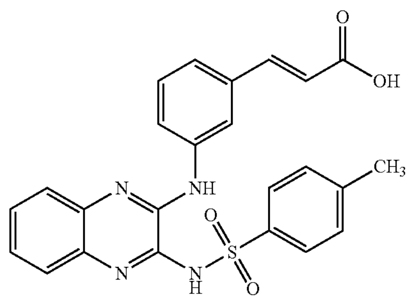 [SMILES: Cc1ccc(S(=O)(=O)Nc2nc3ccccc3nc2Nc2cccc(/C=C/C(=O)O)c2)cc1] | (2E)-3-{3-[(3-{[(4-methylphenyl)sulfonyl]amino}quinoxalin-2-yl)amino]phenyl}prop-2-enoic acid |
| 300 | 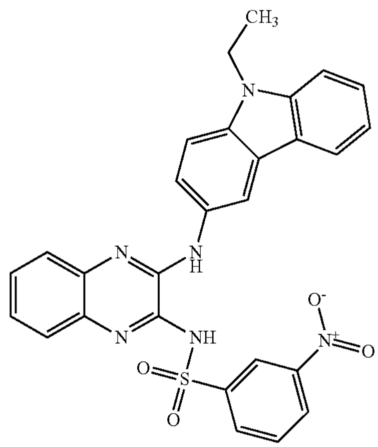 [SMILES: CCn1c2ccccc2c2cc(Nc3nc4ccccc4nc3NS(=O)(=O)c3cccc([N+](=O)[O-])c3)ccc21] | N-{3-[(9-ethyl-9H-carbazol-3-yl)amino]quinoxalin-2-yl}-3-nitrobenzenesulfonamide |
| 301 | 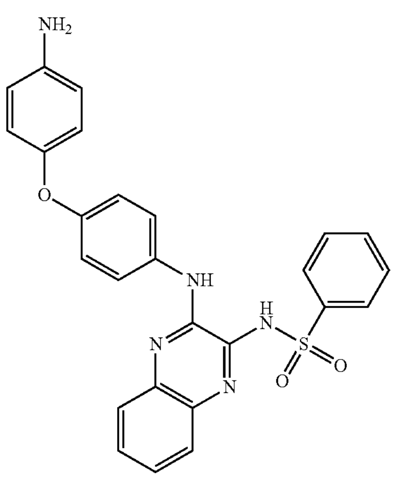 [SMILES: Nc1ccc(Oc2ccc(Nc3nc4ccccc4nc3NS(=O)(=O)c3ccccc3)cc2)cc1] | N-[3-({4-[(4-aminophenyl)oxy]phenyl}amino)quinoxalin-2-yl]benzenesulfonamide |
| 302 | 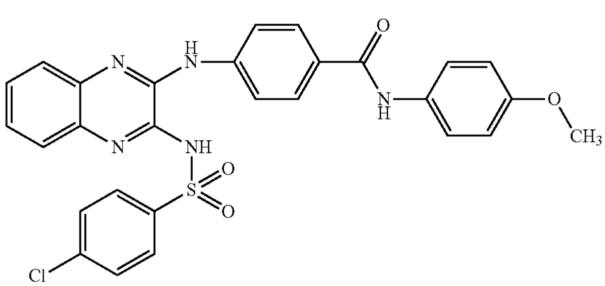 [SMILES: COc1ccc(NC(=O)c2ccc(Nc3nc4ccccc4nc3NS(=O)(=O)c3ccc(Cl)cc3)cc2)cc1] | 4-[(3-{[(4-chlorophenyl)sulfonyl]amino}quinoxalin-2-yl)amino]-N-[4-(methyloxy)phenyl]benzamide |

TABLE 1-continued

| Cpd. No. | Structure | IUPAC Name |
|---|---|---|
| 303 | 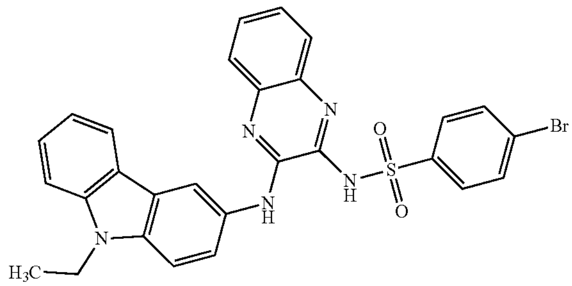 [SMILES: CCn1c2ccccc2c2cc(Nc3nc4ccccc4nc3NS(=O)(=O)c3ccc(Br)cc3)ccc21] | 4-bromo-N-{3-[(9-ethyl-9H-carbazol-3-yl)amino]quinoxalin-2-yl}benzemesulfonamide |
| 304 | 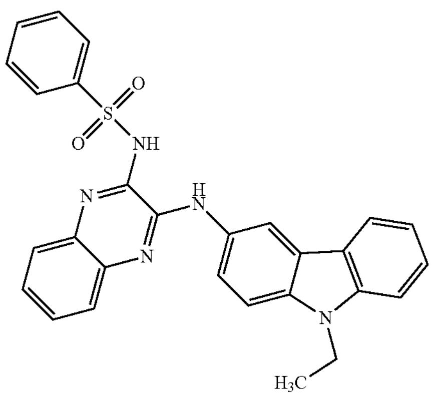 [SMILES: CCn1c2ccccc2c2cc(Nc3nc4ccccc4nc3NS(=O)(=O)c3ccccc3)ccc21] | N-{3-[(9-ethyl-9H-carbazol-3-yl)amino]quinxalin-2-yl}benzenesulfonamide |
| 305 | 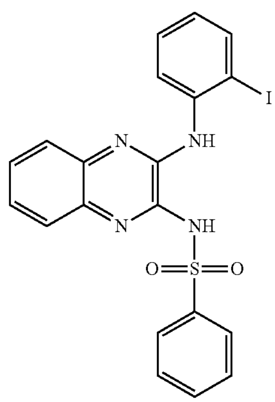 [SMILES: O=S(=O)(Nc1nc2ccccc2nc1Nc1ccccc1I)c1ccccc1] | N-{3-[(2-isodophenyl)amino]quinoxalin-2-yl}benzenesulfonamide |
| 306 | 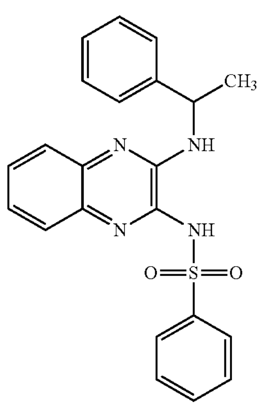 [SMILES: CC(Nc1nc2ccccc2nc1NS(=O)(=O)c1ccccc1)c1ccccc1] | N-{3-[(1-phenylethyl)amino]quinoxalin-2-yl}benzenesulfonamide |

TABLE 1-continued

| Cpd. No. | Structure | IUPAC Name |
|---|---|---|
| 307 | 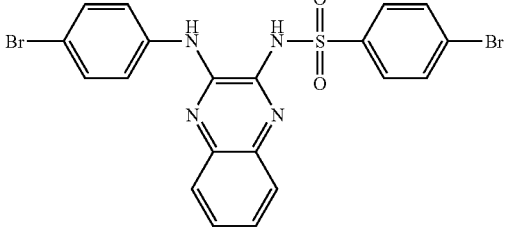 | 4-bromo-N-{3-[(4-bromophenyl)amino]quinoxalin-2-yl}benzenesulfonamide |
| 308 | 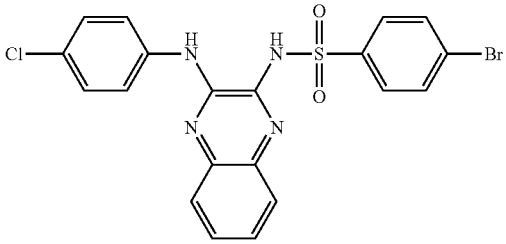 [SMILES: O=S(=O)(Nc1nc2ccccc2nc1Nc1ccc(Cl)cc1)c1ccc(Br)cc1] | 4-bromo-N-{3-[(4-chlorophenyl)amino]quinoxalin-2-yl}benzenesulfonamide |
| 309 | 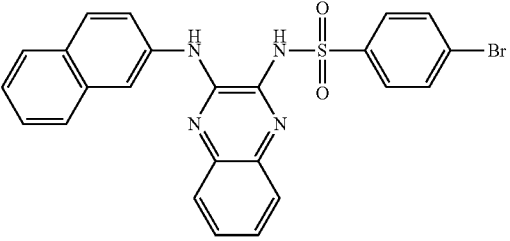 [SMILES: O=S(=O)(Nc1nc2ccccc2nc1Nc1ccc2ccccc2c1)c1ccc(Br)cc1] | 4-bromo-N-[3-(naphthalen-2-ylamino)quinoxalin-2-yl]benzenesulfonamide |
| 310 | 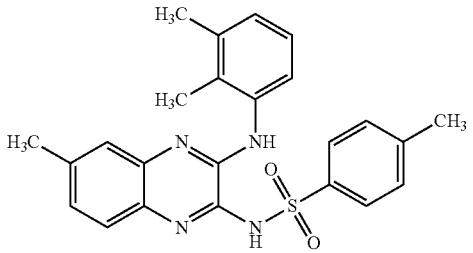 | N-{3-[(2,3-dimethylphenyl)amino]-6-methylquinoxalin-2-yl}-4-methylbenzenesulfonamide |
| 311 | 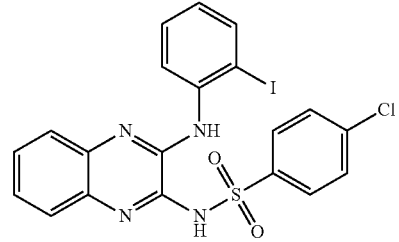 [SMILES: O=S(=O)(Nc1nc2ccccc2nc1Nc1ccccc1I)c1ccc(Cl)cc1] | 4-chloro-N-{3-[(2-isodophenyl)amino]quinoxalin-2-yl}benzenesulfonamide |

TABLE 1-continued
| Cpd. No. | Structure | IUPAC Name |
|---|---|---|
| 312 | 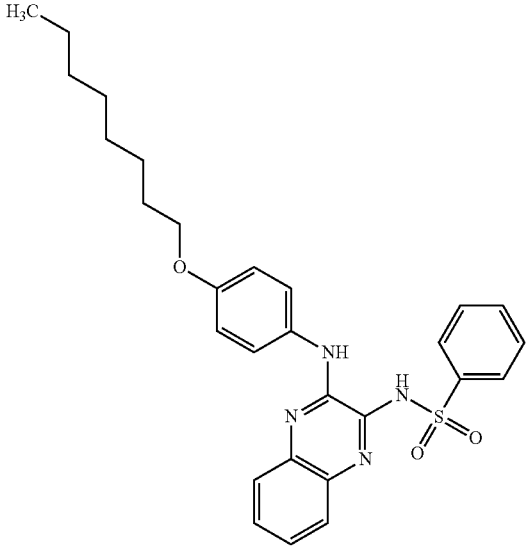 [SMILES: CCCCCCCCOc1ccc(Nc2nc3ccccc3nc2NS(=O)(=O)c2ccccc2)cc1] | N-(3-{[4-(octyloxy)phenyl]amino}quinoxalin-2-yl)benzenesulfonamide |
| 313 | 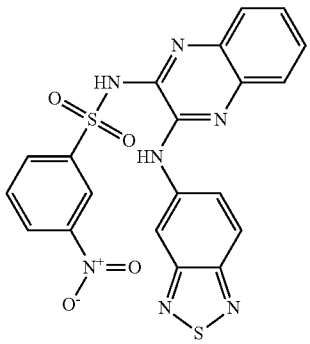 [SMILES: O=[N+]([O-])c1cccc(S(=O)(=O)Nc2nc3ccccc3nc2Nc2ccc3nsnc3c2)c1] | N-[3-(2,1,3-benzothiadiazol-5-ylamino)quinoxalin-2-yl]-3-nitrobenzenesulfonamide |
| 314 | 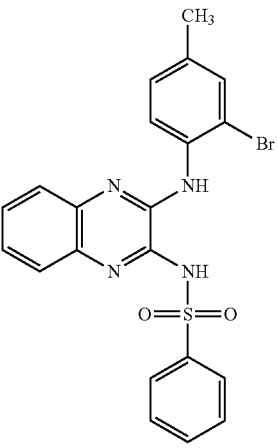 [SMILES: Cc1ccc(Nc2nc3ccccc3nc2NS(=O)(=O)c2ccccc2)c(Br)c1] | N-{3-[(2-bromo-4-methylphenyl)amino]quinoxalin-2-yl}benzenesulfonamide |

TABLE 1-continued

| Cpd. No. | Structure | IUPAC Name |
|---|---|---|
| 315 | 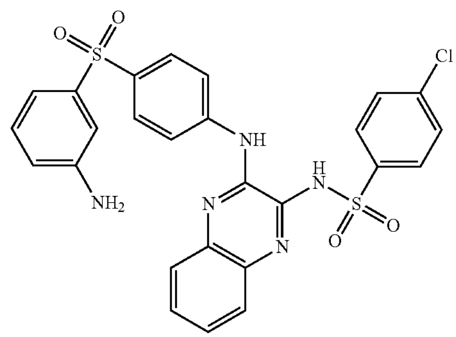 [SMILES: Nc1cccc(S(=O)(=O)c2ccc(Nc3nc4ccccc4nc3NS(=O)(=O)c3ccc(Cl)cc3)cc2)c1] | N-[3-({4-[(3-aminophenyl)sulfonyl]phenyl}amino)quinoxalin-2-yl]-4-chlorobenzenesulfonamide |
| 316 | 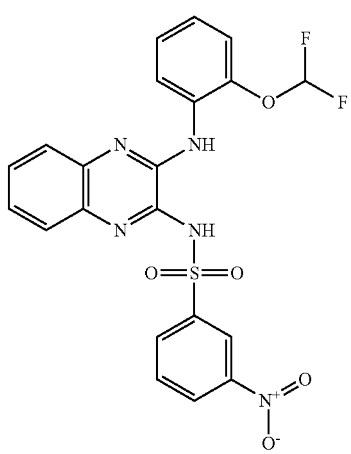 [SMILES: O=[N+]([O-])c1cccc(S(=O)(=O)Nc2nc3ccccc3nc2Nc2ccccc2OC(F)F)c1] | N-[3-({2-[(difluoromethyl)oxy]phenyl}amino)quinoxalin-2-yl]-3-nitrobenzenesulfonamide |
| 317 | 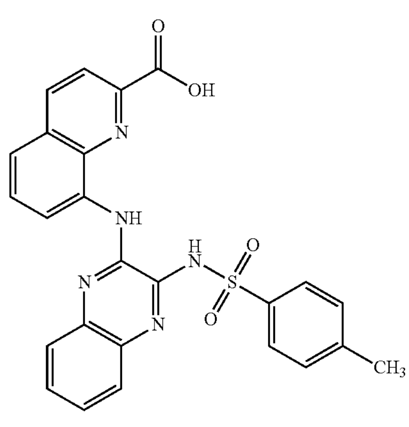 [SMILES: Cc1ccc(S(=O)(=O)Nc2nc3ccccc3nc2Nc2cccc3ccc(C(=O)O)nc23)cc1] | 8-[(3-{[(4-methylphenyl)sulfonyl]amino}quinoxalin-2-yl)amino]quinoline-2-carboxylic acid |

TABLE 1-continued
| Cpd. No. | Structure | IUPAC Name |
|---|---|---|
| 318 | 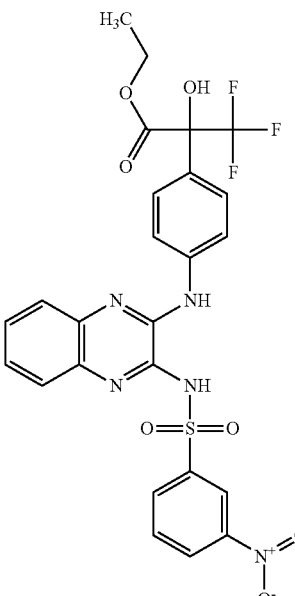 | ethyl 3,3,3-trifluoro-2-hydroxy-2-{4-[(3-{[(3-nitrophenyl)sulfonyl]amino}quinoxalin-2-yl)amino]phenyl}propanoate |
| 319 | 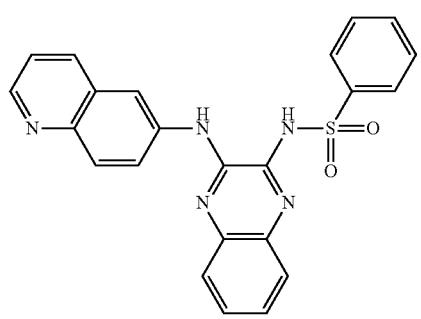 [SMILES: O=S(=O)(Nc1nc2ccccc2nc1Nc1ccc2ncccc2c1)c1ccccc1] | N-[3-quinolin-6-ylamino)quinoxalin-2-yl]benzenesulfonamide |
| 320 | 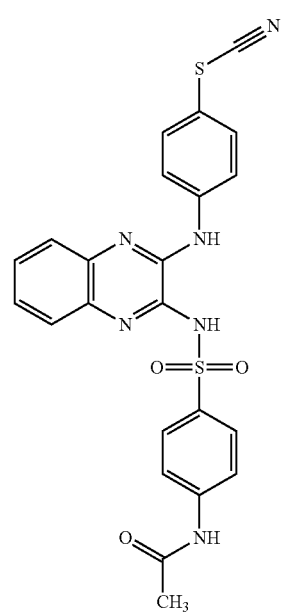 [SMILES: CC(=O)Nc1ccc(S(=O)(=O)Nc2nc3ccccc3nc2Nc2ccc(SC#N)cc2)cc1] | N-{[3-({[4-(acetylamino)phenyl]sulfonyl}amino)quinoxalin-2-yl]amino}phenyl thisocyanate |

TABLE 1-continued

| Cpd. No. | Structure | IUPAC Name |
|---|---|---|
| 321 | 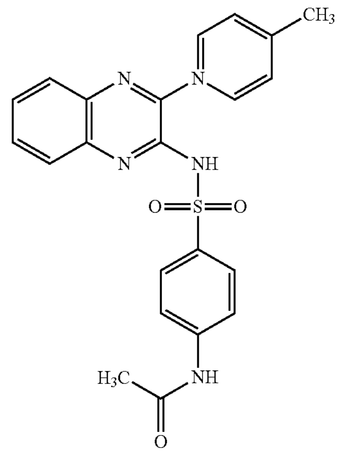 | 1-[3-({[4-(acetylamino)phenyl]sulfonyl}amino)quinoxalin-2-yl]-4-methylpyrimidin |
| 322 | 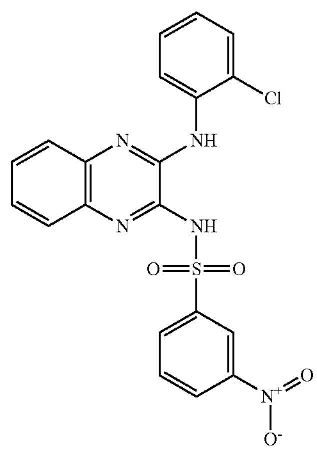 [SMILES: O=[N+]([O-])c1cccc(S(=O)(=O)Nc2nc3ccccc3nc2Nc2ccccc2Cl)c1] | N-{3-[(2-chlorophenyl)amino]quinoxalin-2-yl}-3-nitrobenzenesulfonamide |
| 323 | 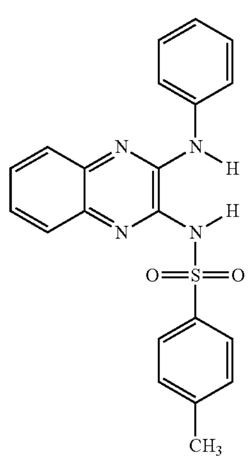 [SMILES: Cc1ccc(S(=O)(=O)Nc2nc3ccccc3nc2Nc2ccccc2)cc1] | 4-methyl-N-[3-(phenylamino)quinoxalin-2-yl]benzenesulfonamide |

TABLE 1-continued

| Cpd. No. | Structure | IUPAC Name |
|---|---|---|
| 324 | 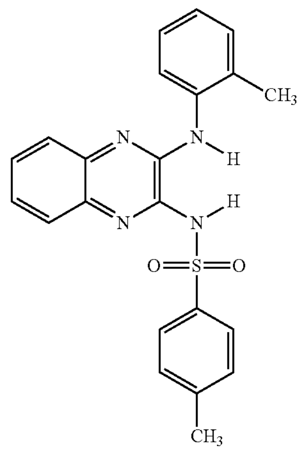 [SMILES: Cc1ccc(S(=O)(=O)Nc2nc3ccccc3nc2Nc2ccccc2C)cc1] | 4-methyl-N-{3-[(2-methylphenyl)amino]quinoxalin-2-yl}benzenesulfonamide |
| 325 | 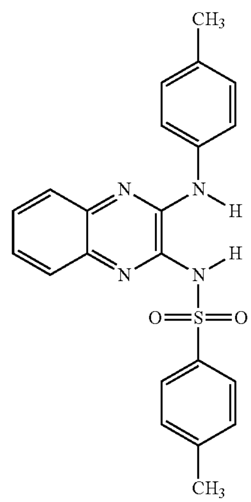 [SMILES: Cc1ccc(Nc2nc3ccccc3nc2NS(=O)(=O)c2ccc(C)cc2)cc1] | 4-methyl-N-{3-[(4-methylphenyl)amino]quinoxalin-2-yl}benzenesulfonamide |
| 326 | 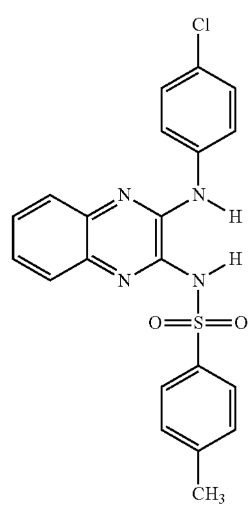 [SMILES: Cc1ccc(S(=O)(=O)Nc2nc3ccccc3nc2Nc2ccc(Cl)cc2)cc1] | N-{3-[(4-chlorophenyl)amino]quinoxalin-2-yl}-4-methylbenzenesulfonamide |

TABLE 1-continued

| Cpd. No. | Structure | IUPAC Name |
|---|---|---|
| 327 | 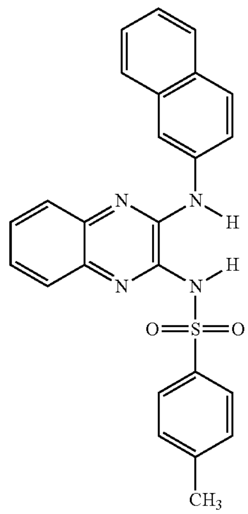 [SMILES: Cc1ccc(S(=O)(=O)Nc2nc3ccccc3nc2Nc2ccc3ccccc3c2)cc1] | 4-methyl-N-[3-(naphthalen-2-ylamino)quinoxalin-2-yl]benzenesulfonamide |
| 328 | 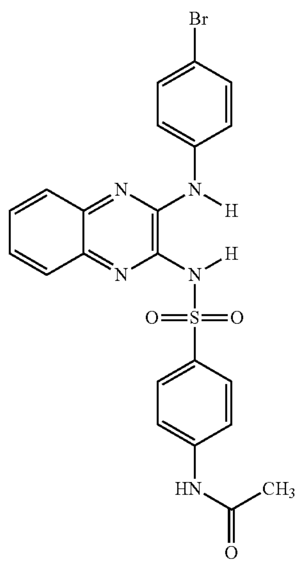 [SMILES: CC(=O)Nc1ccc(S(=O)(=O)Nc2nc3ccccc3nc2Nc2ccc(Br)cc2)cc1] | N-{4-[({3-[(4-bomophenyl)amino]quinoxalin-2-yl}amino)sulfonyl]phenyl}acetamide |
| 329 | 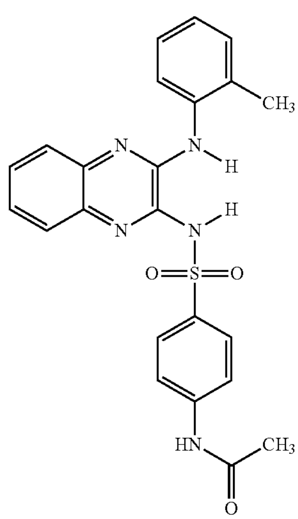 [SMILES: CC(=O)Nc1ccc(S(=O)(=O)Nc2nc3ccccc3nc2Nc2ccccc2C)cc1] | N-{4-[({3-[(2-methylphenyl)amino]quinoxalin-2-yl}amino)sulfonyl]phenyl}acetamide |

TABLE 1-continued

| Cpd. No. | Structure | IUPAC Name |
|---|---|---|
| 330 | 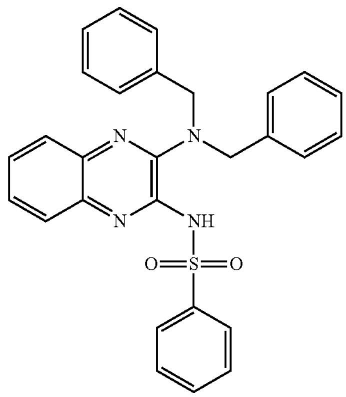 [SMILES: O=S(=O)(Nc1nc2ccccc2nc1N(Cc1ccccc1)Cc1ccccc1)c1ccccc1] | N-{3-[bis(phenylmethyl)amino]quinoxalin-2-yl}benzenesulfonamide |
| 331 | 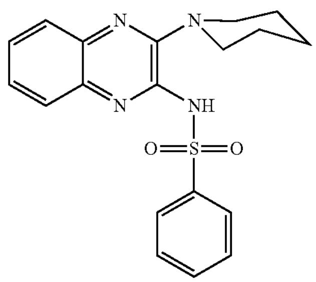 [SMILES: O=S(=O)(Nc1nc2ccccc2nc1N1CCCCC1)c1ccccc1] | N-(3-piperidin-1-ylquinoxalin-2-yl)benzenesulfonamide |
| 332 | 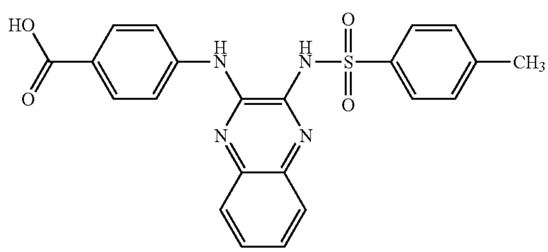 [SMILES: Cc1ccc(S(=O)(=O)Nc2nc3ccccc3nc2Nc2ccc(C(=O)O)cc2)cc1] | 4-[(3-{[(4-methylphenyl)sulfonyl]amino}quinoxalin-2-yl}amino]benzoic acid |
| 333 | 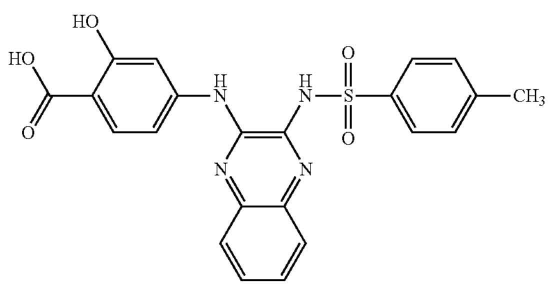 [SMILES: Cc1ccc(S(=O)(=O)Nc2nc3ccccc3nc2Nc2ccc(C(=O)O)c(O)c2)cc1] | 2-hydroxy-4-[(3-{[(4-methylphenyl)sulfonyl]amino}quinoxalin-2-yl)amino]benzoic acid |
| 334 | 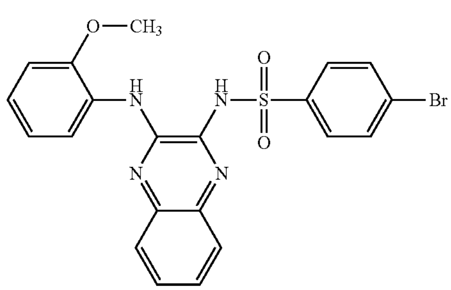 [SMILES: COc1ccccc1Nc1nc2ccccc2nc1NS(=O)(=O)c1ccc(Br)cc1] | 4-bromo-N-(3-{[2-(methyloxy)phenyl]amino}quinoxalin-2-yl)benzenesulfonamide |

| Cpd. No. | Structure | IUPAC Name |
|---|---|---|
| 335 | 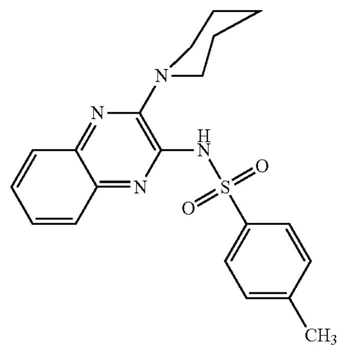 [SMILES: Cc1ccc(S(=O)(=O)Nc2nc3ccccc3nc2N2CCCCC2)cc1] | 4-methyl-N-(3-piperidin-1-ylquinoxalin-2-yl)benzenesulfonamide |
| 336 | 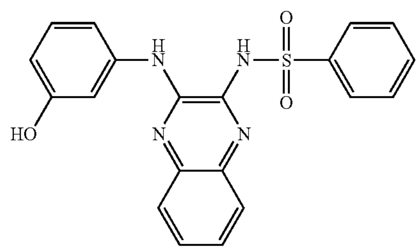 [SMILES: O=S(=O)(Nc1nc2ccccc2nc1Nc1cccc(O)c1)c1ccccc1] | N-{3-[(3-hydroxyphenyl)amino]quinoxalin-2-yl}benzenesulfonamide |
| 337 | 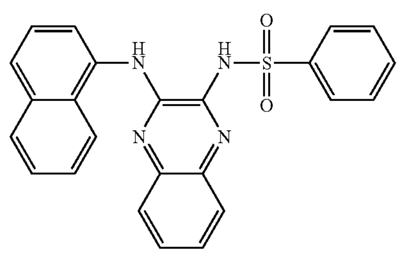 [SMILES: O=S(=O)(Nc1nc2ccccc2nc1Nc1cccc2ccccc12)c1ccccc1] | N-[3-(naphthalen-1-ylamino)quinoxalin-2-yl]benzenesulfonamide |
| 338 | 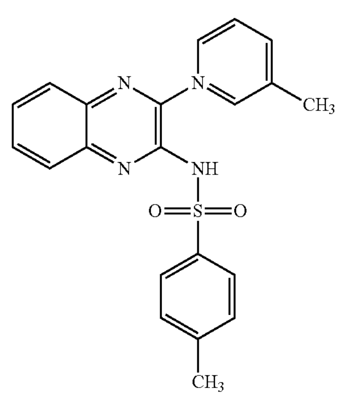 | 3-methyl-1-(3-{[(4-methylphenyl)sulfonyl]amino}quinoxalin-2-yl)pyrimidinium |
| 339 | 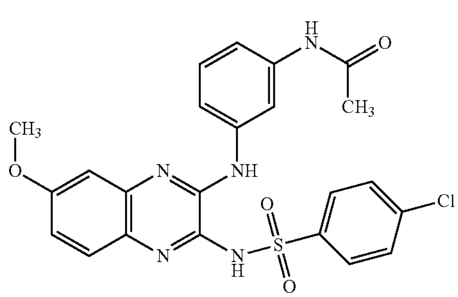 [SMILES: COc1ccc2nc(NS(=O)(=O)c3ccc(Cl)cc3)c(Nc3cccc(NC(C)=O)c3)nc2c1] | N-(3-{[3-{[(4-chlorophenyl)sulfonyl]amino}-7-(methyloxy)quinoxalin-2-yl]amino}phenyl)acetamide |

TABLE 1-continued

| Cpd. No. | Structure | IUPAC Name |
|---|---|---|
| 340 | 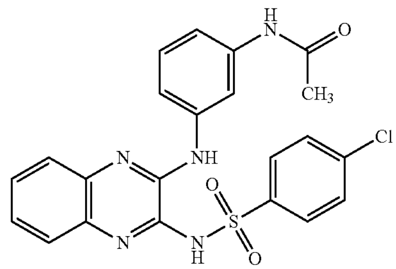 [SMILES: CC(=O)Nc1cccc(Nc2nc3ccccc3nc2NS(=O)(=O)c2ccc(Cl)cc2)c1] | N-{3-[(3-{[(4-chlorophenyl)sulfonyl]amino}quinoxalin-2-yl)amino]phenyl}acetamide |
| 341 | 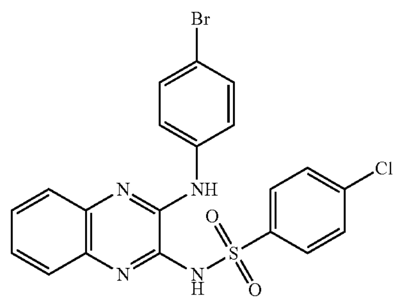 [SMILES: O=S(=O)(Nc1nc2ccccc2nc1Nc1ccc(Br)cc1)c1ccc(Cl)cc1] | N-{3-[(4-bromophenyl)amino]quinoxalin-2-yl}-4-chlorobenzenesulfonamide |
| 342 | 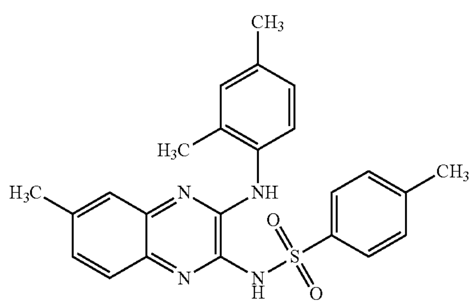 | N-{3-[(2,4-dimethylphenyl)amino]-6-methylquinoxalin-2-yl}-4-methylbenzenesulfonamide |
| 343 | 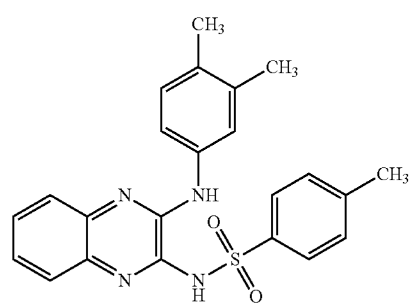 [SMILES: Cc1ccc(S(=O)(=O)Nc2nc3ccccc3nc2Nc2ccc(C)c(C)c2)cc1] | N-{3-[(3,4-dimethylphenyl)amino]quinoxalin-2-yl}-4-methylbenzenesulfonamide |
| 344 | 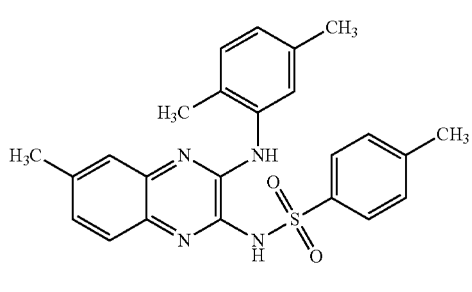 | N-{3-[(2,5-dimethylphenyl)amino]-6-methylquinoxalin-2-yl}-4-methylbenzenesulfonamide |

TABLE 1-continued

| Cpd. No. | Structure | IUPAC Name |
|---|---|---|
| 345 | 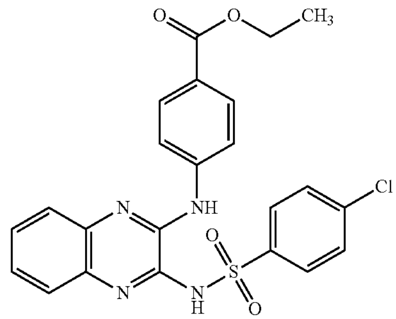 [SMILES: CCOC(=O)c1ccc(Nc2nc3ccccc3nc2NS(=O)(=O)c2ccc(Cl)cc2)cc1] | ethyl 4-[(3-{[(4-chlorophenyl)sulfonyl]amino}quinoxalin-2-yl)amino]benzoate |
| 346 | 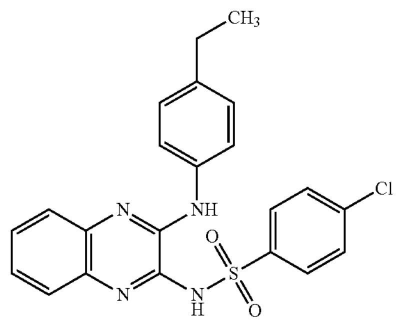 [SMILES: CCc1ccc(Nc2nc3ccccc3nc2NS(=O)(=O)c2ccc(Cl)cc2)cc1] | 4-chloro-N-{3-[(4-ethylphenyl)amino]quinoxalin-2-yl}benzenesulfonamide |
| 347 | 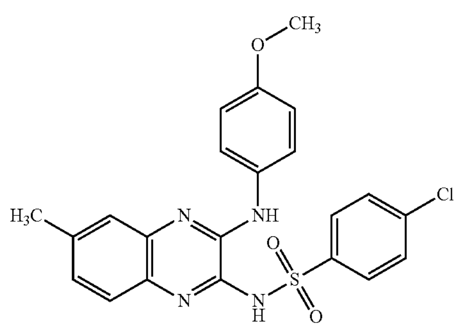 [SMILES: COc1ccc(Nc2nc3cc(C)ccc3nc2NS(=O)(=O)c2ccc(Cl)cc2)cc1] | 4-chloro-N-(6-methyl-3-{[4-(methyloxy)phenyl]amino}quinoxalin-2-yl)benzenesulfonamide |
| 348 | 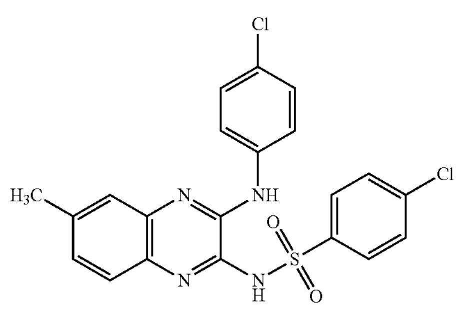 [SMILES: Cc1ccc2nc(NS(=O)(=O)c3ccc(Cl)cc3)c(Nc3ccc(Cl)cc3)nc2c1] | 4-chloro-N-{3-[(4-chlorophenyl)amino]-6-methylquinoxalin-2-yl}benzenesulfonamide |

| Cpd. No. | Structure | IUPAC Name |
|---|---|---|
| 349 | 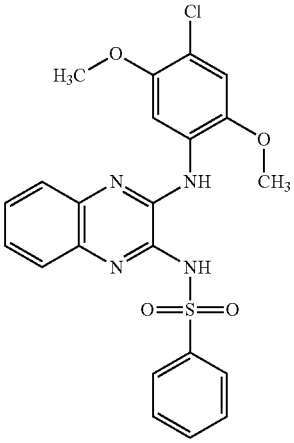 [SMILES: COc1cc(Nc2nc3ccccc3nc2NS(=O)(=O)c2ccccc2)c(OC)cc1Cl] | N-(3-{[4-chloro-2,5-bis(methyloxy)phenyl]amino}quinoxalin-2-yl)benzenesulfonamide |
| 350 | 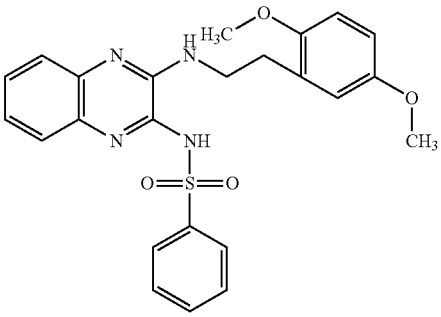 [SMILES: COc1ccc(OC)c(CCNc2nc3ccccc3nc2NS(=O)(=O)c2ccccc2)c1] | N-[3-({2-[2,5-bis(methyloxy)phenyl]ethyl}amino)quinoxalin-2-yl]benzenesulfonamide |
| 351 | 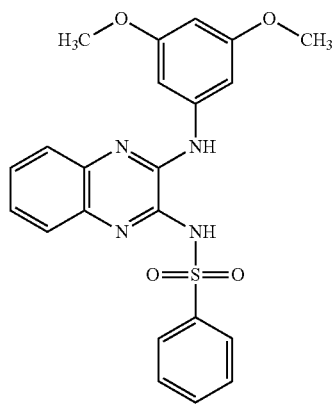 [SMILES: COc1cc(Nc2nc3ccccc3nc2NS(=O)(=O)c2ccccc2)cc(OC)c1] | N-(3-{[3,5-bis(methyloxy)phenyl]amino}quinoxalin-2-yl)benzenesulfonamide |

TABLE 1-continued
| Cpd. No. | Structure | IUPAC Name |
|---|---|---|
| 352 | 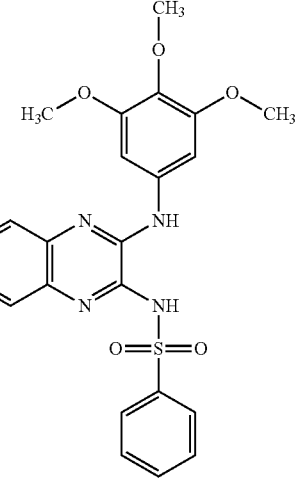 | N-(3-{[3,4,5-tris(methyloxy)phenyl]amino}quinoxalin-2-yl)benzenesulfonamide |
| 353 | 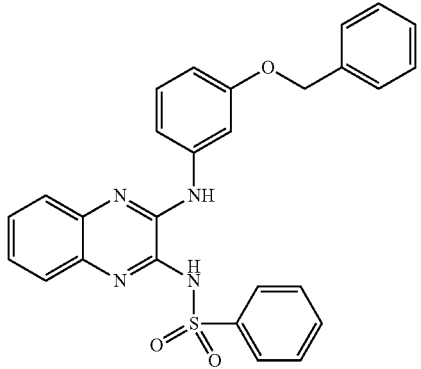 [SMILES: O=S(=O)(Nc1nc2ccccc2nc1Nc1cccc(OCc2ccccc2)c1)c1ccccc1] | N-[3-({3-[(phenylmethyl)oxy]phenyl}amino)quinoxalin-2-yl]benzenesulfonamide |
| 354 | 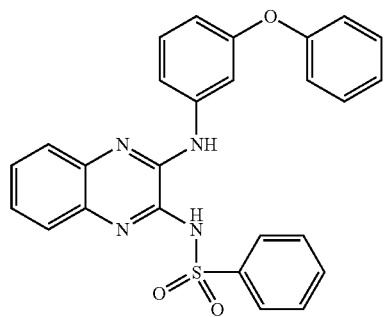 [SMILES: O=S(=O)(Nc1nc2ccccc2nc1Nc1cccc(Oc2ccccc2)c1)c1ccccc1] | N-(3-{[3-(phenyloxy)phenyl]amino}quinoxalin-2-yl)benzenesulfonamide |
| 355 | 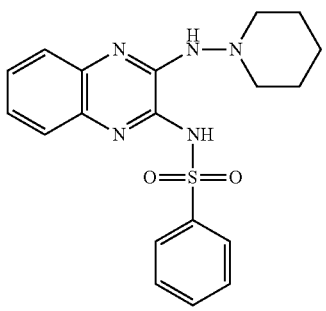 [SMILES: O=S(=O)(Nc1nc2ccccc2nc1NN1CCCCC1)c1ccccc1] | N-[3-(piperidin-1-ylamino)quinoxalin-2-yl]benzenesulfonamide |

TABLE 1-continued

| Cpd. No. | Structure | IUPAC Name |
|---|---|---|
| 356 | 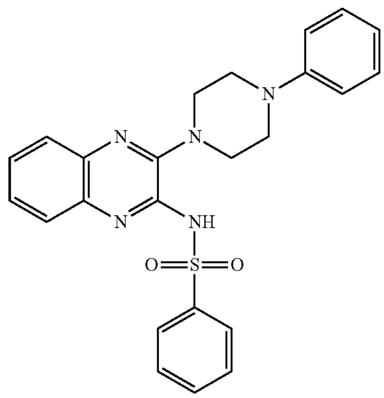 [SMILES: O=S(=O)(Nc1nc2ccccc2nc1N1CCN(c2ccccc2)CC1)c1ccccc1] | N-[3-(4-phenylpiperazin-1-yl)quinoxalin-2-yl]benzenesulfonamide |
| 357 | 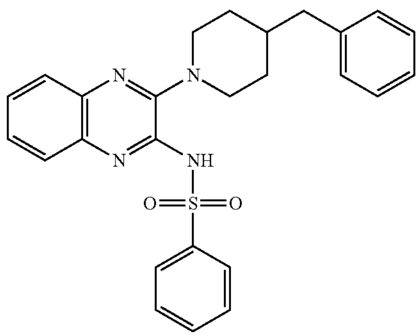 [SMILES: O=S(=O)(Nc1nc2ccccc2nc1N1CCC(Cc2ccccc2)CC1)c1ccccc1] | N-{3-[(phenylmethyl)piperidin-1-yl]quinoxalin-2-yl}benzenesulfonamide |
| 358 | 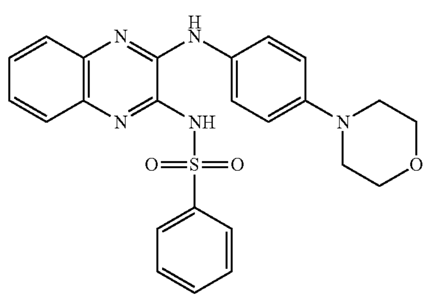 [SMILES: O=S(=O)(Nc1nc2ccccc2nc1Nc1ccc(N2CCOCC2)cc1)c1ccccc1] | N-{3-[(4-mopholin-4-ylphenyl)amino]quinoxalin-2-yl}benzenesulfonamide |
| 359 | 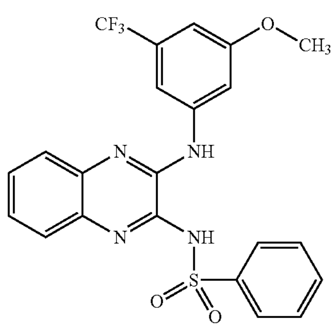 [SMILES: COc1cc(Nc2nc3ccccc3nc2NS(=O)(=O)c2ccccc2)cc(C(F)(F)F)c1] | N-(3-{[3-(methyloxy)-5-(trifluoromethyl)phenyl]amino}quinoxalin-2-yl)benzenesulfonamide |

TABLE 1-continued

| Cpd. No. | Structure | IUPAC Name |
|---|---|---|
| 360 | 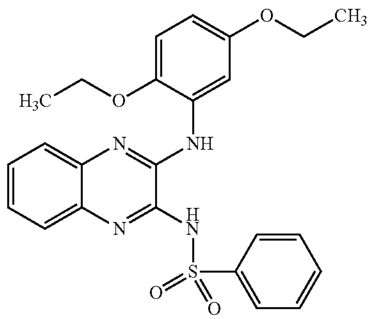 [SMILES: CCOc1ccc(OCC)c(Nc2nc3ccccc3nc2NS(=O)(=O)c2ccccc2)c1] | N-(3-{[2,5-bis(ethyloxy)phenyl]amino}quinoxalin-2-yl)benzenesulfonamide |
| 361 | 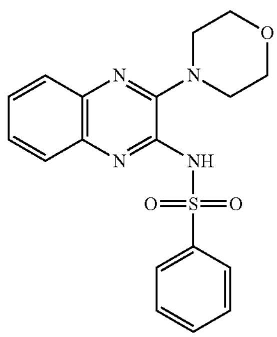 [SMILES: O=S(=O)(Nc1nc2ccccc2nc1N1CCOCC1)c1ccccc1] | N-(3-morpholin-4-ylquinoxalin-2-yl)benzenesulfonamide |
| 362 | 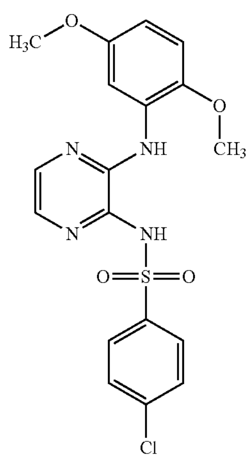 [SMILES: COc1ccc(OC)c(Nc2nccnc2NS(=O)(=O)c2ccc(Cl)cc2)c1] | N-(3-{[2,5-bis(methyloxy)phenyl]amino}pyrazin-2-yl)-4-chlorobenzenesulfonamide |
| 363 | 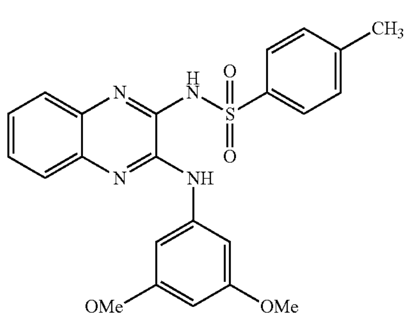 [SMILES: COc1cc(Nc2nc3ccccc3nc2NS(=O)(=O)c2ccc(C)cc2)cc(OC)c1] | N-(3-{[3,5-bis(methyloxy)phenyl]amino}quinoxalin-2-yl)-4-methylbenzenesulfonamide |

TABLE 1-continued

| Cpd. No. | Structure | IUPAC Name |
| --- | --- | --- |
| 364 | 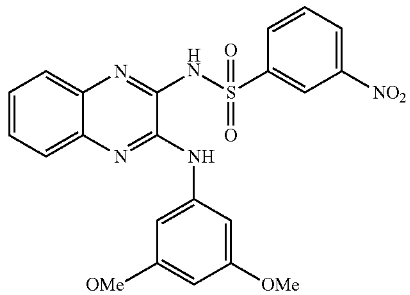 [SMILES: COc1cc(Nc2nc3ccccc3nc2NS(=O)(=O)c2cccc([N+](=O)[O-])c2)cc(OC)c1] | N-(3-{[3,5-bis(methyloxy)phenyl]amino}quinoxalin-2-yl)-3-nitrobenzenesulfonamide |
| 365 | 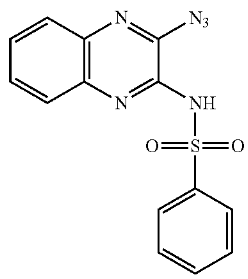 [SMILES: [N-]=[N+]=Nc1nc2ccccc2nc1NS(=O)(=O)c1ccccc1] | N-(3-azidoquinoxalin-2-yl)benzenesulfonamide |
| 366 | 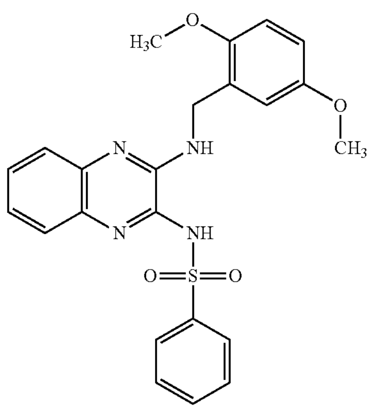 [SMILES: COc1ccc(OC)c(CNc2nc3ccccc3nc2NS(=O)(=O)c2ccccc2)c1] | N-[3-({[2,5-bis(methyloxy)phenyl]methyl}amino)quinoxalin-2-yl]benzenesulfonamide |
| 367 | 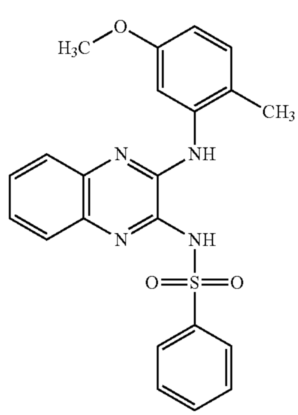 [SMILES: COc1ccc(C)c(Nc2nc3ccccc3nc2NS(=O)(=O)c2ccccc2)c1] | N-(3-{[2-methyl-5-(methyloxy)phenyl]amino}quinoxalin-2-yl)benzenesulfonamide |

TABLE 1-continued

| Cpd. No. | Structure | IUPAC Name |
|---|---|---|
| 368 | 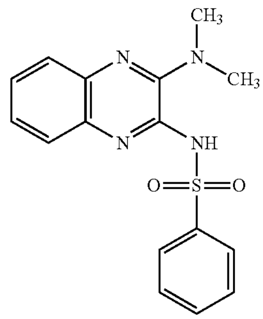 [SMILES: CN(C)c1nc2ccccc2nc1NS(=O)(=O)c1ccccc1] | N-[3-(dimethylamino)quinoxalin-2-yl]benzenesulfonamide |
| 369 | 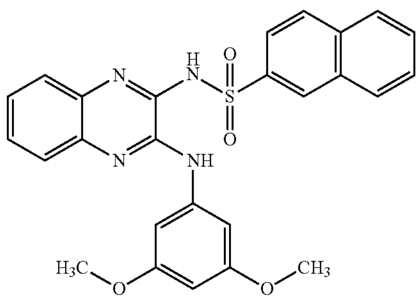 [SMILES: COc1cc(Nc2nc3ccccc3nc2NS(=O)(=O)c2ccc3ccccc3c2)cc(OC)c1] | N-(3-{[3,5-bis(methyloxy)phenyl]amino}quinoxalin-2-yl)naphthalene-2-sulfonamide |
| 370 | 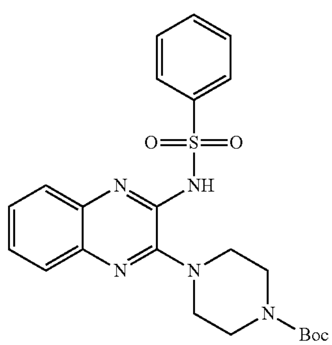 [SMILES: CC(C)(C)OC(=O)N1CCN(c2nc3ccccc3nc2NS(=O)(=O)c2ccccc2)CC1] | 4-(3-Benzenesulfonylamino-quinoxalin-2-yl)piperazine-1-carboxylic acid tert-butyl ester |
| 371 | 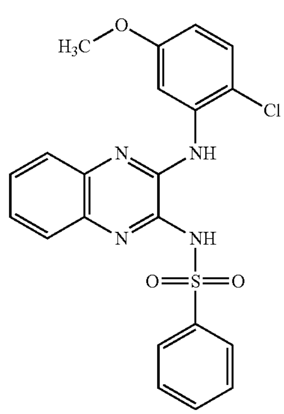 [SMILES: COc1ccc(Cl)c(Nc2nc3ccccc3nc2NS(=O)(=O)c2ccccc2)c1] | N-[3-(2-Chloro-5-methoxy-phenylamino)-quinoxalin-2-yl]-benzenesulfonamide |

TABLE 1-continued

| Cpd. No. | Structure | IUPAC Name |
| --- | --- | --- |
| 372 | 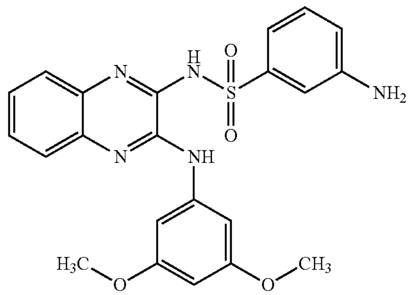 [SMILES: COc1cc(Nc2nc3ccccc3nc2NS(=O)(=O)c2cccc(N)c2)cc(OC)c1] | 3-amino-N-(3-{[3,5-bis(methyloxy)phenyl]amino}quinoxalin-2-yl)benzenesulfonamide |
| 373 | 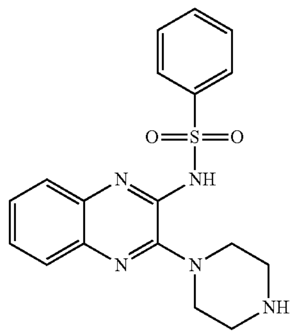 [SMILES: O=S(=O)(Nc1nc2ccccc2nc1N1CCNCC1)c1ccccc1] | N-(3-piperazin-1-ylquinoxalin-2-yl)benzenesulfonamide |
| 374 | 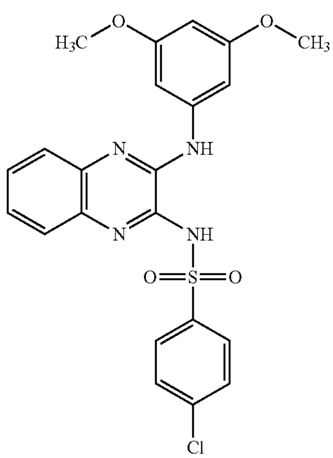 [SMILES: COc1cc(Nc2nc3ccccc3nc2NS(=O)(=O)c2ccc(Cl)cc2)cc(OC)c1] | N-(3-{[3,5-bis(methyloxy)phenyl]amino}quinoxalin-2-yl)-4-chlorobenzenesulfonamide |
| 375 | 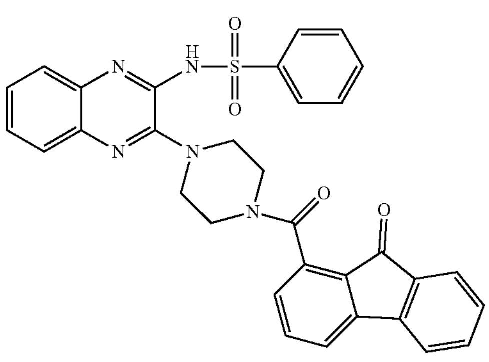 [SMILES: O=C1c2ccccc2-c2cccc(C(=O)N3CCN(c4nc5ccccc5nc4NS(=O)(=O)c4ccccc4)CC3)c21] | N-(3-{4-[9-oxo-9H-fluoren-1-yl)carbonyl]piperazin-1-yl}quinoxalin-2-yl)benzenesulfonamide |

TABLE 1-continued

| Cpd. No. | Structure | IUPAC Name |
|---|---|---|
| 376 | 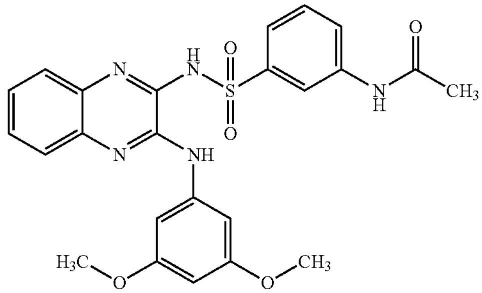 [SMILES: COc1cc(Nc2nc3ccccc3nc2NS(=O)(=O)c2cccc(NC(C)=O)c2)cc(OC)c1] | N-(3-{[(3-{[3,5-bis(methyloxy)phenyl]amino}quinoxalin-2-yl)amino]sulfonyl}phenyl)acetamide |
| 377 | 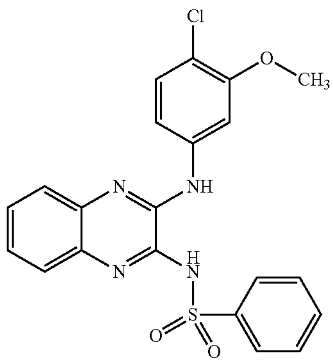 [SMILES: COc1cc(Nc2nc3ccccc3nc2NS(=O)(=O)c2ccccc2)ccc1Cl] | N-(3-{[4-chloro-3-(methyloxy)phenyl]amino}quinoxalin-2-yl)benzenesulfonamide |
| 378 | 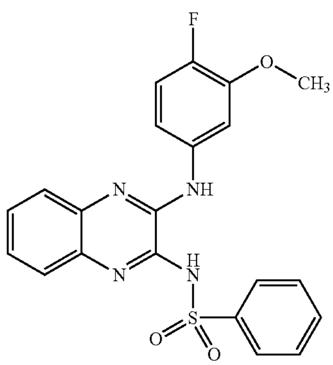 [SMILES: COc1cc(Nc2nc3ccccc3nc2NS(=O)(=O)c2ccccc2)ccc1F] | N-(3-{[4-fluoro-3-(methyloxy)phenyl]amino}quinoxalin-2-yl)benzenesulfonamide |
| 379 | 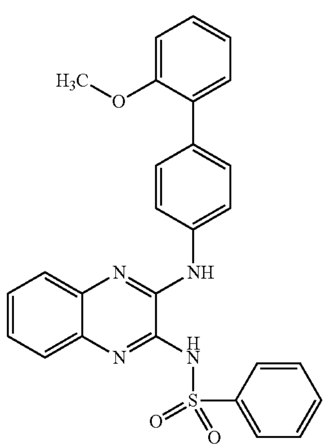 [SMILES: COc1ccccc1-c1ccc(Nc2nc3ccccc3nc2NS(=O)(=O)c2ccccc2)cc1] | N-(3-{[2'-(methyloxy)biphenyl-4-yl]amino}quinoxalin-2-yl)benzenesulfonamide |

TABLE 1-continued

| Cpd. No. | Structure | IUPAC Name |
|---|---|---|
| 380 | 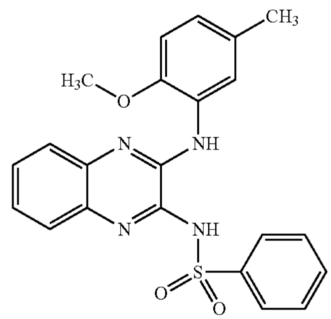 [SMILES: COc1ccc(C)cc1Nc1nc2ccccc2nc1NS(=O)(=O)c1ccccc1] | N-(3-{[5-methyl-2-(methyloxy)phenyl]amino}quinoxalin-2-yl)benzenesulfonamide |
| 381 | 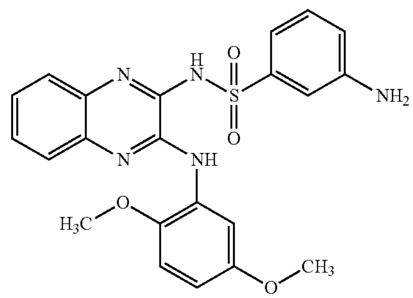 [SMILES: COc1ccc(OC)c(Nc2nc3ccccc3nc2NS(=O)(=O)c2cccc(N)c2)c1] | 3-amino-N-(3-{[2,5-bis(methyloxy)phenyl]amino}quinoxalin-2-yl)benzenesulfonamide |
| 382 | 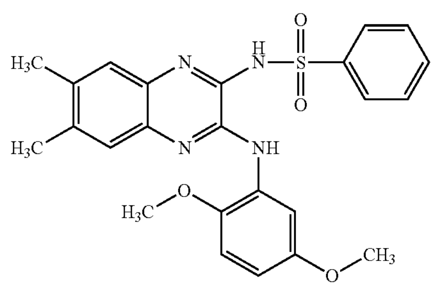 [SMILES: COc1ccc(OC)c(Nc2nc3cc(C)c(C)cc3nc2NS(=O)(=O)c2ccccc2)c1] | N-(3-{[2,5-bis(methyloxy)phenyl]amino}-6,7-dimethylquinoxalin-2-yl)benzenesulfonamide |
| 383 | 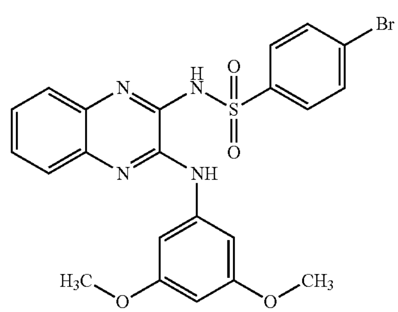 [SMILES: COc1cc(Nc2nc3ccccc3nc2NS(=O)(=O)c2ccc(Br)cc2)cc(OC)c1] | N-(3-{[3,5-bis(methyloxy)phenyl]amino}quinoxalin-2-yl)-4-bromobenzenesulfonamide |
| 384 | 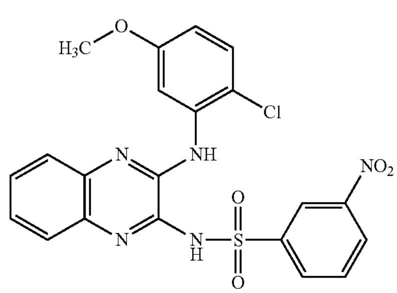 [SMILES: COc1ccc(Cl)c(Nc2nc3ccccc3nc2NS(=O)(=O)c2cccc([N+](=O)[O-])c2)c1] | N-(3-{[2-chloro-5-(methyloxy)phenyl]amino}quinoxalin-2-yl)-3-nitrobenzenesulfonamide |

TABLE 1-continued

| Cpd. No. | Structure | IUPAC Name |
|---|---|---|
| 385 | 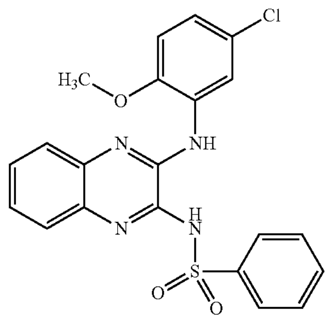 [SMILES: COc1ccc(Cl)cc1Nc1nc2ccccc2nc1NS(=O)(=O)c1ccccc1] | N-(3-{[5-chloro-2-(methyloxy)phenyl]amino}quinoxalin-2-yl)benzenesulfonamide |
| 386 | 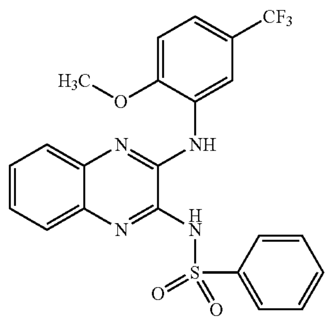 [SMILES: COc1ccc(C(F)(F)F)cc1Nc1nc2ccccc2nc1NS(=O)(=O)c1ccccc1] | N-(3-{[2-(methyloxy)-5-(trifluoromethyl)phenyl]amino}quinoxalin-2-yl)benzenesulfonamide |
| 387 | 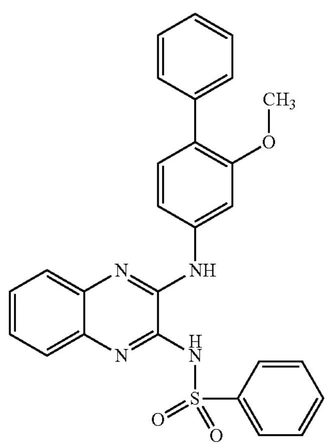 [SMILES: COc1cc(Nc2nc3ccccc3nc2NS(=O)(=O)c2ccccc2)ccc1-c1ccccc1] | N-(3-{[2-(methyloxy)biphenyl-4-yl]amino}quinoxalin-2-yl)benzenesulfonamide |
| 388 | 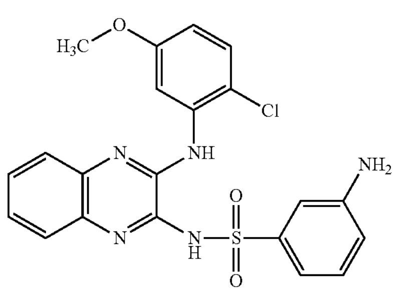 | 3-amino-N-(3-{[2-chloro-5-(methyloxy)phenyl]amino}quinoxalin-2-yl)benzenesulfonamide |

TABLE 1-continued

| Cpd. No. | Structure | IUPAC Name |
|---|---|---|
| 389 | 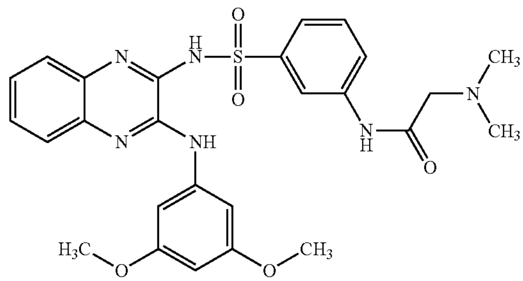 [SMILES: COc1cc(Nc2nc3ccccc3nc2NS(=O)(=O)c2cccc(NC(=O)CN(C)C)c2)cc(OC)c1] | N-(3-{[(3-{[3,5-bis(methyloxy)phenyl]amino}quinoxalin-2-yl)amino]sulfonyl}phenyl)-N-2-,N-2-dimethylglycinamide |
| 390 | 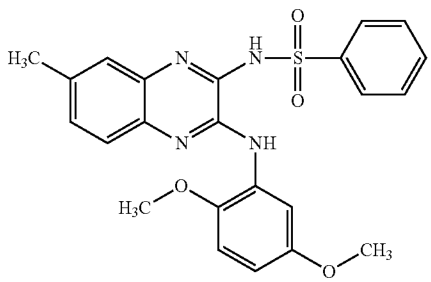 [SMILES: COc1ccc(OC)c(Nc2nc3ccc(C)cc3nc2NS(=O)(=O)c2ccccc2)c1] | N-(3-{[2,5-bis(methyloxy)phenyl]amino}-7-methylquinoxalin-2-yl)benzenesulfonamide |
| 391 | 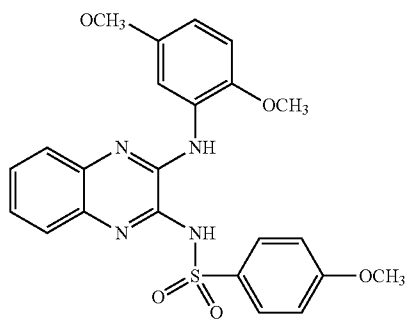 [SMILES: COc1ccc(S(=O)(=O)Nc2nc3ccccc3nc2Nc2cc(OC)ccc2OC)cc1] | N-(3-{[2,5-bis(methyloxy)phenyl]amino}quinoxalin-2-yl)-4-(methyloxy)benzenesulfonamide |
| 392 | 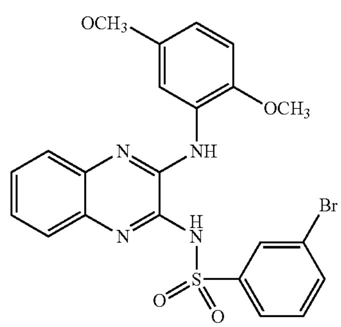 [SMILES: COc1ccc(OC)c(Nc2nc3ccccc3nc2NS(=O)(=O)c2cccc(Br)c2)c1] | N-(3-{[2,5-bis(methyloxy)phenyl]amino}quinoxalin-2-yl)-3-bromobenzenesulfonamide |
| 393 | 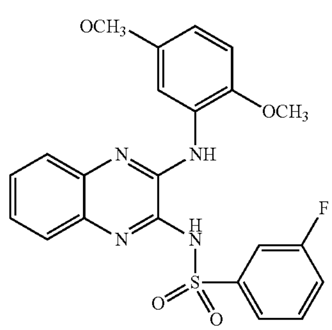 [SMILES: COc1ccc(OC)c(Nc2nc3ccccc3nc2NS(=O)(=O)c2cccc(F)c2)c1] | N-(3-{[2,5-bis(methyloxy)phenyl]amino}quinoxalin-2-yl)-3-fluorobenzenesulfonamide |

TABLE 1-continued

| Cpd. No. | Structure | IUPAC Name |
|---|---|---|
| 394 | 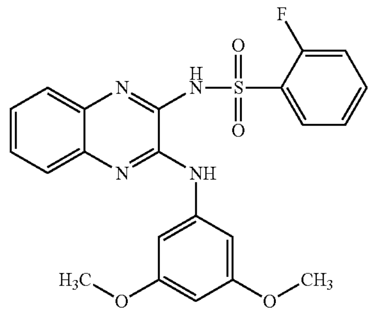 [SMILES: COc1cc(Nc2nc3ccccc3nc2NS(=O)(=O)c2ccccc2F)cc(OC)c1] | N-(3-{[3,5-bis(methyloxy)phenyl]amino}quinoxalin-2-yl)-2-fluorobenzenesulfonamide |
| 395 | 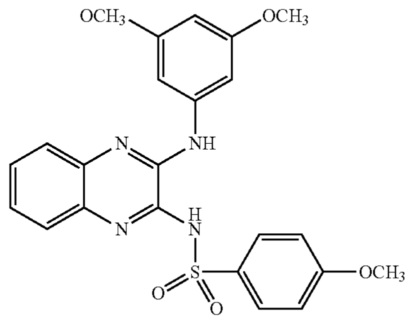 [SMILES: COc1ccc(S(=O)(=O)Nc2nc3ccccc3nc2Nc2cc(OC)cc(OC)c2)cc1] | N-(3-{[3,5-bis(methyloxy)phenyl]amino}quinoxalin-2-yl)-4-(methyloxy)benzenesulfonamide |
| 396 | 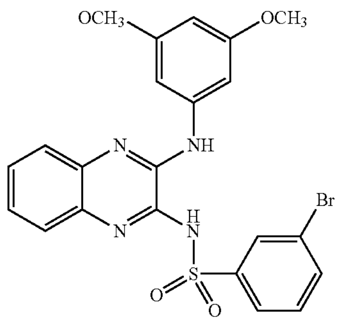 [SMILES: COc1cc(Nc2nc3ccccc3nc2NS(=O)(=O)c2cccc(Br)c2)cc(OC)c1] | N-(3-{[3,5-bis(methyloxy)phenyl]amino}quinoxalin-2-yl)-3-bromobenzenesulfonamide |
| 397 | 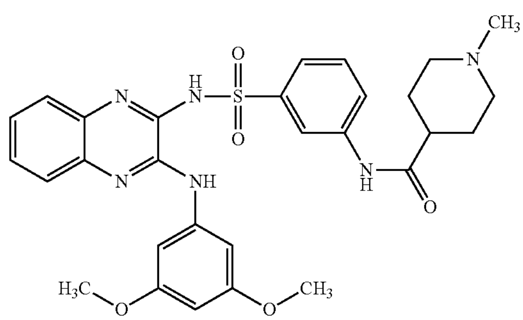 [SMILES: COc1cc(Nc2nc3ccccc3nc2NS(=O)(=O)c2cccc(NC(=O)C3CCN(C)CC3)c2)cc(OC)c1] | N-(3-{[(3-{[3,5-bis(methyloxy)phenyl]amino}quinoxalin-2-yl)amino]sulfonyl}phenyl)-1-methylpiperidine-4-carboxamide |
| 398 | 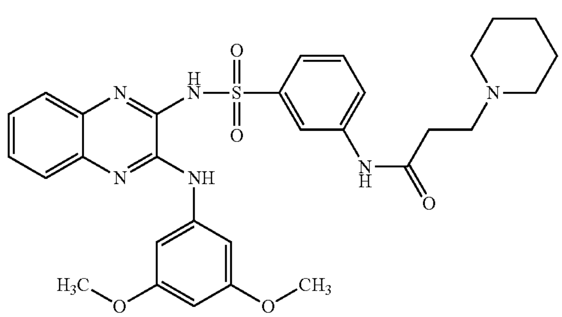 [SMILES: COc1cc(Nc2nc3ccccc3nc2NS(=O)(=O)c2cccc(NC(=O)CCN3CCCCC3)c2)cc(OC)c1] | N-(3-{[(3-{[3,5-bis(methyloxy)phenyl]amino}quinoxalin-2-yl)amino]sulfonyl}phenyl)-3-piperidin-1-ylpropanamide |

TABLE 1-continued

| Cpd. No. | Structure | IUPAC Name |
|---|---|---|
| 399 | 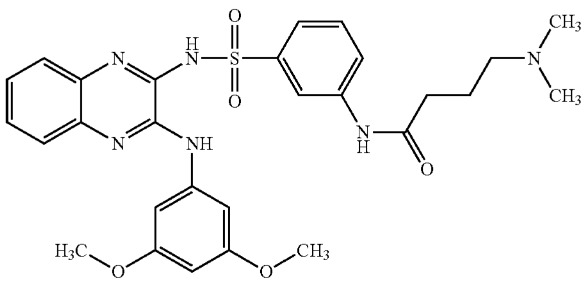 [SMILES: COc1cc(Nc2nc3ccccc3nc2NS(=O)(=O)c2cccc(NC(=O)CCCN(C)C)c2)cc(OC)c1] | N-(3-{[(3-{[3,5-bis(methyloxy)phenyl]amino}quinoxalin-2-yl)amino]sulfonyl}phenyl)-4-(dimethylamino)butanamide |
| 400 | 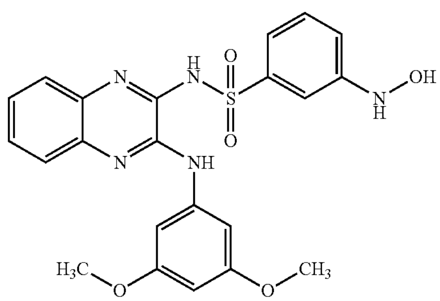 [SMILES: COc1cc(Nc2nc3ccccc3nc2NS(=O)(=O)c2cccc(NO)c2)cc(OC)c1] | N-(3-{[3,5-bis(methyloxy)phenyl]amino}quinoxalin-2-yl)-3-(hydroxyamino)benzenesulfonamide |
| 401 | 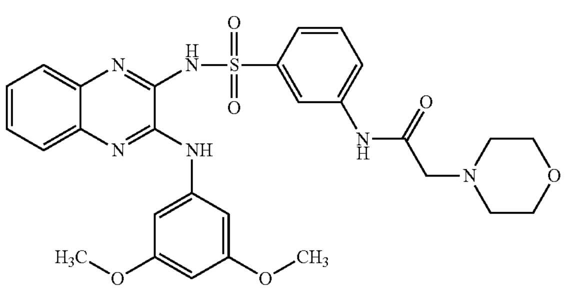 [SMILES: COc1cc(Nc2nc3ccccc3nc2NS(=O)(=O)c2cccc(NC(=O)CN3CCOCC3)c2)cc(OC)c1] | N-(3-{[(3-{[3,5-bis(methyloxy)phenyl]amino}quinoxalin-2-yl)amino]sulfonyl}phenyl)-2-mopholin-4-ylacetamide |
| 402 | 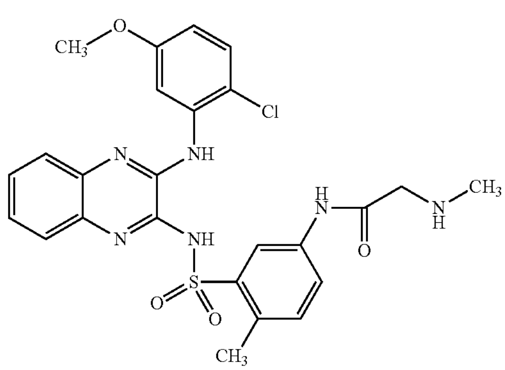 [SMILES: CNCC(=O)Nc1ccc(C)c(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}-4-methylphenyl)-N-2-methylglycinamide |

TABLE 1-continued

| Cpd. No. | Structure | IUPAC Name |
|---|---|---|
| 403 | 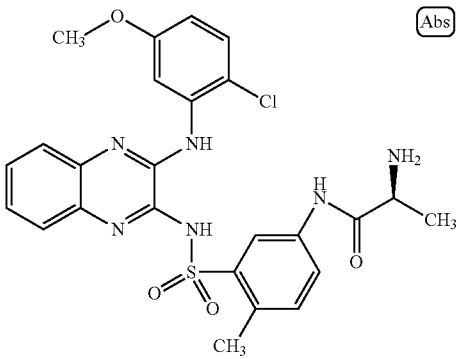 [SMILES: COc1ccc(Cl)c(Nc2nc3ccccc3nc2NS(=O)(=O)c2cc(NC(=O)[C@H](C)N)ccc2C)c1] | N-(3-{[(3-{[2-chloro-5-(methyloxy)phenyl]amino}quinoxalin-2-yl)amino]sulfonyl}-4-methylphenyl)-L-alaninamide |
| 404 | 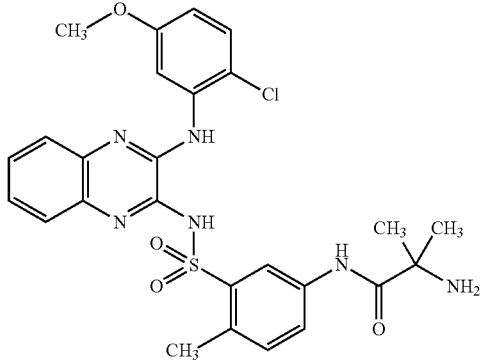 [SMILES: COc1ccc(Cl)c(Nc2nc3ccccc3nc2NS(=O)(=O)c2cc(NC(=O)C(C)(C)N)ccc2C)c1] | N-(3-{[(3-{[2-chloro-5-(methyloxy)phenyl]amino}quinoxalin-2-yl)amino]sulfonyl}-4-methylphenyl)-2-methylalaninamide |
| 405 | 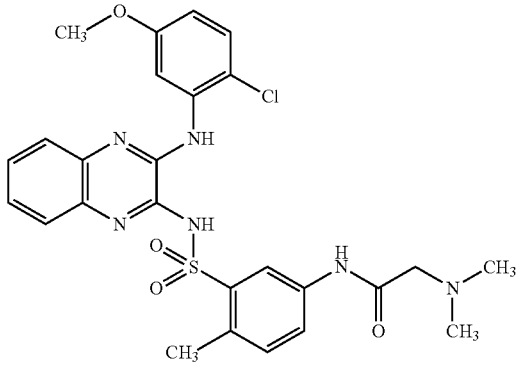 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methyloxy)phenyl]amino}quinoxalin-2-yl)amino]sulfonyl}-4-methylphenyl)-N-2-,N-2-dimethylglycinamide |
| 406 | 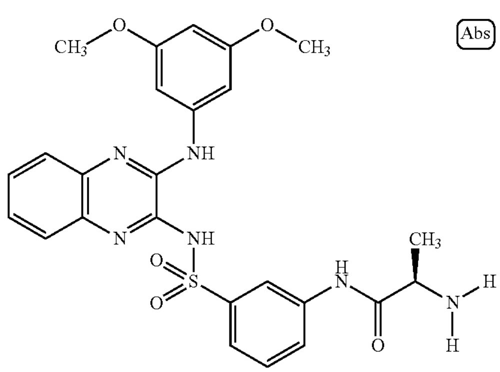 [SMILES: COc1cc(Nc2nc3ccccc3nc2NS(=O)(=O)c2cccc(NC(=O)[C@@H](C)N)c2)cc(OC)c1] | N-(3-{[(3-{[3,5-bis(methyloxy)phenyl]amino}quinoxalin-2-yl)amino]sulfonyl}phenyl)-D-alaninamide |

TABLE 1-continued

| Cpd. No. | Structure | IUPAC Name |
|---|---|---|
| 407 | 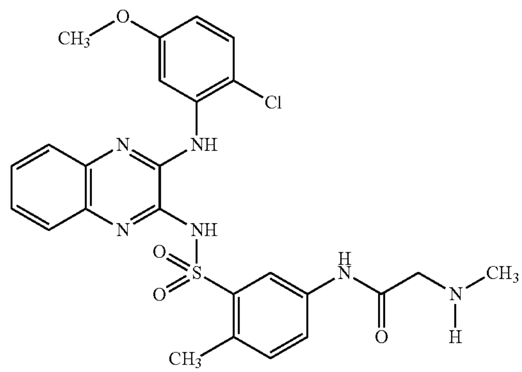 [SMILES: CNCC(=O)Nc1ccc(C)c(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}phenyl)-N-2-methylglycinamide |
| 408 | 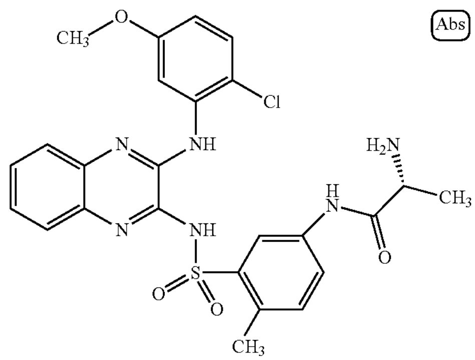 [SMILES: COc1ccc(Cl)c(Nc2nc3ccccc3nc2NS(=O)(=O)c2cc(NC(=O)[C@@H](C)N)ccc2C)c1] | N-(3-{[(3-{[2-chloro-5-(methyloxy)phenyl]amino}quinoxalin-2-yl)amino]sulfonyl}-4-methylphenyl)-D-alaninamide |
| 409 | 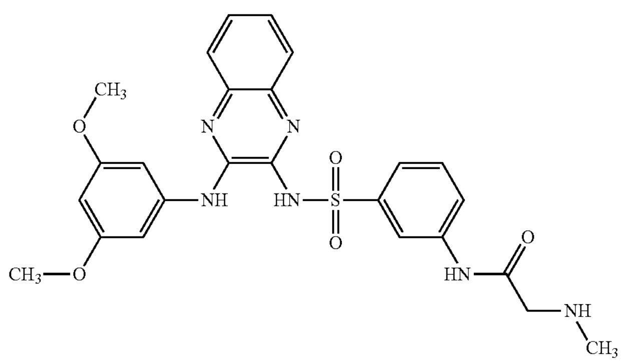 | N-(3-{[(3-{[3,5-bis(methyloxy)phenyl]amino}quinoxalin-2-yl)amino]sulfonyl}phenyl)-N-2-methylglycinamide |
| 410 | 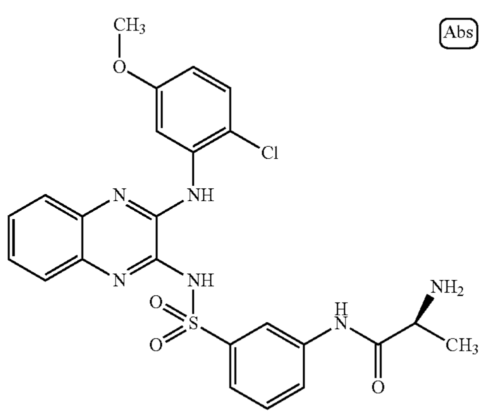 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methyloxy)phenyl]amino}quinoxalin-2-yl)amino]sulfonyl}phenyl)-L-alaninamide |

TABLE 1-continued

| Cpd. No. | Structure | IUPAC Name |
|---|---|---|
| 411 | 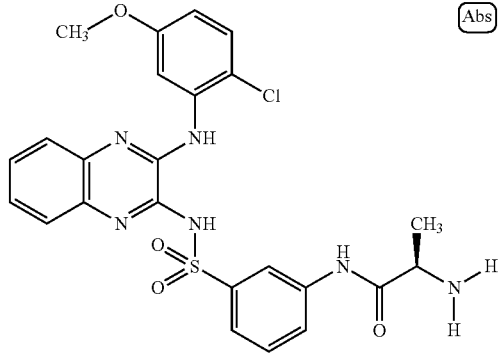 [SMILES: COc1ccc(Cl)c(Nc2nc3ccccc3nc2NS(=O)(=O)c2cccc(NC(=O)[C@@H](C)N)c2)c1] | N-(3-{[(3-{[2-chloro-5-(methyloxy)phenyl]amino}quinoxalin-2-yl)amino]sulfonyl}phenyl)-D-alaninamide |
| 412 | 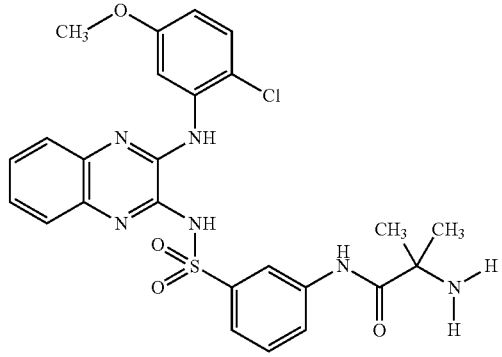 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methyloxy)phenyl]amino}quinoxalin-2-yl)amino]sulfonyl}phenyl)-2-methylalaninamide |
| 413 | 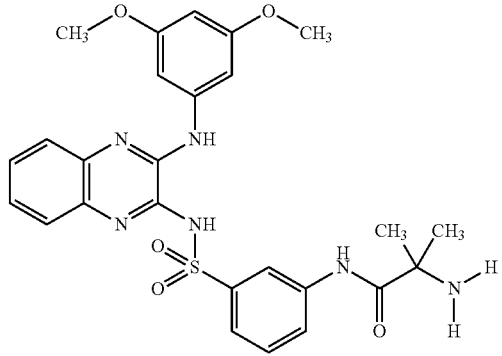 [SMILES: COc1cc(Nc2nc3ccccc3nc2NS(=O)(=O)c2cccc(NC(=O)C(C)(C)N)c2)cc(OC)c1] | N-(3-{[(3-{[3,5-bis(methyloxy)phenyl]amino}quinoxalin-2-yl)amino]sulfonyl}phenyl)-2-methylalaninamide |
| 414 | 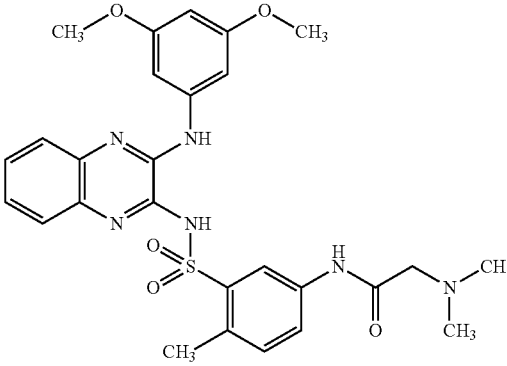 [SMILES: COc1cc(Nc2nc3ccccc3nc2NS(=O)(=O)c2cc(NC(=O)CN(C)C)ccc2C)cc(OC)c1] | N-(3-{[(3-{[3,5-bis(methyloxy)phenyl]amino}quinoxalin-2-yl)amino]sulfonyl}-4-methylphenyl)-N-2-,N-2-dimethylglycinamide |

TABLE 1-continued

| Cpd. No. | Structure | IUPAC Name |
|---|---|---|
| 415 | 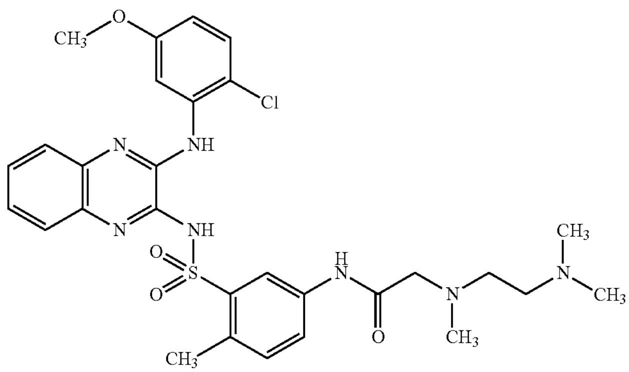 [SMILES: COc1ccc(Cl)c(Nc2nc3ccccc3nc2NS(=O)(=O)c2cc(NC(=O)CN(C)CCN(C)C)ccc2C)c1] | N-(3-{[(3-{[2-chloro-5-(methyloxy)phenyl]amino}quinoxalin-2-yl)amino]sulfonyl}phenyl)-N-2-[2-(dimethylamino)ethyl]-N-2-methylglycinamide |
| 416 | 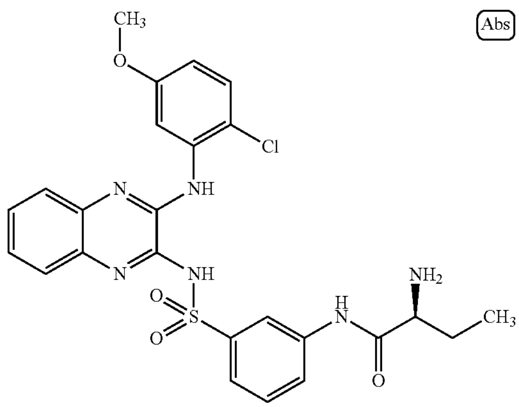 [SMILES: CC[C@H](N)C(=O)Nc1cccc(S(=O)(=O)Nc2nc3ccccc3nc2Nc2cc(OC)ccc2Cl)c1] | (2S)-2-amino-N-(3-{[(3-{[2-chloro-5-(methyloxy)phenyl]amino}quinoxalin-2-yl)amino]sulfonyl}phenyl)butanamide |
| 417 | 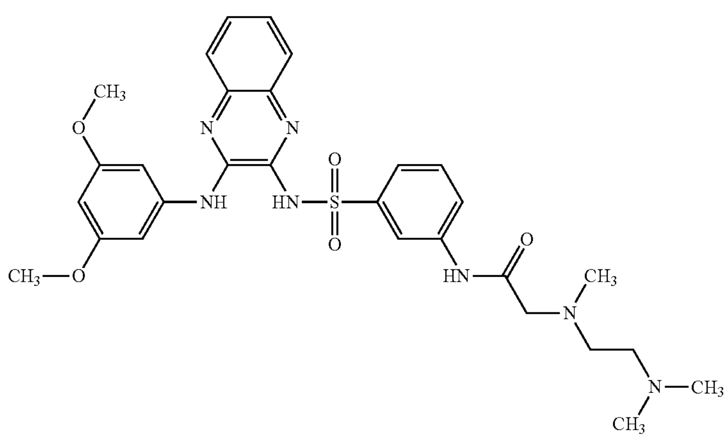 | N-(3-{[(3-{[3,5-bis(methyloxy)phenyl]amino}quinoxalin-2-yl)amino]sulfonyl}phenyl)-N-2-[2-(dimethylamino)ethyl]-N-2-methylglycinamide |
| 418 | 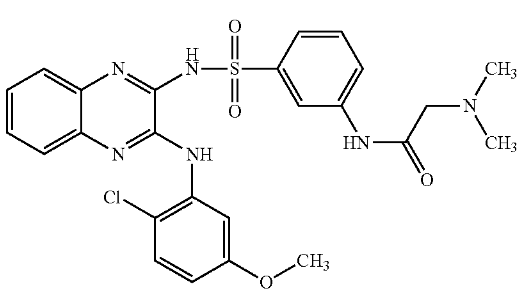 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methyloxy)phenyl]amino}quinoxalin-2-yl)amino]sulfonyl}phenyl)-N-2-,N-2-dimethylglycinamide |

TABLE 1-continued

| Cpd. No. | Structure | IUPAC Name |
|---|---|---|
| 419 | 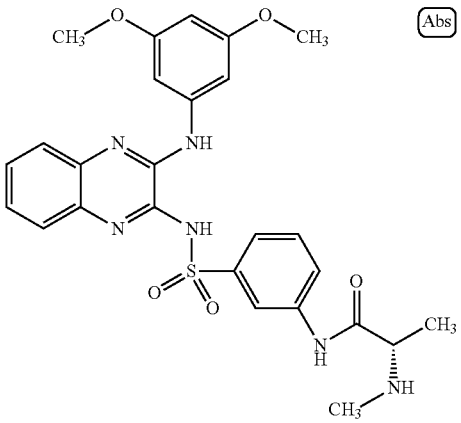 [SMILES: CN[C@@H](C)C(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-methyl-L-alaninamide |
| 420 | 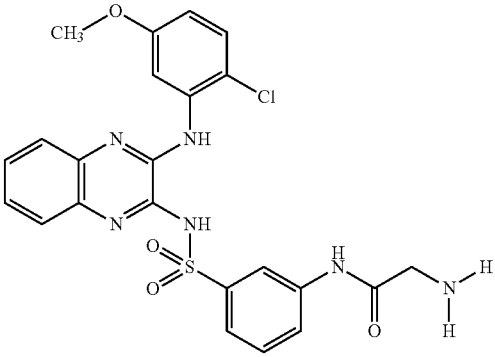 [SMILES: COc1ccc(Cl)c(Nc2nc3ccccc3nc2NS(=O)(=O)c2cccc(NC(=O)CN)c2)c1] | N-(3-{[(3-{[2-chloro-5-(methyloxy)phenyl]amino}quinoxalin-2-yl)amino]sulfonyl}phenyl)glycinamide |
| 421 | 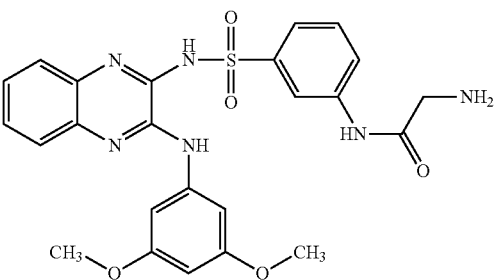 [SMILES: COc1cc(Nc2nc3ccccc3nc2NS(=O)(=O)c2cccc(NC(=O)CN)c2)cc(OC)c1] | N-(3-{[(3-{[3,5-bis(methyloxy)phenyl]amino}quinoxalin-2-yl)amino]sulfonyl}phenyl)glycinamide |
| 422 | 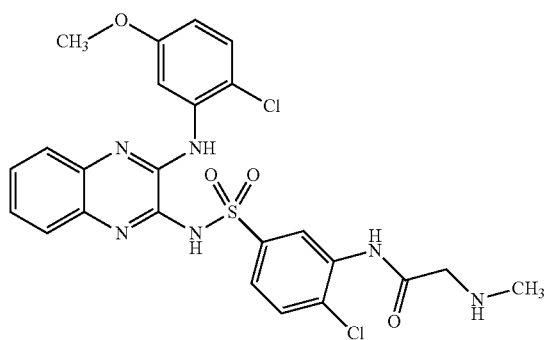 [SMILES: CNCC(=O)Nc1cc(S(=O)(=O)Nc2nc3ccccc3nc2Nc2cc(OC)ccc2Cl)ccc1Cl] | N-(2-chloro-5-{[(3-{[2-chloro-5-(methyloxy)phenyl]amino}quinoxalin-2-yl)amino]sulfonyl}phenyl)-N-2-methylglycinamide |

TABLE 1-continued

| Cpd. No. | Structure | IUPAC Name |
|---|---|---|
| 423 | 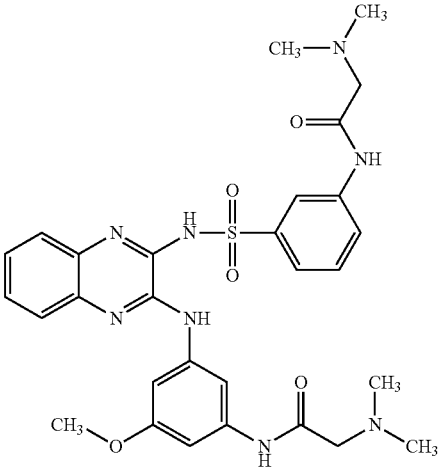 [SMILES: COc1cc(NC(=O)CN(C)C)cc(Nc2nc3ccccc3nc2NS(=O)(=O)c2cccc(NC(=O)CN(C)C)c2)c1] | 2-(dimethylamino)-N-(3-(N-(3-(3-(2-(dimethylamino)acetamido)-5-methoxyphenylamino)quinoxalin-2-yl)sulfamoxyl)phenyl)acetamide |
| 424 | 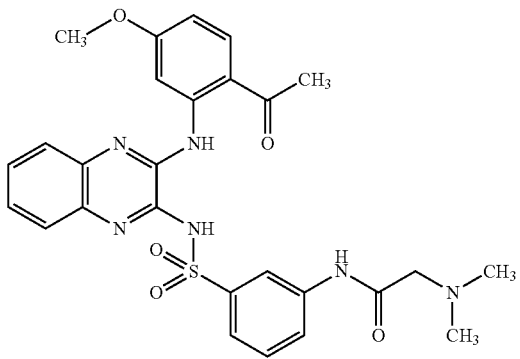 [SMILES: COc1ccc(C(C)=O)c(Nc2nc3ccccc3nc2NS(=O)(=O)c2cccc(NC(=O)CN(C)C)c2)c1] | N-(3-{[(3-{[2-acetyl-5-(methyloxy)phenyl]amino}quinoxalin-2-yl)amino]sulfonyl}phenyl)-N-2-,N-2-dimethylglycinamide |
| 425 | 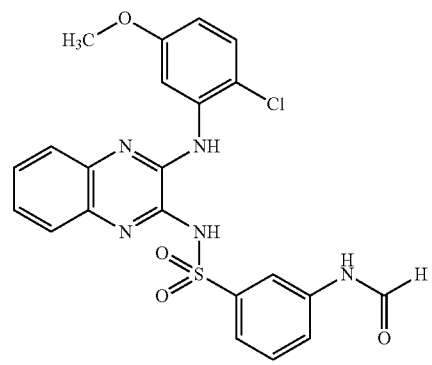 [SMILES: COc1ccc(Cl)c(Nc2nc3ccccc3nc2NS(=O)(=O)c2cccc(NC=O)c2)c1] | N-(3-{[2-chloro-5-(methyloxy)phenyl]amino}quinoxalin-2-yl)-3-(formylamino)benzenesulfonamide |
| 426 | 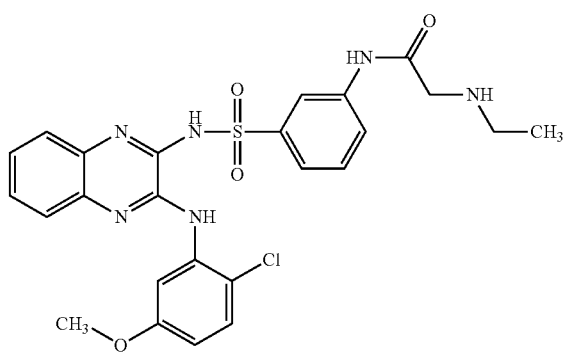 [SMILES: CCNCC(=O)Nc1cccc(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}phenyl)-N-2-thylglycinamide |

TABLE 1-continued

| Cpd. No. | Structure | IUPAC Name |
|---|---|---|
| 427 | 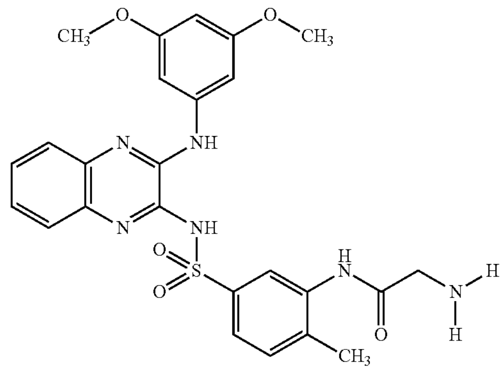 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methyloxy)phenyl]amino}quinoxalin-2-yl)amino]sulfonyl-2-methylphenyl)glycinamide |
| 428 | 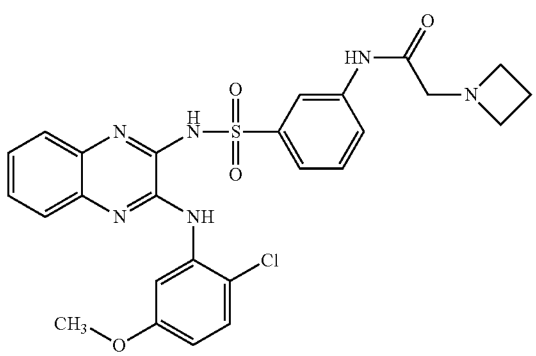 [SMILES: COc1ccc(Cl)c(Nc2nc3ccccc3nc2NS(=O)(=O)c2cccc(NC(=O)CN3CCC3)c2)c1] | 2-azetidin-21-1-N-(3-[{[(3-{[2-chloro-5-(methyloxy)phenyl]amino}quinoxalin-2-yl)amino]sulfonyl}phenyl)acetamide |
| 429 | [Abs] | N-(3-{[(3-{[2-chloro-5-(methyloxy)phenyl]amino}quinoxalin-2-yl)amino]sulfonyl}phenyl)-L-prolinamide |
| 430 | 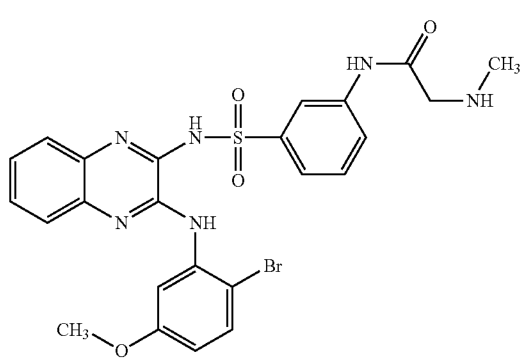 [SMILES: CNCC(=O)Nc1cccc(S(=O)(=O)Nc2nc3ccccc3nc2Nc2cc(OC)ccc2Br)c1] | N-(3-{[(3-{[2-bromo-5-(methyloxy)phenyl]amino}quinoxalin-2-yl)amino]sulfonyl}phenyl)-N-2-methylglycinamide |

TABLE 1-continued

| Cpd. No. | Structure | IUPAC Name |
|---|---|---|
| 431 | 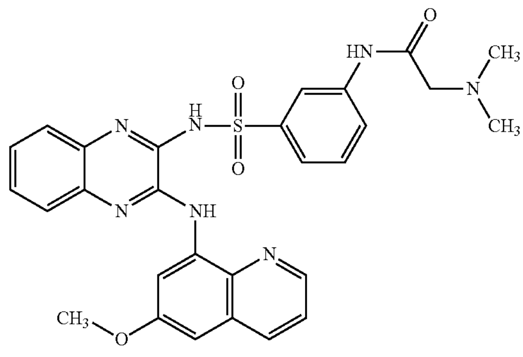 [SMILES: COc1cc(Nc2nc3ccccc3nc2NS(=O)(=O)c2cccc(NC(=O)CN(C)C)c2)c2ncccc2c1] | N-2-,N-2-dimethyl-N-(3-{[(3-{[6-(methyloxy)quinolin-8-yl]amino}quinoxalin-2-yl)amino]sulfonyl}phenyl)glycinamide |
| 432 | 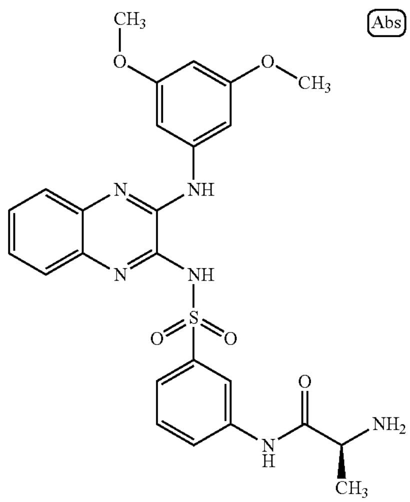 [SMILES: COc1cc(Nc2nc3ccccc3nc2NS(=O)(=O)c2cccc(NC(=O)[C@H](C)N)c2)cc(OC)c1] | N-(3-{[(3-{[3,5-bis(methyloxy)phenyl]amino}quinoxalin-2-yl)amino]sulfonyl}phenyl)-L-alaninamide |
| 433 | 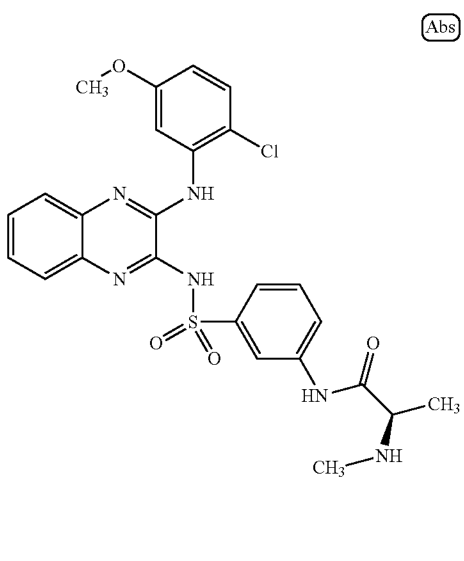 [SMILES: CN[C@H](C)C(=O)Nc1cccc(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}phenyl)-N-2-methyl-D-alaninamide |

TABLE 1-continued

| Cpd. No. | Structure | IUPAC Name |
|---|---|---|
| 434 | 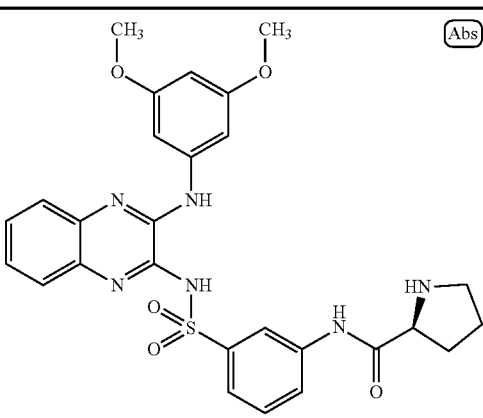 | N-(3-{[(3-{[3,5-bis(methyloxy)phenyl]amino}quinoxalin-2-yl)amino]sulfonyl}phenyl)-L-prolinamide |
| 435 | 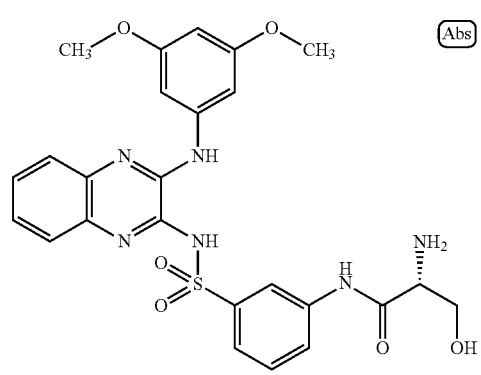 [SMILES: COc1cc(Nc2nc3ccccc3nc2NS(=O)(=O)c2cccc(NC(=O)[C@H](N)CO)c2)cc(OC)c1] | N-(3-{[(3-{[3,5-bis(methyloxy)phenyl]amino}quinoxalin-2-yl)amino]sulfonyl}phenyl)-D-serinamide |
| 436 | 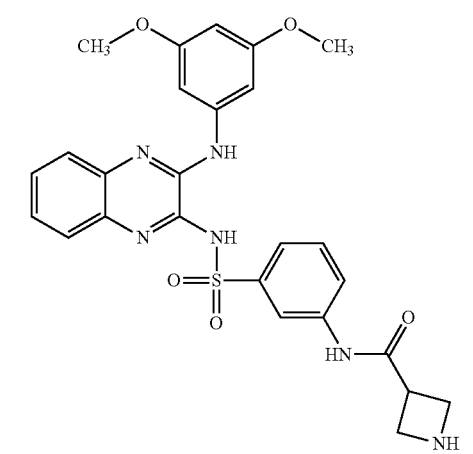 [SMILES: COc1cc(Nc2nc3ccccc3nc2NS(=O)(=O)c2cccc(NC(=O)C3CNC3)c2)cc(OC)c1] | N-(3-{[(3-{[3,5-bis(methyloxy)phenyl]amino}quinoxalin-2-yl)amino]sulfonyl}phenyl)azeidine-3-carboxamide |
| 437 | 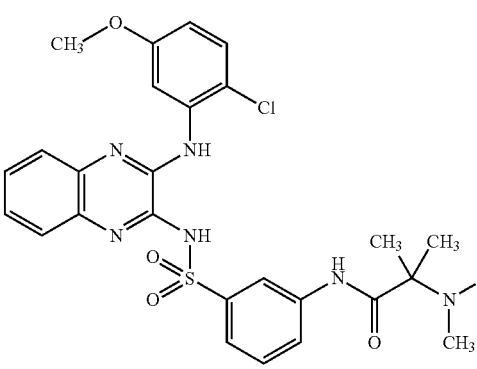 | N-(3-{[(3-{[2-chloro-5-(methyloxy)phenyl]amino}quinoxalin-2-yl)amino]sulfonyl}phenyl)-N-2-,2-dimethylalaninamide |

TABLE 1-continued

| Cpd. No. | Structure | IUPAC Name |
|---|---|---|
| 438 | 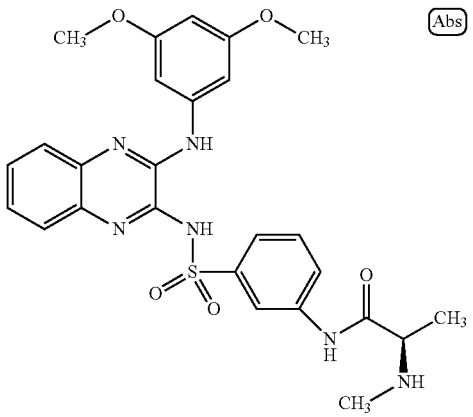 [SMILES: CN[C@H](C)C(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-methyl-D-alanine |
| 439 | 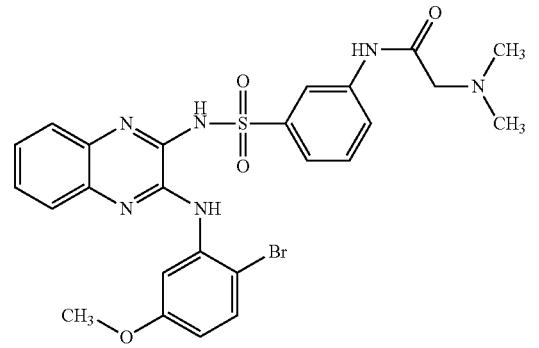 [SMILES: COc1ccc(Br)c(Nc2nc3ccccc3nc2NS(=O)(=O)c2cccc(NC(=O)CN(C)C)c2)c1] | N-(3-{[(3-{[2-bromo-5-(methyloxy)phenyl]amino}quinoxalin-2-yl)amino]sulfonyl}phenyl)-N-2-,N-2-dimethylglycinamide |
| 440 | 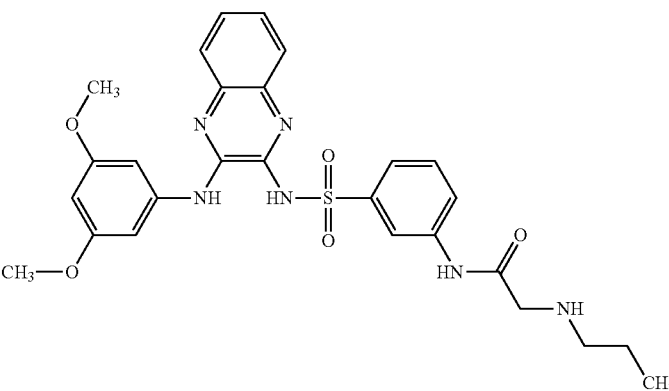 | N-(3-{[(3-{[3,5-bis(methyloxy)phenyl]amino}quinoxalin-2-yl)amino]sulfonyl}phenyl)-N-2-propylglycinamide |
| 441 | 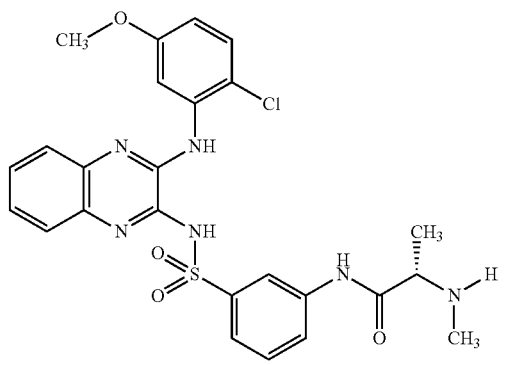 [SMILES: CN[C@@H](C)C(=O)Nc1cccc(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}phenyl)-N-2-methyl-L-alaninamide |

TABLE 1-continued

| Cpd. No. | Structure | IUPAC Name |
|---|---|---|
| 442 | 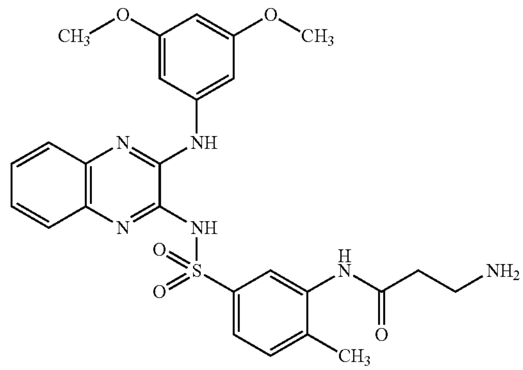 [SMILES: COc1cc(Nc2nc3ccccc3nc2NS(=O)(=O)c2ccc(C)c(NC(=O)CCN)c2)cc(OC)c1] | N-(5-{[(3-{[3,5-bis(methyloxy)phenyl]amino}quinoxalin-2-yl)amino]sulfonyl}-2-methylphenyl)-beta-alaninamide |
| 443 | 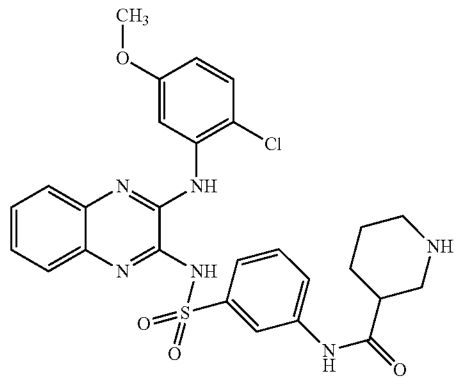 [SMILES: COc1ccc(Cl)c(Nc2nc3ccccc3nc2NS(=O)(=O)c2cccc(NC(=O)C3CCCNC3)c2)c1] | N-(3-{[(3-{[2-chloro-5-(methyloxy)phenyl]amino}quinoxalin-2-yl)amino]sulfonyl}phenyl)piperidine-3-carboxamide |
| 444 | 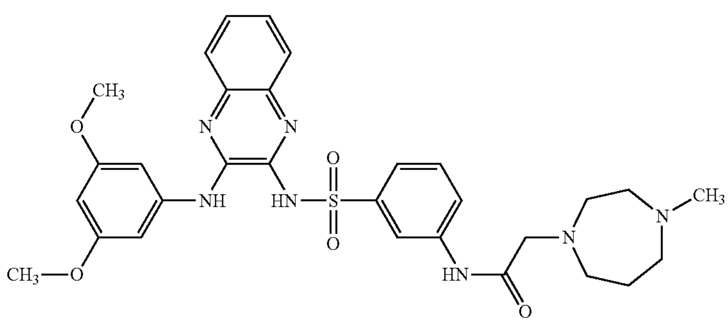 | N-(3-{[(3-{[3,5-bis(methyloxy)phenyl]amino}quinoxalin-2-yl)amino]sulfonyl}phenyl)-2-(4-methyl-1,4-diazepan-1-yl)acetamide |
| 445 | 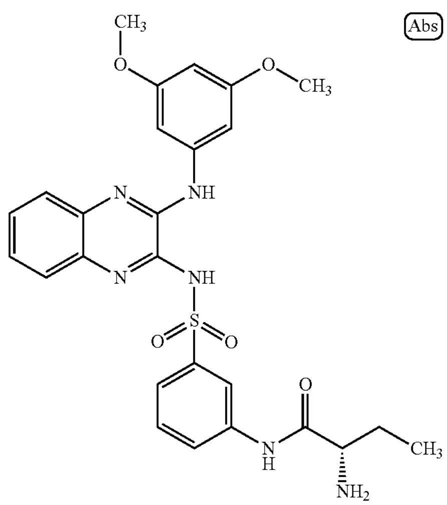 [SMILES: CC[C@H](N)C(=O)Nc1cccc(S(=O)(=O)Nc2nc3ccccc3nc2Nc2cc(OC)cc(OC)c2)c1] | (2S)-2-amino-N-(3-{[(3-{[3,5-bis(methyloxy)phenyl]amino}quinoxalin-2-yl)amino]sulfonyl}phenyl)butanamide |

TABLE 1-continued

| Cpd. No. | Structure | IUPAC Name |
|---|---|---|
| 446 | 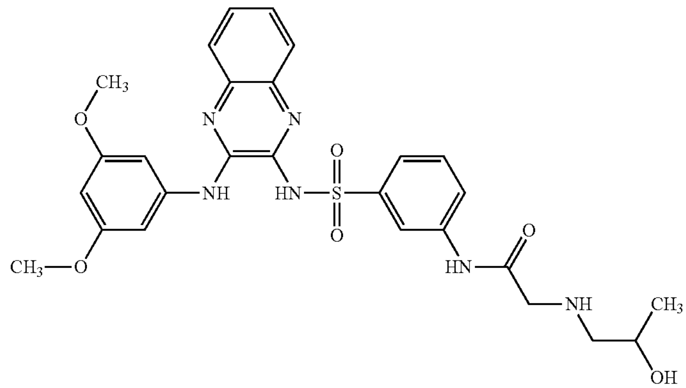 [SMILES: COc1cc(Nc2nc3ccccc3nc2NS(=O)(=O)c2cccc(NC(=O)CNCC(C)O)c2)cc(OC)c1] | N-(3-{[(3-{[3,5-bis(methyloxy)phenyl]amino}quinoxalin-2-yl)amino]sulfonyl}phenyl)-N-2-(2-hydroxypropyl)glycinamide |
| 447 | 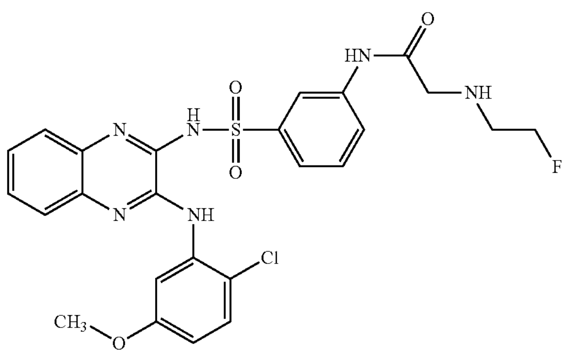 [SMILES: COc1ccc(Cl)c(Nc2nc3ccccc3nc2NS(=O)(=O)c2cccc(NC(=O)CNCCF)c2)c1] | N-(3-{[(3-{[2-chloro-5-(methyloxy)phenyl]amino}quinoxalin-2-yl)amino]sulfonyl}phenyl)-N-2-(2-fluoroethyl)gloxycinamide |
| 448 | 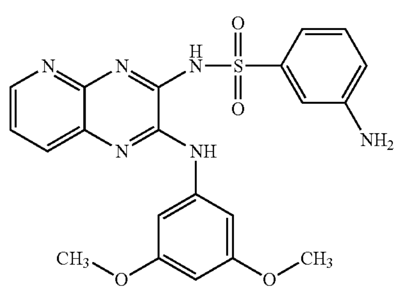 [SMILES: COc1cc(Nc2nc3cccnc3nc2NS(=O)(=O)c2cccc(N)c2)cc(OC)c1] | 3-amino-N-(2-{[3,5-bis(methyloxy)phenyl]amino}pyrido[2,3-b]pyrazin-3-yl)benzenesulfonamide |
| 449 | 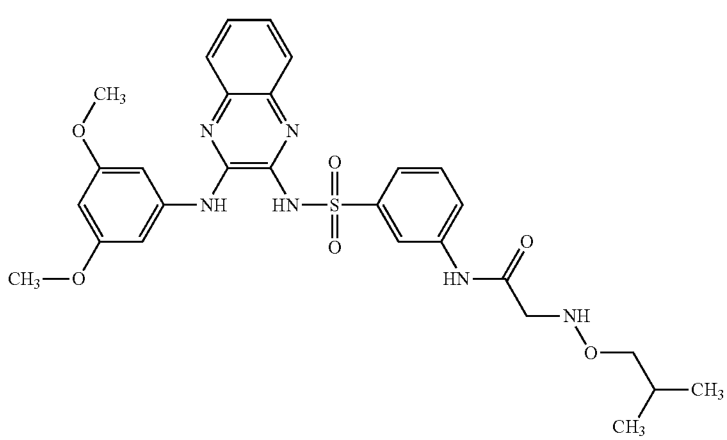 [SMILES: COc1cc(Nc2nc3ccccc3nc2NS(=O)(=O)c2cccc(NC(=O)CNOCC(C)C)c2)cc(OC)c1] | N-(3-{[(3-{[3,5-bis(methyloxy)phenyl]amino}quinoxalin-2-yl)amino]sulfonyl}phenyl)-N-2-[(2-methylpropyl)oxy]glycinamide |

TABLE 1-continued

| Cpd. No. | Structure | IUPAC Name |
|---|---|---|
| 450 | 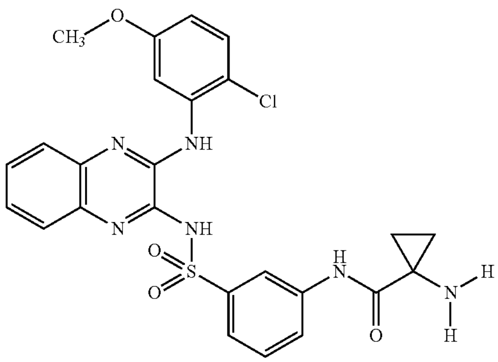 [SMILES: COc1ccc(Cl)c(Nc2nc3ccccc3nc2NS(=O)(=O)c2cccc(NC(=O)C3(N)CC3)c2)c1] | 1-amino-N-(3-{[(3-{[2-chloro-5-(methyloxy)phenyl]amino)quinoxalin-2-yl)amino]sulfonyl}phenyl)cyclopropane-carboxamide |
| 451 | 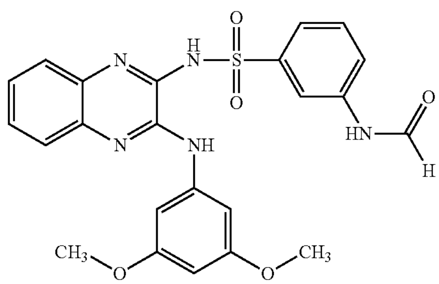 [SMILES: COc1cc(Nc2nc3ccccc3nc2NS(=O)(=O)c2cccc(NC=O)c2)cc(OC)c1] | N-(3-{[3,5-bis(methyloxy)phenyl]amino}quinoxalin-2-yl)-3-(formylamino)benzenesulfonamide |
| 452 | 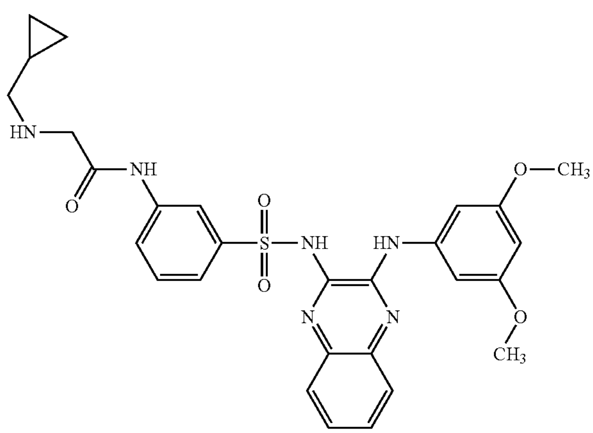 [SMILES: COc1cc(Nc2nc3ccccc3nc2NS(=O)(=O)c2cccc(NC(=O)CNCC3CC3)c2)cc(OC)c1] | N-(3-{[(3-{[3,5-bis(methyloxy)[phenyl]amino}quinoxalin-2-yl)amino]sulfonyl}phenyl)-N-2-(cyclopropylmethyl)glycinamide |
| 453 | 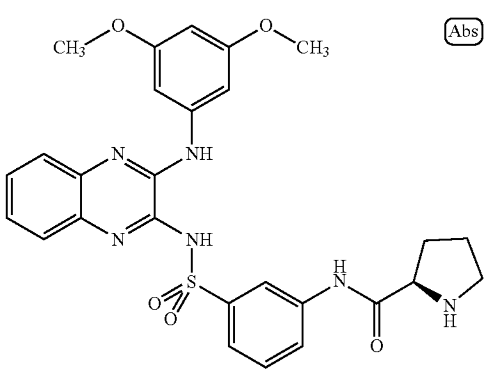 [SMILES: COc1cc(Nc2nc3ccccc3nc2NS(=O)(=O)c2cccc(NC(=O)[C@H]3CCCN3)c2)cc(OC)c1] | N-(3-{[(3-{[3,5-bis(methyloxy)phenyl]amino}quinoxalin-2-yl)amino]sulfonyl}phenyl)-D-prolinamide |

| Cpd. No. | Structure | IUPAC Name |
|---|---|---|
| 454 | 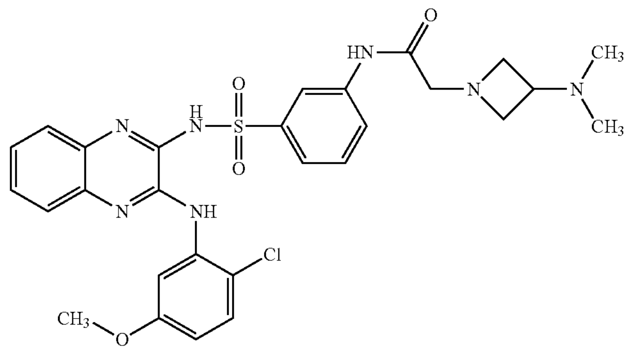 [SMILES: COc1ccc(Cl)c(Nc2nc3ccccc3nc2NS(=O)(=O)c2cccc(NC(=O)CN3CC(N(C)C)C3)c2)c1] | N-(3-{[(3-[{2-chloro-5-(methyloxy)phenyl]amino}quinoxalin-2-yl)amino]sulfonyl}phenyl)-2-[3-(dimethylamino)azetidin-1-yl]acetamide |
| 455 | 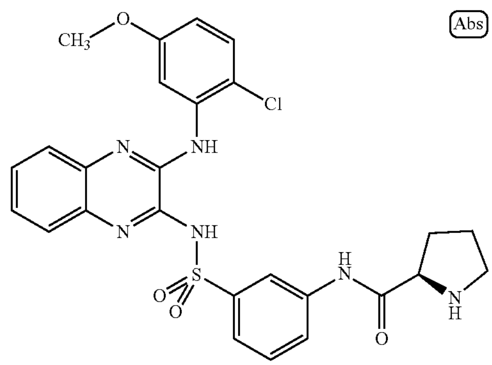 [SMILES: COc1ccc(Cl)c(Nc2nc3ccccc3nc2NS(=O)(=O)c2cccc(NC(=O)[C@H]3CCCN3)c2)c1] | N-(3-{[(3-{[2-chloro-5-(methyloxy)phenyl]amino}quinoxalin-2-yl)amino]sulfonyl}phenyl)-D-prolinamide |
| 456 | 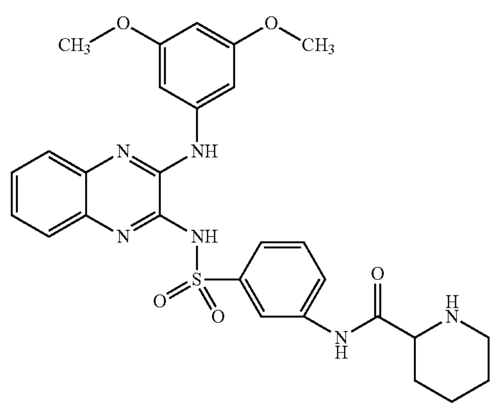 [SMILES: COc1cc(Nc2nc3ccccc3nc2NS(=O)(=O)c2cccc(NC(=O)C3CCCCN3)c2)cc(OC)c1] | N-(3-{[(3-{[3,5-bis(methyloxy)phenyl]amino}quinoxalin-2-yl)amino]sulfonyl}phenyl)piperidine-2-carboxamide |
| 457 | 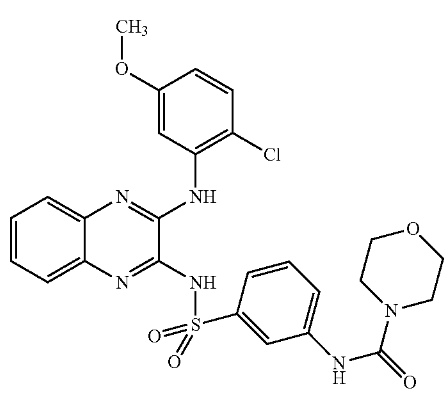 [SMILES: COc1ccc(Cl)c(Nc2nc3ccccc3nc2NS(=O)(=O)c2cccc(NC(=O)N3CCOCC3)c2)c1] | N-(3-{[(3-{[2-chloro-5-(methyloxy)phenyl]amino}quinoxalin-2-yl)amino]sulfonyl}phenyl)morpholine-4-carboxamide |

TABLE 1-continued

| Cpd. No. | Structure | IUPAC Name |
|---|---|---|
| 458 | 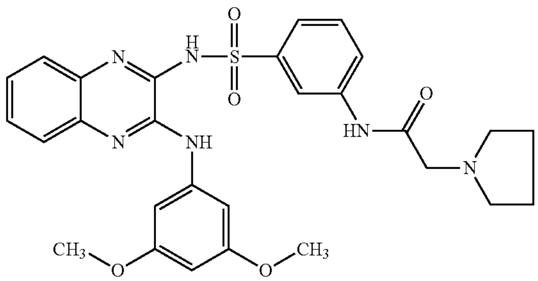 [SMILES: COc1cc(Nc2nc3ccccc3nc2NS(=O)(=O)c2cccc(NC(=O)CN3CCCC3)c2)cc(OC)c1] | N-(3-{[(3-{[3,5-bis(methyloxy)phenyl]amino}quinoxalin-2-yl)amino]sulfonyl}phenyl)-2-pyrrolidin-1-ylacetamide |
| 459 | 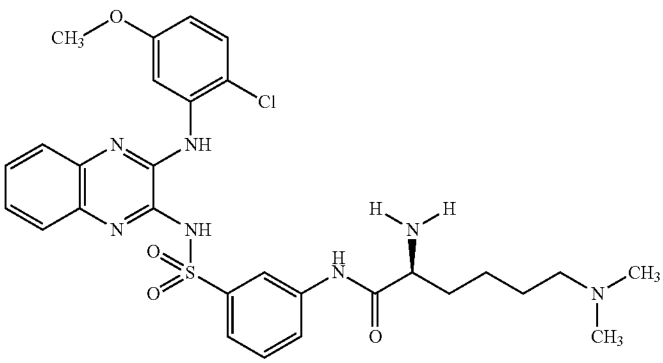 [SMILES: COc1ccc(Cl)c(Nc2nc3ccccc3nc2NS(=O)(=O)c2cccc(NC(=O)[C@@H](N)CCCCN(C)C)c2)c1] | N-(3-{[(3-{[2-chloro-5-(methyloxy)phenyl]amino}quinoxalin-2-yl)amino]sulfonyl}phenyl)-N-6-,N-6-dimethyl-L-lysinamide |
| 460 | 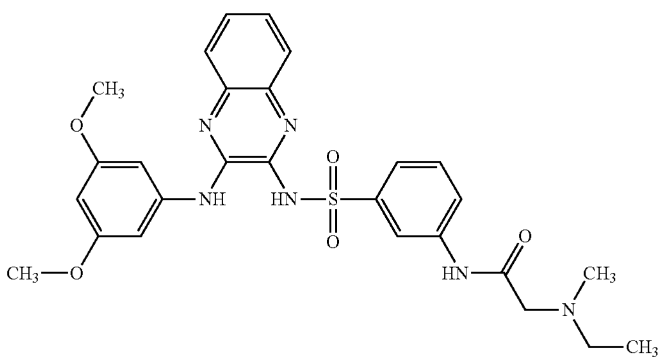 [SMILES: CCN(C)CC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-ethyl-N-2-methylglycinamide |
| 461 | 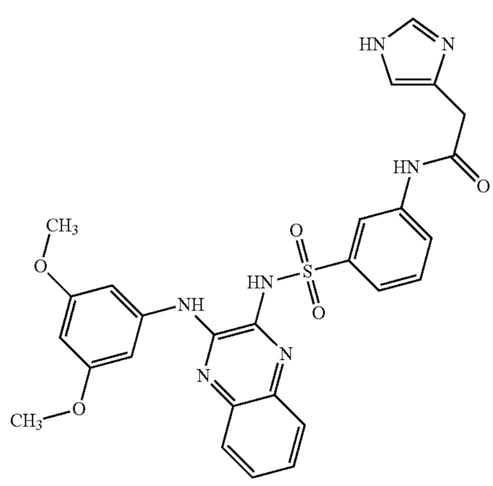 [SMILES: COc1cc(Nc2nc3ccccc3nc2NS(=O)(=O)c2cccc(NC(=O)Cc3c[nH]cn3)c2)cc(OC)c1] | N-(3-{[(3-{[3,5-bis(methyloxy)phenyl]amino}quinoxalin-2-yl)amino]sulfonyl}phenyl)-2-(1H-imidazol-4-yl)acetamide |

TABLE 1-continued

| Cpd. No. | Structure | IUPAC Name |
| --- | --- | --- |
| 462 | 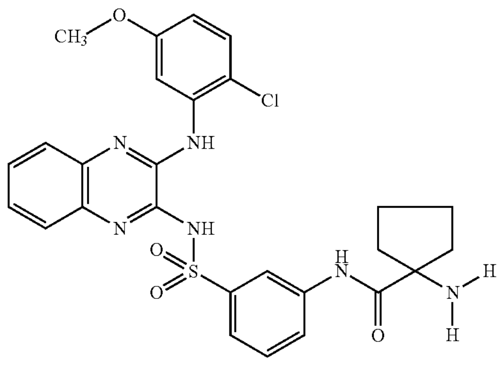 [SMILES: COc1ccc(Cl)c(Nc2nc3ccccc3nc2NS(=O)(=O)c2cccc(NC(=O)C3(N)CCCC3)c2)c1] | 1-amino-N-(3-{[(3-{[2-chloro-5-(methyloxy)phenyl]amino}quinoxalin-2-yl)amino]sulfonyl}phenyl)cyclopentane-carboxamide |
| 463 | 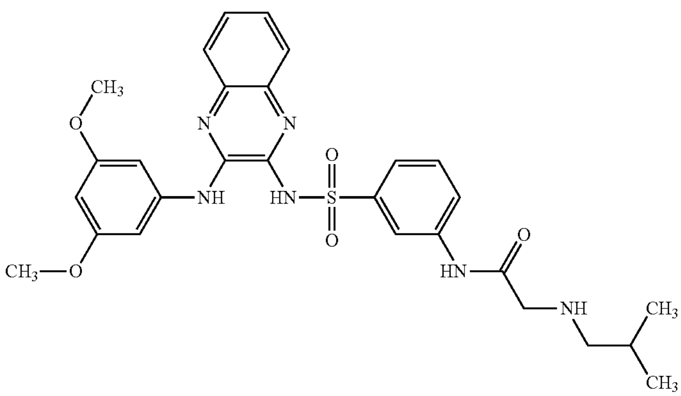 [SMILES: COc1cc(Nc2nc3ccccc3nc2NS(=O)(=O)c2cccc(NC(=O)CNCC(C)C)c2)cc(OC)c1] | N-(3-{[(3-{[3,5-bis(methyloxy)phenyl]amino}quinoxalin-2-yl)amino]sulfonyl}phenyl)-N-2-(2-methylpropyl)glycinamide |
| 464 | 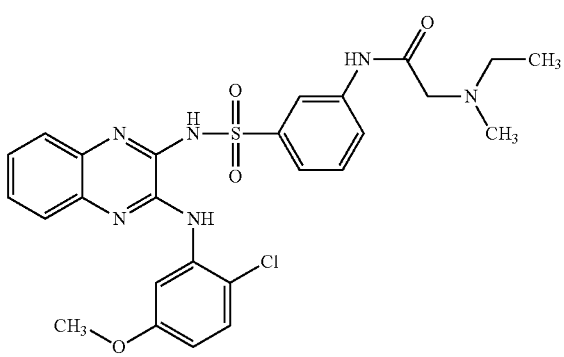 [SMILES: CCN(C)CC(=O)Nc1cccc(S(=O)(=O)Nc2nc3ccccc3nc2Nc2cc(OC)ccc2Cl)c1] | N-(3-{[(3-{[2-chloro-5-(methyloxy)phenyl]amino}quinoxalin-2-yl)amino]sulfonyl}phenyl)-N-2-ethyl-N-2-methylglycinamide |
| 465 | 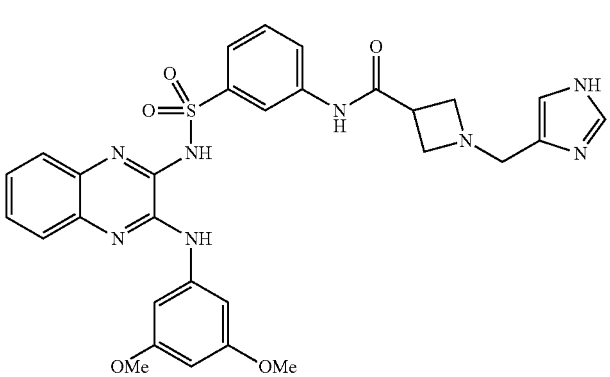 [SMILES: COc1cc(Nc2nc3ccccc3nc2NS(=O)(=O)c2cccc(NC(=O)C3CN(Cc4c[nH]cn4)C3)c2)cc(OC)c1] | N-(3-{[(3-{[3,5-bis(methyloxy)phenyl]amino}quinoxalin-2-yl)amino]sulfonyl}phenyl)-1-(1H-imidazol-4-ylmethyl)azetidine-3-carboxamide |

TABLE 1-continued
| Cpd. No. | Structure | IUPAC Name |
|---|---|---|
| 466 | 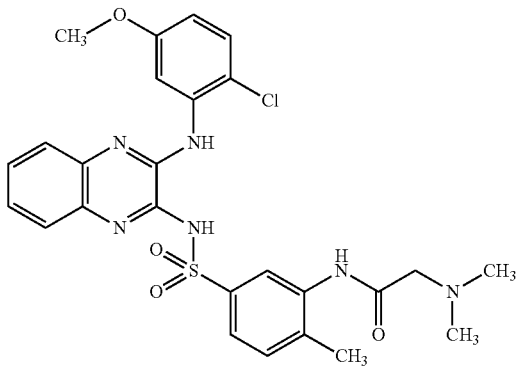 [SMILES: COc1ccc(Cl)c(Nc2nc3ccccc3nc2NS(=O)(=O)c2ccc(C)c(NC(=O)CN(C)C)c2)c1] | N-(5-{[(3-{[2-chloro-5-(methyloxy)phenyl]amino}quinoxalin-2-yl)amino]sulfonyl}-2-methylphenyl)-N-2-,N-2-dimethylglycinamide |
| 467 | 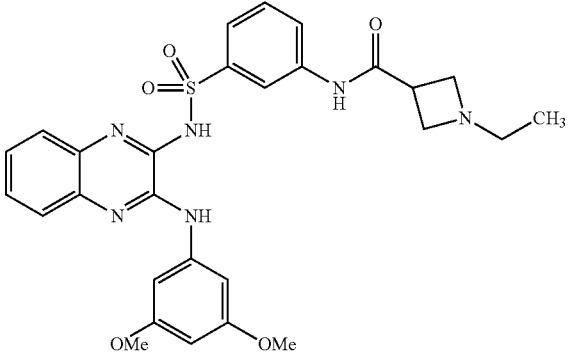 [SMILES: CCN1CC(C(=O)Nc2cccc(S(=O)(=O)Nc3nc4ccccc4nc3Nc3cc(OC)cc(OC)c3)c2)C1] | N-(3-{[(3-{[3,5-bis(methyloxy)phenyl]amino}quinoxalin-2-yl)amino]sulfonyl}phenyl)-1-ethylazetidine-3-carboxamide |
| 468 | 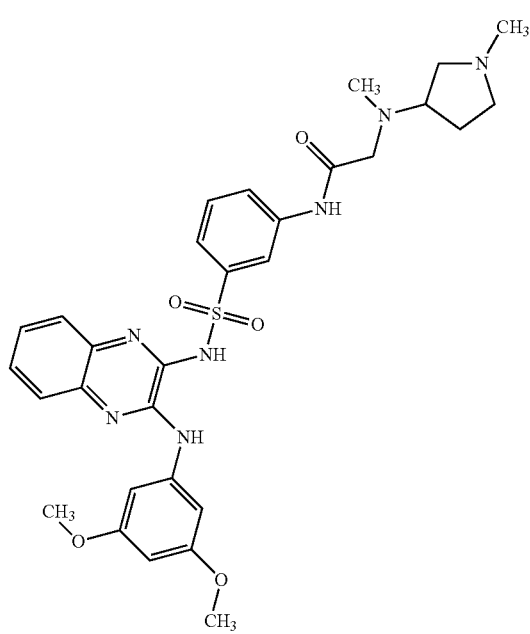 [SMILES: COc1cc(Nc2nc3ccccc3nc2NS(=O)(=O)c2cccc(NC(=O)CN(C)C3CCN(C)C3)c2)cc(OC)c1] | N-(3-{[(3-{[3,5-bis(methyloxy)phenyl]amino}quinoxalin-2-yl)amino[sulfonyl}phenyl)-N-2-methyl-N-2-(1-methylpyrrolidin-3-yl)glycinamide |

TABLE 1-continued
| Cpd. No. | Structure | IUPAC Name |
|---|---|---|
| 469 | 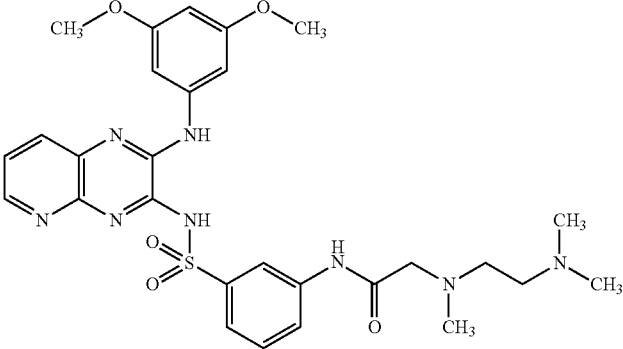 [SMILES: COc1cc(Nc2nc3cccnc3nc2NS(=O)(=O)c2cccc(NC(=O)CN(C)CCN(C)C)c2)cc(OC)c1] | N-(3-{[(2-{[3,5-bis(methyloxy)phenyl]amino}pyrido[2,3-b]pyrazin-3-yl)amino]sulfonyl}phenyl)-N-2-[2-(dimethylamino)ethyl]-N-2-methylglycinamide |
| 470 | 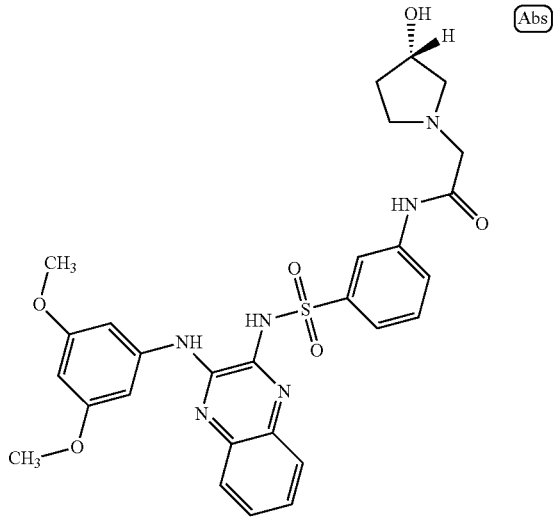 [SMILES: COc1cc(Nc2nc3ccccc3nc2NS(=O)(=O)c2cccc(NC(=O)CN3CC[C@H](O)C3)c2)cc(OC)c1] | N-(3-{[(3-{[3,5-bis(methyloxy)phenyl]amino}quinoxalin-2-yl)amino]sulfonyl}phenyl)-2-[(3S)-3-hydroxypyrolidin-1-yl]acetamide |
| 471 | 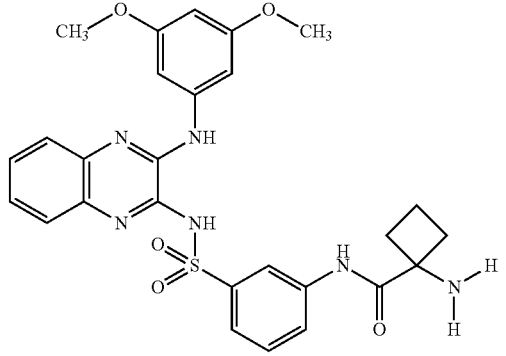 [SMILES: COc1cc(Nc2nc3ccccc3nc2NS(=O)(=O)c2cccc(NC(=O)C3(N)CCC3)c2)cc(OC)c1] | 1-amino-N-(3-{[(3-{[3,5-bis(methyloxy)phenyl]amino}quinoxalin-2-yl)amino]sulfonyl}phenyl)cyclobutanecarboxamide |

TABLE 1-continued

| Cpd. No. | Structure | IUPAC Name |
|---|---|---|
| 472 | 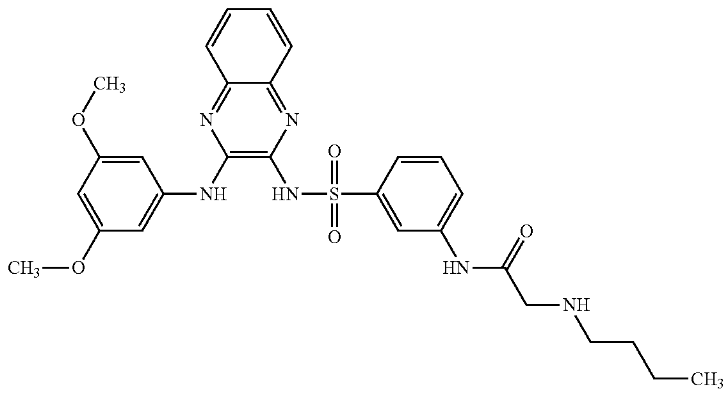 [SMILES: CCCCNCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-butylglycinamide |
| 473 | 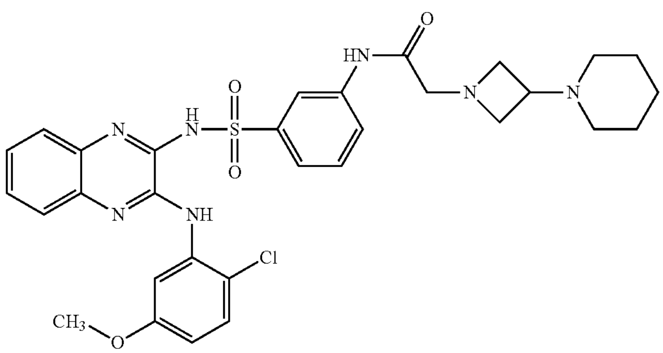 [SMILES: COc1ccc(Cl)c(Nc2nc3ccccc3nc2NS(=O)(=O)c2cccc(NC(=O)CN3CC(N4CCCCC4)C3)c2)c1] | N-(3-{[(3-{[2-chloro-5-(methyloxy)phenyl]amino}quinoxalin-2-yl)amino]sulfonyl}phenyl)-2-(3-piperidin-1-ylazetidin-1-yl)acetamide |
| 474 | 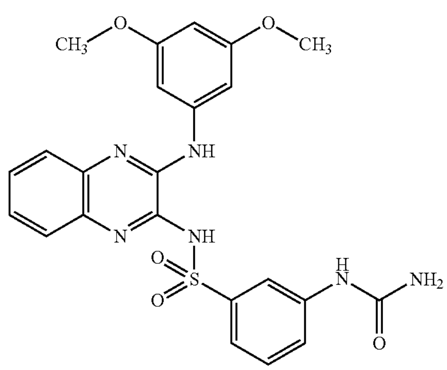 [SMILES: COc1cc(Nc2nc3ccccc3nc2NS(=O)(=O)c2cccc(NC(N)=O)c2)cc(OC)c1] | 3-[(aminocarbonyl)amino]-N-(3-{[3,5-bis(methyloxy)phenyl]amino}quinoxalin-2-yl)benzenesulfonamide |
| 475 | 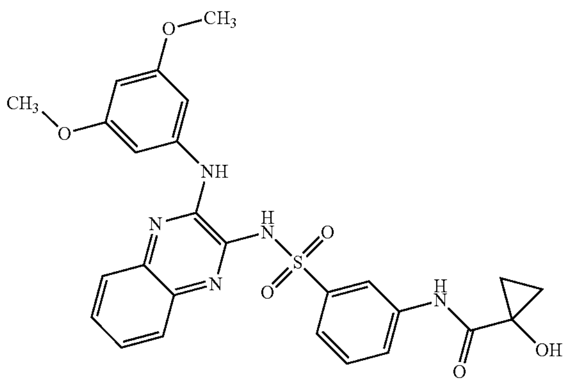 [SMILES: COc1cc(Nc2nc3ccccc3nc2NS(=O)(=O)c2cccc(NC(=O)C3(O)CC3)c2)cc(OC)c1] | N-(3-{[(3-{[3,5-bis(methyloxy)phenyl]amino}quinoxalin-2-yl)amino]sulfonyl}phenyl)-1-hydroxycyclopropanecarboxamide |

TABLE 1-continued

| Cpd. No. | Structure | IUPAC Name |
|---|---|---|
| 476 | 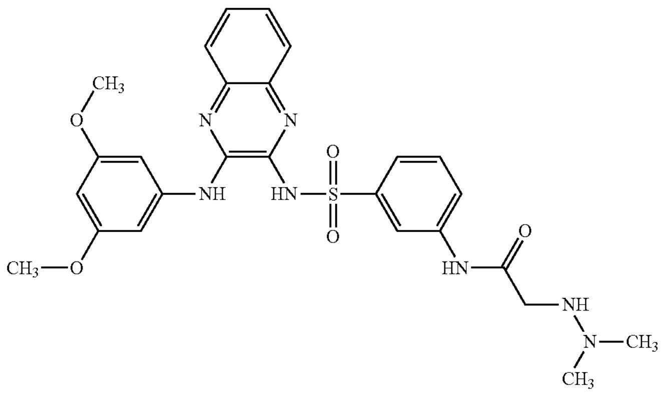 | N-(3-{[(3-{[3,5-bis(methyloxy)phenyl]amino}quinoxalin-2-yl)amino]sulfonyl}phenyl)-2-(2,2-dimethylhydrazino)acetamide |
| 477 | 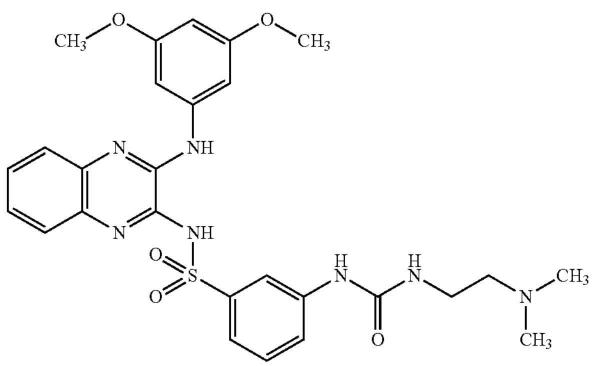 [SMILES: COc1cc(Nc2nc3ccccc3nc2NS(=O)(=O)c2cccc(NC(=O)NCCN(C)C)c2)cc(OC)c1] | N-(3-{[3,5-bis(methyloxy)phenyl]amino}quinoxalin-2-yl)-3-[({[2-(dimethylamino)ethyl]amino}carbonyl)amino]benzenesulfonamide |
| 478 | 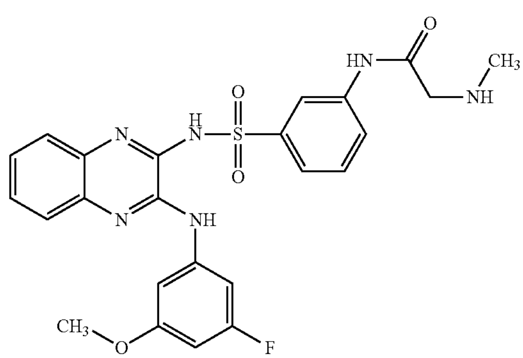 [SMILES: CNCC(=O)Nc1cccc(S(=O)(=O)Nc2nc3ccccc3nc2Nc2cc(F)cc(OC)c2)c1] | N-(3-{[(3-{[3-fluoro-5-(methyloxy)phenyl]amino}quinoxalin-2-yl)amino]sulfonyl}phenyl)-N-2-methylglycinamide |
| 479 | 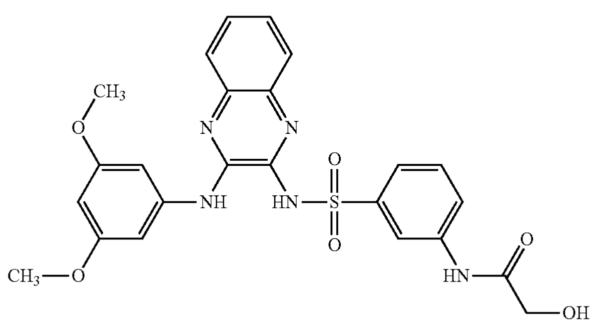 [SMILES: COc1cc(Nc2nc3ccccc3nc2NS(=O)(=O)c2cccc(NC(=O)CO)c2)cc(OC)c1] | N-(3-{[(3-{[3,5-bis(methyloxy)phenyl]amino}quinoxalin-2-yl)amino]sulfonyl}phenyl)-2-hydroxyacetamide |

| Cpd. No. | Structure | IUPAC Name |
|---|---|---|
| 480 | 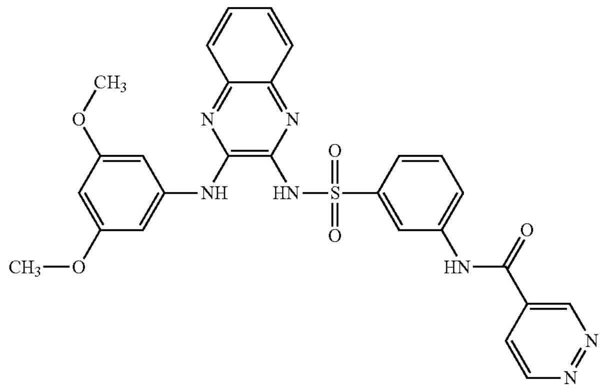 [SMILES: COc1cc(Nc2nc3ccccc3nc2NS(=O)(=O)c2cccc(NC(=O)c3ccnnc3)c2)cc(OC)c1] | N-(3-{[(3-{[3,5-bis(methyloxy)phenyl]amino}quinoxalin-2-yl)amino]sulfonyl}phenyl)pyridazine-4-carboxamide |
| 481 | 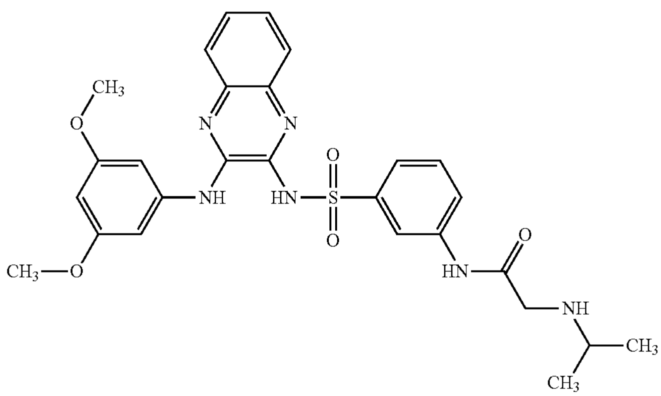 [SMILES: COc1cc(Nc2nc3ccccc3nc2NS(=O)(=O)c2cccc(NC(=O)CNC(C)C)c2)cc(OC)c1] | N-(3-{[(3-{[3,5-bis(methyloxy)phenyl]amino}quinoxalin-2-yl)amino]sulfonyl}phenyl)-N-2-(1-methylethyl)glycinamide |
| 482 | 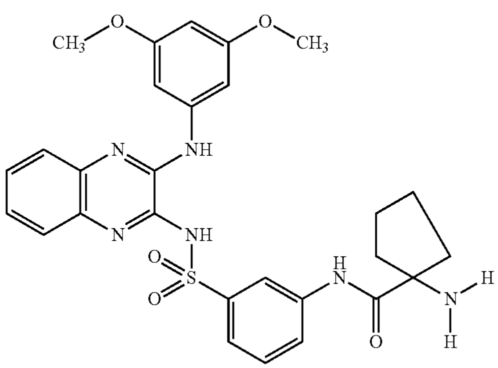 [SMILES: COc1cc(Nc2nc3ccccc3nc2NS(=O)(=O)c2cccc(NC(=O)C3(N)CCCC3)c2)cc(OC)c1] | 1-amino-N-(3-{[(3-{[3,5-bis(methyloxy)phenyl]amino}quinoxalin-2-yl)amino]sulfonyl}phenyl)cyclopentane-carboxamide |
| 483 | 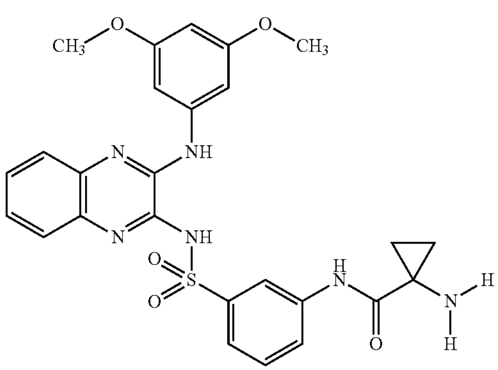 [SMILES: COc1cc(Nc2nc3ccccc3nc2NS(=O)(=O)c2cccc(NC(=O)C3(N)CC3)c2)cc(OC)c1] | 1-amino-N-(3-{[(3-{[3,5-bis(methyloxy)phenyl]amino}quinoxalin-2-yl)amino]sulfonyl}phenyl)cyclopropane-carboxamide |

TABLE 1-continued

| Cpd. No. | Structure | IUPAC Name |
|---|---|---|
| 484 | 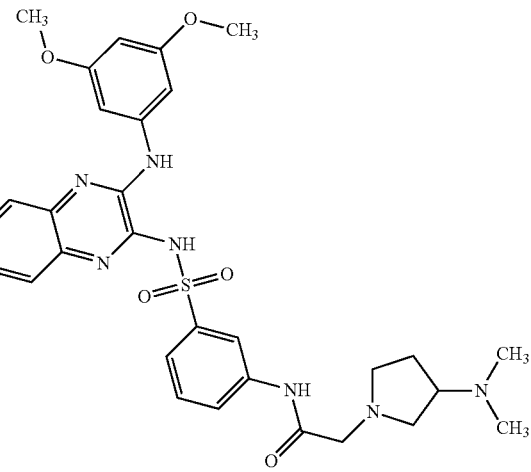 | N-(3-{[(3-{[3,5-bis(methyloxy)phenyl]amino}quinoxalin-2-yl)amino]sulfonyl}phenyl)-2-[3-(dimethylamino)pyrrolidin-1-yl]acetamide |
| 485 | 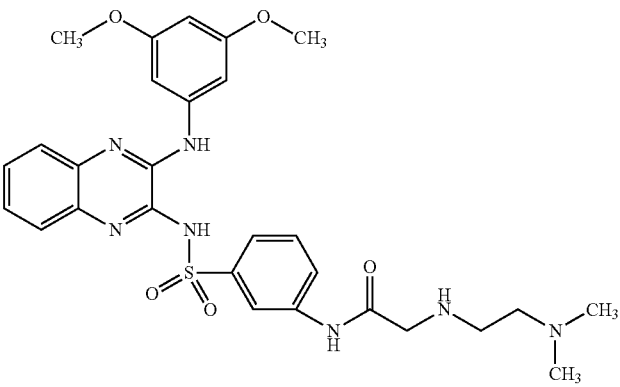 [SMILES: COc1cc(Nc2nc3ccccc3nc2NS(=O)(=O)c2cccc(NC(=O)CNCCN(C)C)c2)cc(OC)c1] | N-(3-{[(3-{[3,5-bis(methyloxy)phenyl]amino}quinoxalin-2-yl)amino]sulfonyl}phenyl)-N-2-[2-(dimethylamino)ethyl]glycinamide |
| 486 | 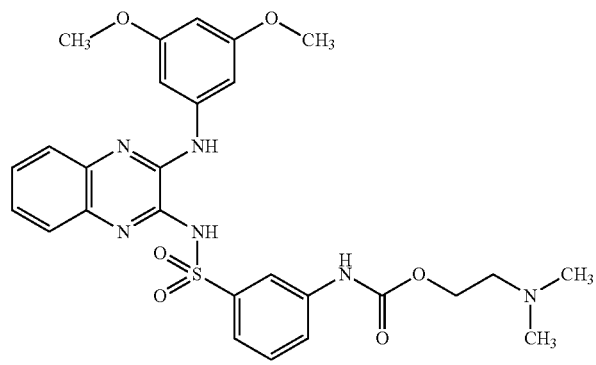 [SMILES: COc1cc(Nc2nc3ccccc3nc2NS(=O)(=O)c2cccc(NC(=O)OCCN(C)C)c2)cc(OC)c1] | 2-(dimethylamino)ethyl(3-{[(3-{[3,5-bis(methyloxy)phenyl]amino}quinoxalin-2-yl)amino]sulfonyl}phenyl)carbamate |
| 487 | 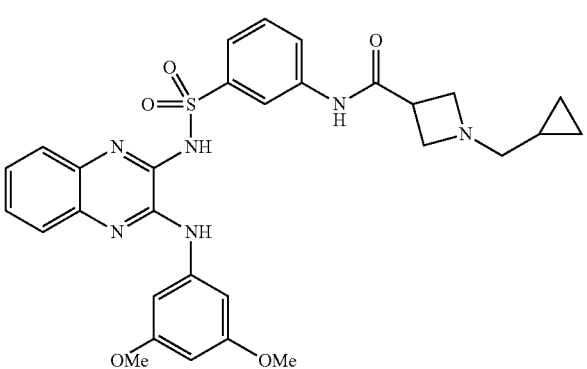 [SMILES: COc1cc(Nc2nc3ccccc3nc2NS(=O)(=O)c2cccc(NC(=O)C3CN(CC4CC4)C3)c2)cc(OC)c1] | N-(3-{[(3-{[3,5-bis(methyloxy)phenyl]amino}quinoxalin-2-yl)amino]sulfonyl}phenyl)-1-(cyclopropylmethyl)azetidine-3-carboxamide |

TABLE 1-continued

| Cpd. No. | Structure | IUPAC Name |
|---|---|---|
| 488 | 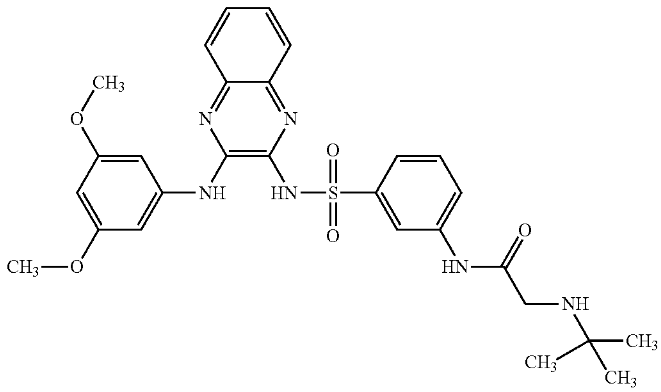 [SMILES: COc1cc(Nc2nc3ccccc3nc2NS(=O)(=O)c2cccc(NC(=O)CNC(C)(C)C)c2)cc(OC)c1] | N-(3-{[(3-{[3,5-bis(methyloxy)phenyl]amino}quinoxalin-2-yl)amino]sulfonyl}phenyl)-N-2-(1,1-dimethylethyl)glycinamide |
| 489 | 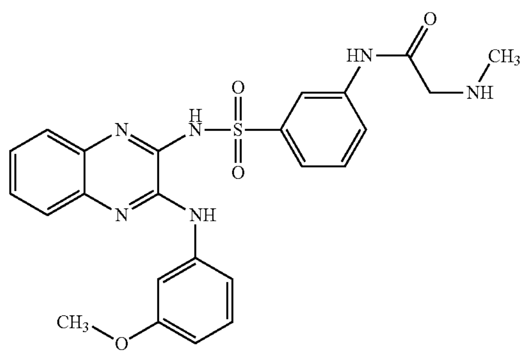 [SMILES: CNCC(=O)Nc1cccc(S(=O)(=O)Nc2nc3ccccc3nc2Nc2cccc(OC)c2)c1] | N-2-methyl-N-(3-{[(3-{[3-(methyloxy)phenyl]amino}quinoxalin-2-yl)amino]sulfonyl}phenyl)glycinamide |
| 490 | 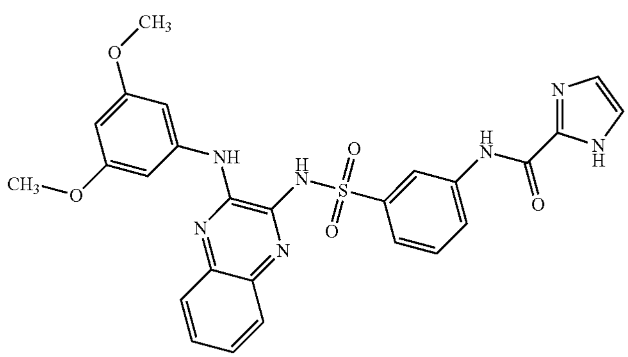 [SMILES: COc1cc(Nc2nc3ccccc3nc2NS(=O)(=O)c2cccc(NC(=O)c3ncc[nH]3)c2)cc(OC)c1] | N-(3-{[(3-{[3,5-bis(methyloxy)phenyl]amino}quinoxalin-2-yl)amino]sulfonyl}phenyl)-1H-imidazole-2-carboxamide |
| 491 | 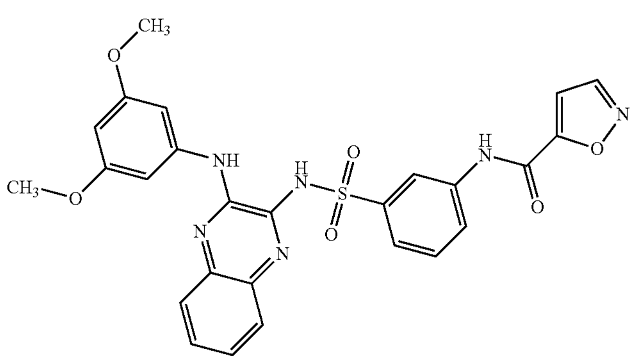 [SMILES: COc1cc(Nc2nc3ccccc3nc2NS(=O)(=O)c2cccc(NC(=O)c3ccno3)c2)cc(OC)c1] | N-(3-{[(3-{[3,5-bis(methyloxy)phenyl]amino}quinoxalin-2-yl)amino]sulfonyl}phenyl)isoxazole-5-carboxamide |

TABLE 1-continued

| Cpd. No. | Structure | IUPAC Name |
| --- | --- | --- |
| 492 | 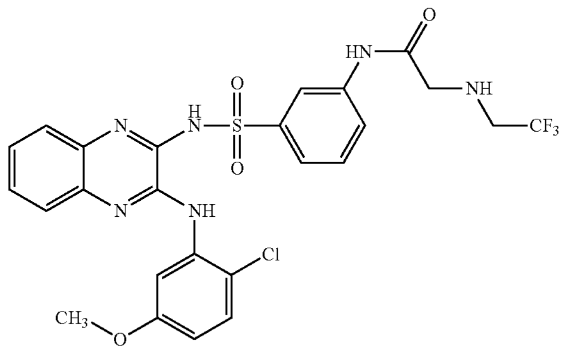 [SMILES: COc1ccc(Cl)c(Nc2nc3ccccc3nc2NS(=O)(=O)c2cccc(NC(=O)CNCC(F)(F)F)c2)c1] | N-(3-{[(3-{[2-chloro-5-(methyloxy)phenyl]amino}quinoxalin-2-yl)amino]sulfonyl}phenyl)-N-2-(2,2,2-trifluoroethyl)glycinamide |
| 493 | 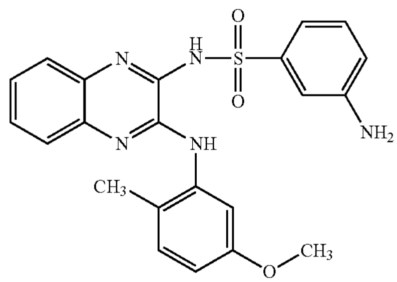 | 3-amino-N-(3-{[3-methyl-5-(methyloxy)phenyl]amino}quinoxalin-2-yl)benzenesulfonamide |
| 494 | 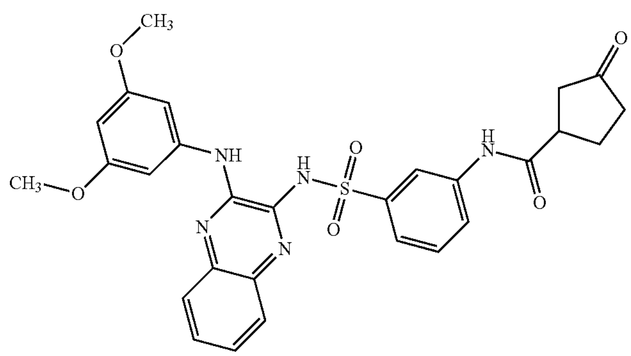 [SMILES: COc1cc(Nc2nc3ccccc3nc2NS(=O)(=O)c2cccc(NC(=O)C3CCC(=O)C3)c2)cc(OC)c1] | N-(3-{[(3-{[3,5-bis(methyloxy)phenyl]amino}quinoxalin-2-yl)amino]sulfonyl}phenyl)-3-oxocyclopentanecarboxamide |
| 495 | 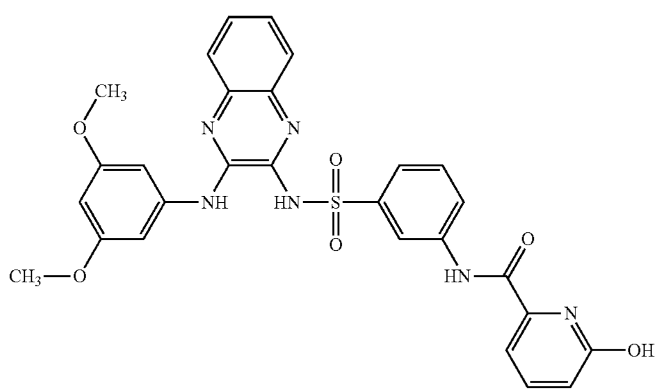 [SMILES: COc1cc(Nc2nc3ccccc3nc2NS(=O)(=O)c2cccc(NC(=O)c3cccc(O)n3)c2)cc(OC)c1] | N-(3-{[(3-{[3,5-bis(methyloxy)phenyl]amino}quinoxalin-2-yl)amino]sulfonyl}phenyl)-6-hydroxypyridine-2-carboxamide |

TABLE 1-continued

| Cpd. No. | Structure | IUPAC Name |
|---|---|---|
| 496 | 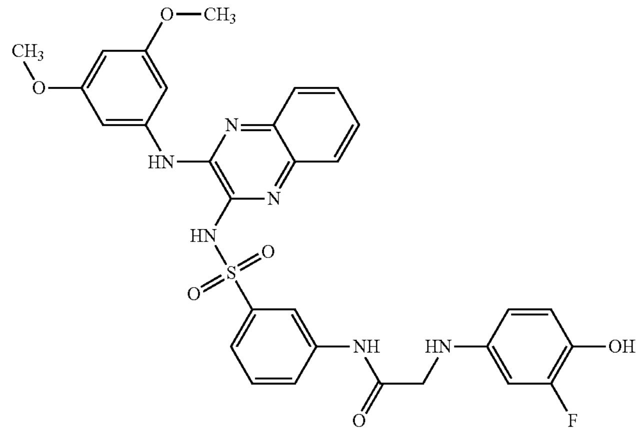 [SMILES: COc1cc(Nc2nc3ccccc3nc2NS(=O)(=O)c2cccc(NC(=O)CNc3ccc(O)c(F)c3)c2)cc(OC)c1] | N-(3-{[(3-{[3,5-bis(methyloxy)phenyl]amino}quinoxalin-2-yl)amino]sulfonyl}phenyl)-N-2-(3-fluoro-4-hydroxyphenyl)glycinamide |
| 497 | 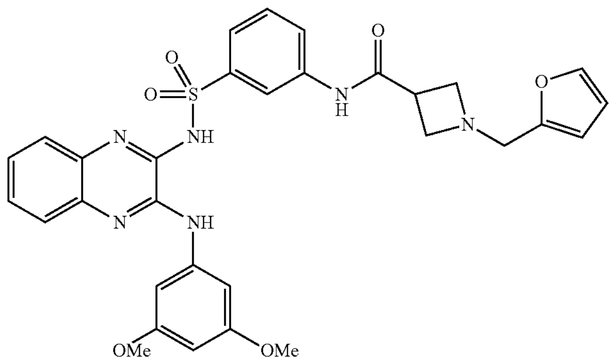 [SMILES: COc1cc(Nc2nc3ccccc3nc2NS(=O)(=O)c2cccc(NC(=O)C3CN(Cc4ccco4)C3)c2)cc(OC)c1] | N-(3-{[(3-{[3,5-bis(methyloxy)phenyl]amino}quinoxalin-2-yl)amino]sulfonyl}phenyl)-1-(furan-2-ylmethyl)azetidine-3-carboxamide |
| 498 | 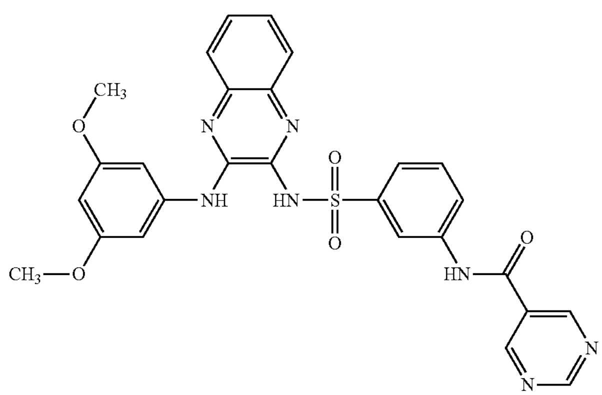 [SMILES: COc1cc(Nc2nc3ccccc3nc2NS(=O)(=O)c2cccc(NC(=O)c3cncnc3)c2)cc(OC)c1] | N-(3-{[(3-{[3,5-bis(methyloxy)phenyl]amino}quinoxalin-2-yl)amino]sulfonyl}phenyl)pyrimidine-5-carboxamide |
| 499 | 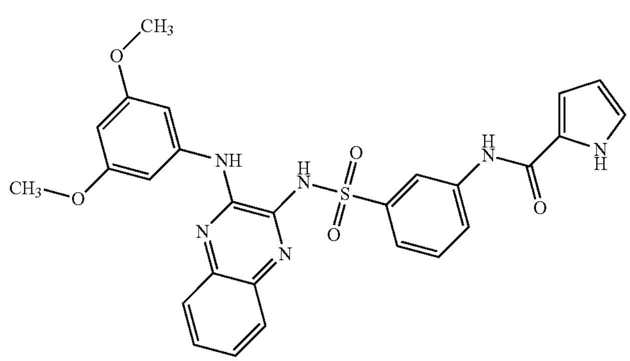 [SMILES: COc1cc(Nc2nc3ccccc3nc2NS(=O)(=O)c2cccc(NC(=O)c3ccc[nH]3)c2)cc(OC)c1] | N-(3-{[(3-{[3,5-bis(methyloxy)phenyl]amino}quinoxalin-2-yl)amino]sulfonyl}phenyl)-1H-pyrrole-2-carboxamide |

TABLE 1-continued

| Cpd. No. | Structure | IUPAC Name |
|---|---|---|
| 500 | 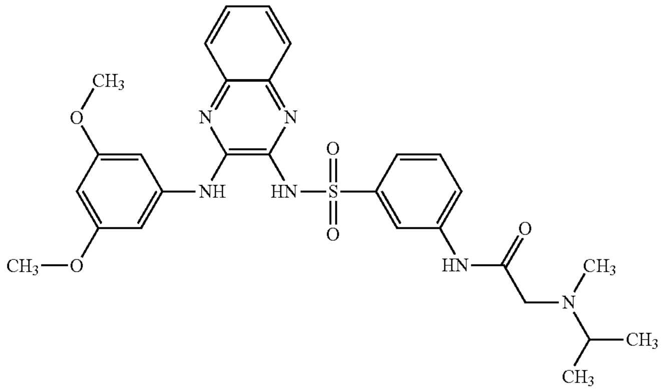 [SMILES: COc1cc(Nc2nc3ccccc3nc2NS(=O)(=O)c2cccc(NC(=O)CN(C)C(C)C)c2)cc(OC)c1] | N-(3-{[(3-{[3,5-bis(methyloxy)phenyl]amino}quinoxalin-2-yl)amino]sulfonyl}phenyl)-N-2-methyl-N-2-(1-methylethyl)glycinamide |
| 501 | 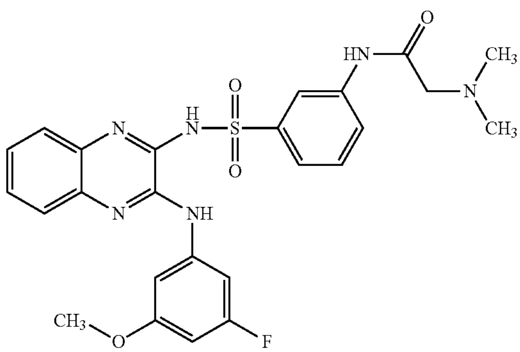 [SMILES: COc1cc(F)cc(Nc2nc3ccccc3nc2NS(=O)(=O)c2cccc(NC(=O)CN(C)C)c2)c1] | N-(3-{[(3-{[3-fluoro-5-(methyloxy)phenyl]amino}quinoxalin-2-yl)amino]sulfonyl}phenyl)-N-2-,N-2-dimethylglycinamide |
| 502 | 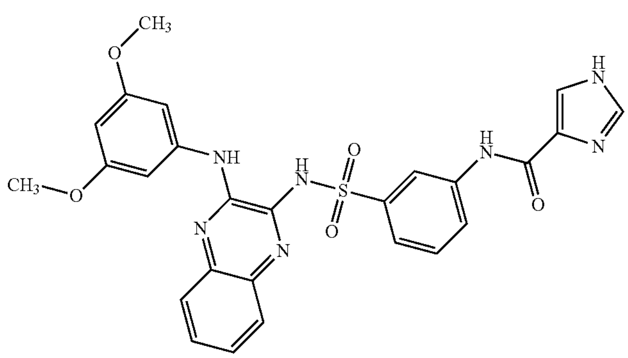 [SMILES: COc1cc(Nc2nc3ccccc3nc2NS(=O)(=O)c2cccc(NC(=O)c3c[nH]cn3)c2)cc(OC)c1] | N-(3-{[(3-{[3,5-bis(methyloxy)phenyl]amino}quinoxalin-2-yl)amino]sulfonyl}phenyl)-1H-imidazole-4-carboxamide |
| 503 | 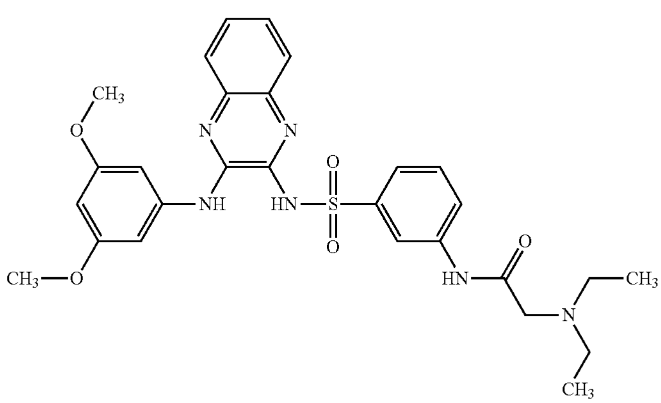 [SMILES: CCN(CC)CC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-,N-2-diethylglycinamide |

| Cpd. No. | Structure | IUPAC Name |
|---|---|---|
| 504 | 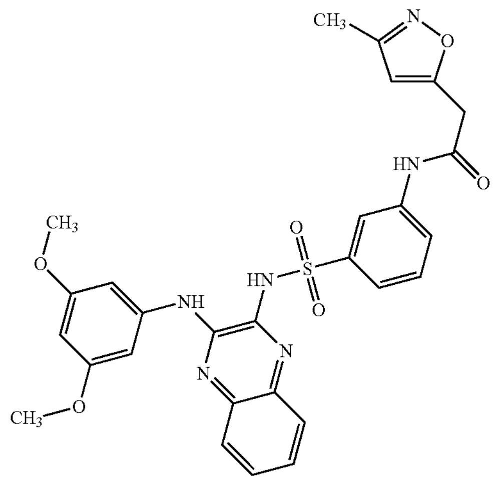 [SMILES: COc1cc(Nc2nc3ccccc3nc2NS(=O)(=O)c2cccc(NC(=O)Cc3cc(C)no3)c2)cc(OC)c1] | N-(3-{[(3-{[3,5-bis(methyloxy)phenyl]amino}quinoxalin-2-yl)amino]sulfonyl}phenyl)-2-(3-methylisoxazol-5-yl)acetamide |
| 505 | 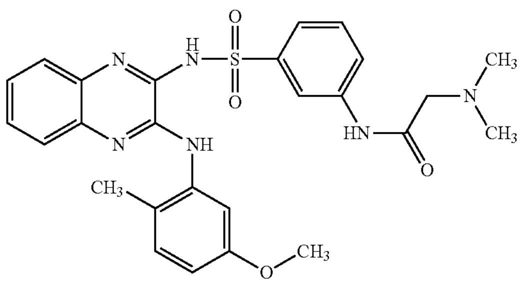 [SMILES: COc1ccc(C)c(Nc2nc3ccccc3nc2NS(=O)(=O)c2cccc(NC(=O)CN(C)C)c2)c1] | N-2-,N-2-dimethyl-N-(3-{[(3-{[2-methyl-5-(methyloxy)phenyl]amino}quinoxalin-2-yl)amino]sulfonyl}phenyl)glycinamide |
| 506 | 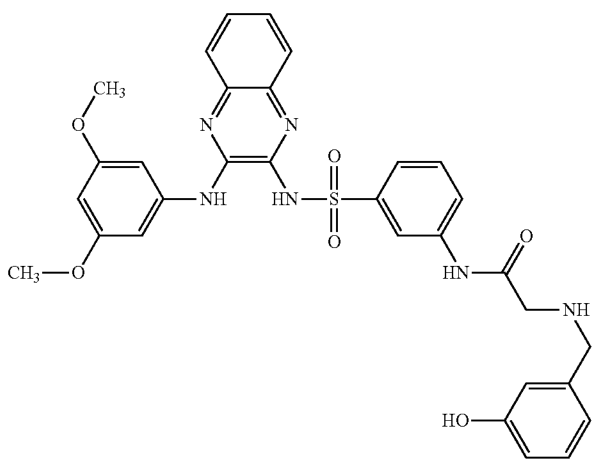 [SMILES: COc1cc(Nc2nc3ccccc3nc2NS(=O)(=O)c2cccc(NC(=O)CNCc3cccc(O)c3)c2)cc(OC)c1] | N-(3-{[(3-{[3,5-bis(methyloxy)phenyl]amino}quinoxalin-2-yl)amino]sulfonyl}phenyl)-N-2-[(3-hydroxyphenyl)methyl]glycinamide |
| 507 | 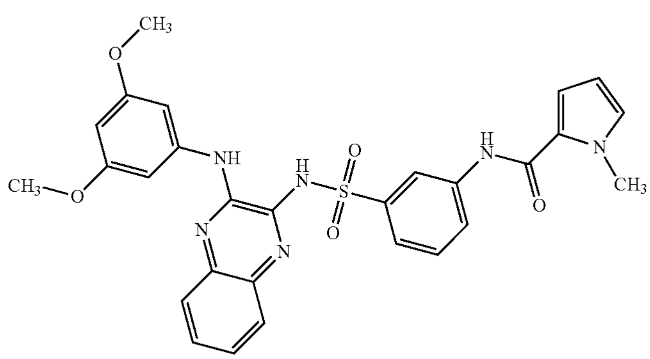 [SMILES: COc1cc(Nc2nc3ccccc3nc2NS(=O)(=O)c2cccc(NC(=O)c3cccn3C)c2)cc(OC)c1] | N-(3-{[(3-{[3,5-bis(methyloxy)phenyl]amino}quinoxalin-2-yl)amino]sulfonyl}phenyl)-1-methyl-1H-pyrole-2-carboxamide |

TABLE 1-continued
| Cpd. No. | Structure | IUPAC Name |
|---|---|---|
| 508 | 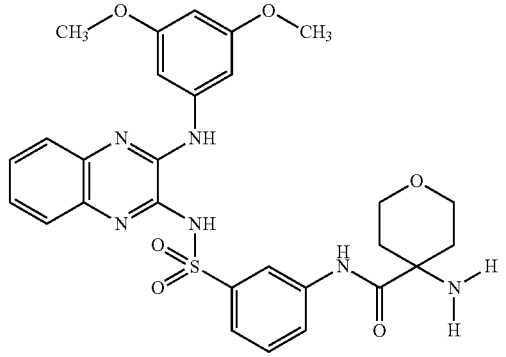 [SMILES: COc1cc(Nc2nc3ccccc3nc2NS(=O)(=O)c2cccc(NC(=O)C3(N)CCOCC3)c2)cc(OC)c1] | 4-amino-N-(3-{[(3-{[3,5-bis(methyloxy)phenyl)amino}quinoxalin-2-yl)amino]sulfonyl}phenyl)tetrahydro-2H-pyran-4-carboxamide |
| 509 | 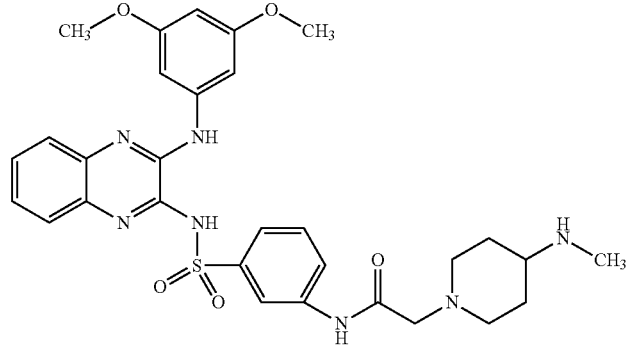 [SMILES: CNC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methyloxy)phenyl]amino}quinoxalin-2-yl)amino]sulfonyl}phenyl)-2-[4-(methylamino)piperidin-1-yl]acetamide |
| 510 | 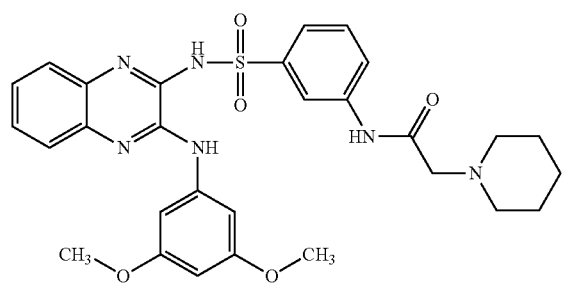 [SMILES: COc1cc(Nc2nc3ccccc3nc2NS(=O)(=O)c2cccc(NC(=O)CN3CCCCC3)c2)cc(OC)c1] | N-(3-{[(3-{[3,5-bis(methyloxy)phenyl]amino}quinoxalin-2-yl)amino]sulfonyl}phenyl)-2-piperidin-1-ylacetamide |

TABLE 1-continued
| Cpd. No. | Structure | IUPAC Name |
|---|---|---|
| 511 | 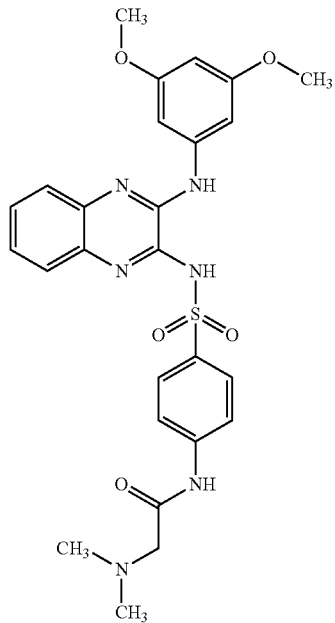 [SMILES: COc1cc(Nc2nc3ccccc3nc2NS(=O)(=O)c2ccc(NC(=O)CN(C)C)cc2)cc(OC)c1] | N-(4-{[(3-{[3,5-bis(methyloxy)phenyl]amino}quinoxalin-2-yl)amino]sulfonyl}phenyl)-N-2-,N-2-dimethylglycinamide |
| 512 | 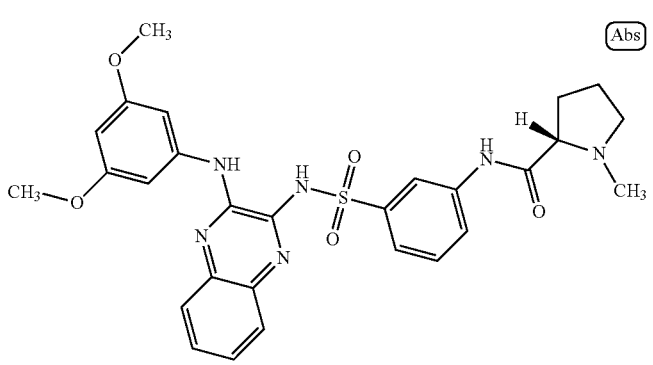 [SMILES: COc1cc(Nc2nc3ccccc3nc2NS(=O)(=O)c2cccc(NC(=O)[C@@H]3CCCN3C)c2)cc(OC)c1] | N-(3-{[(3-{[3,5-bis(methyloxy)phenyl]amino}quinoxalin-2-yl)amino]sulfonyl}phenyl)-1-methyl-L-prolinamide |
| 513 | 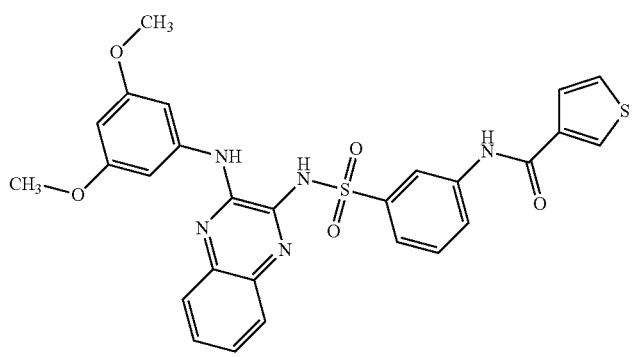 [SMILES: COc1cc(Nc2nc3ccccc3nc2NS(=O)(=O)c2cccc(NC(=O)c3ccsc3)c2)cc(OC)c1] | N-(3-{[(3-{[3,5-bis(methyloxy)phenyl]amino}quinoxalin-2-yl)amino]sulfonyl}phenyl)ethisophene-3-carboxamide |

TABLE 1-continued

| Cpd. No. | Structure | IUPAC Name |
|---|---|---|
| 514 | 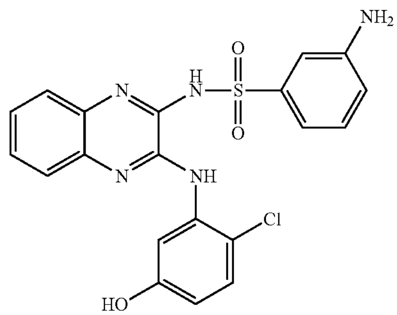 [SMILES: Nc1cccc(S(=O)(=O)Nc2nc3ccccc3nc2Nc2cc(O)ccc2Cl)c1] | 3-amino-N-{3-[(2-chloro-5-hydroxyphenyl)amino]quinoxalin-2-yl}benzenesulfonamide |
| 515 | 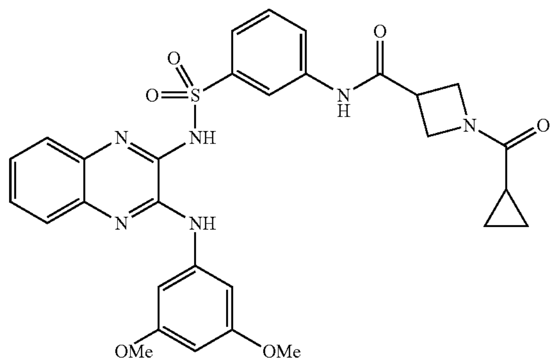 [SMILES: COc1cc(Nc2nc3ccccc3nc2NS(=O)(=O)c2cccc(NC(=O)C3CN(C(=O)C4CC4)C3)c2)cc(OC)c1] | N-(3-{[(3-{[3,5-bis(methyloxy)phenyl]amino}quinoxalin-2-yl)amino]sulfonyl}phenyl)-1-(cyclopropylcarbonyl)azetidine-3-carboxamide |
| 516 | 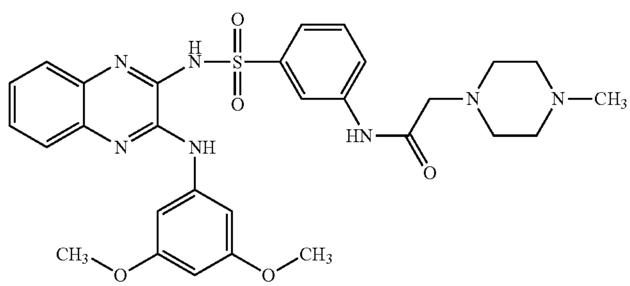 [SMILES: COc1cc(Nc2nc3ccccc3nc2NS(=O)(=O)c2cccc(NC(=O)CN3CCN(C)CC3)c2)cc(OC)c1] | N-(3-{[(3-{[3,5-bis(methyloxy)phenyl]amino}quinoxalin-2-yl)amino]sulfonyl}phenyl)-2-(4-methylpiperazin-1-yl)acetamide |
| 517 | 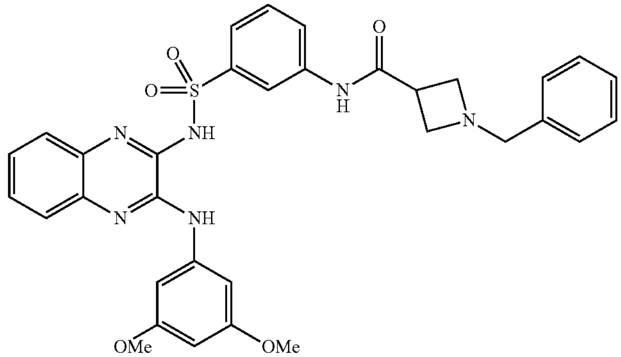 [SMILES: COc1cc(Nc2nc3ccccc3nc2NS(=O)(=O)c2cccc(NC(=O)C3CN(Cc4ccccc4)C3)c2)cc(OC)c1] | N-(3-{[(3-{[3,5-bis(methyloxy)phenyl]amino}quinoxalin-2-yl)amino]sulfonyl}phenyl)-1-(phenylethyl)azetidine-3-carboxamide |

TABLE 1-continued

| Cpd. No. | Structure | IUPAC Name |
|---|---|---|
| 518 | 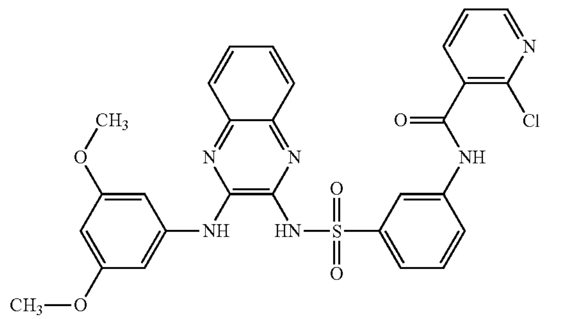 [SMILES: COc1cc(Nc2nc3ccccc3nc2NS(=O)(=O)c2cccc(NC(=O)c3cccnc3Cl)c2)cc(OC)c1] | N-(3-{[(3-{[3,5-bis(methyloxy)phenyl]amino}quinoxalin-2-yl)amino]sulfonyl}phenyl)-2-chloropyridine-3-carboxamide |
| 519 | 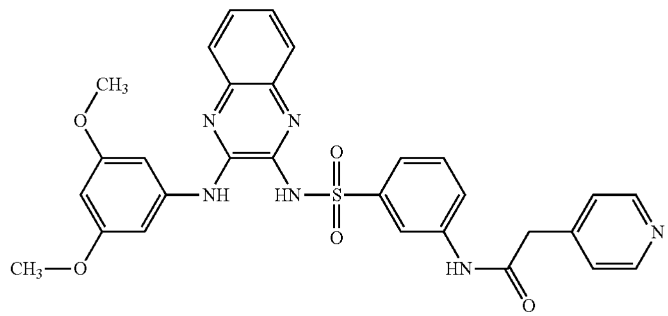 [SMILES: COc1cc(Nc2nc3ccccc3nc2NS(=O)(=O)c2cccc(NC(=O)Cc3ccncc3)c2)cc(OC)c1] | N-(3-{[(3-{[3,5-bis(methyloxy)phenyl]amino}quinoxalin-2-yl)amino]sulfonyl}phenyl)-2-pyridin-4-ylacetamide |
| 520 | 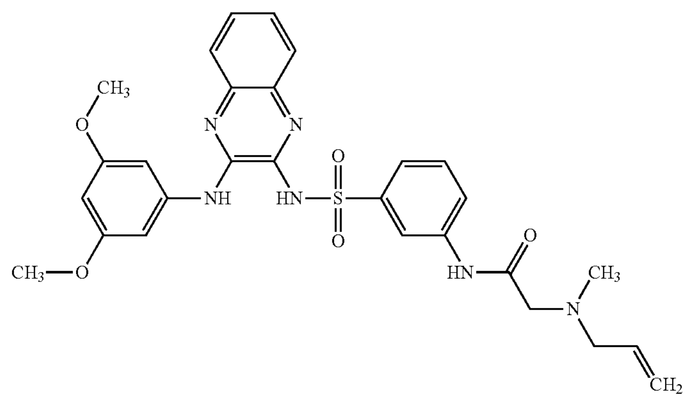 [SMILES: C=CCN(C)CC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-methyl-N-2-prop-2-en-1-ylglycinamide |
| 521 | 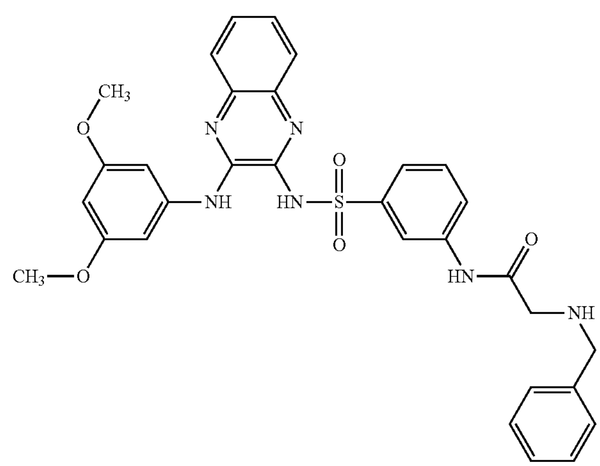 [SMILES: COc1cc(Nc2nc3ccccc3nc2NS(=O)(=O)c2cccc(NC(=O)CNCc3ccccc3)c2)cc(OC)c1] | N-(3-{[(3-{[3,5-bis(methyloxy)(phenyl]amino}quinoxalin-2-yl)amino]sulfonyl}phenyl)-N-2-(phenylmethyl)glycinamide |

TABLE 1-continued

| Cpd. No. | Structure | IUPAC Name |
|---|---|---|
| 522 | 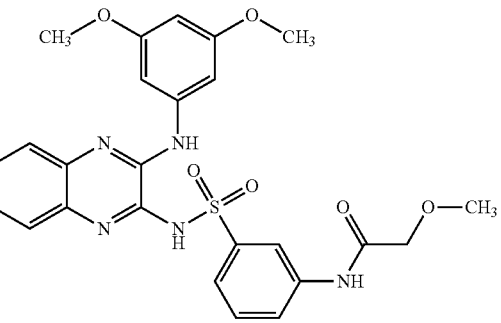 | N-(3-{[(3-{[3,5-bis(methyloxy)phenyl]amino}quinoxalin-2-yl)amino]sulfonyl}phenyl)-2-(methyloxy)acetamide |
| 523 | 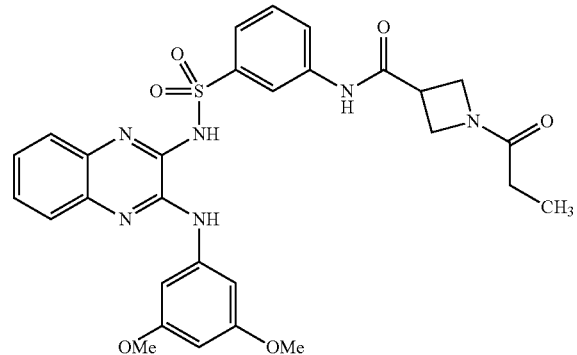 [SMILES: CCC(=O)N1CC(C(=O)Nc2cccc(S(=O)(=O)Nc3nc4ccccc4nc3Nc3cc(OC)cc(OC)c3)c2)C1] | N-(3-{[(3-{[3,5-bis(methyloxy)phenyl]amino}quinoxalin-2-yl)amino]sulfonyl}phenyl)-1-propanoxylazetidine-3-carboxamide |
| 524 | 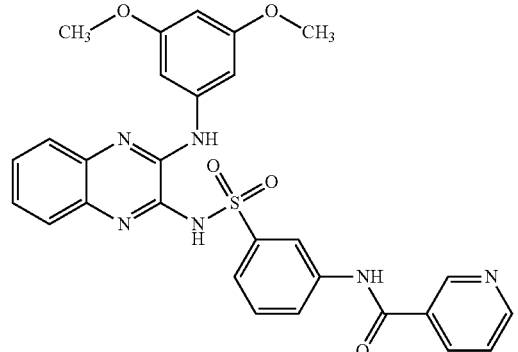 | N-(3-{[(3-{[3,5-bis(methyloxy)phenyl]amino}quinoxalin-2-yl)amino]sulfonyl}phenyl)pyridine-3-carboxamide |
| 525 | 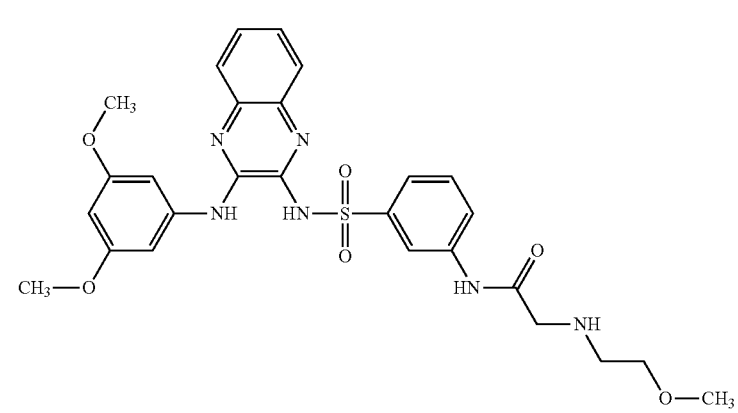 | N-(3-{[(3-{[3,5-bis(methyloxy)phenyl]amino}quinoxalin-2-yl)amino]sulfonyl}phenyl)-N-2-[2-(methyloxy)ethyl]glycinamide |

TABLE 1-continued
| Cpd. No. | Structure | IUPAC Name |
|---|---|---|
| 526 | 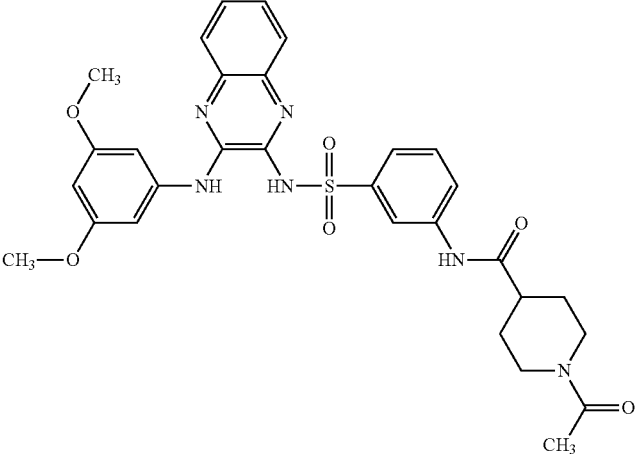 [SMILES: COc1cc(Nc2nc3ccccc3nc2NS(=O)(=O)c2cccc(NC(=O)C3CCN(C(C)=O)CC3)c2)cc(OC)c1] | 1-acetyl-N-(3-{[(3-{[3,5-bis(methyloxy)phenyl]amino}quinoxalin-2-yl)amino]sulfonyl}phenyl)piperidine-4-carboxamide |
| 527 | 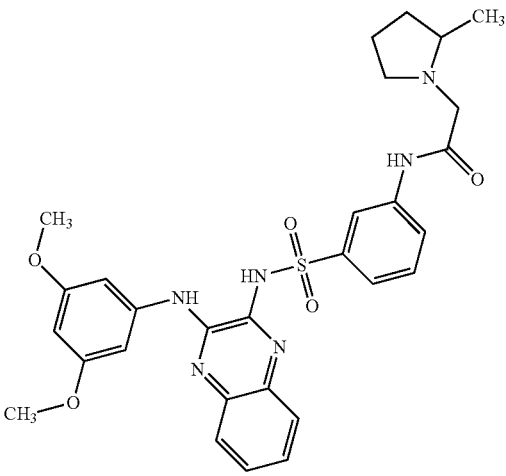 | N-(3-{[(3-{[3,5-bismethyloxy)phenyl]amino}quinoxalin-2-yl)amino]sulfonyl}phenyl)-2-(2-methylpyrrolidin-1-yl)acetamide |
| 528 | 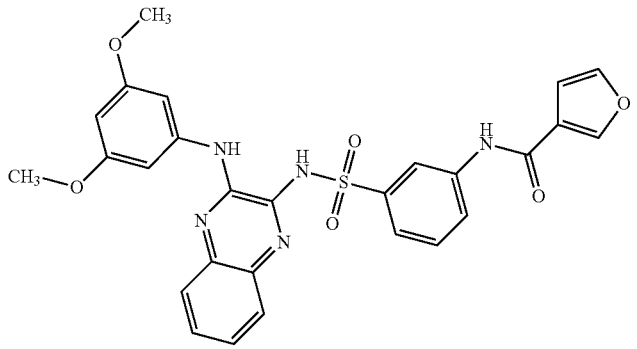 [SMILES: COc1cc(Nc2nc3ccccc3nc2NS(=O)(=O)c2cccc(NC(=O)c3ccoc3)c2)cc(OC)c1] | N-(3-{[(3-{[3,5-bis(methyloxy)phenyl]amino}quinoxalin-2-yl)amino]sulfonyl}phenyl)furan-3-carboxamide |

| Cpd. No. | Structure | IUPAC Name |
|---|---|---|
| 529 | 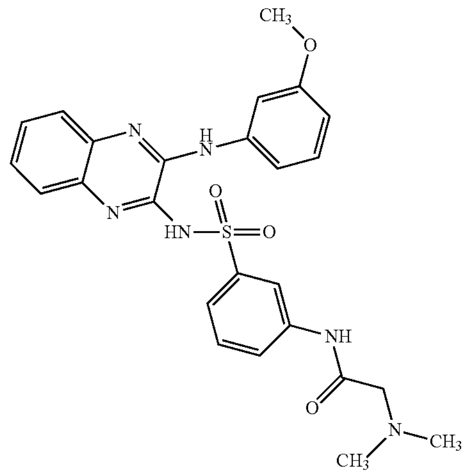 [SMILES: COc1cccc(Nc2nc3ccccc3nc2NS(=O)(=O)c2cccc(NC(=O)CN(C)C)c2)c1] | N-2-,N-2-dimethyl-N-(3-{[(3-{[3-(methyloxy)phenyl]amino}quinoxalin-2-yl)amino]sulfonyl}phenyl)glycinamide |
| 530 | 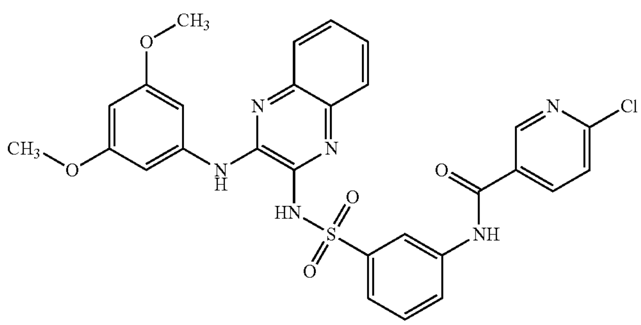 [SMILES: COc1cc(Nc2nc3ccccc3nc2NS(=O)(=O)c2cccc(NC(=O)c3ccc(Cl)nc3)c2)cc(OC)c1] | N-(3-{[(3-{[3,5-bis(methyloxy)phenyl]amino}quinoxalin-2-yl)amino]sulfonyl}phenyl)-6-chloropyridine-3-carboxamide |
| 531 | 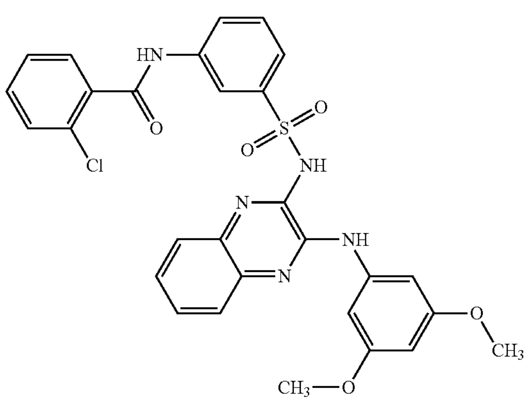 | N-(3-{[(3-{[3,5-bis(methyloxy)phenyl]amino}quinoxalin-2-yl)amino]sulfonyl}phenyl)-2-chlorobenzamide |
| 532 | 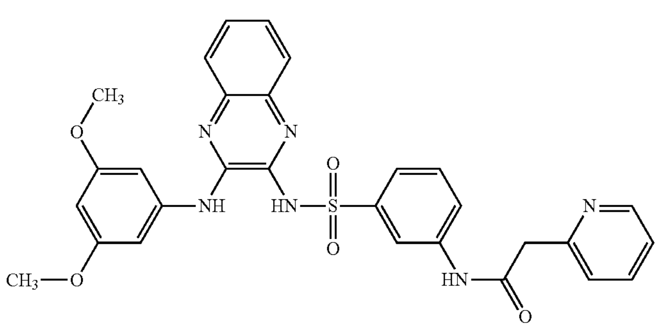 [SMILES: COc1cc(Nc2nc3ccccc3nc2NS(=O)(=O)c2cccc(NC(=O)Cc3ccccn3)c2)cc(OC)c1] | N-(3-{[(3-{[3,5-bis(methyloxy)phenyl]amino}quinoxalin-2-yl)amino]sulfonyl}phenyl)-2-pyridin-2-ylacetamide |

TABLE 1-continued

| Cpd. No. | Structure | IUPAC Name |
|---|---|---|
| 533 | 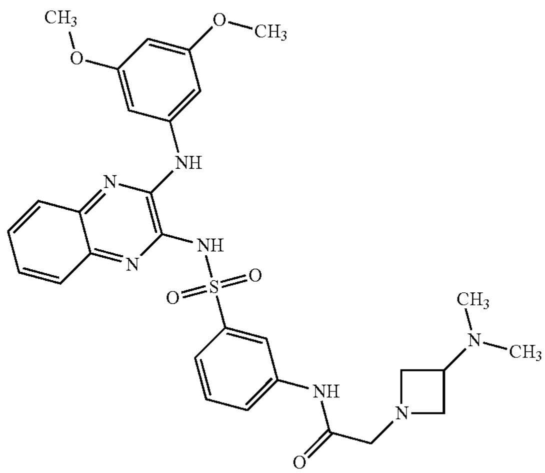 [SMILES: COc1cc(Nc2nc3ccccc3nc2NS(=O)(=O)c2cccc(NC(=O)CN3CC(N(C)C)C3)c2)cc(OC)c1] | N-(3-{[(3-{[3,5-bis(methyloxy)phenyl]amino}quinoxalin-2-yl)amino]sulfonyl}phenyl)-2-[3-(dimethylamino)azetidin-1-yl]acetamide |
| 534 | 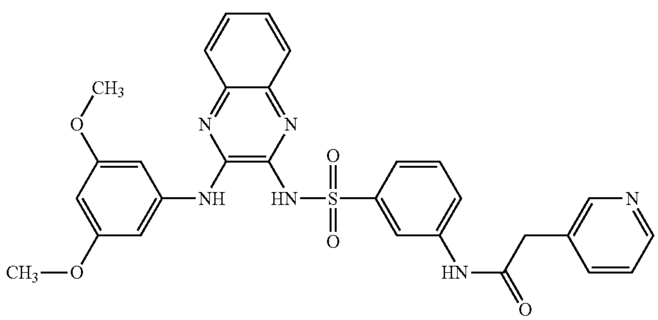 | N-(3-{[(3-{[3,5-bis(methyloxy)phenyl]amino}quinoxalin-2-yl)amino]sulfonyl}phenyl)-2-pyridin-3-ylacetamide |
| 535 | 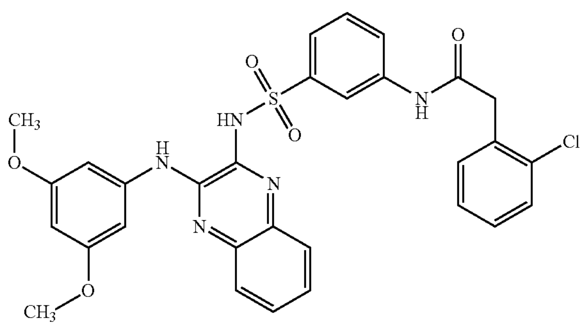 [SMILES: COc1cc(Nc2nc3ccccc3nc2NS(=O)(=O)c2cccc(NC(=O)Cc3ccccc3Cl)c2)cc(OC)c1] | N-(3-{[(3-{[3,5-bis(methyloxy)phenyl]amino}quinoxalin-2-yl)amino]sulfonyl}phenyl)-2-(2-chlorophenyl)acetamide |
| 536 | 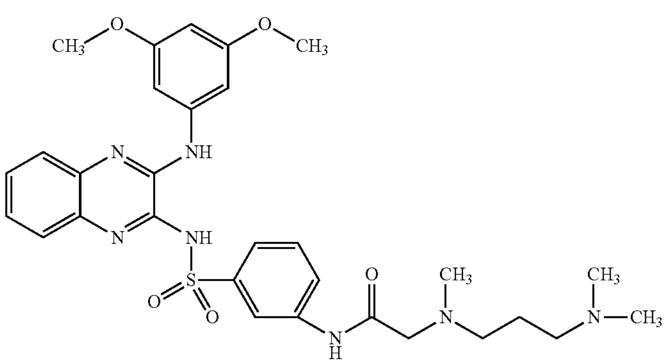 [SMILES: COc1cc(Nc2nc3ccccc3nc2NS(=O)(=O)c2cccc(NC(=O)CN(C)CCCN(C)C)c2)cc(OC)c1] | N-(3-{[(3-{[3,5-bis(methyloxy)phenyl]amino}quinoxalin-2-yl)amino]sulfonyl}phenyl)-N-2-[3-(dimethylamino)propyl]-N-2-methylglycinamide |

TABLE 1-continued
| Cpd. No. | Structure | IUPAC Name |
|---|---|---|
| 537 | 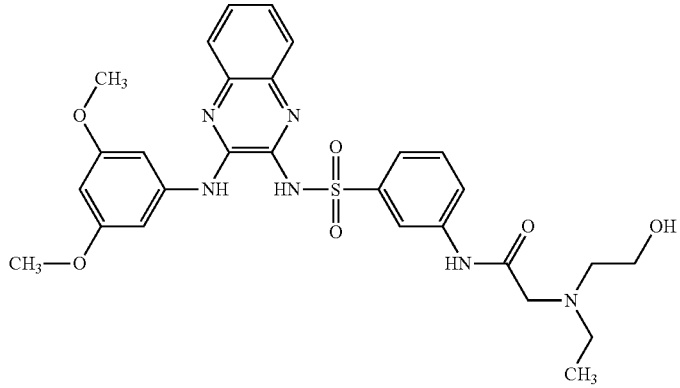 [SMILES: CCN(CCO)CC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-ethyl-N-2-(2-hydroxyethyl)glycinamide |
| 538 | 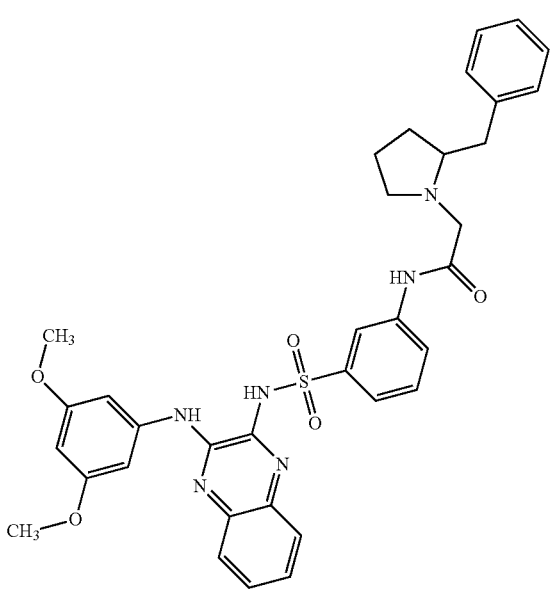 [SMILES: COc1cc(Nc2nc3ccccc3nc2NS(=O)(=O)c2cccc(NC(=O)CN3CCCC3Cc3ccccc3)c2)cc(OC)c1] | N-(3-{[(3-{[3,5-bis(methyloxy)phenyl]amino}quinoxalin-2-yl)amino]sulfonyl}phenyl)-2-[2-(phenylmethyl)pyrrolidin-1-yl]acetamide |
| 539 | 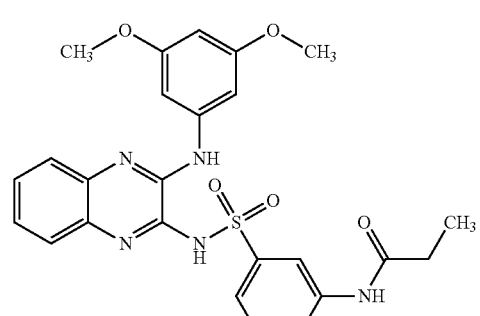 | N-(3-{[(3-{[3,5-bis(methyloxy)phenyl]amino}quinoxalin-2-yl)amino]sulfonyl}phenyl)propanamide |

TABLE 1-continued

| Cpd. No. | Structure | IUPAC Name |
| --- | --- | --- |
| 540 | 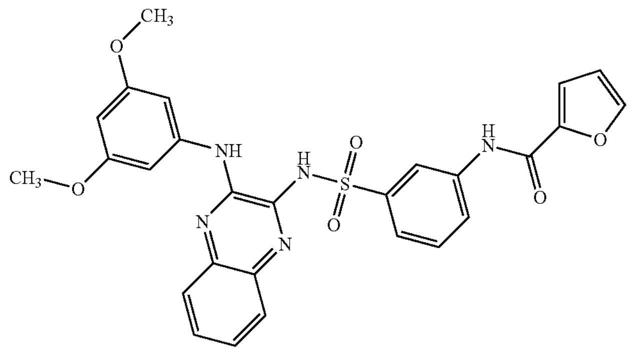 [SMILES: COc1cc(Nc2nc3ccccc3nc2NS(=O)(=O)c2cccc(NC(=O)c3ccco3)c2)cc(OC)c1] | N-(3-{[(3-{[3,5-bis(methyloxy)phenyl]amino}quinoxalin-2-yl)amino]sulfonyl}phenyl)furan-2-carboxamide |
| 541 | 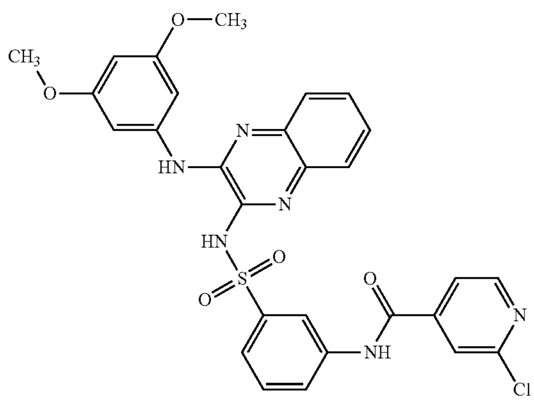 [SMILES: COc1cc(Nc2nc3ccccc3nc2NS(=O)(=O)c2cccc(NC(=O)c3ccnc(Cl)c3)c2)cc(OC)c1] | N-(3-{[(3-{[3,5-bis(methyloxy)phenyl]amino}quinoxalin-2-yl)amino]sulfonyl}phenyl)-2-chloropyridine-4-carboxamide |
| 542 | 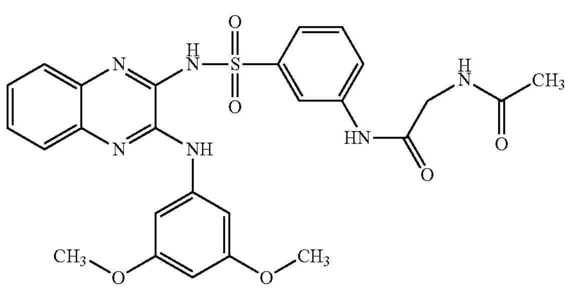 [SMILES: COc1cc(Nc2nc3ccccc3nc2NS(=O)(=O)c2cccc(NC(=O)CNC(C)=O)c2)cc(OC)c1] | N-2-acetyl-N-(3-{[(3-{[3,5-bis(methyloxy)phenyl]amino}quinoxalin-2-yl)amino]sulfonyl}phenyl)glycinamide |
| 543 | 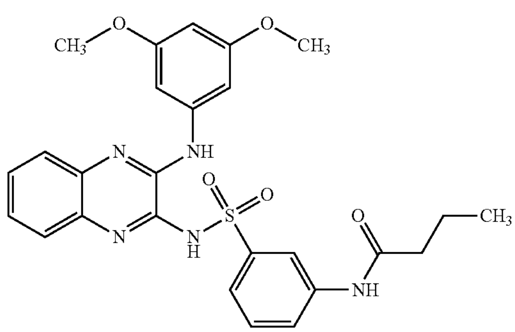 [SMILES: CCCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)butanamide |

TABLE 1-continued

| Cpd. No. | Structure | IUPAC Name |
|---|---|---|
| 544 | 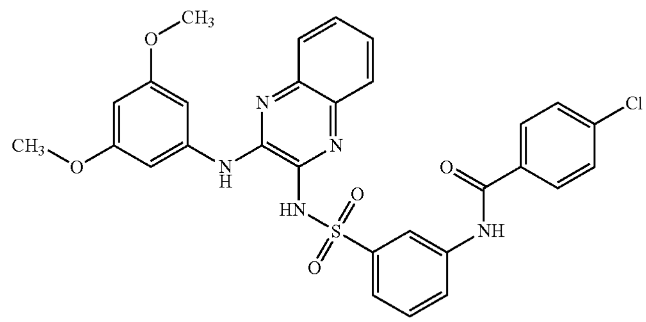 [SMILES: COc1cc(Nc2nc3ccccc3nc2NS(=O)(=O)c2cccc(NC(=O)c3ccc(Cl)cc3)c2)cc(OC)c1] | N-(3-{[(3-{[3,5-bis(methyloxy)phenyl]amino}quinoxalin-2-yl)amino]sulfonyl}phenyl)-4-chlorobenzamide |
| 545 | 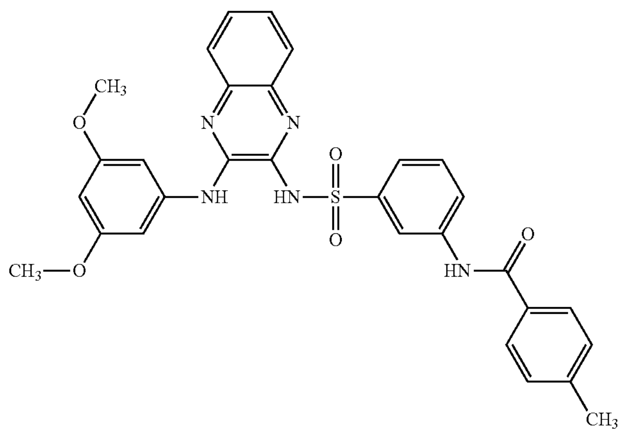 | N-(3-{[(3-{[3,5-bis(methyloxy)phenyl]amino}quinoxalin-2-yl)amino]sulfonyl}phenyl)-4-methylbenzamide |
| 546 | 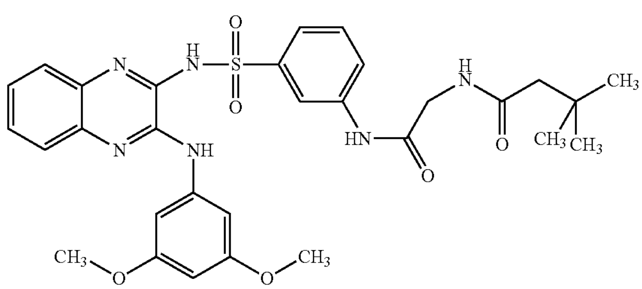 [SMILES: COc1cc(Nc2nc3ccccc3nc2NS(=O)(=O)c2cccc(NC(=O)CNC(=O)CC(C)(C)C)c2)cc(OC)c1] | 1,1-dimethylethyl{2-[(3-{[(3-{[3,5-bis(methyloxy)phenyl]amino}quinoxalin-2-yl)amino]sulfonyl}phenyl)amino]-2-oxoethyl}carbamate |
| 547 | 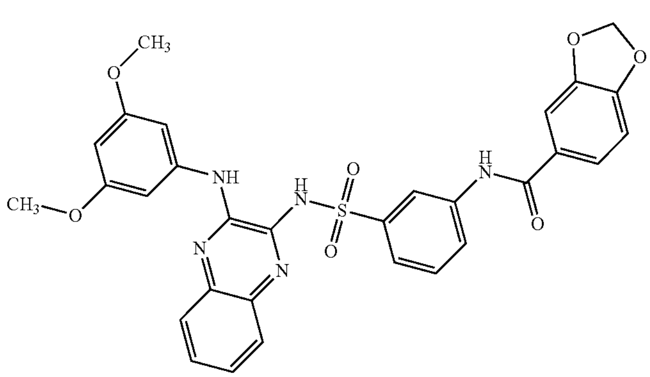 [SMILES: COc1cc(Nc2nc3ccccc3nc2NS(=O)(=O)c2cccc(NC(=O)c3ccc4c(c3)OCO4)c2)cc(OC)c1] | N-(3-{[(3-{[3,5-bis(methyloxy)phenyl]amino}quinoxalin-2-yl)amino]sulfonyl}phenyl)-1,3-benzodisoxole-5-carboxamide |

TABLE 1-continued
| Cpd. No. | Structure | IUPAC Name |
|---|---|---|
| 548 | 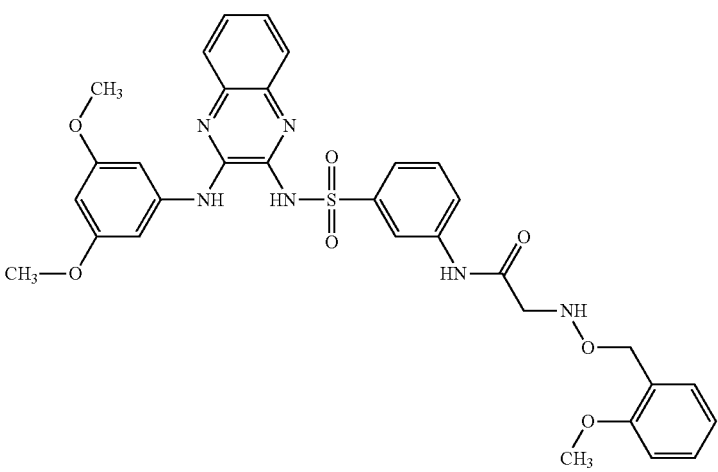 [SMILES: COc1cc(Nc2nc3ccccc3nc2NS(=O)(=O)c2cccc(NC(=O)CNOCc3ccccc3OC)c2)cc(OC)c1] | N-(3-{[(3-{[3,5-bis(methyloxy)phenyl]amino}quinoxalin-2-yl)amino]sulfonyl}phenyl)-N-2-({[2-(methyloxy)phenyl]methyl}oxy)glycinamide |
| 549 | 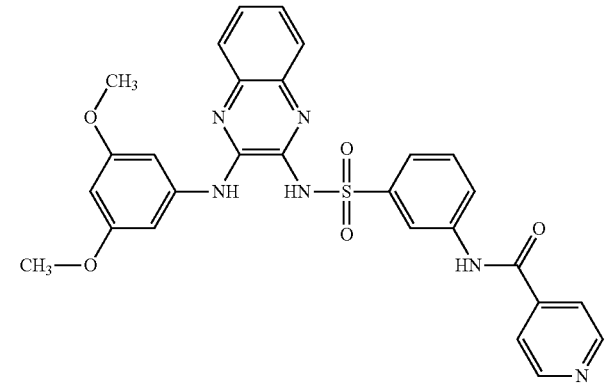 [SMILES: COc1cc(Nc2nc3ccccc3nc2NS(=O)(=O)c2cccc(NC(=O)c3ccncc3)c2)cc(OC)c1] | N-(3-{[(3-{[3,5-bis(methyloxy)phenyl]amino}quinoxalin-2-yl)amino]sulfonyl}phenyl)pyridine-4-carboxamide |
| 550 | 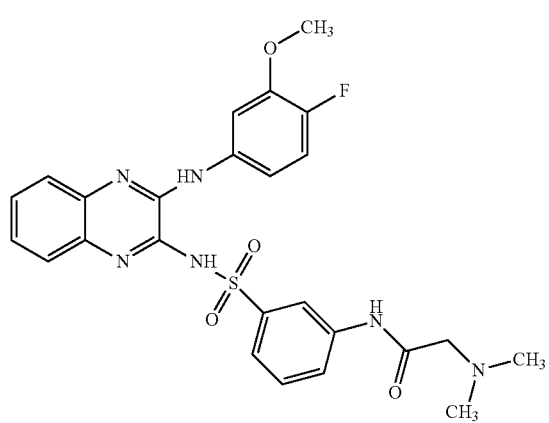 [SMILES: COc1cc(Nc2nc3ccccc3nc2NS(=O)(=O)c2cccc(NC(=O)CN(C)C)c2)ccc1F] | N-(3-{[(3-{[4-fluoro-3-(methyloxy)phenyl]amino}quinoxalin-2-yl)amino]sulfonyl}phenyl)-N-2-,N-2-dimethylglycinamide |

TABLE 1-continued

| Cpd. No. | Structure | IUPAC Name |
|---|---|---|
| 551 | 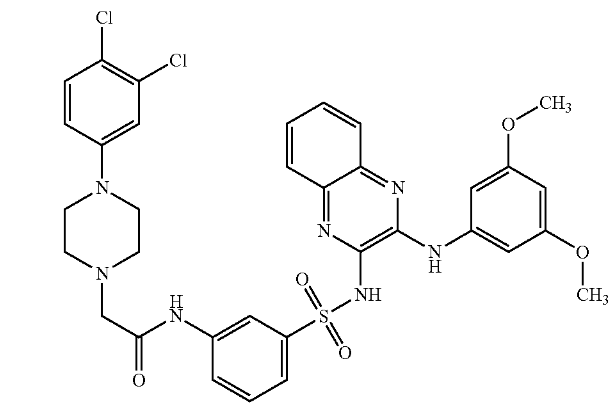 [SMILES: COc1cc(Nc2nc3ccccc3nc2NS(=O)(=O)c2cccc(NC(=O)CN3CCN(c4ccc(Cl)c(Cl)c4)CC3)c2)cc(OC)c1] | N-(3-{[(3-{[3,5-bis(methyloxy)phenyl]amino}quinoxalin-2-yl)amino]sulfonyl}phenyl)-2-[4-(3,4-dichlorophenyl)piperazin-1-yl]acetamide |
| 552 | 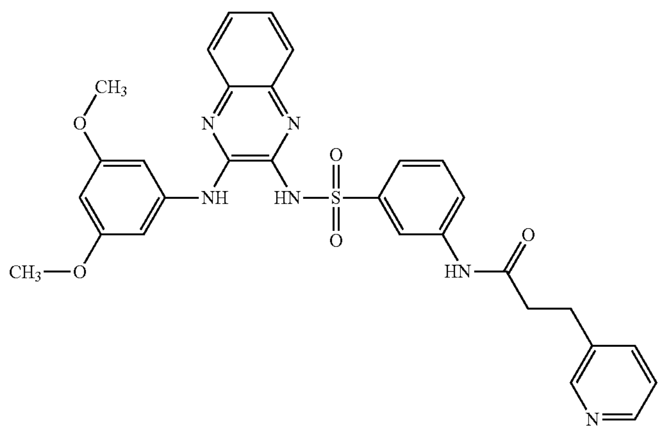 [SMILES: COc1cc(Nc2nc3ccccc3nc2NS(=O)(=O)c2cccc(NC(=O)CCc3cccnc3)c2)cc(OC)c1] | N-(3-{[(3-{[3,5-bis(methyloxy)phenyl]amino}quinoxalin-2-yl)amino]sulfonyl}phenyl)-3-pyridin-3-ylpropanamide |
| 553 | 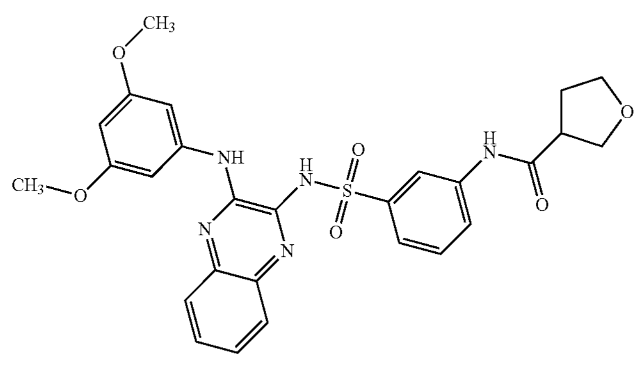 [SMILES: COc1cc(Nc2nc3ccccc3nc2NS(=O)(=O)c2cccc(NC(=O)C3CCOC3)c2)cc(OC)c1] | N-(3-{[(3-{[3,5-bis(methyloxy)phenyl]amino}quinoxalin-2-yl)amino]sulfonyl}phenyl)tetrahydrofuran-3-carboxamide |
| 554 | 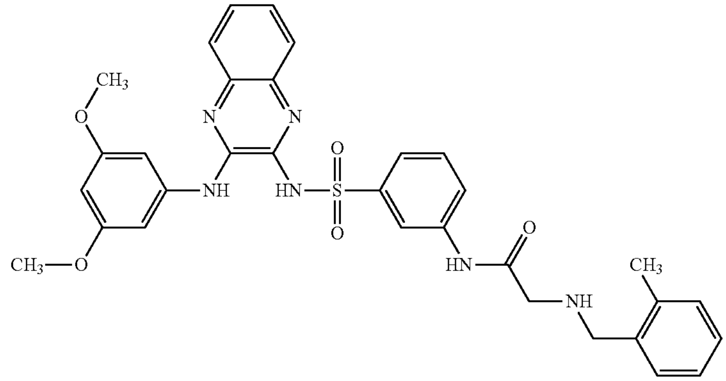 [SMILES: COc1cc(Nc2nc3ccccc3nc2NS(=O)(=O)c2cccc(NC(=O)CNCc3ccccc3C)c2)cc(OC)c1] | N-(3-{[(3-{[3,5-bis(methyloxy)phenyl]amino}quinoxalin-2-yl)amino]sulfonyl}phenyl)-N-2-[(2-methylphenyl)methyl]glycinamide |

TABLE 1-continued

| Cpd. No. | Structure | IUPAC Name |
|---|---|---|
| 555 | 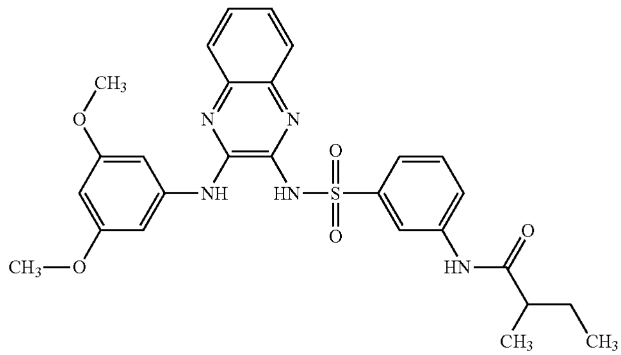 [SMILES: CCC(C)C(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-2-methylbutanamide |
| 556 | 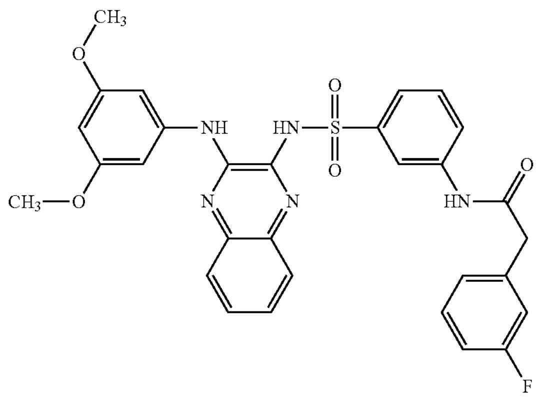 [SMILES: COc1cc(Nc2nc3ccccc3nc2NS(=O)(=O)c2cccc(NC(=O)Cc3cccc(F)c3)c2)cc(OC)c1] | N-(3-{[(3-{[3,5-bis(methylethyl)phenyl]amino}quinoxalin-2-yl)amino]sulfonyl}phenyl)-2-(3-fluorophenyl)acetamide |
| 557 | 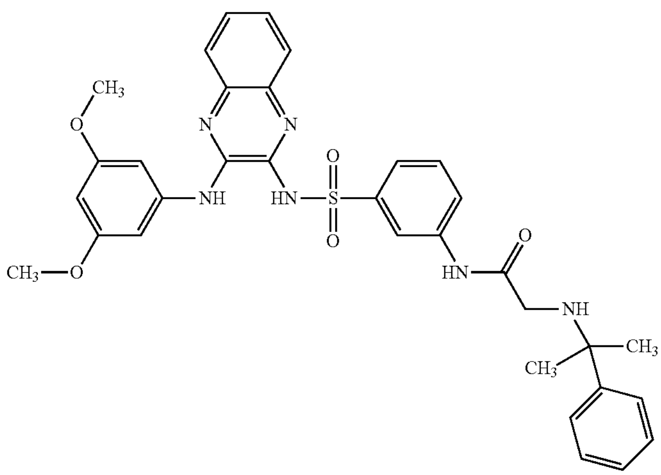 [SMILES: COc1cc(Nc2nc3ccccc3nc2NS(=O)(=O)c2cccc(NC(=O)CNC(C)(C)c3ccccc3)c2)cc(OC)c1] | N-(3-{[(3-{[3,5-bis(methyloxy)phenyl]amino}quinoxalin-2-yl)amino]sulfonyl}phenyl)-N-2-(1-methyl-1-phenylethyl)glycinamide |
| 558 | 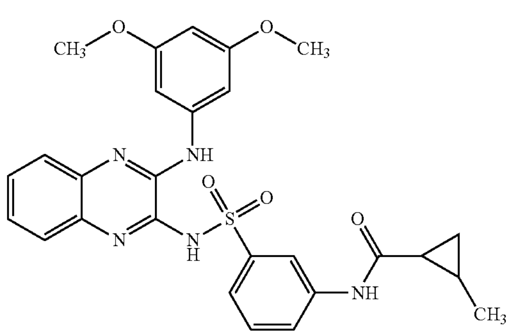 [SMILES: COc1cc(Nc2nc3ccccc3nc2NS(=O)(=O)c2cccc(NC(=O)C3CC3C)c2)cc(OC)c1] | N-(3-{[(3-{[3,5-bis(methyloxy)phenyl]amino}quinoxalin-2-yl)amino]sulfonyl}phenyl)-2-methylcyclopropanecarboxamide |

TABLE 1-continued

| Cpd. No. | Structure | IUPAC Name |
|---|---|---|
| 559 | 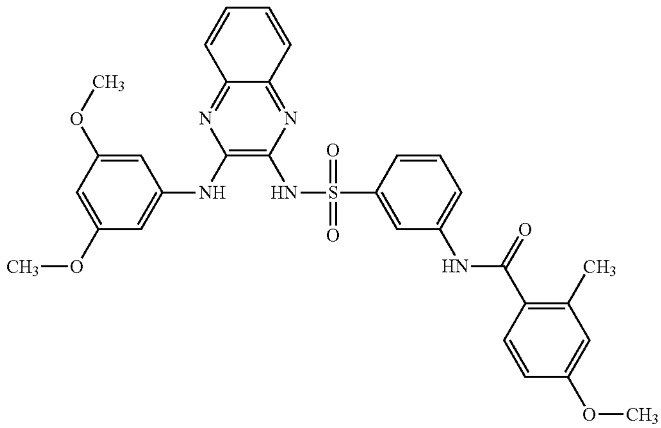 | N-(3-{[(3-{[3,5-bis(methyloxy)phenyl]amino}quinoxalin-2-yl)amino]sulfonyl}phenyl)-2-methyl-4-(methyloxy)benzamide |
| 560 | 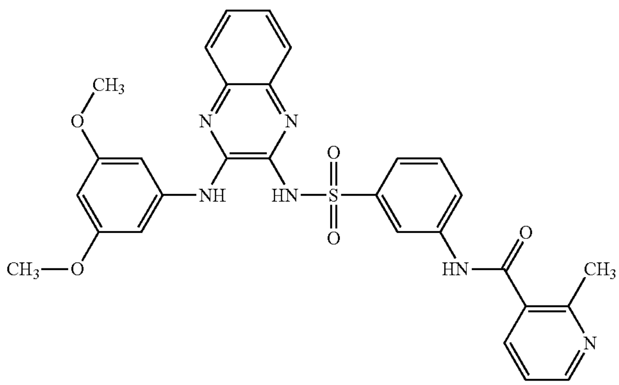 | N-(3-{[(3-{[3,5-bis(methyloxy)phenyl]amino}quinoxalin-2-yl)amino]sulfonyl}phenyl)-2-methylpyridine-3-carboxamide |
| 561 | 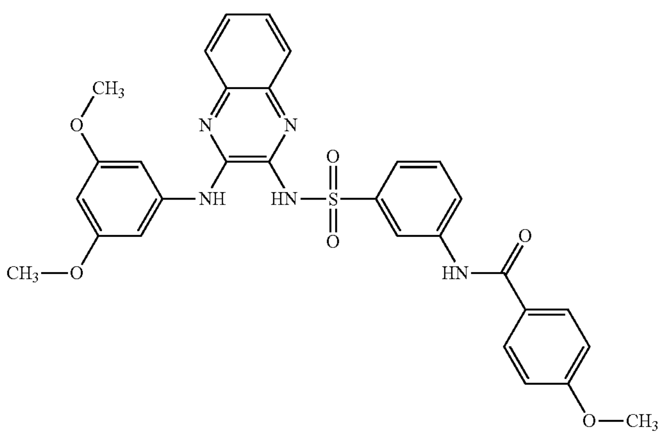 | N-(3-{[(3-{[3,5-bis(methyloxy)phenyl]amino}quinoxalin-2-yl)amino]sulfonyl}phenyl)-4-(methyloxy)benzamide |
| 562 | 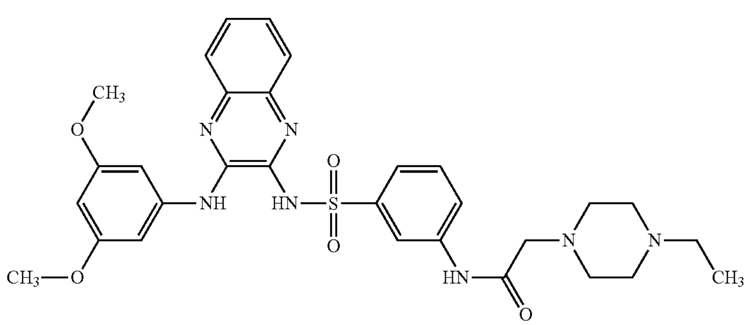 [SMILES: CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methyloxy)phenyl]amino}quinoxalin-2-yl)amino]sulfonyl}phenyl)-2-(4-ethylpiperazin-1-yl)acetamide |

TABLE 1-continued

| Cpd. No. | Structure | IUPAC Name |
|---|---|---|
| 563 | 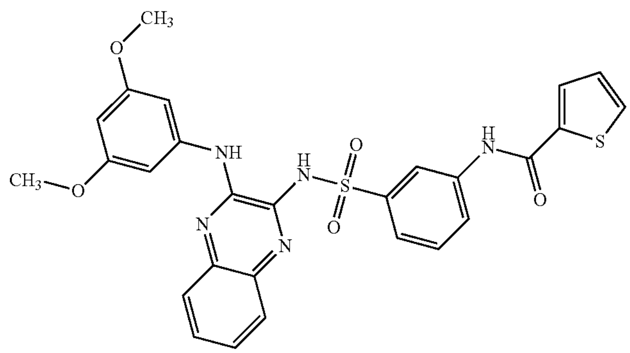 [SMILES: COc1cc(Nc2nc3ccccc3nc2NS(=O)(=O)c2cccc(NC(=O)c3cccs3)c2)cc(OC)c1] | N-(3-{[(3-{[3,5-bis(methyloxy)phenyl]amino}quinoxalin-2-yl)amino]sulfonyl}phenyl)ethisophene-2-carboxamide |
| 564 | 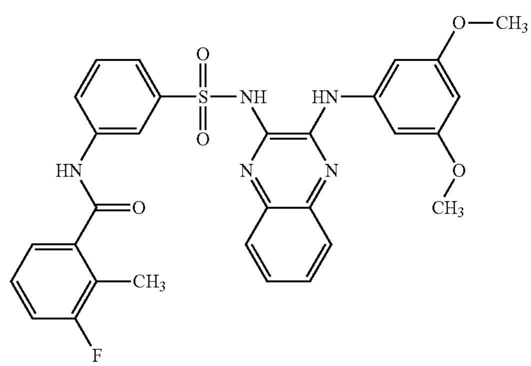 [SMILES: COc1cc(Nc2nc3ccccc3nc2NS(=O)(=O)c2cccc(NC(=O)c3cccc(F)c3C)c2)cc(OC)c1] | N-(3-{[(3-{[3,5-bis(methyloxy)phenyl]amino}quinoxalin-2-yl)amino]sulfonyl}phenyl)-3-fluoro-2-methylbenzamide |
| 565 | 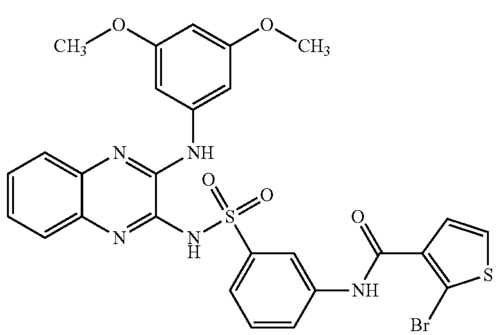 [SMILES: COc1cc(Nc2nc3ccccc3nc2NS(=O)(=O)c2cccc(NC(=O)c3ccsc3Br)c2)cc(OC)c1] | N-(3-{[(3-{[3,5-bis(methyloxy)phenyl]amino}quinoxalin-2-yl)amino]sulfonyl}phenyl)-2-bromothisophene-3-carboxamide |
| 566 | 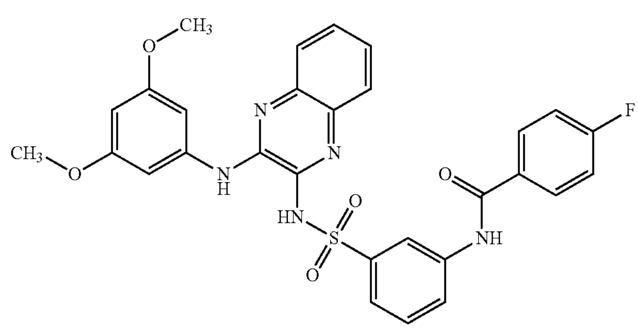 [SMILES: COc1cc(Nc2nc3ccccc3nc2NS(=O)(=O)c2cccc(NC(=O)c3ccc(F)cc3)c2)cc(OC)c1] | N-(3-{[(3-{[3,5-bis(methyloxy)phenyl]amino}quinoxalin-2-yl)amino]sulfonyl}phenyl)-4-fluorobenzamide |

TABLE 1-continued

| Cpd. No. | Structure | IUPAC Name |
|---|---|---|
| 567 | 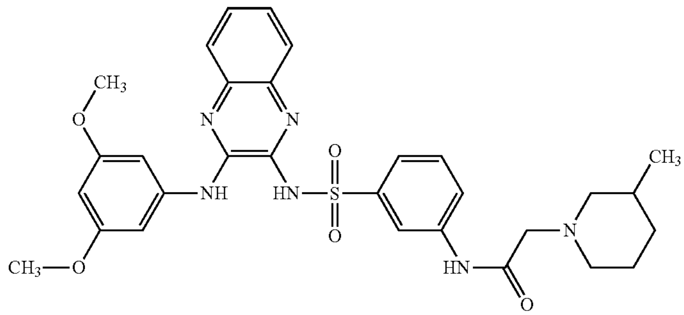 | N-(3-{[(3-{[3,5-bis(methyloxy)phenyl]amino}quinoxalin-2-yl)amino]sulfonyl}phenyl)-2-(3-methylpiperidin-1-yl)acetamide |
| 568 | 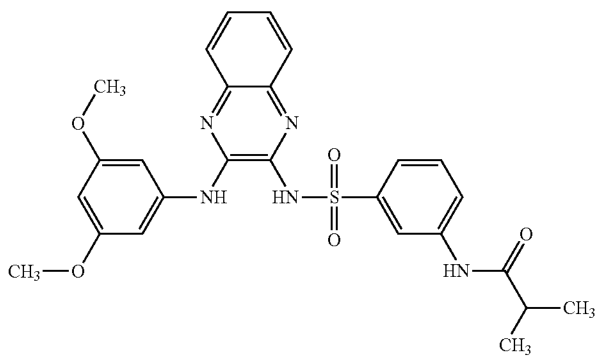 [SMILES: COc1cc(Nc2nc3ccccc3nc2NS(=O)(=O)c2cccc(NC(=O)C(C)C)c2)cc(OC)c1] | N-(3-{[(3-{[3,5-bis(methyloxy)phenyl]amino}quinoxalin-2-yl)amino]sulfonyl}phenyl)-2-methylpropanamide |
| 569 | 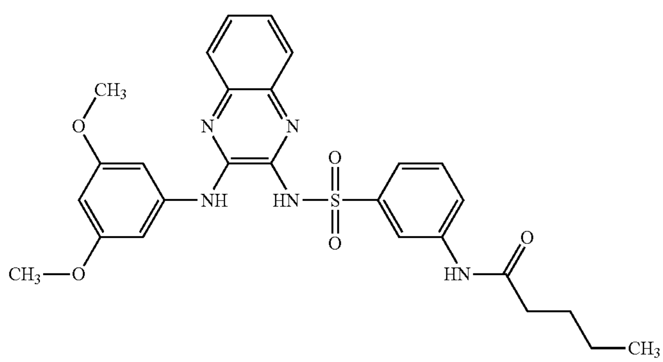 [SMILES: CCCCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)pentanamide |
| 570 | 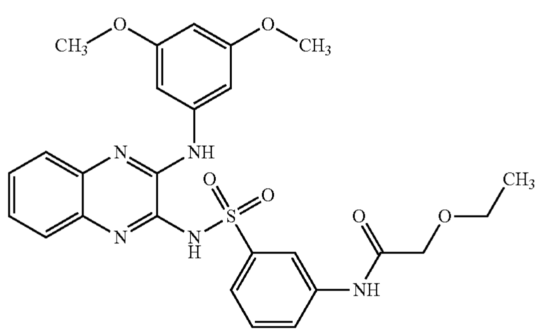 [SMILES: CCOCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-2-(ethyloxy)acetamide |

TABLE 1-continued

| Cpd. No. | Structure | IUPAC Name |
|---|---|---|
| 571 | 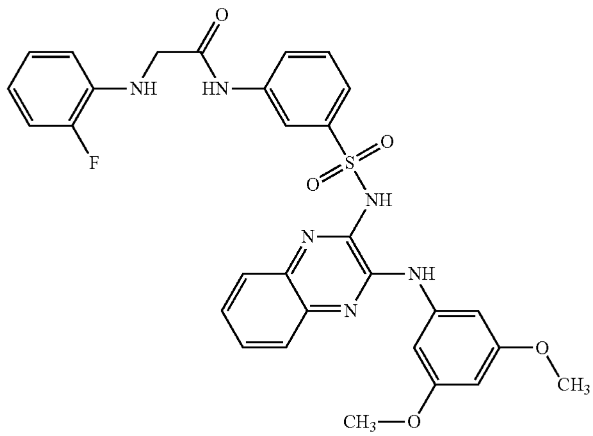 [SMILES: COc1cc(Nc2nc3ccccc3nc2NS(=O)(=O)c2cccc(NC(=O)CNc3ccccc3F)c2)cc(OC)c1] | N-(3-{[(3-{[3,5-bis(methyloxy)phenyl]amino}quinoxalin-2-yl)amino]sulfonyl}phenyl)-N-2-(2-fluorophenyl)glycinamide |
| 572 | 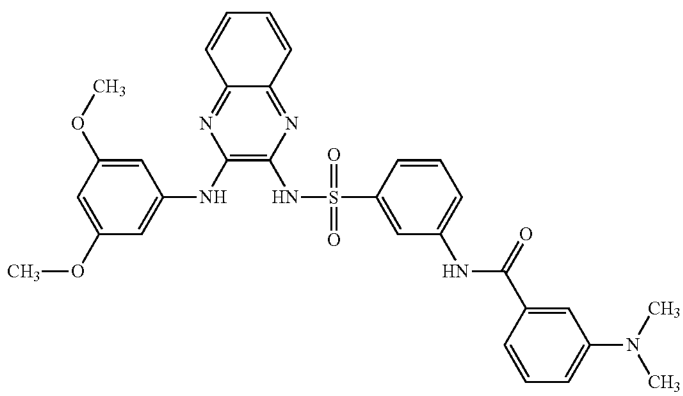 | N-(3-{[(3-{[3,5-bis(methyloxy)phenyl]amino}quinoxalin-2-yl)amino]sulfonyl}phenyl)-3-(dimethylamino)benzamide |
| 573 | 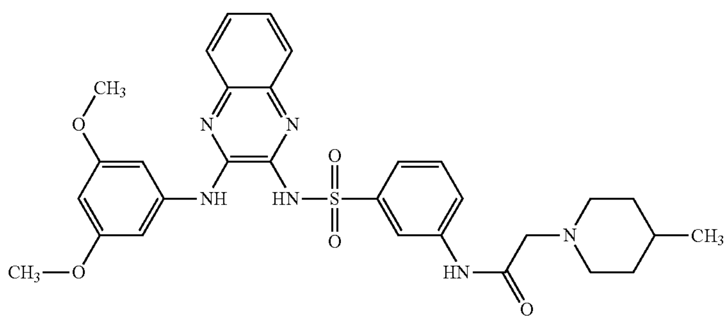 | N-(3-{[(3-{[3,5-bis(methyloxy)phenyl]amino}quinoxalin-2-yl)amino]sulfonyl}phenyl)-2-(4-methylpiperidin-1-yl)acetamide |
| 574 | 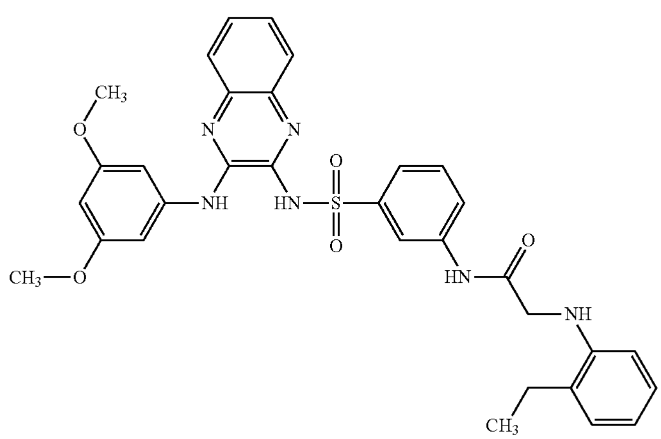 [SMILES: CCc1ccccc1NCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-N-2-(2-propylphenyl)glycinamide |

TABLE 1-continued

| Cpd. No. | Structure | IUPAC Name |
|---|---|---|
| 575 | 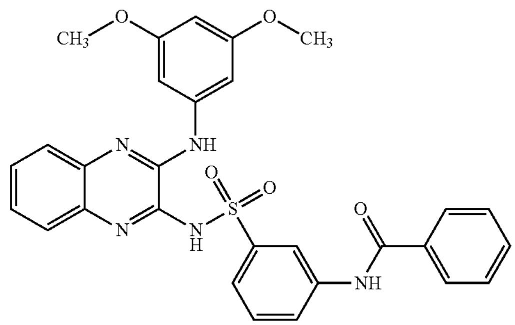 [SMILES: COc1cc(Nc2nc3ccccc3nc2NS(=O)(=O)c2cccc(NC(=O)c3ccccc3)c2)cc(OC)c1] | N-(3-{[(3-{[3,5-bis(methyloxy)phenyl]amino}quinoxalin-2-yl)amino]sulfonyl}phenyl)benzamide |
| 576 | 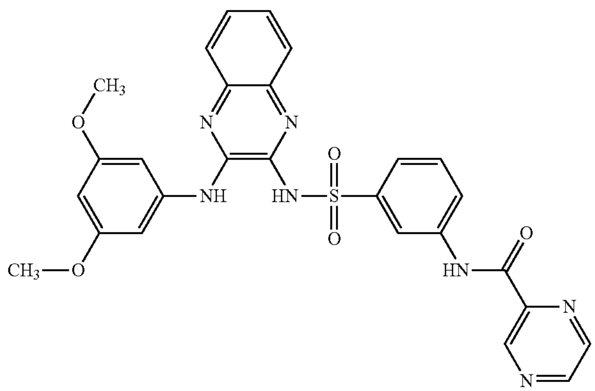 [SMILES: COc1cc(Nc2nc3ccccc3nc2NS(=O)(=O)c2cccc(NC(=O)c3cnccn3)c2)cc(OC)c1] | N-(3-{[(3-{[3,5-bis(methyloxy)phenyl]amino}quinoxalin-2-yl)amino]sulfonyl}phenyl)pyrazine-2-carboxamide |
| 577 | 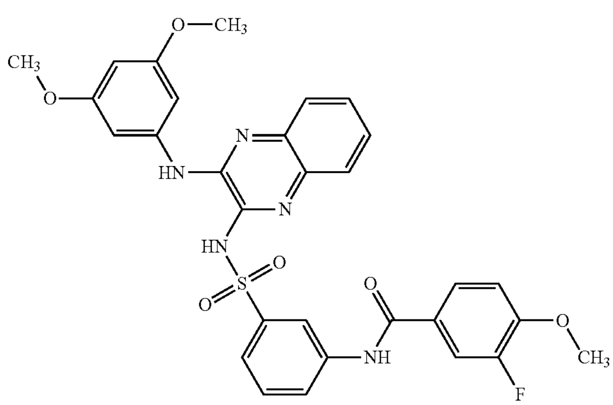 | N-(3-{[(3-{[3,5-bis(methyloxy)phenyl]amino}quinoxalin-2-yl)amino]sulfonyl}phenyl)-3-fluoro-4-(methyloxy)benzamide |
| 578 | 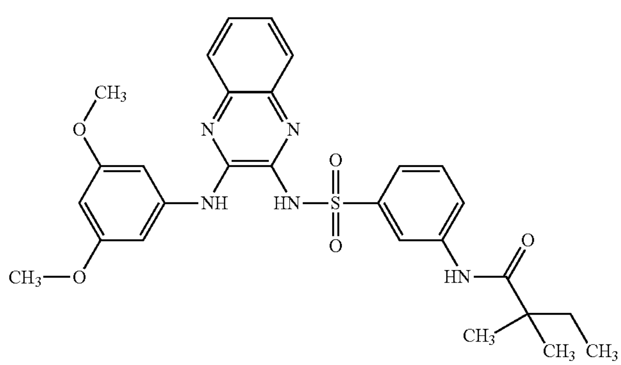 [SMILES: CCC(C)(C)C(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-2,2-dimethylbutanamide |

TABLE 1-continued

| Cpd. No. | Structure | IUPAC Name |
|---|---|---|
| 579 | 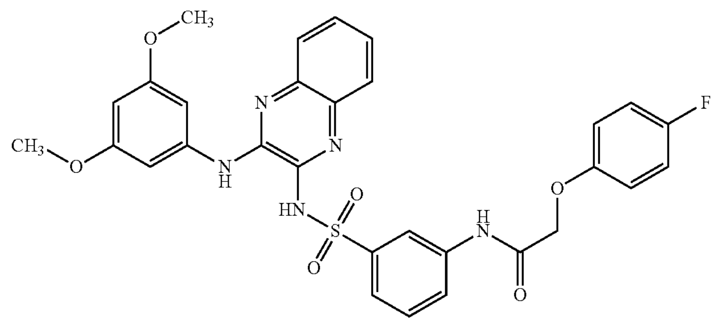 [SMILES: COc1cc(Nc2nc3ccccc3nc2NS(=O)(=O)c2cccc(NC(=O)COc3ccc(F)cc3)c2)cc(OC)c1] | N-(3-{[(3-{[3,5-bis(methyloxy)phenyl]amino}quinoxalin-2-yl)amino]sulfonyl}phenyl)-2-[(4-fluorophenyl)oxy]acetamide |
| 580 | 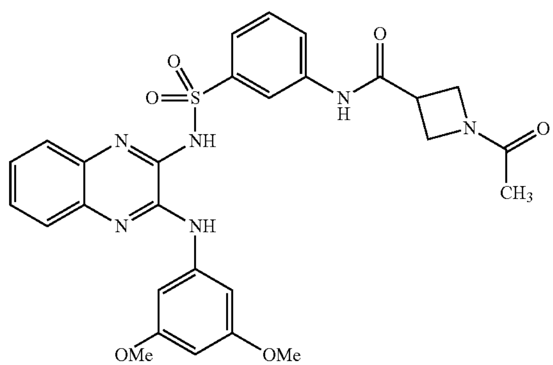 [SMILES: COc1cc(Nc2nc3ccccc3nc2NS(=O)(=O)c2cccc(NC(=O)C3CN(C(C)=O)C3)c2)cc(OC)c1] | 1-acetyl-N-(3-{[(3-{[3,5-bis(methyloxy)phenyl]amino}quinoxalin-2-yl)amino]sulfonyl}phenyl)azetidine-3-carboxamide |
| 581 | 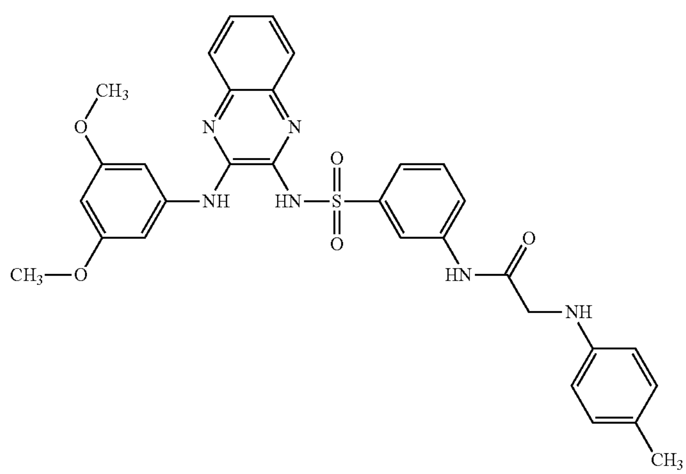 | N-(3-{[(3-{[3,5-bis(methyloxy)phenyl]amino}quinoxalin-2-yl)amino]sulfonyl}phenyl)-N-2-(4-methylphenyl)glycinamide |
| 582 | 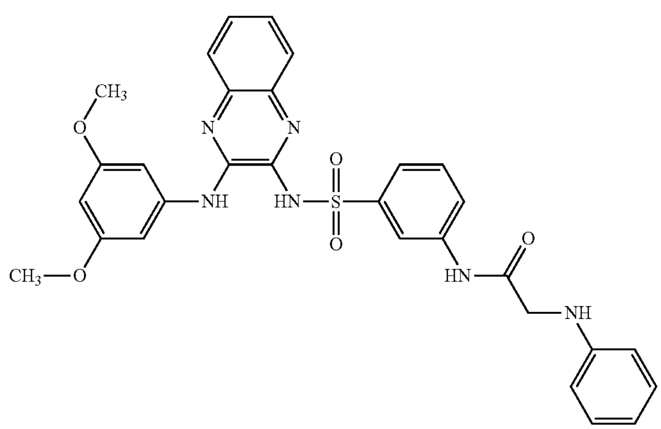 [SMILES: COc1cc(Nc2nc3ccccc3nc2NS(=O)(=O)c2cccc(NC(=O)CNc3ccccc3)c2)cc(OC)c1] | N-(3-{[(3-{[3,5-bis(methyloxy)phenyl]amino}quinoxalin-2-yl)amino]sulfonyl}phenyl)-N-2-phenylglycinamide |

TABLE 1-continued

| Cpd. No. | Structure | IUPAC Name |
| --- | --- | --- |
| 583 | 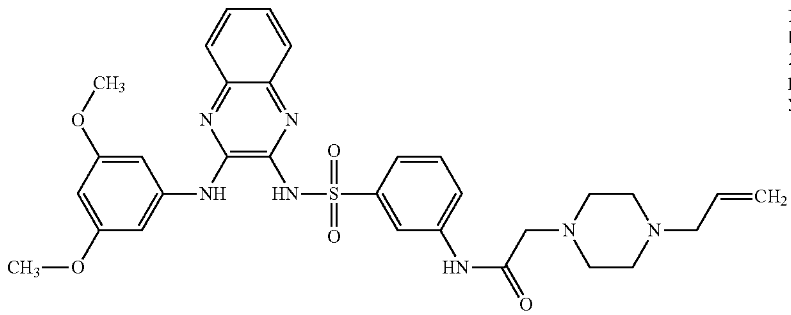 [SMILES: C=CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methyloxy)phenyl]amino}quinoxalin-2-yl)amino]sulfonyl}phenyl)-2-(4-prop-2-en-1-ylpiperazin-1-yl)acetamide |
| 584 | 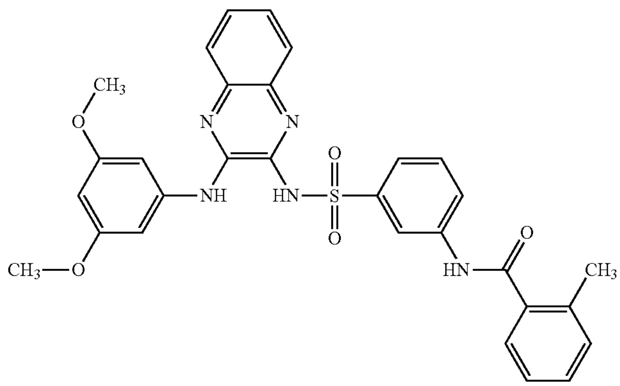 | N-(3-{[(3-{[3,5-bis(methyloxy)phenyl]amino}quinoxalin-2-yl)amino]sulfonyl}phenyl)-2-methylbenzamide |
| 585 | 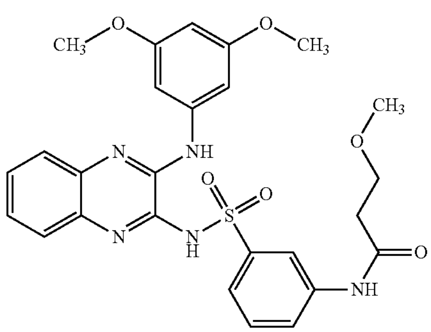 [SMILES: COCCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-3-(methyloxy)propanamide |
| 586 | 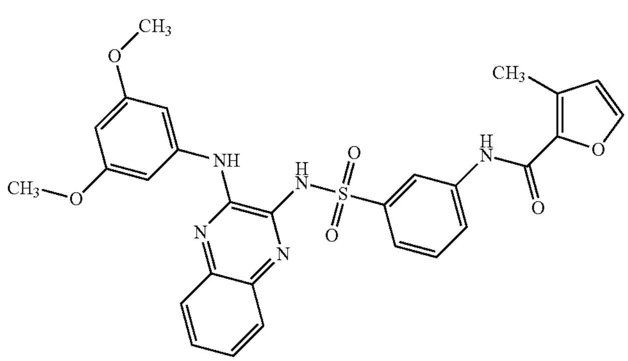 [SMILES: COc1cc(Nc2nc3ccccc3nc2NS(=O)(=O)c2cccc(NC(=O)c3occc3C)c2)cc(OC)c1] | N-(3-{[(3-{[3,5-bis(methyloxy)phenyl]amino}quinoxalin-2-yl)amino]sulfonyl}phenyl)-3-methylfuran-2-carboxamide |

TABLE 1-continued

| Cpd. No. | Structure | IUPAC Name |
|---|---|---|
| 587 | 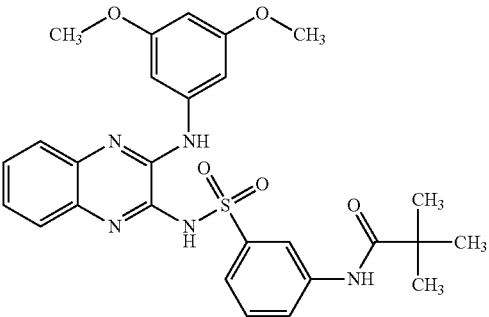 [SMILES: COc1cc(Nc2nc3ccccc3nc2NS(=O)(=O)c2cccc(NC(=O)C(C)(C)C)c2)cc(OC)c1] | N-(3-{[(3-{[3,5-bis(methyloxy)phenyl]amino}quinoxalin-2-yl)amino]sulfonyl}phenyl)-2,2-dimethylpropanamide |
| 588 | 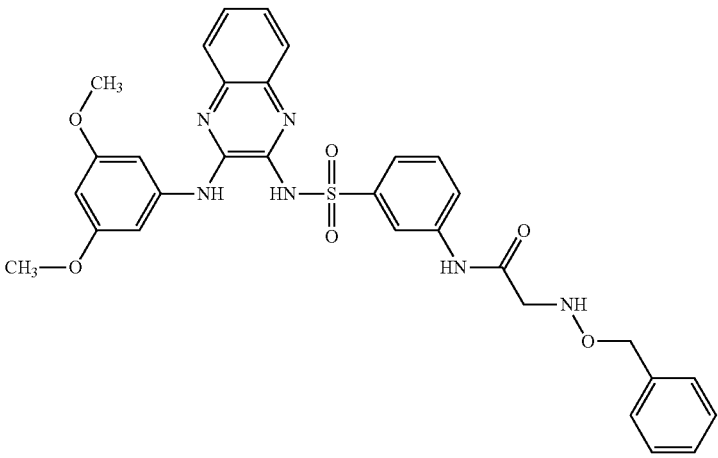 [SMILES: COc1cc(Nc2nc3ccccc3nc2NS(=O)(=O)c2cccc(NC(=O)CNOCc3ccccc3)c2)cc(OC)c1] | N-(3-{[(3-{[3,5-bis(methyloxy)phenyl]amino}quinoxalin-2-yl)amino]sulfonyl}phenyl)-N-2-[(phenylmethyl)oxy]glycinamide |
| 589 | 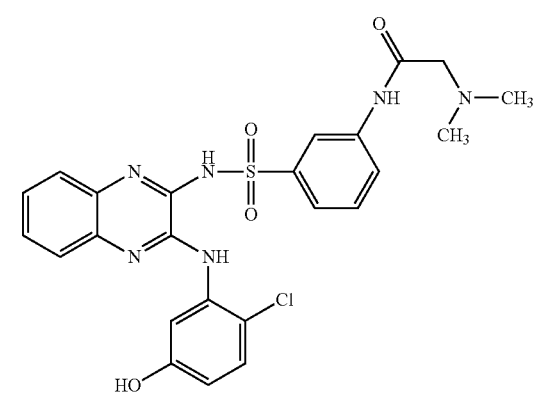 [SMILES: CN(C)CC(=O)Nc1cccc(S(=O)(=O)Nc2nc3ccccc3nc2Nc2cc(O)ccc2Cl)c1] | N-{3-[({3-[(2-chloro-5-hydroxyphenyl)amino]quinoxalin-2-yl}amino)sulfonyl]phenyl}-N-2-,N-2-dimethylglycinamide |
| 590 | 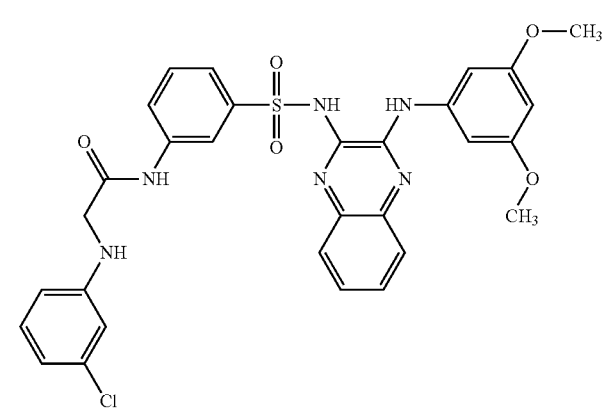 [SMILES: COc1cc(Nc2nc3ccccc3nc2NS(=O)(=O)c2cccc(NC(=O)CNc3cccc(Cl)c3)c2)cc(OC)c1] | N-(3-{[(3-{[3,5-bis(methyloxy)phenyl]amino}quinoxalin-2-yl)amino]sulfonyl}[phenyl)-N-2-(3-chlorophenyl)glycinamide |

TABLE 1-continued

| Cpd. No. | Structure | IUPAC Name |
|---|---|---|
| 591 | 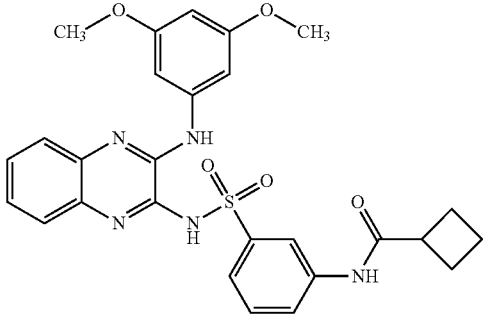 [SMILES: COc1cc(Nc2nc3ccccc3nc2NS(=O)(=O)c2cccc(NC(=O)C3CCC3)c2)cc(OC)c1] | N-(3-{[(3-{[3,5-bis(methyloxy)phenyl]amino}quinoxalin-2-yl)amino]sulfonyl}phenyl)cyclobutanecarboxamide |
| 592 | 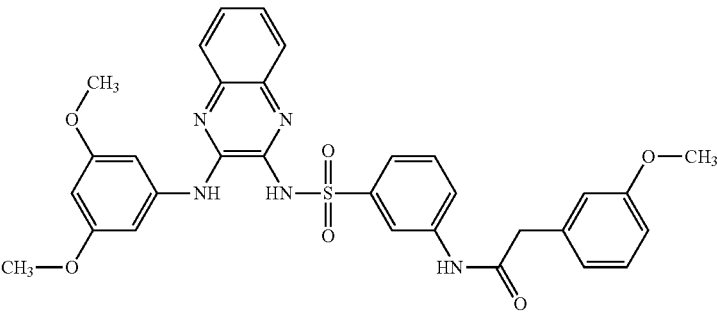 | N-(3-{[(3-{[3,5-bis(methyloxy)phenyl]amino}quinoxalin-2-yl)amino]sulfonyl}phenyl)-2-[3-(methyloxy)phenyl]acetamide |
| 593 | 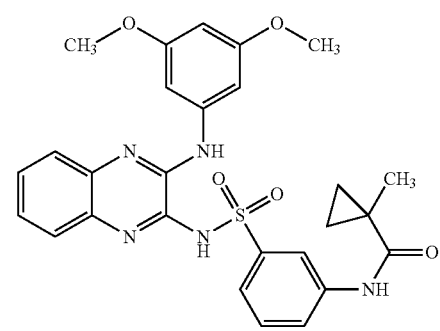 [SMILES: COc1cc(Nc2nc3ccccc3nc2NS(=O)(=O)c2cccc(NC(=O)C3(C)CC3)c2)cc(OC)c1] | N-(3-{[(3-{[3,5-bis(methyloxy)phenyl]amino}quinoxalin-2-yl)amino]sulfonyl}phenyl)-1-methylcyclopropanecarboxamide |
| 594 | 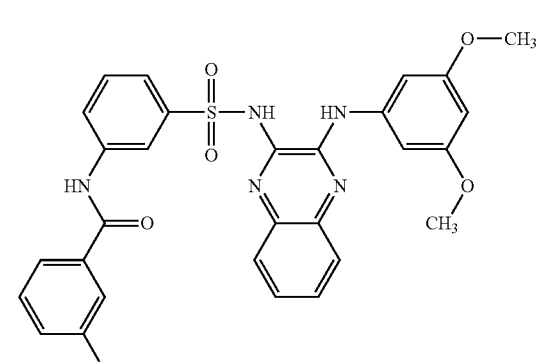 | N-(3-{[(3-{[3,5-bis(methyloxy)phenyl]amino}quinoxalin-2-yl)amino]sulfonyl}phenyl)-3-fluorobenzamide |

TABLE 1-continued

| Cpd. No. | Structure | IUPAC Name |
|---|---|---|
| 595 | 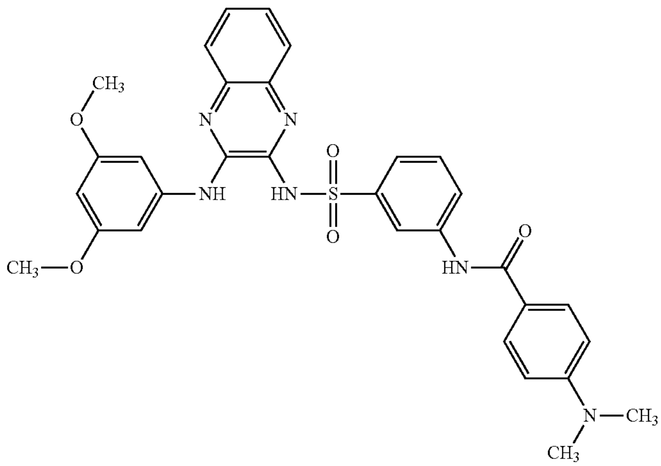 | N-(3-{[(3-{[3,5-bis(methyloxy)phenyl]amino}quinoxalin-2-yl)amino]sulfonyl}phenyl)-4-(dimethylamino)benzamide |
| 596 | 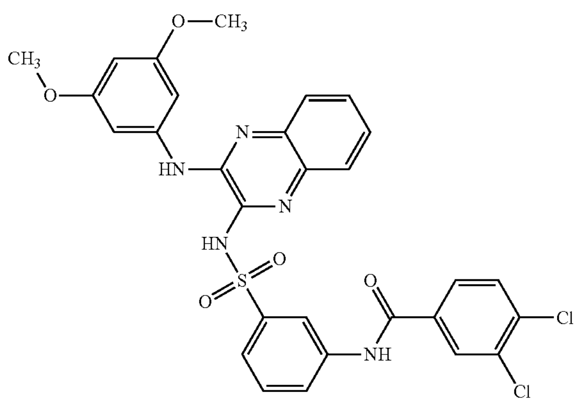 [SMILES: COc1cc(Nc2nc3ccccc3nc2NS(=O)(=O)c2cccc(NC(=O)c3ccc(Cl)c(Cl)c3)c2)cc(OC)c1] | N-(3-{[(3-{[3,5-bis(methyloxy)phenyl]amino}quinoxalin-2-yl)amino]sulfonyl}phenyl)-3,4-dichlorobenzamide |
| 597 | 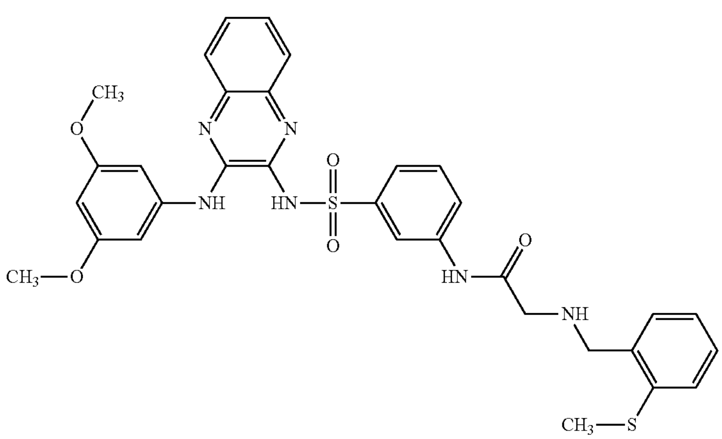 [SMILES: COc1cc(Nc2nc3ccccc3nc2NS(=O)(=O)c2cccc(NC(=O)CNCc3ccccc3SC)c2)cc(OC)c1] | N-(3-{[(3-{[3,5-bis(methyloxy)phenyl]amino}quinoxalin-2-yl)amino]sulfonyl}phenyl)-N-2-{[2-(methylthiso)phenyl]methyl}glycinamide |

TABLE 1-continued

| Cpd. No. | Structure | IUPAC Name |
|---|---|---|
| 598 | 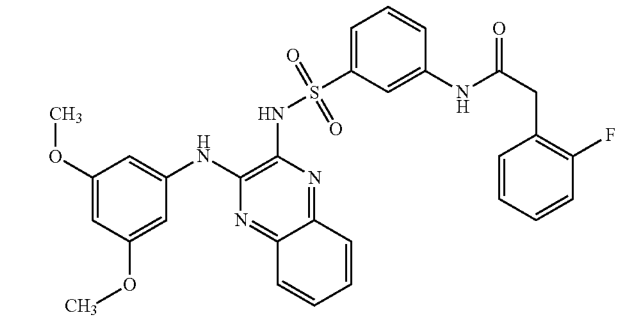 [SMILES: COc1cc(Nc2nc3ccccc3nc2NS(=O)(=O)c2cccc(NC(=O)Cc3ccccc3F)c2)cc(OC)c1] | N-(3-{[(3-{[3,5-bis(methyloxy)phenyl]amino}quinoxalin-2-yl)amino]sulfonyl}phenyl)-2-(2-fluorophenyl)acetamide |
| 599 | 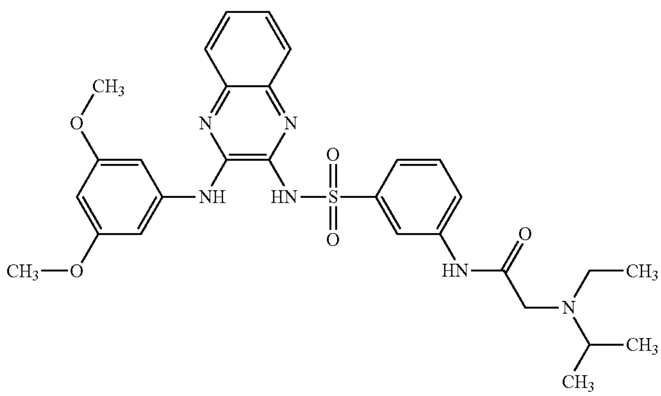 [SMILES: CCN(CC(=O)Nc1cccc(S(=O)(=O)Nc2nc3ccccc3nc2Nc2cc(OC)cc(OC)c2)c1)C(C)C] | N-(3-{[(3-{[3,5-bis(methyloxy)phenyl]amino}quinoxalin-2-yl)amino]sulfonyl}phenyl)-N-2-ethyl-N-2-(1-methylethyl)glycinamide |
| 600 | 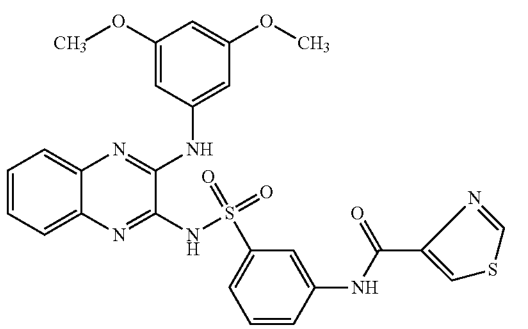 [SMILES: COc1cc(Nc2nc3ccccc3nc2NS(=O)(=O)c2cccc(NC(=O)c3cscn3)c2)cc(OC)c1] | N-(3-{[(3-{[3,5-bis(methyloxy)phenyl]amino}quinoxalin-2-yl)amino]sulfonyl}phenyl)-1,3-thiazole-4-carboxamide |
| 601 | 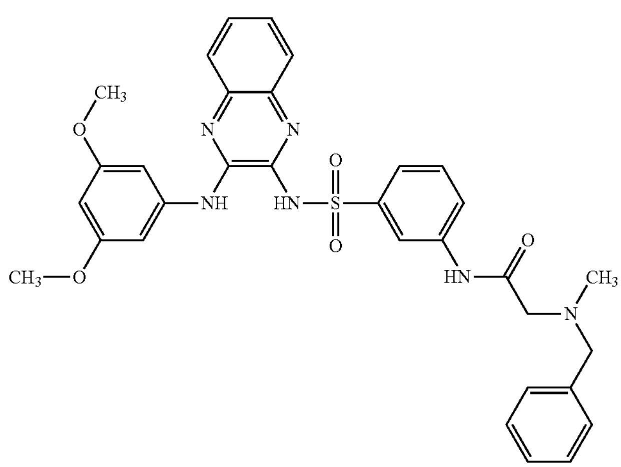 | N-(3-{[(3-{[3,5-bis(methyloxy)phenyl]amino}quinoxalin-2-yl)amino]sulfonyl}phenyl)-N-2-methyl-N-2-(phenylmethyl)glycinamide |

TABLE 1-continued
| Cpd. No. | Structure | IUPAC Name |
|---|---|---|
| 602 | 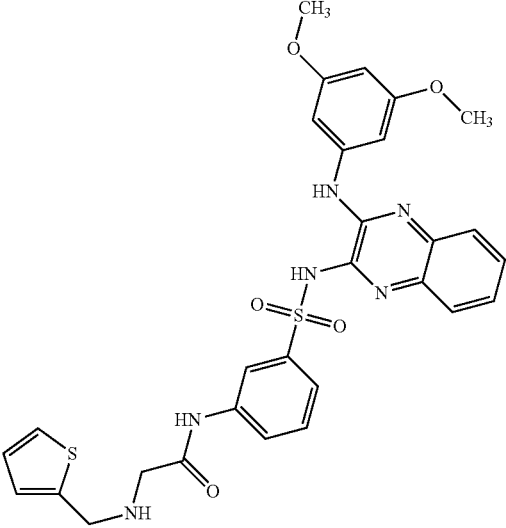 [SMILES: COc1cc(Nc2nc3ccccc3nc2NS(=O)(=O)c2cccc(NC(=O)CNCc3cccs3)c2)cc(OC)c1] | N-(3-{[(3-{[3,5-bis(methyloxy)phenyl]amino}quinoxalin-2-yl)amino]sulfonyl}phenyl)-N-2-(2-thienylmethyl)glycinamide |
| 603 | 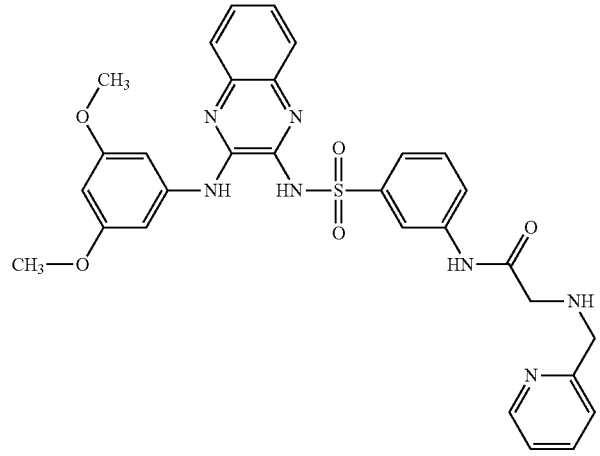 [SMILES: COc1cc(Nc2nc3ccccc3nc2NS(=O)(=O)c2cccc(NC(=O)CNCc3ccccn3)c2)cc(OC)c1] | N-(3-{[(3-{[3,5-bis(methyloxy)phenyl]amino}quinoxalin-2-yl)amino]sulfonyl}phenyl)-N-2-(pyridin-2-ylmethyl)glycinamide |
| 604 | 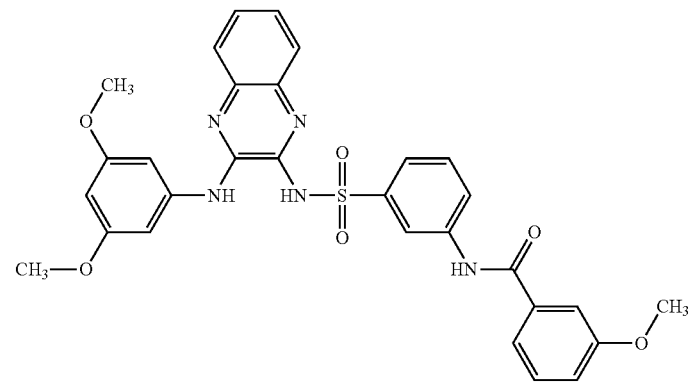 | N-(3-{[(3-{[3,5-bis(methyloxy)phenyl]amino}quinoxalin-2-yl)amino]sulfonyl}phenyl)-3-(methyloxy)benzamide |

TABLE 1-continued

| Cpd. No. | Structure | IUPAC Name |
|---|---|---|
| 605 | 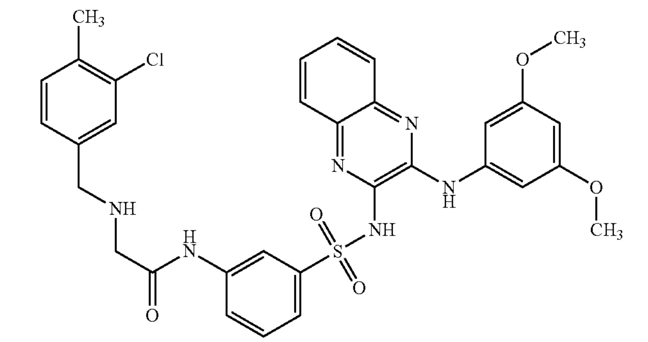 [SMILES: COc1cc(Nc2nc3ccccc3nc2NS(=O)(=O)c2cccc(NC(=O)CNCc3ccc(C)c(Cl)c3)c2)cc(OC)c1] | N-(3-{[(3-{[3,5-bis(methyloxy)phenyl]amino}quinoxalin-2-yl)amino]sulfonyl}phenyl)-N-2-[(3-chloro-4-methylphenyl)methyl]glycinamide |
| 606 | 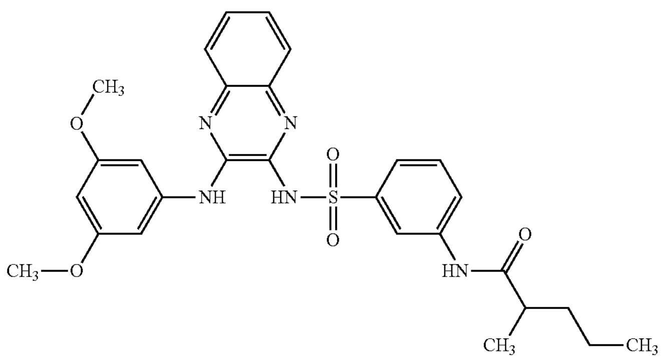 [SMILES: CCCC(C)C(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)-2-methylpentanamide |
| 607 | 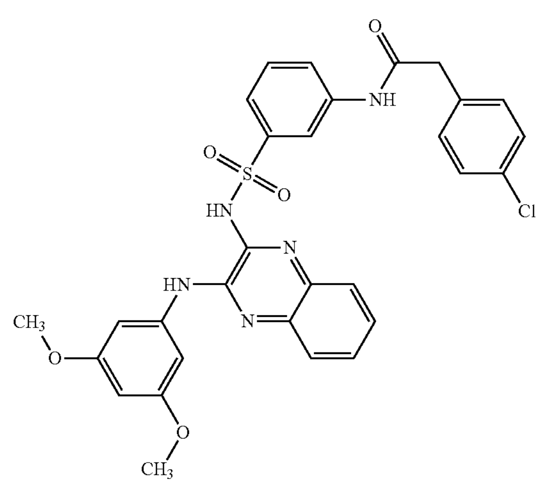 [SMILES: COc1cc(Nc2nc3ccccc3nc2NS(=O)(=O)c2cccc(NC(=O)Cc3ccc(Cl)cc3)c2)cc(OC)c1] | N-(3-{[(3-{[3,5-bis(metyloxy)phenyl]amino}quinoxalin-2-yl)amino]sulfonyl}phenyl)-2-(4-chlorophenyl)acetamide |
| 608 | 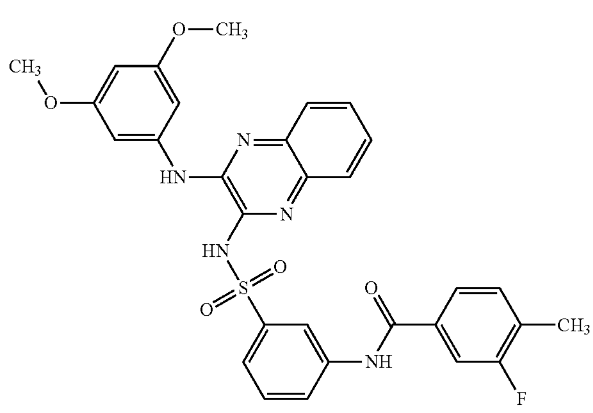 | N-(3-{[(3-{[3,5-bis(methyloxy)phenyl]amino}quinoxalin-2-yl)amino]sulfonyl}phenyl)-3-fluoro-4-methylbenzamide |

TABLE 1-continued

| Cpd. No. | Structure | IUPAC Name |
|---|---|---|
| 609 | 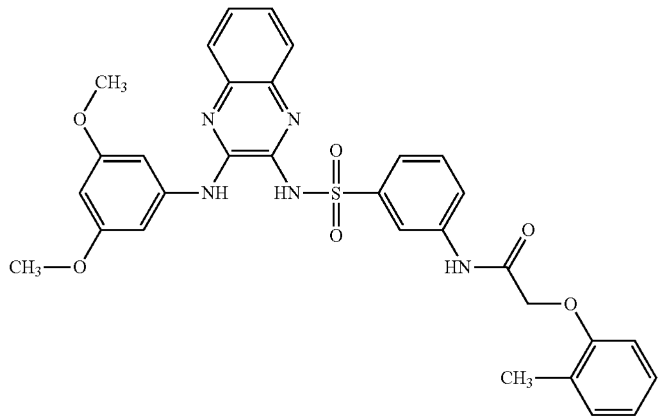 [SMILES: COc1cc(Nc2nc3ccccc3nc2NS(=O)(=O)c2cccc(NC(=O)COc3ccccc3C)c2)cc(OC)c1] | N-(3-{[(3-{[3,5-bis(methyloxy)phenyl]amino}quinoxalin-2-yl)amino]sulfonyl}phenyl)-2-[(2-methylphenyl)oxy]acetamide |
| 610 | 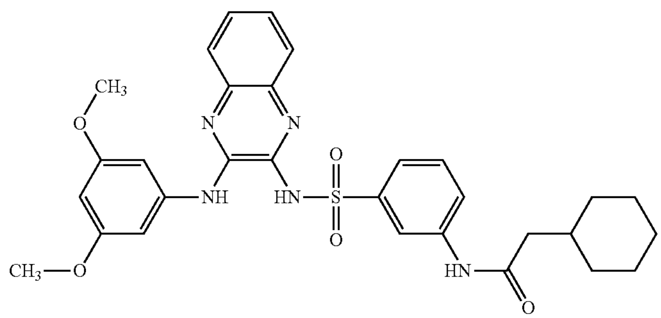 [SMILES: COc1cc(Nc2nc3ccccc3nc2NS(=O)(=O)c2cccc(NC(=O)CC3CCCCC3)c2)cc(OC)c1] | N-(3-{[(3-{[3,5-bis(methyloxy)phenyl]amino}quinoxalin-2-yl)amino]sulfonyl}phenyl)-2-cyclohexylacetamide |
| 611 | [Abs] | (1R,2R)-N-(3-{[3-{[3,5-bis(methyloxy)phenyl]amino}quinoxalin-2-yl)amino]sulfonyl}phenyl)-2-phenylcyclopropanecarboxamide |
| 612 | 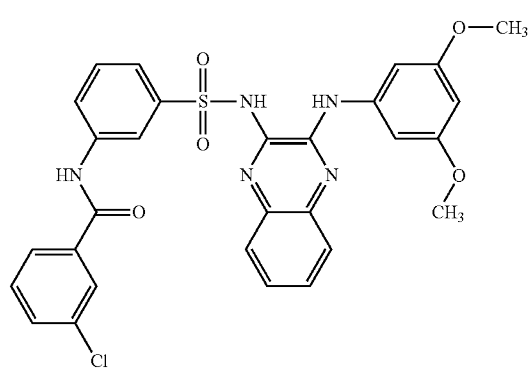 [SMILES: COc1cc(Nc2nc3ccccc3nc2NS(=O)(=O)c2cccc(NC(=O)c3cccc(Cl)c3)c2)cc(OC)c1] | N-(3-{[(3-{[3,5-bis(methyloxy)phenyl]amino}quinoxalin-2-yl)amino]sulfonyl}phenyl)-3-chlorobenzamide |

TABLE 1-continued

| Cpd. No. | Structure | IUPAC Name |
| --- | --- | --- |
| 613 | 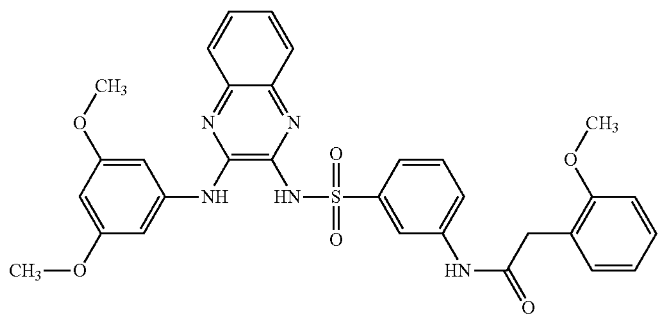 [SMILES: COc1cc(Nc2nc3ccccc3nc2NS(=O)(=O)c2cccc(NC(=O)Cc3ccccc3OC)c2)cc(OC)c1] | N-(3-{[(3-{[3,5-bis(methyloxy)phenyl]amino}quinoxalin-2-yl)amino]sulfonyl}phenyl)-2-[2-(methyloxy)phenyl]acetamide |
| 614 | 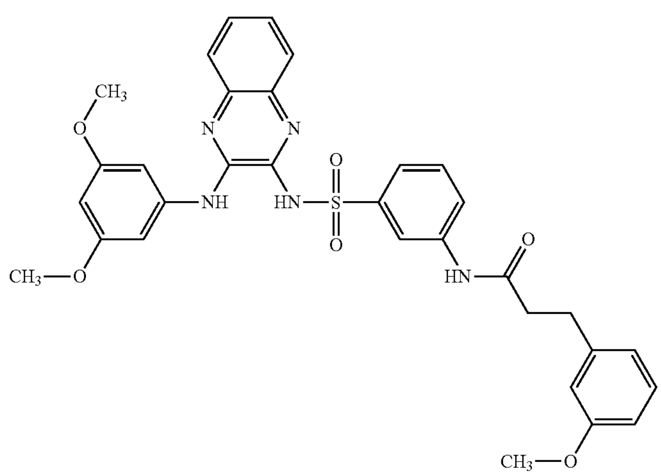 [SMILES: COc1cccc(CCC(=O)Nc2cccc(S(=O)(=O)Nc3nc4ccccc4nc3Nc3cc(OC)cc(OC)c3)c2)c1] | N-(3-{[(3-{[3,5-bis(methyloxy)phenyl]amino}quinoxalin-2-yl)amino]sulfonyl}phenyl)-3-[3-(methyloxy)phenyl]propanamide |
| 615 | 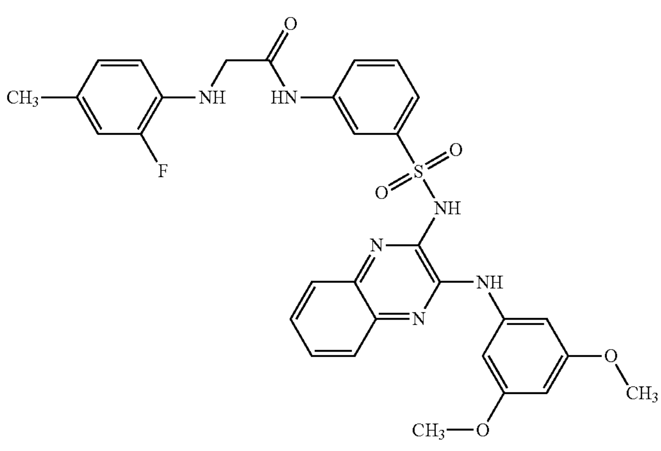 | N-(3-{[(3-[{3,5-bis(methyloxy)phenyl]amino}quinoxalin-2-yl)amino]sulfonyl}phenyl)-N-2-(2-fluoro-4-methylphenyl)glycinamide |

TABLE 1-continued

| Cpd. No. | Structure | IUPAC Name |
|---|---|---|
| 616 | 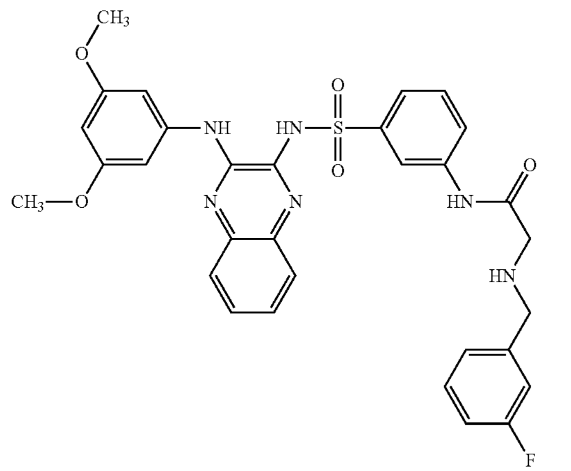 [SMILES: COc1cc(Nc2nc3ccccc3nc2NS(=O)(=O)c2cccc(NC(=O)CNCc3cccc(F)c3)c2)cc(OC)c1] | N-(3-{[(3-{[3,5-bis(methyloxy)phenyl]amino}quinoxalin-2-yl)amino]sulfonyl}phenyl)-N-2-[(3-fluorophenyl)methyl]glycinamide |
| 617 | 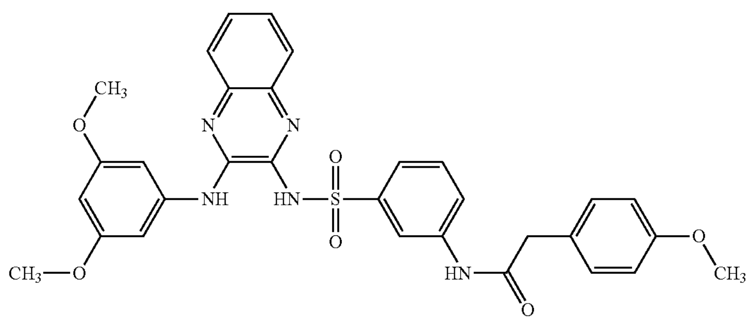 | N-(3-{[(3-{[3,5-bis(methyloxy)phenyl]amino}quinoxalin-2-yl)amino]sulfonyl}phenyl)-2-[4-(methyloxy)phenyl]acetamide |
| 618 | 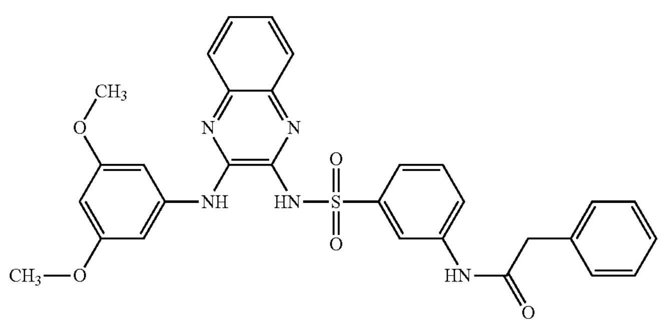 [SMILES: COc1cc(Nc2nc3ccccc3nc2NS(=O)(=O)c2cccc(NC(=O)Cc3ccccc3)c2)cc(OC)c1] | N-(3-{[(3-{[3,5-bis(methyloxy)phenyl]amino}quinoxalin-2-yl)amino]sulfonyl}phenyl)-2-phenylacetamide |
| 619 | 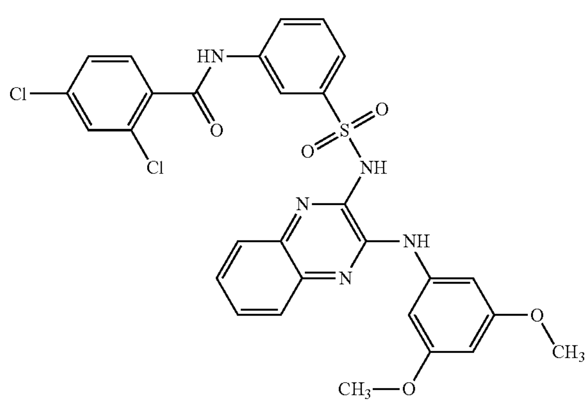 [SMILES: COc1cc(Nc2nc3ccccc3nc2NS(=O)(=O)c2cccc(NC(=O)c3ccc(Cl)cc3Cl)c2)cc(OC)c1] | N-(3-{[(3-{[3,5-bis(methyloxy)phenyl]amino}quinoxalin-2-yl)amino]sulfonyl}phenyl)-2,4-dichlorobenzamide |

TABLE 1-continued

| Cpd. No. | Structure | IUPAC Name |
|---|---|---|
| 620 | 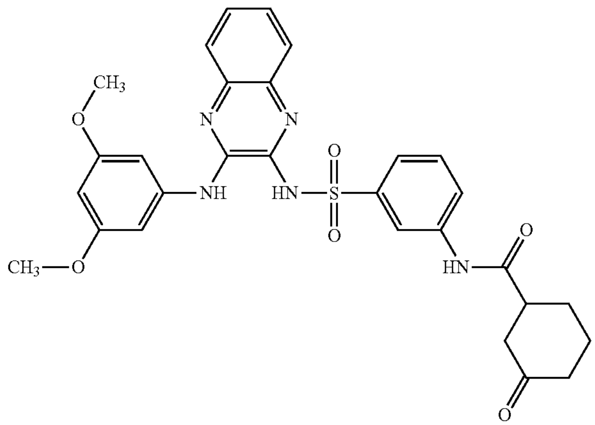 [SMILES: COc1cc(Nc2nc3ccccc3nc2NS(=O)(=O)c2cccc(NC(=O)C3CCCC(=O)C3)c2)cc(OC)c1] | N-(3-{[(3-{[3,5-bis(methyloxy)phenyl]amino}quinoxalin-2-yl)amino]sulfonyl}phenyl)-3-oxocyclohexanecarboxamide |
| 621 | 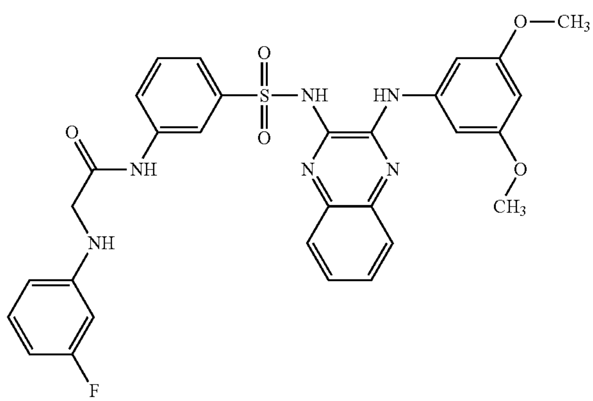 [SMILES: COc1cc(Nc2nc3ccccc3nc2NS(=O)(=O)c2cccc(NC(=O)CNc3cccc(F)c3)c2)cc(OC)c1] | N-(3-{[(3-{[3,5-bis(methyloxy)phenyl]amino}quinoxalin-2-yl)amino]sulfonyl}phenyl)-N-2-(3-fluorophenyl)glycinamide |
| 622 | 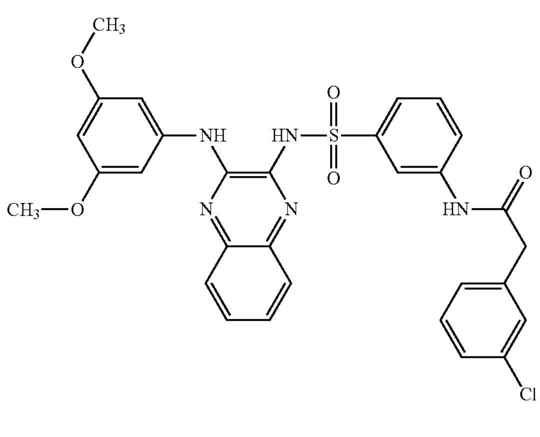 [SMILES: COc1cc(Nc2nc3ccccc3nc2NS(=O)(=O)c2cccc(NC(=O)Cc3cccc(Cl)c3)c2)cc(OC)c1] | N-(3-{[(3-{[3,5-bis(methyloxy)phenyl]amino}quinoxalin-2-yl)amino]sulfonyl}phenyl)-2-(3-chlorophenyl)acetamide |

TABLE 1-continued

| Cpd. No. | Structure | IUPAC Name |
|---|---|---|
| 623 | 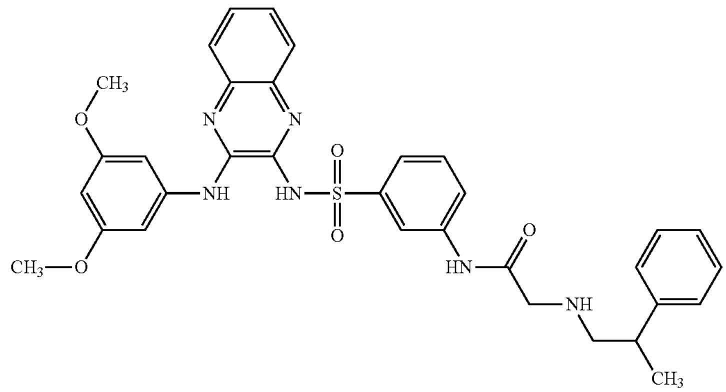 [SMILES: COc1cc(Nc2nc3ccccc3nc2NS(=O)(=O)c2cccc(NC(=O)CNCC(C)c3ccccc3)c2)cc(OC)c1] | N-(3-{[(3-{[3,5-bis(methyloxy)phenyl]amino}quinoxalin-2-yl)amino]sulfonyl}phenyl)-N-2-(2-phenylpropyl)glycinamide |
| 624 | 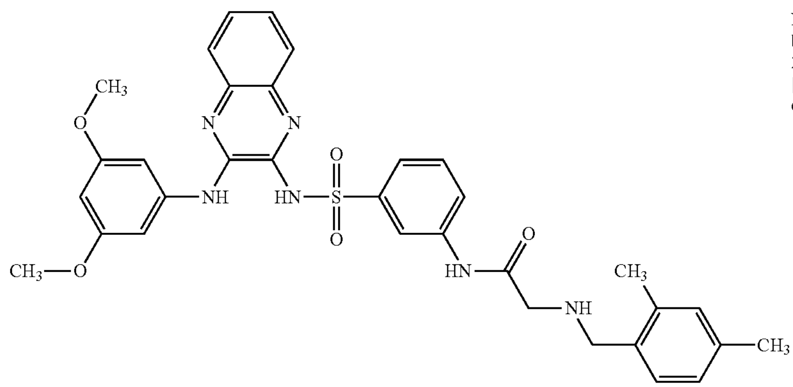 | N-(3-{[(3-{[3,5-bis(methyloxy)phenyl]amino}quinoxalin-2-yl)amino]sulfonyl}phenyl)-N-2-[(2,4-dimethylphenyl)methyl]glycinamide |
| 625 | 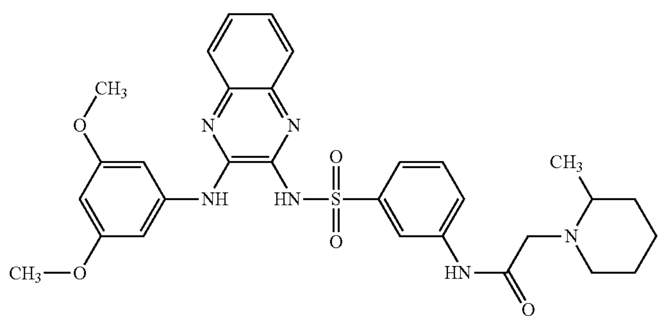 [SMILES: COc1cc(Nc2nc3ccccc3nc2NS(=O)(=O)c2cccc(NC(=O)CN3CCCCC3C)c2)cc(OC)c1] | N-(3-{[(3-{[3,5-bis(methyloxy)phenyl]amino}quinoxalin-2-yl)amino]sulfonyl}phenyl)-2-(2-methylpiperidin-1-yl)acetamide |
| 626 | 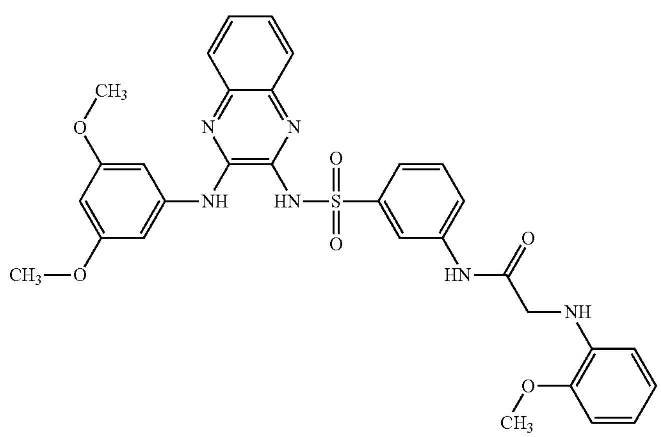 [SMILES: COc1cc(Nc2nc3ccccc3nc2NS(=O)(=O)c2cccc(NC(=O)CNc3ccccc3OC)c2)cc(OC)c1] | N-(3-{[(3-{[3,5-bis(methyloxy)phenyl]amino}quinoxalin-2-yl)amino]sulfonyl}phenyl)-N-2-[2-(methyloxy)phenyl]glycinamide |

TABLE 1-continued

| Cpd. No. | Structure | IUPAC Name |
| --- | --- | --- |
| 627 | 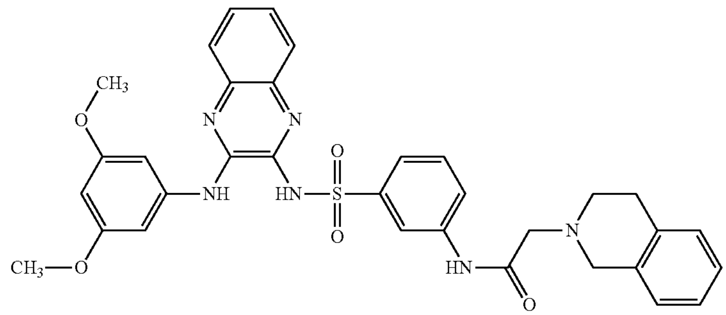 [SMILES: COc1cc(Nc2nc3ccccc3nc2NS(=O)(=O)c2cccc(NC(=O)CN3CCc4ccccc4C3)c2)cc(OC)c1] | N-(3-{[(3-{[3,5-bis(methyloxy)phenyl]amino}quinoxalin-2-yl)amino]sulfonyl}phenyl)-2-(3,4-dichloroisoquinolin-2(1H)-yl)acetamide |
| 628 | 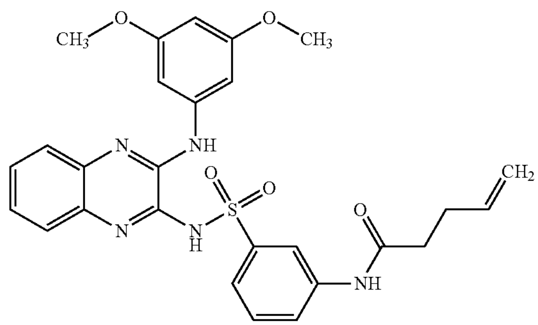 [SMILES: C=CCCC(=O)Nc1cccc(S(=O)(=O)Nc2nc3ccccc3nc2Nc2cc(OC)cc(OC)c2)c1] | N-(3-{[(3-{[3,5-bis(methyloxy)phenyl]amino}quinoxalin-2-yl)amino]sulfonyl}phenyl)pent-4-enamide |
| 629 | 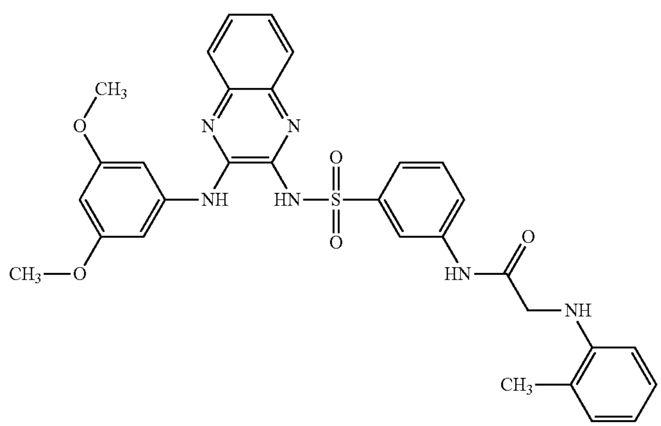 [SMILES: COc1cc(Nc2nc3ccccc3nc2NS(=O)(=O)c2cccc(NC(=O)CNc3ccccc3C)c2)cc(OC)c1] | N-(3-{[(3-{[3,5-bis(methyloxy)phenyl]amino}quinoxalin-2-yl)amino]sulfonyl}phenyl)-N-2-(2-methylphenyl)glycinamide |
| 630 | 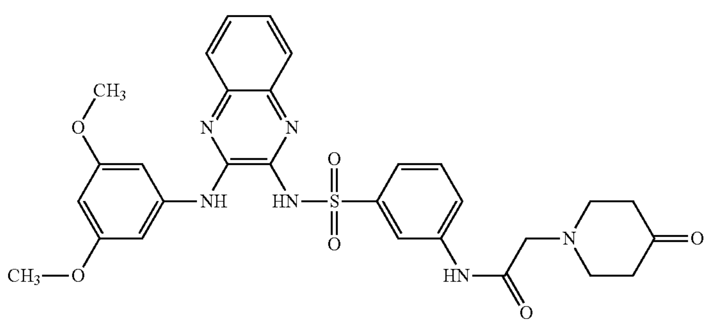 [SMILES: COc1cc(Nc2nc3ccccc3nc2NS(=O)(=O)c2cccc(NC(=O)CN3CCC(=O)CC3)c2)cc(OC)c1] | N-(3-{[(3-{[3,5-bis(methyloxy)phenyl]amino}quinoxalin-2-yl)amino]sulfonyl}phenyl)-2-(4-oxopiperidin-1-yl)acetamide |

TABLE 1-continued
| Cpd. No. | Structure | IUPAC Name |
|---|---|---|
| 631 | 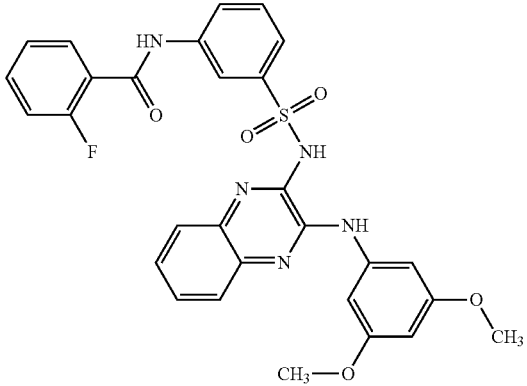 [SMILES: COc1cc(Nc2nc3ccccc3nc2NS(=O)(=O)c2cccc(NC(=O)c3ccccc3F)c2)cc(OC)c1] | N-(3-{[(3-{[3,5-bis(methyloxy)phenyl]amino}quinoxalin-2-yl)amino]sulfonyl}phenyl)-2-fluorobenzamide |
| 632 | 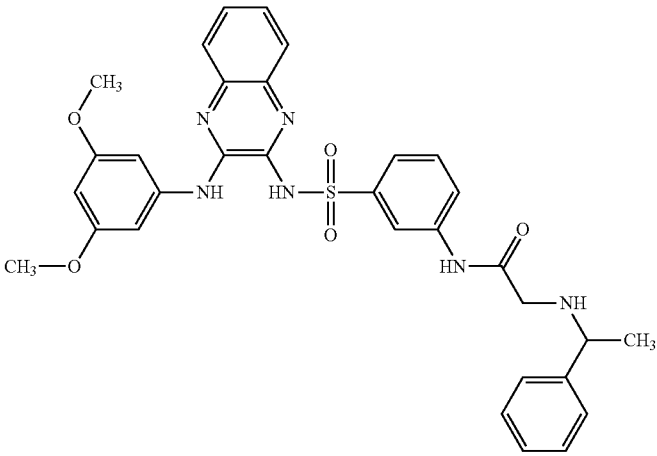 [SMILES: COc1cc(Nc2nc3ccccc3nc2NS(=O)(=O)c2cccc(NC(=O)CNC(C)c3ccccc3)c2)cc(OC)c1] | N-(3-{[(3-{[3,5-bis(methyloxy)phenyl]amino}quinoxalin-2-yl)amino]sulfonyl}phenyl)-N-2-(1-phenylethyl)glycinamide |
| 633 | 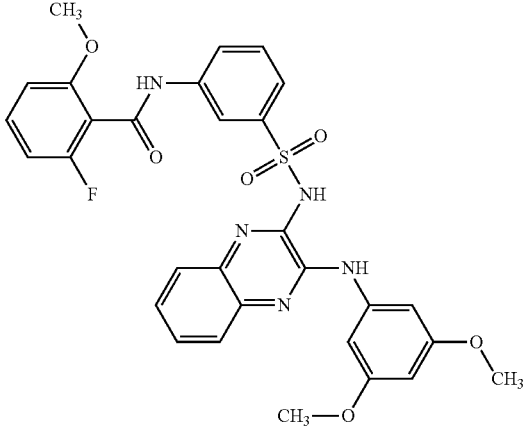 [SMILES: COc1cc(Nc2nc3ccccc3nc2NS(=O)(=O)c2cccc(NC(=O)c3c(F)cccc3OC)c2)cc(OC)c1] | N-(3-{[(3-{[3,5-bis(methyloxy)phenyl]amino}quinoxalin-2-yl)amino]sulfonyl}phenyl)-2-fluoro-6-(methyloxy)benzamide |

TABLE 1-continued

| Cpd. No. | Structure | IUPAC Name |
|---|---|---|
| 634 | 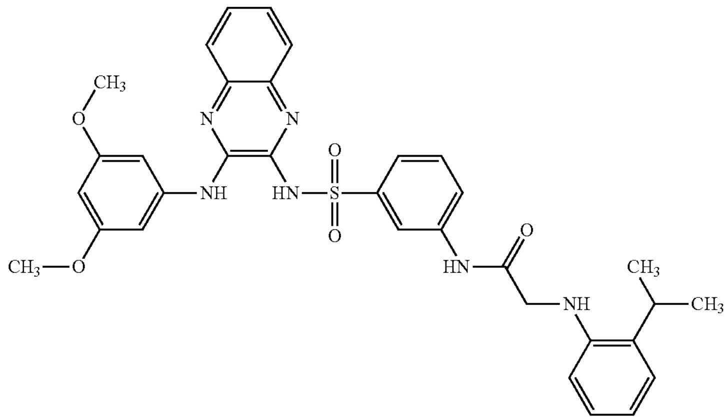 [SMILES: COc1cc(Nc2nc3ccccc3nc2NS(=O)(=O)c2cccc(NC(=O)CNc3ccccc3C(C)C)c2)cc(OC)c1] | N-(3-{[(3-{[3,5-bis(methyloxy)phenyl]amino}quinoxalin-2-yl)amino]sulfonyl}phenyl)-N-2-[2-(1-methylethyl)phenyl]glycinamide |
| 635 | 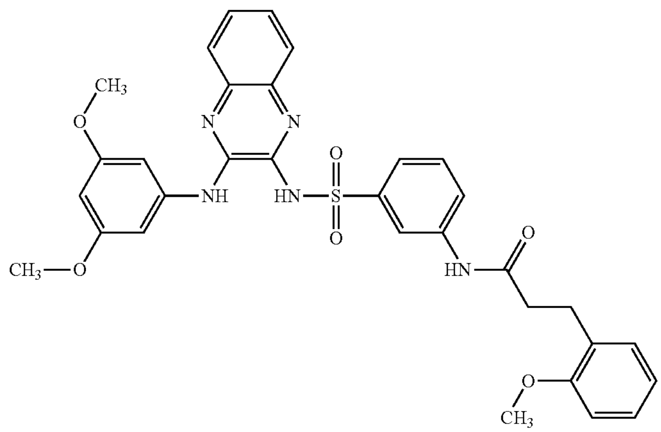 [SMILES: COc1cc(Nc2nc3ccccc3nc2NS(=O)(=O)c2cccc(NC(=O)CCc3ccccc3OC)c2)cc(OC)c1] | N-(3-{[(3-{[3,5-bis(methyloxy)phenyl]amino}quinoxalin-2-yl)amino]sulfonyl}phenyl)-3-[2-(methyloxy)phenyl]propanamide |
| 636 | 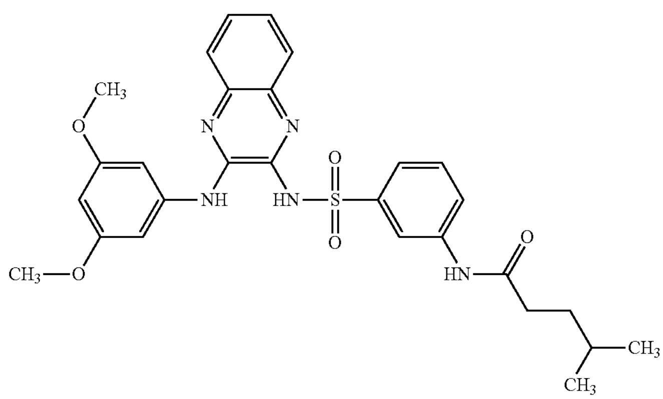 [SMILES: COc1cc(Nc2nc3ccccc3nc2NS(=O)(=O)c2cccc(NC(=O)CCC(C)C)c2)cc(OC)c1] | N-(3-{[(3-{[3,5-bis(methyloxy)phenyl]amino}quinoxalin-2-yl)amino]sulfonyl}phenyl)-4-methylpentanamide |
| 637 | 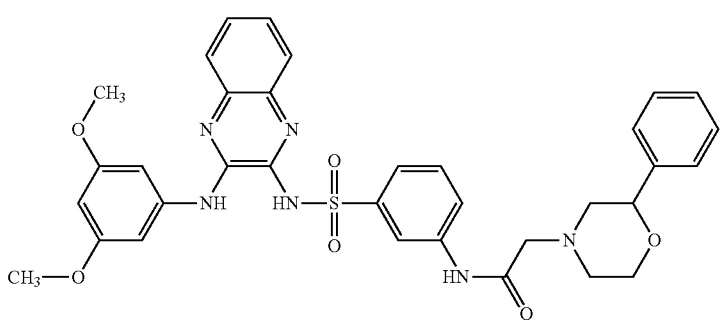 [SMILES: COc1cc(Nc2nc3ccccc3nc2NS(=O)(=O)c2cccc(NC(=O)CN3CCOC(c4ccccc4)C3)c2)cc(OC)c1] | N-(3-{[(3-{[3,5-bis(methyloxy)phenyl]amino}quinoxalin-2-yl)amino]sulfonyl}phenyl)-2-(2-phenylmorpholin-4-yl)acetamide |

US 8,642,584 B2
455 456
TABLE 1-continued
| Cpd. No. | Structure | IUPAC Name |
|---|---|---|
| 638 | 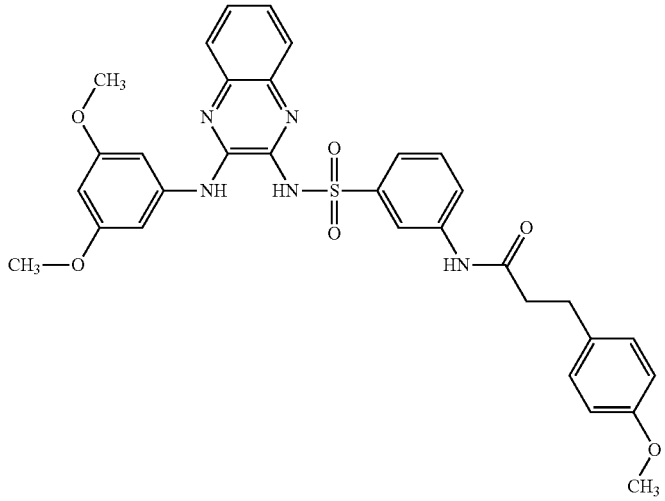 [SMILES: COc1ccc(CCC(=O)Nc2cccc(S(=O)(=O)Nc3nc4ccccc4nc3Nc3cc(OC)cc(OC)c3)c2)cc1] | N-(3-{[(3-{[3,5-bis(methyloxy)phenyl]amino}quinoxalin-2-yl)amino]sulfonyl}phenyl)-3-[4-(methyloxy)phenyl]propanamide |
| 639 | 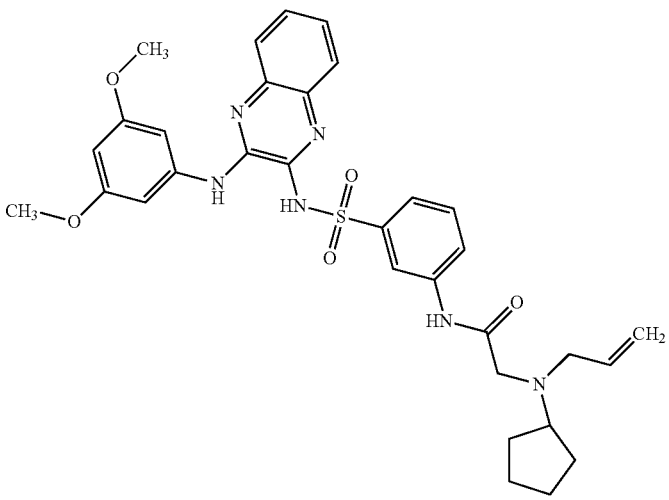 [SMILES: C=CCN(CC(=O)Nc1cccc(S(=O)(=O)Nc2nc3ccccc3nc2Nc2cc(OC)cc(OC)c2)c1)C1CCCC1] | N-(3-{[(3-{[3,5-bis(methyloxy)phenyl]amino}quinoxalin-2-yl)amino]sulfonyl}phenyl)-N-2-cyclopentyl-N-2-prop-2-en-1-ylglycinamide |
| 640 | 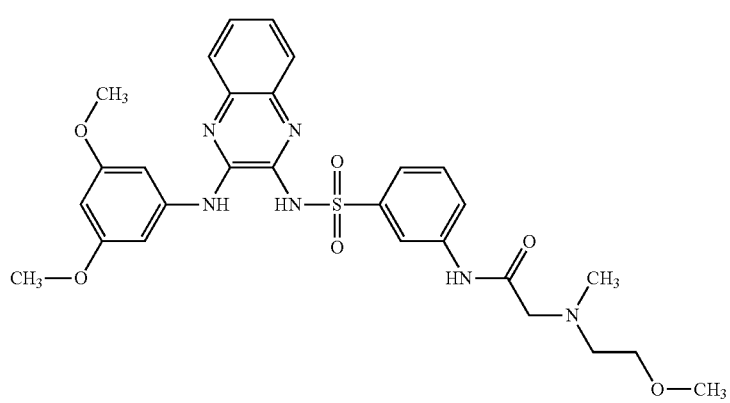 | N-(3-{[(3-{[3,5-bis(methyloxy)phenyl]amino}quinoxalin-2-yl)amino]sulfonyl}phenyl)-N-2-methyl-N-2-[2-(methyloxy)ethyl]glycinamide |

TABLE 1-continued

| Cpd. No. | Structure | IUPAC Name |
|---|---|---|
| 641 | 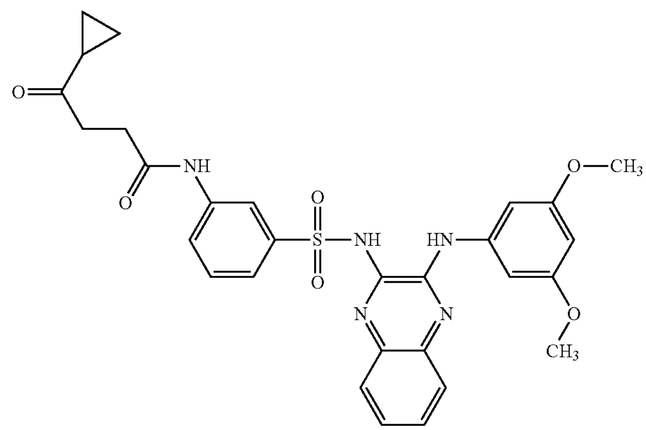 [SMILES: COc1cc(Nc2nc3ccccc3nc2NS(=O)(=O)c2cccc(NC(=O)CCC(=O)C3CC3)c2)cc(OC)c1] | N-(3-{[(3-{[3,5-bis(methyloxy)phenyl]amino}quinoxalin-2-yl)amino]sulfonyl}phenyl)-4-cyclopropyl-4-oxobutanamide |
| 642 | 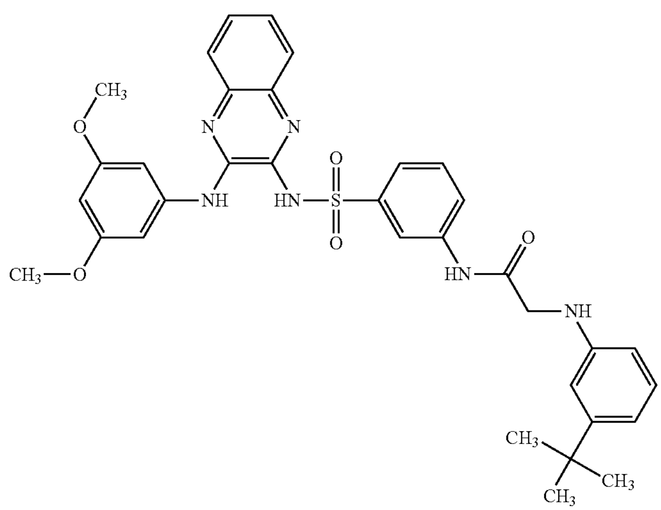 [SMILES: COc1cc(Nc2nc3ccccc3nc2NS(=O)(=O)c2cccc(NC(=O)CNc3cccc(C(C)(C)C)c3)c2)cc(OC)c1] | N-(3-{[(3-{[3,5-bis(methyloxy)phenyl]amino}quinoxalin-2-yl)amino]sulfonyl}phenyl)-N-2-[3-(1,1-dimethylethyl)phenyl]glycinamide |
| 643 | 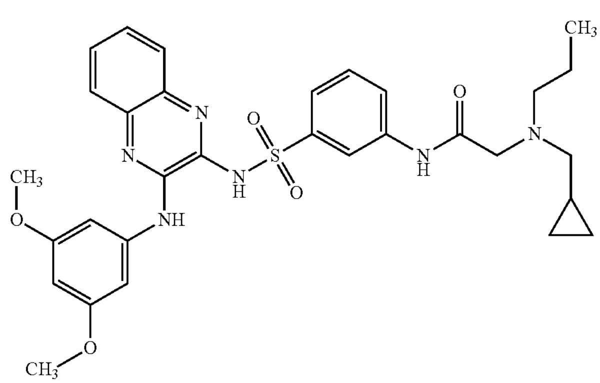 [SMILES: CCCN(CC(=O)Nc1cccc(S(=O)(=O)Nc2nc3ccccc3nc2Nc2cc(OC)cc(OC)c2)c1)CC1CC1] | N-(3-{[(3-{[3,5-bis(methyloxy)phenyl]amino}quinoxalin-2-yl)amino]sulfonyl}phenyl)-N-2-(cyclopropylmethyl)-N-2-propylglycinamide |

TABLE 1-continued

| Cpd. No. | Structure | IUPAC Name |
|---|---|---|
| 644 | 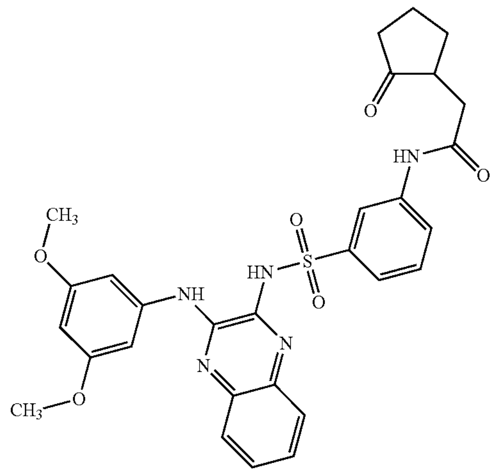 [SMILES: COc1cc(Nc2nc3ccccc3nc2NS(=O)(=O)c2cccc(NC(=O)CC3CCCC3=O)c2)cc(OC)c1] | N-(3-{[(3-{[3,5-bis(methyloxy)phenyl]amino}quinoxalin-2-yl)amino]sulfonyl}phenyl)-2-(2-oxocyclopentyl)acetamide |
| 645 | 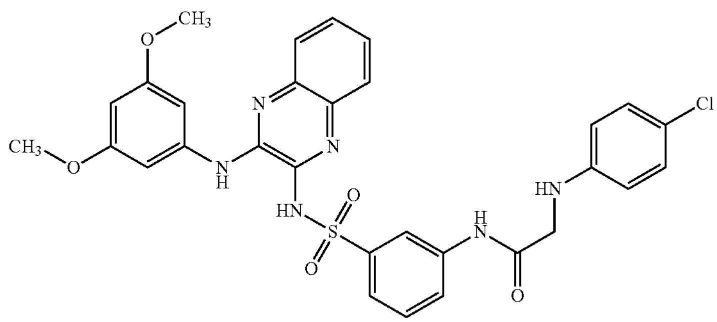 [SMILES: COc1cc(Nc2nc3ccccc3nc2NS(=O)(=O)c2cccc(NC(=O)CNc3ccc(Cl)cc3)c2)cc(OC)c1] | N-(3-{[(3-{[3,5-bis(methyloxy)phenyl]amino}quinoxalin-2-yl)amino]sulfonyl}phenyl)-N-2-(4-chlorophenyl)glycinamide |
| 646 | 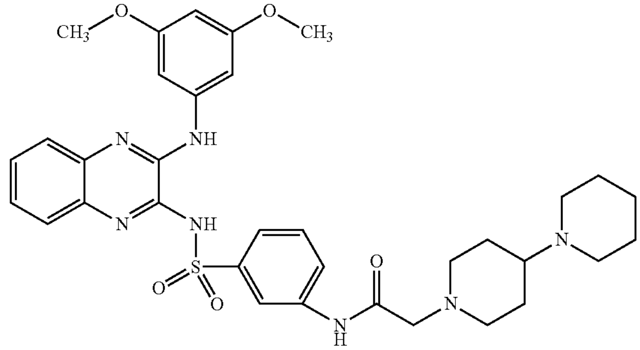 [SMILES: COc1cc(Nc2nc3ccccc3nc2NS(=O)(=O)c2cccc(NC(=O)CN3CCC(N4CCCCC4)CC3)c2)cc(OC)c1] | 2-(1,4'-bipiperidin-1'-yl)-N-(N-(3-{[(3-{[3,5-bis(methyloxy)phenyl]amino}quinoxalin-2-yl)amino]sulfonyl}phenyl)acetamide |

TABLE 1-continued
| Cpd. No. | Structure | IUPAC Name |
|---|---|---|
| 647 | 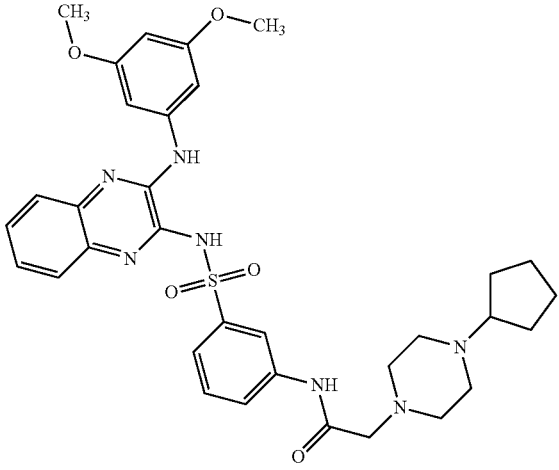 [SMILES: COc1cc(Nc2nc3ccccc3nc2NS(=O)(=O)c2cccc(NC(=O)CN3CCN(C4CCCC4)CC3)c2)cc(OC)c1] | N-(3-{[(3-{[3,5-bis(methyloxy)phenyl]amino}quinoxalin-2-yl)amino]sulfonyl}phenyl)-2-(4-cyclopentylpiperazin-1-yl)acetamide |
| 648 | 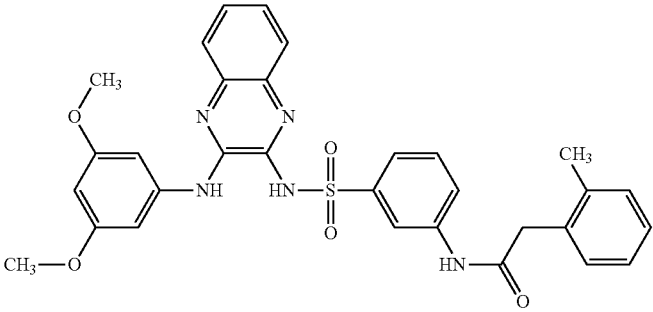 [SMILES: COc1cc(Nc2nc3ccccc3nc2NS(=O)(=O)c2cccc(NC(=O)Cc3ccccc3C)c2)cc(OC)c1] | N-(3-{[(3-{[3,5-bis(methyloxy)phenyl]amino}quinoxalin-2-yl)amino]sulfonyl}phenyl)-2-(2-methylphenyl)acetamide |
| 649 | 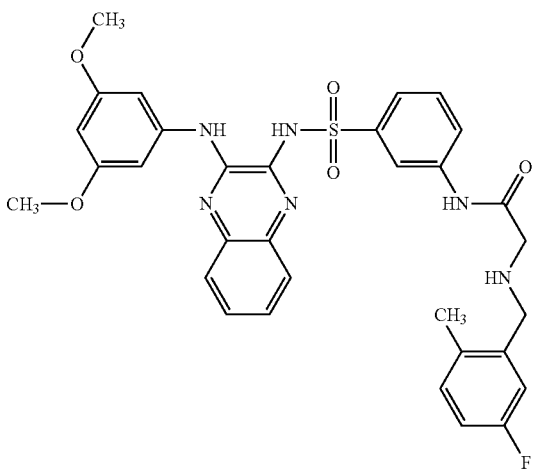 [SMILES: COc1cc(Nc2nc3ccccc3nc2NS(=O)(=O)c2cccc(NC(=O)CNCc3cc(F)ccc3C)c2)cc(OC)c1] | N-(3-{[(3-{[3,5-bis(methyloxy)phenyl]amino}quinoxalin-2-yl)amino]sulfonyl}phenyl)-N-2-[(5-fluoro-2-methylphenyl)methyl]glycinamide |

TABLE 1-continued

| Cpd. No. | Structure | IUPAC Name |
|---|---|---|
| 650 | 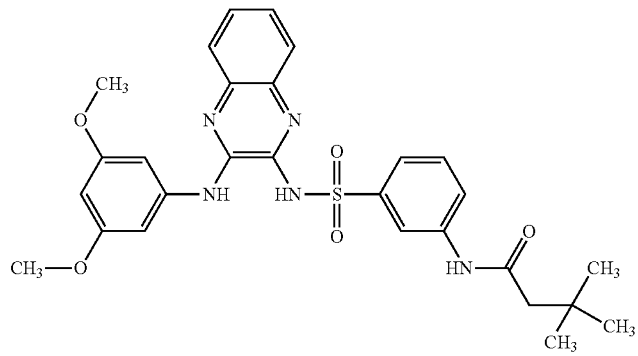 [SMILES: COc1cc(Nc2nc3ccccc3nc2NS(=O)(=O)c2cccc(NC(=O)CC(C)(C)C)c2)cc(OC)c1] | N-(3-{[(3-{[3,5-bis(methyloxy)phenyl]amino}quinoxalin-2-yl)amino]sulfonyl}phenyl)-3,3-dimethylbutanamide |
| 651 | 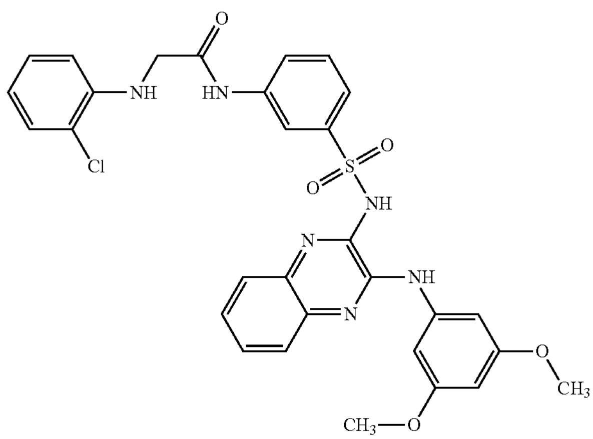 | 2-(2-chlorophenylamino)-N-(3-(N-(3-(3,5-dimethoxyphenylamino)quinoxalin-2-yl)sulfamoxyl)phenyl)acetamide |
| 652 | 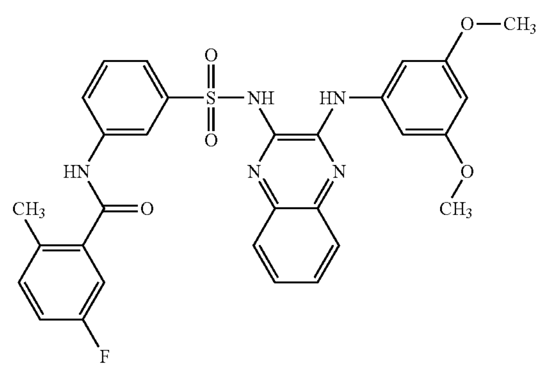 [SMILES: COc1cc(Nc2nc3ccccc3nc2NS(=O)(=O)c2cccc(NC(=O)c3cc(F)ccc3C)c2)cc(OC)c1] | N-(3-{[(3-{[3,5-bis(methyloxy)phenyl]amino}quinoxalin-2-yl)amino]sulfonyl}phenyl)-5-fluoro-2-methylbenzamide |
| 653 | 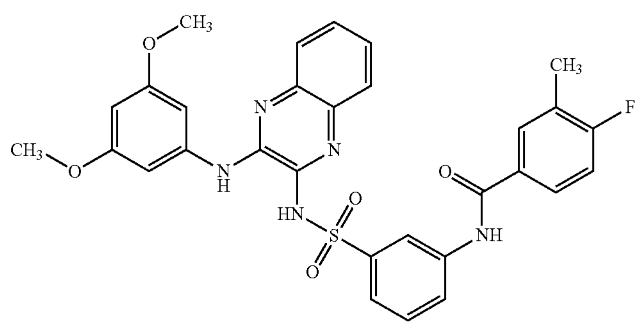 [SMILES: COc1cc(Nc2nc3ccccc3nc2NS(=O)(=O)c2cccc(NC(=O)c3ccc(F)c(C)c3)c2)cc(OC)c1] | N-(3-{[(3-{[3,5-bis(methyloxy)phenyl]amino}quinoxalin-2-yl)amino]sulfonyl}phenyl)-4-fluoro-3-methylbenzamide |

TABLE 1-continued

| Cpd. No. | Structure | IUPAC Name |
|---|---|---|
| 654 | 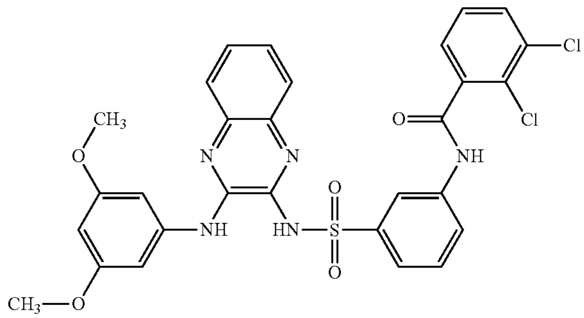 [SMILES: COc1cc(Nc2nc3ccccc3nc2NS(=O)(=O)c2cccc(NC(=O)c3cccc(Cl)c3Cl)c2)cc(OC)c1] | N-(3-{[(3-{[3,5-bis(methyloxy)phenyl]amino}quinoxalin-2-yl)amino]sulfonyl}phenyl)-2,3-dichlorobenzamide |
| 655 | 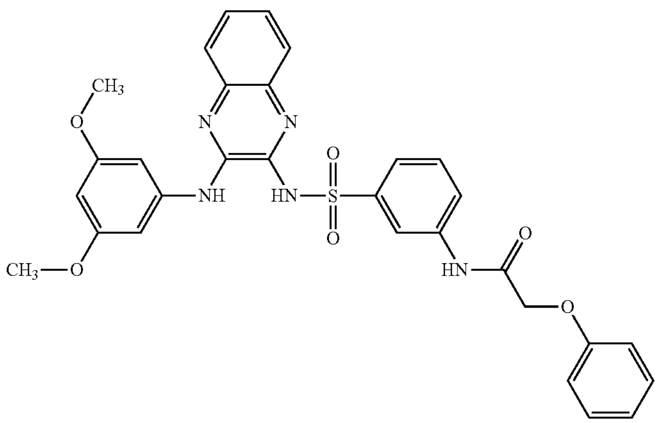 [SMILES: COc1cc(Nc2nc3ccccc3nc2NS(=O)(=O)c2cccc(NC(=O)COc3ccccc3)c2)cc(OC)c1] | N-(3-{[(3-{[3,5-bis(methyloxy)phenyl]amino}quinoxalin-2-yl)amino]sulfonyl}phenyl)-2-(phenyloxy)acetamide |
| 656 | 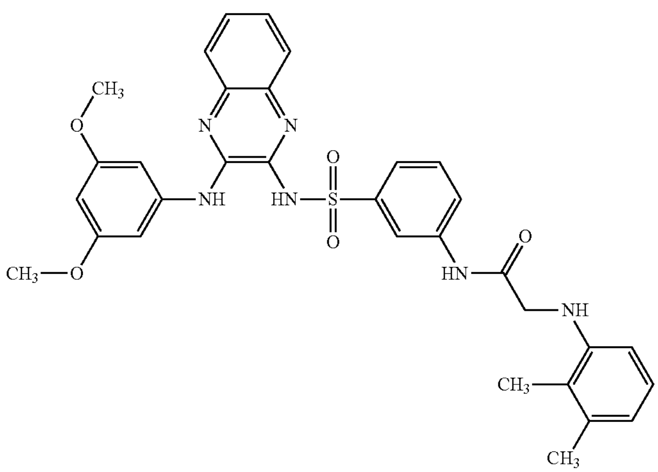 [SMILES: COc1cc(Nc2nc3ccccc3nc2NS(=O)(=O)c2cccc(NC(=O)CNc3cccc(C)c3C)c2)cc(OC)c1] | N-(3-{[(3-{[3,5-bis(methyloxy)phenyl]amino}quinoxalin-2-yl)amino]sulfonyl}phenyl)-N-2-(2,3-dimethylphenyl)glycinamide |
| 657 | 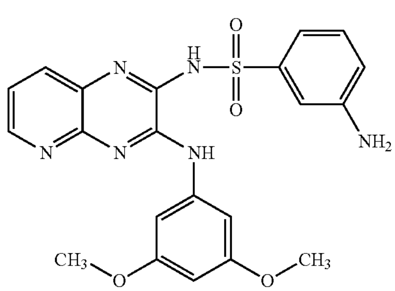 | 3-amino-N-(3-{[3,5-bis(methyloxy)phenyl]amino}pyrido[2,3-b]pyrazin-2-yl)benzenesulfonamide |

| Cpd. No. | Structure | IUPAC Name |
|---|---|---|
| 658 | 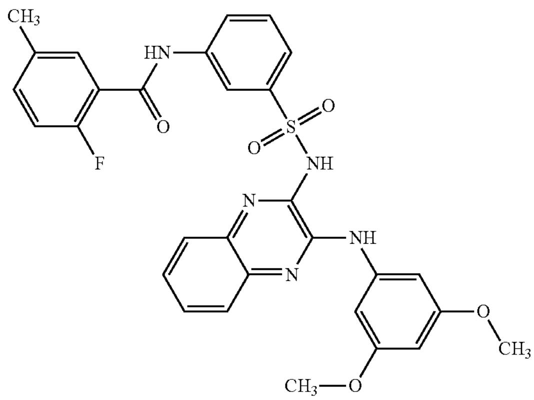 [SMILES: COc1cc(Nc2nc3ccccc3nc2NS(=O)(=O)c2cccc(NC(=O)c3cc(C)ccc3F)c2)cc(OC)c1] | N-(3-{[(3-{[3,5-bis(methyloxy)phenyl]amino}quinoxalin-2-yl)amino]sulfonyl}phenyl)-2-fluoro-5-methylbenzamide |
| 659 | 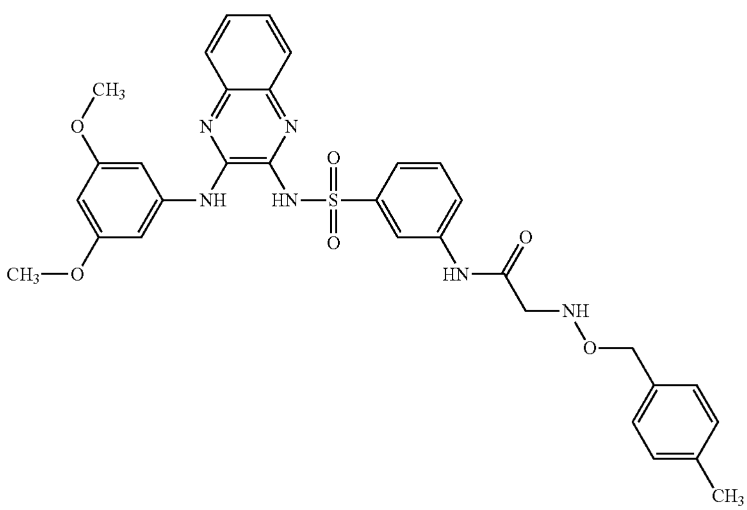 | N-(3-{[(3-{[3,5-bis(methyloxy)phenyl]amino}quinoxalin-2-yl)amino]sulfonyl}phenyl)-N-2-{[(4-methylphenyl)methyl]oxy}glycinamide |
| 660 | 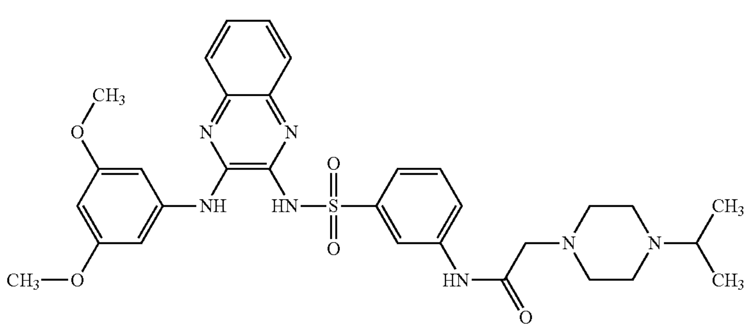 [SMILES: COc1cc(Nc2nc3ccccc3nc2NS(=O)(=O)c2cccc(NC(=O)CN3CCN(C(C)C)CC3)c2)cc(OC)c1] | N-(3-{[(3-{[3,5-bis(methyloxy)phenyl]amino}quinoxalin-2-yl)amino]sulfonyl}phenyl)-2-[4-(1-methylethyl)piperazin-1-yl]acetamide |

TABLE 1-continued

| Cpd. No. | Structure | IUPAC Name |
|---|---|---|
| 661 | 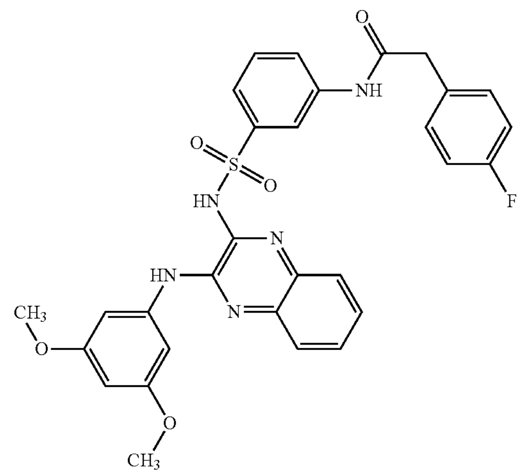 [SMILES: COc1cc(Nc2nc3ccccc3nc2NS(=O)(=O)c2cccc(NC(=O)Cc3ccc(F)cc3)c2)cc(OC)c1] | N-(3-{[(3-{[3,5-bis(methyloxy)phenyl]amino}quinoxalin-2-yl)amino]sulfonyl}phenyl)-2-(4-fluorophenyl)acetamide |
| 662 | 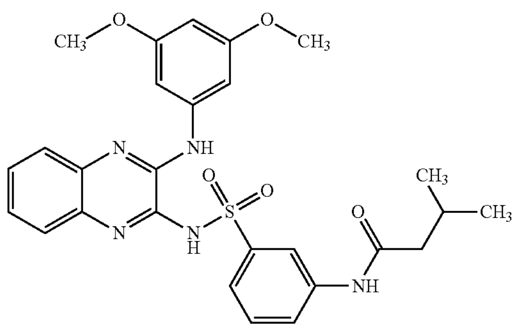 [SMILES: COc1cc(Nc2nc3ccccc3nc2NS(=O)(=O)c2cccc(NC(=O)CC(C)C)c2)cc(OC)c1] | N-(3-{[(3-{[3,5-bis(methyloxy)phenyl]amino}quinoxalin-2-yl)amino]sulfonyl}phenyl)-3-methylbutanamide |
| 663 | 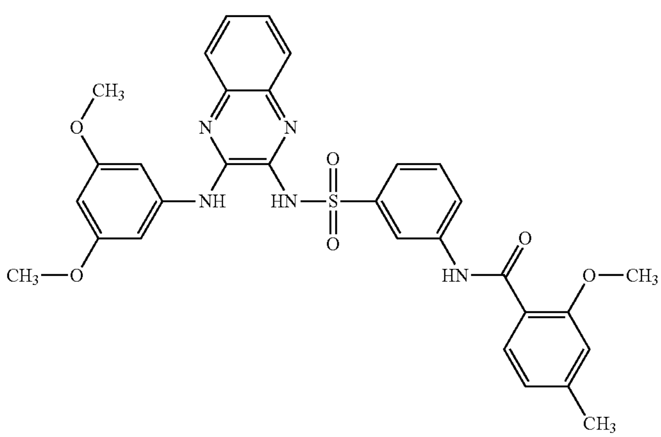 | N-(3-{[(3-{[3,5-bis(methyloxy)phenyl]amino}quinoxalin-2-yl)amino]sulfonyl}phenyl)-4-methyl-2-(methyloxy)benzamide |
| 664 | 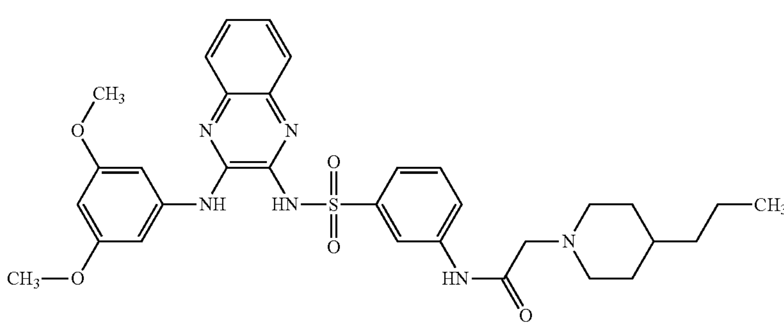 [SMILES: CCCC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methyloxy)phenyl]amino}quinoxalin-2-yl)amino]sulfonyl}phenyl)-2-(4-propylpiperidin-1-yl)acetamide |

TABLE 1-continued

| Cpd. No. | Structure | IUPAC Name |
|---|---|---|
| 665 | 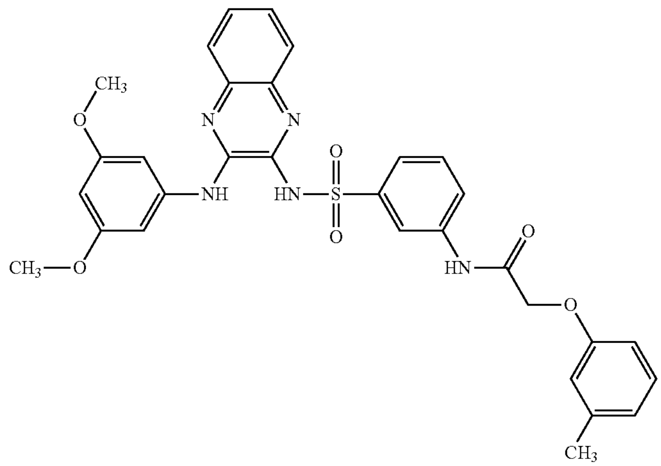 [SMILES: COc1cc(Nc2nc3ccccc3nc2NS(=O)(=O)c2cccc(NC(=O)COc3cccc(C)c3)c2)cc(OC)c1] | N-(3-{[(3-{[3,5-bis(methyloxy)phenyl]amino}quinoxalin-2-yl)amino]sulfonyl}phenyl)-2-[(3-methylphenyl)oxy]acetamide |
| 666 | 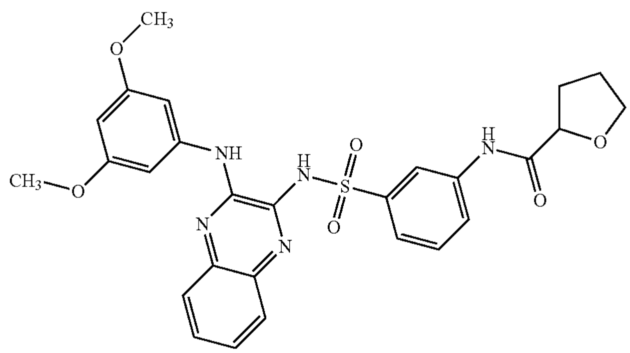 [SMILES: COc1cc(Nc2nc3ccccc3nc2NS(=O)(=O)c2cccc(NC(=O)C3CCCO3)c2)cc(OC)c1] | N-(3-{[(3-{[3,5-bis(methyloxy)phenyl]amino}quinoxalin-2-yl)amino]sulfonyl}phenyl)-tetrahydro-furan-2-carboxamide |
| 667 | 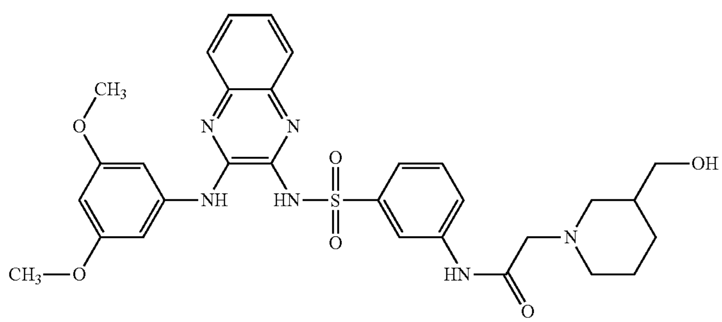 [SMILES: COc1cc(Nc2nc3ccccc3nc2NS(=O)(=O)c2cccc(NC(=O)CN3CCCC(CO)C3)c2)cc(OC)c1] | N-(3-{[(3-{[3,5-bis(methyloxy)phenyl]amino}quinoxalin-2-yl)amino]sulfonyl}phenyl)-2-[3-(hydroxymethyl)piperidin-1-yl]acetamide |
| 668 | 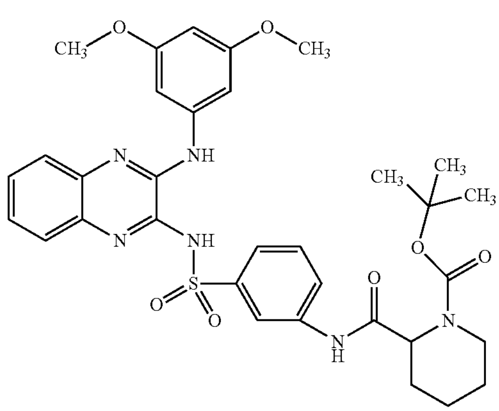 [SMILES: COc1cc(Nc2nc3ccccc3nc2NS(=O)(=O)c2cccc(NC(=O)C3CCCCN3C(=O)OC(C)(C)C)c2)cc(OC)c1] | 1,1-dimethylethyl[2-{[(3-{[(3-{[3,5-bis(methyloxy)phenyl]amino}quinoxalin-2-yl)amino]sulfonyl}phenyl)amino]carbonyl}piperidine-1-carboxylate |

TABLE 1-continued

| Cpd. No. | Structure | IUPAC Name |
|---|---|---|
| 669 | 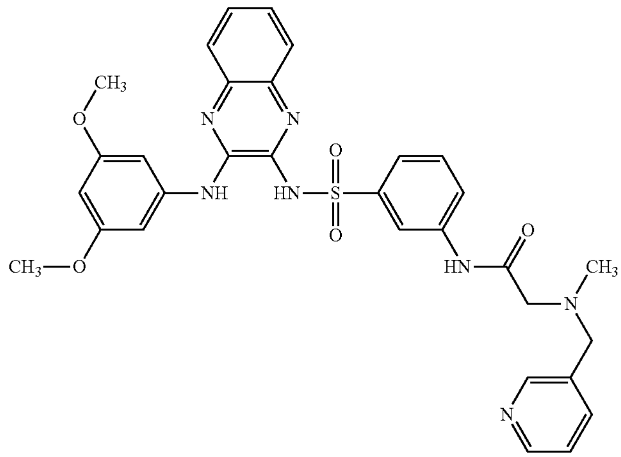 | N-(3-{[(3-{[3,5-bis(methyloxy)phenyl]amino}quinoxalin-2-yl)amino]sulfonyl}phenyl)-N-2-methyl-N-2-(pyridin-3-ylmethyl)glycinamide |
| 670 | 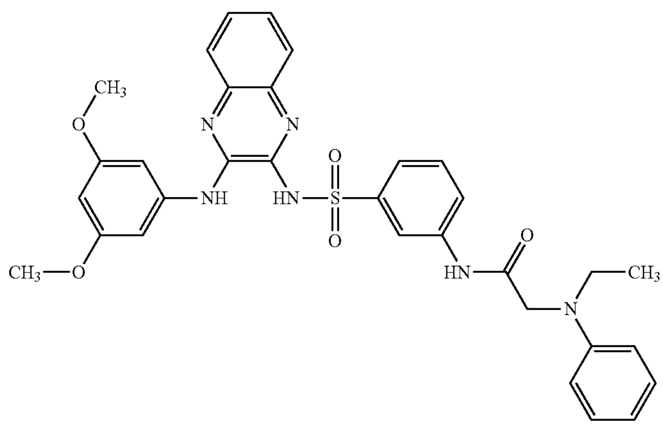 [SMILES: CCN(CC(=O)Nc1cccc(S(=O)(=O)Nc2nc3ccccc3nc2Nc2cc(OC)cc(OC)c2)c1)c1ccccc1] | N-(3-{[(3-{[3,5-bis(methyloxy)phenyl]amino}quinoxalin-2-yl)amino]sulfonyl}phenyl)-N-2-ethyl-N-2-phenylglycinamide |
| 671 | 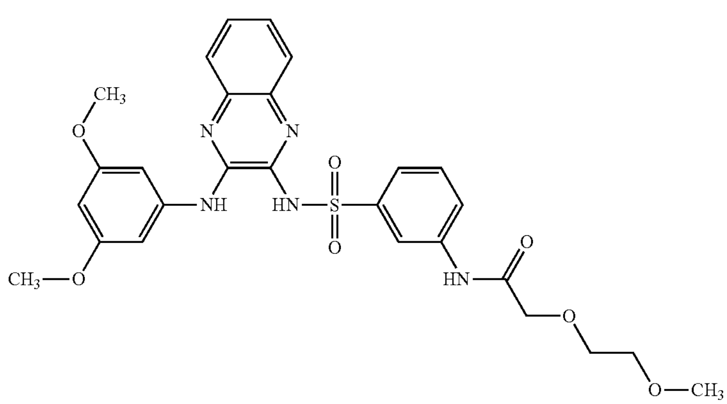 | N-(3-{[(3-{[3,5-bis(methyloxy)phenyl]amino}quinoxalin-2-yl)amino]sulfonyl}phenyl)-2-{[2-(methyloxy)ethyl]oxy}acetamide |

TABLE 1-continued

| Cpd. No. | Structure | IUPAC Name |
| --- | --- | --- |
| 672 | 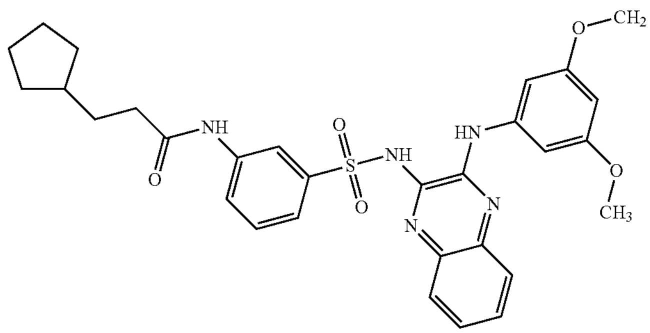 [SMILES: COc1cc(Nc2nc3ccccc3nc2NS(=O)(=O)c2cccc(NC(=O)CCC3CCCC3)c2)cc(OC)c1] | N-(3-{[(3-{[3,5-bis(methyloxy)phenyl]amino}quinoxalin-2-yl)amino]sulfonyl}phenyl)-3-cyclopentylpropanamide |
| 673 | 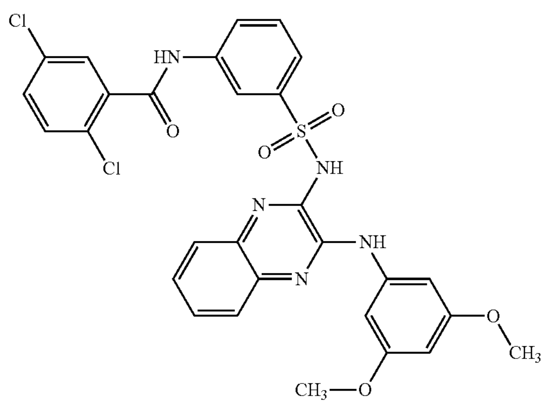 [SMILES: COc1cc(Nc2nc3ccccc3nc2NS(=O)(=O)c2cccc(NC(=O)c3cc(Cl)ccc3Cl)c2)cc(OC)c1] | N-(3-{[(3-{[3,5-bis(methyloxy)phenyl]amino}quinoxalin-2-yl)amino]sulfonyl}phenyl)-2,5-dichlorobenzamide |
| 674 | 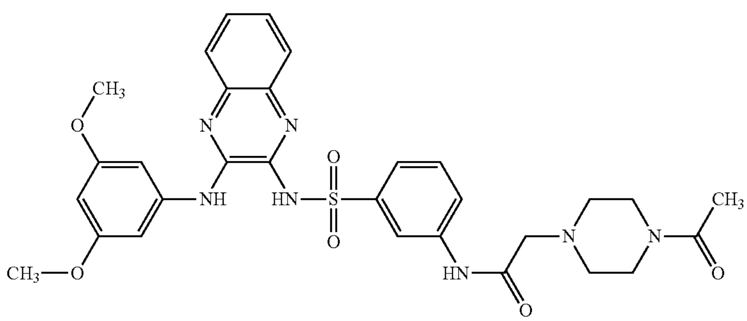 [SMILES: COc1cc(Nc2nc3ccccc3nc2NS(=O)(=O)c2cccc(NC(=O)CN3CCN(C(C)=O)CC3)c2)cc(OC)c1] | 2-(4-acetylpiperazin-1-yl)-N-N-(3-{[(3-{[3,5-bis(methyloxy)phenyl]amino}quinoxalin-2-yl)amino]sulfonyl}phenyl)acetamide |
| 675 | 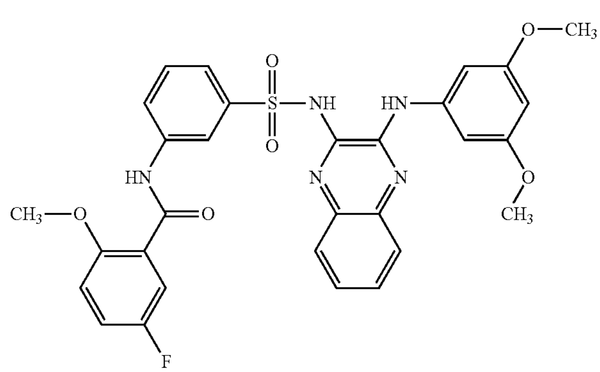 | N-(3-{[(3-{[3,5-bis(methyloxy)phenyl]amino}quinoxalin-2-yl)amino]sulfonyl}phenyl)-5-fluoro-2-(methyloxy)benzamide |

TABLE 1-continued

| Cpd. No. | Structure | IUPAC Name |
|---|---|---|
| 676 | 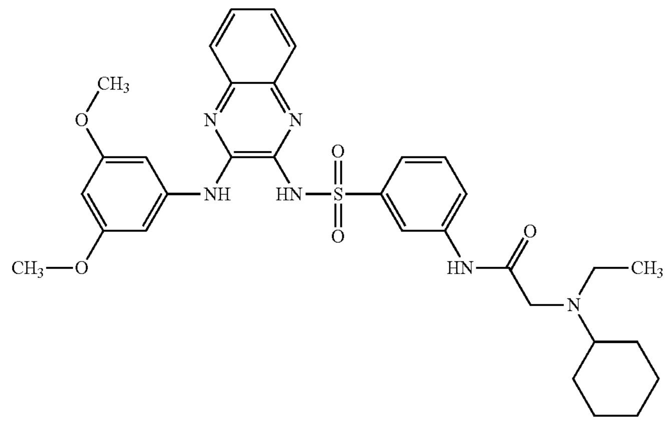 [SMILES: CCN(CC(=O)Nc1cccc(S(=O)(=O)Nc2nc3ccccc3nc2Nc2cc(OC)cc(OC)c2)c1)C1CCCCC1] | N-(3-{[(3-{[3,5-bis(methyloxy)phenyl]amino}quinoxalin-2-yl)amino]sulfonyl}phenyl)-N-2-cyclohexyl-N-2-ethylglycinamide |
| 677 | 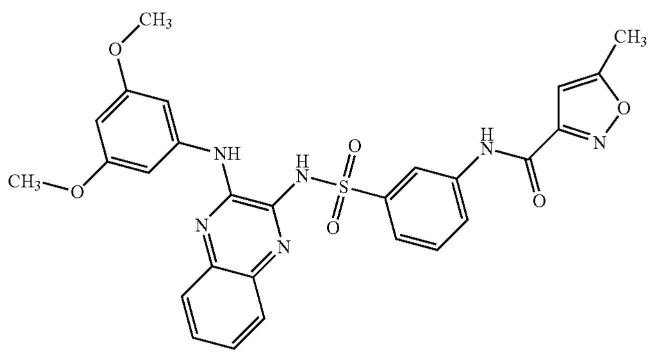 [SMILES: COc1cc(Nc2nc3ccccc3nc2NS(=O)(=O)c2cccc(NC(=O)c3cc(C)on3)c2)cc(OC)c1] | N-(3-{[(3-{[3,5-bis(methyloxy)phenyl]amino}quinoxalin-2-yl)amino]sulfonyl}phenyl)-5-methylisoxazole-3-carboxamide |
| 678 | 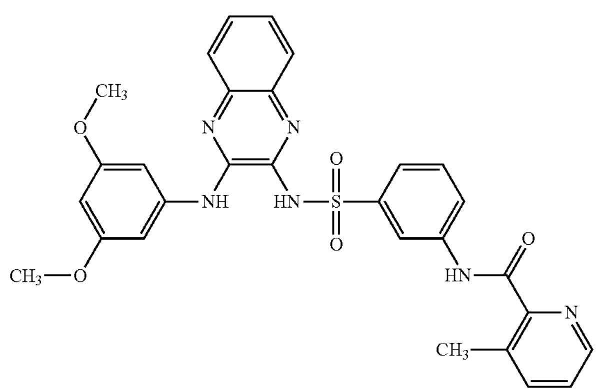 [SMILES: COc1cc(Nc2nc3ccccc3nc2NS(=O)(=O)c2cccc(NC(=O)c3ncccc3C)c2)cc(OC)c1] | N-(3-{[(3-{[3,5-bis(methyloxy)phenyl]amino}quinoxalin-2-yl)amino]sulfonyl}phenyl)-3-methylpiperidine-2-carboxamide |
| 679 | 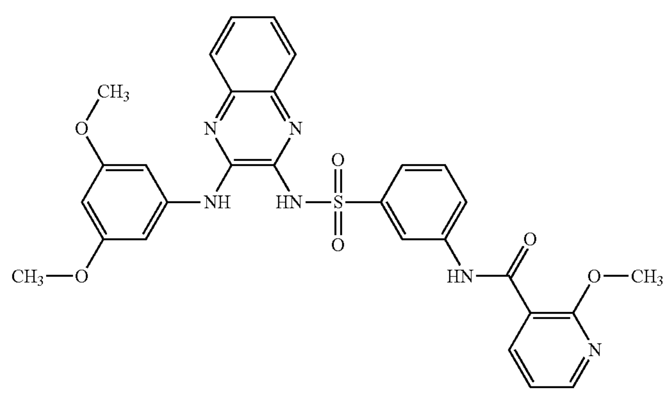 | N-(3-{[(3-{[3,5-bis(methyloxy)phenyl]amino}quinoxalin-2-yl)amino]sulfonyl}phenyl)-2-(methyloxy)pyridine-3-carboxamide |

TABLE 1-continued

| Cpd. No. | Structure | IUPAC Name |
|---|---|---|
| 680 | 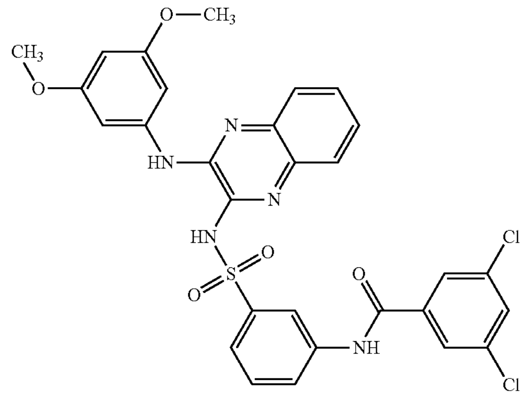 [SMILES: COc1cc(Nc2nc3ccccc3nc2NS(=O)(=O)c2cccc(NC(=O)c3cc(Cl)cc(Cl)c3)c2)cc(OC)c1] | N-(3-{[(3-{[3,5-bis(methyloxy)phenyl]amino}quinoxalin-2-yl)amino]sulfonyl}phenyl)-3,5-dichlorobenzamide |
| 681 | 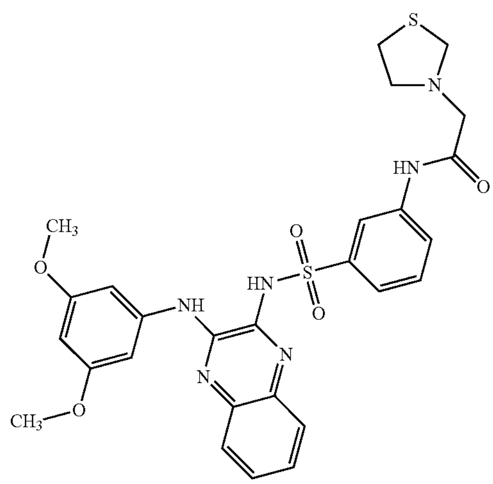 [SMILES: COc1cc(Nc2nc3ccccc3nc2NS(=O)(=O)c2cccc(NC(=O)CN3CCSC3)c2)cc(OC)c1] | N-(3-{[(3-{[3,5-bis(methyloxy)phenyl]amino}quinoxalin-2-yl)amino]sulfonyl}phenyl)-2-(1,3-thiazolidin-3-yl)acetamide |
| 682 | 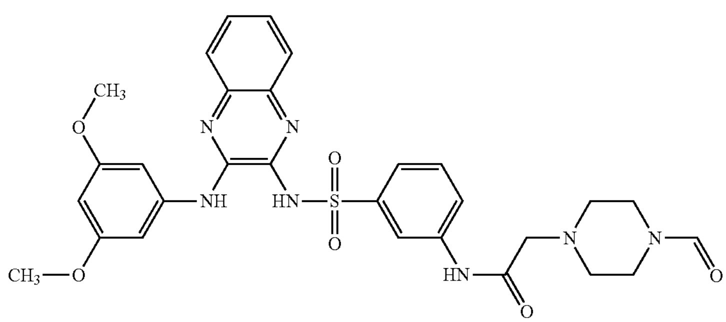 [SMILES: COc1cc(Nc2nc3ccccc3nc2NS(=O)(=O)c2cccc(NC(=O)CN3CCN(C=O)CC3)c2)cc(OC)c1] | N-(3-{[(3-{[3,5-bis(methyloxy)phenyl]amino}quinoxalin-2-yl)amino]sulfonyl}phenyl)-2-(4-formylpiperazin-1-yl)acetamide |
| 683 | 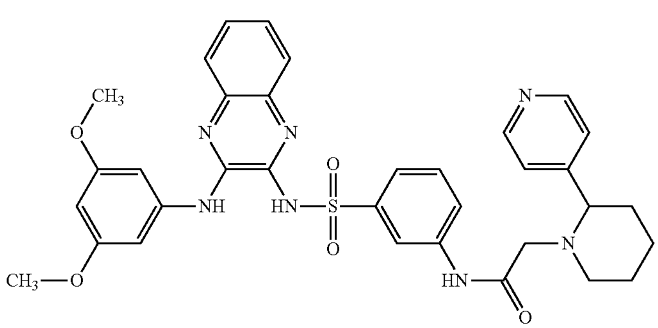 [SMILES: COc1cc(Nc2nc3ccccc3nc2NS(=O)(=O)c2cccc(NC(=O)CN3CCCCC3c3ccncc3)c2)cc(OC)c1] | N-(3-{[(3-{[3,5-bis(methyloxy)phenyl]amino}quinoxalin-2-yl)amino]sulfonyl}phenyl)-2-(2-pyridin-4-ylpiperidin-1-yl)acetamide |

TABLE 1-continued

| Cpd. No. | Structure | IUPAC Name |
|---|---|---|
| 684 | 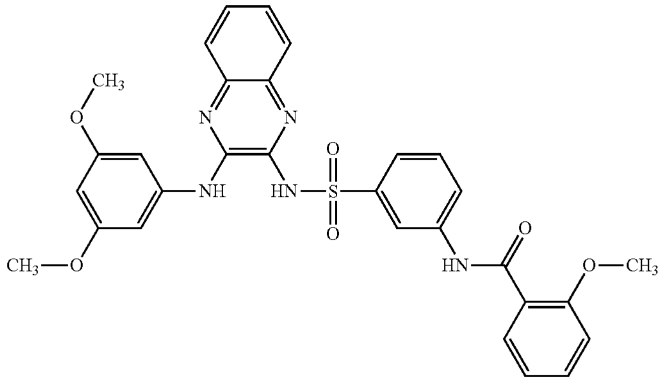 | N-(3-{[(3-{[3,5-bis(methyloxy)phenyl]amino}quinoxalin-2-yl)amino]sulfonyl}phenyl)-2-(methyloxy)benzamide |
| 685 | 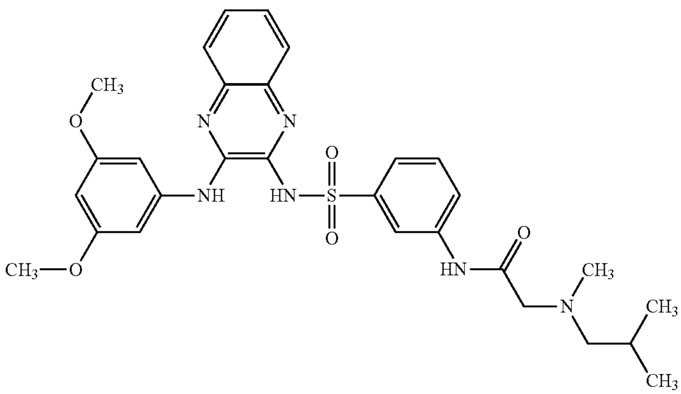 [SMILES: COc1cc(Nc2nc3ccccc3nc2NS(=O)(=O)c2cccc(NC(=O)CN(C)CC(C)C)c2)cc(OC)c1] | N-(3-{[(3-{[3,5-bis(methyloxy)phenyl]amino}quinoxalin-2-yl)amino]sulfonyl}phenyl)-N-2-methyl-N-2-(2-methylpropyl)glycinamide |
| 686 | 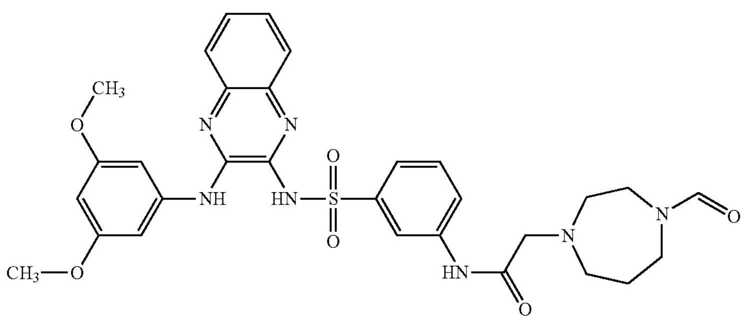 [SMILES: COc1cc(Nc2nc3ccccc3nc2NS(=O)(=O)c2cccc(NC(=O)CN3CCCN(C=O)CC3)c2)cc(OC)c1] | N-(3-{[(3-{[3,5-bis(methyloxy)phenyl]amino}quinoxalin-2-yl)amino]sulfonyl}phenyl)-2-(4-formyl-1,4-diazepan-1-yl)acetamide |
| 687 | 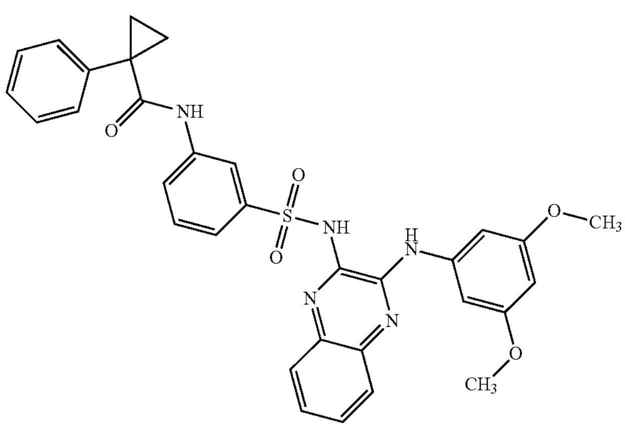 [SMILES: COc1cc(Nc2nc3ccccc3nc2NS(=O)(=O)c2cccc(NC(=O)C3(c4ccccc4)CC3)c2)cc(OC)c1] | N-(3-{[(3-{[3,5-bis(methyloxy)phenyl]amino}quinoxalin-2-yl)amino]sulfonyl}phenyl)-1-phenylcyclopropanecarboxamide |

TABLE 1-continued

| Cpd. No. | Structure | IUPAC Name |
|---|---|---|
| 688 | 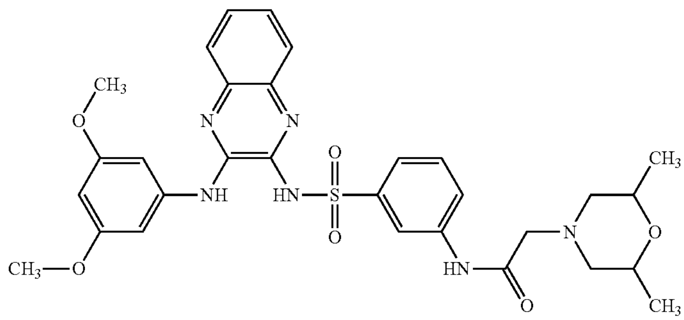 | N-(3-{[(3-{[3,5-bis(methyloxy)phenyl]amino}quinoxalin-2-yl)amino]sulfonyl}phenyl)-2-(2,6-dimethylmorpholin-4-yl)acetamide |
| 689 | 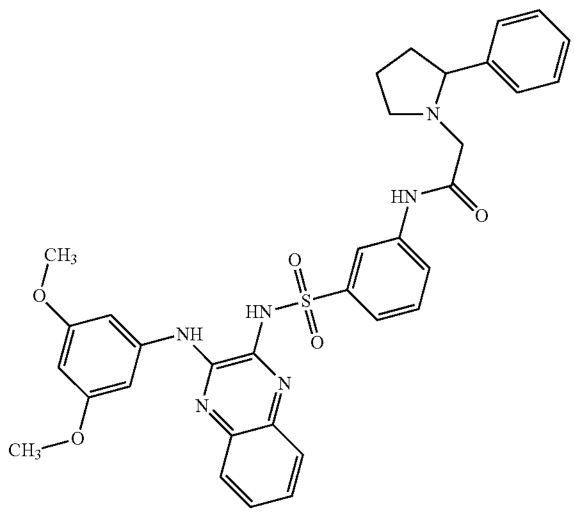 [SMILES: COc1cc(Nc2nc3ccccc3nc2NS(=O)(=O)c2cccc(NC(=O)CN3CCCC3c3ccccc3)c2)cc(OC)c1] | N-(3-{[(3-{[3,5-bis(methyloxy)phenyl]amino}quinoxalin-2-yl)amino]sulfonyl}phenyl)-2-(2-phenylpyrrolidin-1-yl)acetamide |
| 690 | 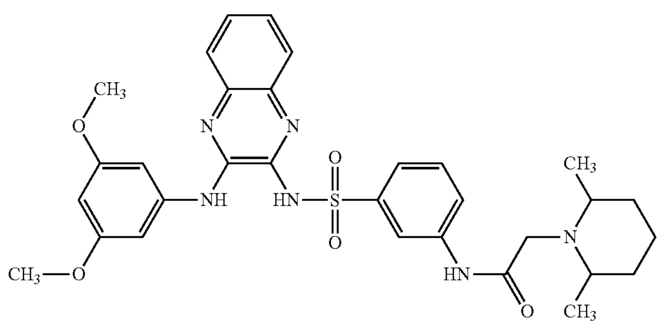 [SMILES: COc1cc(Nc2nc3ccccc3nc2NS(=O)(=O)c2cccc(NC(=O)CN3C(C)CCCC3C)c2)cc(OC)c1] | N-(3-{[(3-{[3,5-bis(methyloxy)phenyl]amino}quinoxalin-2-yl)amino]sulfonyl}phenyl)-2-(2,6-dimethyl[piperidin-1-yl)acetamide |
| 691 | 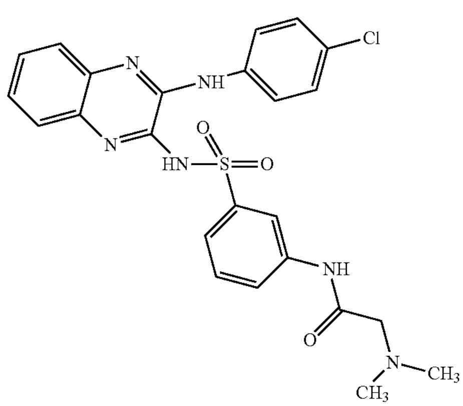 [SMILES: CN(C)CC(=O)Nc1cccc(S(=O)(=O)Nc2nc3ccccc3nc2Nc2ccc(Cl)cc2)c1] | N-{3-[({3-[(4-chlorophenyl)amino]quinoxalin-2-yl}amino)sulfonyl]phenyl}-N-2-,N-2-dimethylglycinamide |

TABLE 1-continued
| Cpd. No. | Structure | IUPAC Name |
|---|---|---|
| 692 | 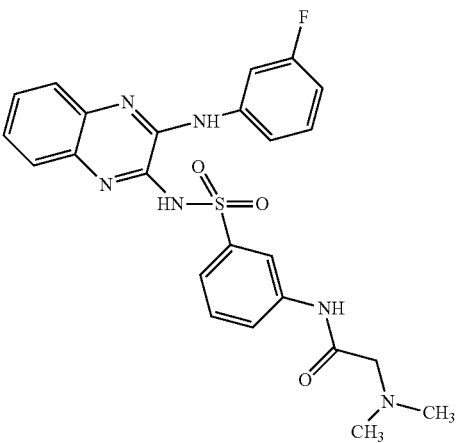 [SMILES: CN(C)CC(=O)Nc1cccc(S(=O)(=O)Nc2nc3ccccc3nc2Nc2cccc(F)c2)c1] | N-{3-[({3-[(3-fluorophenyl)amino]quinoxalin-2-yl}amino)sulfonyl]phenyl}-N-2-,N-2-dimethylglycinamide |
| 693 | 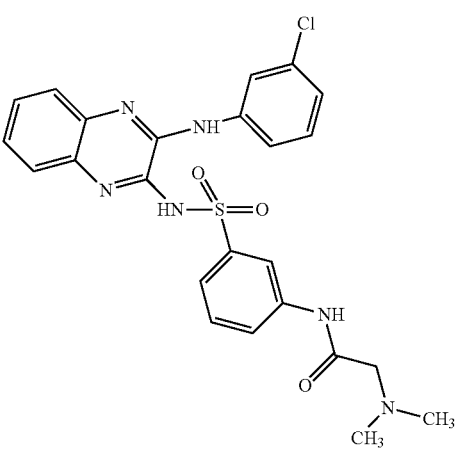 [SMILES: CN(C)CC(=O)Nc1cccc(S(=O)(=O)Nc2nc3ccccc3nc2Nc2cccc(Cl)c2)c1] | N-{3-[({3-[(3-chlorophenyl)amino]quinoxalin-2-yl}amino)sulfonyl]phenyl}-N-2-,N-2-dimethylglycinamide |
| 694 | 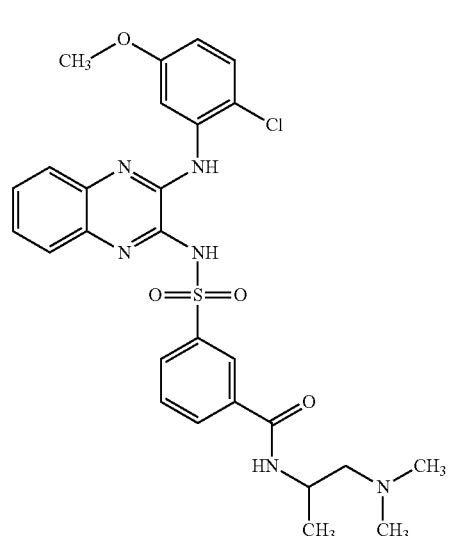 | 3-{[(3-{[2-chloro-5-(methyloxy)phenyl]amino}quinoxalin-2-yl)amino]sulfonyl}-N-[2-(dimethylamino)-1-methylethyl]benzamide |

TABLE 1-continued

| Cpd. No. | Structure | IUPAC Name |
|---|---|---|
| 695 | 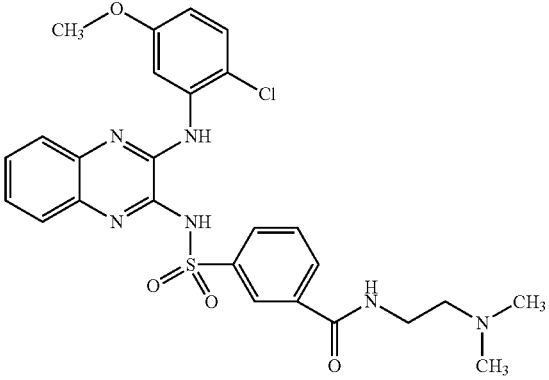 [SMILES: COc1ccc(Cl)c(Nc2nc3ccccc3nc2NS(=O)(=O)c2cccc(C(=O)NCCN(C)C)c2)c1] | 3-{[(3-{[2-chloro-5-(methyloxy)phenyl]amino}quinoxalin-2-yl)amino]sulfonyl}-N-[2-(dimethylamino)ethyl]benzamide |
| 696 | 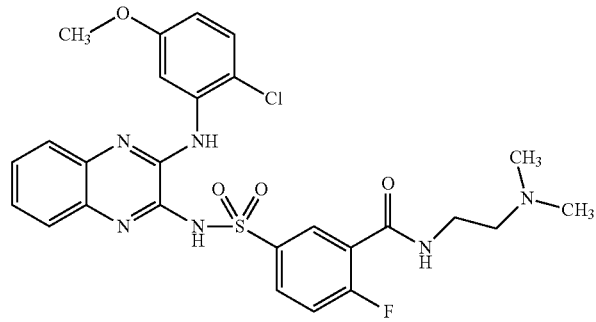 [SMILES: COc1ccc(Cl)c(Nc2nc3ccccc3nc2NS(=O)(=O)c2ccc(F)c(C(=O)NCCN(C)C)c2)c1] | 5-{[(3-{[2-chloro-5-(methyloxy)phenyl]amino}quinoxalin-2-yl)amino]sulfonyl}-N-[2-(dimethylamino)ethyl]-2-fluorobenzamide |
| 697 | 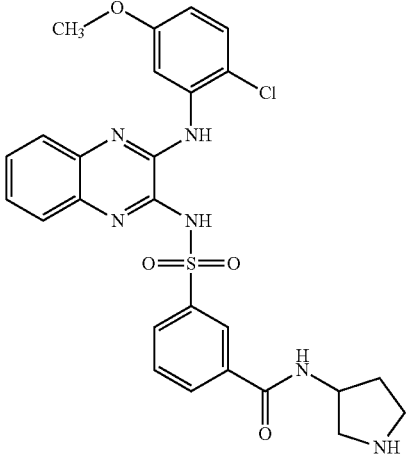 [SMILES: COc1ccc(Cl)c(Nc2nc3ccccc3nc2NS(=O)(=O)c2cccc(C(=O)NC3CCNC3)c2)c1] | 3-{[(3-{[2-chloro-5-(methyloxy)phenyl]amino}quinoxalin-2-yl)amino]sulfonyl}-N-pyrrolidin-3-ylbenzamide |
| 698 | 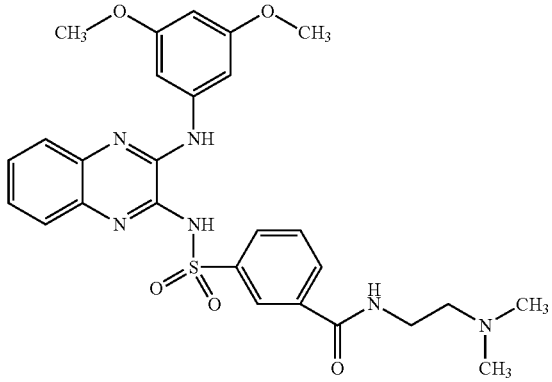 [SMILES: COc1cc(Nc2nc3ccccc3nc2NS(=O)(=O)c2cccc(C(=O)NCCN(C)C)c2)cc(OC)c1] | 3-{[(3-{[3,5-bis(methyloxy)phenyl]amino}quinoxalin-2-yl)amino]sulfonyl}-N-[2-(dimethylamino)ethyl]benzamide |

TABLE 1-continued

| Cpd. No. | Structure | IUPAC Name |
|---|---|---|
| 699 | 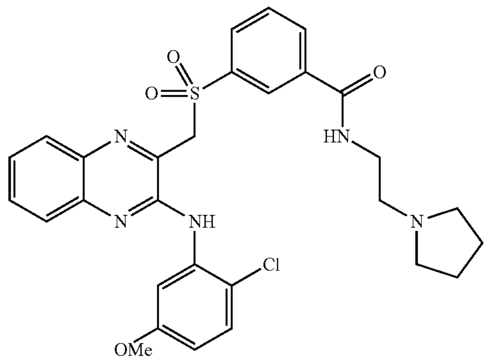 [SMILES: COc1ccc(Cl)c(Nc2nc3ccccc3nc2CS(=O)(=O)c2cccc(C(=O)NCCN3CCCC3)c2)c1] | 3-{[(3-{[2-chloro-5-(methyloxy)phenyl]amino}quinoxalin-2-yl)amino]sulfonyl}-N-(2-pyrrolidin-1-ylethyl)benzamide |
| 700 | 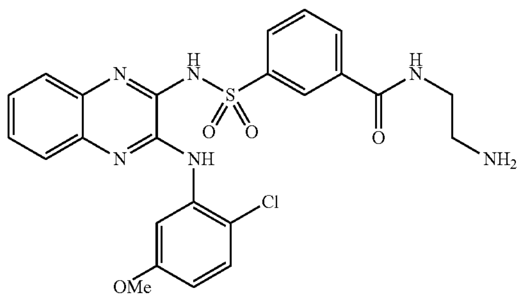 [SMILES: COc1ccc(Cl)c(Nc2nc3ccccc3nc2NS(=O)(=O)c2cccc(C(=O)NCCN)c2)c1] | N-(2-aminomethyl)-3-{[(3-{[2-chloro-5-(methyloxy)phenyl]amino}quinoxalin-2-yl)amino]sulfonyl}benzamide |
| 701 | 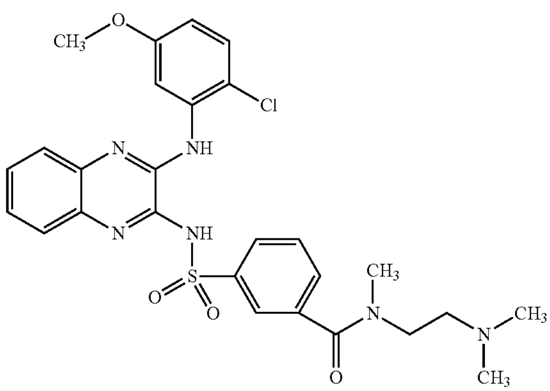 [SMILES: COc1ccc(Cl)c(Nc2nc3ccccc3nc2NS(=O)(=O)c2cccc(C(=O)N(C)CCN(C)C)c2)c1] | 3-{[(3-{[2-chloro-5-(methyloxy)phenyl]amino}quinoxalin-2-yl)amino]sulfonyl}-N-[2-(dimethylamino)ethyl]-N-methylbenzamide |
| 702 | 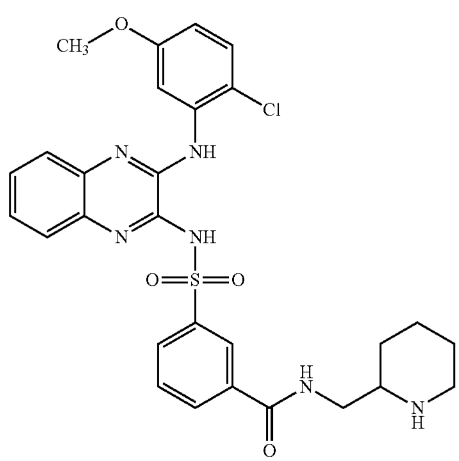 [SMILES: COc1ccc(Cl)c(Nc2nc3ccccc3nc2NS(=O)(=O)c2cccc(C(=O)NCC3CCCCN3)c2)c1] | 3-{[(3-{[2-chloro-5-(methyloxy)phenyl]amino}quinoxalin-2-yl)amino]sulfonyl}-N-(piperidin-2-ylmethyl)benzamide |

| Cpd. No. | Structure | IUPAC Name |
|---|---|---|
| 703 | 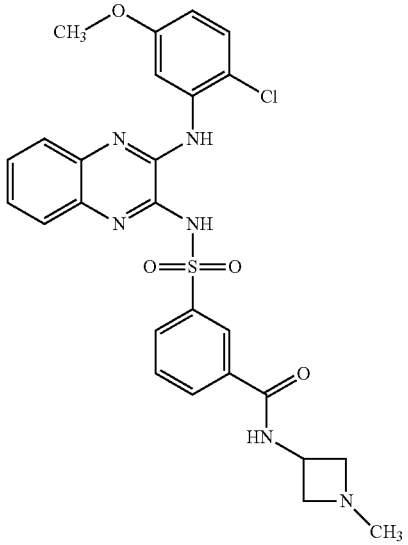 [SMILES: COc1ccc(Cl)c(Nc2nc3ccccc3nc2NS(=O)(=O)c2cccc(C(=O)NC3CN(C)C3)c2)c1] | 3-{[(3-{[2-chloro-5-(methyloxy)phenyl]amino}quinoxalin-2-yl)amino]sulfonyl}-N-(1-methylazetidin-3-yl)benzamide |
| 704 | 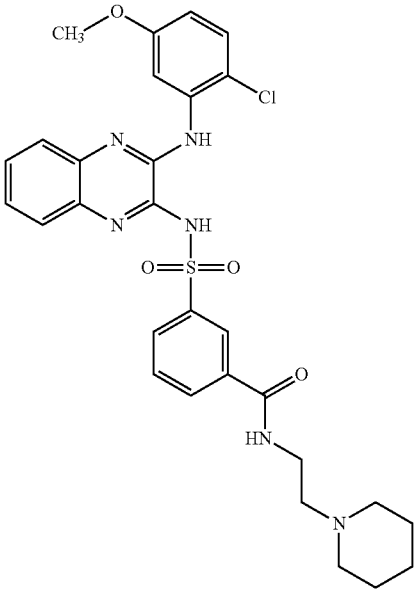 [SMILES: COc1ccc(Cl)c(Nc2nc3ccccc3nc2NS(=O)(=O)c2cccc(C(=O)NCCN3CCCCC3)c2)c1] | 3-{[(3-{[2-chloro-5-(methyloxy)phenyl]amino}quinoxalin-2-yl)amino]sulfonyl}-N-(2-piperidin-1-ylethyl)benzamide |

TABLE 1-continued
| Cpd. No. | Structure | IUPAC Name |
|---|---|---|
| 705 | 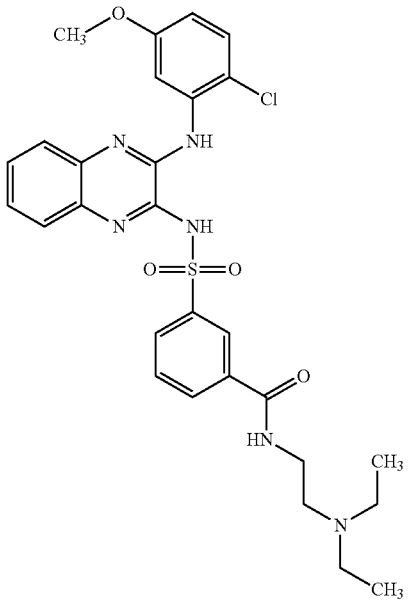 [SMILES: CCN(CC)CCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[2-(diethylamino)ethyl]benzamide |
| 706 | 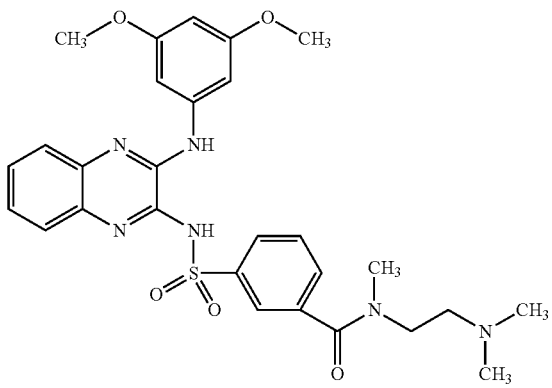 [SMILES: COc1cc(Nc2nc3ccccc3nc2NS(=O)(=O)c2cccc(C(=O)N(C)CCN(C)C)c2)cc(OC)c1] | 3-{[(3-{[3,5-bis(methyloxy)phenyl]amino}quinoxalin-2-yl)amino]sulfonyl}-N-[2-(dimethylamino)ethyl]-N-methylbenzamide |
| 707 | 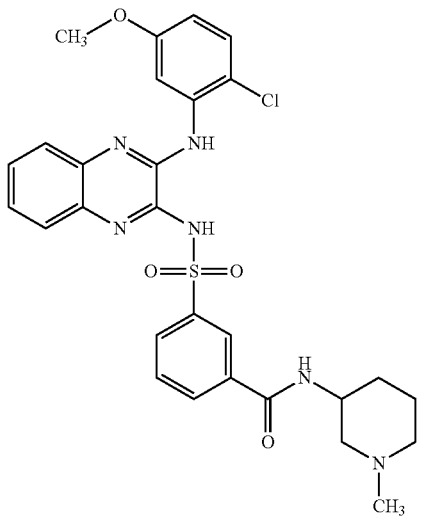 [SMILES: COc1ccc(Cl)c(Nc2nc3ccccc3nc2NS(=O)(=O)c2cccc(C(=O)NC3CCCN(C)C3)c2)c1] | 3-{[(3-{[2-chloro-5-(methyloxy)phenyl]amino}quinoxalin-2-yl)amino]sulfonyl}-N-(1-methylpiperidin-3-yl)benzamide |

| Cpd. No. | Structure | IUPAC Name |
|---|---|---|
| 708 | 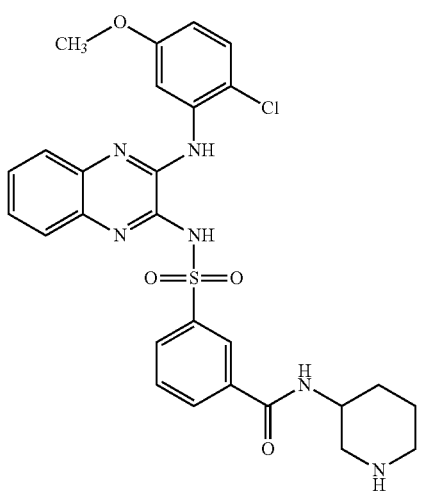 [SMILES: COc1ccc(Cl)c(Nc2nc3ccccc3nc2NS(=O)(=O)c2cccc(C(=O)NC3CCCNC3)c2)c1] | 3-{[(3-{[2-chloro-5-(methyloxy)phenyl]amino}quinoxalin-2-yl)amino]sulfonyl}-N-piperidin-3-ylbenzamide |
| 709 | 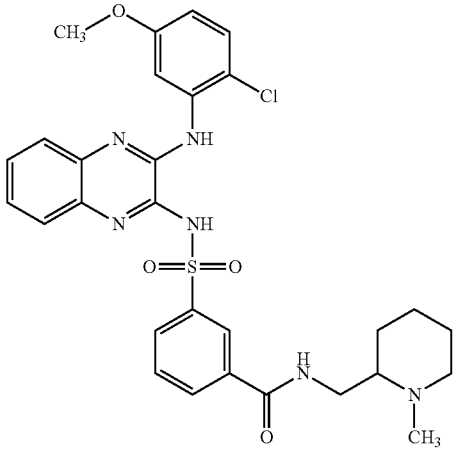 [SMILES: COc1ccc(Cl)c(Nc2nc3ccccc3nc2NS(=O)(=O)c2cccc(C(=O)NCC3CCCCN3C)c2)c1] | 3-{[(3-{[2-chloro-5-(methyloxy)phenyl]amino}quinoxalin-2-yl)amino]sulfonyl}-N-[(1-methylpiperidin-2-yl)methyl]benzamide |
| 710 | 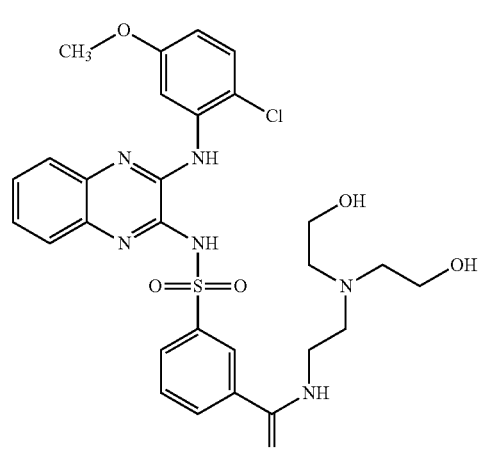 | N-{2-[bis(2-hydroxyethyl)amino]ethyl}-3-{[(3-{[2-chloro-5-(methyloxy)phenyl]amino}quinoxalin-2-yl)amino]sulfonyl}benzamide |

TABLE 1-continued
| Cpd. No. | Structure | IUPAC Name |
|---|---|---|
| 711 | 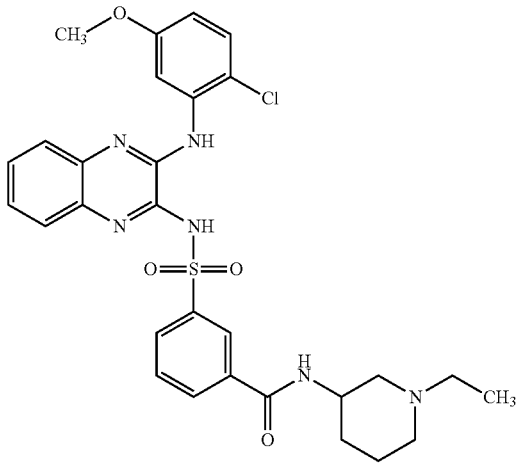 [SMILES: CCN1CCCC(NC(=O)c2cccc(S(=O)(=O)Nc3nc4ccccc4nc3Nc3cc(OC)ccc3Cl)c2)C1] | 3-{[(3-{[2-chloro-5-(methyloxy)phenyl]amino}quinoxalin-2-yl)amino]sulfonyl}-N-(1-ethylpiperidin-3-yl)benzamide |
| 712 | 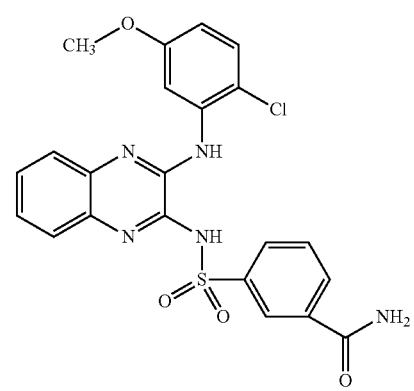 [SMILES: COc1ccc(Cl)c(Nc2nc3ccccc3nc2NS(=O)(=O)c2cccc(C(N)=O)c2)c1] | 3-{[(3-{[2-chloro-5-(methyloxy)phenyl]amino}quinoxalin-2-yl)amino]sulfonyl}benzamide |
| 713 | 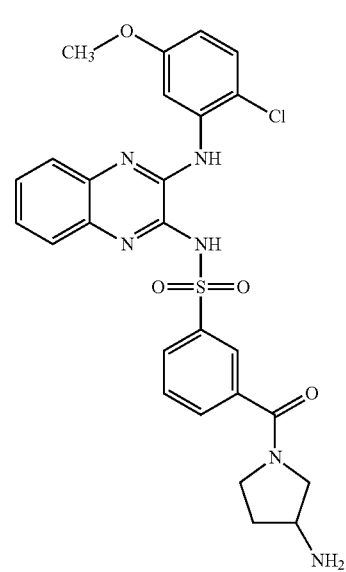 [SMILES: COc1ccc(Cl)c(Nc2nc3ccccc3nc2NS(=O)(=O)c2cccc(C(=O)N3CCC(N)C3)c2)c1] | 3-[(3-aminopyrrolidin-1-yl)carbonyl]-N-(3-{[2-chloro-5-(methyloxy)phenyl]amino}quinoxalin-2-yl)benzenesulfonamide |

TABLE 1-continued

| Cpd. No. | Structure | IUPAC Name |
|---|---|---|
| 714 | 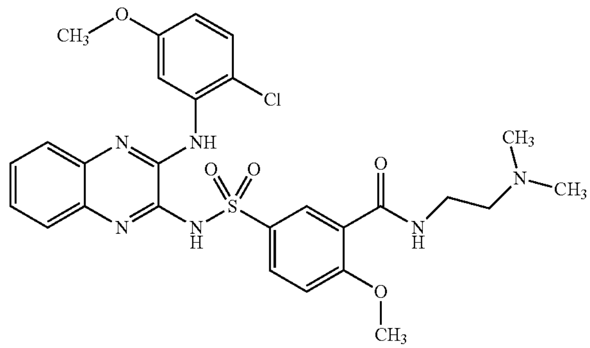 [SMILES: COc1ccc(Cl)c(Nc2nc3ccccc3nc2NS(=O)(=O)c2ccc(OC)c(C(=O)NCCN(C)C)c2)c1] | 5-{[(3-{[2-chloro-5-(methyloxy)phenyl]amino}quinoxalin-2-yl)amino]sulfonyl}-N-[2-(dimethylamino)ethyl]-2-(methyloxy)benzamide |
| 715 | 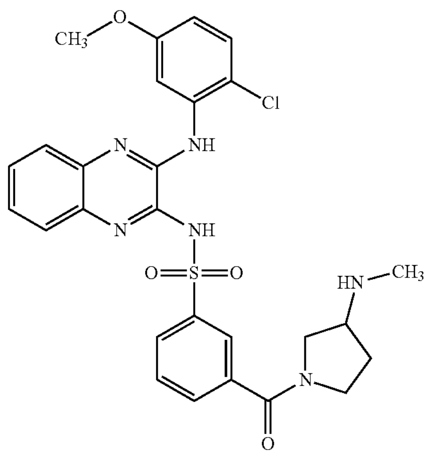 [SMILES: CNC1CCN(C(=O)c2cccc(S(=O)(=O)Nc3nc4ccccc4nc3Nc3cc(OC)ccc3Cl)c2)C1] | N-(3-{[2-chloro-5-(methyloxy)phenyl]amino}quinoxalin-2-yl)-3-{[3-(methylamino)pyrrolidin-1-yl]carbonyl}benzenesulfonamide |
| 716 | 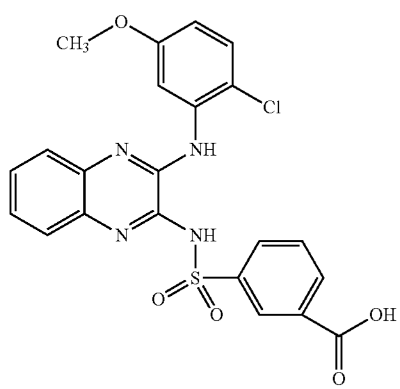 [SMILES: COc1ccc(Cl)c(Nc2nc3ccccc3nc2NS(=O)(=O)c2cccc(C(=O)O)c2)c1] | 3-{[(3-{[2-chloro-5-(methyloxy)phenyl]amino}quinoxalin-2-yl)amino]sulfonyl}benzoicacid |
| 717 | 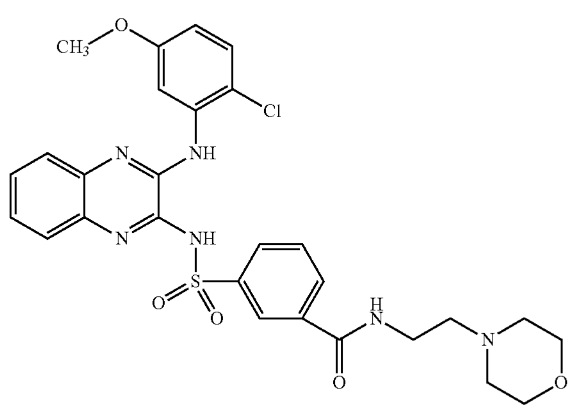 [SMILES: COc1ccc(Cl)c(Nc2nc3ccccc3nc2NS(=O)(=O)c2cccc(C(=O)NCCN3CCOCC3)c2)c1] | 3-{[(3-{[2-chloro-5-(methyloxy)phenyl]amino}quinoxalin-2-yl)amino]sulfonyl}-N-(2-morpholin-4-ylethyl)benzamide |

TABLE 1-continued
| Cpd. No. | Structure | IUPAC Name |
|---|---|---|
| 718 | 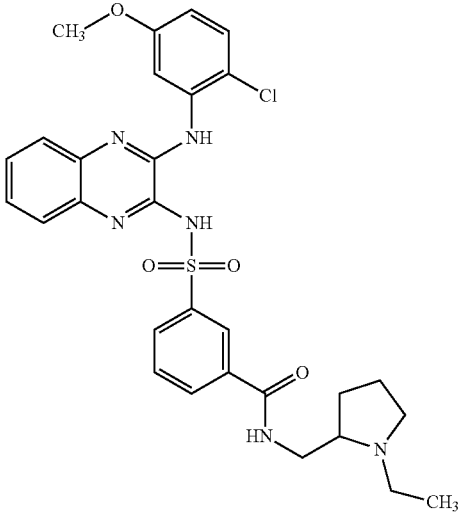 [SMILES: CCN1CCCC1CNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[(1-ethylpyrrolidin-2-yl)methyl]benzamide |
| 719 | 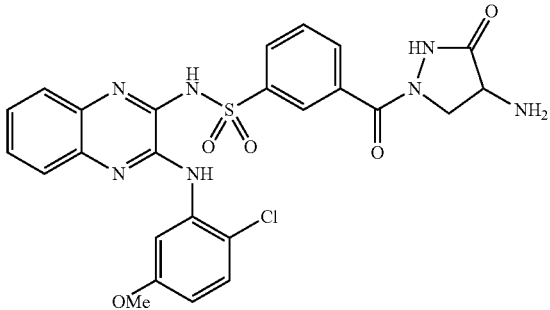 [SMILES: COc1ccc(Cl)c(Nc2nc3ccccc3nc2NS(=O)(=O)c2cccc(C(=O)N3CC(N)C(=O)N3)c2)c1] | 3-{(4-amino-3-oxopyrazolidin-1-yl)carbonyl]-N-(3-{[2-chloro-5-(methyloxy)phenyl]amino}quinoxalin-2-yl)benzenesulfonamide |
| 720 | 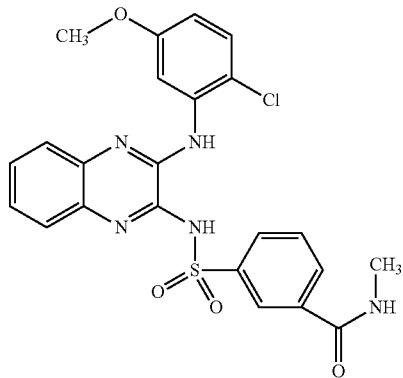 [SMILES: CNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-methylbenzamide |

TABLE 1-continued

| Cpd. No. | Structure | IUPAC Name |
|---|---|---|
| 721 | 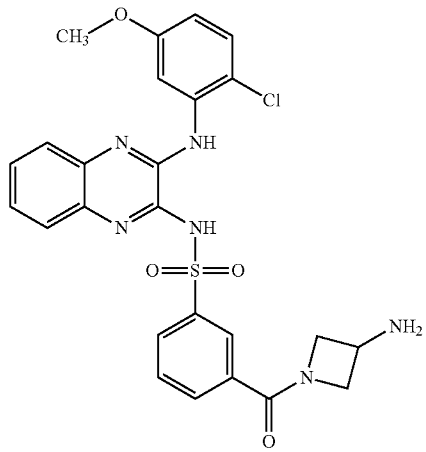 [SMILES: COc1ccc(Cl)c(Nc2nc3ccccc3nc2NS(=O)(=O)c2cccc(C(=O)N3CC(N)C3)c2)c1] | 3-[(3-aminoazetidin-1-yl)carbonyl]-N-(3-{[2-chloro-5-(methyloxy)phenyl]amino}quinoxalin-2-yl)benzenesulfonamide |
| 722 | 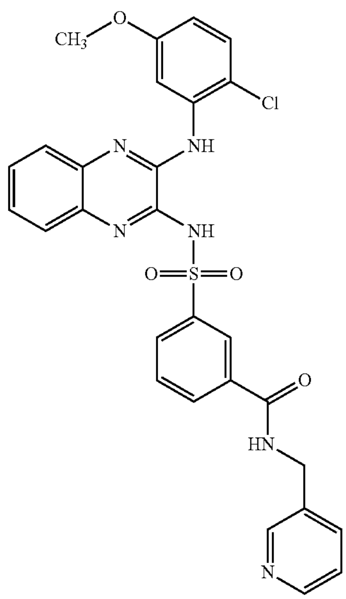 [SMILES: COc1ccc(Cl)c(Nc2nc3ccccc3nc2NS(=O)(=O)c2cccc(C(=O)NCc3cccnc3)c2)c1] | 3-{[(3-{[2-chloro-5-(methyloxy)phenyl]amino}quinoxalin-2-yl)amino]sulfonyl}-N-(pyridin-3-ylmethyl)benzamide |
| 723 | 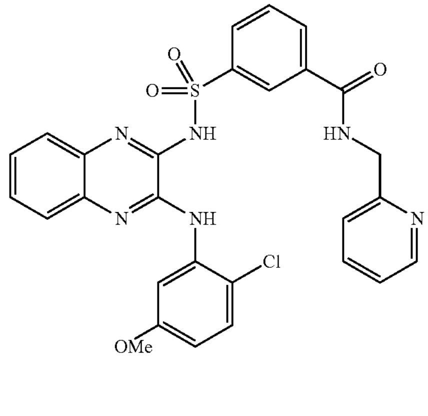 [SMILES: COc1ccc(Cl)c(Nc2nc3ccccc3nc2NS(=O)(=O)c2cccc(C(=O)NCc3ccccn3)c2)c1] | 3-{[(3-{[2-chloro-5-(methyloxy)phenyl]amino}quinoxalin-2-yl)amino]sulfonyl}-N-(pyridin-2-ylmethyl)benzamide |

TABLE 1-continued
| Cpd. No. | Structure | IUPAC Name |
|---|---|---|
| 724 | 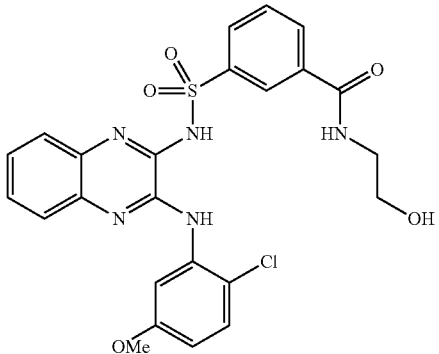 [SMILES: COc1ccc(Cl)c(Nc2nc3ccccc3nc2NS(=O)(=O)c2cccc(C(=O)NCCO)c2)c1] | 3-{[(3-{[2-chloro-5-(methyloxy)phenyl]amino}quinoxalin-2-yl)amino]sulfonyl}-N-(2-hydroxyethyl)benzamide |
| 725 | 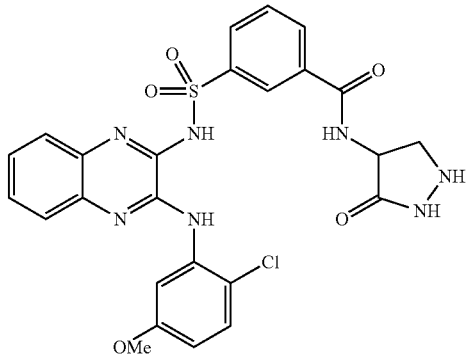 [SMILES: COc1ccc(Cl)c(Nc2nc3ccccc3nc2NS(=O)(=O)c2cccc(C(=O)NC3CNNC3=O)c2)c1] | 3-{[(3-{[2-chloro-5-(methyloxy)phenyl]amino}quinoxalin-2-yl)amino]sulfonyl}-N-(3-oxopyrazolidin-4-yl)benzamide |
| 726 | 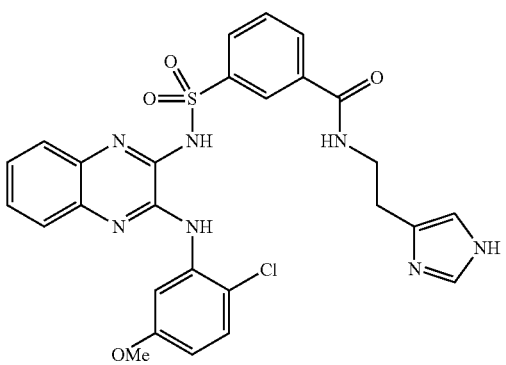 [SMILES: COc1ccc(Cl)c(Nc2nc3ccccc3nc2NS(=O)(=O)c2cccc(C(=O)NCCc3c[nH]cn3)c2)c1] | 3-{[(3-{[2-chloro-5-(methyloxy)phenyl]amino}quinoxalin-2-yl)amino]sulfonyl}-N-[2-(1H-imidazol-4-yl)ethyl]benzamide |

| Cpd. No. | Structure | IUPAC Name |
|---|---|---|
| 727 | 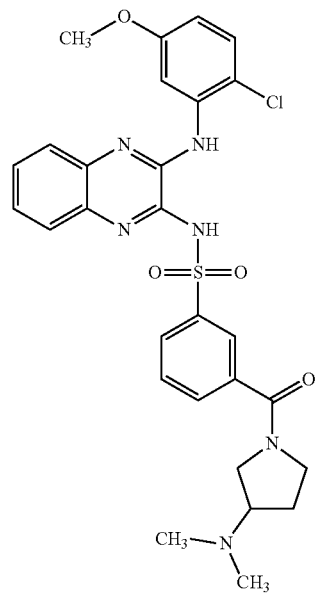 [SMILES: COc1ccc(Cl)c(Nc2nc3ccccc3nc2NS(=O)(=O)c2cccc(C(=O)N3CCC(N(C)C)C3)c2)c1] | N-(3-{[2-chloro-5-(methyloxy)phenyl]amino}quinoxalin-2-yl)-3-{[3-(dimethylamino)pyrrolidin-1-yl]carbonyl}benzenesulfonamide |
| 728 | 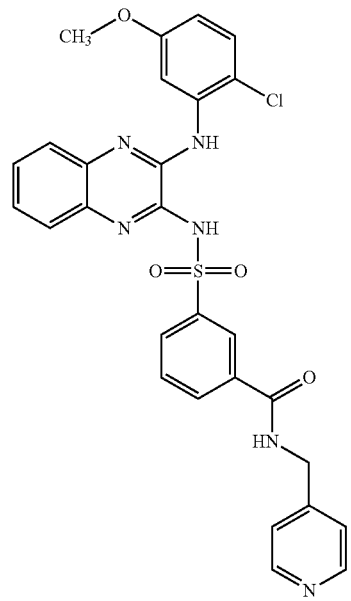 [SMILES: COc1ccc(Cl)c(Nc2nc3ccccc3nc2NS(=O)(=O)c2cccc(C(=O)NCc3ccncc3)c2)c1] | 3-{[(3-{[2-chloro-5-(methyloxy)phenyl]amino}quinoxalin-2-yl)amino]sulfonyl}-N-(pyridin-4-ylmethyl)benzamide |

TABLE 1-continued

| Cpd. No. | Structure | IUPAC Name |
|---|---|---|
| 729 | 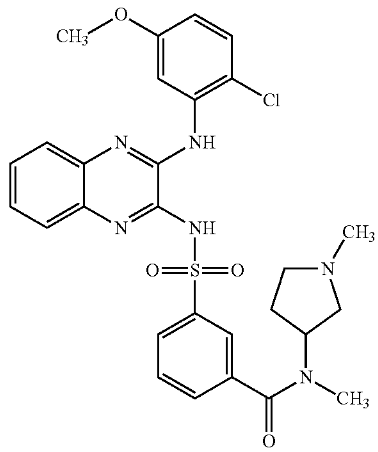 [SMILES: COc1ccc(Cl)c(Nc2nc3ccccc3nc2NS(=O)(=O)c2cccc(C(=O)N(C)C3CCN(C)C3)c2)c1] | 3-{[(3-{[2-chloro-5-(methyloxy)phenyl]amino}quinoxalin-2-yl)amino]sulfonyl}-N-methyl-N-(1-methylpyrrolidin-3-yl)benzamide |
| 730 | 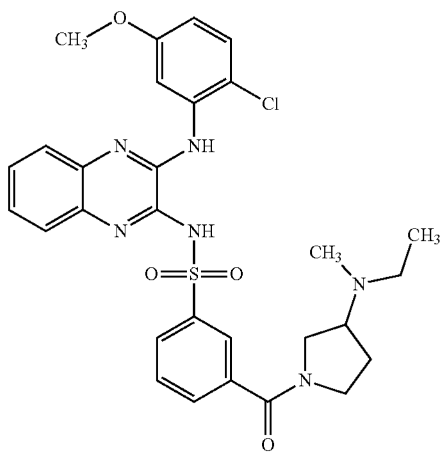 [SMILES: CCN(C)C1CCN(C(=O)c2cccc(S(=O)(=O)Nc3nc4ccccc4nc3Nc3cc(OC)ccc3Cl)c2)C1] | N-(3-{[2-chloro-5-(methyloxy)phenyl]amino}quinoxalin-2-yl)-3-{[3-(diethylamino)pyrrolidin-1-yl]carbonyl}benzenesulfonamide |
| 731 | 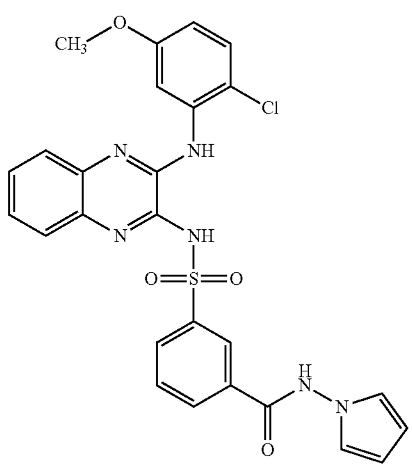 [SMILES: COc1ccc(Cl)c(Nc2nc3ccccc3nc2NS(=O)(=O)c2cccc(C(=O)Nn3cccc3)c2)c1] | 3-{[(3-{[2-chloro-5-(methyloxy)phenyl]amino}quinoxalin-2-yl)amino]sulfonyl}-N-1H-pyrrol-1-ylbenzamide |

TABLE 1-continued
| Cpd. No. | Structure | IUPAC Name |
|---|---|---|
| 732 | 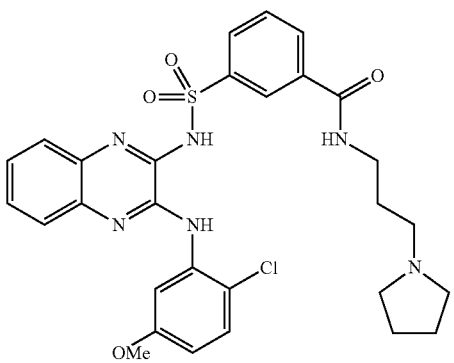 [SMILES: COc1ccc(Cl)c(Nc2nc3ccccc3nc2NS(=O)(=O)c2cccc(C(=O)NCCCN3CCCC3)c2)c1] | 3-{[(3-{[2-chloro-5-(methyloxy)phenyl]amino}quinoxalin-2-yl)amino]sulfonyl}-N-(3-pyrolidin-1-ylpropyl)benzamide |
| 733 | 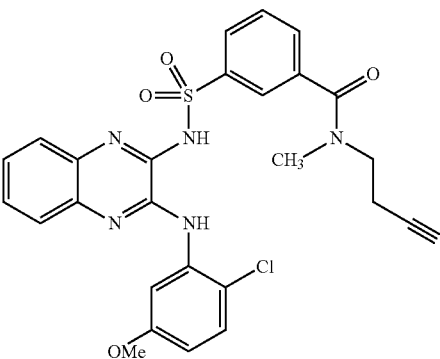 | 3-{[(3-{[2-chloro-5-(methyloxy)phenyl]amino}quinoxalin-2-yl)amino]sulfonyl}-N-(2-cyanoethyl)-N-methylbenzamide |
| 734 | 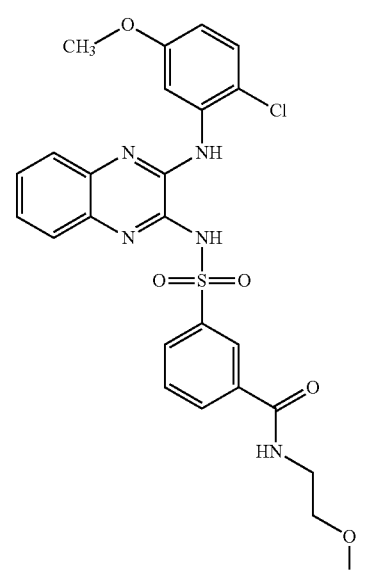 | 3-{[(3-{[2-chloro-5-(methyloxy)phenyl]amino}quinoxalin-2-yl)amino]sulfonyl}-N-[2-(methyloxy)ethyl]benzamide |

TABLE 1-continued

| Cpd. No. | Structure | IUPAC Name |
|---|---|---|
| 735 | 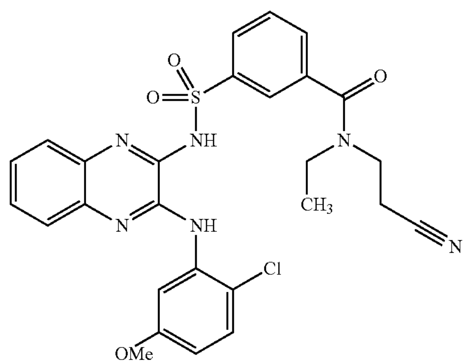 [SMILES: CCN(CCC#N)C(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-(2-cyanoethyl)-N-ethylbenzamide |
| 736 | 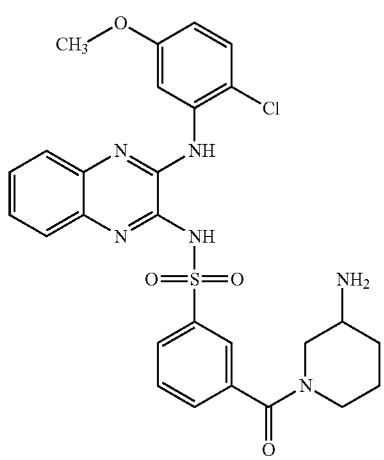 [SMILES: COc1ccc(Cl)c(Nc2nc3ccccc3nc2NS(=O)(=O)c2cccc(C(=O)N3CCCC(N)C3)c2)c1] | 3-[(3-aminopiperidin-1-yl)carbonyl]-N-(3-{[2-chloro-5-(methyloxy)phenyl]amino}quinoxalin-2-yl)benzenesulfonamide |
| 737 | 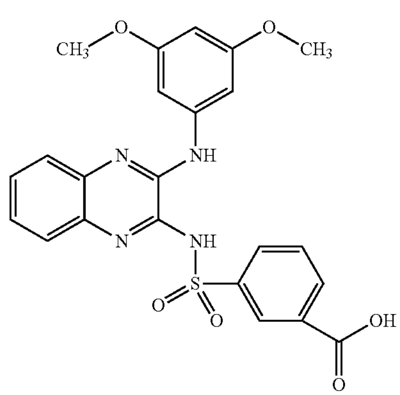 [SMILES: COc1cc(Nc2nc3ccccc3nc2NS(=O)(=O)c2cccc(C(=O)O)c2)cc(OC)c1] | 3-{[(3-{[3,5-bis(methyloxy)phenyl]amino}quinoxalin-2-yl)amino]sulfonyl}benzoicacid |

TABLE 1-continued
| Cpd. No. | Structure | IUPAC Name |
|---|---|---|
| 738 | 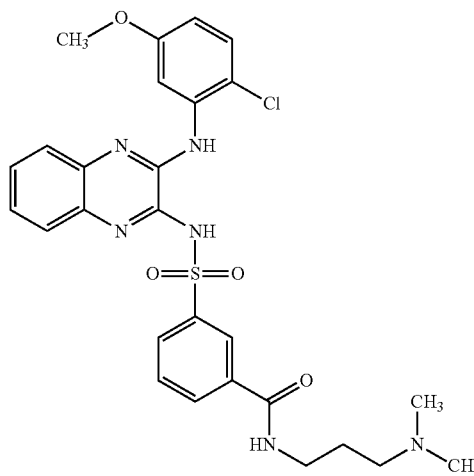 | 3-{[(3-{[2-chloro-5-(methyloxy)phenyl]amino}quinoxalin-2-yl)amino]sulfonyl}-N-[3-(dimethylamino)propyl]benzamide |
| 739 | 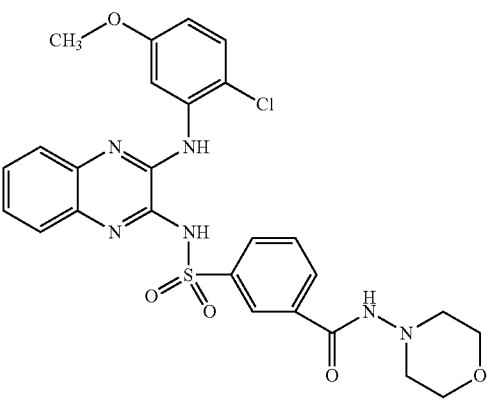 [SMILES: COc1ccc(Cl)c(Nc2nc3ccccc3nc2NS(=O)(=O)c2cccc(C(=O)NN3CCOCC3)c2)c1] | 3-{[(3-{[2-chloro-5-(methyloxy)phenyl]amino}quinoxalin-2-yl)amino]sulfonyl}-N-morpholin-4-ylbenzamide |
| 740 | 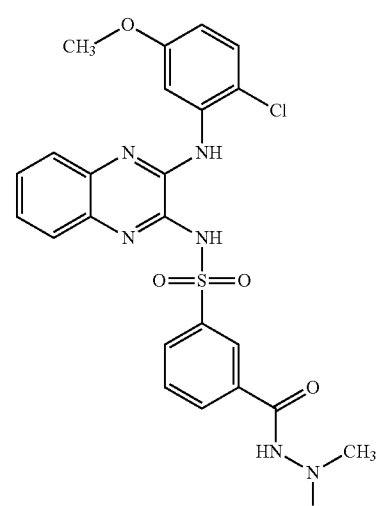 | N-(3-{[2-chloro-5-(methyloxy)phenyl]amino}quinoxalin-2-yl)-3-[(2,2-dimethylhydrazino)carbonyl]benzenesulfonamide |

TABLE 1-continued

| Cpd. No. | Structure | IUPAC Name |
|---|---|---|
| 741 | 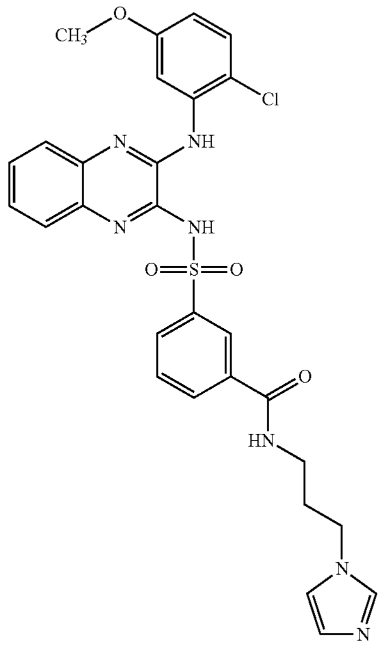 [SMILES: COc1ccc(Cl)c(Nc2nc3ccccc3nc2NS(=O)(=O)c2cccc(C(=O)NCCCn3ccnc3)c2)c1] | 3-{[(3-{[2-chloro-5-(methyloxy)phenyl]amino}quinoxalin-2-yl)amino]sulfonyl}-N-[3-(1H-imidazol-1-yl)propyl]benzamide |
| 742 | 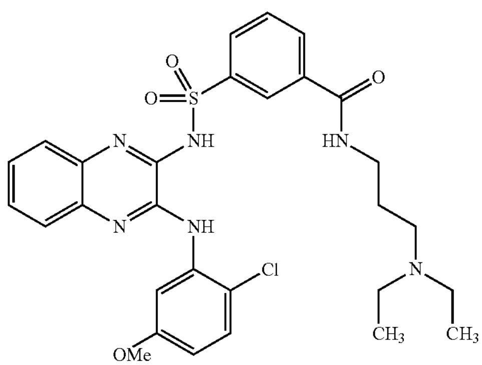 [SMILES: CCN(CC)CCCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[3-(diethylamino)propyl]benzamide |
| 743 | 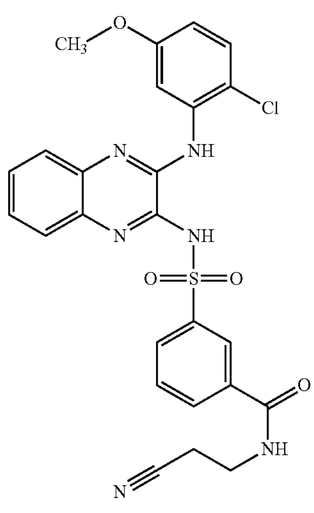 [SMILES: COc1ccc(Cl)c(Nc2nc3ccccc3nc2NS(=O)(=O)c2cccc(C(=O)NCCC#N)c2)c1] | 3-{[(3-{[2-chloro-5-(methyloxy)phenyl]amino}quinoxalin-2-yl)amino]sulfonyl}-N-(2-cyanoethyl)benzamide |

| Cpd. No. | Structure | IUPAC Name |
|---|---|---|
| 744 | 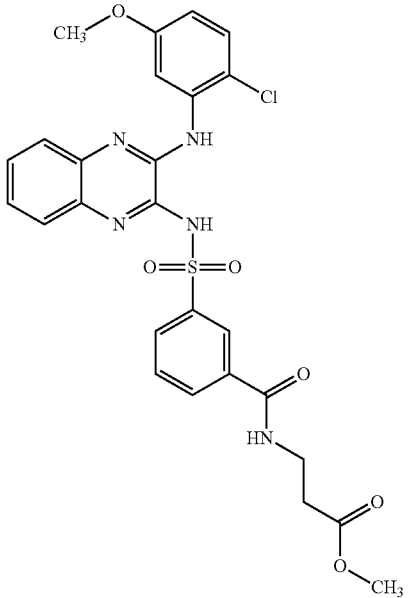 [SMILES: COC(=O)CCNC(=O)c1cccc(S(=O)(=O)Nc2nc3ccccc3nc2Nc2cc(OC)ccc2Cl)c1] | methylN-[(3-{[(3-{[2-chloro-5-(methyloxy)phenyl]amino}quinoxalin-2-yl)amino]sulfonyl}phenyl)carbonyl]-beta-alanine |
| 745 | 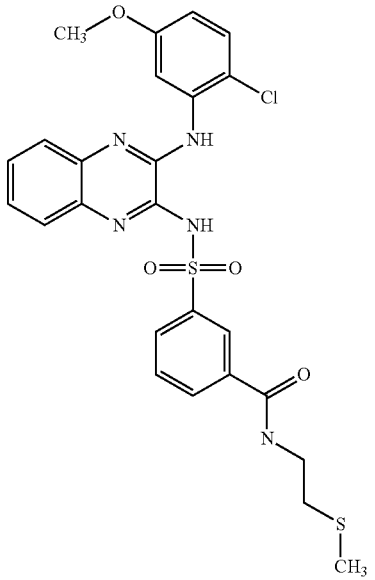 [SMILES: COc1ccc(Cl)c(Nc2nc3ccccc3nc2NS(=O)(=O)c2cccc(C(=O)NCCSC)c2)c1] | 3-{[(3-{[2-chloro-5-(methyloxy)phenyl]amino}quinoxalin-2-yl)amino]sulfonyl}-N-[2-(methylthiso)ethyl]benzamide |
| 746 | 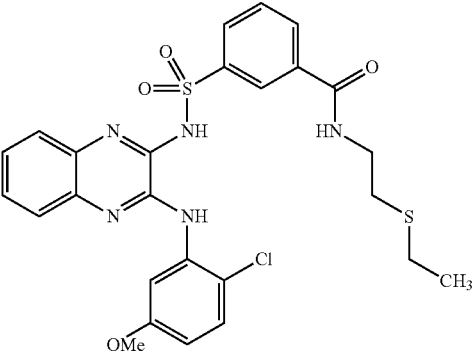 [SMILES: CCSCCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[2-(ethylthiso)ethyl]benzamide |

TABLE 1-continued
| Cpd. No. | Structure | IUPAC Name |
|---|---|---|
| 747 | 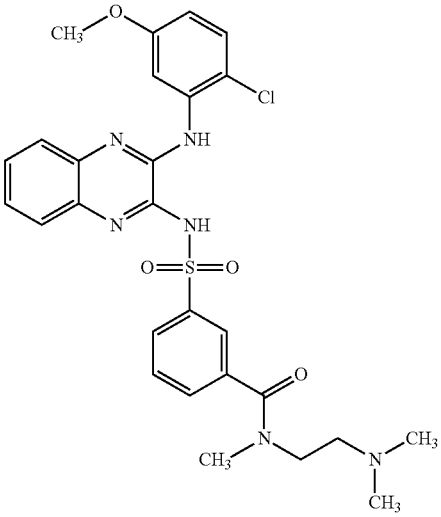 [SMILES: COc1ccc(Cl)c(Nc2nc3ccccc3nc2NS(=O)(=O)c2cccc(C(=O)N(C)CCN(C)C)c2)c1] | 3-{[(3-{[2-chloro-5-(methyloxy)phenyl]amino}quinoxalin-2-yl)amino]sulfonyl}-N-[2-(dimethylamino)ethyl]-N-ethylbenzamide |
| 748 | 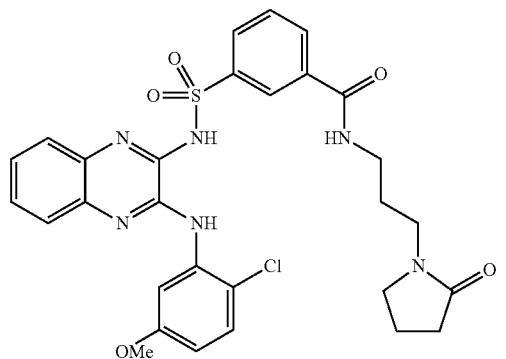 [SMILES: COc1ccc(Cl)c(Nc2nc3ccccc3nc2NS(=O)(=O)c2cccc(C(=O)NCCCN3CCCC3=O)c2)c1] | 3-{[(3-{[2-chloro-5-(methyloxy)phenyl]amino}quinoxalin-2-yl)amino]sulfonyl}-N-[3-(2-oxopyrrolidin-1-yl)propyl]benzamide |
| 749 | 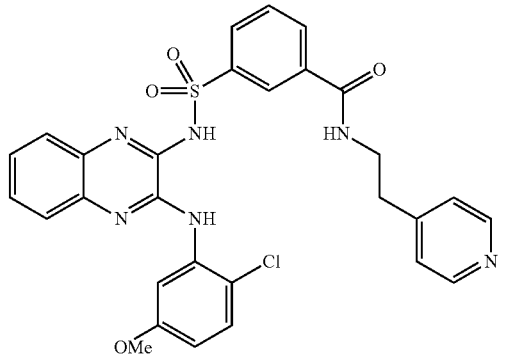 [SMILES: COc1ccc(Cl)c(Nc2nc3ccccc3nc2NS(=O)(=O)c2cccc(C(=O)NCCc3ccncc3)c2)c1] | 3-{[(3-{[2-chloro-5-(methyloxy)phenyl]amino}quinoxalin-2-yl)amino]sulfonyl}-N-(2-pyridin-4-ylethyl)benzamide |

TABLE 1-continued
| Cpd. No. | Structure | IUPAC Name |
|---|---|---|
| 750 | 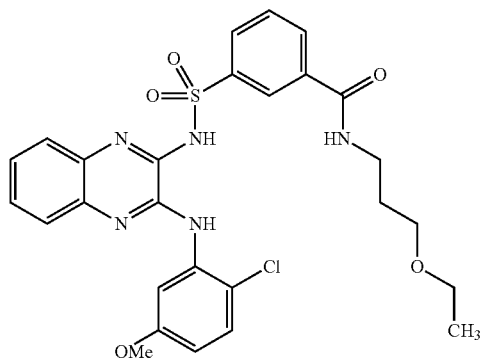 [SMILES: CCOCCCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[3-(ethyloxy)propyl]benzamide |
| 751 | 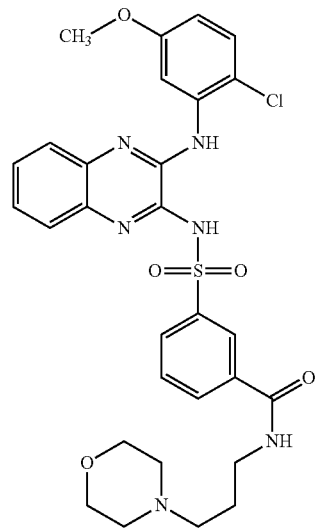 [SMILES: COc1ccc(Cl)c(Nc2nc3ccccc3nc2NS(=O)(=O)c2cccc(C(=O)NCCCN3CCOCC3)c2)c1] | 3-{[(3-{[2-chloro-5-(methyloxy)phenyl]amino}quinoxalin-2-yl)amino]sulfonyl}-N-(3-morpholin-4-ylpropyl)benzamide |
| 752 | 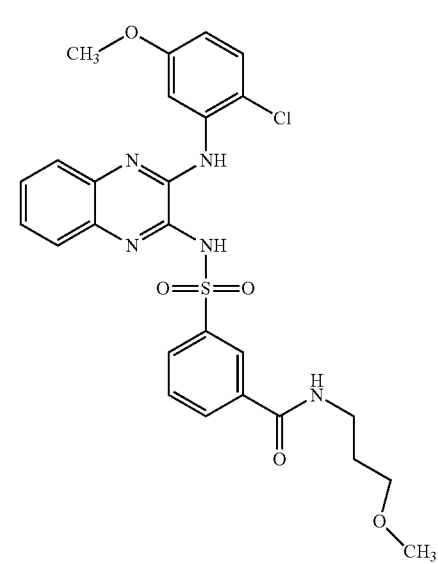 [SMILES: COCCCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[3-(methyloxy)propyl]benzamide |

| Cpd. No. | Structure | IUPAC Name |
|---|---|---|
| 753 | 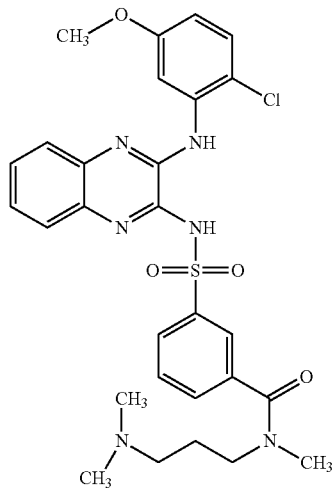 [SMILES: COc1ccc(Cl)c(Nc2nc3ccccc3nc2NS(=O)(=O)c2cccc(C(=O)N(C)CCCN(C)C)c2)c1] | 3-{[(3-{[2-chloro-5-(methyloxy)phenyl]amino}quinoxalin-2-yl)amino]sulfonyl}-N-[3-(dimethylamino)propyl]-N-methylbenzamide |
| 754 | 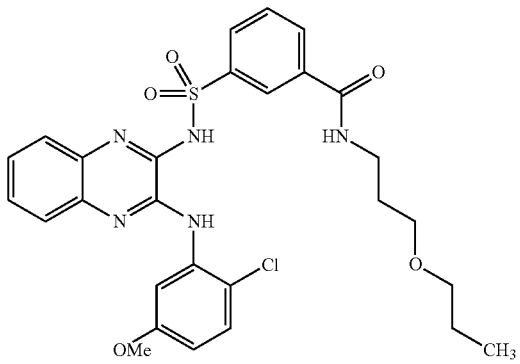 [SMILES: CCCOCCCNC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[3-(propyloxy)propyl]benzamide |
| 755 | 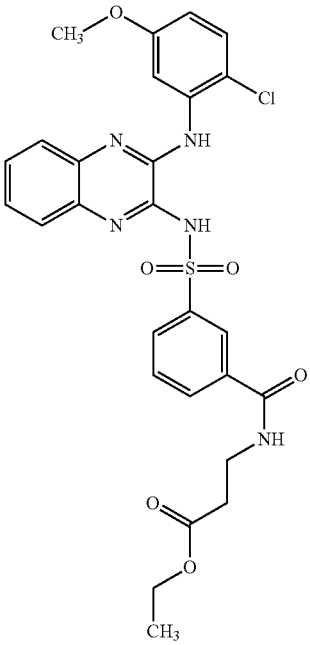 [SMILES: CCOC(=O)CCNC(=O)c1cccc(S(=O)(=O)Nc2nc3ccccc3nc2Nc2cc(OC)ccc2Cl)c1] | ethylN-[(3-{[(3-{[2-chloro-5-(methyloxy)phenyl]amino}quinoxalin-2-yl)amino]sulfonyl}phenyl)carbonyl]-beta-alanine |

TABLE 1-continued
| Cpd. No. | Structure | IUPAC Name |
|---|---|---|
| 756 | 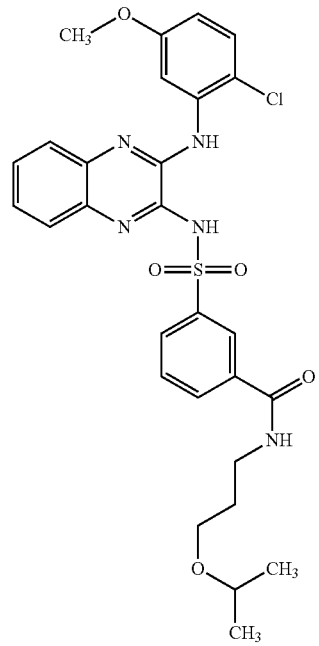 [SMILES: COc1ccc(Cl)c(Nc2nc3ccccc3nc2NS(=O)(=O)c2cccc(C(=O)NCCCOC(C)C)c2)c1] | 3-{[(3-{[2-chloro-5-(methyloxy)phenyl]amino}quinoxalin-2-yl)amino]sulfonyl}-N-{3-[(1-methylethyl)oxy]propyl}benzamide |
| 757 | 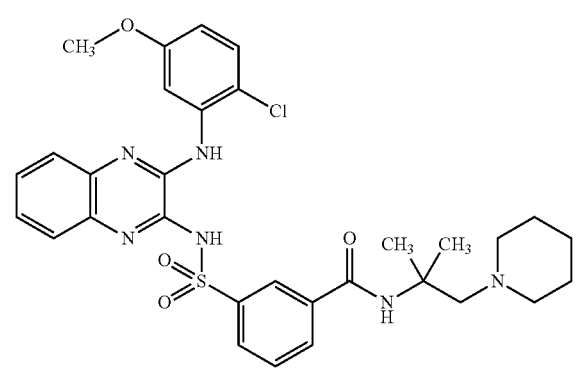 [SMILES: COc1ccc(Cl)c(Nc2nc3ccccc3nc2NS(=O)(=O)c2cccc(C(=O)NC(C)(C)CN3CCCCC3)c2)c1] | 3-{[(3-{[2-chloro-5-(methyloxy)phenyl]amino}quinoxalin-2-yl)amino]sulfonyl}-N-(1,1-dimethyl-2-piperidin-1-ylethyl)benzamide |
| 758 | 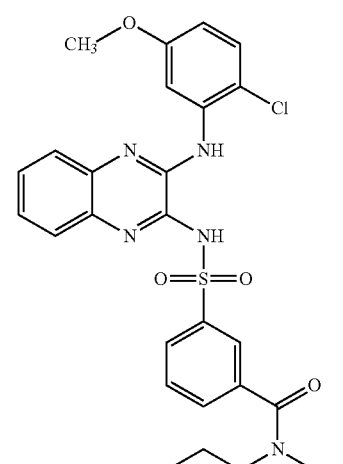 | 3-{[(3-{[2-chloro-5-(methyloxy)phenyl]amino}quinoxalin-2-yl)amino]sulfonyl}-N-methyl-N-propylbenzamide |

| Cpd. No. | Structure | IUPAC Name |
|---|---|---|
| 759 | 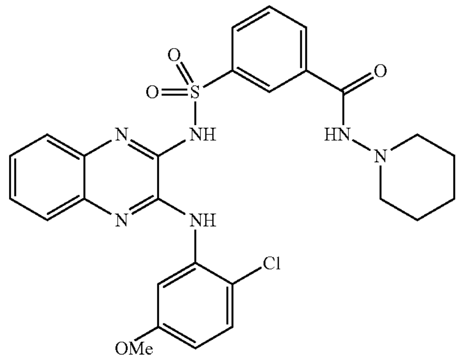 [SMILES: COc1ccc(Cl)c(Nc2nc3ccccc3nc2NS(=O)(=O)c2cccc(C(=O)NN3CCCCC3)c2)c1] | 3-{[(3-{[2-chloro-5-(methyloxy)phenyl]amino}quinoxalin-2-yl)amino]sulfonyl}-N-piperidin-1-ylbenzamide |
| 760 | 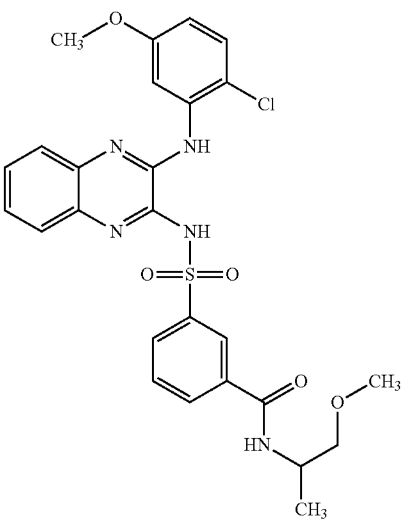 [SMILES: COCC(C)NC(=O)c1cccc(S(=O)(=O)Nc2nc3ccccc3nc2Nc2cc(OC)ccc2Cl)c1] | 3-{[(3-{[2-chloro-5-(methyloxy)phenyl]amino}quinoxalin-2-yl)amino]sulfonyl}-N-[1-methyl-2-(methyloxy)ethyl]benzamide |
| 761 | 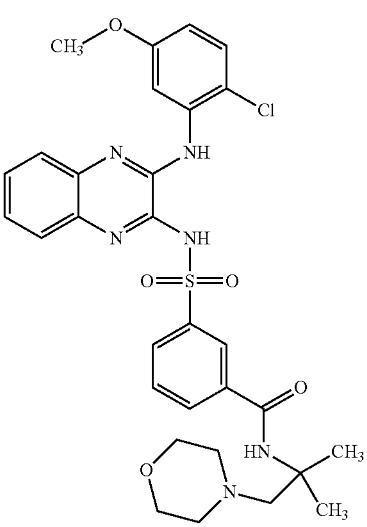 [SMILES: COc1ccc(Cl)c(Nc2nc3ccccc3nc2NS(=O)(=O)c2cccc(C(=O)NC(C)(C)CN3CCOCC3)c2)c1] | 3-{[(3-{[2-chloro-5-(methyloxy)phenyl]amino}quinoxalin-2-yl)amino]sulfonyl}-N-(1,1-dimethyl-2-mopholin-4-ylethyl)benzamide |

TABLE 1-continued

| Cpd. No. | Structure | IUPAC Name |
|---|---|---|
| 762 | 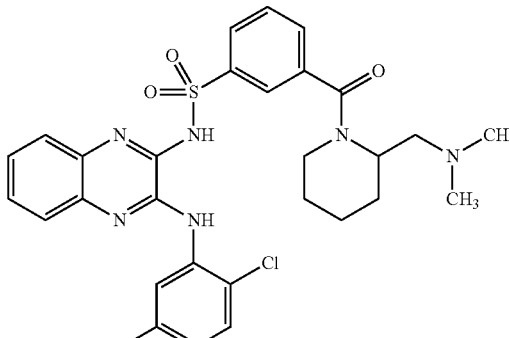 | N-(3-{[2-chloro-5-(methyloxy)phenyl]amino}quinoxalin-2-yl)-3-({2-[(dimethylamino)methyl]piperidin-1-yl}carbonyl)benzenesulfonamide |
| 763 | 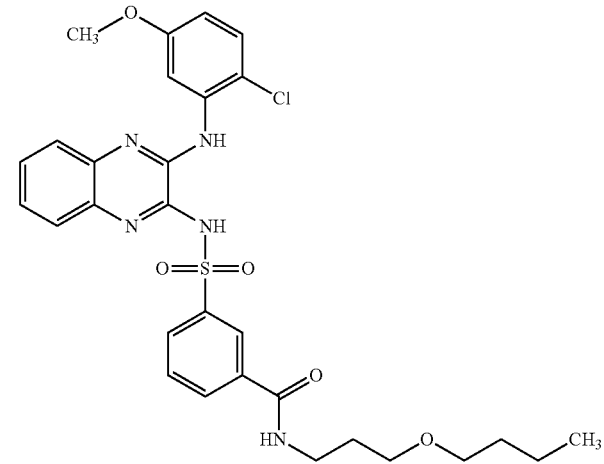 [SMILES: CCCCOCCCNC(=O)c1cccc(S(=O)(=O)Nc2nc3ccccc3nc2Nc2cc(OC)ccc2Cl)c1] | N-[3-(butyloxy)propyl]-3-{[(3-{[2-chloro-5-(methyloxy)phenyl]amino}quinoxalin-2-yl)amino]sulfonyl}benzamide |
| 764 | 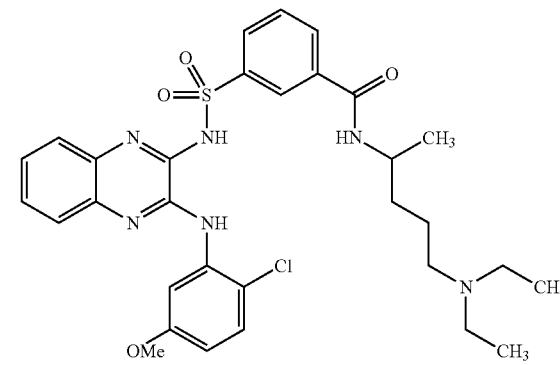 | 3-{[(3-{[2-chloro-5-(methyloxy)phenyl]amino}quinoxalin-2-yl)amino]sulfonyl}-N-[4-(diethylamino)-1-methylbutyl]benzamide |
| 765 | 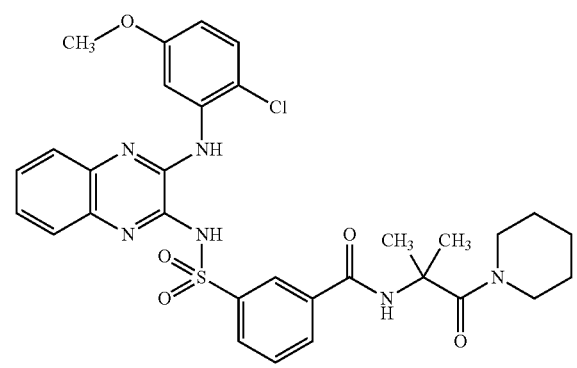 [SMILES: COc1ccc(Cl)c(Nc2nc3ccccc3nc2NS(=O)(=O)c2cccc(C(=O)NC(C)(C)C(=O)N3CCCCC3)c2)c1] | 3-{[(3-{[2-chloro-5-(methyloxy)phenyl]amino}quinoxalin-2-yl)amino]sulfonyl}-N-(1,1-dimethyl-2-oxo-2-piperidin-1-ylethyl)benzamide |

TABLE 1-continued

| Cpd. No. | Structure | IUPAC Name |
|---|---|---|
| 766 | 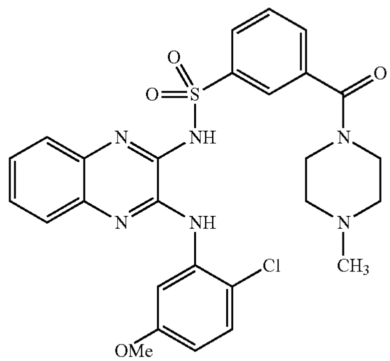 [SMILES: COc1ccc(Cl)c(Nc2nc3ccccc3nc2NS(=O)(=O)c2cccc(C(=O)N3CCN(C)CC3)c2)c1] | N-(3-{[2-chloro-5-(methyloxy)phenyl]amino}quinoxalin-2-yl)-3-[(4-methylpiperazin-1-yl)carbonyl]benzenesulfonamide |
| 767 | 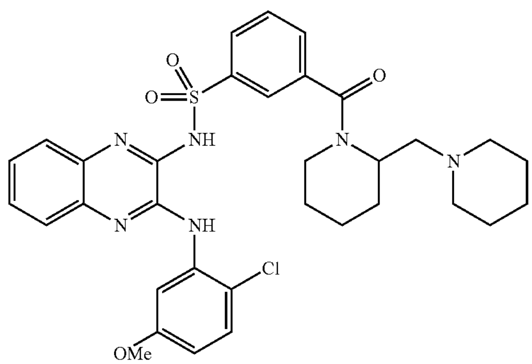 [SMILES: COc1ccc(Cl)c(Nc2nc3ccccc3nc2NS(=O)(=O)c2cccc(C(=O)N3CCCCC3CN3CCCCC3)c2)c1] | N-(3-{[2-chloro-5-(methyloxy)phenyl]amino}quinoxalin-2-yl)-3-{[2-(piperidin-1-ylmethyl)piperidin-1-yl]carbonyl}benzenesulfonamide |
| 768 | 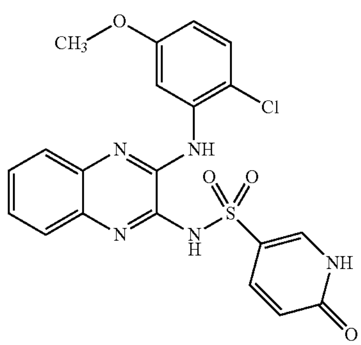 [SMILES: COc1ccc(Cl)c(Nc2nc3ccccc3nc2NS(=O)(=O)c2ccc(=O)[nH]c2)c1] | N-(3-{[2-chloro-5-(methyloxy)phenyl]amino}quinoxalin-2-yl)-6-oxo-1,6-dihydropyridine-3-sulfonamide |
| 769 | 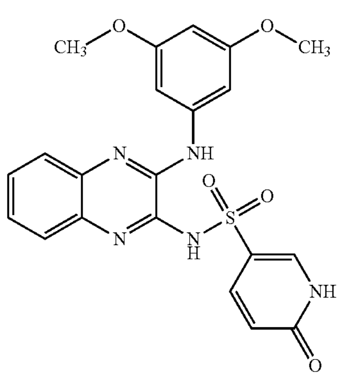 [SMILES: COc1cc(Nc2nc3ccccc3nc2NS(=O)(=O)c2ccc(=O)[nH]c2)cc(OC)c1] | N-(3-{[3,5-bis(methyloxy)phenyl]amino}quinoxalin-2-yl)-6-oxo-1,6-dihydropyridine-3-sulfonamide |

TABLE 1-continued

| Cpd. No. | Structure | IUPAC Name |
|---|---|---|
| 770 | 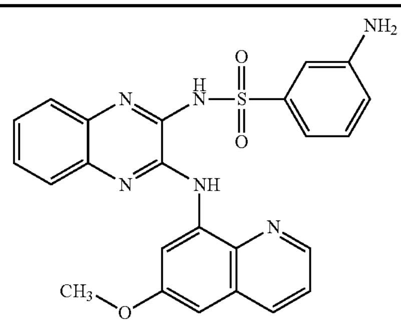 | 3-amino-N-(3-{[6-(methyloxy)quinolin-8-yl]amino}quinoxalin-2-yl)benzenesulfonamide |
| 771 | 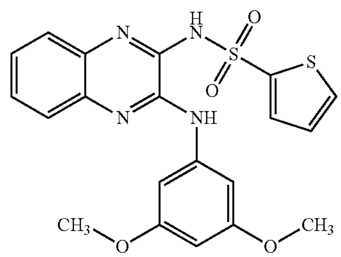 [SMILES: COc1cc(Nc2nc3ccccc3nc2NS(=O)(=O)c2cccs2)cc(OC)c1] | N-(3-{[3,5-bis(methyloxy)phenyl]amino}quinoxalin-2-yl)ethisophene-2-sulfonamide |
| 772 | 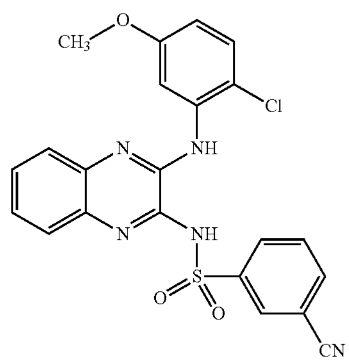 [SMILES: COc1ccc(Cl)c(Nc2nc3ccccc3nc2NS(=O)(=O)c2cccc(C#N)c2)c1] | N-(3-{[2-chloro-5-(methyloxy)phenyl]amino}quinoxalin-2-yl)-3-cyanobenzenesulfonamide |
| 773 | 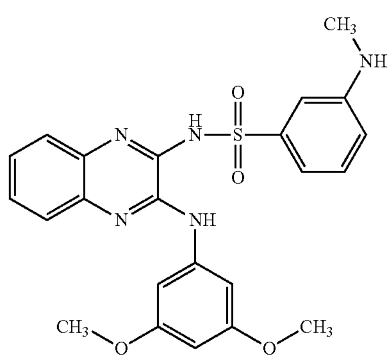 [SMILES: CNc1cccc(S(=O)(=O)Nc2nc3ccccc3nc2Nc2cc(OC)cc(OC)c2)c1] | N-(3-{[3,5-bis(methyloxy)phenyl]amino}quinoxalin-2-yl)-3-(methylamino)benzenesulfonamide |
| 774 | 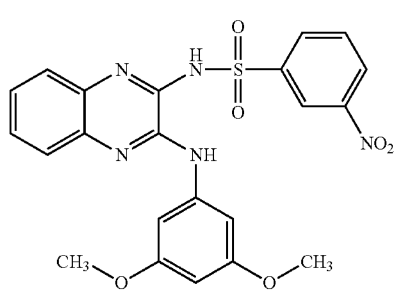 [SMILES: COc1cc(Nc2nc3ccccc3nc2NS(=O)(=O)c2cccc([N+](=O)[O-])c2)cc(OC)c1] | N-(2-{[3,5-bis(methyloxy)phenyl]amino}pyrido[2,3-b]pyrazin-3-yl)-3-nitrobenzenesulfonamide |

TABLE 1-continued

| Cpd. No. | Structure | IUPAC Name |
|---|---|---|
| 775 | 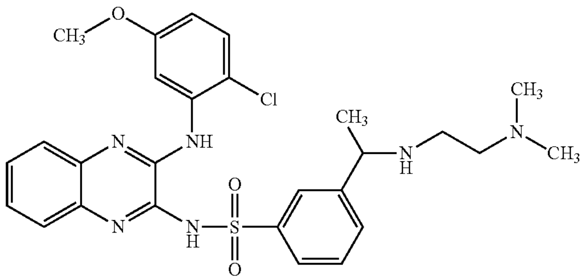 [SMILES: COc1ccc(Cl)c(Nc2nc3ccccc3nc2NS(=O)(=O)c2cccc(C(C)NCCN(C)C)c2)c1] | N-(3-{[2-chloro-5-(methyloxy)phenyl]amino}quinoxalin-2-yl)-3-(1-{[2-(dimethylamino)ethyl]amino}ethyl)benzenesulfonamide |
| 776 | 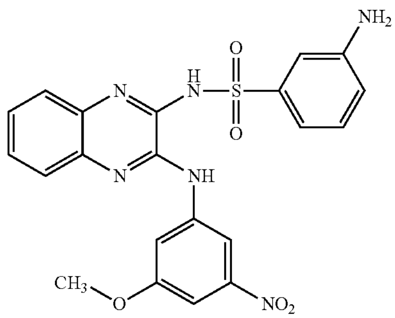 [SMILES: COc1cc(Nc2nc3ccccc3nc2NS(=O)(=O)c2cccc(N)c2)cc([N+](=O)[O-])c1] | 3-amino-N-(3-{[3-(methyloxy)-5-nitrophenyl]amino}quinoxalin-2-yl)benzenesulfonamide |
| 777 | 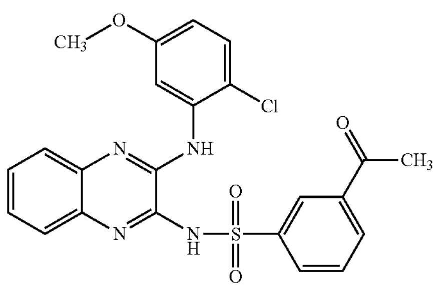 [SMILES: COc1ccc(Cl)c(Nc2nc3ccccc3nc2NS(=O)(=O)c2cccc(C(C)=O)c2)c1] | 3-acetyl-N-(3-{[2-chloro-5-(methyloxy)phenyl]amino}quinoxalin-2-yl)benzenesulfonamide |
| 778 | 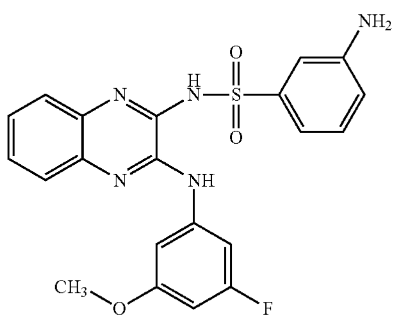 [SMILES: COc1cc(F)cc(Nc2nc3ccccc3nc2NS(=O)(=O)c2cccc(N)c2)c1] | 3-amino-N-(3-{[3-fluoro-5-(methyloxy)phenyl]amino}quinoxalin-2-yl)benzenesulfonamide |
| 779 | 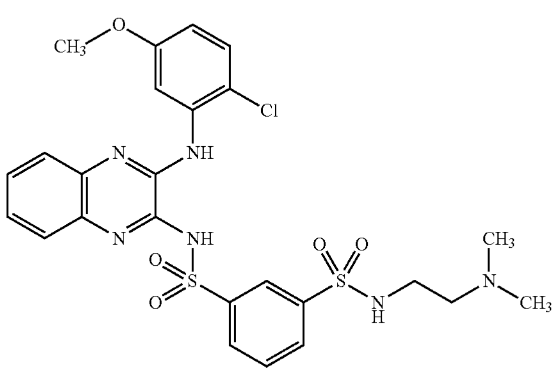 [SMILES: COc1ccc(Cl)c(Nc2nc3ccccc3nc2NS(=O)(=O)c2cccc(S(=O)(=O)NCCN(C)C)c2)c1] | N-(3-{[2-chloro-5-(methyloxy)phenyl]amino}quinoxalin-2-yl)-N'-[2-(dimethylamino)ethyl]benzamide-1,3-disulfonamide |

TABLE 1-continued

| Cpd. No. | Structure | IUPAC Name |
|---|---|---|
| 780 | 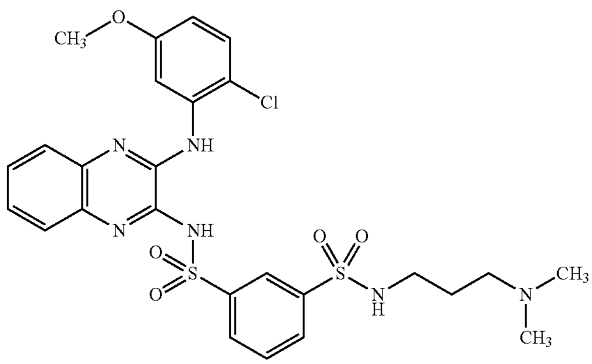 [SMILES: COc1ccc(Cl)c(Nc2nc3ccccc3nc2NS(=O)(=O)c2cccc(S(=O)(=O)NCCCN(C)C)c2)c1] | N-(3-{[2-chloro-5-(methyloxy)phenyl]amino}quinoxalin-2-yl)-N'-[3-(dimethylamino)propyl]benzene-1,3-disulfonamide |
| 781 | 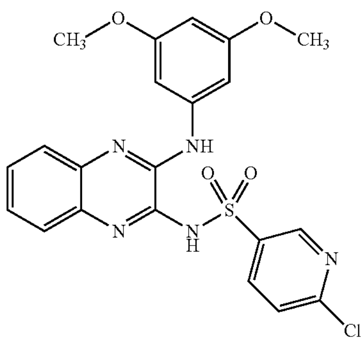 [SMILES: COc1cc(Nc2nc3ccccc3nc2NS(=O)(=O)c2ccc(Cl)nc2)cc(OC)c1] | N-(3-{[3,5-bis(methyloxy)phenyl]amino}quinoxalin-2-yl)-6-chloropyridine-3-sulfonamide |
| 782 | 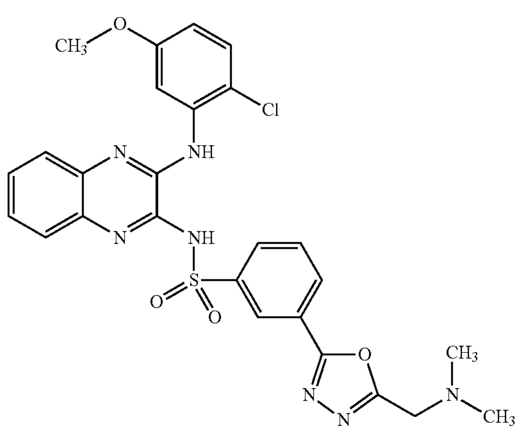 [SMILES: COc1ccc(Cl)c(Nc2nc3ccccc3nc2NS(=O)(=O)c2cccc(-c3nnc(CN(C)C)o3)c2)c1] | N-(3-{[2-chloro-5-(methyloxy)phenyl]amino}quinoxalin-2-yl)-3-{5-[(dimethylamino)methyl]-1,3,4-oxadiazol-2-yl}benzenesulfonamide |
| 783 | 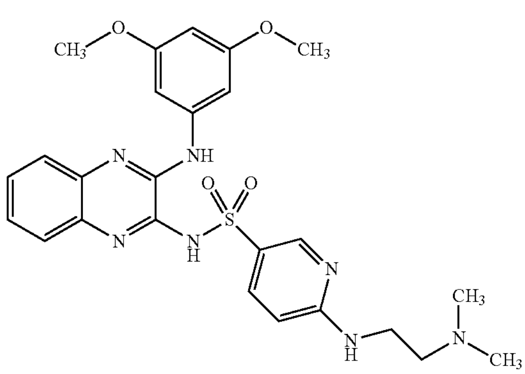 [SMILES: COc1cc(Nc2nc3ccccc3nc2NS(=O)(=O)c2ccc(NCCN(C)C)nc2)cc(OC)c1] | N-(3-{[3,5-bis(methyloxy)phenyl]amino}quinoxalin-2-yl)-6-{[2-(dimethylamino)ethyl]amino}pyridine-3-sulfonamide |

| Cpd. No. | Structure | IUPAC Name |
|---|---|---|
| 784 | 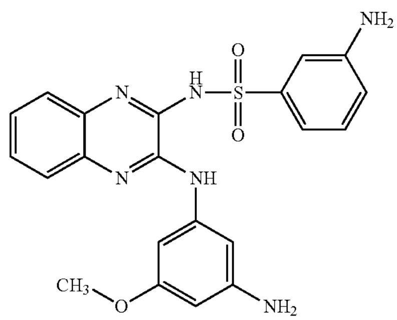 | 3-amino-N-(3-{[3-amino-5-(methyloxy)phenyl]amino}quinoxalin-2-yl)benzenesulfonamide |
| 785 | 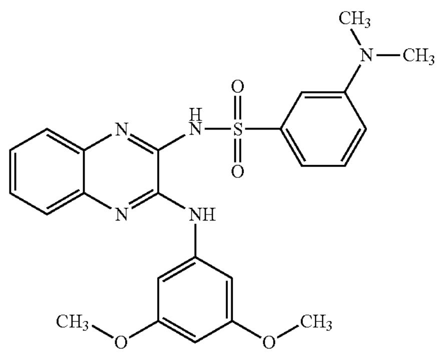 [SMILES: COc1cc(Nc2nc3ccccc3nc2NS(=O)(=O)c2cccc(N(C)C)c2)cc(OC)c1] | N-(3-{[3,5-(methyloxy)phenyl]amino}quinoxalin-2-yl)-3-(dimethylamino)benzenesulfonamide |
| 786 | 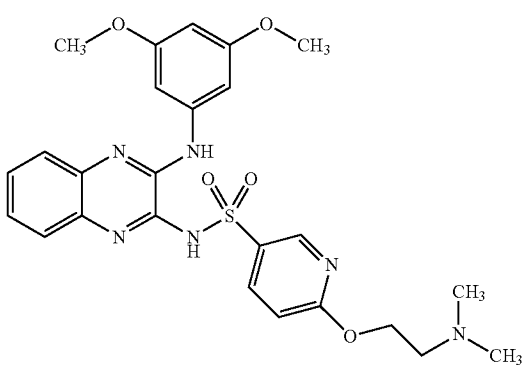 [SMILES: COc1cc(Nc2nc3ccccc3nc2NS(=O)(=O)c2ccc(OCCN(C)C)nc2)cc(OC)c1] | N-(3-{[3,5-(methyloxy)phenyl]amino}quinoxalin-2-yl)-6-{[2-(dimethylamino)ethyl]oxy}pyridine-3-sulfonamide |
| 787 | 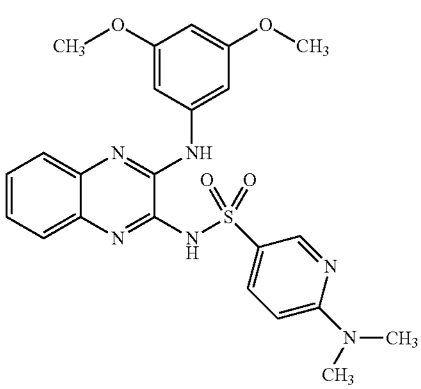 [SMILES: COc1cc(Nc2nc3ccccc3nc2NS(=O)(=O)c2ccc(N(C)C)nc2)cc(OC)c1] | N-(3-{[3,5-(methyloxy)phenyl]amino}quinoxalin-2-yl)-6-(dimethylamino)pyridine-3-sulfonamide |

TABLE 1-continued

| Cpd. No. | Structure | IUPAC Name |
|---|---|---|
| 788 | 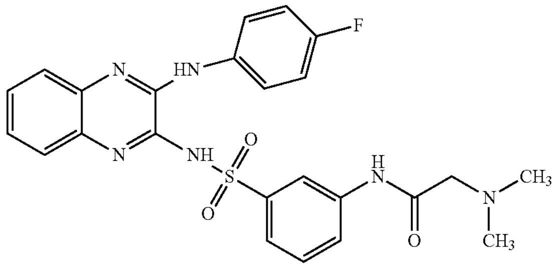 [SMILES: CN(C)CC(=O)Nc1cccc(S(=O)(=O)Nc2nc3ccccc3nc2Nc2ccc(F)cc2)c1] | N-{3-[({3-[(4-fluorophenyl)amino]quinoxalin-2-yl}amino)sulfonyl]phenyl}-N-2-,N-2-dimethylglycinamide |
| 789 | 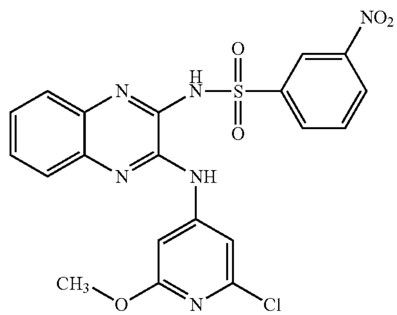 [SMILES: COc1cc(Nc2nc3ccccc3nc2NS(=O)(=O)c2cccc([N+](=O)[O-])c2)cc(Cl)n1] | N-(3-{[2-chloro-6-(methyloxy)pyridin-4-yl]amino}quinoxalin-2-yl)-3-nitrobenzenesulfonamide |
| 790 | 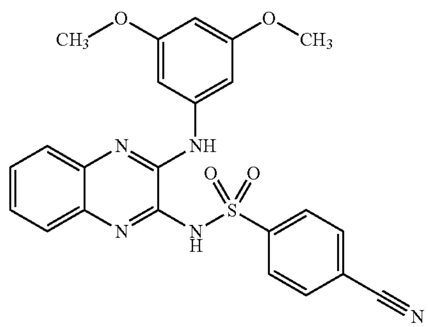 [SMILES: COc1cc(Nc2nc3ccccc3nc2NS(=O)(=O)c2ccc(C#N)cc2)cc(OC)c1] | N-(3-{[3,5-bis(methyloxy)phenyl]amino}quinoxalin-2-yl)-4-cyanobenzenesulfonamide |
| 791 | 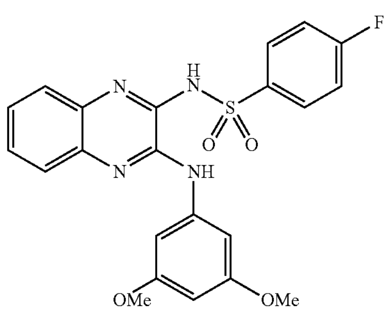 [SMILES: COc1cc(Nc2nc3ccccc3nc2NS(=O)(=O)c2ccc(F)cc2)cc(OC)c1] | N-(3-{[3,5-bis(methyloxy)phenyl]amino}quinoxalin-2-yl)-4-fluorobenzenesulfonamide |
| 792 | 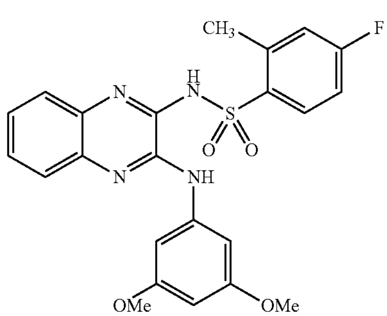 [SMILES: COc1cc(Nc2nc3ccccc3nc2NS(=O)(=O)c2ccc(F)cc2C)cc(OC)c1] | N-(3-{[3,5-bis(methyloxy)phenyl]amino}quinoxalin-2-yl)-4-fluoro-2-methylbenzenesulfonamide |

TABLE 1-continued
| Cpd. No. | Structure | IUPAC Name |
|---|---|---|
| 793 | 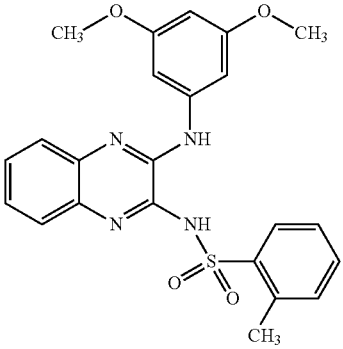 [SMILES: COc1cc(Nc2nc3ccccc3nc2NS(=O)(=O)c2ccccc2C)cc(OC)c1] | N-(3-{[3,5-(methyloxy)phenyl]amino}quinoxalin-2-yl)-2-methylbenzenesulfonamide |
| 794 | 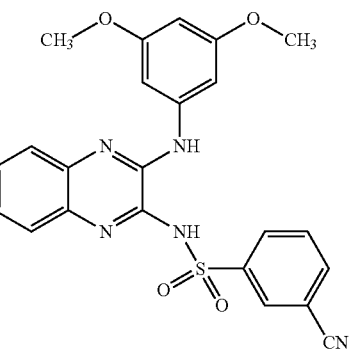 | N-(3-{[3,5-(methyloxy)phenyl]amino}quinoxalin-2-yl)-3-cyanobenzenesulfonamide |
| 795 | 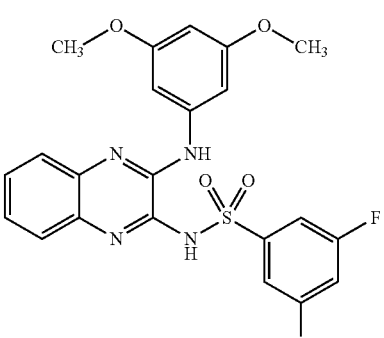 | N-(3-{[3,5-bis(methyloxy)phenyl]amino}quinoxalin-2-yl)-3,5-difluorobenzenesulfonamide |
| 796 | 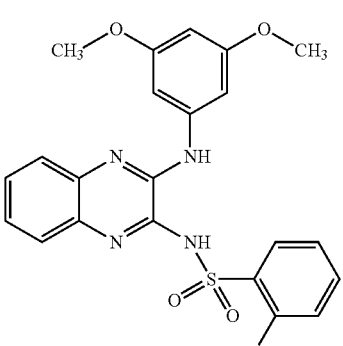 | N-(3-{[3,5-bis(methyloxy)phenyl]amino}quinoxalin-2-yl)-2-chlorobenzenesulfonamide |

TABLE 1-continued

| Cpd. No. | Structure | IUPAC Name |
|---|---|---|
| 797 | 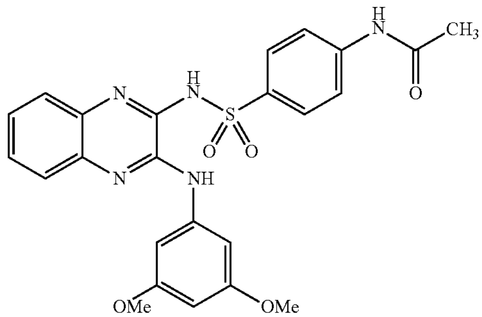 [SMILES: COc1cc(Nc2nc3ccccc3nc2NS(=O)(=O)c2ccc(NC(C)=O)cc2)cc(OC)c1] | N-(4-{[(3-{[3,5-bis(methyloxy)phenyl]amino}quinoxalin-2-yl)amino]sulfonyl}phenyl)acetamide |
| 798 | 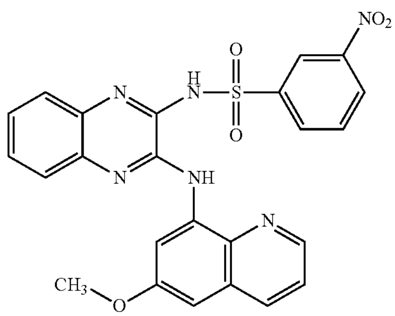 | N-(3-{[6-(methyloxy)quinolin-8-yl]amino}quinoxalin-2-yl)-3-nitrobenzenesulfonamide |
| 799 | 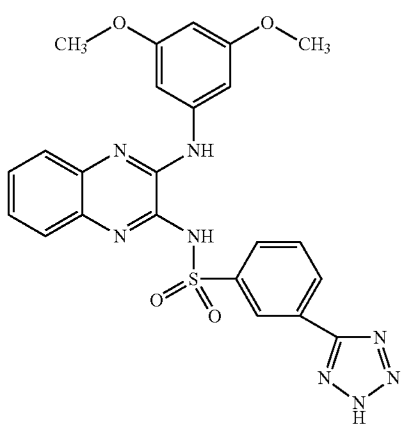 [SMILES: COc1cc(Nc2nc3ccccc3nc2NS(=O)(=O)c2cccc(-c3nn[nH]n3)c2)cc(OC)c1] | N-(3-{[3,5-bis(methyloxy)phenyl]amino}quinoxalin-2-yl)-3-(2H-tetrazol-5-yl)benzenesulfonamide |
| 800 | 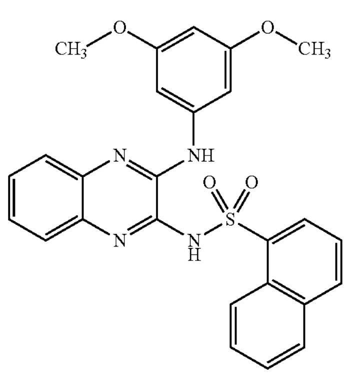 [SMILES: COc1cc(Nc2nc3ccccc3nc2NS(=O)(=O)c2cccc3ccccc23)cc(OC)c1] | N-(3-{[3,5-bis(methyloxy)phenyl]amino}quinoxalin-2-yl)naphthalene-1-sulfonamide |

TABLE 1-continued

| Cpd. No. | Structure | IUPAC Name |
|---|---|---|
| 801 | 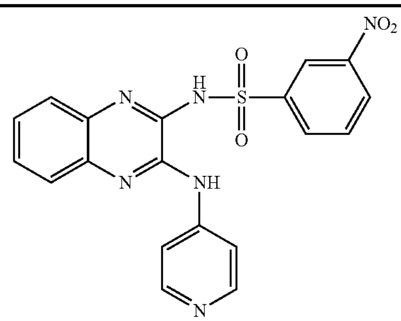 | 3-nitro-N-[3-(pyridin-4-ylamino)quinoxalin-2-yl]benzenesulfonamide |
| 802 | 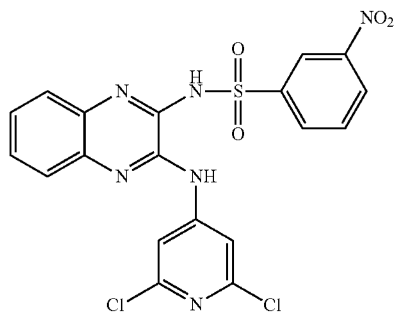 [SMILES: O=[N+]([O-])c1cccc(S(=O)(=O)Nc2nc3ccccc3nc2Nc2cc(Cl)nc(Cl)c2)c1] | N-{3-[(2,6-dichloropyridin-4-yl)amino]quinoxalin-2-yl}-3-nitrobenzenesulfonamide |
| 803 | 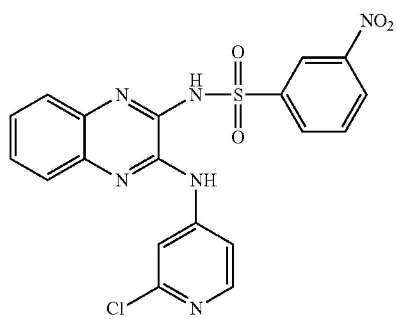 [SMILES: O=[N+]([O-])c1cccc(S(=O)(=O)Nc2nc3ccccc3nc2Nc2ccnc(Cl)c2)c1] | N-{3-[(2-chloropyridin-4-yl)amino]quinoxalin-2-yl}-3-nitrobenzenesulfonamide |
| 804 | 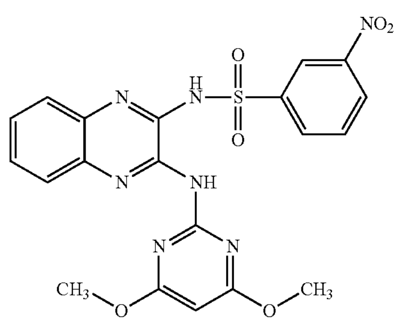 [SMILES: COc1cc(OC)nc(Nc2nc3ccccc3nc2NS(=O)(=O)c2cccc([N+](=O)[O-])c2)n1] | N-(3-{[4,6-bis(methyloxy)pyrimidin-2-yl]amino}quinoxalin-2-yl)-3-nitrobenzenesulfonamide |
| 805 | 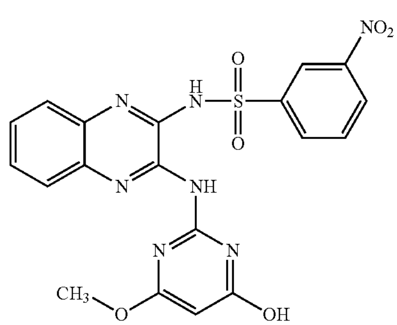 [SMILES: COc1cc(O)nc(Nc2nc3ccccc3nc2NS(=O)(=O)c2cccc([N+](=O)[O-])c2)n1] | N-(3-{[4-hydroxy-6-(methyloxy)pyrimidin-2-yl]amino}quinoxalin-2-yl)-3-nitrobenzenesulfonamide |

TABLE 1-continued

| Cpd. No. | Structure | IUPAC Name |
| --- | --- | --- |
| 806 | 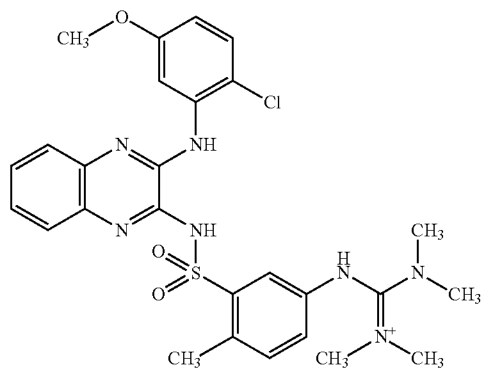 [SMILES: COc1ccc(Cl)c(Nc2nc3ccccc3nc2NS(=O)(=O)c2cc(NC(N(C)C)=[N+](C)C)ccc2C)c1] | N-{[(3-{[(3-{[2-chloro-5-(methyloxy)phenyl]amino}quinoxalin-2-yl)amino]sulfonyl}-4-methylphenyl)amino](dimethylamino)methylidene}-N-methylmethanaminium |
| 807 | 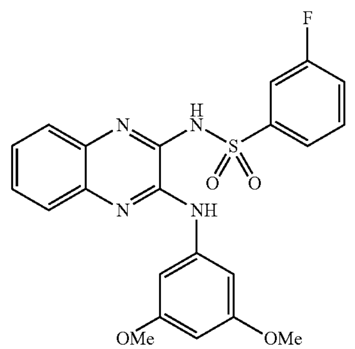 [SMILES: COc1cc(Nc2nc3ccccc3nc2NS(=O)(=O)c2cccc(F)c2)cc(OC)c1] | N-(3-{[3,5-bis(methyloxy)phenyl]amino}quinoxalin-2-yl)-3-fluorobenzenesulfonamide |
| 808 | 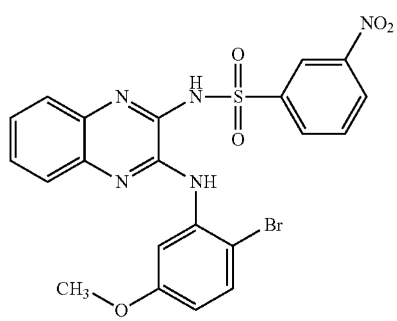 [SMILES: COc1ccc(Br)c(Nc2nc3ccccc3nc2NS(=O)(=O)c2cccc([N+](=O)[O-])c2)c1] | N-(3-{[2-bromo-5-(methyloxy)phenyl]amino}quinoxalin-2-yl)-3-nitrobenzenesulfonamide |
| 809 | 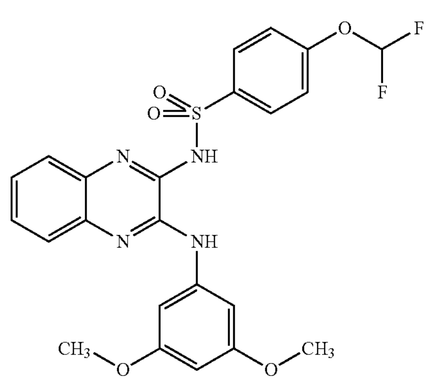 [SMILES: COc1cc(Nc2nc3ccccc3nc2NS(=O)(=O)c2ccc(OC(F)F)cc2)cc(OC)c1] | N-(3-{[3,5-bis(methyloxy)phenyl]amino}quinoxalin-2-yl)-4-[(difluoromethyl)oxy]benzenesulfonamide |

TABLE 1-continued

| Cpd. No. | Structure | IUPAC Name |
|---|---|---|
| 810 | 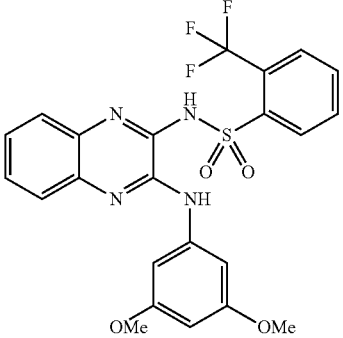 [SMILES: COc1cc(Nc2nc3ccccc3nc2NS(=O)(=O)c2ccccc2C(F)(F)F)cc(OC)c1] | N-(3-{[3,5-bis(methyloxy)phenyl]amino}quinoxalin-2-yl)-2-(trifluoromethyl)benzenesulfonamide |
| 811 | 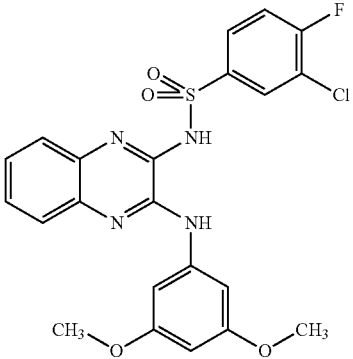 [SMILES: COc1cc(Nc2nc3ccccc3nc2NS(=O)(=O)c2ccc(F)c(Cl)c2)cc(OC)c1] | N-(3-{[3,5-bis(methyloxy)phenyl]amino}quinoxalin-2-yl)-3-chloro-4-fluorobenzenesulfonamide |
| 812 | 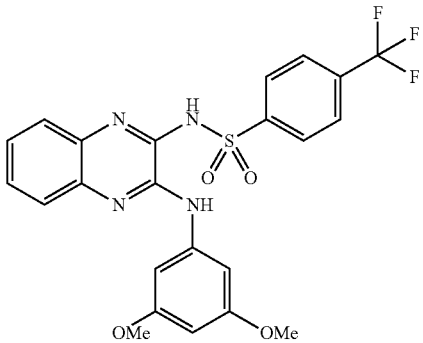 [SMILES: COc1cc(Nc2nc3ccccc3nc2NS(=O)(=O)c2ccc(C(F)(F)F)cc2)cc(OC)c1] | N-(3-{[3,5-bis(methyloxy)phenyl]amino}quinoxalin-2-yl)-4-(trifluoromethyl)benzenesulfonamide |
| 813 | 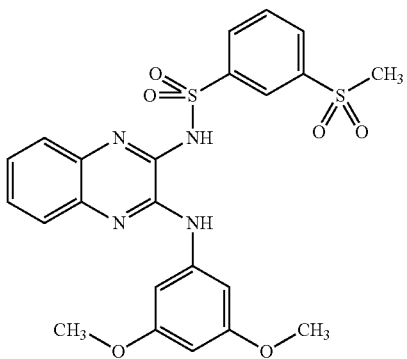 [SMILES: COc1cc(Nc2nc3ccccc3nc2NS(=O)(=O)c2cccc(S(C)(=O)=O)c2)cc(OC)c1] | N-(3-{[3,5-bis(methyloxy)phenyl]amino}quinoxalin-2-yl)-3-(methylsulfonyl)benzenesulfonamide |

TABLE 1-continued

| Cpd. No. | Structure | IUPAC Name |
|---|---|---|
| 814 | 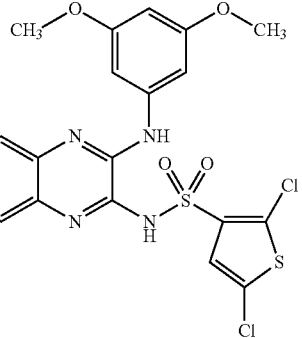 | N-(3-{[3,5-bis(methyloxy)phenyl]amino}quinoxalin-2-yl)-2,5-dichlorothisophene-3-sulfonamide |
| 815 | 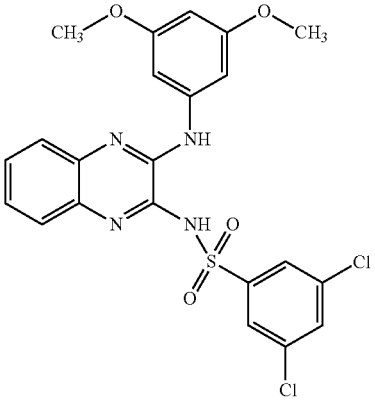 [SMILES: COc1cc(Nc2nc3ccccc3nc2NS(=O)(=O)c2cc(Cl)cc(Cl)c2)cc(OC)c1] | N-(3-{[3,5-bis(methyloxy)phenyl]amino}quinoxalin-2-yl)-3,5-dichlorobenzenesulfonamide |
| 816 | 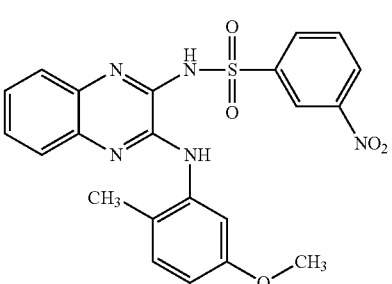 | N-(3-{[2-methyl-5-bis(methyloxy)phenyl]amino}quinoxalin-2-yl)-3-nitrobenzenesulfonamide |
| 817 | 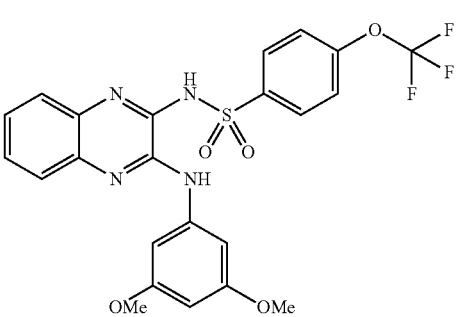 [SMILES: COc1cc(Nc2nc3ccccc3nc2NS(=O)(=O)c2ccc(OC(F)(F)F)cc2)cc(OC)c1] | N-(3-{[3,5-bis(methyloxy)phenyl]amino}quinoxalin-2-yl)-4-[(trifluoromethyl)oxy]benzenesulfonamide |

TABLE 1-continued

| Cpd. No. | Structure | IUPAC Name |
|---|---|---|
| 818 | 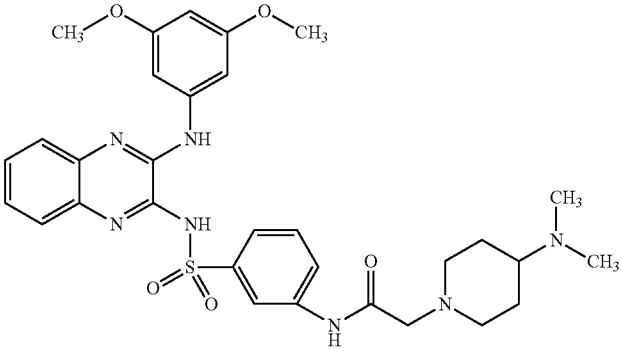 [SMILES: COc1cc(Nc2nc3ccccc3nc2NS(=O)(=O)c2cccc(NC(=O)CN3CCC(N(C)C)CC3)c2)cc(OC)c1] | N-(3-{[(3-{[3,5-bis(methyloxy)phenyl]amino}quinoxalin-2-yl)amino]sulfonyl}phenyl)-2-[4-(dimethylamino)piperidin-1-yl]acetamide |
| 819 | 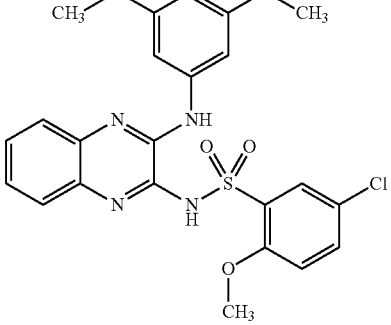 | N-(3-{[3,5-bis(methyloxy)phenyl]amino}quinoxalin-2-yl)-5-chloro-2-(methyloxy)benzenesulfonamide |
| 820 | 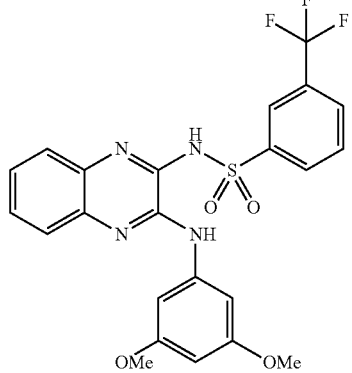 | N-(3-{[3,5-bis(methyloxy)phenyl]amino}quinoxalin-2-yl)-3-(trifluoromethyl)benzenesulfonamide |
| 821 | 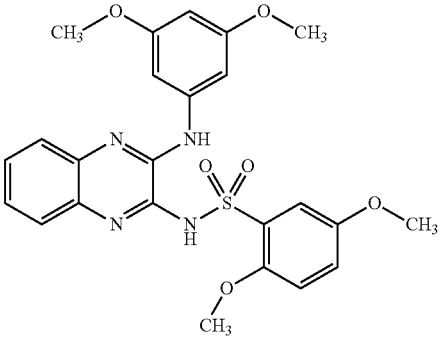 [SMILES: COc1cc(Nc2nc3ccccc3nc2NS(=O)(=O)c2cc(OC)ccc2OC)cc(OC)c1] | N-(3-{[3,5-bis(methyloxy)phenyl]amino}quinoxalin-2-yl)-2,5-bis(methyloxy)benzenesulfonamide |

TABLE 1-continued

| Cpd. No. | Structure | IUPAC Name |
|---|---|---|
| 822 | 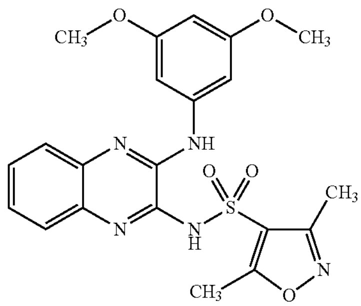 [SMILES: COc1cc(Nc2nc3ccccc3nc2NS(=O)(=O)c2c(C)noc2C)cc(OC)c1] | N-(3-{[3,5-bis(methyloxy)phenyl]amino}quinoxalin-2-yl)-3,5-dimethylisoxazole-4-sulfonamide |
| 823 | 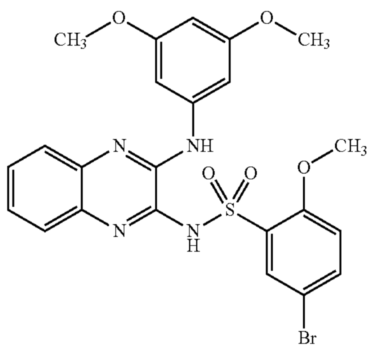 [SMILES: COc1cc(Nc2nc3ccccc3nc2NS(=O)(=O)c2cc(Br)ccc2OC)cc(OC)c1] | N-(3-{[3,5-bis(methyloxy)phenyl]amino}quinoxalin-2-yl)-5-bromo-2-(methyloxy)benzenesulfonamide |
| 824 | 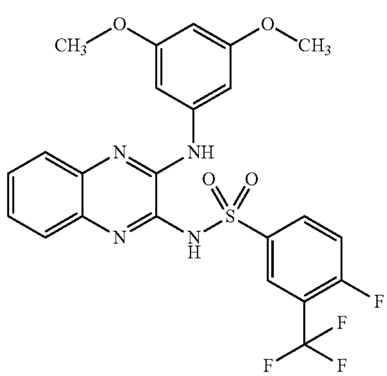 [SMILES: COc1cc(Nc2nc3ccccc3nc2NS(=O)(=O)c2ccc(F)c(C(F)(F)F)c2)cc(OC)c1] | N-(3-{[3,5-bis(methyloxy)phenyl]amino}quinoxalin-2-yl)-4-fluoro-3-(trifluoromethyl)benzenesulfonamide |
| 825 | 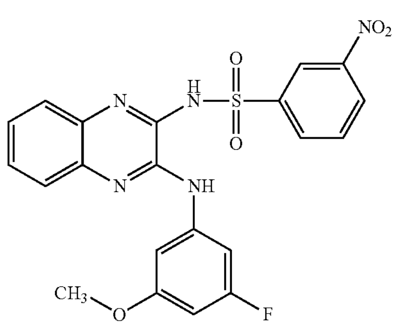 | N-(3-{[3-fluoro-5-(methyloxy)phenyl]amino}quinoxalin-2-yl)-3-nitrobenzenesulfonamide |

TABLE 1-continued
| Cpd. No. | Structure | IUPAC Name |
|---|---|---|
| 826 | 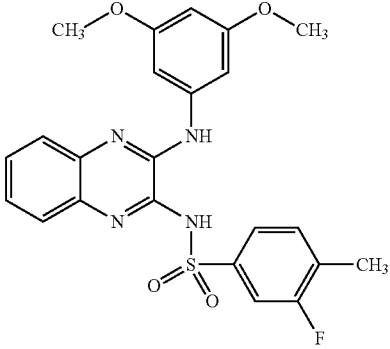 [SMILES: COc1cc(Nc2nc3ccccc3nc2NS(=O)(=O)c2ccc(C)c(F)c2)cc(OC)c1] | N-(3-{[3,5-bis(methyloxy)phenyl]amino}quinoxalin-2-yl)-3-fluoro-4-methylbenzenesulfonamide |
| 827 | 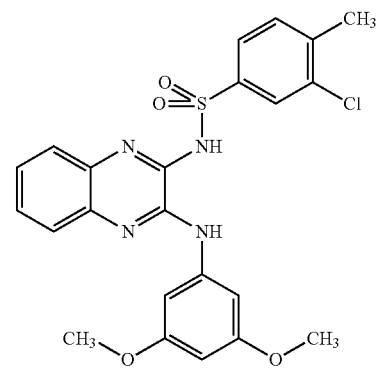 [SMILES: COc1cc(Nc2nc3ccccc3nc2NS(=O)(=O)c2ccc(C)c(Cl)c2)cc(OC)c1] | N-(3-{[3,5-bis(methyloxy)phenyl]amino}quinoxalin-2-yl)-3-chloro-4-methylbenzenesulfonamide |
| 828 | 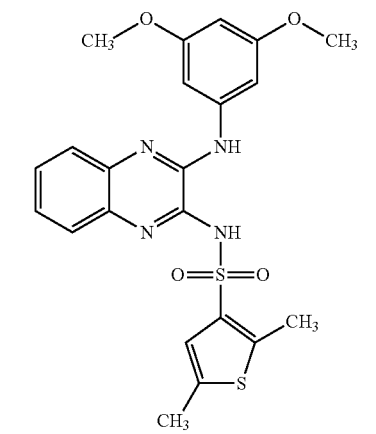 [SMILES: COc1cc(Nc2nc3ccccc3nc2NS(=O)(=O)c2cc(C)sc2C)cc(OC)c1] | N-(3-{[3,5-bis(methyloxy)phenyl]amino}quinoxalin-2-yl)-2,5-dimethylthisophene-3-sulfonamide |
| 829 | 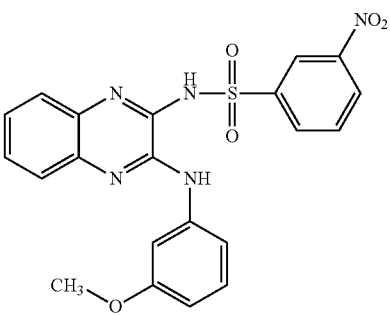 [SMILES: COc1cccc(Nc2nc3ccccc3nc2NS(=O)(=O)c2cccc([N+](=O)[O-])c2)c1] | N-(3-{[3-(methyloxy)phenyl]amino}quinoxalin-2-yl)-3-nitrobenzenesulfonamie |

TABLE 1-continued

| Cpd. No. | Structure | IUPAC Name |
| --- | --- | --- |
| 830 | 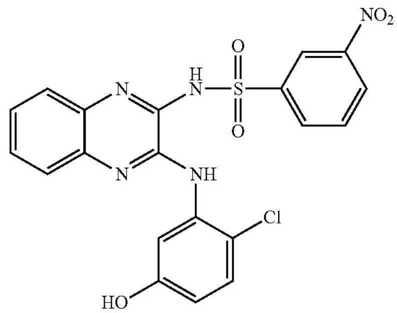 [SMILES: O=[N+]([O-])c1cccc(S(=O)(=O)Nc2nc3ccccc3nc2Nc2cc(O)ccc2Cl)c1] | N-{3-[(2-chloro-5-hydroxyphenyl)amino]quinoxalin-2-yl}-3-nitrobenzenesulfonamide |
| 831 | 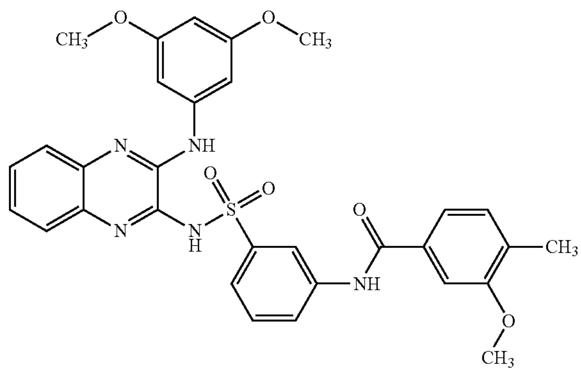 [SMILES: COc1cc(Nc2nc3ccccc3nc2NS(=O)(=O)c2cccc(NC(=O)c3ccc(C)c(OC)c3)c2)cc(OC)c1] | N-(3-{[(3-{[3,5-bis(methyloxy)phenyl]amino}quinoxalin-2-yl)amino]sulfonyl}phenyl)-4-methyl-3-(methyloxy)benzamide |
| 832 | 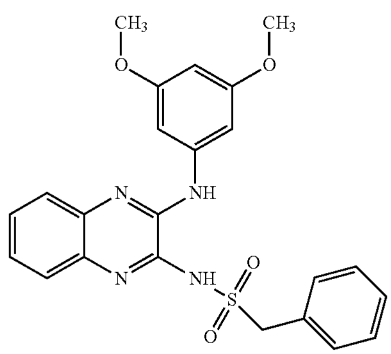 [SMILES: COc1cc(Nc2nc3ccccc3nc2NS(=O)(=O)Cc2ccccc2)cc(OC)c1] | N-(3-{[3,5-bis(methyloxy)phenyl]amino}quinoxalin-2-yl)-1-phenylmethanesulfonamide |
| 833 | 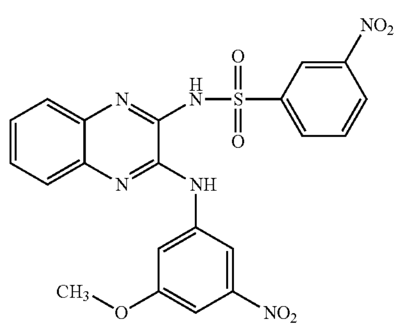 | N-(3-{[3-(methyloxy)-5-nitrophenyl]amino}quinoxalin-2-yl)-3-nitrobenzenesulfonamide |

TABLE 1-continued
| Cpd. No. | Structure | IUPAC Name |
|---|---|---|
| 834 | 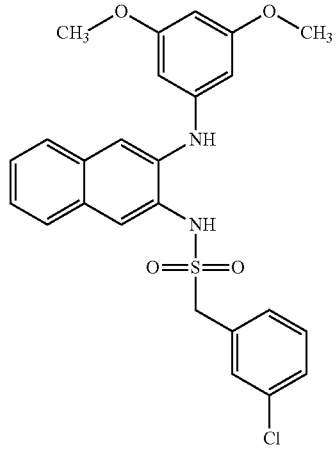 [SMILES: COc1cc(Nc2cc3ccccc3cc2NS(=O)(=O)Cc2cccc(Cl)c2)cc(OC)c1] | N-(3-{[3,5-bis(methyloxy)phenyl]amino}quinoxalin-2-yl)-1-(3-chlorophenyl)methanesulfonamide |
| 835 | 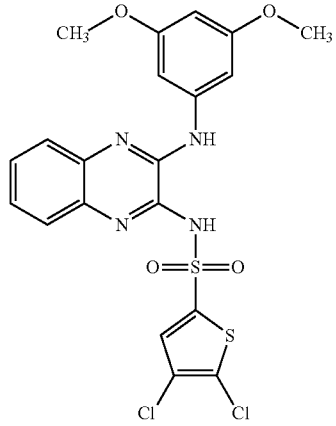 [SMILES: COc1cc(Nc2nc3ccccc3nc2NS(=O)(=O)c2cc(Cl)c(Cl)s2)cc(OC)c1] | N-(3-{[3,5-bis(methyloxy)phenyl]amino}quinoxalin-2-yl)-4,5-dichlorothisophene-2-sulfonamide |
| 836 | 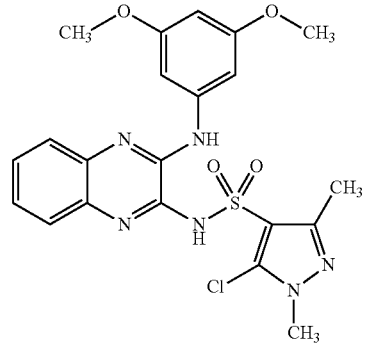 [SMILES: COc1cc(Nc2nc3ccccc3nc2NS(=O)(=O)c2c(C)nn(C)c2Cl)cc(OC)c1] | N-(3-{[3,5-bis(methyloxy)phenyl]amino}quinoxalin-2-yl)-5-chloro-1,3-dimethyl-1H-pyrazole-4-sulfonamide |

TABLE 1-continued

| Cpd. No. | Structure | IUPAC Name |
|---|---|---|
| 837 | 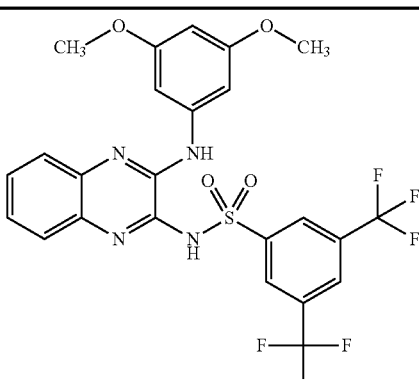 | N-(3-{[3,5-bis(methyloxy)phenyl]amino}quinoxalin-2-yl)-3,5-bis(trifluoromethyl)benzenesulfonamide |
| 838 | 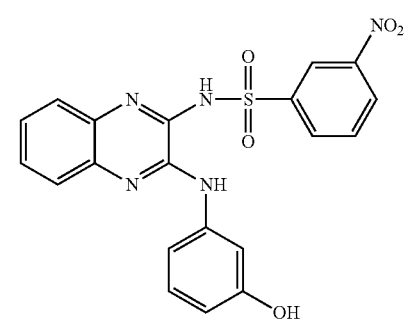 [SMILES: O=[N+]([O-])c1cccc(S(=O)(=O)Nc2nc3ccccc3nc2Nc2cccc(O)c2)c1] | N-{3-[(3-hydroxyphenyl)amino]quinoxalin-2-yl}-3-nitrobenzenesulfonamide |
| 839 | 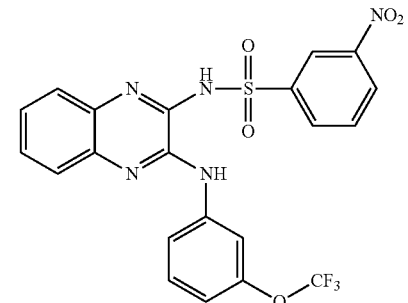 | 3-nitro-N-[3-({3-[(trifluoromethyl)oxy]phenyl}amino)quinoxalin-2-yl]benzenesulfonamide |
| 840 | 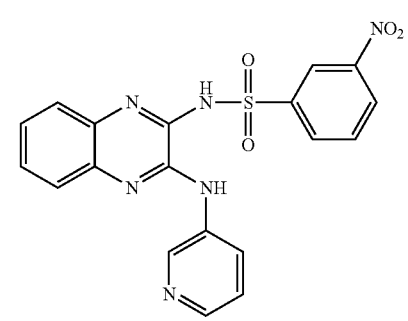 [SMILES: O=[N+]([O-])c1cccc(S(=O)(=O)Nc2nc3ccccc3nc2Nc2cccnc2)c1] | 3-nitro-N-[3-(pyridin-3-ylamino)quinoxalin-2-yl]benzenesulfonamide |
| 841 | 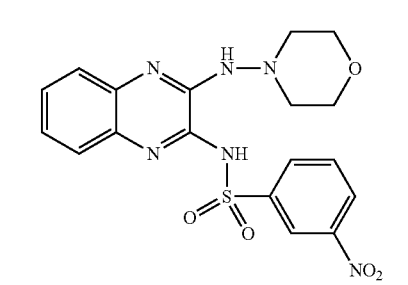 [SMILES: O=[N+]([O-])c1cccc(S(=O)(=O)Nc2nc3ccccc3nc2NN2CCOCC2)c1] | N-[3-(morpholin-4-ylamino)quinoxalin-2-yl]-3-nitrobenzenesulfonamide |

TABLE 1-continued

| Cpd. No. | Structure | IUPAC Name |
|---|---|---|
| 842 | 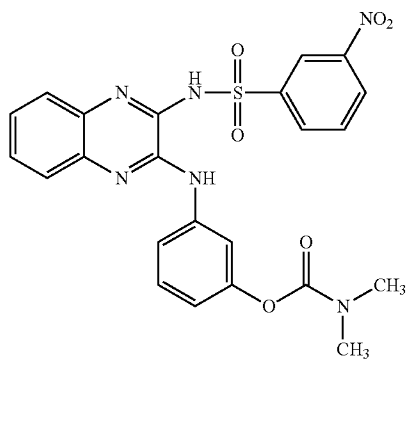 [SMILES: CN(C)C(=O)Oc1cccc(Nc2nc3ccccc3nc2NS(=O)(=O)c2cccc([N+](=O)[O-])c2)c1] | 3-[(3-{[(3-nitrophenyl)sulfonyl]amino}quinoxalin-2-yl)amino]phenyldimethylcarbamate |
| 843 | 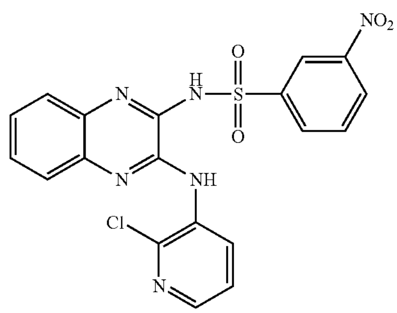 [SMILES: O=[N+]([O-])c1cccc(S(=O)(=O)Nc2nc3ccccc3nc2Nc2cccnc2Cl)c1] | N-{3-[(2-chloropyridin-3-yl)amino]quinoxalin-2-yl}-3-nitrobenzenesulfonamide |
| 844 | 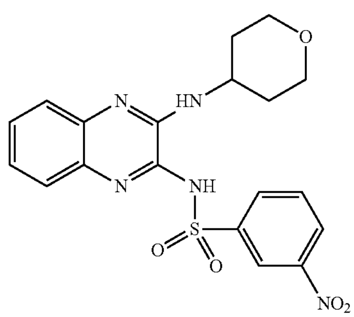 [SMILES: O=[N+]([O-])c1cccc(S(=O)(=O)Nc2nc3ccccc3nc2NC2CCOCC2)c1] | 3-nitro-N-[3-(tetrahydro-2H-pyran-4-ylamino)quinoxalin-2-yl]benzenesulfonamide |
| 845 | 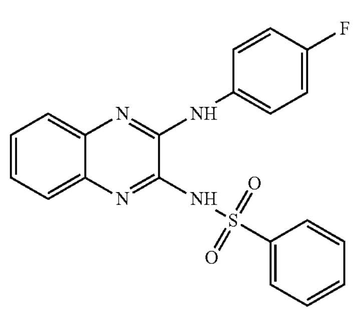 [SMILES: O=S(=O)(Nc1nc2ccccc2nc1Nc1ccc(F)cc1)c1ccccc1] | N-{3-[(4-fluorophenyl)amino]quinoxalin-2-yl}benzenesulfonamide |

TABLE 1-continued

| Cpd. No. | Structure | IUPAC Name |
|---|---|---|
| 846 | 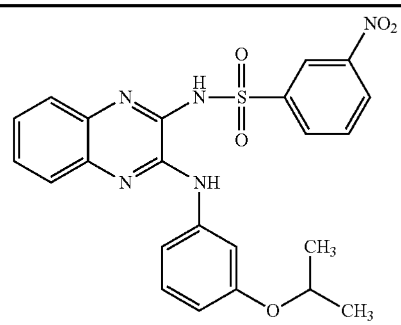 | N-[3-({3-[(1-methylethyl)oxy]phenyl}amino)quinoxalin-2-yl]-3-nitrobenzenesulfonamide |
| 847 | 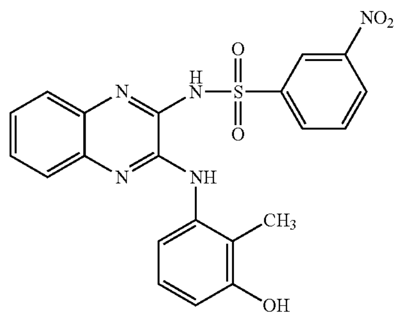 [SMILES: Cc1c(O)cccc1Nc1nc2ccccc2nc1NS(=O)(=O)c1cccc([N+](=O)[O-])c1] | N-{3-[(3-hydroxy-2-methylphenyl)amino]quinoxalin-2-yl}-3-nitrobenzenesulfonamide |
| 848 | 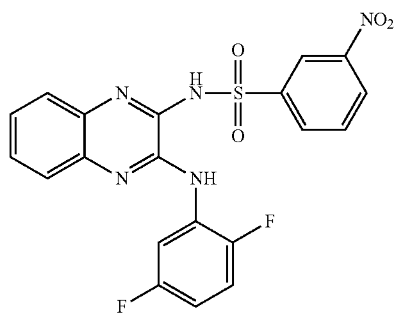 [SMILES: O=[N+]([O-])c1cccc(S(=O)(=O)Nc2nc3ccccc3nc2Nc2cc(F)ccc2F)c1] | N-{3-[(2,5-difluorophenyl)amino]quinoxalin-2-yl}-3-nitrobenzenesulfonamide |
| 849 | 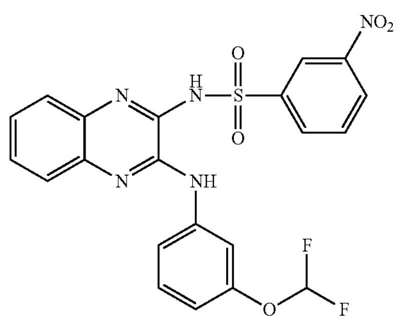 [SMILES: O=[N+]([O-])c1cccc(S(=O)(=O)Nc2nc3ccccc3nc2Nc2cccc(OC(F)F)c2)c1] | N-[3-({3-[(difluoromethyl)oxy]phenyl}amino)quinoxalin-2-yl]-3-nitrobenzenesulfonamide |
| 850 | 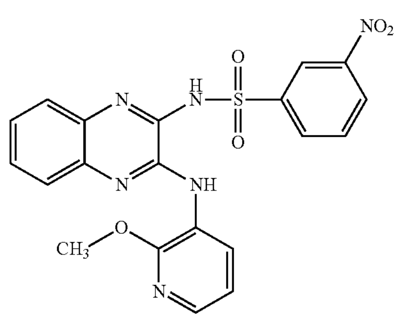 [SMILES: COc1ncccc1Nc1nc2ccccc2nc1NS(=O)(=O)c1cccc([N+](=O)[O-])c1] | N-(3-{[2-(methyloxy)pyridin-3-yl]amino}quinyloxalin-2-yl)-3-nitrobenzenesulfonamide |

TABLE 1-continued

| Cpd. No. | Structure | IUPAC Name |
|---|---|---|
| 851 | 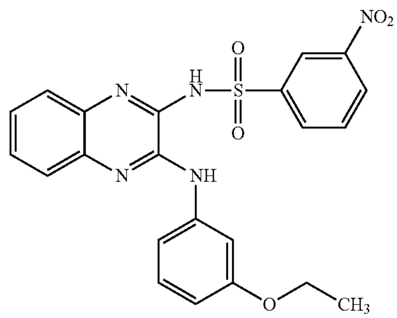 [SMILES: CCOc1cccc(Nc2nc3ccccc3nc2NS(=O)(=O)c2cccc([N+](=O)[O-])c2)c1] | N-(3-{[3-(ethyloxy)phenyl]amino}quinoxalin-2-yl)-3-nitrobenzenesulfonamide |
| 852 | 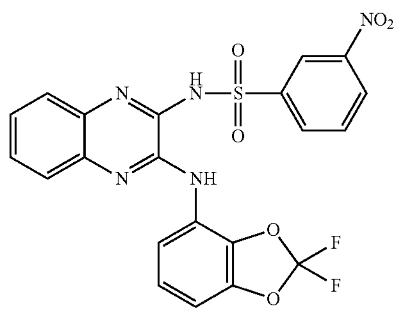 [SMILES: O=[N+]([O-])c1cccc(S(=O)(=O)Nc2nc3ccccc3nc2Nc2cccc3c2OC(F)(F)O3)c1] | N-{3-[(2,2-difluoro-1,3-benzodisoxol-4-yl)amino]quinoxalin-2-yl}-3-nitrobenzenesulfonamide |
| 853 | 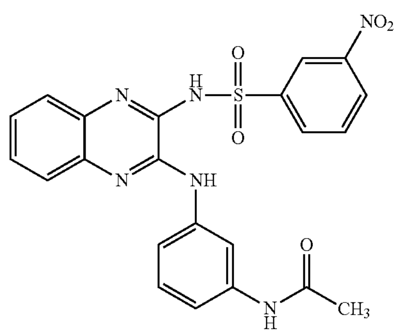 [SMILES: CC(=O)Nc1cccc(Nc2nc3ccccc3nc2NS(=O)(=O)c2cccc([N+](=O)[O-])c2)c1] | N-{3-[(3-{[(3-nitrophenyl)sulfonyl]amino}quinoxalin-2-yl)amino]phenyl}acetamide |
| 854 | 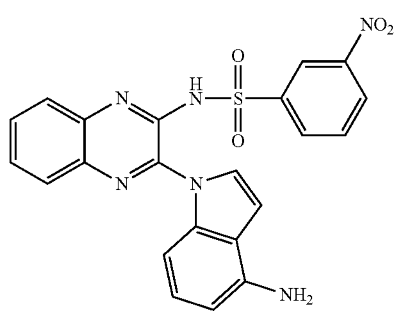 [SMILES: Nc1cccc2c1ccn2-c1nc2ccccc2nc1NS(=O)(=O)c1cccc([N+](=O)[O-])c1] | N-[3-(4-amino-1H-indol-1-yl)quinoxalin-2-yl]-3-nitrobenzenesulfonamide |
| 855 | 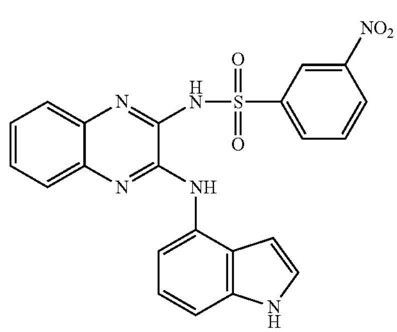 [SMILES: O=[N+]([O-])c1cccc(S(=O)(=O)Nc2nc3ccccc3nc2Nc2cccc3[nH]ccc23)c1] | N-[3-(1H-indol-4-ylamino)quinoxalin-2-yl]-3-nitrobenzenesulfonamide |

| Cpd. No. | Structure | IUPAC Name |
|---|---|---|
| 856 | 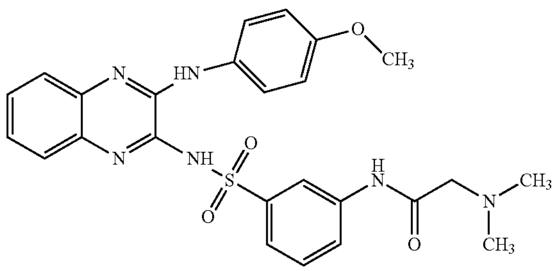 [SMILES: COc1ccc(Nc2nc3ccccc3nc2NS(=O)(=O)c2cccc(NC(=O)CN(C)C)c2)cc1] | N-2-,N-2-dimethyl-N-(3-{[(3-{[4-(methyloxy)phenyl]amino}quinoxalin-2-yl)amino]sulfonyl}phenyl)glycinamide |
| 857 | 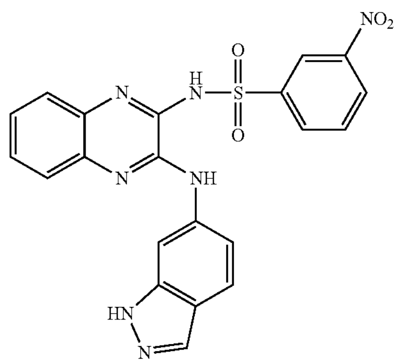 [SMILES: O=[N+]([O-])c1cccc(S(=O)(=O)Nc2nc3ccccc3nc2Nc2ccc3cn[nH]c3c2)c1] | N-[3-(1H-indazol-6-ylamino)quinoxalin-2-yl]-3-nitrobenzenesulfonamide |
| 858 | 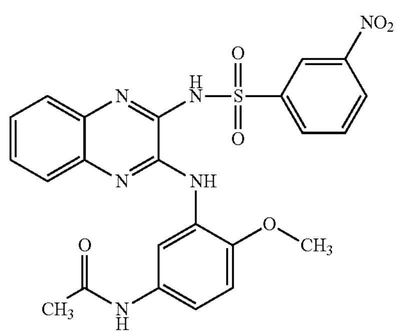 [SMILES: COc1ccc(NC(C)=O)cc1Nc1nc2ccccc2nc1NS(=O)(=O)c1cccc([N+](=O)[O-])c1] | N-{4-(methyloxy)-3-[3-{[(3-nitrophenyl)sulfonyl]amino}quinoxalin-2-yl)amino]phenyl}acetamide |
| 859 | 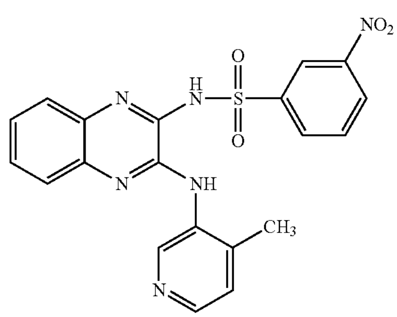 [SMILES: Cc1ccncc1Nc1nc2ccccc2nc1NS(=O)(=O)c1cccc([N+](=O)[O-])c1] | N-{3-[(4-methylpyridin-3-yl)amino]quinoxalin-2-yl}-3-nitrobenzenesulfonamide |

TABLE 1-continued

| Cpd. No. | Structure | IUPAC Name |
|---|---|---|
| 860 | 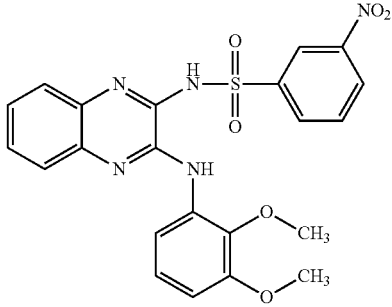 [SMILES: COc1cccc(Nc2nc3ccccc3nc2NS(=O)(=O)c2cccc([N+](=O)[O-])c2)c1OC] | N-(3-{[2,3-bis(methyloxy)phenyl]amino}quinoxalin-2-yl)-3-nirobenzenesulfonamide |
| 861 | 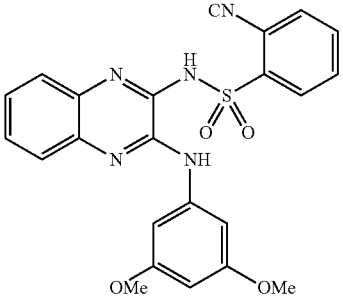 | N-(3[{[3,5-bis(methyloxy)phenyl]amino}quinoxalin-2-yl)-2-cyanobenzenesulfonamide |
| 862 | 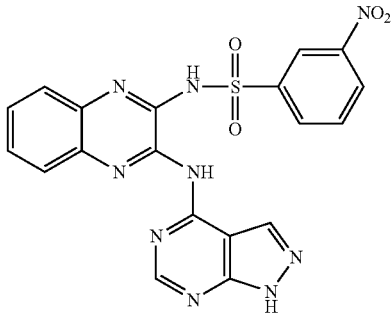 [SMILES: O=[N+]([O-])c1cccc(S(=O)(=O)Nc2nc3ccccc3nc2Nc2ncnc3[nH]ncc23)c1] | 3-nitro-N-[3-(1H-pyrazolo[3,4-d]pyrimidin-4-ylamino)quinoxalin-2-yl]benzenesulfonamide |
| 863 | 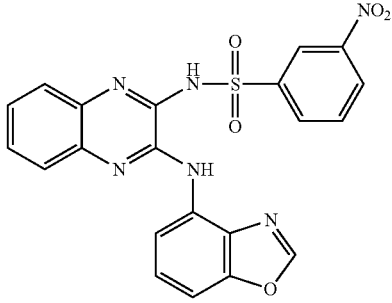 [SMILES: O=[N+]([O-])c1cccc(S(=O)(=O)Nc2nc3ccccc3nc2Nc2cccc3ocnc23)c1] | N-[3-(1,3-benzoxazol-4-ylamino)quinoxalin-2-yl]-3-nitrobenzenesulfonamide |
| 864 | 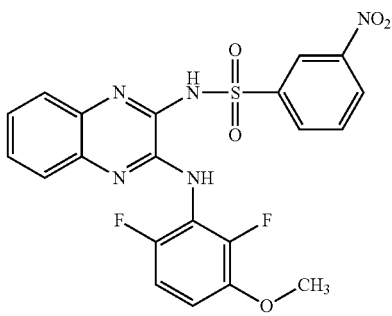 [SMILES: COc1ccc(F)c(Nc2nc3ccccc3nc2NS(=O)(=O)c2cccc([N+](=O)[O-])c2)c1F] | N-(3-{[2,6-difluoro-3-(methyloxy)phenyl]amino}quinoxalin-2-yl)-3-nitrobenzenesulfonamide |

TABLE 1-continued

| Cpd. No. | Structure | IUPAC Name |
|---|---|---|
| 865 | 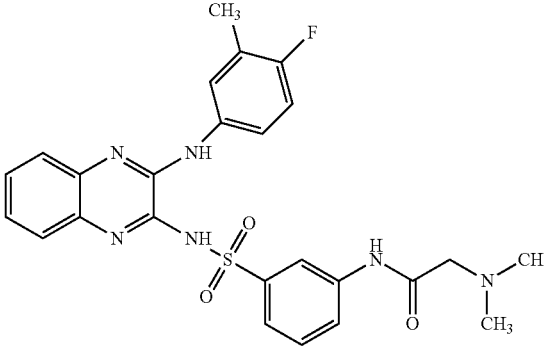 | N-{3-[({3-[(4-fluoro-3-methylphenyl)amino]quinoxalin-2-yl}amino)sulfonyl]phenyl}-N-2-,N-2-dimethylglycinamide |
| 866 | 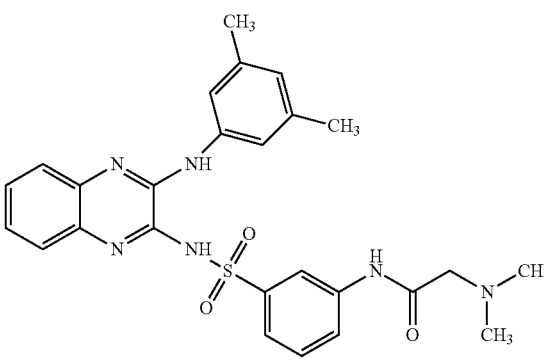 | N-{3-[({3-{[3,5-dimethylphenyl)amino]quinoxalin-2-yl}amino)sulfonyl]phenyl}-N-2-,N-2-dimethylglycinamide |
| 867 | 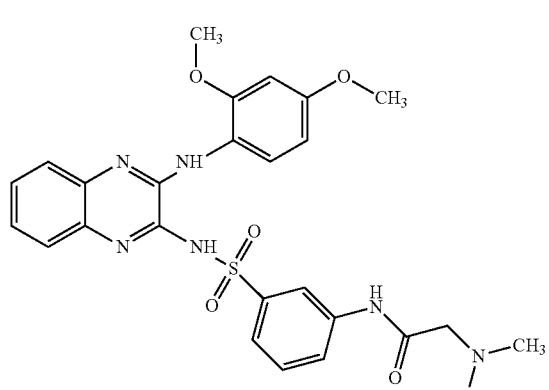 | N-(3-{[(3-{[2,4-bis(methyloxy)phenyl]amino}quinoxalin-2-yl)amino]sulfonyl}phenyl)-N-2-,N-2-dimethylglycinamide |
| 868 | 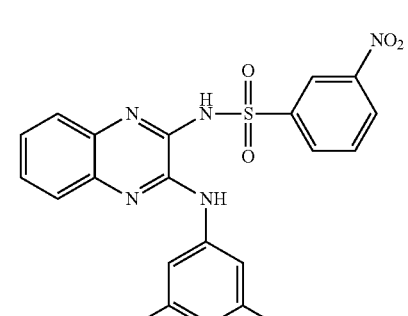 | N-{3-[(3,5-dihydroxyphenyl)amino]quinoxalin-2-yl}-3-nitrobenzenesulfonamide |

TABLE 1-continued

| Cpd. No. | Structure | IUPAC Name |
|---|---|---|
| 869 | 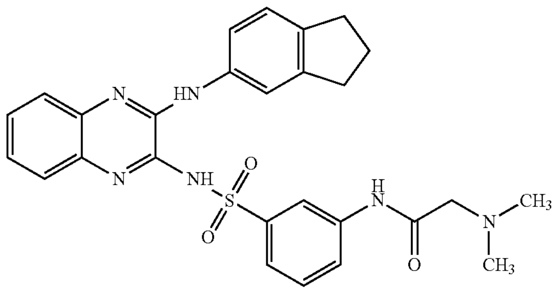 [SMILES: CN(C)CC(=O)Nc1cccc(S(=O)(=O)Nc2nc3ccccc3nc2Nc2ccc3c(c2)CCC3)c1] | N-[3-({[3-(2,3-dihydro-1H-inden-5-ylamino)quinoxalin-2-yl]amino}sulfonyl)phenyl]-N-2-,N-2-dimethylglycinamide |
| 870 | 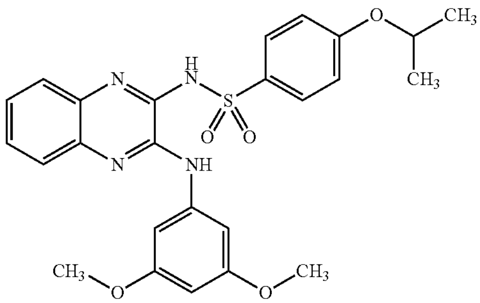 [SMILES: COc1cc(Nc2nc3ccccc3nc2NS(=O)(=O)c2ccc(OC(C)C)cc2)cc(OC)c1] | N-(3-{[3,5-bis(methyloxy)phenyl]amino}quinoxalin-2-yl)-4-[(1-methylethyl)oxy]benzenesulfonamide |
| 871 | 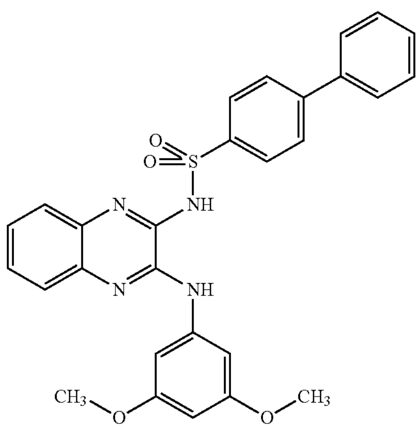 [SMILES: COc1cc(Nc2nc3ccccc3nc2NS(=O)(=O)c2ccc(-c3ccccc3)cc2)cc(OC)c1] | N-(3-{[3,5-bis(methyloxy)phenyl]amino}quinoxalin-2-yl)biphenyl-4-sulfonamide |
| 872 | 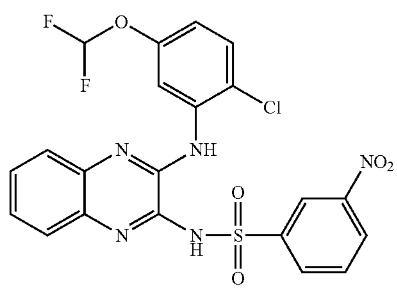 [SMILES: O=[N+]([O-])c1cccc(S(=O)(=O)Nc2nc3ccccc3nc2Nc2cc(OC(F)F)ccc2Cl)c1] | N-[3-({2-chloro-5-[(difluoromethyl)oxy]phenyl}amino)quinoxalin-2-yl]-3-nitrobenzenesulfonamide |

In addition to the preferred embodiments recited hereinabove, also preferred are embodiments comprising combinations of preferred embodiments.

One of ordinary skill in the art would understand that certain crystallized, protein-ligand complexes, in particular PI3K-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an embodiment of the invention.

In one embodiment of the invention, the PI3K inhibitor is selected from the compounds in Table I having a PI3K-binding affinity of about 8 μM or less. In another embodiment, the PI3K inhibitor is selected from the compounds in Table I having a PI3K-binding affinity of about 4 µM or less. In another embodiment, the PI3K inhibitor is selected from the compounds in Table I having a PI3K-binding affinity of about 3 µM or less. In another embodiment, the PI3K inhibitor is selected from the compounds in Table I having a PI3K-binding affinity of about 2 µM or less. In another embodiment, the PI3K inhibitor is selected from the compounds in Table I having a PI3K-binding affinity of about 1.5 µM or less. In another embodiment, the PI3K inhibitor is selected from the compounds in Table I having a PI3K-binding affinity of about 1 µM or less. In another embodiment, the PI3K inhibitor is selected from the compounds in Table I having a PI3K-binding affinity of about 0.750 µM or less. In another embodiment, the PI3K inhibitor is selected from the compounds in Table I having a PI3K-binding affinity of about 0.5 µM or less. In another embodiment, the PI3K inhibitor is selected from the compounds in Table I having a PI3K-binding affinity of about 0.3 µM or less. In another embodiment, the PI3K inhibitor is selected from the compounds in Table I having a PI3K-binding affinity of about 0.2 µM or less. In another embodiment, the PI3K inhibitor is selected from the compounds in Table I having a PI3K-binding affinity of about 0.1 µM or less. In another embodiment, the PI3K inhibitor is selected from the compounds in Table I having a PI3K-binding affinity of about 0.075 µM or less. In another embodiment, the PI3K inhibitor is selected from the compounds in Table I having a PI3K-binding affinity of about 0.050 µM or less.

Synthetic Procedures

Fusion of the reagents at 180° C. in the presence of $K_2CO_3$ and metallic copper was known to provide these compounds in low yield (S. H. Dandegaonker and C. K. Mesta, *J Med. Chem.* 1965, 8, 884). New method was utilized that brief heating of the reagents in DMF in the presence of $K_2CO_3$, commercially available 2,3-dichloroquinoxaline and substituted arysulfonamides were formed in quantitative yields (S. V. Litvinenko, V. I. Savich, D. D. Bobrovnik, *Chem. Heterocycl. Compd.* (Engl. Transl), 1994, 30, 340).

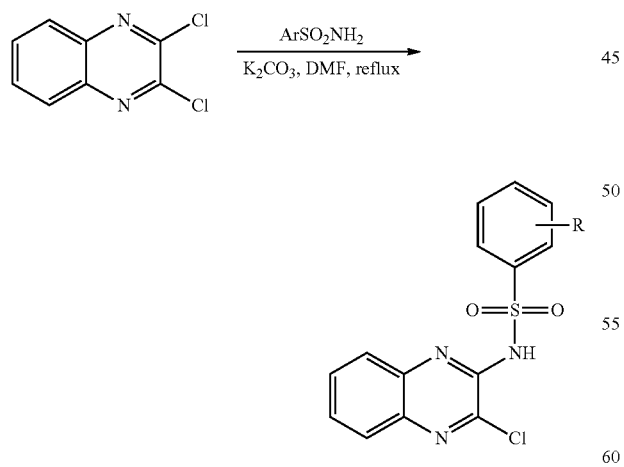

The displacement of the active chlorine atom in above compounds was treated with 2,5-dimethoxy-phenylamine (nucleophile) in refluxing DMF to give the desired compounds in quantitative yields (S. V. Litvinenko, V. I. Savich, D. D. Bobrovnik, *Chem. Heterocycl. Compd.* (Engl. Transl), 1994, 30, 340).

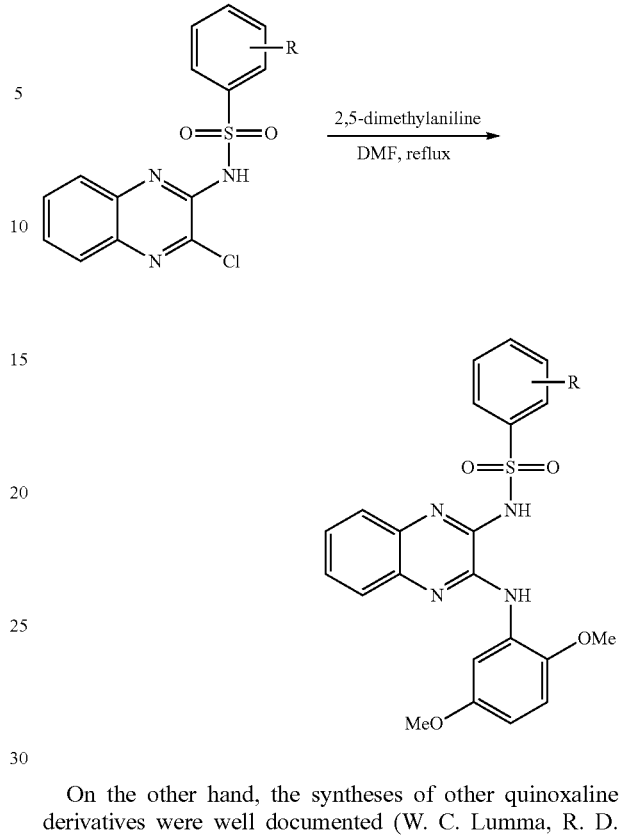

On the other hand, the syntheses of other quinoxaline derivatives were well documented (W. C. Lumma, R. D. Hartman, *J. Med. Chem.* 1981, 24, 93).

The following compounds were prepared in a manner similar to that described above: N-(3-{[2,5-bis(methyloxy)phenyl]amino}quinoxalin-2-yl)-3-nitrobenzenesulfonamide; N-(3-{[2,5-bis(methyloxy)phenyl]amino}quinoxalin-2-yl)-4-chlorobenzenesulfonamide; N-(3-chloroquinoxalin-2-yl)-3-nitrobenzenesulfonamide; and 4-chloro-N-(3-chloroquinoxalin-2-yl)benzenesulfonamide.

SYNTHETIC EXAMPLES

Example 1

6-chloro-N-(3-(3,5-dimethoxyphenylamino)quinoxalin-2-yl)pyridine-3-sulfonamide

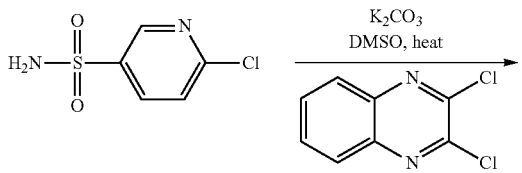

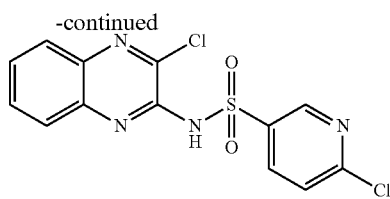

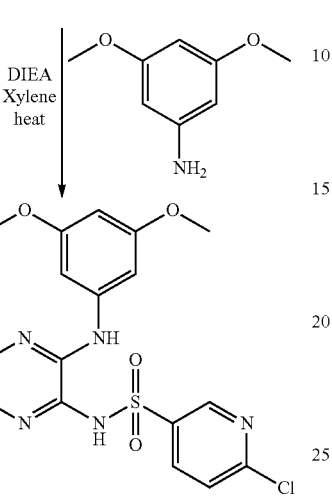

6-chloropyridine-3-sulfonamide 6-chloropyridine-3-sulfonyl chloride (4.1 g, 19.3 mmol) was stirred in ammonium hydroxide (30 mL) at room temperature for 2 hr. The reaction mixture was diluted with EtOAc (150 mL) and any insoluble material filtered. The filtrate was transferred to a separatory funnel and the phases were separated. The aqueous phase was further extracted with EtOAc (1×15 mL). The combined EtOAc extractions were washed with $H_2O$ (1×50 mL), saturated NaCl (1×50 mL), dried ($Na_2SO_4$), and concentrated in vacuo to give 6-chloro-pyridine-3-sulfonamide (2.58 g, 69%). MS (EI) for $C_5H_3Cl_2NO_2S$: 190.9 (MH−).

6-chloro-N-(3-chloroquinoxalin-2-yl)pyridine-3-sulfonamide 2,3-dichloroquinoxaline (1.09 g, 5.48 mmol), 6-chloropyridine-3-sulfonamide (1.05 g, 5.45 mmol), $K_2CO_3$ (753 mg, 5.45 mmol) and dry DMSO (30 mL) were combined and heated to 150 C with vigorous stirring for 3-4 hr. The reaction mixture was allowed to cool to room temperature, then poured into 1% AcOH in ice water (300 mL) with vigorous stirring. The resulting solids were filtered, washed with $H_2O$ and dried under high vacuum to give 6-chloro-N-(3-chloro-quinoxalin-2-yl)pyridine-3-sulfonamide (1.87 g, 96%). MS (EI) for $C_{13}H_8Cl_2N_4O_2S$: 354.99 (MH+).

6-chloro-N-(3-(3,5-dimethoxyphenylamino)quinoxa-lin-2-yl)pyridine-3-sulfonamide

6-Chloro-N-(3-chloroquinoxalin-2-yl)pyridine-3-sulfonamide (775 mg, 2.2 mmol), 3,5-dimethoxyaniline (355 mg, 2.3 mmol) and toluene (12 mL) were combined and heated to 125 C with stirring overnight. The reaction was allowed to cool to room temperature and diluted with $Et_2O$ with vigorous stirring. The resulting solids were filtered, washed with $Et_2O$ and dried to give 6-chloro-N-(3-(3,5-dimethoxyphenylamino)quinoxalin-2-yl)pyridine-3-sulfonamide (920 mg, 89%). 1H NMR (400 MHz, DMSO-d6) δ 12.20 (br s, 1H), 9.12 (d, 1H), 9.01 (br s, 1H), 8.53 (dd, 1H), 7.91 (br d, 1H), 7.77 (d, 1H), 7.60 (dd, 1H), 7.40 (m, 4H), 6.26 (m, 1H), 3.78 (s, 6H). MS (EI) for $C_{21}H_{18}ClN_5O_4S$: 472.0 (MH+).

Example 2

N-(3-(3,5-dimethoxyphenylamino)quinoxalin-2-yl)-6-(2-(dimethylamino)ethylamino)pyridine-3-sulfonamide

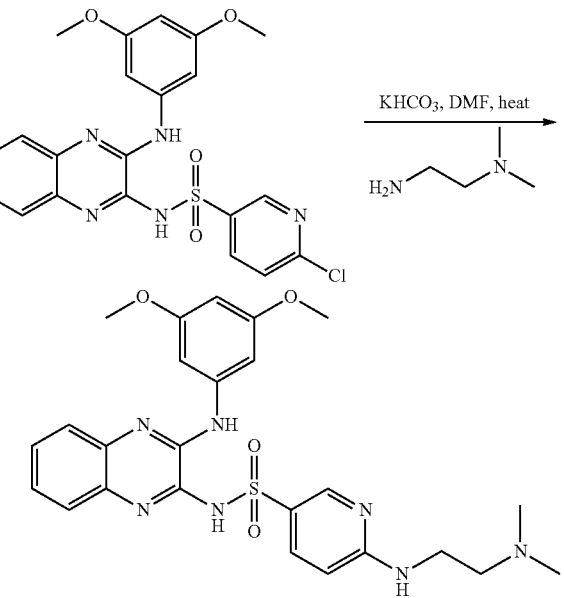

N-(3-(3,5-dimethoxyphenylamino)quinoxalin-2-yl)pyridine-3-sulfonamide (100 mg, 0.21 mmol), $KHCO_3$ (40 mg, 0.40 mmol), $N^1,N^1$-dimethylethane-1,2-diamine (225 µl, 2.0 mmol) and dry DMF (1.0 mL) were combined and heated to 130 C. with stirring overnight. The reaction mixture was concentrated in vacuo and purified by preparative HPLC to give N-(3-(3,5-dimethoxyphenylamino)quinoxalin-2-yl)-6-(2-(dimethylamino)ethylamino)pyridine-3-sulfonamide (21.0 mg, 19%). 1H NMR (400 MHz, DMSO-d6) δ 8.76 (br s, 1H), 8.63 (d, 1H), 8.07 (dd, 1H), 7.40 (m, 1H), 7.34 (m, 1H), 7.28 (d, 2H), 7.14 (m, 4H), 6.47 (d, 1H), 6.12 (m, 1H), 3.75 (s, 6H), 3.35 (m, 2H), 3.14 (m, 2H), 2.74 (s, 6H). MS (EI) for $C_{25}H_{29}N_7O_4S$: 524.1 (MH+).

Example 3

N-(3-(3,5-dimethoxyphenylamino)quinoxalin-2-yl)-6-(dimethylamino)pyridine-3-sulfonamide The title compound was prepared according to the Examples above. 1H NMR (400 MHz, DMSO-d6) δ 12.00 (br s, 1H), 8.92 (br s, 1H), 8.74 (d, 1H), 8.10 (dd, 1H), 7.38 (br s, 1H), 7.54 (m, 1H), 7.33 (m, 4H), 6.70 (d, 1H), 6.22 (s, 1H), 3.77 (s, 6H), 3.08 (s, 6H). MS (EI) for $C_{23}H_{24}N_6O_4S$: 481.1 (MH+).

Example 4

N-(3-(3,5-dimethoxyphenylamino)quinoxalin-2-yl)-6-(2-(dimethylamino)ethoxy)pyridine-3-sulfonamide

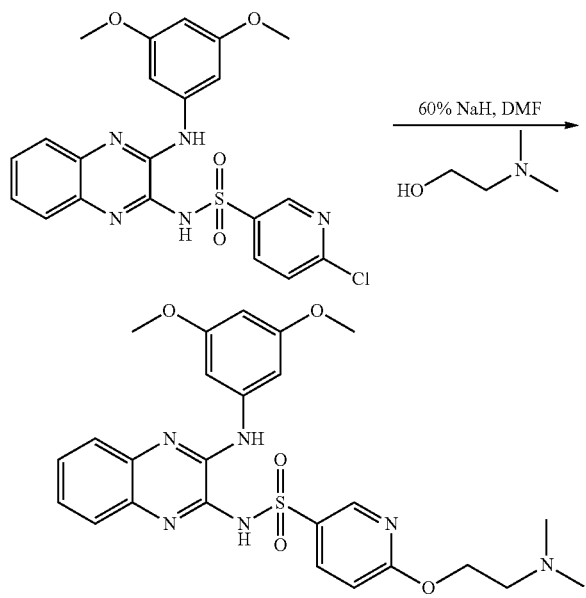

N-(3-(3,5-dimethoxyphenylamino)quinoxalin-2-yl)pyridine-3-sulfonamide (100 mg, 0.21 mmol), 2-(dimethylamino)ethanol (50 μl, 0.50 mmol) and dry DMF were combined and 60% NaH in oil (80 mg, 2.0 mmol) added. The mixture was stirred at room temperature overnight. The reaction mixture was concentrated in vacuo and purified by preparative HPLC to give N-(3-(3,5-dimethoxyphenylamino) quinoxalin-2-yl)-6-(2-(dimethylamino)ethoxy)pyridine-3-sulfonamide (23 mg, 21%). 1H NMR (400 MHz, DMSO-d6) δ 8.78 (d, 1H), 8.73 (s, 1H), 8.38 (dd, 1H), 7.40 (dd, 1H), 7.31 (m, 3H), 7.14 (tn, 2H), 6.85 (d, 1H), 6.12 (m, 1H), 4.56 (m, 2H), 3.76 (s, 6H), 3.43 (m, 2H), 2.77 (s, 6H). MS (EI) for $C_{25}H_{28}N_6O_5S$: 525.1 (MH+).

Example 5

N-(3-(3,5-dimethoxyphenylamino)quinoxalin-2-yl)-6-oxo-1,6-dihydropyridine-3-sulfonamide

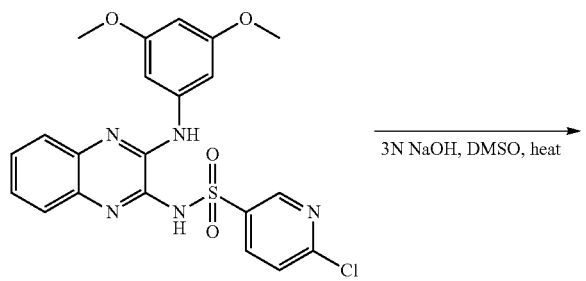

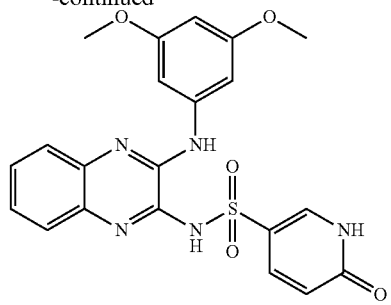

N-(3-(3,5-dimethoxyphenylamino)quinoxalin-2-yl)pyridine-3-sulfonamide (220 mg, 0.47 mmol), DMSO (5 mL), and 3N NaOH (5 mL) are combined and heated to 100 C. overnight with stirring. Upon cooling to room temperature, the reaction mixture was diluted with $H_2O$ and the pH was adjusted to 7.0 with 1N HCl. The resulting solid was filtered, washed with $H_2O$, and air-dried. The solid was then sonicated in EtOAc, filtered, washed with EtOAc, and dried under high vacuum to give N-(3-(3,5-dimethoxyphenylamino)quinoxalin-2-yl)-6-oxo-1,6-dihydropyridine-3-sulfonamide (190 mg, 90%). 1H NMR (400 MHz, DMSO-d6) δ 12.23 (br s, 1H), 12.10 (br s, 1H), 8.97 (s, 1H), 8.23 (s, 1H), 7.95 (m, 2H), 7.59 (m, 1H), 7.37 (m, 4H), 6.43 (d, 1H), 6.25 (s, 1H), 3.77 (s, 6H). MS (EI) for $C_{21}H_{19}N_5O_5S$: 454.0 (MH+).

The following title compounds were prepared according to the above Examples.

Example 6

N-(3-(2-chloro-5-methoxyphenylamino)quinoxalin-2-yl)-6-oxo-1,6-dihydropyridine-3-sulfonamide 1H NMR (400 MHz, DMSO-d6) δ 12.22 (br s, 1H), 12.10 (br s, 1H), 9.16 (s, 1H), 8.60 (s, 1H), 8.14 (d, 1H), 7.94 (m, 1H), 7.85 (dd, 1H), 7.62 (m, 1H), 7.40 (m, 3H) 6.69 (dd, 1H), 6.43 (d, 1H), 3.81 (s, 3H). MS (EI) for $C_{20}H_{16}ClN_5O_4S$: 456.0 (MH−).

Example 7

5-(N-(3-(2-chloro-5-methoxyphenylamino)quinoxalin-2-yl)sulfamoyl)-N-(2-(dimethylamino)ethyl)-2-methoxybenzamide 1H NMR (400 MHz, DMSO-d6) δ 9.45 (s, 1H), 8.95 (d, 1H), 8.57 (d, 1H), 8.28 (t, 1H), 8.14 (dd, 1H), 7.46 (dd, 1H), 7.39 (m, 2H), 7.17 (m, 4H), 6.60 (dd, 1H), 3.89 (s, 3H), 3.82 (s, 3H), 3.38 (m, 2H), 2.43 (m, 2H), 2.21 (s, 6H). MS (EI) for $C_{27}H_{29}ClN_6O_5S$: 585.3 (MH+).

Example 8

5-(N-(3-(2-chloro-5-methoxyphenylamino)quinoxalin-2-yl)sulfamoyl)-N-(2-(dimethylamino)ethyl)-2-fluorobenzamide 1H NMR (400 MHz, DMSO-d6) δ 9.40 (br s, 1H), 9.16 (s, 1H), 8.73 (m, 1H), 8.67 (d, 1H), 8.36 (dd, 1H), 8.26 (m, 1H), 7.94 (br s, 1H), 7.66 (m, 1H), 7.59 (t, 1H), 7.43 (m, 3H), 6.71 (dd, 1H), 3.83 (s, 3H), 3.62 (m, 2H), 3.27 (m, 2H), 2.85 (d, 6H). MS (EI) for $C_{26}H_{26}ClFN_6O_4S$: 573.1 (MH+).

Example 9

N-(2-chloro-5-(N-(3-(2-chloro-5-methoxyphenylamino)quinoxalin-2-yl)sulfamoyl)phenyl)-2-(methylamino)acetamide The title compound was prepared according to the Examples above. 1H NMR (400 MHz, DMSO-d6) δ 10.50 (s, 1H), 9.14 (s, 1H), 9.03 (m, 2H), 8.63 (d, 1H), 8.44 (d, 1H), 7.98 (m, 1H), 7.91 (dd, 1H), 7.80 (d, 1H), 7.67 (m, 1H), 7.44 (m, 3H), 6.71 (dd, 1H), 4.06 (m, 2H), 3.83 (s, 3H), 2.64 (t, 3H). MS (EI) for $C_{24}H_{22}Cl_2N_6O_4S$: 561.0 (MH+).

Example 10

(S)-2-amino-N-(3-(N-(3-(2-chloro-5-methoxyphenylamino)quinoxalin-2-yl)sulfamoyl)phenyl)propanamide hydrochloride 1H NMR (400 MHz, CD3OD) δ 8.72-8.71 (d, 1H), 8.48-8.46 (t, 1H), 7.86-7.84 (m, 1H), 7.80-7.78 (m, 1H), 7.63-7.59 (m, 2H), 7.58-7.55 (t, 1H), 7.41-7.38 (m, 2H), 7.24-7.22 (d, 1H), 6.60-6.58 (dd, 1H), 4.10-4.04 (q, 1H), 3.83 (s, 3H), 1.61-1.60 (d, 3H); MS (EI) for $C_{24}H_{23}ClN_6O_4S \cdot HCl$: 527.2 (MH+).

Example 11

(S)-2-amino-N-(3-(N-(3-(2-chloro-5-methoxyphenylamino)quinoxalin-2-yl)sulfamoyl)phenyl)butanamide hydrochloride 1H NMR (400 MHz, CD3OD) δ 8.74-8.73 (d, 1H), 8.80-8.47 (t, 1H), 7.87-7.85 (m, 1H), 7.80-7.78 (m, 1H), 7.67-7.61 (m, 2H), 7.59-7.55 (t, 1H), 7.42-7.39 (m, 2H), 7.26-7.24 (d, 1H), 6.62-6.59 (dd, 1H), 3.96-3.93 (t, 1H), 3.84 (s, 3H), 2.02-1.94 (m, 2H, 1.09-1.06 (t, 3H); MS (EI) for $C_{25}H_{25}ClN_6O_4S \cdot HCl$: 541.3 (MH+).

Example 12

(S)—N-(3-(N-(3-(2-chloro-5-methoxyphenylamino)quinoxalin-2-yl)sulfamoyl)phenyl)pyrrolidine-2-carboxamide hydrochloride 1H NMR (400 MHz, CD3OD) δ 8.78-8.77 (d, 1H), 8.47-8.46 (t, 1H), 7.87-7.85 (m, 1H), 7.80-7.75 (m, 1H), 7.69-7.65 (m, 2H), 7.59-7.55 (t, 1H), 7.45-7.41 (m, 2H), 7.31-7.28 (d, 1H), 6.65-6.63 (dd, 1H), 4.42-4.38 (m, 1H), 3.86 (s, 3H), 3.48-3.42 (m, 2H), 2.55-2.49 (m 1H), 2.18-2.08 (m, 3H); MS (EI) for $C_{26}H_{25}ClN_6O_4S \cdot HCl$: 553.3 (MH+).

Exmaple 13

(S)—N-(3-(N-(3-(3,5-dimethoxy-phenylamino)quinoxalin-2-yl)sulfamoyl)phenyl)pyrrolidine-2-carboxamide hydrochloride 1H NMR (400 MHz, CD3OD) δ 10.62 (br s, 1H), 8.50-8.49 (t, 1H), 7.90-7.87 (m, 1H), 7.76-7.73 (m, 1H), 7.63-7.58 (m, 3H), 7.43-7.35 (m, 2H), 7.14 (s, 2H), 6.27-6.26 (t, 1H), 4.43-4.38 (m, 1H), 3.78 (s, 6H), 3.48-3.41 (m, 1H), 3.40-3.36 (m, 1H), 2.54-2.48 (m, 1H), 2.19-2.05 (m, 3H); MS (EI) for $C_{27}H_{28}N_6O_5S \cdot HCl$: 549.3 (MH+).

Example 14

(R)-2-amino-N-(3-(N-(3-(3,5-dimethoxy-phenylamino)quinoxalin-2-yl)sulfamoyl)phenyl)-3-hydroxypropanamide hydrochloride 1H NMR (400 MHz, CD3OD) δ 8.49-8.48 (t, 1H), 7.89-7.87 (m, 1H), 7.75-7.72 (m, 1H), 7.65-7.62 (m, 2H), 7.62-7.55 (t, 1H), 7.44-7.38 (m, 2H), 7.23-7.22 (d, 2H), 6.27-6.26 (t, 1H), 4.07-4.05 (m, 1H), 3.99-3.93 (m, 2H), 3.80 (s, 6H); MS (EI) for $C_{25}H_{26}N_6O_6S \cdot HCl$: 539.1 (MH+).

Example 15

N-(3-(N-(3-(2-chloro-5-methoxy-phenylamino)quinoxalin-hydrochloride

1H NMR (400 MHz, CD3OD) δ 8.79-8.78 (d, 1H), 8.45 (m, 1H), 7.83-7.81 (d, 1H), 7.76-7.74 (m, 1H), 7.636 (m, 2H), 7.54-7.50 (t, 1H), 7.41 (m, 2H), 7.30-7.28 (d, 1H), 6.65-6.62 (dd, 1H), 3.86 (s, 3H), 3.40-3.32 (m, 2H), 3.20-3.13 (m, 3H), 2.93 (m, 1H), 2.15-2.11 (m, 1H), 1.98-1.93 (m, 2H), 1.83 (m, 1H); MS (EI) for $C_{27}H_{27}ClN_6O_4S \cdot HCl$: 567.3 (MH+).

Example 16

(S)-2-amino-N-(3-(N-(3-(3,5-dimethoxyphenylamino)quinoxalin-2-yl)sulfamoyl)phenyl)butanamide hydrochloride MS (EI) for $C_{26}H_{28}N_6O_5S \cdot HCl$: 537.1 (MH+).

Example 17

(R)—N-(3-(N-(3-(3,5-dimethoxy-phenylamino)quinoxalin-2-yl)sulfamoyl)phenyl)pyrrolidine-2-carboxamide hydrochloride MS (EI) for $C_{27}H_{28}N_6O_5S \cdot HCl$: 549.1 (MH+).

Example 18

(R)—N-(3-(N-(3-(2-chloro-5-methoxy-phenylamino)quinoxalin-2-yl)sulfamoyl)phenyl)pyrrolidine-2-carboxamide hydrochloride MS (EI) for $C_{26}H_{25}ClN_6O_4S \cdot HCl$: 553 (MH+).

Example 19

N-(3-(N-(3-(2-chloro-5-methoxy-phenylamino)quinoxalin-2-yl)sulfamoyl)phenyl)morpholine-4-carboxamide MS (EI) for $C_{26}H_{25}ClN_6O_5S$: 567 (MH−).

Example 20

N-(3-(N-(3-(3,5-dimethoxy-phenylamino)quinoxalin-2-yl)sulfamoyl)phenyl)-2-(dimethylamino)acetamide MS (EI) for $C_{26}H_{29}N_6O_5S$: 535.1 (MH−).

Example 21

(S)-2-amino-N-(3-(N-(3-(3,5-dimethoxyphenylamino)quinoxalin-2-yl)sulfamoyl)phenyl)propanamide hydrochloride

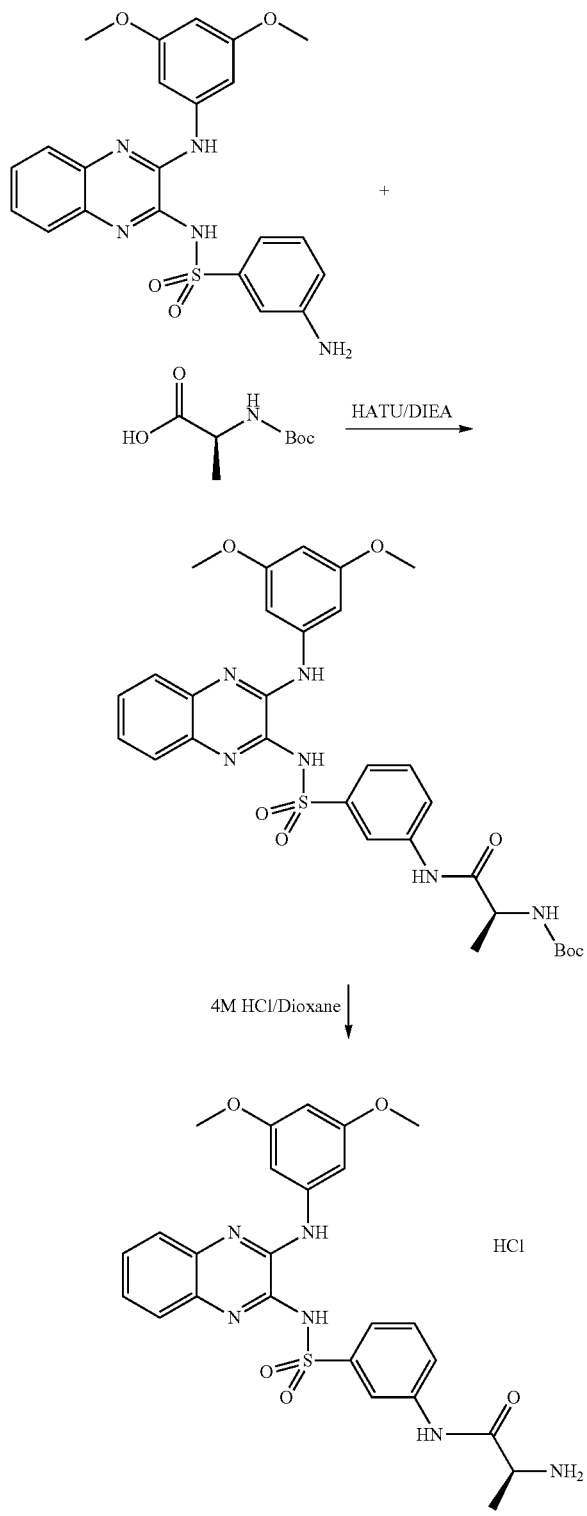

(S)-tert-butyl 1-(3-(N-(3-(3,5-dimethoxyphenylamino)quinoxalin-2-yl)sulfamoyl)phenylamino)-1-oxopropan-2-ylcarbamate 3-amino-N-(3-(3,5-dimethoxyphenylamino)quinoxalin-2-yl)benzenesulfonamide (1.1 mmol, 500 mg), (L)-Boc-Ala-OH (1.5 mmol, 284 mg), dichloromethane (15 mL), DMF (10 mL), DIEA (2 mmol, 330 ul), and HATU (2 mmol, 760 mg) stirred at r.t. over night. The crude mixture was column purified using 1/1 ethyl acetate/hexanes on silica to gave 160 mg.

(S)-2-amino-N-(3-(N-(3-(3,5-dimethoxyphenylamino)quinoxalin-2-yl)sulfamoyl)phenyl)propanamide hydrochloride 4 M HCl is dioxane (10 mL) was added to a solution of (S)-tert-butyl 1-(3-(N-(3-(3,5-dimethoxyphenylamino)quinoxalin-2-yl)sulfamoyl)phenylamino)-1-oxopropan-2-ylcarbamate (160 mg) and DCM (15 mL). The mixture was stirred at r.t. for 3 hours. The solvent decanted and ether added to the solid, ether decanted to gave 80 mg product as HCl salt. 1H NMR (400 MHz, CD3OD) δ 8.50-8.49 (t, 1H), 7.89-7.87 (m, 1H), 7.74-7.72 (m, 1H), 7.61-7.5 (m, 3H), 7.40-7.36 (m, 2H), 7.21-7.20 (d, 2H), 6.23-6.21 (t, 1H), 4.09-4.03 (q, 1H), 3.78 (s, 6H), 1.60-1.58 (d, 3H); MS (EI) for $C_{25}H_{26}N_6O_5S \cdot HCl$: 523.1 (MH+).

The following title compounds were prepared according to the above Examples.

Example 22

4-chloro-N-(3-(2,5-dimethoxyphenylamino)quinoxalin-2-yl)benzenesulfonamide

1H NMR (400 MHz, DMSO-d6) δ 9.18 (s, 1H), 8.78 (s, 1H), 8.40-8.60 (m, 3H), 7.98 (t, 2H), 7.62 (d, 1H), 7.41 (m, 2H), 6.98 (d, 1H), 6.59 (d, 1H), 3.78 (s, 3H), 3.76 (s, 3H); MS (EI) for $C_{22}H_{19}N_5O_6S$: 482.1 (MH+).

Example 23

N-(3-(2,5-dimethoxyphenylamino)quinoxalin-2-yl)-3-nitrobenzenesulfonamide

1H NMR (400 MHz, CDCl$_3$) δ 12.68 (br s, 1H), 9.18 (s, 1H), 8.55 (s, 1H), 8.08 (d, 2H), 7.98 (d, 1H), 7.78 (d, 2H), 7.62 (dd, 1H), 7.40 (m, 2H), 7.00 (d, 1H), 6.60 (dd, 1H), 3.78 (s, 6H); MS (EI) for $C_{22}H_{19}ClN_4O_4S$: 471.1 (MH+).

Example 24

N-(3-(N-(3-(2-chloro-5-methoxyphenylamino)quinoxalin-2-yl)sulfamoyl)-4-methylphenyl)-2-(dimethylamino)acetamide 1H NMR (400 MHz, DMSO-d6) δ 12.0 (br s, 1H), 10.6 (s, 1H), 10.0 (br s, 1H), 9.52 (s, 1H), 8.91 (d, 1H), 8.25 (d, 1H), 7.69 (dd, 1H), 7.47 (m, 1H), 7.39 (d, 1H), 7.16 (m, 3H), 6.01 (dd, 1H); MS (EI) for $C_{26}H_{27}ClN_6O_4S$: 555 (MH+).

Example 25

(R)-2-amino-N-(3-(N-(3-(3,5-dimethoxyphenylamino)quinoxalin-2-yl)sulfamoyl)phenyl)propanamide 1H NMR (400 MHz, DMSO-d6) δ 10.2 (br s, 1H), 8.82 (s, 1H), 8.27 (m, 1H), 7.75 (m, 2H), 7.33 (m, 5H), 7.13 (m, 2H), 6.14 (t, 1H), 3.77 (s, 6H), 1.39 (d, 3H); MS (EI) for $C_{25}H_{26}N_6O_5S$: 523 (MH+).

Example 26

N-(3-(N-(3-(2-chloro-5-methoxy-phenylamino)quinoxalin-2-yl)sulfamoyl)phenyl)-2-(methylamino)acetamide 1H NMR (400 MHz, DMSO-d6) δ 10.6 (s, 1H), 9.48 (s, 1H), 8.95 (br s, 1H), 8.75 (br s, 1H), 8.19 (br s, 1H), 7.77 (dd, 1H), 7.69 (dd, 1H), 7.41 (m, 4H), 7.17 (m, 2H), 6.60 (dd, 1H), 3.91 (s, 2H), 3.82 (s, 6H), 2.62 (s, 3H); MS (EI) for $C_{24}H_{23}ClN_6O_4S$: 527 (MH+).

Example 27

(R)-2-amino-N-(3-(N-(3-(2-chloro-5-methoxy-phenylamino)quinoxalin-2-yl)sulfamoyl)phenyl)propanamide 1H NMR (400 MHz, DMSO-d6) δ 10.5 (s, 1H), 9.47 (s, 1H), 8.95 (d, 1H), 8.22 (d, 2H), 8.14 (br s, 2H), 7.76 (m, 2H), 7.40 (m, 4H), 7.17 (m, 2H), 6.60 (m, 1H), 3.97 (q, 1H), 3.96 (s, 3H), 1.45 (d, 3H); MS (EI) for $C_{24}H_{23}ClN_6O_4S$: 527 (MH+).

Example 28

2-amino-N-(3-(N-(3-(2-chloro-5-methoxy-phenylamino)quinoxalin-2-yl)sulfamoyl)phenyl)-2-methylpropanamide 1H NMR (400 MHz, DMSO-d6) δ 10.1 (s, 1H), 9.46 (s, 1H), 8.95 (d, 1H), 8.50 (br s, 1H), 8.27 (m, 1H), 7.81 (m, 2H), 7.47 (m, 1H), 7.37 (m, 3H), 7.17 (m, 2H), 6.61 (dd, 1H), 3.83 (s, 3H), 1.60 (s, 6H); MS (EI) for $C_{25}H_{25}ClN_6O_4S$: 541 (MH+).

Example 29

2-amino-N-(3-(N-(3-(3,5-dimethoxy-phenylamino)quinoxalin-2-yl)sulfamoyl)phenyl)-2-methylpropanamide 1H NMR (400 MHz, DMSO-d6) δ 10.33 (s, 1H), 8.89 (s, 1H), 8.32 (br s, 4H), 7.92 (m, 3H), 7.59 (m, 2H), 7.37 (m, 4H), 6.24 (s, 1H), 3.76 (s, 6H), 1.61 (s, 6H); MS (EI) for $C_{26}H_{28}N_6O_5S$: 537 (MH+).

Example 30

N-(3-(N-(3-(3,5-dimethoxy-phenylamino)quinoxalin-2-yl)sulfamoyl)-4-methylphenyl)-2-(dimethylamino)acetamide 1H NMR (400 MHz, DMSO-d6) δ 10.58 (s, 1H), 9.80 (br s, 1H), 8.85 (s, 1H), 8.25 (s, 1H), 7.67 (dd, 1H), 7.30 (m, 7H), 6.16 (m, 1H), 4.02 (br s, 2H), 3.77 (s, 6H), 2.81 (s, 6H), 2.54 (s, 3H); MS (EI) for $C_{27}H_{30}N_6O_5S$: 551 (MH+).

Example 31

N-(3-(N-(3-(2-chloro-5-methoxy-phenylamino)quinoxalin-2-yl)sulfamoyl)phenyl)-2-((2-(dimethylamino)ethyl)(methyl)amino)acetamide 1H NMR (400 MHz, DMSO-d6) δ 10.0 (s, 1H), 9.48 (s, 1H), 8.96 (d, 1H), 8.16 (m, 1H), 7.76 (m, 2H), 7.39 (m, 4H), 7.17 (m, 2H), 6.61 (dd, 1H), 3.82 (s, 3H), 3.40 (br s, 2H), 2.94 (br s, 2H), 2.71 (br t, 2H), 2.60 (s, 6H), 2.33 (s, 3H); MS (EI) for $C_{28}H_{32}ClN_7O_4S$: 598 (MH+).

Example 32

2-amino-N-(3-(N-(3-(2-chloro-5-methoxy-phenylamino)quinoxalin-2-yl)sulfamoyl)phenyl)acetamide 1H NMR (400 MHz, DMSO-d6) δ 10.5 (s, 1H), 9.48 (s, 1H), 8.94 (s, 1H), 8.15 (s, 1H), 8.06 (br s, 3H), 7.74 (m, 2H), 7.39 (m, 4H), 7.18 (m, 2H), 6.61 (dd, 1H), 3.83 (s, 3H), 3.77 (s, 2H); MS (EI) for $C_{23}H_{21}ClN_6O_4S$: 513 (MH+).

Example 33

N-(3-(N-(3-(2-acetyl-5-methoxy-phenylamino)quinoxalin-2-yl)sulfamoyl)phenyl)-2-(dimethylamino)acetamide 1H NMR (400 MHz, DMSO-d6) δ 12.4 (s, 1H), 10.5 (s, 1H), 9.27 (s, 1H), 8.25 (s, 1H), 8.01 (d, 1H), 7.82 (d, 1H), 7.71 (d, 1H), 7.42 (m, 3H), 7.21 (m, 2H), 6.63 (dd, 1H), 3.91 (m, 5H), 2.75 (s, 6H), 2.61 (s, 3H); MS (EI) for $C_{27}H_{28}N_6O_5S$: 549 (MH+).

Example 34

N-(3-(N-(3-(2-chloro-5-methoxy-phenylamino)quinoxalin-2-yl)sulfamoyl)phenyl)formamide 1H NMR (400 MHz, DMSO-d6) δ 12.6 (s, 1H), 10.5 (s, 1H), 9.16 (s, 1H), 8.53 (br s, 1H), 8.35 (m, 2H), 8.02 (s, 1H), 7.56 (m, 7H), 6.70 (dd, 1H), 3.83 (s, 3H); MS (EI) for $C_{22}H_{18}ClN_5O_4S$: 484 (MH+).

Example 35

2-amino-N-(5-(N-(3-(3,5-dimethoxy-phenylamino)quinoxalin-2-yl)sulfamoyl)-2-methylphenyl)acetamide 1H NMR (400 MHz, DMSO-d6) δ 12.4 (s, 1H), 10.1 (br s, 1H), 8.82 (s, 1H), 8.20 (m, 3H), 7.82 (r, 1H), 7.30 (m, 6H), 6.20 (s, 1H), 3.85 (s, 2H), 3.77 (s, 6H), 2.26 (s, 3H); MS (EI) for $C_{25}H_{26}N_6O_5S$: 523 (MH+).

Example 36

N-(3-(N-(3-(2-chloro-5-methoxy-phenylamino)quinoxalin-2-yl)sulfamoyl)phenyl)-2-methyl-2-(methylamino)propanamide 1H NMR (400 MHz, DMSO-d6) δ 10.09 (s, 1H), 9.46 (s, 1H), 8.95 (m, 3H), 8.28 (s, 1H), 7.81 (m, 2H), 7.41 (m, 4H), 7.17 (m, 2H), 6.60 (dd, 1H), 3.82 (s, 3H), 2.53 (s, 3H), 1.60 (s, 6H); MS (EI) for $C_{26}H_{27}ClN_6O_4S$: 555 (MH+).

Example 37

(S)—N-(3-(N-(3-(2-chloro-5-methoxy-phenylamino)quinoxalin-2-yl)sulfamoyl)phenyl)-2-(methylamino)propanamide 1H NMR (400 MHz, DMSO-d6) δ 10.61 (s, 1H), 9.47 (s, 1H), 8.95 (s, 1H), 8.82 (br s, 2H), 8.27 (m, 1H), 7.74 (m, 2H), 7.42 (m, 4H), 7.17 (m, 2H), 6.60 (dd, 1H), 3.90 (m, 1H), 3.82

Example 38

3-amino-N-(5-(N-(3-(2-chloro-5-methoxyphenylamino)quinoxalin-2-yl)sulfamoyl)-2-methylphenyl)propanamide 1H NMR (400 MHz, DMSO-d6) δ 12.25 (s, 1H), 9.77 (s, 1H), 8.82 (s, 1H), 7.84 (m, 5H), 7.50 (d, 1H), 7.37 (m, 5H), 6.22 (m, 1H), 3.74 (s, 6H), 3.08 (m, 2H), 2.77 (m, 2H), 2.27 (s, 3H); MS (EI) for $C_{26}H_{28}N_6O_5S$: 537 (MH+).

Example 39

1-amino-N-(3-(N-(3-(2-chloro-5-methoxy-phenylamino)quinoxalin-2-yl)sulfamoyl)phenyl)cyclopropanecarboxamide 1H NMR (400 MHz, DMSO-d6) δ 9.54 (br s, 1H), 9.42 (s, 1H), 8.91 (s, 1H), 8.21 (s, 1H), 8.20 (br s, 2H), 7.81 (m, 2H), 7.48 (m, 4H), 7.22 (m, 2H), 6.61 (dd, 1H), 3.82 (s, 3H), 1.63 (m, 2H), 1.26 (m, 2H); MS (EI) for $C_{25}H_{23}ClN_6O_4S$: 539 (MH+).

Example 40

(S)-2-amino-N-(3-(N-(3-(2-chloro-5-methoxy-phenylamino)quinoxalin-2-yl)sulfamoyl)phenyl)-6-(dimethylamino)hexanamide 1H NMR (400 MHz, DMSO-d6) δ 9.47 (br s, 1H), 8.95 (d, 1H), 8.26 (m, 1H), 7.73 (m, 2H), 7.30 (m, 4H), 7.26 (m, 4H), 7.16 (m, 2H), 6.59 (dd, 1H), 3.82 (s, 3.14), 3.34 (m, 1H), 2.20 (m, 2H), 2.09 (s, 6H), 1.50 (m, 6H); MS (EI) for $C_{29}H_{34}ClN_7O_4S$: 610 (MH+).

Example 41

1-amino-N-(3-(N-(3-(2-chloro-5-methoxy-phenylamino)quinoxalin-2-yl)sulfamoyl)phenyl)cyclopentanecarboxamide 1H NMR (400 MHz, DMSO-d6) δ 10.12 (br s, 1H), 9.46 (s, 1H), 8.95 (d, 1H), 8.26 (m, 1H), 8.16 (m, 3H), 7.84 (m, 2H), 7.35 (m, 6H), 6.60 (dd, 1H), 3.82 (s, 3H), 2.34 (m, 2H), 1.91 (m, 6H); MS (EI) for $C_{27}H_{27}ClN_6O_4S$: 567 (MH+).

Example 42

2-amino-N-(5-(N-(3-(3,5-dimethoxy-phenylamino)quinoxalin-2-yl)sulfamoyl)-2-methylphenyl)acetamide

Example

N-(5-(N-(3-(2-chloro-5-methoxyphenylamino)quinoxalin-2-yl)sulfamoyl)-2-methylphenyl)-2-(dimethylamino)acetamide 1H NMR (400 MHz, DMSO-d6) δ 12.0 (br s, 1H), 9.98 (s, 1H), 9.43 (s, 1H), 8.91 (m, 1H), 8.08 (s, 1H), 7.84 (dd, 1H), 7.32 (m, 6H), 6.61 (dd, 1H), 4.07 (s, 2H), 3.82 (s, 3H), 2.82 (s, 6H), 2.21 (s, 3H); MS (EI) for $C_{26}H_{27}ClN_6O_4S$: 555 (MH+).

Example 43

1-amino-N-(3-(N-(3-(3,5-dimethoxy-phenylamino)quinoxalin-2-yl)sulfamoyl)phenyl)cyclobutanecarboxamide 1H NMR (400 MHz, DMSO-d6) δ 10.34 (br s, 1H), 8.81 (s, 1H), 8.49 (br s, 3H), 8.34 (s, 1H), 7.83 (m, 2H), 7.43 (m, 3H), 7.31 (m, 2H), 7.16 (m, 2H), 6.16 (s, 1H), 3.77 (s, 6H), 2.83 (m, 2H), 2.25 (m, 3H), 2.05 (m, 1H); MS (EI) for $C_{27}H_{28}N_6O_5S$: 549 (MH+).

Example 44

N-(3-(3,5-dimethoxyphenylamino)quinoxalin-2-yl)-3-(3-(2-(dimethylamino)ethyl)ureido)benzenesulfonamide 1H NMR (400 MHz, DMSO-d6) δ 8.91 (br s, 1H), 8.81 (s, 1H), 8.08 (s, 1H), 7.60 (s, 1H), 7.38 (m, 9H), 6.28 (m, 1H), 6.15 (s, 1H), 3.78 (s, 6H), 3.40 (m, 2H), 3.08 (m, 2H), 2.74 (s, 6H); MS (EI) for $C_{27}H_{31}N_7O_5S$: 566 (MH+).

Example 45

1-amino-N-(3-(N-(3-(3,5-dimethoxy-phenylamino)quinoxalin-2-yl)sulfamoyl)phenyl)cyclopentanecarboxamide 1H NMR (400 MHz, DMSO-d6) δ 12.40 (br s, 1H), 10.58 (s, 1H), 8.46 (m, 4H), 7.80 (m, 3H), 7.59 (m, 2H), 7.34 (m, 4H), 6.25 (m, 1H), 3.76 (s, 6H), 2.35 (m, 2H), 1.90 (m, 8H); MS (EI) for $C_{28}H_{30}N_6O_5S$: 563 (MH+).

Example 46

1-amino-N-(3-(N-(3-(3,5-dimethoxy-phenylamino)quinoxalin-2-yl)sulfamoyl)phenyl)cyclopropanecarboxamide 1H NMR (400 MHz, DMSO-d6) δ 9.54 (br s, 1H), 8.84 (s, 1H), 8.29 (s, 1H), 7.75 (m, 2H), 7.39 (m, 6H), 7.17 (m, 2H), 6.16 (m, 1H), 3.78 (s, 6H), 1.52 (m, 2H), 1.17 (m, 2H); MS (EI) for $C_{26}H_{26}N_6O_5S$: 535 (MH+).

Example 47

2-(dimethylamino)ethyl 3-(N-(3-(3,5-dimethoxyphenylamino)quinoxalin-2-yl)sulfamoyl)phenylcarbamate 1H NMR (400 MHz, DMSO-d6) δ 9.78 (br s, 1H), 8.79 (s, 1H), 8.19 (s, 1H), 7.66 (d, 1H), 7.31 (m, 9H), 6.14 (m, 1H), 4.17 (t, 2H), 3.78 (s, 6H), 2.54 (t, 2H), 2.21 (s, 6H): MS (EI) for $C_{27}H_{30}N_6O_6S$: 567 (MH+).

Example 48

4-amino-N-(3-(N-(3-(3,5-dimethoxy-phenylamino)quinoxalin-2-yl)sulfamoyl)phenyl)tetrahydro-2H-pyran-4-carboxamide 1H NMR (400 MHz, DMSO-d6) δ 12.2 (br s, 1H), 10.6 (s, 1H), 8.74 (m, 5H), 7.93 (m, 2H), 7.47 (m, 6H), 6.24 (m, 1H), 3.77 (m, 10H), 2.45 (m, 2H), 1.81 (m, 2H); MS (EI) for $C_{28}H_{30}N_6O_6S$: 579 (MH+).

(beginning of page, continuation from prior example:)
(s, 3H), 2.59 (s, 3H), 1.49 (d, 3H); MS (EI) for $C_{25}H_{25}ClN_6O_4S$: 541 (MH+).

Example 49

N1-(3-(2-chloro-5-methoxy-phenylamino)quinoxalin-2-yl)-N-3-(2-(dimethylamino)ethyl)benzene-1,3-disulfonamide 1H NMR (400 MHz, DMSO-d6) δ 9.35 (m, 2H), 8.92 (m, 1H), 8.64 (s, 1H), 8.30 (m, 1H), 8.11 (s, 1H), 7.86 (m, 1H), 7.68 (m, 1H), 7.49 (s, 1H), 7.42 (m, 2H), 7.21 (m, 2H), 6.61 (m, 1H), 3.82 (s, 3H), 3.05 (m, 4H), 2.74 (s, 6H); MS (EI) for $C_{25}H_{27}ClN_6O_5S_2$: 591 (MH+).

Example 50

N1-(3-(2-chloro-5-methoxy-phenylamino)quinoxalin-2-yl)-N-3-(3-(dimethylamino)propyl)benzene-1,3-disulfonamide 1H NMR (400 MHz, DMSO-d6) δ 9.38 (m, 2H), 8.90 (m, 1H), 8.60 (s, 1H), 8.32 (m, 1H), 8.12 (s, 1H), 7.88 (m, 1H), 7.72 (m, 1H), 7.59 (s, 1H), 7.40 (m, 2H), 7.20 (m, 2H), 6.67 (m, 1H), 3.82 (s, 3H), 2.97 (m, 2H), 2.78 (m, 2H), 2.71 (s, 6H), 1.70 (m, 2H); MS (EI) for $C_{26}H_{29}ClN_6O_5S_2$: 605 (MH+).

Example 51

N-(3-(N-(3-(2-chloro-5-methoxy-phenylamino)quinoxalin-2-yl)sulfamoyl)-4-methylphenyl)-2-(methylamino)acetamide MS (EI) for $C_{25}H_{25}ClN_6O_4S$: 541.0 (MH+).

Example 52

(S)-2-amino-N-(3-(N-(3-(2-chloro-5-methoxy-phenylamino)quinoxalin-2-yl)sulfamoyl)-4-methylphenyl)propanamide MS (EI) for $C_{25}H_{25}ClN_6O_4S$: 541.2 (MH+).

Example 53

(R)-2-amino-N-(3-(N-(3-(2-chloro-5-methoxy-phenylamino)quinoxalin-2-yl)sulfamoyl)-4-methylphenyl)propanamide MS (EI) for $C_{25}H_{25}ClN_6O_4S$: 541.0 (MH+).

Example 54

(S)—N-(3-(N-(3-(3,5-dimethoxy-phenylamino)quinoxalin-2-yl)sulfamoyl)phenyl)-2-(methylamino)propanamide MS (EI) for $C_{26}H_{28}N_6O_5S$: 537.1 (MH+).

Example 55

(R)—N-(3-(N-(3-(2-chloro-5-methoxy-phenylamino)quinoxalin-2-yl)sulfamoyl)phenyl)-2-(methylamino)propanamide MS (EI) for $C_{25}H_{25}ClN_6O_4S$: 541.1 (MH+).

Example 56

(R)—N-(3-(N-(3-(3,5-dimethoxy-phenylamino)quinoxalin-2-yl)sulfamoyl)phenyl)-2-(methylamino)propanamide MS (EI) for $C_{26}H_{28}N_6O_5S$: 537.3 (MH+).

Example 57

N-(3-(N-(3-(3,5-dimethoxy-phenylamino)quinoxalin-2-yl)sulfamoyl)phenyl)piperidine-2-carboxamide MS (EI) for $C_{28}H_{30}N_6O_5S$: 563.1 (MH+).

Example 58

N-(3-(N-(3-(3,5-dimethoxy-phenylamino)quinoxalin-2-yl)sulfamoyl)phenyl)-2-(2-(dimethylamino)ethylamino)acetamide MS (EI) for $C_{28}H_{33}N_7O_5S$: 580.1 (MH+).

Example 59

N-(3-(N-(3-(3,5-dimethoxy-phenylamino)quinoxalin-2-yl)sulfamoyl)phenyl)-2-(4-(methylamino)piperidin-1-yl)acetamide MS (EI) for $C_{30}H_{35}N_7O_6S$: 606.1 (MH+).

Example 60

N-(3-(N-(3-(3,5-dimethoxy-phenylamino)quinoxalin-2-yl)sulfamoyl)phenyl)-2-((3-(dimethylamino)propyl)(methyl)amino)acetamide MS (EI) for $C_{30}H_{37}N_7O_5S$: 608.1 (MH+).

Example 61

2-(1,4'-bipiperidin-1'-yl)-N-(3-(N-(3-(3,5-dimethoxy-phenylamino)quinoxalin-2-yl)sulfamoyl)phenyl)acetamide MS (EI) for $C_{34}H_{41}N_7O_5S$: 660.1 (MH+).

Example 62 tert-butyl 2-(3-(N-(3-(3,5-dimethoxy-phenylamino)quinoxalin-2-yl)sulfamoyl)phenylcarbamoyl)piperidine-1-carboxylate MS (EI) for $C_{33}H_{38}N_6O_7S$: 663.1 (MH+).

Example 63

3-(N-(3-(2-chloro-5-methoxy-phenylamino)quinoxalin-2-yl)sulfamoyl)-N-(1-(dimethylamino)propan-2-yl)benzamide MS (EI) for $C_{27}H_{29}ClN_6O_4S$: 569.0 (MH+).

Example 64

3-{[(3-{[2-chloro-5-(methyloxy)phenyl]amino}quinoxalin-2-yl)amino]sulfonyl}-N-[2-(dimethylamino)ethyl]benzamide

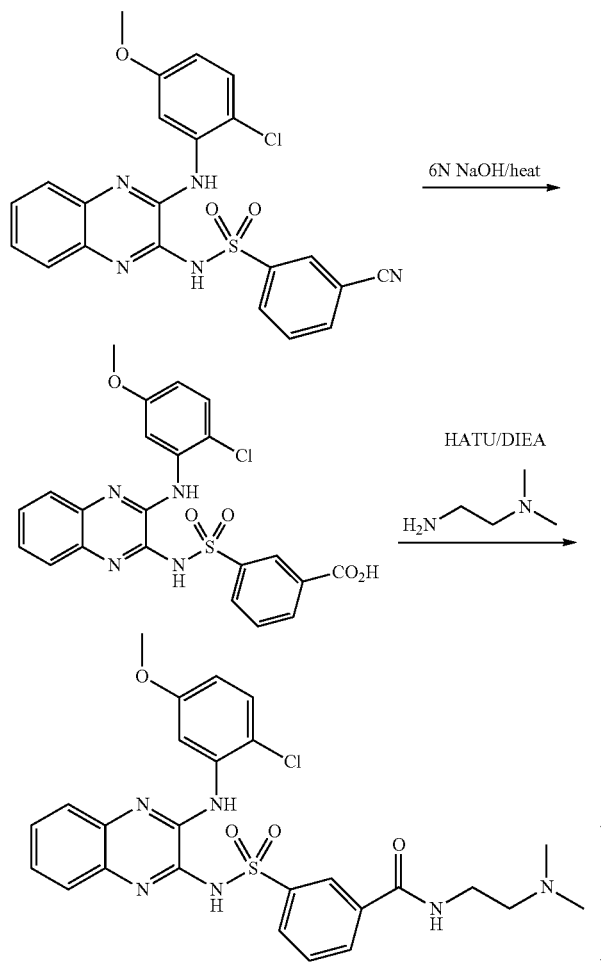

3-{[(3-{[2-chloro-5-(methyloxy)phenyl]amino}quinoxalin-2-yl)amino]sulfonyl}benzoic acid To a solution of N-(3-{[2-chloro-5-(methyloxy)phenyl]amino}quinoxalin-2-yl)-3-cyanobenzenesulfonamide (6.02 g, 12.95 mmol) in methanol (20 mL) and 1,4-dioxane (20 mL) was added 6.0 N aqueous sodium hydroxide (40 mL) at room temperature. The solution was stirred at 90° C. for 3.5 h. The reaction was cooled to room temperature and neutralized slowly by adding 2.0 N hydrochloric acid until the pH of the solution became in the 2-3 range at 0° C. The solution was diluted with ethyl acetate (300 mL). The organic layer was washed with saturated aqueous sodium chloride (50 mL) and dried over magnesium sulfate. Filtration and concentration at reduced pressure afforded 3-{[(3-{[2-chloro-5-(methyloxy)phenyl]amino}quinoxalin-2-yl)amino]sulfonyl}benzoic acid (5.921 g, 94%). MS (EI) for $C_{22}H_{17}ClN_4O_5S$: 485.0 (MH+)

3-{[(3-{[2-chloro-5-(methyloxy)phenyl]amino}quinoxalin-2-yl)amino]sulfonyl}-N-[2-(dimethylamino)ethyl]benzamide To a solution of 3-{[(3-{[2-chloro-5-(methyloxy)phenyl]amino}quinoxalin-2-yl)amino]sulfonyl}benzoic acid (0.20 g, 0.42 mmol) in dimethylformamide (4 mL) were added 2-(7-Aza-1H-benzotriazole-1-yl)-1,1,3,3-tetramethyluronium hexafluorophosphate (HATU, 0.32 g, 0.83 mmol) and N-ethyldiisopropylamine (DIEA, 0.13 g, 1.04 mmol) at room temperature. The reaction was stirred for 15 min before N,N-dimethylethane-1,2-diamine (73 mg, 0.83 mmol) was added. The reaction mixture was allowed to stir overnight. The reaction was diluted with ethyl acetate (200 mL) and washed with water (50 mL), saturated aqueous sodium bicarbonate (40 mL), 1.0 N aqueous hydrochloric acid (30 mL), and saturated aqueous sodium chloride (25 mL). The organic layer was dried over magnesium sulfate, filtered and concentrated at reduced pressure to afford 3-{[(3-{[2-chloro-5-(methyloxy)phenyl]amino}quinoxalin-2-yl)amino]sulfonyl}-N-[2-(dimethylamino)ethyl]benzamide (0.20 g, 87%) as yellow solid. MS (EI) for $C_{26}H_{27}ClN_6O_4S$: 555.1 (MH+).

The following title compounds were prepared according to the above Examples.

Example 65

3-(N-(3-(3,5-dimethoxyphenylamino)quinoxalin-2-yl)sulfamoyl)-N-(2-(dimethylamino)ethyl)benzamide MS (EI) for $C_{27}H_{30}N_6O_5S$: 551.1 (MH+).

Example 66

3-(N-(3-(2-chloro-5-methoxyphenylamino)quinoxalin-2-yl)sulfamoyl)-N-(2-(dimethylamino)ethyl)-N-methylbenzamide MS (EI) for $C_{27}H_{29}ClN_6O_4S$: 569.1 (MH+).

Example 67

3-(N-(3-(3,5-dimethoxyphenylamino)quinoxalin-2-yl)sulfamoyl)-N-(2-(dimethylamino)ethyl)-N-methylbenzamide MS (EI) for $C_{28}H_{32}N_6O_5S$: 565.1 (MH+).

Example 69

3-(N-(3-(2-chloro-5-methoxy-phenylamino)quinoxalin-2-yl)sulfamoyl)benzamide

MS (EI) for $C_{22}H ClN_5O_4S$: 484.0 (MH+).

Example 70

3-(N-(3-(2-chloro-5-methoxy-phenylamino)quinoxalin-2-yl)sulfamoyl)benzoic acid

MS (EI) for $C_{22}H_{17}ClN_4O_5S$: 485.0 (MH+).

Example 71

3-(N-(3-(2-chloro-5-methoxy-phenylamino)quinoxalin-2-yl)sulfamoyl)-N-(2-morpholinoethyl)benzamide MS (EI) for $C_{28}H_{29}ClN_6O_5S$: 597.0 (MH+).

Example 72

3-(N-(3-(2-chloro-5-methoxy-phenylamino)quinoxalin-2-yl)sulfamoyl)-N-methylbenzamide MS (EI) for $C_{23}H_{20}ClN_5O_4S$: 498.0 (MH+).

Example 73

3-(N-(3-(3,5-dimethoxyphenylamino)quinoxalin-2-yl)sulfamoyl)benzoic acid

MS (EI) for $C_{23}H_{20}N_4O_6S$: 481.0 (MH+).

Example 74

3-(N-(3-(2-chloro-5-methoxy-phenylamino)quinoxalin-2-yl)sulfamoyl)-N-morpholinobenzamide MS (EI) for $C_{26}H_{25}ClN_6O_5S$: 569.0 (MH+).

Example 75

N-(3-(2-chloro-5-methoxyphenylamino)quinoxalin-2-yl)-3-cyanobenzenesulfonamide

MS (EI) for $C_{22}H_{16}ClN_5O_3S$: 465.9 (MH+).

Example 76

N-(3-{[2-chloro-5-(methyloxy)phenyl]amino}quinoxalin-2-yl)-3-{5-[(dimethylamino)methyl]-1,3,4-oxadiazol-2-yl}benzenesulfonamide

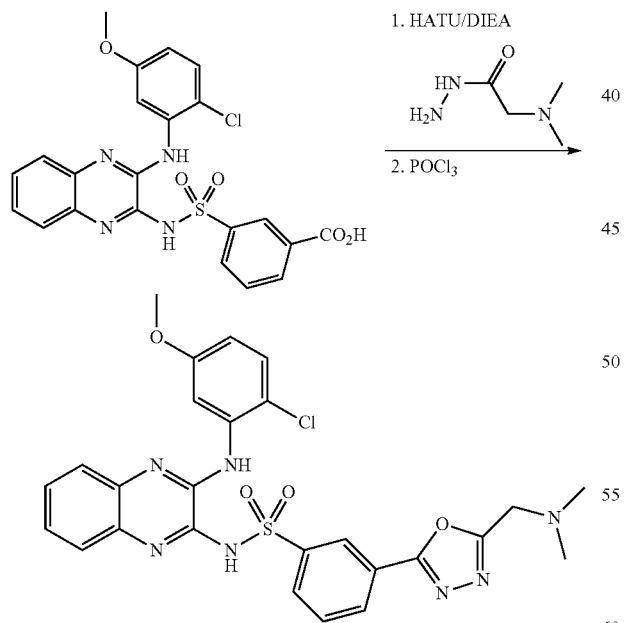

To a solution of 3-{[(3-{[2-chloro-5-(methyloxy)phenyl]amino}quinoxalin-2-yl)amino]sulfonyl}benzoic acid (0.25 g, 0.52 mmol) in dimethylformamide (2.6 mL) were added 2-(7-Aza-1H-benzotriazole-1-yl)-1,1,3,3-tetramethyluronium hexafluorophosphate (HATU, 0.25 g, 0.67 mmol) and N-ethyldiisopropylamine (DIEA, 0.11 g, 0.88 mmol) at room temperature. The reaction was stirred for 15 min before 2-(dimethylamino)acetohydrazide (78 mg, 0.67 mmol) was added. The reaction mixture was allowed to stir overnight. The reaction was diluted with ethyl acetate (200 mL) and washed with water (30 mL), saturated aqueous sodium bicarbonate (30 mL), 1.0 N aqueous hydrochloric acid (20 mL), and saturated aqueous sodium chloride (25 mL). The organic layer was dried over magnesium sulfate, filtered and concentrated at reduced pressure to afford 180 mg of a coupled intermediate which was then heated in phosphorus oxychloride (5 mL) at 100° C. for 4 h. The reaction was cooled to room temperature and treated with ice water (50 mL) and extracted with dichloromethane (3×50 mL). The organic layer was dried over magnesium sulfate, filtered and concentrated at reduced pressure to afford a crude product which was subjected to reverse phase HPLC to afford N-(3-{[2-chloro-5-(methyloxy)phenyl]amino}quinoxalin-2-yl)-3-{5-[(dimethylamino)methyl]-1,3,4-oxadiazol-2-yl}benzenesulfonamide (16 mg, 5%) as yellow solid. MS (EI) for $C_{26}H_{24}ClN_7O_4S$: 566.0 (MH+).

Example 78

N-(3-{[3,5-bis(methyloxy)phenyl]amino}quinoxalin-2-yl)-3-(2H-tetrazol-5-yl)benzenesulfonamide

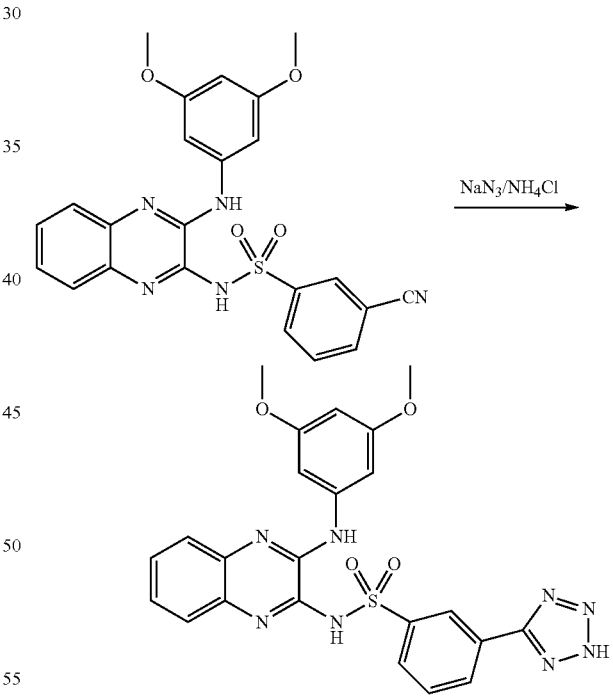

To a stirred solution of 3-cyano-N-(3-(3,5-dimethoxyphenylamino)quinoxalin-2-yl)benzenesulfonamide (0.20 g, 0.44 mmol) in dimethylformamide (1.2 mL) at 50° C. were added sodium azide (0.11 g, 1.76 mmol) and ammonium chloride (94 mg, 1.76 mmol). The crude mixture was heated at 100° C. overnight. The reaction was cooled to room temperature treated with ice water (20 mL) followed by concentrated hydrochloric acid (10 mL). The solid obtained was filtered under reduced pressure and washed with hexane (20 mL), diethyl ether (20 mL), and ethyl acetate (5 mL) to afford N-(3-{[3,5-bis(methyloxy)phenyl]amino}quinoxalin-2-yl)-3-(2H-tetrazol-5-yl)benzenesulfonamide (55 mg, 25%) as light yellow solid. MS (EI) for $C_{23}H_{20}N_8O_4S$: 505.0 (MH+).

The following title compounds were prepared according to the above Examples.

Example 77

3-cyano-N-(3-(3,5-dimethoxyphenylamino)quinoxalin-2-yl)benzenesulfonamide

MS (EI) for $C_{23}H_{19}N_5O_4S$: 462.3 (MH+).

Example 79

N-(3-(N-(3-(3,5-dimethoxyphenylamino)quinoxalin-2-yl)sulfamoyl)phenyl)-2-(4-(dimethylamino)piperidin-1-yl)acetamide MS (EI) for $C_{31}H_{37}N_7O_5S$: 620.1 (MH+).

Example 80

N-(3-(2,5-dimethoxyphenylamino)quinoxalin-2-yl)-3-fluorobenzenesulfonamide

MS (EI) for $C_{22}H_{19}FN_4O_4S$: 456.0 (MH+).

Example 81

3-bromo-N-(3-(3,5-dimethoxyphenylamino)quinoxalin-2-yl)benzenesulfonamide

MS (EI) for $C_{22}H_{19}BrN_4O_4S$: 516.9 (MH+).

Example 82

3-bromo-N-(3-(2,5-dimethoxy-phenylamino)quinoxalin-2-yl)benzenesulfonamide

MS (EI) for $C_{22}H_{19}BrN_4O_4S$: 516.9 (MH+).

Example 83

N-(3-(3-methoxyphenylamino)quinoxalin-2-yl)benzenesulfonamide

MS (EI) for $C_{21}H_{18}N_4O_3S$: 407.0 (MH+).

Example 84

N-(3-(morpholinoamino)quinoxalin-2-yl)-3-nitrobenzenesulfonamide

MS (EI) for $C_{18}H_{18}N_6O_5S$: 431.0 (MH+).

Example 85

3-nitro-N-(3-(tetrahydro-2H-pyran-4-ylamino)quinoxalin-2-yl)benzenesulfonamide

MS (EI) for $C_{19}H_{19}N_5O_5S$: 430.0 (MH+)

Example 86

N-(3-(4-fluoro-3-methoxyphenylamino)quinoxalin-2-yl)benzenesulfonamide

MS (EI) for $C_{21}H_{17}FN_4O_3S$: 425.0 (MH+).

Example 87

N-(3-(2,5-dimethoxyphenylamino)quinoxalin-2-yl)-4-methoxybenzenesulfonamide

MS (EI) for $C_{23}H_{22}N_4O_5S$: 467.0 (MH+).

Example 88

N-(3-(3,5-dimethoxyphenylamino)quinoxalin-2-yl)-4-methoxybenzenesulfonamide

MS (EI) for $C_{23}H_{22}N_4O_5S$: 467.0 (MH+).

Example 89

N-(3-(4-chloro-3-methoxyphenylamino)quinoxalin-2-yl)benzenesulfonamide

MS (EI) for $C_{21}H_{17}ClN_4O_3S$: 440.9 (MH+).

Example 90

N-(3-(2-methoxyphenylamino)quinoxalin-2-yl)benzenesulfonamide

MS (EI) for $C_{21}H_{18}N_4O_3S$: 407.0 (MH+).

Example 91

N-(3-(3-(benzyloxy)phenylamino)quinoxalin-2-yl)benzenesulfonamide

MS (EI) for $C_{27}H_{22}N_4O_3S$: 483.0 (MH+).

Example 92

N-(3-(3-phenoxyphenylamino)quinoxalin-2-yl)benzenesulfonamide

MS (EI) for $C_{26}H_{20}N_4O_3S$: 469.0 (MH+).

Example 93

N-(3-(3-methoxy-5-(trifluoromethyl)phenylamino)quinoxalin-2-yl)benzenesulfonamide MS (EI) for $C_{22}H_{17}F_3N_4O_3S$: 475.0 (MH+).

Example 94

N-(3-(2,5-diethoxyphenylamino)quinoxalin-2-yl)benzenesulfonamide

MS (EI) for $C_{24}H_{24}N_4O_4S$: 465.0 (MH+).

Example 95

N-(3-(2'-methoxybiphenyl-4-ylamino)quinoxalin-2-yl)benzenesulfonamide

MS (EI) for $C_{27}H_{22}N_4O_3S$: 483.0 (MH+).

Example 96

N-(3-(2-methoxy-5-methyl-phenylamino)quinoxalin-2-yl)benzenesulfonamide

MS (EI) for $C_{22}H_{20}N_4O_3S$: 421.0 (MH+).

Example 97

N-(3-(5-chloro-2-methoxyphenylamino)quinoxalin-2-yl)benzenesulfonamide

MS (EI) for $C_{21}H_{17}ClN_4O_3S$: 441.0 (MH+).

Example 98

N-(3-(2-methoxy-5-(trifluoromethyl)-phenylamino)quinoxalin-2-yl)benzenesulfonamide MS (EI) for $C_{22}H_{17}F_3N_4O_3S$: 475.0 (MH+).

Example 99

N-(3-(2-methoxybiphenyl-4-ylamino)quinoxalin-2-yl)benzenesulfonamide

MS (EI) for $C_{27}H_{22}N_4O_3S$: 483.3 (MH+).

Example 100

N-(3-(N-(3-(3,5-dimethoxyphenylamino)quinoxalin-2-yl)sulfamoyl)phenyl)-2-(dimethylamino)acetamide 1H NMR (400 MHz, DMSO) δ 12.4 (br s, 1H), 10.9 (s, 1H), 9.8 (s, 1H), 8.9 (s, 1H), 8.3 (br s, 1H), 7.9 (d, 2H), 7.8 (d, 1H), 7.6 (t, 2H), 7.4 (q, 2H), 7.3 (s, 1H), 6.25 (s, 1H), 4.15 (s, 2H), 3.8 (s, 6H), 2.9 (s, 6H). MS (EI) for $C_{26}H_{28}N_6O_5S$ $2.0 \times C_2H_1O_2F_3$: 537.1 (MH+).

Example 101

2-(dimethylamino)-N-(3-(N-(3-(3-(2-(dimethylamino)acetamido)-5-methoxyphenylamino)quinoxalin-2-yl)sulfamoyl)phenyl)acetamide

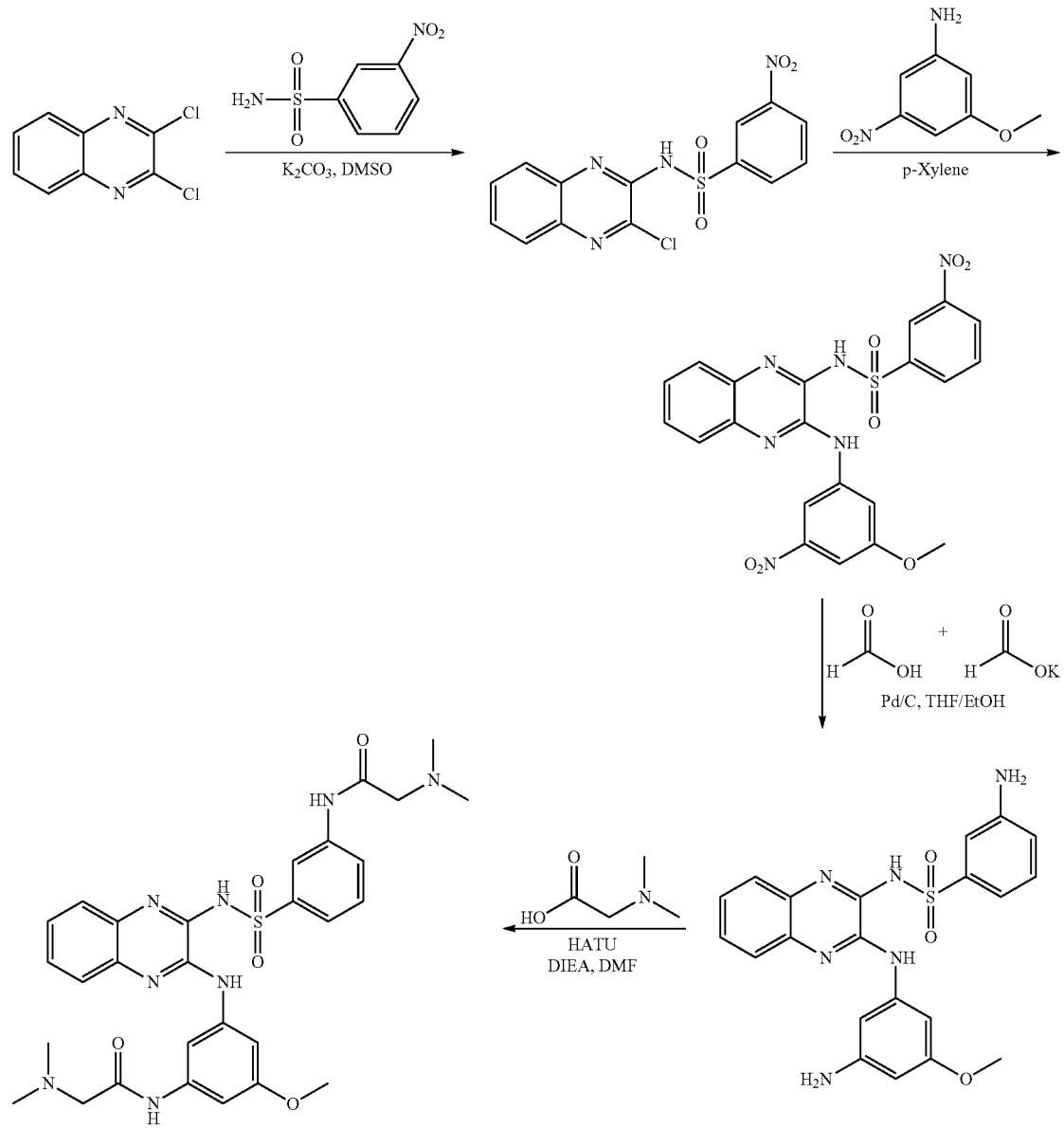

N-(3-chloroquinoxalin-2-yl)-3-nitrobenzenesulfonamide 2,3-Dichloroquinoxaline (26.1 g, 131.1 mmol), m-Nitrobenzene sulfonamide (26.5 g, 131.1 mmol) and potassium carbonate (18.1 g, 131.1) were dissolved in anhydrous DMSO (500 mL). The reaction was heated to 150° C. for 2 h. The reaction mixture was poured into water (400 mL), followed by addition of 2M HCl (60 mL). The product was extracted with EtOAc (3×500 mL). The organic layers were combined and washed water (2×500 mL) and brine (2×500 mL). The product was then dried with sodium sulfate to give N-(3-chloroquinoxalin-2-yl)-3-nitrobenzenesulfonamide. MS (EI) for $C_{14}H_9ClN_4O_4S$: 364.94, 366.97 (MH+)

N-(3-(3-methoxy-5-nitrophenylamino)quinoxalin-2-yl)-3-nitro-benzenesulfonamide N-(3-chloroquinoxalin-2-yl)-3-nitrobenzenesulfonamide (700 mg, 1.92 mmol), 3-methoxy-5-nitroaniline (645 mg, 3.84 mmol) and p-xylene (7 mL) were combined and heated to 140° C., then stirred for 16 hours at 130° C. The reaction was allowed to cool, placed in a sep. funnel, diluted with DCM, and washed with 2M HCl and brine and concentrated in vacuo. The resulting solid was washed with $Et_2O$ to give N-(3-(3-methoxy-5-nitrophenylamino)quinoxalin-2-yl)-3-nitrobenzenesulfonamide (400 mg, 42%). MS (EI) for $C_{21}H_{16}N_6O_7S$: 496.94 (MH+)

3-amino-N-(3-(3-amino-5-methoxyphenylamino)quinoxalin-2-yl)benzenesulfonamide N-(3-(3-Methoxy-5-nitrophenylamino)quinoxalin-2-yl)-3-nitrobenzenesulfonamide (400 mg, 0.81 mmol) was dissolved in 1:1 THF:EtOH (4 mL), to which was added formic acid (938 µl, 2.42 mmol) and potassium formate (203 mg, 2.42 mmol). The system was flushed with nitrogen, and then 10% wt Pd/C (50 mg) was added. The reaction was then heated to 60° C. Once the reaction was determined complete by LC-MS, it was allowed to cool, and DMF was added for solubility. The solution was then filtered through a nylon frit to remove the catalyst. The filtrate was diluted water and the pH adjusted to 7 and extracted with DCM (2×) and EtOAc (2×). All organic layers were combined and evaporated to dryness to give 3-amino-N-(3-(3-amino-5-methoxyphenylamino)quinoxalin-2-yl)benzenesulfonamide (330 mg, 93%). MS (EI) for $C_{21}H_{20}N_6O_3S$: 437.06 (MH+)

2-(dimethylamino)-N-(3-(N-(3-(3-(2-(dimethylamino)acetamido)-5-methoxyphenylamino)quinoxalin-2-yl)-sulfamoyl)phenyl)acetamide 3-Amino-N-(3-(3-amino-5-methoxyphenylamino)quinoxalin-2-yl)benzenesulfonamide (330 mg, 0.76 mmol), DMF (4 mL), N,N,-Dimethylglycine (312 mg, 3.02 mmol), HATU (1.15 g, 3.02 mmol), and 1.29 (mL) (7.56 mmol) DIEA (1.29 mL, 7.56 mmol) were combined and heated to 90° C., followed by heating at 50° C. for over 16 hours. The reaction was allowed to cool, placed into a sep. funnel diluted with water and aqueous LiCl and extracted with EtOAc. The final compound was then purified by prep. HPLC to give 2-(dimethylamino)-N-(3-(N-(3-(3-(2-(dimethylamino)acetamido)-5-methoxy-phenylamino)-quinoxalin-2-yl)sulfamoyl)phenyl)acetamide. 1H NMR (400 MHz, CD3OD) δ 8.45 (t, 1H), 7.93 (t, 1H), 7.85-7.88 (m, 1H), 7.70-7.74 (m, 1H), 7.65-7.68 (m, 1H), 7.58-7.62 (m, 1H), 7.58 (t, 1H), 7.34-7.42 (m, 3H), 7.0 (t, 1H), 4.05 (d, 2H), 3.8 (s, 3H), 2.9-3.0 (d, 12H). MS (EI) for $C_{29}H_{34}N_8O_5S$: 607.2 (MH+).

The following title compounds were prepared according to the above Examples.

Example 102

N-(3-(N-(3-(2-chloro-5-methoxyphenylamino)quinoxalin-2-yl)sulfamoyl)phenyl)-2-(ethylamino)acetamide 1H NMR (400 MHz, DMSO) δ 10.8 (s, 1H), 9.20 (s, 1H), 8.84 (br s, 2H), 8.64 (br s, 1H), 8.30 (s, 1H), 7.9-8.0 (br s, 1H), 7.80 (t, 2H), 7.55-7.68 (m, 2H), 7.4 (d, 3H), 6.70 (m, 1H), 3.97 (br s, 2H), 3.83 (s, 3H), 3.04 (br s, 2H), 1.3 (t, 3H). MS (EI) for $C_{25}H_{25}ClN_6O_4S$ $2.0×C_2H_1O_2F_3$: 541.3, 543.2 (MH+).

Example 103

2-(azetidin-1-yl)-N-(3-(N-(3-(2-chloro-5-methoxyphenylamino)quinoxalin-2-yl)sulfamoyl)phenyl)acetamide 1H NMR (400 MHz, DMSO) δ 10.8 (s, 1H), 10.2 (s, 1H), 9.2 (s, 1H), 8.7 (s, 1H), 8.3 (s, 1H), 7.9-8.0 (br s, 1H), 7.80 (d, 1H), 7.72 (d, 1H), 7.65 (br s, 1H), 7.56 (t, 1H), 7.40 (d, 3H), 6.70 (m, 1H), 4.28 (s, 2H), 4.15 (m, 4H), 3.82 (s, 3H), 2.32 (br s, 1H). MS (EI) for $C_{26}H_{25}ClN_6O_4S$ $2.0×C_2H_1O_2F_3$: 553.3, 555.2 (MH+).

Example 104

N-(3-(N-(3-(2-bromo-5-methoxy-phenylamino)quinoxalin-2-yl)sulfamoyl)phenyl)-2-(methylamino)acetamide The title compound was prepared according to the Examples above. 1H NMR (400 MHz, DMSO) δ 10.6 (s, 1H), 9.5 (s, 1H), 8.95 (d, 1H), 8.18 (t, 1H), 7.78 (m, 1H), 7.70 (m, 1H), 7.54 (d, 1H), 7.46 (m, 1H), 7.38 (t, 1H), 7.32 (d, 1H), 7.12-7.22 (m, 2H), 6.56 (m, 1H), 3.90 (s, 2H), 3.82 (s, 3H), 2.62 (s, 3H). MS (EI) for $C_{24}H_{23}BrN_6O_4S$: 572.77, 570.90 (MH+).

Example 105

2-(dimethylamino)-N-(3-(N-(3-(6-methoxy-quinolin-8-ylamino)quinoxalin-2-yl)sulfamoyl)phenyl)acetamide The title compound was prepared according to the Examples above. 1H NMR (400 MHz, DMSO) δ 10.9 (s, 1H), 10.6 (s, 1H), 9.13 (s, 1H), 8.80 (d, 1H), 8.26-8.30 (m, 2H), 7.85 (d, 1H), 7.70 (d, 1H), 7.60 (q, 1H), 7.54 (m, 1H), 7.44 (t, 2H), 7.20 (t, 2H), 6.80 (d, 1H), 4.00 (s, 2H), 3.94 (s, 3H), 2.78 (s, 6H). MS (EI) for $C_{28}H_{27}N_7O_4S$: 558.3 (MH+).

Example 106

N-(3-(N-(3-(2-bromo-5-methoxy-phenylamino)quinoxalin-2-yl)sulfamoyl)phenyl)-2-(dimethylamino)acetamide The title compound was prepared according to the Examples above. 1H NMR (400 MHz, DMSO) δ 10.6 (s, 1H), 9.4 (s, 1H), 8.9 (s, 1H), 8.25 (s, 1H), 7.78 (d, 1H), 7.70 (d, 1H), 7.54 (d, 1H), 7.48 (d, 1H), 7.40 (t, 2H), 6.56 (d, 1H), 4.02 (s, 2H), 3.82 (s, 3H), 2.80 (s, 6H). MS (EI) for $C_{25}H_{25}BrN_6O_4S$: 586.79, 584.91 (MH+).

Example 107

N-(3-(3,5-dimethoxyphenylamino)quinoxalin-2-yl)-3-(hydroxyamino)benzenesulfonamide MS (EI) for $C_{22}H_{21}N_5O_5S$: 468.1 (MH+).

Example 108

N-(3-(N-(3-(2-chloro-5-methoxy-phenylamino)quinoxalin-2-yl)sulfamoyl)phenyl)-2-(2-fluoroethylamino)acetamide The title compound was prepared according to the Examples above. 1H NMR (400 MHz, DMSO) δ 10.6 (s, 1H), 9.4 (s, 1H), 8.9 (d, 1H), 8.20 (s, 1H), 7.78 (d, 1H), 7.70 (d, 1H), 7.48 (m, 1H), 7.36-7.44 (m, 3H), 7.20 (q, 3H), 6.6 (m, 1H), 4.78 (t, 1H), 4.66 (t, 1H), 3.94 (s, 2H), 3.82 (s, 3H), 3.4 (t, 1H), 3.3 (t, 1H). MS (EI) for $C_{25}H_{24}ClFN_6O_4S$: 559.2, 561.2 (MH+).

Example 109

N-(3-(N-(3-(3,5-dimethoxy-phenylamino)quinoxalin-2-yl)sulfamoyl)phenyl)formamide 1H NMR (400 MHz, DMSO) δ 12.4 (br s, 1H), 10.5 (s, 1H), 8.90 (s, 1H), 8.3 (s, 1H), 7.9 (br s, 1H), 7.85 (d, 1H), 7.75 (d, 1H), 7.5-7.6 (m, 2H), 7.3-7.4 (m, 4H), 6.2 (s, 1H), 3.8 (s, 3H). MS (EI) for $C_{23}H_{21}N_5O_5S$: 480.1 (MH+).

Example 110

N-(3-(N-(3-(2-chloro-5-methoxy-phenylamino)quinoxalin-2-yl)sulfamoyl)phenyl)-2-(3-(dimethylamino)azetidin-1-yl)acetamide 1H NMR (400 MHz, DMSO) δ 10.2 (br s, 1H), 9.5 (s, 1H), 8.95 (d, 1H), 8.2 (s, 1H), 7.75 (d, 1H), 7.65 (d, 1H), 7.45 (d, 1H), 7.40 (d, 1H), 7.30-7.35 (t, 1H), 7.1-7.2 (q, 2H), 6.60 (m, 1H), 3.82 (s, 3H). MS (EI) for $C_{28}H_{30}ClN_7O_4S$: 480.1 (MH+).

Example 111

N-(3-(N-(3-(3,5-dimethoxy-phenylamino)quinoxalin-2-yl)sulfamoyl)phenyl)-2-(pyrrolidin-1-yl)acetamide MS (EI) for $C_{28}H_{30}N_6O_5S$: 563.18 (MH+).

Example 112

3-amino-N-(3-(3,5-dimethoxy-phenylamino)quinoxalin-2-yl)benzenesulfonamide

1H NMR (400 MHz, DMSO) δ 12.2 (br s, 1H), 8.85 (s, 1H), 7.90 (br s, 1H), 7.50-7.60 (m, 1H), 7.3-7.4 (m, 4H), 7.2 (m, 3H), 6.74 (m, 1H), 6.24 (m, 1H), 5.56 (br s, 2H), 3.76 (s, 6H). MS (EI) for $C_{22}H_{21}N_5O_4S$: 452.0 (MH+).

Example 113

N-(3-(N-(3-(2-chloro-5-methoxyphenylamino)quinoxalin-2-yl)sulfamoyl)phenyl)-2-(ethyl(methyl)amino)acetamide 1H NMR (400 MHz, DMSO) δ 12.0 (s, 1H), 10.6 (s, 1H), 9.65 (s, 1H), 9.5 (s, 1H), 8.95 (s, 1H), 8.25 (s, 1H), 7.8 (d, 1H), 7.70 (d, 1H), 7.45-7.50 (d, 1H), 7.3-7.4 (m, 3H), 7.2 (t, 2H), 6.60 (d, 1H), 4.02 (br s, 2H), 3.82 (s, 3H), 3.14 (br s, 2H), 2.80 (s, 3H) 1.2 (t, 3H). MS (EI) for $C_{26}H_{27}ClN_6O_4S$: 555.2, 557.3 (MH+).

Example 114

N-(3-(N-(3-(2-chloro-5-methoxy-phenylamino)quinoxalin-2-yl)sulfamoyl)phenyl)-2-(3-(piperidin-1-yl)azetidin-1-yl)acetamide MS (EI) for $C_{31}H_{34}ClN_7O_4S \; 2.0 \times C_2H_1O_2F_3$: 636.3, 638.3 (MH+).

Example 115

N-(3-(N-(3-(3-fluoro-5-methoxy-phenylamino)quinoxalin-2-yl)sulfamoyl)phenyl)-2-(methylamino)acetamide MS (EI) for $C_{24}H_{23}FN_6O_4S$: 511.04 (MH+).

Example 116

N-(3-(N-(3-(3,5-dimethoxy-phenylamino)quinoxalin-2-yl)sulfamoyl)phenyl)-1-methylpiperidine-4-carboxamide MS (EI) for $C_{29}H_{32}N_6O_5S \; 1.0 \times C_2H_4O_2$: 577.2 (MH+).

Example 117

N-(3-(N-(3-(3-methoxyphenylamino)quinoxalin-2-yl)sulfamoyl)phenyl)-2-(methylamino)acetamide 1H NMR (400 MHz, DMSO) δ 10.6 (s, 1H), 8.82 (s, 1H), 8.22 (t, 1H), 7.86 (t, 1H), 7.76 (m, 1H), 7.66 (m, 1H), 7.46 (m, 1H), 7.41 (m, 1H), 7.38 (t, 1H), 7.28 (m 1H), 7.24 (t, 1H), 7.12 (m, 2H), 6.56 (d, 1H), 3.88 (s, 2H), 3.80 (s, 3H), 2.60 (s, 3H). MS (EI) for $C_{24}H_{24}N_6O_4S$: 492.99 (MH+).

Example 118

N-(3-(N-(3-(2-chloro-5-methoxy-phenylamino)quinoxalin-2-yl)sulfamoyl)phenyl)-2-(2,2,2-trifluoroethylamino)acetamide 1H NMR (400 MHz, DMSO) δ 10.4 (s, 1H), 9.2 (s, 1H), 8.65 (s, 1H), 8.4 (s, 1H), 8.00 (m, 1H), 7.80 (d, 1H), 7.75 (d, 1H), 7.65 (q, 1H), 7.55 (t, 1H), 7.40-7.5 (m, 3H), 6.7 (m, 1H), 3.82 (s, 3H), 3.62 (br s, 2H), 3.55 (br d, 2H). MS (EI) for $C_{25}H_{22}ClF_3N_6O_4S \; 1.0 \times C_2H_1O_2F_3$: 595.0, 597.0 (MH+).

Example 119

N-(3-(N-(3-(3,5-dimethoxy-phenylamino)quinoxalin-2-yl)sulfamoyl)phenyl)-3-(piperidin-1-yl)propanamide MS (EI) for $C_{30}H_{34}N_6O_5S$: 591.2 (MH+).

Example 120

3-amino-N-(3-(2,5-dimethoxy-phenylamino)quinoxalin-2-yl)benzenesulfonamide

1H NMR (400 MHz, DMSO) δ 12.4 (br s, 1H), 9.20 (s, 1H), 8.56 (d, 1H), 7.95 (d, 1H), 7.62 (m, 1H), 7.38 (m, 2H), 7.24 (q, 2H), 7.14 (d, 1H), 6.98 (d, 1H), 6.8 (m, 1H), 6.60 (m, 1H), 5.6 (br s, 2H), 3.78 (d, 6H). MS (EI) for $C_{22}H_{21}N_5O_4S$: 452.3 (MH+).

Example 121

N-(3-(N-(3-(3,5-dimethoxy-phenylamino)quinoxalin-2-yl)sulfamoyl)phenyl)-4-(dimethylamino)butanamide MS (EI) for $C_{28}H_{32}N_6O_5S$ $1.0 \times C_2H_4O_2$: 565.2 (MH+).

Example 122

2-(dimethylamino)-N-(3-(N-(3-(3-fluoro-5-methoxy-phenylamino)quinoxalin-2-yl)sulfamoyl)phenyl)acetamide 1H NMR (400 MHz, DMSO) δ 10.9 (s, 1H), 9.8 (br s, 1H), 9.1 (s, 1H), 8.34 (s, 1H), 7.90 (d, 1H), 7.76 (d, 1H), 7.52-7.68 (m, 4H), 7.40 (m, 2H), 6.54 (m, 1H), 4.16 (s, 2H), 3.82 (s, 3H), 2.86 (s, 6H). MS (EI) for $C_{25}H_{25}FN_6O_4S$: 525.05 (MH+).

Example 123

N-(3-(N-(3-(3,5-dimethoxy-phenylamino)quinoxalin-2-yl)sulfamoyl)phenyl)-2-(piperidin-1-yl)acetamide MS (EI) for $C_{29}H_{32}N_6O_5S$: 577.37 (MH+).

Example 124

3-amino-N-(3-(2-chloro-5-hydroxy-phenylamino)quinoxalin-2-yl)benzenesulfonamide

MS (EI) for $C_{20}H_{16}ClN_5O_3S$ $1.0 \times C_2H_1O_2F_3$: 442.2, 444.2 (MH+).

Example 125

2-(dimethylamino)-N-(3-(N-(3-(3-methoxy-phenylamino)quinoxalin-2-yl)sulfamoyl)phenyl)acetamide 1H NMR (400 MHz, DMSO) δ 10.5 (s, 1H), 8.8 (s, 1H), 8.25 (s, 1H), 7.83 (t, 1H), 7.76 (d, 1H), 7.64 (d, 1H), 7.3-7.48 (m, 4H), 7.22 (t, 1H), 7.12 (t, 2H), 6.56 (m, 1H), 3.96 (s, 2H), 3.78 (s, 3H), 2.76 (s, 6H). MS (EI) for $C_{25}H_{26}N_6O_4S$: 507.1 (MH+).

Example 126

N-(3-(N-(3-(2-chloro-5-hydroxy-phenylamino)quinoxalin-2-yl)sulfamoyl)phenyl)-2-(dimethylamino)acetamide 1H NMR (400 MHz, DMSO) δ 10.8 (s, 1H), 9.9 (s, 1H), 9.8 (s, 1H), 9.1 (s, 1H), 8.55 (s, 1H), 8.34 (s, 1H), 7.9-8.0 (br s, 1H), 7.82 (d, 1H), 7.76 (d, 1H), 7.52-7.66 (m, 2H), 7.42 (t, 1H), 7.26 (d, 1H), 6.50 (m, 1H), 4.16 (s, 2H), 2.86 (s, 6H). MS (EI) for $C_{24}H_{23}ClN_6O_4S$: 527.1, 529.0 (MH+).

Example 127

N-(3-(N-(3-(3,5-dimethoxy-phenylamino)quinoxalin-2-yl)sulfamoyl)phenyl)-2-morpholinoacetamide MS (EI) for $C_{28}H_{30}N_6O_6S$: 579.1 (MH+).

Example 128

3-amino-N-(3-(6-methoxyquinolin-8-ylamino)quinoxalin-2-yl)benzenesulfonamide

MS (EI) for $C_{24}H_{20}N_6O_3S$: 473.0 (MH+).

Example 129

N-(3-(3,5-dimethoxyphenylamino)quinoxalin-2-yl)thiophene-2-sulfonamide

MS (EI) for $C_{20}H_{18}N_4O_4S_2$: 443.0 (MH+).

Example 130

N-(3-(3,5-dimethoxyphenylamino)quinoxalin-2-yl)-3-(methylamino)benzenesulfonamide MS (EI) for $C_{23}H_{23}N_5O_4S$: 466.05 (MH+).

Example 131

3-amino-N-(3-(3-methoxy-5-nitro-phenylamino)quinoxalin-2-yl)benzenesulfonamide

MS (EI) for $C_{21}H_{18}N_6O_5S$: 467.00 (MH+).

Example 132

3-amino-N-(3-(3-fluoro-5-methoxy-phenylamino)quinoxalin-2-yl)benzenesulfonamide

MS (EI) for $C_{21}H_{18}FN_5O_3S$: 439.99 (MH+).

Example 134

3-amino-N-(3-(3-amino-5-methoxy-phenylamino)quinoxalin-2-yl)benzenesulfonamide

MS (EI) for $C_{21}H_{20}N_6O_3S$: 437.2 (MH+).

Example 135

N-(3-(3,5-dimethoxyphenylamino)quinoxalin-2-yl)-3-(dimethylamino)benzenesulfonamide MS (EI) for $C_{24}H_{25}N_5O_4S$: 480.04 (MH+).

Example 136

N-(3-(2-chloro-6-methoxypyridin-4-ylamino)quinoxalin-2-yl)-3-nitrobenzenesulfonamide MS (EI) for $C_{20}H_{15}ClN_6O_5S$: 496.94 (MH+).

Example 137

N-(3-(6-methoxyquinolin-8-ylamino)quinoxalin-2-yl)-3-nitrobenzenesulfonamide

MS (EI) for $C_{24}H_{18}N_6O_5S$: 502.95 (MH+).

Example 138

3-nitro-N-(3-(pyridin-4-ylamino)quinoxalin-2-yl)benzenesulfonamide

MS (EI) for $C_{19}H_{14}N_6O_4S$: 423.2 (MH+).

Example 139

N-(3-(2,6-dichloropyridin-4-ylamino)quinoxalin-2-yl)-3-nitrobenzenesulfonamide

MS (EI) for $C_{19}H_{12}Cl_2N_6O_4S$: 491.1, 493.1 (MH+).

Example 140

N-(3-(2-chloropyridin-4-ylamino)quinoxalin-2-yl)-3-nitrobenzenesulfonamide

MS (EI) for $C_{19}H_{13}ClN_6O_4S$: 456.93, 458.90 (MH+).

Example 141

N-(3-(4,6-dimethoxypyrimidin-2-ylamino)quinoxalin-2-yl)-3-nitrobenzenesulfonamide MS (EI) for $C_{20}H_{17}N_7O_6S$: 484.03 (MH+).

Example 142

N-(3-(4-hydroxy-6-methoxypyrimidin-2-ylamino)quinoxalin-2-yl)-3-nitrobenzenesulfonamide MS (EI) for $C_{19}H_{15}N_7O_6S$: 469.97 (MH+).

Example 143

N-(3-(3,5-dimethoxyphenylamino)quinoxalin-2-yl)-2-fluorobenzenesulfonamide

MS (EI) for $C_{22}H_{19}FN_4O_4S$: 455.3 (MH+).

Example 144

N-(3-(2-bromo-5-methoxyphenylamino)quinoxalin-2-yl)-3-nitrobenzenesulfonamide

MS (EI) for $C_{21}H_{16}BrN_5O_5S$: 531.82, 532.84 (MH+).

Example 145

N-(3-(3,5-dimethoxyphenylamino)quinoxalin-2-yl)-4-methylbenzenesulfonamide

MS (EI) for $C_{23}H_{22}N_4O_4S$: 451.0 (MH+).

Example 146

N-(3-(2,5-dimethoxyphenylamino)-7-methylquinoxalin-2-yl)benzenesulfonamide

MS (EI) for $C_{23}H_{22}N_4O_4S$: 451.0 (MH+).

Example 147

N-(3-(3,5-dimethoxyphenylamino)quinoxalin-2-yl)-3-nitrobenzenesulfonamide

MS (EI) for $C_{22}H_{19}N_5O_6S$: 481.9 (MH+).

Example 148

N-(3-(N-(3-(3,5-dimethoxy-phenylamino)quinoxalin-2-yl)sulfamoyl)phenyl)acetamide MS (EI) for $C_{24}H_{23}N_5O_5S$: 494.0 (MH+).

Example 149

N-(3-(2,5-dimethoxyphenylamino)quinoxalin-2-yl)-4-methylbenzenesulfonamide

MS (EI) for $C_{23}H_{22}N_4O_4S$: 451.0 (MH+).

Example 150

N-(3-(3-fluoro-5-methoxy-phenylamino)quinoxalin-2-yl)-3-nitrobenzenesulfonamide

MS (EI) for $C_{21}H_{16}FN_5O_5S$: 470.0 (MH+).

Example 151

4-bromo-N-(3-(3,5-dimethoxy-phenylamino)quinoxalin-2-yl)benzenesulfonamide

MS (EI) for $C_{22}H_{19}BrN_4O_4S$: 516.9, 514.9 (MH+).

Example 152

N-(3-(3-methoxyphenylamino)quinoxalin-2-yl)-3-nitro-benzenesulfonamide

MS (EI) for $C_{21}H_{17}N_5O_5S$: 451.93 (MH+).

Example 153

N-(3-(2-chloro-5-hydroxy-phenylamino)quinoxalin-2-yl)-3-nitrobenzenesulfonamide

MS (EI) for $C_{20}H_{14}ClN_5O_5S$: 472.15, 474.13 (MH+).

Example 154

N-(3-(3-methoxy-5-nitro-phenylamino)quinoxalin-2-yl)-3-nitrobenzenesulfonamide

MS (EI) for $C_{21}H_{16}N_6O_7S$: 496.94 (MH+).

Example 155

N-(3-(benzo[d][1,3]dioxol-5-ylamino)quinoxalin-2-yl)-3-nitrobenzenesulfonamide

MS (EI) for $C_{21}H_{15}N_5O_6S$: 466.2 (MH+).

Example 156

N-(3-(3-hydroxyphenylamino)quinoxalin-2-yl)-3-nitro-benzenesulfonamide

MS (EI) for $C_{20}H_{15}N_5O_5S$: 438.16 (MH+).

Example 157

3-nitro-N-(3-(3-(trifluoromethoxy)-phenylamino) quinoxalin-2-yl)benzenesulfonamide MS (EI) for $C_{21}H_{14}F_3N_5O_5S$: 506.19 (MH+).

Example 158

3-nitro-N-(3-(pyridin-3-ylamino)quinoxalin-2-yl) benzenesulfonamide

MS (EI) for $C_{19}H_{14}N_6O_4S$: 423.15 (MH+).

Example 159

3-(3-(3-nitrophenylsulfonamido)quinoxalin-2-ylamino)phenyl dimethylcarbamate

MS (EI) for $C_{23}H_{20}N_6O_6S$: 509.01 (MH+).

Example 160

N-(3-(2-chloropyridin-3-ylamino)quinoxalin-2-yl)-3-nitrobenzenesulfonamide

MS (EI) for $C_{19}H_{13}ClN_6O_4S$: 456.91 (MH+).

Example 161

N-(3-(3-isopropoxyphenylamino)quinoxalin-2-yl)-3-nitrobenzenesulfonamide

MS (EI) for $C_{23}H_{21}N_5O_5S$: 480.3 (MH+).

Example 162

N-(3-(3-hydroxy-2-methyl-phenylamino)quinoxalin-2-yl)-3-nitrobenzenesulfonamide

MS (EI) for $C_{21}H_{17}N_5O_5S$: 452.2 (MH+).

Example 163

N-(3-(2,5-difluorophenylamino)quinoxalin-2-yl)-3-nitrobenzenesulfonamide

MS (EI) for $C_{20}H_{13}F_2N_5O_4S$: 458.2 (MH+).

Example 164

N-(3-(3-(difluoromethoxy)phenylamino)quinoxalin-2-yl)-3-nitrobenzenesulfonamide

MS (EI) for $C_{21}H_{15}F_2N_5O_5S$: 488.2 (MH+).

Example 165

N-(3-(2-methoxypyridin-3-ylamino)quinoxalin-2-yl)-3-nitrobenzenesulfonamide

MS (EI) for $C_{20}H_{16}N_6O_5S$: 453.01 (MH+).

Example 166

N-(3-(3-ethoxyphenylamino)quinoxalin-2-yl)-3-nitrobenzenesulfonamide

MS (EI) for $C_{22}H_{19}N_5O_5S$: 466.2 (MH+).

Example 167

N-(3-(2,2-difluorobenzo[d][1,3]dioxol-4-ylamino) quinoxalin-2-yl)-3-nitrobenzenesulfonamide MS (EI) for $C_{21}H_{13}F_2N_5O_6S$: 502.2 (MH+).

Example 168

N-(3-(3-(3-nitrophenylsulfonamido)quinoxalin-2-ylamino)phenyl)acetamide

MS (EI) for $C_{22}H_{18}N_6O_5S$: 479.2 (MH+).

Example 169

N-(3-(4-amino-1H-indol-1-yl)quinoxalin-2-yl)-3-nitrobenzenesulfonamide

MS (EI) for $C_{22}H_{16}N_6O_4S$: 461.2 (MH+).

Example 170

N-(3-(1H-indol-4-ylamino)quinoxalin-2-yl)-3-nitrobenzenesulfonamide

MS (EI) for $C_{22}H_{16}N_6O_4S$: 461.2 (MH+).

Example 171

N-(3-(1H-indazol-6-ylamino)quinoxalin-2-yl)-3-nitrobenzenesulfonamide

MS (EI) for $C_{21}H_{15}N_7O_4S$: 461.96 (MH+).

Example 172

N-(4-methoxy-3-(3-(3-nitro-phenylsulfonamido) quinoxalin-2-ylamino)phenyl)acetamide MS (EI) for $C_{23}H_{20}N_6O_6S$: 508.97 (MH+).

Example 173

N-(3-(4-methylpyridin-3-ylamino)quinoxalin-2-yl)-3-nitrobenzenesulfonamide

MS (EI) for $C_{20}H_{16}N_6O_4S$: 436.93 (MH+).

Example 174

N-(3-(2,3-dimethoxyphenylamino)quinoxalin-2-yl)-3-nitrobenzenesulfonamide

MS (EI) for $C_{22}H_{19}N_5O_6S$: 481.94 (MH+).

Example 175

N-(3-(1H-pyrazolo[3,4-d]pyrimidin-4-ylamino)quinoxalin-2-yl)-3-nitrobenzenesulfonamide MS (EI) for $C_{19}H_{13}N_9O_4S$: 463.96 (MH+).

Example 176

N-(3-(benzo[d]oxazol-4-ylamino)quinoxalin-2-yl)-3-nitrobenzenesulfonamide

MS (EI) for $C_{21}H_{14}N_6O_5S$: 462.99 (MH+).

Example 177

N-(3-(2,6-difluoro-3-methoxy-phenylamino)quinoxalin-2-yl)-3-nitrobenzenesulfonamide MS (EI) for $C_{21}H_{15}F_2N_5O_5S$: 487.89 (MH+).

Example 178

N-(3-(3,5-dihydroxyphenylamino)quinoxalin-2-yl)-3-nitrobenzenesulfonamide

MS (EI) for $C_{20}H_{15}N_5O_6S$: 453.96 (MH+).

Example 179

N-(3-(3,5-dimethoxyphenylamino)quinoxalin-2-yl) naphthalene-2-sulfonamide

MS (EI) for $C_{26}H_{22}N_4O_4S$: 487.0 (MH+).

Example 180

N-(3-(2,5-dimethoxyphenylamino)-6,7-dimethylquinoxalin-2-yl)benzenesulfonamide

MS (EI) for $C_{24}H_{24}N_4O_4S$: 465.3 (MH+).

Example 181

2-amino-N-(3-(N-(3-(2-chloro-5-methoxy-phenylamino)quinoxalin-2-yl)sulfamoyl)-4-methylphenyl)-2-methylpropanamide MS (EI) for $C_{26}H_{27}ClN_6O_4S$: 556.12 (MH+).

Example 182

N-(3-(N-(3-(2-chloro-5-methoxy-phenylamino)quinoxalin-2-yl)sulfamoyl)phenyl)-2-(dimethylamino) acetamide MS (EI) for $C_{25}H_{25}ClN_6O_4S$: 542.05 (MH+).

Example 183

2-amino-N-(3-(N-(3-(3,5-dimethoxy-phenylamino) quinoxalin-2-yl)sulfamoyl)phenyl)acetamide MS (EI) for $C_{24}H_{24}N_6O_5S$: 509.59 (MH+).

Example 184

3-amino-N-(3-(2-chloro-5-methoxy-phenylamino) quinoxalin-2-yl)benzenesulfonamide MS (EI) for $C_{21}H_{18}ClN_5O_3S$: 457.02 (MH+).

Example 185

3-amino-N-(2-(3,5-dimethoxy-phenylamino)pyrido [2,3-b]pyrazin-3-yl)benzenesulfonamide MS (EI) for $C_{21}H_{20}N_6O_4S$: 453.62 (MH+).

Example 186

N-(3-{[(2-{[3,5-bis(methyloxy)phenyl]amino}pyrido[2,3-b]pyrazin-3-yl)amino]sulfonyl}phenyl)-N-2-[2-(dimethylamino)ethyl]-N-2-methylglycinamide

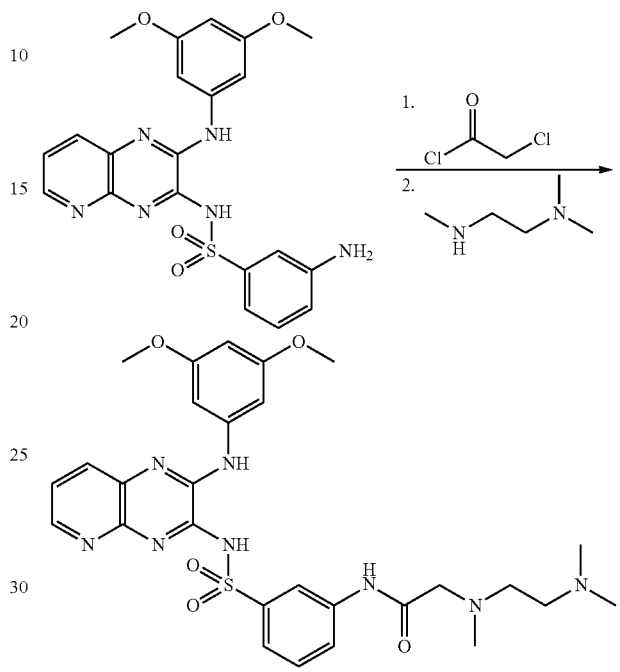

To a THF suspension (1.3 mL) of 3-amino-N-(3-{[3,5-bis (methyloxy)phenyl]amino}quinoxalin-2-yl)benzenesulfonamide (126 mg, 0.28 mmol) was added 0.143 mL of 2M aqueous $Na_2CO_3$. To this yellow suspension is added dropwise 33 uL (0.42 mmol) of chlororacetyl chloride. The reaction mixture turns clear after a few minutes and is allowed to stir at 23° C. for 1 h. To the reaction is added a DMSO (1 mL) solution containing 180 uL (1.4 mmol) of N,N',N' trimethylethelyenediamine. The reaction is then warmed to 60° C. and stirred for 18 h. The product is isolated by preparative RP-HPLC ($NH_4OAc$/ACN) gradient, the appropriate fractions were pooled and lyophilize to give a solid yellow as the acetic acid salt: 59 mg (51%). $^1$H-NMR (400 MHz, $CDCL_3$): δ10.1 (br s, 1), 8.37 (br s, 2), 8.18 (d, 1), 7.97 (d, 1), 7.60 (br d, 1), 7.27 (s, 2), 7.20 (br s, 3), 6.15 (s, 1), 3.82 (m, 2), 3.65 (s, 6), 3.20 (br m, 2), 2.82 (br s, 8), 2.42 (s, 3), 2.02 (s, 3). MS (EI) for $C_{28}H_{34}N_8O_5S$: 595.84 (MH+).

The following title compounds were prepared according to the above Examples.

Example 187

N-(3-(3,5-dimethoxyphenylamino)quinoxalin-2-yl)-3-ureidobenzenesulfonamide

MS (EI) for $C_{23}H_{22}N_6O_5S$: 495.40 (MH+).

Example 188

3-amino-N-(3-(5-methoxy-2-methyl-phenylamino) quinoxalin-2-yl)benzenesulfonamide MS (EI) for $C_{22}H_{21}N_5O_3S$: 436.32 (MH+).

Example 189

2-(dimethylamino)-N-(3-(N-(3-(5-methoxy-2-methylphenylamino)quinoxalin-2-yl)sulfamoyl)phenyl)acetamide MS (EI) for $C_{26}H_{28}N_6O_4S$: 521.69 (MH+).

Example 190

N-(3-(N-(3-(3,5-dimethoxy-phenylamino)quinoxalin-2-yl)sulfamoyl)phenyl)-2-(4-methylpiperazin-1-yl)acetamide MS (EI) for $C_{29}H_{33}N_7O_5S$: 592.61 (MH+).

Example 191

2-acetamido-N-(3-(N-(3-(3,5-dimethoxyphenylamino)quinoxalin-2-yl)sulfamoyl)phenyl)acetamide MS (EI) for $C_{26}H_{26}N_6O_6S$: 550.59 (MH+).

Example 192 tert-butyl 2-(3-(N-(3-(3,5-dimethoxy-phenylamino)quinoxalin-2-yl)sulfamoyl)phenylamino)-2-oxoethylcarbamate MS (EI) for $C_{29}H_{32}N_6O_7S$: 609.32 (MH+).

Example 193

3-amino-N-(3-{[3,5-bis(methyloxy)phenyl]amino}pyrido[2,3-b]pyrazin-2-yl)benzenesulfonamide

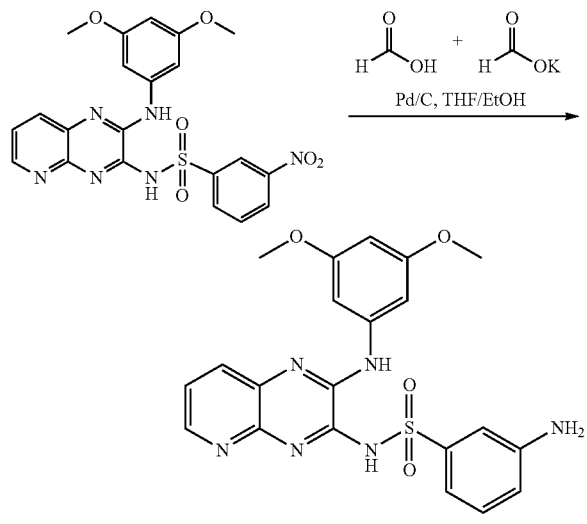

To a 1:1 THF/EtOH suspension (1 mL) of 3-nitro-N-(3-{[3,5-bis(methyloxy)-phenyl]amino}pyrido[2,3-b]pyrazin-2-yl)benzenesulfonamide (100 mg, 0.21 mmol) was added 46 uL (0.63 mmol) of formic acid plus 100 mg (0.63 mmol) of potassium formate and 100 mg of 10% palladium on charcoal. After refluxing the reaction for 1 h, hot filtration through celite, and concentration, the product is isolated by preparative RP-HPLC ($NH_4OAc$/ACN) gradient. The appropriate fractions were pooled and lyophilize to give solid yellow product: 3.2 mg (4%). $^1$H-NMR (400 MHz, $CDCl_3$): δ 8.62 (d, 1), 8.52 (s, 1), 7.62 (d, 1), 7.3 (m, 4), 7.18 (d, 2), 6.88 (d, 1), 6.27 (t, 1), 3.96 (br s, 2), 3.83 (s, 6). MS (EI) for $C_{21}H_{20}N_6O_4S$: 453.22 (MH+).

The following title compounds were prepared according to the above Examples.

Example 194

3-(N-(3-(2-chloro-5-methoxyphenylamino)quinoxalin-2-yl)sulfamoyl)-N-(2-methyl-1-(piperidin-1-yl)propan-2-yl)benzamide MS (EI) for $C_{31}H_{35}ClN_6O_4S$: 623.06 (MH+).

Example 195

3-(N-(3-(2-chloro-5-methoxy-phenylamino)quinoxalin-2-yl)sulfamoyl)-N-(2-methyl-1-oxo-1-(piperidin-1-yl)propan-2-yl)benzamide MS (EI) for $C_{31}H_{33}ClN_6O_5S$: 637.65 (MH+).

Example 196

N-(2-(3,5-dimethoxyphenylamino)pyrido[2,3-b]pyrazin-3-yl)-3-nitrobenzenesulfonamide MS (EI) for $C_{21}H_{18}N_6O_6S$: 483.78 (MH+).

Example 197

N-(3-{[2-chloro-5-(methyloxy)phenyl]amino}quinoxalin-2-yl)-3-(1-{[2-(dimethylamino)-ethyl]amino}ethyl)benzenesulfonamide trifluoracetic acid salt

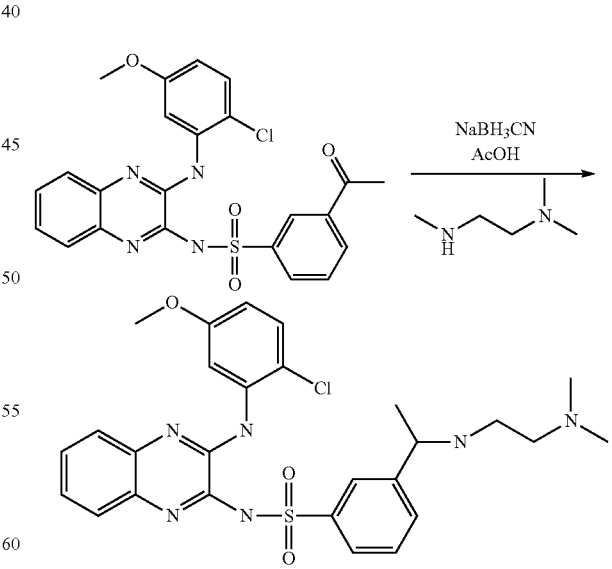

To a dichloroethane solution (0.6 mL) of 3-acetyl-N-(3-{[2-chloro-5-(methyloxy)-phenyl]amino}quinoxalin-2-yl)benzenesulfonamide (150 mg, 0.31 mmol) and 51 uL (0.37 mmol) of N,N-dimethylethelyenediamine was added 19 uL of acetic acid followed by 132 mg (0.62 mmol) of sodium cyanoborohydride. The reaction mixture was refluxed for 18 h under a nitrogen atmosphere. After concentration (in vacuo), the product is isolated by preparative RP-HPLC (0.1% TFA/AC/V) gradient, followed by lyophilization of appropriate fractions to give solid yellow solid: 189 mg (90%). $^1$H-NMR (400 MHz, d$_3$-MeOD): δ 8.74 (s, 1), 8.18 (s, 1), 8.12 (d, 1), 7.71 (m, 3), 7.48 (m, 4), 7.28 (d, 1), 6.63 (d, 1), 4.38 (q, 1), 3.80 (s, 3), 3.30 (m, 3), 3.12 (m, 1), 2.84 (s, 3), 1.60 (d, 3). MS (EI) for $C_{27}H_{31}ClN_6O_3S$: 555.56 (MH+).

Example 198

N,N-{[(3-{[(3-{[2-chloro-5-(methyloxy)phenyl]amino}quinoxalin-2-yl)amino]sulfonyl}-4-methylphenyl)amino](dimethylamino)methylidene}-N-methylmethanaminium

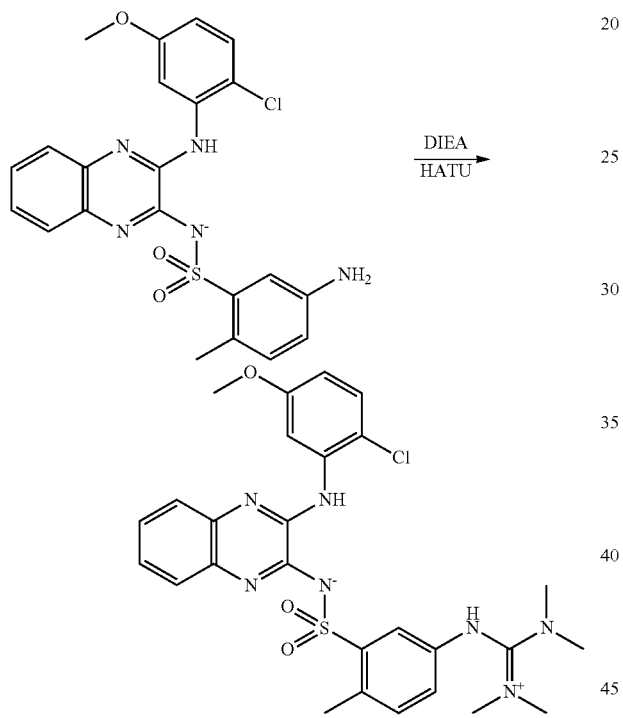

To a dimethylformamide solution (1 mL) of 3-amino-N-(3-{([2-chloro-5-(methyloxy)-phenyl]amino}quinoxalin-2-yl)-2-methylbenzenesulfonamide (200 mg, 0.40 mmol) is added 312 uL (1.8 mmol) of hunigs base and 122 mg (0.6 mmol) of HATU. After stirring for 18 h at 60° C., the product was precipitated from a 1:1 mixture of hexane/ethyl acetate, filtered and dried to afford 60 mg (26%). 1H NMR (400 MHz, d$_6$-DMSO): δ 9.26 (b rs, 1), 8.96 (br s, 1), 7.80 (s, 1), 7.51 (br s, 1), 7.45 (d, 1), 7.18 (brm, 4), 6.91 (br s, 1), 6.60 (br d, 1), 3.82 (s, 3), 3.36 (s, 3), 2.85 (s, 6), 2.58 (s, 3). MS (EI) for $C_{27}H_{31}ClN_7O_3S+$: 569.32 (MH+).

The following title compounds were prepared according to the above Examples.

Example 199

3-acetyl-N-(3-(2-chloro-5-methoxy-phenylamino)quinoxalin-2-yl)benzenesulfonamide MS (EI) for $C_{23}H_{19}ClN_4O_4S$: 483.08 (MH+).

Example 200

N-(3-(3,5-dimethoxyphenylamino)quinoxalin-2-yl)benzenesulfonamide

MS (EI) for $C_{22}H_{20}N_4O_4S$: 437.49 (MH+).

Example 201

N-(3-(5-methoxy-2-methyl-phenylamino)quinoxalin-2-yl)benzenesulfonamide

MS (EI) for $C_{22}H_{20}N_4O_3S$: 421.46 (MH+).

Example 202

N-(3-(2-chloro-5-methoxy-phenylamino)quinoxalin-2-yl)benzenesulfonamide

MS (EI) for $C_{21}H_{17}ClN_4O_3S$: 440.59 (MH+).

Example 203

N-(3-(2,5-dimethoxyphenylamino)quinoxalin-2-yl)benzenesulfonamide

MS (EI) for $C_{22}H_{20}N_4O_4S$: 437.53 (MH+).

Example 204

4-chloro-N-(3-(3,5-dimethoxy-phenylamino)quinoxalin-2-yl)benzenesulfonamide

MS (EI) for $C_{22}H_{19}ClN_4O_4S$: 470.54 (MH+).

Example 205

N-(3-(5-methoxy-2-methyl-phenylamino)quinoxalin-2-yl)-3-nitrobenzenesulfonamide

MS (EI) for $C_{22}H_{19}N_5O_5S$: 466.32 (MH+).

Example 206

N-(3-(2-chloro-5-methoxy-phenylamino)quinoxalin-2-yl)-3-nitrobenzenesulfonamide

MS (EI) for $C_{21}H_{16}ClN_5O_5S$: 485.86 (MH+).

Example 207

N-(3-(2-chloro-5-(difluoromethoxy)-phenylamino)quinoxalin-2-yl)-3-nitrobenzenesulfonamide MS (EI) for $C_{21}H_{14}ClF_2N_5O_5S$: 521.92 (MH+).

Example 208

N-(3-(4-chloro-2,5-dimethoxy-phenylamino)quinoxalin-2-yl)benzenesulfonamide

MS (EI) for $C_{22}H_{19}ClN_4O_4S$: 470.99 (MH+).

Example 209

N-(3-(4-morpholinophenylamino)quinoxalin-2-yl)benzenesulfonamide

MS (EI) for $C_{24}H_{23}N_5O_3S$: 461.54 (MH+).

Example 210

3-amino-N-(3-(3,5-dimethoxyphenylamino)quinoxalin-2-yl)benzenesulfonamide

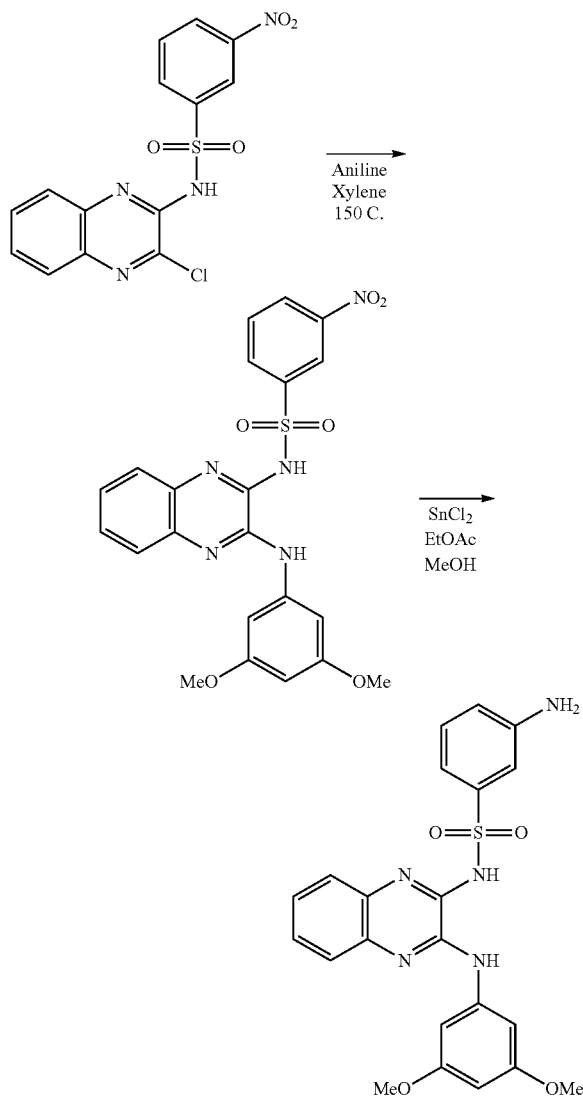

N-(3-(3,5-dimethoxyphenylamino)quinoxalin-2-yl)-3-nitrobenzenesulfonamide

A flask was charged with N-(3-chloroquinoxalin-2-yl)-3-nitrobenzenesulfonamide (5 g, 13.7 mmol), 3,5-dimethoxyaniline (4.2 g, 27.4 mmol), and 80 mL of Xylene. The reaction mixture was stirred under an $N_2$ atmosphere at 150° C. for 3 hours, after which time, solvent was removed on a rotary evaporator, and 10 mL of Dichloromethane and 50 mL of Methanol were added. The slurry was heated to reflux and filtered while hot, resulting in 4.6 g (69.7%) of N-(3-(3,5-dimethoxyphenylamino)quinoxalin-2-yl)-3-nitrobenzenesulfonamide MS (EI) for $C_{22}H_{19}N_5O_6S$: 482.2 (MH+).

Example 211

3-amino-N-(3-(3,5-dimethoxyphenylamino)quinoxalin-2-yl)benzenesulfonamide

A flask was charged with N-(3-(3,5-dimethoxyphenylamino)quinoxalin-2-yl)-3-nitro-benzenesulfonamide (3.4 g, 7.06 mmol), tin chloride hydrate (6.4 g, 28.2 mmol), and 30 mL of DMA. A few drops of water were added and the reaction mixture was stirred at 80° C. for 3 hours, after which time, solvent was removed on a rotary evaporator, and 50 mL of water and 10 mL of Methanol were added. The slurry was filtered, and the filtrate was washed with MeOH, water, and diethyl ether (20 mL of each), resulting in 3.25 g 3-amino-N-(3-(3,5-dimethoxy-phenylamino)quinoxalin-2-yl)benzene-sulfonamide. MS (EI) for $C_{22}H_{21}N_5O_4S$: 461.5 (MH+).

General Library Alkylation Procedure 1

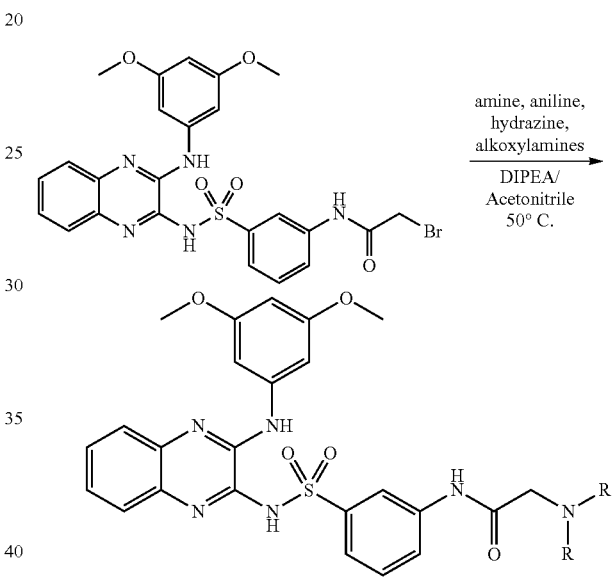

Into a 2-dram vial was placed 2-bromo-N-(3-(N-(3-(3,5-dimethoxy-phenylamino)quinoxalin-2-yl)sulfamoyl)phenyl)acetamide (86 mg, 0.15 mmol) along with 2 mL of acetonitrile. Eight equivalents (1.2 mmol) of the desired amine, aniline, hydrazine or alkoxylamine were added followed by the addition of Hunig's Base (41 µL, 0.25 mmol). The reaction then was stirred at 50° C. for one hour (overnight for aniline reagents). Preparative reverse-phase HPLC was used to isolate the desired product directly from the crude reaction mixture. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification.

The following title compounds were prepared according to General Library Alkylation Procedure 1

Example 212

N-(3-(N-(3-(3,5-dimethoxy-phenylamino)quinoxalin-2-yl)sulfamoyl)phenyl)-2-(methylamino)acetamide $^1$H-NMR (400 MHz, $d_6$-DMSO): 8.81 (s, 1H), 8.23 (t, 1H), 7.75 (d, 1H), 7.66 (d, 1H), 7.41-7.38 (m, 1H), 7.35 (m, 1H), 7.32 (d, 2H), 7.29-7.27 (m, 1H), 7.14-7.11 (m, 2H), 6.14 (t, 1H), 3.80 (s, 1H), 3.78 (s, 6H), 2.58 (s, 3H), 1.91 (s, 2H); MS (EI) $C_{25}H_{26}N_6O_5S$: 523.6 (MH$^+$).

Example 213

2-(cyclopropylmethylamino)-N-(3-(N-(3-(3,5-dimethoxyphenylamino)quinoxalin-2-yl)sulfamoyl)phenyl)acetamide $^1$H-NMR (400 MHz, d$_6$-DMSO): 10.58 (s, 1H), 8.81 (s, 1H), 8.20 (t, 1H), 7.76 (d, 1H), 7.67 (d, 1H), 7.42-7.36 (m, 2H), 7.32 (d, 2H), 7.27 (s, 1H), 7.14-7.12 (m, 2H), 6.15 (t, 1H), 3.93 (s, 2H), 3.78 (s, 6H), 2.89 (s, 1H), 2.88 (s, 1H), 1.05-1.00 (m, 1H), 0.59 (d, 1H), 0.57 (d, 1H), 0.35 (d, 1H), 0.34 (d, 1H); MS (EI) $C_{28}H_{30}N_6O_5S$: 563.6 (MH$^+$).

Example 214

N-(3-(N-(3-(3,5-dimethoxy-phenylamino)quinoxalin-2-yl)sulfamoyl)phenyl)-2-(2-hydroxypropylamino)acetamide $^1$H-NMR (400 MHz, d$_6$-DMSO): 10.49 ppm (s, 1H), 8.81 ppm (s, 1H), 8.23 ppm (t, 1H), 8.13 ppm (s, 1H), 7.76 ppm (d, 1H), 7.765-7.763 (dd, 1H), 7.41-7.37 ppm (m, 2H), 7.33-7.32 ppm (d, 1H), 7.30-7.28 ppm (m, 1H), 7.16-7.09 ppm (m, 2H), 6.55 ppm (s, 1H), 6.14 ppm (t, 1H), 5.49 ppm (d, 2H), 5.25 ppm (s, 1H), 3.85 ppm (s, 1H), 3.78 ppm (s, 6H) 3.67-3.59 ppm (m, 1H), 3.00-2.89 ppm (dd, 1H), 2.79-2.76 ppm (m, 1H), 1.10 ppm (d, 1H), 1.01-0.99 ppm (d, 1H); MS (EI) $C_{27}H_{30}N_6O_6S$: 566.6 (MH$^+$).

Example 215

N-(3-(N-(3-(3,5-dimethoxy-phenylamino)quinoxalin-2-yl)sulfamoyl)phenyl)-2-(3-fluorobenzylamino)acetamide $^1$H-NMR (400 MHz, d$_6$-DMSO): 10.42 ppm (s, 1H), 8.82 ppm (s, 1H), 8.23 ppm (s, 1H), 8.14 ppm (s, 1H), 7.75 ppm (d, 1H), 7.65 ppm (d, 1H), 7.49-7.32 ppm (m, 6H), 7.25-7.20 ppm (m, 1H), 7.14-7.12 ppm (m, 2H), 6.55 ppm (s, 1H), 6.15 ppm (t, 1H), 4.14 ppm (s, 2H), 3.78 ppm (s, 6H), 3.74 ppm (s, 2H); MS (EI) $C_{31}H_{29}FN_6O_5S$: 616.7 (MH$^+$).

Example 216

2-(benzylamino)-N-(3-(N-(3-(3,5-dimethoxyphenylamino)quinoxalin-2-yl)sulfamoyl)phenyl)acetamide

MS (EI) $C_{31}H_{30}N_6O_5S$: 599 (MH$^+$).

Example 217

2-(diethylamino)-N-(3-(N-(3-(3,5-dimethoxy-phenylamino)quinoxalin-2-yl)sulfamoyl)phenyl)acetamide

MS (EI) $C_{28}H_{32}N_6O_5S$: 565 (MH$^+$).

Example 218

2-(4-(3,4-dichlorophenyl)piperazin-1-yl)-N-(3-(N-(3-(3,5-dimethoxyphenylamino)quinoxalin-2-yl)sulfamoyl)phenyl)acetamide MS (EI) $C_{34}H_{33}Cl_2N_7O_5S$: 722 (MH$^+$).

Example 219

N-(3-(N-(3-(3,5-dimethoxy-phenylamino)quinoxalin-2-yl)sulfamoyl)phenyl)-2-(2,2-dimethylhydrazinyl)acetamide

MS (EI) $C_{26}H_{29}N_7O_5S$: 552 (MH$^+$).

Example 220

N-(3-(N-(3-(3,5-dimethoxy-phenylamino)quinoxalin-2-yl)sulfamoyl)phenyl)-2-(p-tolylamino)acetamide

MS (EI) $C_{31}H_{30}N_6O_5S$: 599 (MH$^+$).

Example 221

2-(benzyloxyamino)-N-(3-(N-(3-(3,5-dimethoxyphenylamino)quinoxalin-2-yl)sulfamoyl)phenyl)acetamide

MS (EI) $C_{31}H_{30}N_6O_6S$: 615 (MH$^+$).

Example 222

2-(2-chlorophenylamino)-N-(3-(N-(3-(3,5-dimethoxyphenylamino)quinoxalin-2-yl)sulfamoyl)phenyl)acetamide MS (EI) $C_{30}H_{27}ClN_6O_5S$: 619 (MH$^+$).

Example 223

N-(3-(N-(3-(3,5-dimethoxyphenylamino)quinoxalin-2-yl)sulfamoyl)phenyl)-2-(isopropylamino)acetamide

MS (EI) $C_{27}H_{30}N_6O_5S$: 551 (MH$^+$).

Example 224

2-(4-cyclopentylpiperazin-1-yl)-N-(3-(N-(3-(3,5-dimethoxyphenylamino)quinoxalin-2-yl)sulfamoyl)phenyl)acetamide

MS (EI) $C_{33}H_{39}N_7O_5S$: 646 (MH$^+$).

Example 225

N-(3-(N-(3-(3,5-dimethoxy-phenylamino)quinoxalin-2-yl)sulfamoyl)phenyl)-2-(4-propylpiperidin-1-yl)acetamide

MS (EI) $C_{32}H_{38}N_6O_5S$: 619 (MH$^+$).

Example 226

N-(3-(N-(3-(3,5-dimethoxy-phenylamino)quinoxalin-2-yl)sulfamoyl)phenyl)-2-(isobutoxyamino)acetamide

MS (EI) $C_{28}H_{32}N_6O_6S$: 581 (MH$^+$).

Example 227

2-(3-tert-butylphenylamino)-N-(3-(N-(3-(3,5-dimethoxyphenylamino)quinoxalin-2-yl)sulfamoyl)phenyl)acetamide

MS (EI) $C_{34}H_{36}N_6O_5S$: 641 (MH$^+$).

Example 228

N-(3-(N-(3-(3,5-dimethoxy-phenylamino)quinoxalin-2-yl)sulfamoyl)phenyl)-2-(2-phenylpropan-2-ylamino)acetamide

MS (EI) $C_{33}H_{34}N_6O_5S$: 627 (MH$^+$).

Example 229

N-(3-(N-(3-(3,5-dimethoxy-phenylamino)quinoxalin-2-yl)sulfamoyl)phenyl)-2-(3-fluoro-4-hydroxyphenylamino)acetamide

MS (EI) $C_{30}H_{27}FN_6O_6S$: 619 (MH$^+$).

Example 230

N-(3-(N-(3-(3,5-dimethoxy-phenylamino)quinoxalin-2-yl)sulfamoyl)phenyl)-2-(2-(methylthio)benzylamino)acetamide

MS (EI) $C_{32}H_{32}N_6O_5S_2$: 645 (MH$^+$).

Example 231

N-(3-(N-(3-(3,5-dimethoxy-phenylamino)quinoxalin-2-yl)sulfamoyl)phenyl)-2-(5-fluoro-2-methylbenzylamino)acetamide

MS (EI) $C_{32}H_{31}FN_6O_5S$: 631 (MH$^+$).

Example 232

N-(3-(N-(3-(3,5-dimethoxy-phenylamino)quinoxalin-2-yl)sulfamoyl)phenyl)-2-(2-phenylpyrrolidin-1-yl)acetamide

MS (EI) $C_{34}H_{34}N_6O_5S$: 639 (MH$^+$).

Example 233

2-(2-benzylpyrrolidin-1-yl)-N-(3-(N-(3-(3,5-dimethoxy-phenylamino)quinoxalin-2-yl)sulfamoyl)phenyl)acetamide

MS (EI) $C_{35}H_{36}N_6O_5S$: 653 (MH$^+$).

Example 234

N-(3-(N-(3-(3,5-dimethoxy-phenylamino)quinoxalin-2-yl)sulfamoyl)phenyl)-2-(2-phenylmorpholino)acetamide

MS (EI) $C_{34}H_{34}N_6O_6S$: 655 (MH$^+$).

Example 235

N-(3-(N-(3-(3,5-dimethoxy-phenylamino)quinoxalin-2-yl)sulfamoyl)phenyl)-2-(2-(pyridin-4-yl)piperidin-1-yl)acetamide

MS (EI) $C_{34}H_{35}N_7O_5S$: 654 (MH$^+$).

Example 236

N-(3-(N-(3-(3,5-dimethoxy-phenylamino)quinoxalin-2-yl)sulfamoyl)phenyl)-2-(o-tolylamino)acetamide

MS (EI) $C_{31}H_{30}N_6O_5S$: 599 (MH$^+$).

Example 237

N-(3-(N-(3-(3,5-dimethoxy-phenylamino)quinoxalin-2-yl)sulfamoyl)phenyl)-2-(2,4-dimethylbenzylamino)acetamide

MS (EI) $C_{33}H_{34}N_6O_5S$: 627 (MH$^+$).

Example 238

N-(3-(N-(3-(3,5-dimethoxy-phenylamino)quinoxalin-2-yl)sulfamoyl)phenyl)-2-(methyl(pyridin-3-ylmethyl)amino)acetamide

MS (EI) $C_{31}H_{31}N_7O_5S$: 614 (MH$^+$).

Example 239

2-(3-chloro-4-methylbenzylamino)-N-(3-(N-(3-(3,5-dimethoxyphenylamino)quinoxalin-2-yl)sulfamoyl)phenyl)acetamide MS (EI) $C_{32}H_{31}ClN_6O_5S$: 647 (MH$^+$).

Example 240

N-(3-(N-(3-(3,5-dimethoxy-phenylamino)quinoxalin-2-yl)sulfamoyl)phenyl)-2-((2-(dimethylamino)ethyl)(methyl)amino)acetamide

MS (EI) $C_{29}H_{35}N_7O_5S$: 594 (MH$^+$).

Example 241

2-(4-acetylpiperazin-1-yl)-N-(3-(N-(3-(3,5-dimethoxyphenylamino)quinoxalin-2-yl)sulfamoyl)phenyl)acetamide

MS (EI) $C_{30}H_{33}N_7O_6S$: 620 (MH$^+$).

Example 242

N-(3-(N-(3-(3,5-dimethoxyphenylamino)quinoxalin-2-yl)sulfamoyl)phenyl)-2-(methyl(1-methylpyrrolidin-3-yl)amino)acetamide

MS (EI) $C_{30}H_{35}N_7O_5S$: 606 (MH$^+$).

Example 243

N-(3-(N-(3-(3,5-dimethoxyphenylamino)quinoxalin-2-yl)sulfamoyl)phenyl)-2-(4-methyl-1,4-diazepan-1-yl)acetamide

MS (EI) $C_{30}H_{35}N_7O_5S$: 606 (MH$^+$).

Example 244

2-(4-allylpiperazin-1-yl)-N-(3-(N-(3-(3,5-dimethoxyphenylamino)quinoxalin-2-yl)sulfamoyl)phenyl)acetamide

MS (EI) $C_{31}H_{35}N_7O_5S$: 618 (MH$^+$).

Example 245

N-(3-(N-(3-(3,5-dimethoxyphenylamino)quinoxalin-2-yl)sulfamoyl)phenyl)-2-(4-isopropylpiperazin-1-yl)acetamide

MS (EI) $C_{31}H_{37}N_7O_5S$: 620 (MH$^+$).

Example 246

N-(3-(N-(3-(3,5-dimethoxyphenylamino)quinoxalin-2-yl)sulfamoyl)phenyl)-2-(3-(dimethylamino)pyrrolidin-1-yl)acetamide

MS (EI)$C_{30}H_{35}N_7O_5S$: 606 (MH$^+$).

Example 247

N-(3-(N-(3-(3,5-dimethoxyphenylamino)quinoxalin-2-yl)sulfamoyl)phenyl)-2-(3-(dimethylamino)azetidin-1-yl)acetamide

MS (EI) $C_{29}H_{33}N_7O_5S$: 592 (MH$^+$).

Example 248

N-(3-(N-(3-(3,5-dimethoxyphenylamino)quinoxalin-2-yl)sulfamoyl)phenyl)-2-(4-oxopiperidin-1-yl)acetamide

MS (EI) $C_{29}H_{30}N_6O_6S$: 591 (MH$^+$).

Example 249

N-(3-(N-(3-(3,5-dimethoxyphenylamino)quinoxalin-2-yl)sulfamoyl)phenyl)-2-((2-methoxyethyl)(methyl)amino)acetamide

MS (EI) $C_{28}H_{32}N_6O_6S$: 581 (MH$^+$).

Example 250

N-(3-(N-(3-(3,5-dimethoxyphenylamino)quinoxalin-2-yl)sulfamoyl)phenyl)-2-(4-methylbenzyloxyamino)acetamide

MS (EI) $C_{32}H_{32}N_6O_6S$: 629 (MH$^+$).

Example 251

N-(3-(N-(3-(3,5-dimethoxyphenylamino)quinoxalin-2-yl)sulfamoyl)phenyl)-2-(2-methoxybenzyloxyamino)acetamide

MS (EI) $C_{32}H_{32}N_6O_7S$: 645 (MH$^+$).

Example 252

N-(3-(N-(3-(3,5-dimethoxyphenylamino)quinoxalin-2-yl)sulfamoyl)phenyl)-2-(propylamino)acetamide

MS (EI) $C_{27}H_{30}N_6O_5S$: 551 (MH$^+$).

Example 253

N-(3-(N-(3-(3,5-dimethoxyphenylamino)quinoxalin-2-yl)sulfamoyl)phenyl)-2-(ethyl(methyl)amino)acetamide

MS (EI) $C_{27}H_{30}N_6O_5S$: 551 (MH$^+$).

Example 254

2-(allyl(methyl)amino)-N-(3-(N-(3-(3,5-dimethoxyphenylamino)quinoxalin-2-yl)sulfamoyl)phenyl)acetamide

MS (EI) $C_{28}H_{30}N_6O_5S$: 563 (MH$^+$).

Example 255

2-(tert-butylamino)-N-(3-(N-(3-(3,5-dimethoxyphenylamino)quinoxalin-2-yl)sulfamoyl)phenyl)acetamide

MS (EI) $C_{28}H_{32}N_6O_5S$: 565 (MH$^+$).

Example 256

N-(3-(N-(3-(3,5-dimethoxyphenylamino)quinoxalin-2-yl)sulfamoyl)phenyl)-2-(isobutylamino)acetamide

MS (EI) $C_{28}H_{32}N_6O_5S$: 565 (MH$^+$).

Example 257

2-(butylamino)-N-(3-(N-(3-(3,5-dimethoxyphenylamino)quinoxalin-2-yl)sulfamoyl)phenyl)acetamide

MS (EI) $C_{28}H_{32}N_6O_5S$: 565 (MH$^+$).

Example 258

N-(3-(N-(3-(3,5-dimethoxyphenylamino)quinoxalin-2-yl)sulfamoyl)phenyl)-2-(isopropyl(methyl)amino)acetamide

MS (EI) $C_{28}H_{32}N_6O_5S$: 565 (MH$^+$).

Example 259

N-(3-(N-(3-(3,5-dimethoxyphenylamino)quinoxalin-2-yl)sulfamoyl)phenyl)-2-(4-formylpiperazin-1-yl)acetamide

MS (EI) $C_{29}H_{31}N_7O_6S$: 606 (MH$^+$).

Example 260

N-(3-(N-(3-(3,5-dimethoxyphenylamino)quinoxalin-2-yl)sulfamoyl)phenyl)-2-(4-ethylpiperazin-1-yl)acetamide

MS (EI) $C_{30}H_{35}N_7O_5S$: 606 (MH$^+$).

Example 261

N-(3-(N-(3-(3,5-dimethoxyphenylamino)quinoxalin-2-yl)sulfamoyl)phenyl)-2-(4-formyl-1,4-diazepan-1-yl)acetamide

MS (EI) $C_{30}H_{33}N_7O_6S$: 620 (MH$^+$).

Example 262

N-(3-(N-(3-(3,5-dimethoxyphenylamino)quinoxalin-2-yl)sulfamoyl)phenyl)-2-(ethyl(2-hydroxyethyl)amino)acetamide

MS (EI) $C_{28}H_{32}N_6O_6S$: 581 (MH$^+$).

Example 263

(S)—N-(3-(N-(3-(3,5-dimethoxyphenylamino)quinoxalin-2-yl)sulfamoyl)phenyl)-2-(3-hydroxypyrrolidin-1-yl)acetamide

MS (EI) $C_{28}H_{30}N_6O_6S$: 579 (MH$^+$).

Example 264

N-(3-(N-(3-(3,5-dimethoxyphenylamino)quinoxalin-2-yl)sulfamoyl)phenyl)-2-(2,6-dimethylmorpholino)acetamide

MS (EI) $C_{30}H_{34}N_6O_6S$: 607 (MH$^+$).

Example 265

N-(3-(N-(3-(3,5-dimethoxyphenylamino)quinoxalin-2-yl)sulfamoyl)phenyl)-2-(2-methylbenzylamino)acetamide

MS (EI) $C_{32}H_{32}N_6O_5S$: 613 (MH$^+$).

Example 266

N-(3-(N-(3-(3,5-dimethoxyphenylamino)quinoxalin-2-yl)sulfamoyl)phenyl)-2-(2-methoxyethylamino)acetamide

MS (EI) $C_{27}H_{30}N_6O_6S$: 567 (MH$^+$).

Example 267

N-(3-(N-(3-(3,5-dimethoxyphenylamino)quinoxalin-2-yl)sulfamoyl)phenyl)-2-(thiazolidin-3-yl)acetamide

MS (EI) $C_{27}H_{28}N_6O_5S_2$: 581 (MH$^+$).

Example 268

N-(3-(N-(3-(3,5-dimethoxyphenylamino)quinoxalin-2-yl)sulfamoyl)phenyl)-2-(3-(hydroxymethyl)piperidin-1-yl)acetamide

MS (EI) $C_{30}H_{34}N_6O_6S$: 607 (MH$^+$).

Example 268

N-(3-(N-(3-(3,5-dimethoxyphenylamino)quinoxalin-2-yl)sulfamoyl)phenyl)-2-(2-phenylpropylamino)acetamide

MS (EI) $C_{33}H_{34}N_6O_5S$: 627 (MH$^+$).

Example 269

N-(3-(N-(3-(3,5-dimethoxyphenylamino)quinoxalin-2-yl)sulfamoyl)phenyl)-2-(isobutyl(methyl)amino)acetamide

MS (EI) $C_{29}H_{34}N_6O_5S$: 579 (MH$^+$).

Example 270

N-(3-(N-(3-(3,5-dimethoxyphenylamino)quinoxalin-2-yl)sulfamoyl)phenyl)-2-(phenylamino)acetamide

MS (EI) $C_{30}H_{28}N_6O_5S$: 585 (MH$^+$).

Example 271

N-(3-(N-(3-(3,5-dimethoxyphenylamino)quinoxalin-2-yl)sulfamoyl)phenyl)-2-(2-propylphenylamino)acetamide

MS (EI) $C_{33}H_{34}N_6O_5S$: 627 (MH$^+$).

Example 272

N-(3-(N-(3-(3,5-dimethoxyphenylamino)quinoxalin-2-yl)sulfamoyl)phenyl)-2-(2-isopropylphenylamino)acetamide

MS (EI) $C_{33}H_{34}N_6O_5S$: 627 (MH$^+$).

Example 273

N-(3-(N-(3-(3,5-dimethoxyphenylamino)quinoxalin-2-yl)sulfamoyl)phenyl)-2-(2-fluoro-4-methylphenylamino)acetamide

MS (EI) $C_{31}H_{29}FN_6O_5S$: 617 (MH$^+$).

Example 274

2-(4-chlorophenylamino)-N-(3-(N-(3-(3,5-dimethoxyphenylamino)quinoxalin-2-yl)sulfamoyl)phenyl)acetamide MS (EI) $C_{30}H_{27}ClN_6O_5S$: 619 (MH$^+$).

Example 275

N-(3-(N-(3-(3,5-dimethoxyphenylamino)quinoxalin-2-yl)sulfamoyl)phenyl)-2-(2-methoxyphenylamino)acetamide

MS (EI) $C_{31}H_{30}N_6O_6S$: 615 (MH$^+$).

Example 276

2-(3-chlorophenylamino)-N-(3-(N-(3-(3,5-dimethoxyphenylamino)quinoxalin-2-yl)sulfamoyl)phenyl)acetamide MS (EI) $C_{30}H_{27}ClN_6O_5S$: 619 (MH$^+$).

Example 277

N-(3-(N-(3-(3,5-dimethoxyphenylamino)quinoxalin-2-yl)sulfamoyl)phenyl)-2-(2,3-dimethylphenylamino)acetamide

MS (EI) $C_{32}H_{32}N_6O_5S$: 613 (MH$^+$).

Example 278

N-(3-(N-(3-(3,5-dimethoxyphenylamino)quinoxalin-2-yl)sulfamoyl)phenyl)-2-(2-fluorophenylamino)acetamide

MS (EI) $C_{30}H_{27}FN_6O_5S$: 603 (MH$^+$).

Example 279

N-(3-(N-(3-(3,5-dimethoxyphenylamino)quinoxalin-2-yl)sulfamoyl)phenyl)-2-(3-fluorophenylamino)acetamide

MS (EI) $C_{30}H_{27}FN_6O_5S$: 603 (MH$^+$).

Example 280

N-(3-(N-(3-(3,5-dimethoxyphenylamino)quinoxalin-2-yl)sulfamoyl)phenyl)-2-(thiophen-2-ylmethylamino)acetamide

MS (EI) $C_{29}H_{28}N_6O_5S_2$: 605 (MH$^+$).

Example 281

2-(cyclohexyl(ethyl)amino)-N-(3-(N-(3-(3,5-dimethoxyphenylamino)quinoxalin-2-yl)sulfamoyl)phenyl)acetamide

MS (EI) $C_{32}H_{38}N_6O_5S$: 619 (MH$^+$).

Example 282

2-((cyclopropylmethyl)(propyl)amino)-N-(3-(N-(3-(3,5-dimethoxyphenylamino)quinoxalin-2-yl)sulfamoyl)phenyl)acetamide

MS (EI) $C_{31}H_{36}N_6O_5S$: 605 (MH$^+$).

Example 283

2-(allyl(cyclopentyl)amino)-N-(3-(N-(3-(3,5-dimethoxyphenylamino)quinoxalin-2-yl)sulfamoyl)phenyl)acetamide

MS (EI) $C_{32}H_{36}N_6O_5S$: 617 (MH$^+$).

Example 284

N-(3-(N-(3-(3,5-dimethoxyphenylamino)quinoxalin-2-yl)sulfamoyl)phenyl)-2-(ethyl(isopropyl)amino)acetamide

MS (EI) $C_{29}H_{34}N_6O_5S$: 579 (MH$^+$).

Example 285

N-(3-(N-(3-(3,5-dimethoxyphenylamino)quinoxalin-2-yl)sulfamoyl)phenyl)-2-(ethyl(phenyl)amino)acetamide

MS (EI) $C_{32}H_{32}N_6O_5S$: 613 (MH$^+$).

Example 286

N-(3-(N-(3-(3,5-dimethoxyphenylamino)quinoxalin-2-yl)sulfamoyl)phenyl)-2-(2-methylpyrrolidin-1-yl)acetamide

MS (EI) $C_{29}H_{32}N_6O_5S$: 577 (MH$^+$).

Example 287

N-(3-(N-(3-(3,5-dimethoxyphenylamino)quinoxalin-2-yl)sulfamoyl)phenyl)-2-(2-methylpiperidin-1-yl)acetamide

MS (EI) $C_{30}H_{34}N_6O_5S$: 591 (MH$^+$).

Example 288

N-(3-(N-(3-(3,5-dimethoxyphenylamino)quinoxalin-2-yl)sulfamoyl)phenyl)-2-(pyridin-2-ylmethylamino)acetamide

MS (EI) $C_{30}H_{29}N_7O_5S$: 600 (MH$^+$).

Example 289

2-(benzyl(methyl)amino)-N-(3-(N-(3-(3,5-dimethoxyphenylamino)quinoxalin-2-yl)sulfamoyl)phenyl)acetamide

MS (EI) $C_{32}H_{32}N_6O_5S$: 613 (MH$^+$).

Example 290

N-(3-(N-(3-(3,5-dimethoxyphenylamino)quinoxalin-2-yl)sulfamoyl)phenyl)-2-(1-phenylethylamino)acetamide

MS (EI) $C_{32}H_{32}N_6O_5S$: 613 (MH$^+$).

Example 291

N-(3-(N-(3-(3,5-dimethoxyphenylamino)quinoxalin-2-yl)sulfamoyl)phenyl)-2-(3-methylpiperidin-1-yl)acetamide

MS (EI) $C_{30}H_{34}N_6O_5S$: 591 (MH$^+$).

Example 292

N-(3-(N-(3-(3,5-dimethoxyphenylamino)quinoxalin-2-yl)sulfamoyl)phenyl)-2-(4-methylpiperidin-1-yl)acetamide

MS (EI) $C_{30}H_{34}N_6O_5S$: 591 (MH$^+$).

Example 293

2-(3,4-dihydroisoquinolin-2(1H)-yl)-N-(3-(N-(3-(3,5-dimethoxyphenylamino)quinoxalin-2-yl)sulfamoyl)phenyl)acetamide

MS (EI) $C_{33}H_{32}N_6O_5S$: 625 (MH$^+$).

Example 294

N-(3-(N-(3-(3,5-dimethoxyphenylamino)quinoxalin-2-yl)sulfamoyl)phenyl)-2-(2,6-dimethylpiperidin-1-yl)acetamide

MS (EI) $C_{31}H_{36}N_6O_5S$: 605 (MH$^+$).

Example 295

N-(3-(N-(3-(3,5-dimethoxyphenylamino)quinoxalin-2-yl)sulfamoyl)phenyl)-2-(3-hydroxybenzylamino)acetamide

MS (EI) $C_{31}H_{30}N_6O_6S$: 615 (MH$^+$).

General Library Acylation Procedure 2

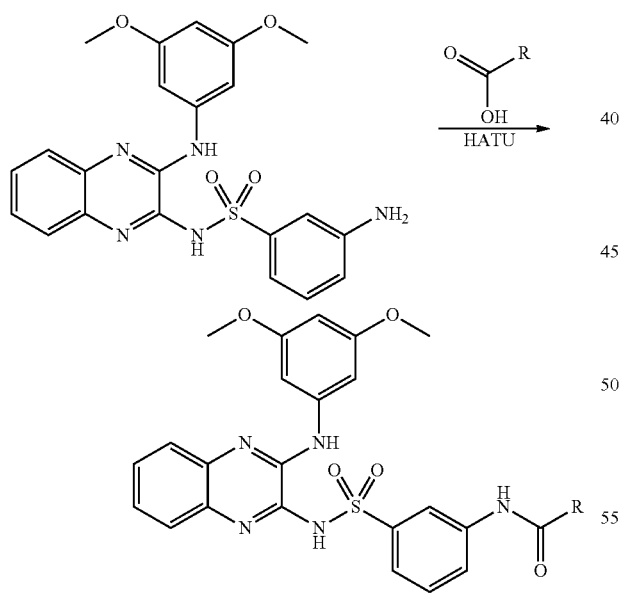

Into a 2-dram vial were added 3-amino-N-(3-(3,5-dimethoxyphenylamino)quinoxalin-2-yl)benzenesulfonamide (54 mg, 0.12 mmol), DMA O$_2$ mL) and the desired carboxylic acid (0.17 mmol). Hunig's Base (70 □L, 0.4 mmol) followed by HATU (53 mg, 0.14 mmol) were added to the vial and the reaction mixture stirred at 50° C. overnight. Preparative reverse-phase HPLC was used to isolate the desired product directly from the crude reaction mixture. A Waters Fractionlynx preparative reverse-phase HPLC; equipped with a Waters SunFire Prep C18, OCD 5 □M, 30×70 mm column and running a 5-100% gradient with a binary solvent system of 25 mM ammonium acetate in water/acetonitrile; was used to carry out the purification.

The following title compounds were prepared according to General Library Acylation Procedure 2.

Example 296

N-(3-(N-(3-(3,5-dimethoxyphenylamino)quinoxalin-2-yl)sulfamoyl)phenyl)propionamide $^1$H-NMR (400 MHz, d$_6$-DMSO): 12.37 (s, 1H), 10.20 (s, 1H), 8.88 (s, 1H), 8.37 (s, 1H), 7.93 (s, 1H), 7.77 (t, 2H), 7.59 (t, 1H), 7.51 (t, 1H), 7.41-7.34 (m, 4H), 6.24 (t, 1H), 3.76 (s, 6H), 2.36-2.31 (dd, 2H), 1.10 (s, 1H), 1.08 (s, 1H), 1.06 (s, 1H); MS (EI) $C_{25}H_{25}N_5O_5S$: 508.6 (MH$^+$).

Example 297

N-(3-(N-(3-(3,5-dimethoxyphenylamino)quinoxalin-2-yl)sulfamoyl)phenyl)pyridazine-4-carboxamide $^1$H-NMR (400 MHz, d$_6$-DMSO): 11.01 (s, 1H), 9.66 (dd, 1H), 9.52 (dd, 1H), 8.90 (s, 1H), 8.55 (s, 1H), 8.13 (dd, 1H), 7.99 (d, 1H), 7.93 (d, 1H), 7.65-7.58 (m, 2H), 7.42-7.35 (m, 4H), 6.24 (t, 1H), 3.75 (s, 6H); MS (EI) $C_{27}H_{23}N_7O_5S$: 558.6 (MH$^+$).

Example 298

N-(3-(N-(3-(3,5-dimethoxyphenylamino)quinoxalin-2-yl)sulfamoyl)phenyl)-2-methylnicotinamide $^1$H-NMR (400 MHz, d$_6$-DMSO): 10.78 ppm (s, 1H), 8.90 ppm (s, 1H), 8.58-8.57 ppm (dd, 2H), 7.90-7.86 (m, 4H), 7.60-7.56 ppm (m, 2H), 7.42-7.34 (m, 5H), 6.23 ppm (t, 1H), 3.74 ppm (s, 6H), 2.57 ppm (s, 3H); MS (EI) $C_{29}H_{26}N_5O_5S$: 570.6 (MH$^+$).

Example 299

N-(3-(N-(3-(3,5-dimethoxyphenylamino)quinoxalin-2-yl)sulfamoyl)phenyl)-2-(o-tolyloxy)acetamide $^1$H-NMR (400 MHz, d$_6$-DMSO): 12.37 ppm (s, 1H), 10.41 ppm (s, 1H), 8.90 ppm (s, 1H), 8.41 ppm (s, 1H), 7.93 ppm (s, 1H), 7.90-7.8 (m, 2H), 7.59-7.53 ppm (m, 2H), 7.42-7.33 ppm (m, 4H), 7.17-7.12 ppm (m, 2H), 6.89-6.85 ppm (m, 2H), 6.24 ppm (t, 1H), 4.74 ppm (s, 2H), 3.76 ppm (s, 6H), 2.33 ppm (s, 2H); MS (EI) $C_{31}H_{29}N_5O_6S$: 599.7 (MH$^+$).

Example 300

N-(3-(N-(3-(3,5-dimethoxyphenylamino)quinoxalin-2-yl)sulfamoyl)phenyl)-3-methoxy-4-methylbenzamide

MS (EI) $C_{31}H_{29}N_5O_6S$: 600 (MH$^+$).

Example 301

N-(3-(N-(3-(3,5-dimethoxyphenylamino)quinoxalin-2-yl)sulfamoyl)phenyl)-3-methoxy-4-methylbenzamide

MS (EI) $C_{28}H_{24}N_6O_5S$: 557 (MH$^+$).

Example 302

N-(3-(N-(3-(3,5-dimethoxyphenylamino)quinoxalin-2-yl)sulfamoyl)phenyl)thiazole-4-carboxamide

MS (EI) $C_{26}H_{22}N_6O_5S_2$: 563 (MH$^+$).

Example 303

2-bromo-N-(3-(N-(3-(3,5-dimethoxyphenylamino)quinoxalin-2-yl)sulfamoyl)phenyl)thiophene-3-carboxamide MS (EI) $C_{27}H_{22}BrN_5O_5S_2$ 640 (MH$^+$).

Example 304

N-(3-(N-(3-(3,5-dimethoxyphenylamino)quinoxalin-2-yl)sulfamoyl)phenyl)pivalamide

MS (EI) $C_{27}H_{29}N_5O_5S$: 536 (MH$^+$).

Example 305

N-(3-(N-(3-(3,5-dimethoxyphenylamino)quinoxalin-2-yl)sulfamoyl)phenylpent-4-enamide

MS (EI) $C_{27}H_{27}N_5O_5S$: 534 (MH$^+$).

Example 306

N-(3-(N-(3-(3,5-dimethoxyphenylamino)quinoxalin-2-yl)sulfamoyl)phenyl)benzamide

MS (EI) $C_{29}H_{25}N_5O_5S$: 556 (MH$^+$).

Example 307

N-(3-(N-(3-(3,5-dimethoxyphenylamino)quinoxalin-2-yl)sulfamoyl)phenyl)butyramide

MS (EI) $C_{26}H_{27}N_5O_5S$: 522 (MH$^+$).

Example 308

N-(3-(N-(3-(3,5-dimethoxyphenylamino)quinoxalin-2-yl)sulfamoyl)phenyl)-2-methoxyacetamide

MS (EI) $C_{25}H_{25}N_5O_6S$: 524 (MH$^+$).

Example 309

N-(3-(N-(3-(3,5-dimethoxyphenylamino)quinoxalin-2-yl)sulfamoyl)phenyl)cyclobutanecarboxamide

MS (EI) $C_{27}H_{27}N_5O_5S$: 534 (MH$^+$).

Example 310

N-(3-(N-(3-(3,5-dimethoxyphenylamino)quinoxalin-2-yl)sulfamoyl)phenyl)-2-methylcyclopropanecarboxamide

MS (EI) $C_{27}H_{27}N_5O_5S$: 534 (MH$^+$).

Example 311

N-(3-(N-(3-(3,5-dimethoxyphenylamino)quinoxalin-2-yl)sulfamoyl)phenyl)-1-methylcyclopropanecarboxamide

MS (EI) $C_{27}H_{27}N_5O_5S$: 534 (MH$^+$).

Example 312

N-(3-(N-(3-(3,5-dimethoxyphenylamino)quinoxalin-2-yl)sulfamoyl)phenyl)-3-methylbutanamide

MS (EI) $C_{27}H_{29}N_5O_5S$: 536 (MH$^+$).

Example 313

N-(3-(N-(3-(3,5-dimethoxyphenylamino)quinoxalin-2-yl)sulfamoyl)phenyl)-2-ethoxyacetamide

MS (EI) $C_{26}H_{27}N_5O_6S$: 538 (MH$^+$).

Example 314

N-(3-(N-(3-(3,5-dimethoxyphenylamino)quinoxalin-2-yl)sulfamoyl)phenyl)-3-methoxypropanamide

MS (EI) $C_{26}H_{27}N_5O_6S$: 538 (MH$^+$).

Example 315

N-(3-(N-(3-(3,5-dimethoxyphenylamino)quinoxalin-2-yl)sulfamoyl)phenyl)-2-hydroxyacetamide

MS (EI) $C_{24}H_{23}N_5O_6S$: 510 (MH$^+$).

Example 316

N-(3-(N-(3-(3,5-dimethoxyphenylamino)quinoxalin-2-yl)sulfamoyl)phenyl)isobutyramide

MS (EI) $C_{26}H_{27}N_5O_5S$: 522 (MH$^+$).

Example 317

N-(3-(N-(3-(3,5-dimethoxyphenylamino)quinoxalin-2-yl)sulfamoyl)phenyl)-1-hydroxycyclopropanecarboxamide

MS (EI) $C_{26}H_{25}N_5O_6S$: 536 (MH$^+$).

Example 318

N-(3-(N-(3-(3,5-dimethoxyphenylamino)quinoxalin-2-yl)sulfamoyl)phenyl)furan-3-carboxamide

MS (EI) $C_{27}H_{23}N_5O_6S$: 546 (MH$^+$).

Example 319

N-(3-(N-(3-(3,5-dimethoxyphenylamino)quinoxalin-2-yl)sulfamoyl)phenyl)tetrahydrofuran-3-carboxamide

MS (EI) $C_{27}H_{27}N_5O_6S$: 550 (MH$^+$).

Example 320

N-(3-(N-(3-(3,5-dimethoxyphenylamino)quinoxalin-2-yl)sulfamoyl)phenyl)tetrahydrofuran-2-carboxamide

MS (EI) $C_{27}H_{27}N_5O_6S$: 550 (MH$^+$).

Example 321

N-(3-(N-(3-(3,5-dimethoxyphenylamino)quinoxalin-2-yl)sulfamoyl)phenyl)furan-2-carboxamide

MS (EI) $C_{27}H_{23}N_5O_6S$: 546 (MH$^+$).

Example 322

N-(3-(N-(3-(3,5-dimethoxyphenylamino)quinoxalin-2-yl)sulfamoyl)phenyl)isonicotinamide

MS (EI) $C_{28}H_{24}N_6O_5S$: 557 (MH$^+$).

Example 323

N-(3-(N-(3-(3,5-dimethoxyphenylamino)quinoxalin-2-yl)sulfamoyl)phenyl)-1H-pyrrole-2-carboxamide

MS (EI) $C_{27}H_{24}N_6O_5S$: 545 (MH$^+$).

Example 324

N-(3-(N-(3-(3,5-dimethoxyphenylamino)quinoxalin-2-yl)sulfamoyl)phenyl)pyrazine-2-carboxamide

MS (EI) $C_{27}H_{23}N_7O_5S$: 558 (MH$^+$).

Example 325

N-(3-(N-(3-(3,5-dimethoxyphenylamino)quinoxalin-2-yl)sulfamoyl)phenyl)-1-methyl-1H-pyrrole-2-carboxamide

MS (EI) $C_{28}H_{26}N_6O_5S$: 559 (MH$^+$).

Example 326

N-(3-(N-(3-(3,5-dimethoxyphenylamino)quinoxalin-2-yl)sulfamoyl)phenyl)-5-methylisoxazole-3-carboxamide

MS (EI) $C_{27}H_{24}N_6O_6S$: 561 (MH$^+$).

Example 327

N-(3-(N-(3-(3,5-dimethoxyphenylamino)quinoxalin-2-yl)sulfamoyl)phenyl)thiophene-2-carboxamide

MS (EI) $C_{27}H_{23}N_5O_5S_2$: 562 (MH$^+$).

Example 328

(S)—N-(3-(N-(3-(3,5-dimethoxyphenylamino)quinoxalin-2-yl)sulfamoyl)phenyl)-1-methylpyrrolidine-2-carboxamide

MS (EI) $C_{28}H_{30}N_6O_5S$: 563 (MH$^+$).

Example 329

N-(3-(N-(3-(3,5-dimethoxyphenylamino)quinoxalin-2-yl)sulfamoyl)phenyl)-2-methylbenzamide

MS (EI) $C_{30}H_{27}N_5O_5S$: 570 (MH$^+$).

Example 330

N-(3-(N-(3-(3,5-dimethoxyphenylamino)quinoxalin-2-yl)sulfamoyl)phenyl)-2-phenylacetamide

MS (EI) $C_{30}H_{27}N_5O_5S$: 570 (MH$^+$).

Example 331

N-(3-(N-(3-(3,5-dimethoxyphenylamino)quinoxalin-2-yl)sulfamoyl)phenyl)-3-methylpicolinamide

MS (EI) $C_{29}H_{26}N_6O_5S$: 571 (MH$^+$).

Example 332

N-(3-(N-(3-(3,5-dimethoxyphenylamino)quinoxalin-2-yl)sulfamoyl)phenyl)-2-(pyridin-3-yl)acetamide

MS (EI) $C_{29}H_{26}N_6O_5S$: 571 (MH$^+$).

Example 333

N-(3-(N-(3-(3,5-dimethoxyphenylamino)quinoxalin-2-yl)sulfamoyl)phenyl)-6-hydroxypicolinamide

MS (EI) $C_{28}H_{24}N_6O_6S$: 573 (MH$^+$).

Example 334

N-(3-(N-(3-(3,5-dimethoxyphenylamino)quinoxalin-2-yl)sulfamoyl)phenyl)-2-fluorobenzamide

MS (EI) $C_{29}H_{24}FN_5O_5S$: 574 (MH$^+$).

Example 335

N-(3-(N-(3-(3,5-dimethoxyphenylamino)quinoxalin-2-yl)sulfamoyl)phenyl)-4-fluorobenzamide

MS (EI) $C_{29}H_{24}FN_5O_5S$: 574 (MH$^+$).

Example 336

N-(3-(N-(3-(3,5-dimethoxyphenylamino)quinoxalin-2-yl)sulfamoyl)phenyl)-3-fluorobenzamide

MS (EI) $C_{29}H_{24}FN_5O_5S$: 574 (MH$^+$).

Example 337

2-cyclohexyl-N-(3-(N-(3-(3,5-dimethoxyphenylamino)quinoxalin-2-yl)sulfamoyl)phenyl)acetamide

MS (EI) $C_{30}H_{33}N_5O_5S$: 576 (MH$^+$).

Example 338

N-(3-(N-(3-(3,5-dimethoxyphenylamino)quinoxalin-2-yl)sulfamoyl)phenyl)-2-(2-oxocyclopentyl)acetamide

MS (EI) $C_{29}H_{29}N_5O_6S$: 576 (MH$^+$).

Example 339

4-cyclopropyl-N-(3-(N-(3-(3,5-dimethoxyphenylamino)quinoxalin-2-yl)sulfamoyl)phenyl)-4-oxobutanamide

MS (EI) $C_{29}H_{29}N_5O_6S$: 576 (MH$^+$).

Example 340

N-(3-(N-(3-(3,5-dimethoxyphenylamino)quinoxalin-2-yl)sulfamoyl)phenyl)-3-oxocyclohexanecarboxamide

MS (EI) $C_{29}H_{29}N_5O_6S$: 576 (MH$^+$).

Example 341

N-(3-(N-(3-(3,5-dimethoxyphenylamino)quinoxalin-2-yl)sulfamoyl)phenyl)-3-(pyridin-3-yl)propanamide

MS (EI) $C_{30}H_{28}N_6O_5S$: 585 (MH$^+$).

Example 342

N-(3-(N-(3-(3,5-dimethoxyphenylamino)quinoxalin-2-yl)sulfamoyl)phenyl)-2-methoxybenzamide

MS (EI) $C_{30}H_{27}N_5O_6S$: 586 (MH$^+$).

Example 343

N-(3-(N-(3-(3,5-dimethoxyphenylamino)quinoxalin-2-yl)sulfamoyl)phenyl)-3-methoxybenzamide

MS (EI) $C_{30}H_{27}N_5O_6S$: 586 (MH$^+$).

Example 344

N-(3-(N-(3-(3,5-dimethoxyphenylamino)quinoxalin-2-yl)sulfamoyl)phenyl)-2-phenoxyacetamide

MS (EI) $C_{30}H_{27}N_5O_6S$: 586 (MH$^+$).

Example 345

N-(3-(N-(3-(3,5-dimethoxyphenylamino)quinoxalin-2-yl)sulfamoyl)phenyl)-4-methoxybenzamide

MS (EI) $C_{30}H_{27}N_5O_6S$: 586 (MH$^+$).

Example 346

N-(3-(N-(3-(3,5-dimethoxyphenylamino)quinoxalin-2-yl)sulfamoyl)phenyl)-2-(4-fluorophenyl)acetamide

MS (EI) $C_{30}H_{26}FN_5O_5S$: 588 (MH$^+$).

Example 347

N-(3-(N-(3-(3,5-dimethoxyphenylamino)quinoxalin-2-yl)sulfamoyl)phenyl)-2-(2-fluorophenyl)acetamide

MS (EI) $C_{30}H_{26}FN_5O_5S$: 588 (MH$^+$).

Example 348

N-(3-(N-(3-(3,5-dimethoxyphenylamino)quinoxalin-2-yl)sulfamoyl)phenyl)-2-(3-fluorophenyl)acetamide

MS (EI) $C_{30}H_{26}FN_5O_5S$: 588 (MH$^+$).

Example 349

2-chloro-N-(3-(N-(3-(3,5-dimethoxyphenylamino)quinoxalin-2-yl)sulfamoyl)phenyl)benzamide MS (EI) $C_{29}H_{24}ClN_5O_5S$: 590 (MH$^+$).

Example 350

4-chloro-N-(3-(N-(3-(3,5-dimethoxyphenylamino)quinoxalin-2-yl)sulfamoyl)phenyl)benzamide MS (EI) $C_{29}H_{24}ClN_5O_5S$: 590 (MH$^+$).

Example 351

3-chloro-N-(3-(N-(3-(3,5-dimethoxyphenylamino)quinoxalin-2-yl)sulfamoyl)phenyl)benzamide MS (EI) $C_{29}H_{24}ClN_5O_5S$: 590 (MH$^+$).

Example 352

(1R,2R)—N-(3-(N-(3-(3,5-dimethoxyphenylamino)quinoxalin-2-yl)sulfamoyl)phenyl)-2-phenylcyclopropanecarboxamide

MS (EI) $C_{32}H_{29}N_5O_5S$: 596 (MH$^+$).

Example 353

N-(3-(N-(3-(3,5-dimethoxyphenylamino)quinoxalin-2-yl)sulfamoyl)phenyl)-1-phenylcyclopropanecarboxamide

MS (EI) $C_{32}H_{29}N_5O_5S$: 596 (MH$^+$).

Example 354

N-(3-(N-(3-(3,5-dimethoxyphenylamino)quinoxalin-2-yl)sulfamoyl)phenyl)-2-(1H-imidazol-4-yl)acetamide

MS (EI) $C_{27}H_{25}N_7O_5S$: 560 (MH$^+$).

Example 355

N-(3-(N-(3-(3,5-dimethoxyphenylamino)quinoxalin-2-yl)sulfamoyl)phenyl)-4-methoxy-2-methylbenzamide

MS (EI) $C_{31}H_{29}N_5O_6S$: 600 (MH$^+$).

Example 356

N-(3-(N-(3-(3,5-dimethoxyphenylamino)quinoxalin-2-yl)sulfamoyl)phenyl)-2-(4-fluorophenoxy)acetamide

MS (EI) $C_{30}H_{26}FN_5O_6S$: 604 (MH$^+$).

Example 357

N-(3-(N-(3-(3,5-dimethoxyphenylamino)quinoxalin-2-yl)sulfamoyl)phenyl)-5-fluoro-2-methoxybenzamide

MS (EI) $C_{30}H_{26}FN_5O_6S$: 604 (MH$^+$).

Example 358

2-(4-chlorophenyl)-N-(3-(N-(3-(3,5-dimethoxyphenylamino)quinoxalin-2-yl)sulfamoyl)phenyl)acetamide MS (EI) $C_{30}H_{26}ClN_5O_5S$: 604 (MH$^+$).

Example 359

2-(2-chlorophenyl)-N-(3-(N-(3-(3,5-dimethoxyphenylamino)quinoxalin-2-yl)sulfamoyl)phenyl)acetamide MS (EI) $C_{30}H_{26}ClN_5O_5S$: 604 (MH$^+$).

Example 360

2-(3-chlorophenyl)-N-(3-(N-(3-(3,5-dimethoxyphenylamino)quinoxalin-2-yl)sulfamoyl)phenyl)acetamide MS (EI) $C_{30}H_{26}ClN_5O_5S$: 604 (MH$^+$).

Example 361

1-acetyl-N-(3-(N-(3-(3,5-dimethoxyphenylamino)quinoxalin-2-yl)sulfamoyl)phenyl)piperidine-4-carboxamide

MS (EI) $C_{30}H_{32}N_6O_6S$: 605 (MH$^+$).

Example 362

N-(3-(N-(3-(3,5-dimethoxyphenylamino)quinoxalin-2-yl)sulfamoyl)phenyl)-2-(pyridin-4-yl)acetamide

MS (EI) $C_{29}H_{26}N_6O_5S$: 571 (MH$^+$).

Example 363

N-(3-(N-(3-(3,5-dimethoxyphenylamino)quinoxalin-2-yl)sulfamoyl)phenyl)-2-(pyridin-2-yl)acetamide

MS (EI) $C_{29}H_{26}N_6O_5S$: 571 (MH$^+$).

Example 364

2,4-dichloro-N-(3-(N-(3-(3,5-dimethoxyphenylamino)quinoxalin-2-yl)sulfamoyl)phenyl)benzamide MS (EI) $C_{29}H_{23}Cl_2N_5O_5S$: 624 (MH$^+$).

Example 365

3,4-dichloro-N-(3-(N-(3-(3,5-dimethoxyphenylamino)quinoxalin-2-yl)sulfamoyl)phenyl)benzamide MS (EI) $C_{29}H_{23}Cl_2N_5O_5S$: 624 (MH$^+$).

Example 366

2,5-dichloro-N-(3-(N-(3-(3,5-dimethoxyphenylamino)quinoxalin-2-yl)sulfamoyl)phenyl)benzamide MS (EI) $C_{29}H_{23}Cl_2N_5O_5S$: 624 (MH$^+$).

Example 367

3,5-dichloro-N-(3-(N-(3-(3,5-dimethoxyphenylamino)quinoxalin-2-yl)sulfamoyl)phenyl)benzamide MS (EI) $C_{29}H_{23}Cl_2N_5O_5S$: 624 (MH$^+$).

Example 368

2,3-dichloro-N-(3-(N-(3-(3,5-dimethoxyphenylamino)quinoxalin-2-yl)sulfamoyl)phenyl)benzamide MS (EI) $C_{29}H_{23}Cl_2N_5O_5S$: 624 (MH$^+$).

Example 369

N-(3-(N-(3-(3,5-dimethoxyphenylamino)quinoxalin-2-yl)sulfamoyl)phenyl)pentanamide

MS (EI) $C_{27}H_{29}N_5O_5S$: 536 (MH$^+$).

Example 370

N-(3-(N-(3-(3,5-dimethoxyphenylamino)quinoxalin-2-yl)sulfamoyl)phenyl)-2-methylbutanamide

MS (EI) $C_{27}H_{29}N_5O_5S$: 536 (MH$^+$).

Example 371

N-(3-(N-(3-(3,5-dimethoxyphenylamino)quinoxalin-2-yl)sulfamoyl)phenyl)-1H-imidazole-2-carboxamide

MS (EI) $C_{26}H_{23}N_7O_5S$: 546 (MH$^+$).

Example 372

N-(3-(N-(3-(3,5-dimethoxyphenylamino)quinoxalin-2-yl)sulfamoyl)phenyl)-1H-imidazole-4-carboxamide

MS (EI) $C_{26}H_{23}N_7O_5S$: 546 (MH$^+$).

Example 373

N-(3-(N-(3-(3,5-dimethoxyphenylamino)quinoxalin-2-yl)sulfamoyl)phenyl)isoxazole-5-carboxamide

MS (EI) $C_{26}H_{22}N_6O_6S$: 547 (MH$^+$).

Example 374

N-(3-(N-(3-(3,5-dimethoxyphenylamino)quinoxalin-2-yl)sulfamoyl)phenyl)-3,3-dimethylbutanamide

MS (EI) $C_{28}H_{31}N_5O_5S$: 550 (MH$^+$).

Example 375

N-(3-(N-(3-(3,5-dimethoxyphenylamino)quinoxalin-2-yl)sulfamoyl)phenyl)-2-methylpentanamide

MS (EI) $C_{28}H_{31}N_5O_5S$: 550 (MH$^+$).

Example 376

N-(3-(N-(3-(3,5-dimethoxyphenylamino)quinoxalin-2-yl)sulfamoyl)phenyl)-2,2-dimethylbutanamide

MS (EI) $C_{28}H_{31}N_5O_5S$: 550 (MH$^+$).

Example 377

N-(3-(N-(3-(3,5-dimethoxyphenylamino)quinoxalin-2-yl)sulfamoyl)phenyl)-4-methylpentanamide

MS (EI) $C_{23}H_{31}N_5O_5S$: 550 (MH$^+$).

Example 378

N-(3-(N-(3-(3,5-dimethoxyphenylamino)quinoxalin-2-yl)sulfamoyl)phenyl)pyrimidine-5-carboxamide

MS (EI) $C_{27}H_{23}N_7O_5S$: 558 (MH$^+$).

Example 379

N-(3-(N-(3-(3,5-dimethoxyphenylamino)quinoxalin-2-yl)sulfamoyl)phenyl)-3-methylfuran-2-carboxamide

MS (EI) $C_{28}H_{25}N_5O_6S$: 560 (MH$^+$).

Example 380

N-(3-(N-(3-(3,5-dimethoxyphenylamino)quinoxalin-2-yl)sulfamoyl)phenyl)thiophene-3-carboxamide

MS (EI) $C_{27}H_{23}N_5O_5S_2$: 562 (MH$^+$).

Example 381

N-(3-(N-(3-(3,5-dimethoxyphenylamino)quinoxalin-2-yl)sulfamoyl)phenyl)-3-oxocyclopentanecarboxamide

MS (EI) $C_{28}H_{27}N_5O_6S$: 562 (MH$^+$).

Example 382

N-(3-(N-(3-(3,5-dimethoxyphenylamino)quinoxalin-2-yl)sulfamoyl)phenyl)-2-(2-methoxyethoxy)acetamide

MS (EI) $C_{27}H_{29}N_5O_7S$: 568 (MH$^+$).

Example 383

N-(3-(N-(3-(3,5-dimethoxyphenylamino)quinoxalin-2-yl)sulfamoyl)phenyl)-4-methylbenzamide

MS (EI) $C_{30}H_{27}N_5O_5S$: 570 (MH$^+$).

Example 384

N-(3-(N-(3-(3,5-dimethoxyphenylamino)quinoxalin-2-yl)sulfamoyl)phenyl)-2-(3-methylisoxazol-4-yl)acetamide

MS (EI) $C_{28}H_{26}N_6O_6S$: 575 (MH$^+$).

Example 385

3-cyclopentyl-N-(3-(N-(3-(3,5-dimethoxyphenylamino)quinoxalin-2-yl)sulfamoyl)phenyl)propanamide

MS (EI) $C_{30}H_{33}N_5O_5S$: 576 (MH$^+$).

Example 386

N-(3-(N-(3-(3,5-dimethoxyphenylamino)quinoxalin-2-yl)sulfamoyl)phenyl)-2-o-tolylacetamide

MS (EI) $C_{31}H_{29}N_5O_5S$: 584 (MH$^+$).

Example 387

N-(3-(N-(3-(3,5-dimethoxyphenylamino)quinoxalin-2-yl)sulfamoyl)phenyl)-2-methoxynicotinamide

MS (EI) $C_{29}H_{26}N_6O_6S$: 587 (MH$^+$).

Example 388

N-(3-(N-(3-(3,5-dimethoxyphenylamino)quinoxalin-2-yl)sulfamoyl)phenyl)-4-fluoro-3-methylbenzamide

MS (EI) $C_{30}H_{26}FN_5O_5S$: 588 (MH$^+$).

Example 389

N-(3-(N-(3-(3,5-dimethoxyphenylamino)quinoxalin-2-yl)sulfamoyl)phenyl)-3-fluoro-2-methylbenzamide

MS (EI) $C_{30}H_{26}FN_5O_5S$: 588 (MH$^+$).

Example 390

N-(3-(N-(3-(3,5-dimethoxyphenylamino)quinoxalin-2-yl)sulfamoyl)phenyl)-3-fluoro-4-methylbenzamide

MS (EI) $C_{30}H_{26}FN_5O_5S$: 588 (MH$^+$).

Example 391

N-(3-(N-(3-(3,5-dimethoxyphenylamino)quinoxalin-2-yl)sulfamoyl)phenyl)-2-fluoro-5-methylbenzamide

MS (EI) $C_{30}H_{26}FN_5O_5S$: 588 (MH$^+$).

Example 392

N-(3-(N-(3-(3,5-dimethoxyphenylamine)quinoxalin-2-yl)sulfamoyl)phenyl)-5-fluoro-2-methylbenzamide

MS (EI) $C_{30}H_{26}FN_5O_5S$: 588 (MH$^+$).

Example 393

6-chloro-N-(3-(N-(3-(3,5-dimethoxyphenylamino)quinoxalin-2-yl)sulfamoyl)phenyl)nicotinamide MS (EI) $C_{28}H_{23}ClN_6O_5S$: 591 (MH$^+$).

Example 394

2-chloro-N-(3-(N-(3-(3,5-dimethoxyphenylamino)quinoxalin-2-yl)sulfamoyl)phenyl)nicotinamide MS (EI) $C_{28}H_{23}ClN_6O_5S$: 591 (MH$^+$).

Example 395

2-chloro-N-(3-(N-(3-(3,5-dimethoxyphenylamino)quinoxalin-2-yl)sulfamoyl)phenyl)isonicotinamide MS (EI) $C_{28}H_{23}ClN_6O_5S$: 591 (MH$^+$).

Example 396

N-(3-(N-(3-(3,5-dimethoxyphenylamino)quinoxalin-2-yl)sulfamoyl)phenyl)-4-(dimethylamino)benzamide

MS (EI) $C_{31}H_{30}N_6O_5S$: 599 (MH$^+$).

Example 397

N-(3-(N-(3-(3,5-dimethoxyphenylamino)quinoxalin-2-yl)sulfamoyl)phenyl)-3-(dimethylamino)benzamide

MS (EI) $C_{31}H_{30}N_6O_5S$: 599 (MH$^+$).

Example 398

N-(3-(N-(3-(3,5-dimethoxyphenylamino)quinoxalin-2-yl)sulfamoyl)phenyl)benzo[d][1,3]dioxole-5-carboxamide

MS (EI) $C_{30}H_{25}N_5O_7S$: 600 (MH$^+$).

Example 399

N-(3-(N-(3-(3,5-dimethoxyphenylamino)quinoxalin-2-yl)sulfamoyl)phenyl)-2-(m-tolyloxy)acetamide

MS (EI) $C_{31}H_{29}N_5O_6S$: 600 (MH$^+$).

Example 400

N-(3-(N-(3-(3,5-dimethoxyphenylamino)quinoxalin-2-yl)sulfamoyl)phenyl)-2-(4-methoxyphenyl)acetamide

MS (EI) $C_{31}H_{29}N_5O_6S$: 600 (MH$^+$).

Example 401

N-(3-(N-(3-(3,5-dimethoxyphenylamino)quinoxalin-2-yl)sulfamoyl)phenyl)-2-(2-methoxyphenyl)acetamide

MS (EI) $C_{31}H_{29}N_5O_6S$: 600 (MH$^+$).

Example 402

N-(3-(N-(3-(3,5-dimethoxyphenylamino)quinoxalin-2-yl)sulfamoyl)phenyl)-2-(3-methoxyphenyl)acetamide

MS (EI) $C_{31}H_{29}N_5O_6S$: 600 (MH$^+$).

Example 403

N-(3-(N-(3-(3,5-dimethoxyphenylamino)quinoxalin-2-yl)sulfamoyl)phenyl)-2-methoxy-4-methylbenzamide

MS (EI) $C_{31}H_{29}N_5O_6S$: 600 (MH$^+$).

Example 404

N-(3-(N-(3-(3,5-dimethoxyphenylamino)quinoxalin-2-yl)sulfamoyl)phenyl)-3-fluoro-4-methoxybenzamide

MS (EI) $C_{30}H_{26}FN_5O_6S$: 604 (MH$^+$).

Example 405

N-(3-(N-(3-(3,5-dimethoxyphenylamino)quinoxalin-2-yl)sulfamoyl)phenyl)-2-fluoro-6-methoxybenzamide

MS (EI) $C_{30}H_{26}FN_5O_6S$: 604 (MH$^+$).

Example 406

N-(3-(N-(3-(3,5-dimethoxyphenylamino)quinoxalin-2-yl)sulfamoyl)phenyl)-3-(4-methoxyphenyl)propanamide

MS (EI) $C_{32}H_{31}N_5O_6S$: 614 (MH$^+$).

Example 407

N-(3-(N-(3-(3,5-dimethoxyphenylamino)quinoxalin-2-yl)sulfamoyl)phenyl)-3-(2-methoxyphenyl)propanamide

MS (EI) $C_{32}H_{31}N_5O_6S$: 614 (MH$^+$).

Example 408

N-(3-(N-(3-(3,5-dimethoxyphenylamino)quinoxalin-2-yl)sulfamoyl)phenyl)-3-(3-methoxyphenyl)propanamide

MS (EI) $C_{32}H_{31}N_5O_6S$: 614 (MH$^+$).

General Library Acylation Procedure 2a

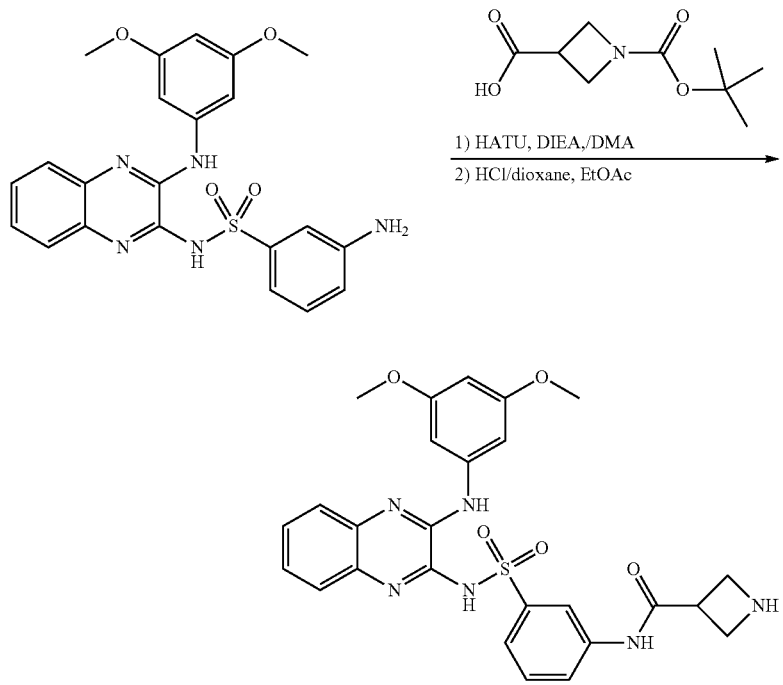 [SMILES: COc1cc(Nc2nc3ccccc3nc2NS(=O)(=O)c2cccc(N)c2)cc(OC)c1 ; CC(C)(C)OC(=O)N1CC(C(=O)O)C1 ; COc1cc(Nc2nc3ccccc3nc2NS(=O)(=O)c2cccc(NC(=O)C3CNC3)c2)cc(OC)c1]

Into a 20 mL vial was added 3-amino-N-(3-(3,5-dimethoxyphenylamino)quinoxalin-2-yl)benzenesulfonamide (0.24 mmol, 1 equiv), DMA (5 mL) and 1-(tert-butoxycarbonyl)azetidine-3-carboxylic acid (0.336 mmol, 1.4 equiv). Hunig's Base (0.792 mmol, 3.3 equiv) and HATU (0.288 mmol, 1.2 equiv) were added to the vial and the reaction mixture was then stirred at room temperature overnight. Completion of the reaction was indicated by LCMS. The solvent was removed by rotary evaporation. The crude mixture was carried forward without further purification. The residue was suspended in 5 mL ethyl acetate and chilled in an ice bath. A solution of 4 N HCl in dioxane (3 mL, 5 equiv) was added with stirring. The reaction mixture was then stirred at room temperature overnight. The solid materials were collected by filtration, washed with ethylacetate then purified further by preparative reverse-phase HPLC (ammonium acetate/ACN). A Waters Fractionlynx preparative reverse-phase HPLC; equipped with a Waters SunFire Prep C18, OCD 5 □M, 30×70 mm column and running a 5-100% gradient with a binary solvent system of 25 mM ammonium acetate in water/acetonitrile; was used to carry out the purification.

The following title compounds were prepared according to General Library Acylation Procedure 2a Example 409

N-(3-(N-(3-(3,5-dimethoxyphenylamino)quinoxalin-2-yl)sulfamoyl)phenyl)azetidine-3-carboxamide $^1$H-NMR (400 MHz, d$_6$-DMSO): 10.26 (s, 1H), 8.81 (s, 1H), 8.25 (t, 1H), 8.14 (s, 1H), 7.74 (d, 1H), 7.69 (d, 1H), 7.41-7.39 (m, 1H), 7.36 (d, 1H), 7.32 (d, 2H), 7.30-7.28 (dd, 1H), 7.14-7.11 (m, 2H), 6.14 (t, 1H), 4.09 (d, 4H), 3.78 (s, 6H); MS (EI) C$_{26}$H$_{26}$N$_6$O$_5$S: 535.6 (MH$^+$).

Procedure 3:
N-(3-chloroquinoxalin-2-yl)benzenesulfonamide

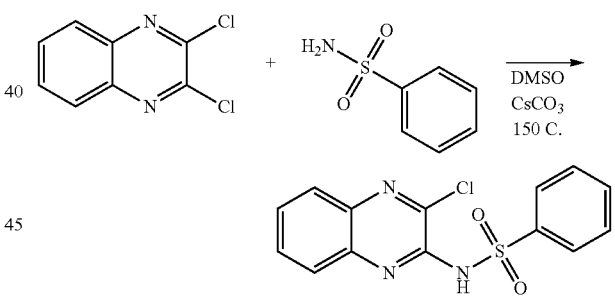

A flask was charged with 2,3-dichloroquinoxaline (3.5 g, 18 mmol), 85 mL of dimethylsulfoxide, benzene sulfonamide (2.8 g, 18 mmol), and cesium carbonate (5.8 g, 18 mmol). The reaction mixture was stirred under an N2 atmosphere for 15 h at 150° C., after which time, it was transferred to a separatory funnel and 100 mL of water were added. Concentrated HCl was then added in order to acidify the reaction mixture to pH<2. The aqueous layer was subsequently washed three times with 90 mL ethyl acetate. The ethyl acetate layers were then washed two times with 150 mL water, three times with 100 mL brine and then dried over sodium sulfate. The ethyl acetate was removed on a rotary-evaporator. A slurry was formed by adding ethyl acetate and dichloromethane to the dried crude product, filtration yielded N-(3-chloroquinoxalin-2-yl)benzenesulfonamide which was submitted to the next step without further purification. MS (EI) C$_{14}$H$_{10}$ClN$_3$O$_2$S: 319.9 (MH+)$^+$.

Example 410

N-(3-(4-fluorophenylamino)quinoxalin-2-yl)benzenesulfonamide

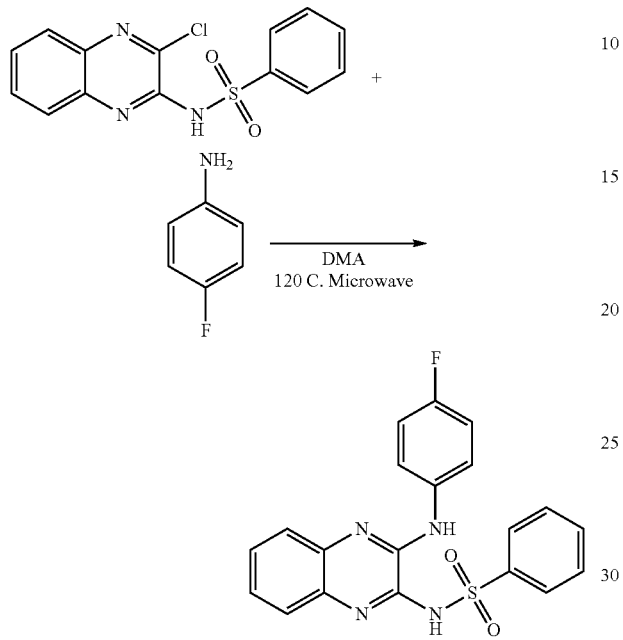

A CEM microwave reaction vessel was charged with N-(3-chloroquinoxalin-2-yl)benzenesulfonamide (52 mg, 0.16 mmol), 4-fluoroaniline (36 mg, 0.32 mmol), and 0.8 mL of dimethylacetamide. The vessel was sealed and the reaction mixture was heated under microwave radiation for 25 m at 120° C. in a CEM Discover microwave instrument. Methanol (1 mL) was added to the reaction mixture and after 20 minutes the product precipitated out of the solution. Filtration yielded 39 mg (62%) of N-(3-(4-fluorophenylamino)quinoxalin-2-yl)benzenesulfonamide. $^1$H-NMR (400 MHz, $d_6$-DMSO): δ 12.30 (s, 1H), 9.11 (s, 1H), 8.16-8.10 (d, 2H), 8.02-7.90 (m, 3H), 7.68-7.58 (m, 3H), 7.55-7.51 (m, 1H), 7.41-7.32 (m, 2H), 7.25-7.16 (m, 2H); MS (EI) $C_{20}H_{15}FN_4O_2S$: 395.0 (MH$^+$).

Procedure 4:
2-(dimethylamino)-N-(3-sulfamoylphenyl)acetamide

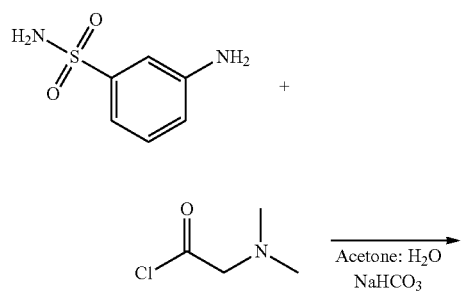

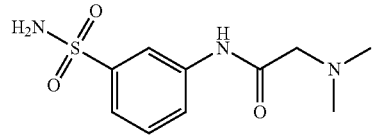

A flask was charged with 3-aminobenzene sulfonamide (3.3 g, 19 mmol), and 20 mL of 1:1 acetone:H$_2$O. The solution was stirred at room temperature until the aminobenzene sulfonamide had dissolved. The flask was then cooled in an ice bath and dimethylamino-acetyl chloride HCl (4.6 g, 29 mmol) was added. To the resulting slurry sodium bicarbonate (4.8 g, 57 mmol) was added over a 15 m period. After 30 min the reaction was removed from the ice bath and allowed to stir at room temperature for 15 h. The reaction mixture was then filtered and washed with methanol and acetonitrile. The filtrate was dried on a rotary evaporator to yield 2-(dimetyhlamino)-N-(3-sulfamoylphenyl)acetamide, which was submitted to the next step without further purification. MS (EI) $C_{10}H_{15}N_3O_3S$: 258.0 (MH+).

Example 411

N-(3-(N-(3-chloroquinoxalin-2-yl)sulfamoyl)phenyl)-2-(dimethylamino)acetamide

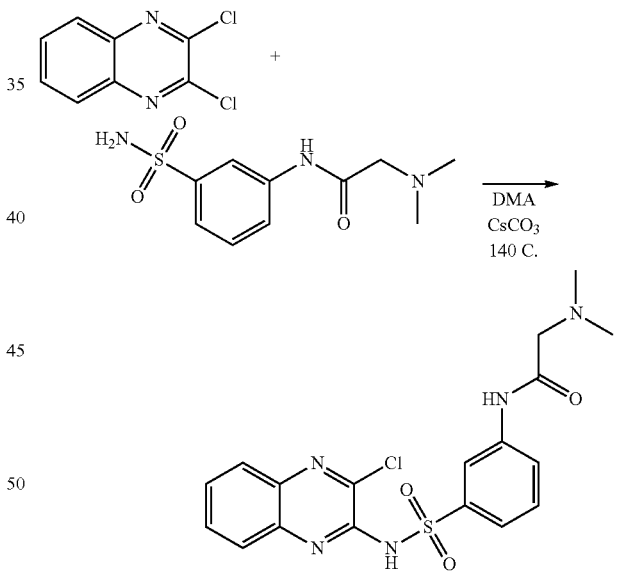

A flask was charged with dichloroquinozaline (1.0 g, 5.8 mmol), 10 mL of dimethylacetamide, 2-(dimetyhlamino)-N-(3-sulfamoylphenyl)acetamide (0.70 g, 2.7 mmol), and cesium carbonate (1.8 g, 5.5 mmol). The reaction mixture was stirred for 3 h at 140° C. and then filtered. The solvent was evaporated from the filtrate on a rotary-evaporator to yield (N-(3-(N-(3-chloroquinoxalin-2-yl)sulfamoyl)phenyl)-2-(dimethylamino)acetamide) which was submitted to the next step without further purification. MS (EI) $C_{18}H_{18}ClN_5O_3S$: 420.0 (MH+).

Two similar procedures were then used to conduct the general reaction shown.

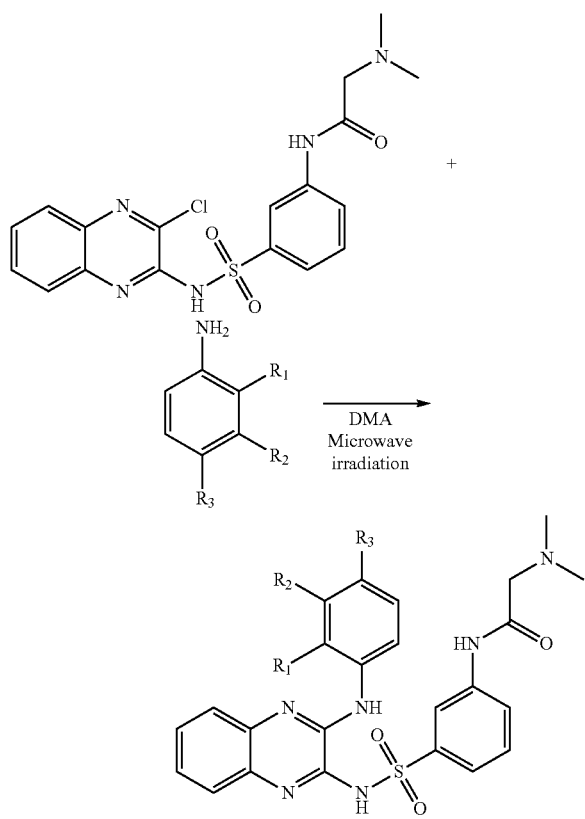

A CEM microwave reaction vessel was charged with N-(3-(N-(3-chloroquinoxalin-2-yl)sulfamoyl)phenyl)-2-(dimethylamino)acetamide (30 mg, 0.071 mmol), the desired aniline (16 mg, 0.14 mmol, 2 eq), and 0.5 mL of Dimethylacetamide. The vessel was sealed and the reaction mixture was heated under microwave radiation for 70 min at 140° C. in a CEM Discover microwave instrument. The solvent was then removed by rotary-evaporation. Purification of the final product was accomplished by preparatory reverse-phase HPLC with the eluents 25 mM aqueous NH$_4$OAc/ACN to yield 2-(dimethylamino)-N-(3-(N-(3-(3-fluorophenylamino)quinoxalin-2-yl)sulfamoyl)phenyl)acetamide.

The following compounds were prepared according to the above Examples.

Example 412

2-(dimethylamino)-N-(3-(N-(3-(3-fluorophenylamino)quinoxalin-2-yl)sulfamoyl)phenyl)acetamide 2-(dimethylamino)-N-(3-(N-(3-(3-fluorophenylamino)quinoxalin-2-yl)sulfamoyl)phenyl)acetamide. $^1$H-NMR (400 MHz, CDCl$_3$): 9.40 ppm (s, 1H), 8.43 ppm (s, 1H), 822 ppm (s, 1H), 8.07-8.02 ppm (d, 1H), 7.97-7.93 ppm (d, 1H), 7.76-7.71 ppm (m, 2H), 7.53-7.48 ppm (t, 1H), 7.45-7.36 ppm (m, 4H), 7.35-7.28 ppm (m, 2H), 6.84-6.77 ppm (t, 1H), 3.10 ppm (s, 2H), 2.38 ppm (s, 6H); MS (EI) C$_{24}$H$_{23}$FN$_6$O$_3$S: 495 (MH$^+$).

Example 413

2-(dimethylamino)-N-(3-(N-(3-(4-fluorophenylamino)quinoxalin-2-yl)sulfamoyl)phenyl)acetamide

MS (EI) C$_{24}$H$_{23}$FN$_6$O$_3$S: 495 (MH$^+$).

Example 414

2-(dimethylamino)-N-(3-(N-(3-(4-methoxyphenylamino)quinoxalin-2-yl)sulfamoyl)phenyl)acetamide

MS (EI) C$_{25}$H$_{26}$N$_6$O$_4$S: 507 (MH$^+$).

Example 415

N-(3-(N-(3-(4-chlorophenylamino)quinoxalin-2-yl)sulfamoyl)phenyl)-2-(dimethylamino)acetamide MS (EI) C$_{24}$H$_{23}$ClN$_6$O$_3$S: 511 (MH$^+$).

Example 416

N-(3-(N-(3-(3-chlorophenylamino)quinoxalin-2-yl)sulfamoyl)phenyl)-2-(dimethylamino)acetamide MS (EI) C$_{24}$H$_{23}$ClN$_6$O$_3$S: 511 (MH$^+$)

A CEM microwave reaction vessel was charged with N-(3-(N-(3-chloroquinoxalin-2-yl)sulfamoyl)phenyl)-2-(dimethylamino)acetamide (62 mg, 0.147 mmol), the desired aniline (0.567 mmol, 4 eq), and 1.0 mL of toluene. The vessel was sealed and the reaction mixture was heated under microwave radiation for 60 min at 180° C. in a CEM Discover microwave instrument. The solvent was removed on a rotary-evaporator. Purification of the final product was done by preparatory HPLC with NH$_4$OAc/ACN as eluent to yield 2-(dimethylamino)-N-(3-(N-(3-(4-fluoro-3-methoxyphenylamino)quinoxalin-2-yl)sulfamoyl)phenyl).

The following compounds were prepared according to the above Examples.

Example 417

2-(dimethylamino)-N-(3-(N-(3-(4-fluoro-3-methoxyphenylamino)quinoxalin-2-yl)sulfamoyl)phenyl)acetamide 2-(dimethylamino)-N-(3-(N-(3-(4-fluoro-3-methoxyphenylamino)quinoxalin-2-yl)sulfamoyl)phenyl). $^1$H-NMR (400 MHz, CDCl$_3$): δ 9.47 (s, 1H), 8.36 (s, 1H), 8.29 (s, 1H), 7.91-7.87 (d, 1H), 7.80-7.73 (m, 2H), 7.66-7.63 (d, 1H), 7.53-7.47 (t, 1H), 7.43-7.30 (m, 4H), 7.10-7.04 (t, 1H), 6.55-5.95 (br s, 1H), 3.96 (s, 3H), 3.12 (s, 2H), 2.39 (s, 6H), 2.08 (s, 3H(AcOH); MS (EI) C$_{25}$H$_{25}$FN$_6$O$_4$S: 525 (MH$^+$).

Example 418

2-(dimethylamino)-N-(3-(N-(3-(4-fluoro-3-methylphenylamino)quinoxalin-2-yl)sulfamoyl)phenyl)acetamide

MS (EI) C$_{25}$H$_{25}$FN$_6$O$_3$S: 509 (MH$^+$).

Example 419

2-(dimethylamino)-N-(3-(N-(3-(3,5-dimethylphenylamino)quinoxalin-2-yl)sulfamoyl)phenyl)acetamide

MS (EI) C$_{26}$H$_{28}$N$_6$O$_3$S: 505 (MH$^+$).

Example 420

N-(3-(N-(3-(2,4-dimethoxyphenylamino)quinoxalin-2-yl)phenyl)-2-(dimethylamino)acetamide

MS (EI) C$_{26}$H$_{28}$N$_6$O$_5$S: 537 (MH$^+$).

Example 421

N-(3-(N-(3-(2,3-dihydro-1H-inden-5-ylamino)quinoxalin-2-yl)sulfamoyl)phenyl)-2-(dimethylamino)acetamide

MS (EI) $C_{27}H_{28}N_6O_3S$: 517 (MH$^+$).

Example 422

Procedure 5

N-(3-(3,5-dimethoxyphenylamino)quinoxalin-2-yl)-4-isopropoxybenzenesulfonamide

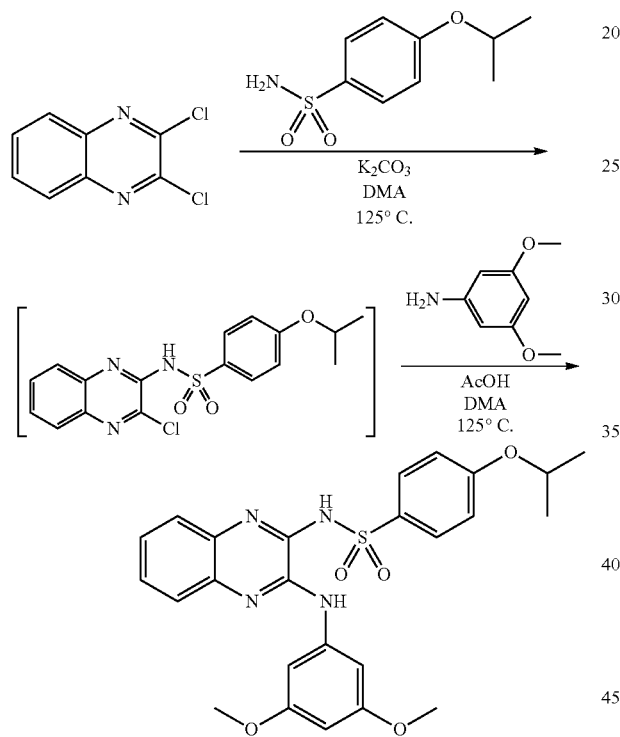

N-(3-(3,5-dimethoxyphenylamino)quinoxalin-2-yl)-4-isopropoxybenzenesulfonamide: A solution of 2,3-dichloroquinoxaline (2.0 mL, 0.38 M) was combined with K$_2$CO$_3$ (105 mg, 0.76 mmol) in a glass vial. A solution of 4-isopropoxybenzene sulfonamide (1.75 mL, 0.43 M) was added and the solution was stirred overnight at 125° C. After cooling, acetic acid (45 mL, 0.79 mmol) and 3,5-dimethoxyaniline (230 mg, 1.5 mmol) were added. The reaction mixture was stirred again at 125° C. overnight. Upon cooling, the reaction mixture was diluted with 8 mL of methanol and then 8 mL of water. The precipitate was collected by filtration and recrystallized from N,N-dimethylacetamide/water to give 45 mg of product. $^1$H-NMR (400 MHz, d$_6$-DMSO): 12.16 (bs, 1H), 8.93 (s, 1H), 8.03 (d, 2H), 7.92 (bs, 1H), 7.56 (d, 1H), 7.36 (m, 4H), 7.07 (d, 2H), 6.24 (s, 1H), 4.72 (m, 1H), 3.76 (s, 6H), 1.27 (d, 6H); MS (EI) $C_{25}H_{26}N_4O_5S$: 495 (MH$^+$).

The remaining examples were synthesized in similar fashion. In the cases where the product did not precipitate, the mixture was purified by reverse phase HPLC.

Example 423

3-chloro-N-(3-(3,5-dimethoxyphenylamino)quinoxalin-2-yl)-4-methylbenzenesulfonamide $^1$H-NMR (400 MHz, d$_6$-DMSO): 12.31 (bs, 1H), 8.96 (s, 1H), 8.18 (s, 1H), 7.98 (d, 1H), 7.92 (bs, 1H), 7.58 (d, 2H), 7.43-7.33 (m, 4H), 6.24 (t, 1H), 3.76 (s, 6H), 2.39 (s, 3H); MS (EI) $C_{23}H_{21}ClN_4O_4S$: 485 (MH$^+$).

Example 424

N-(3-(3,5-dimethoxyphenylamino)quinoxalin-2-yl)naphthalene-1-sulfonamide

MS (EI) $C_{26}H_{22}N_4O_4S$: 487 (MH$^+$).

Example 425

N-(3-(3,5-dimethoxyphenylamino)quinoxalin-2-yl)-4-fluorobenzenesulfonamide

MS (EI) $C_{22}H_{19}FN_4O_4S$: 455 (MH$^+$).

Example 426

N-(3-(3,5-dimethoxyphenylamino)quinoxalin-2-yl)-3-fluorobenzenesulfonamide

MS (EI) $C_{22}H_{19}FN_4O_4S$: 455 (MH$^+$).

Example 427

N-(3-(3,5-dimethoxyphenylamino)quinoxalin-2-yl)-3-(trifluoromethyl)benzenesulfonamide

MS (EI) $C_{23}H_{19}F_3N_4O_4S$: 505 (MH$^+$).

Example 428

N-(3-(3,5-dimethoxyphenylamino)quinoxalin-2-yl)-4-(trifluoromethyl)benzenesulfonamide

MS (EI) $C_{23}H_{19}F_3N_4O_4S$: 505 (MH$^+$).

Example 429

2-cyano-N-(3-(3,5-dimethoxyphenylamino)quinoxalin-2-yl)benzenesulfonamide

MS (EI) $C_{23}H_{19}N_5O_4S$: 462 (MH$^+$).

Example 430

N-(3-(3,5-dimethoxyphenylamino)quinoxalin-2-yl)-4-(trifluoromethoxy)benzenesulfonamide

MS (EI) $C_{23}H_{19}F_3N_4O_5S$: 521 (MH$^+$).

Example 431

N-(4-(N-(3-(3,5-dimethoxyphenylamino)quinoxalin-2-yl)sulfamoyl)phenyl)acetamide

MS (EI) $C_{24}H_{23}N_5O_5S$: 494 (MH$^+$).

Example 432

N-(3-(3,5-dimethoxyphenylamino)quinoxalin-2-yl)-4-fluoro-2-methylbenzenesulfonamide

MS (EI) $C_{23}H_{21}FN_4O_4S$: 469 (MH$^+$).

Example 433

N-(3-(3,5-dimethoxyphenylamino)quinoxalin-2-yl)-2-methylbenzenesulfonamide

MS (EI) $C_{23}H_{22}N_4O_4S$: 451 (MH$^+$).

Example 434

2-chloro-N-(3-(3,5-dimethoxyphenylamino)quinoxalin-2-yl)benzenesulfonamide

MS (EI) $C_{22}H_{19}ClN_4O_4S$: 471 (MH$^+$).

Example 435

N-(3-(3,5-dimethoxyphenylamino)quinoxalin-2-yl)-3,5-difluorobenzenesulfonamide

MS (EI) $C_{22}H_{18}F_2N_4O_4S$: 473 (MH$^+$).

Example 436

3,5-dichloro-N-(3-(3,5-dimethoxyphenylamino)quinoxalin-2-yl)benzenesulfonamide

MS (EI) $C_{22}H_{18}Cl_2N_4O_4S$: 505 (MH$^+$).

Example 437

N-(3-(3,5-dimethoxyphenylamino)quinoxalin-2-yl)-3-fluoro-4-methylbenzenesulfonamide

MS (EI) $C_{23}H_{21}FN_4O_4S$: 469 (MH$^+$).

Example 438

N-(3-(3,5-dimethoxyphenylamino)quinoxalin-2-yl)-2-(trifluoromethyl)benzenesulfonamide

MS (EI) $C_{23}H_{19}F_3N_4O_4S$: 505 (MH$^+$).

Example 439

4-cyano-N-(3-(3,5-dimethoxyphenylamino)quinoxalin-2-yl)benzenesulfonamide

MS (EI) $C_{23}H_{19}N_5O_4S$: 462 (MH$^+$).

Example 440

N-(3-(3,5-dimethoxyphenylamino)quinoxalin-2-yl)-1-phenylmethanesulfonamide

MS (EI) $C_{23}H_{22}N_4O_4S$: 451 (MH$^+$).

Example 441

4,5-dichloro-N-(3-(3,5-dimethoxyphenylamino)quinoxalin-2-yl)thiophene-2-sulfonamide MS (EI) $C_{20}H_{16}Cl_2N_4O_4S_2$: 511 (MH$^+$).

Example 442

1-(3-chlorophenyl)-N-(3-(3,5-dimethoxyphenylamino)quinoxalin-2-yl)methanesulfonamide MS (EI) $C_{23}H_{21}ClN_4O_4S$: 485 (MH$^+$).

Example 443

N-(3-(3,5-dimethoxyphenylamino)quinoxalin-2-yl)-2,5-dimethylthiophene-3-sulfonamide

MS (EI) $C_{22}H_{22}N_4O_4S_2$: 471 (MH$^+$).

Example 444

N-(3-(3,5-dimethoxyphenylamino)quinoxalin-2-yl)-3,5-bis(trifluoromethyl)benzenesulfonamide

MS (EI) $C_{24}H_{18}F_6N_4O_4S$: 573 (MH$^+$).

Example 445

N-(3-(3,5-dimethoxyphenylamino)quinoxalin-2-yl)-4-fluoro-3-(trifluoromethyl)benzenesulfonamide

MS (EI) $C_{23}H_{18}F_4N_4O_4S$: 523 (MH$^+$).

Example 446

5-chloro-N-(3-(3,5-dimethoxyphenylamino)quinoxalin-2-yl)-1,3-dimethyl-1H-pyrazole-4-sulfonamide MS (EI) $C_{21}H_{21}ClN_6O_4S$: 489 (MH$^+$).

Example 447

5-chloro-N-(3-(3,5-dimethoxyphenylamino)quinoxalin-2-yl)-2-methoxybenzenesulfonamide MS (EI) $C_{23}H_{21}ClN_4O_5S$: 501 (MH$^+$).

Example 448

5-bromo-N-(3-(3,5-dimethoxyphenylamino)quinoxalin-2-yl)-2-methoxybenzenesulfonamide MS (EI) $C_{23}H_{21}BrN_4O_5S$: 545 (MH$^+$).

Example 449

2,5-dichloro-N-(3-(3,5-dimethoxyphenylamino)quinoxalin-2-yl)thiophene-3-sulfonamide

MS (EI) $C_{20}H_{16}C_{12}N_4O_4S_2$: 511 (MH$^+$).

Example 450

N-(3-(3,5-dimethoxyphenylamino)quinoxalin-2-yl)-3,5-dimethylisoxazole-4-sulfonamide

MS (EI) $C_{21}H_{21}N_5O_5S$: 456 (MH$^+$).

Example 451

N-(3-(3,5-dimethoxyphenylamino)quinoxalin-2-yl)-2,5-dimethoxybenzenesulfonamide

MS (EI) $C_{24}H_{24}N_4O_6S$: 497 (MH$^+$).

Example 452

3-chloro-N-(3-(3,5-dimethoxyphenylamino)quinoxalin-2-yl)-4-fluorobenzenesulfonamide MS (EI) $C_{22}H_{18}ClFN_4O_4S$: 489 (MH$^+$).

Example 453

N-(3-(3,5-dimethoxyphenylamino)quinoxalin-2-yl) biphenyl-4-sulfonamide

MS (EI) $C_{28}H_{24}N_4O_4S$: 513 (MH$^+$).

Example 454

4-(difluoromethoxy)-N-(3-(3,5-dimethoxyphenylamino)quinoxalin-2-yl)benzenesulfonamide

MS (EI) $C_{23}H_{20}F_2N_4O_5S$: 503 (MH$^+$).

Example 455

N-(3-(3,5-dimethoxyphenylamino)quinoxalin-2-yl)-3-(methylsulfonyl)benzenesulfonamide

MS (EI) $C_{23}H_{22}N_4O_6S_2$: 515 (MH$^+$).

General Procedure 6

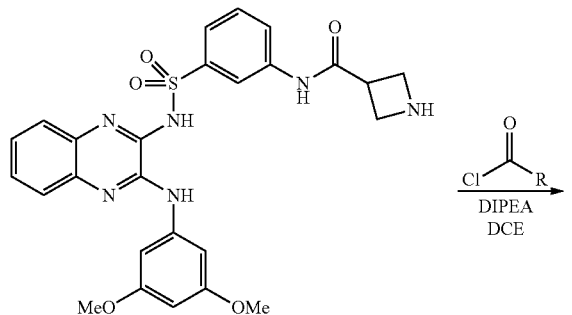

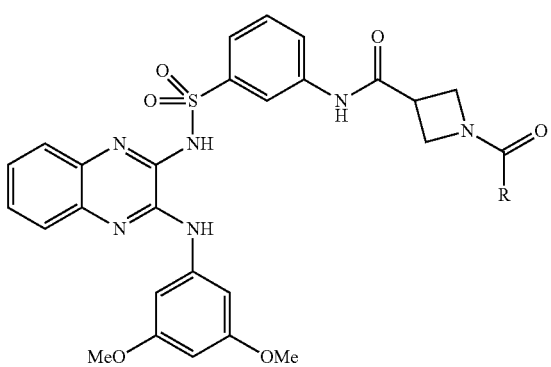

N-(3-(N-(3-(3,5-dimethoxyphenylamino)quinoxalin-2-yl)sulfamoyl)phenyl)azetidine-3-carboxamide (125 mg, 0.23 mmol) was dissolved into 5 mL DCE in a 10 mL round-bottom flask. DIPEA (1.17 mmol, 5.0 eq.) was then added with stirring followed by acid chloride (0.47 mmol, 2.0 eq.). The reaction was then stirred at room temperature for 1 hour or until complete as indicated by LCMS. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC; equipped with a Waters SunFire Prep C18, OCD 5 □M, 30×70 mm column and running a 5-100% gradient with a binary solvent system of 25 mM ammonium acetate in water/acetonitrile; was used to carry out the purification.

The following title compounds were prepared according to General Procedure 6.

Example 456

N-(3-(N-(3-(3,5-dimethoxyphenylamino)quinoxalin-2-yl)sulfamoyl)phenyl)-1-propionylazetidine-3-carboxamide $^1$H-NMR (400 MHz, d$_6$-DMSO): 12.40 (s, 1H), 10.45 (s, 1H), 8.88 (s, 1H), 8.40 (s, 1H), 7.93 (s, 1H), 7.82 (d, 1H), 7.77 (d, 1H), 7.60-7.45 (m, 2H), 7.41-7.30 (m, 4H), 6.24 (s, 1H), 4.26 (t, 1H), 4.22-4.17 (m, 1H), 3.99 (t, 1H), 3.95-3.89 (m, 1H), 3.76 (s, 6H), 3.59-3.45 (m, 1H), 2.05 (dd, 2H), 0.95 (t, 3H); MS (EI) $C_{29}H_{30}N_6O_6S$: 591 (MH$^+$).

Example 457

1-acetyl-N-(3-{[(3-{[3,5-bis(methyloxy)phenyl]amino}quinoxalin-2-yl)amino]sulfonyl}phenyl)azetidine-3-carboxamide

MS (EI) $C_{28}H_{28}N_6O_6S$: 577 (MH$^+$).

Example 458

1-(cyclopropanecarbonyl)-N-(3-(N-(3-(3,5-dimethoxyphenylamino)quinoxalin-2-yl)sulfamoyl)phenyl)azetidine-3-carboxamide

MS (EI) $C_{30}H_{30}N_6O_6S$: 603 (MH$^+$).

General Procedure 7

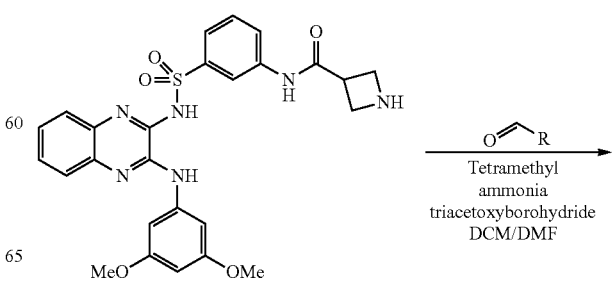

-continued

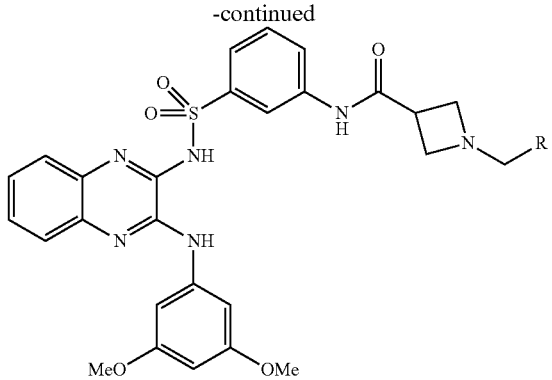

To a solution of N-(3-(N-(3-(3,5-dimethoxyphenylamino)quinoxalin-2-yl)sulfamoyl)phenyl)azetidine-3-carboxamide (110 mg, 0.19 mmol) in 3 mL of DCE and 200 μL of DMF, aldehyde (0.77 mmol, 4.0 eq.)was added slowly followed by tetramethylammonium triacetoxyborohydride (1.16 mmol, 6.0 eq). The reaction was stirred at room temperature overnight. LC/MS indicated the reaction was completed. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC; equipped with a Waters SunFire Prep C18, OCD 5 □M, 30×70 mm column and running a 5-100% gradient with a binary solvent system of 25 mM ammonium acetate in water/acetonitrile; was used to carry out the purification.

The following title compounds were prepared according to General Procedure 7.

Example 459

N-(3-(N-(3-(3,5-dimethoxyphenylamino)quinoxalin-2-yl)sulfamoyl)phenyl)-1-ethylazetidine-3-carboxamide $^1$H-NMR (400 MHz, d$_6$-DMSO): 10.29 (s, 1H), 8.82 (s, 1H), 8.25 (t, 1H), 7.75-7.68 (m, 2H), 7.43-7.38 (m, 1H), 7.375-7.340 (m, 1H), 7.338-7.310 (d, 2H), 7.305-7.262 (m, 1H), 7.15-7.08 (m, 2H), 6.56 (s, 1H), 6.15 (t, 1H), 4.15-4.08 (m, 2H), 4.06-3.95 (m, 2H), 3.78 (s, 6H), 3.65-3.56 (m, 1H), 3.12-3.04 (m, 2H), 1.03 (t, 3H); MS (EI) C$_{28}$H$_{30}$N$_6$O$_5$S: 563 (MH$^+$).

Example 460

1-(cyclopropylmethyl)-N-(3-(N-(3-(3,5-dimethoxyphenylamino)quinoxalin-2-yl)sulfamoyl)phenyl)azetidine-3-carboxamide

MS (EI) C$_{30}$H$_{32}$N$_6$O$_5$S: 589 (MH$^+$).

Example 461

1-benzyl-N-(3-(N-(3-(3,5-dimethoxyphenylamino)quinoxalin-2-yl)sulfamoyl)phenyl)azetidine-3-carboxamide

MS (EI) C$_{33}$H$_{32}$N$_6$O$_5$S: 625 (MH$^+$).

Example 462

N-(3-(N-(3-(3,5-dimethoxyphenylamino)quinoxalin-2-yl)sulfamoyl)phenyl)-1-(furan-2-ylmethyl)azetidine-3-carboxamide

MS (EI) C$_{31}$H$_{30}$N$_6$O$_6$S: 615 (MH$^+$).

Example 463

1-((1H-imidazol-5-yl)methyl)-N-(3-(N-(3-(3,5-dimethoxyphenylamino)quinoxalin-2-yl)sulfamoyl)phenyl)azetidine-3-carboxamide

MS (EI) C$_{30}$H$_{30}$N$_8$O$_5$S: 615 (MH$^+$).

General Library Procedure 8

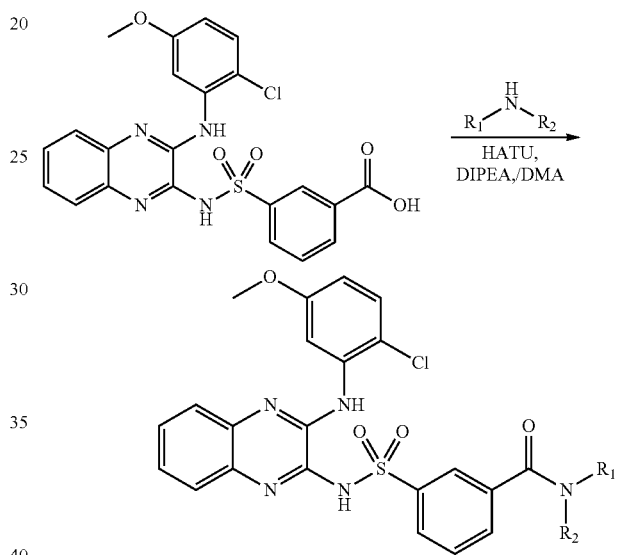

Into a small 1 dram vial was added 3-(N-(3-(2-chloro-5-methoxyphenylamino)quinoxalin-2-yl)sulfamoyl)benzoic acid (61 mg, 0.13 mmol, 1.1 equiv). The acid was dissolved in 1 mL of DMA and DIPEA (42 uL, 0.24 mMol, 2 equiv) was added then added to the solution. The amine reagent (1 mL of 0.12 M solution in DMA) was added to solution with stirring followed by HATU (64 mg, 0.17 mMol, 1.4 equiv). Reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

The following compounds were prepared according to General Library Procedure 8.

Example 464

3-(N-(3-(2-chloro-5-methoxyphenylamino)quinoxalin-2-yl)sulfamoyl)-N-(3-(dimethylamino)propyl)benzamide 3-(N-(3-(2-chloro-5-methoxyphenylamino)quinoxalin-2-yl)sulfamoyl)-N-(3-(dimethylamino)propyl)benzamide: 1H NMR (400 MHz, d$_6$-DMSO): 9.44 (s, 1H), 8.94 (s, 1H), 8.79 (t, 1H), 8.54 (s, 1H), 8.24 (d, 1H), 7.87 (d, 1H), 7.48 (m, 3H), 7.33 (d, 1H), 7.18 (m, 2H), 6.60 (dd, 1H), 3.82 (1H), 3.04 (m, 3H), 2.51 (m, 5H), 1.91 (s, 1H), 1.86 (m, 3H); MS (EI) for C$_{27}$H$_{29}$ClN$_6$O$_4$S: 569 (MH$^+$).

Example 465

3-(N-(3-(2-chloro-5-methoxyphenylamino)quinoxalin-2-yl)sulfamoyl)-N-(1-methylazetidin-3-yl)benzamide 3-(N-(3-(2-chloro-5-methoxyphenylamino)quinoxalin-2-yl)sulfamoyl)-N-(1-methylazetidin-3-yl)benzamide: $^1$H NMR (400 MHz, d$_6$-DMSO): 9.43 (s, 1H), 9.23 (d, 1H), 8.94 (d, 1H), 8.58 (s, 1H), 8.29 (d, 1H), 7.89 (d, 1H), 7.56 (t, 1H), 7.47 (d, 1H), 7.44 (d, 1H), 7.33 (d, 1H), 7.18 (m, 2H), 6.60 (dd, 1H), 4.81 (m, 1H), 4.33 (m, 2H), 4.19 (m, 2H), 3.82 (s, 1H), 2.51 (s, 3H); MS (EI) for C$_{26}$H$_{25}$ClN$_6$O$_4$S: 553 (MH$^+$).

Example 466

3-(N-(3-(2-chloro-5-methoxyphenylamino)quinoxalin-2-yl)sulfamoyl)-N-(Pyridin-4-ylmethyl)benzamide MS (EI) C$_{28}$H$_{23}$ClN$_6$O$_4$S: 575 (MH$^+$).

Example 467

3-(N-(3-(2-chloro-5-methoxyphenylamino)quinoxalin-2-yl)sulfamoyl)-N-(3-(dimethylamino)propyl)benzamide MS (EI) C$_{28}$H$_{26}$ClN$_7$O$_4$S: 592 (MH$^+$).

Example 468

N-(3-(2-chloro-5-methoxyphenylamino)quinoxalin-2-yl)-3-(2,2-dimethylhydrazinecarbonyl)benzenesulfonamide MS (EI) C$_{24}$H$_{23}$ClN$_6$O$_4$S: 527 (MH$^+$).

Example 469

3-(N-(3-(2-chloro-5-methoxyphenylamino)quinoxalin-2-yl)sulfamoyl)-N-(2-methoxyethyl)benzamide MS (EI) C$_{25}$H$_{24}$ClN$_5$O$_5$S: 542 (MH$^+$).

Example 470

N-(3-(2-chloro-5-methoxyphenylamino)quinoxalin-2-yl)-3-(4-methylpiperazine-1-carbonyl)benzenesulfonamide MS (EI) C$_{27}$H$_{27}$ClN$_6$O$_4$S: 567 (MH$^+$).

Example 471

3-(N-(3-(2-chloro-5-methoxyphenylamino)quinoxalin-2-yl)sulfamoyl)-N-(2-(pyrrolidin-1-yl)ethyl)benzamide MS (EI) C$_{28}$H$_{29}$ClN$_6$O$_4$S: 581 (MH$^+$).

Example 472

3-(N-(3-(2-chloro-5-methoxyphenylamino)quinoxalin-2-yl)sulfamoyl)-N-(2-(pyridin-4-yl)ethyl)benzamide MS (EI) C$_{29}$H$_{25}$ClN$_6$O$_4$S: 589 (MH$^+$).

Example 473

N-(2-(1H-imidazol-4-yl)ethyl)-3-(N-(3-(2-chloro-5-methoxyphenylamino)quinoxalin-2-yl)sulfamoyl)benzamide MS (EI) C$_{27}$H$_{24}$ClN$_7$O$_4$S: 578 (MH$^+$).

Example 474

3-(N-(3-(2-chloro-5-methoxyphenylamino)quinoxalin-2-yl)sulfamoyl)-N-(piperidin-1-yl)benzamide MS (EI) C$_{27}$H$_{27}$ClN$_6$O$_4$S: 567 (MH$^+$).

Example 475

3-(N-(3-(2-chloro-5-methoxyphenylamino)quinoxalin-2-yl)sulfamoyl)-N-(2-hydroxyethyl)benzamide MS (EI) C$_{24}$H$_{22}$ClN$_5$O$_5$S: 528 (MH$^+$).

Example 476

3-(N-(3-(2-chloro-5-methoxyphenylamino)quinoxalin-2-yl)sulfamoyl)-N-(3-ethoxypropyl)benzamide MS (EI) C$_{27}$H$_{28}$ClN$_5$O$_5$S: 570 (MH$^+$).

Example 477

3-(N-(3-(2-chloro-5-methoxyphenylamino)quinoxalin-2-yl)sulfamoyl)-N-(3-(pyrrolidin-1-yl)propyl)benzamide MS (EI) C$_{29}$H$_3$ClN$_6$O$_4$S: 595 (MH$^+$).

Example 478111

3-(N-(3-(2-chloro-5-methoxyphenylamino)quinoxalin-2-yl)sulfamoyl)-N-(3-(diethylamino)propyl)benzamide MS (EI) C$_{29}$H$_{33}$ClN$_6$O$_4$S: 597 (MH$^+$).

Example 479

3-(N-(3-(2-chloro-5-methoxyphenylamino)quinoxalin-2-yl)sulfamoyl)-N-(3-(2-oxopyrrolidin-1-yl)propyl)benzamide MS (EI) C$_{29}$H$_{29}$ClN$_6$O$_5$S: 609 (MH$^+$).

Example 480

3-(N-(3-(2-chloro-5-methoxyphenylamino)quinoxalin-2-yl)sulfamoyl)-N-(pyridin-2-ylmethyl)benzamide MS (EI) C$_{28}$H$_{23}$ClN$_6$O$_4$S: 575 (MH$^+$).

Example 481

3-(N-(3-(2-chloro-5-methoxyphenylamino)quinoxalin-2-yl)sulfamoyl)-N-(2-cyanoethyl)-N-methylbenzamide MS (EI) $C_{26}H_{23}ClN_6O_4S$: 551 (MH$^+$).

Example 482

3-(N-(3-(2-chloro-5-methoxyphenylamino)quinoxalin-2-yl)sulfamoyl)-N-(2-cyanoethyl)-N-ethylbenzamide MS (EI) $C_{27}H_{25}ClN_6O_4S$: 565 (MH$^+$).

Example 483

3-(N-(3-(2-chloro-5-methoxyphenylamino)quinoxalin-2-yl)sulfamoyl)-N-(2-(ethylthio)ethyl)benzamide MS (EI) $C_{26}H_{26}ClN_5O_4S_2$: 572 (MH$^+$).

Example 484

3-(N-(3-(2-chloro-5-methoxyphenylamino)quinoxalin-2-yl)sulfamoyl)-N-(3-propoxypropyl)benzamide MS (EI) $C_{28}H_{30}ClN_5O_5S$: 584 (MH$^+$).

Example 485

3-(N-(3-(2-chloro-5-methoxyphenylamino)quinoxalin-2-yl)sulfamoyl)-N-(5-(diethylamino)pentan-2-yl)benzamide MS (EI) $C_{31}H_{37}ClN_6O_4S$: 625 (MH$^+$).

Example 486

3-(N-(3-(2-chloro-5-methoxyphenylamino)quinoxalin-2-yl)sulfamoyl)-N-(3-methoxypropyl)benzamide MS (EI) $C_{26}H_{26}ClN_5O_5S$: 556 (MH$^+$).

Example 487

3-(N-(3-(2-chloro-5-methoxyphenylamino)quinoxalin-2-yl)sulfamoyl)-N-(3-morpholinopropyl)benzamide MS (EI) $C_{29}H_{31}ClN_6O_5S$: 611 (MH$^+$).

Example 488

3-(N-(3-(2-chloro-5-methoxyphenylamino)quinoxalin-2-yl)sulfamoyl)-N-(pyridin-3-ylmethyl)benzamide MS (EI) $C_{28}H_{23}ClN_6O_4S$: 575 (MH$^+$).

Example 489

3-(N-(3-(2-chloro-5-methoxyphenylamino)quinoxalin-2-yl)sulfamoyl)-N-(2-cyanoethyl)benzamide MS (EI) $C_{25}H_{21}ClN_6O_4S$: 537 (MH$^+$).

Example 490

3-(N-(3-(2-chloro-5-methoxyphenylamino)quinoxalin-2-yl)sulfamoyl)-N-(1-methoxypropan-2-yl)benzamide MS (EI) $C_{26}H_{26}ClN_5O_5S$: 556 (MH$^+$).

Example 491

3-(N-(3-(2-chloro-5-methoxyphenylamino)quinoxalin-2-yl)sulfamoyl)-N-(2-(methylthio)ethyl)benzamide MS (EI) $C_{25}H_{24}ClN_5O_4S_2$: 558 (MH$^+$).

Example 492

3-(N-(3-(2-chloro-5-methoxyphenylamino)quinoxalin-2-yl)sulfamoyl)-N-(3-(dimethylamino)propyl)-N-methylbenzamide MS (EI) $C_{28}H_{31}ClN_6O_4S$: 583 (MH$^+$).

Example 493

3-(N-(3-(2-chloro-5-methoxyphenylamino)quinoxalin-2-yl)sulfamoyl)-N-(3-isopropoxypropyl)benzamide MS (EI) $C_{28}H_{30}ClN_5O_5S$: 584 (MH$^+$).

Example 494

3-(N-(3-(2-chloro-5-methoxyphenylamino)quinoxalin-2-yl)sulfamoyl)-N-(2-(dimethylamino)ethyl)-N-ethylbenzamide MS (EI) $C_{28}H_{31}ClN_6O_4S$: 583 (MH$^+$).

Example 495

N-(3-butoxypropyl)-3-(N-(3-(2-chloro-5-methoxyphenylamino)quinoxalin-2-yl)sulfamoyl)benzamide MS (EI) $C_{29}H_{32}ClN_5O_5S$: 598 (MH$^+$).

Example 496

3-(N-(3-(2-chloro-5-methoxyphenylamino)quinoxalin-2-yl)sulfamoyl)-N-(2-(diethylamino)ethyl)benzamide MS (EI) $C_{28}H_{31}ClN_6O_4S$: 583 (MH$^+$).

Example 497XEL-04286749 methyl 3-(3-(N-(3-(2-chloro-5-methoxyphenylamino)quinoxalin-2-yl)sulfamoyl)benzamido)propanoate MS (EI) $C_{26}H_{24}ClN_5O_6S$: 570 (MH$^+$).

Example 498

3-(N-(3-(2-chloro-5-methoxyphenylamino)quinoxalin-2-yl)sulfamoyl)-N-methyl-N-propylbenzamide MS (EI) $C_{26}H_{26}ClN_5O_4S$: 540 (MH$^+$).

Example 499 ethyl 3-(3-(N-(3-(2-chloro-5-methoxyphenylamino) quinoxalin-2-yl)sulfamoyl)benzamido)propanoate MS (EI) $C_{27}H_{26}ClN_5O_6S$: 584 (MH$^+$).

Example 500

3-(N-(3-(2-chloro-5-methoxyphenylamino)quinoxalin-2-yl)sulfamoyl)-N-(2-(piperidin-1-yl)ethyl)benzamide MS (EI) $C_{29}H_{31}ClN_6O_4S$: 595 (MH$^+$).

Example 501

3-(N-(3-(2-chloro-5-methoxyphenylamino)quinoxalin-2-yl)sulfamoyl)-N-((1-ethylpyrrolidin-2-yl)methyl)benzamide MS (EI) $C_{29}H_{31}ClN_6O_4S$: 595 (MH$^+$).

Example 502

N-(2-(bis(2-hydroxyethyl)amino)ethyl)-3-(N-(3-(2-chloro-5-methoxyphenylamino)quinoxalin-2-yl)sulfamoyl)benzamide MS (EI) $C_{28}H_{31}ClN_6O_6S$: 615 (MH$^+$).

Example 503

N-(3-(2-chloro-5-methoxyphenylamino)quinoxalin-2-yl)-3-(3-(diethylamino)pyrrolidine-1-carbonyl)benzenesulfonamide MS (EI) $C_{30}H_{33}ClN_6O_4S$: 609 (MH$^+$).

Example 504

3-(N-(3-(2-chloro-5-methoxyphenylamino)quinoxalin-2-yl)sulfamoyl)-N-methyl-N-(1-methylpyrrolidin-3-yl)benzamide MS (EI) $C_{28}H_{29}ClN_6O_4S$: 581 (MH$^+$).

Example 505

N-(3-(2-chloro-5-methoxyphenylamino)quinoxalin-2-yl)-3-(3-(dimethylamino)pyrrolidine-1-carbonyl)benzenesulfonamide MS (EI) $C_{28}H_{29}ClN_6O_4S$: 581 (MH$^+$).

Example 506

3-(N-(3-(2-chloro-5-methoxyphenylamino)quinoxalin-2-yl)sulfamoyl)-N-(2-methyl-1-morpholinopropan-2-yl)benzamide MS (EI) $C_{30}H_{33}ClN_6O_5S$: 625 (MH$^+$).

Example 507

3-(N-(3-(2-chloro-5-methoxyphenylamino)quinoxalin-2-yl)sulfamoyl)-N-(1H-pyrrol-1-yl)benzamide MS (EI) $C_{26}H_{21}ClN_6O_4S$: 549 (MH$^+$).

Example 508

3-(N-(3-(2-chloro-5-methoxyphenylamino)quinoxalin-2-yl)sulfamoyl)-N-(3-oxopyrazolidin-4-yl)benzamide MS (EI) $C_{25}H_{22}ClN_7O_5S$: 568 (MH$^+$).

Example 509

N-(3-(2-chloro-5-methoxyphenylamino)quinoxalin-2-yl)-3-(2-((dimethylamino)methyl)piperidine-1-carbonyl)benzenesulfonamide MS (EI) $C_{30}H_{33}ClN_6O_4S$: 609 (MH$^+$).

Example 510

N-(3-(2-chloro-5-methoxyphenylamino)quinoxalin-2-yl)-3-(2-(piperidin-1-ylmethyl)piperidine-1-carbonyl)benzenesulfonamide MS (EI) $C_{33}H_{37}ClN_6O_4S$: 649 (MH$^+$).

Example 511

3-(N-(3-(2-chloro-5-methoxyphenylamino)quinoxalin-2-yl)sulfamoyl)-N-(1-ethylpiperidin-3-yl)benzamide MS (EI) $C_{29}H_{31}ClN_6O_4S$: 595 (MH$^+$).

General Procedure 8A

The General Library Procedure outlined in Procedure 8 was used to incorporate a number of amines that contained a second amine group protected as the tert-butylcarbamate. A subsequent deprotection after HPLC purification was performed to unmask this second amine group. Into a small 1 dram vial was added 3-(N-(3-(2-chloro-5-methoxyphenylamino)quinoxalin-2-yl)sulfamoyl)benzoic acid (61 mg, 0.13 mmol, 1.1 equiv). The acid was dissolved in 1 mL of DMA and DIPEA (42 uL, 0.24 mmol, 2 equiv) was added then added to the solution. The mono-Boc-protected diamine reagent (1 mL of 0.12 M solution in DMA, 1 equiv) was added to solution with stirring followed by HATU (64 mg, 0.17 mmol, 1.4 equiv). Reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification. The product fractions were combined and concentrated to dryness under reduced pressure by rotary evaporation. A solution of 4 N HCl in dioxane (2 mL) was added. The solution was then stirred at room temperature until no starting material was detected. The deprotected product precipitated out of solution as an HCL salt and was collected by filtration, washed with ether and dried under vacuum.

The following compounds were prepared according to General Procedure 8A

Example 512

3-(N-(3-(2-chloro-5-methoxyphenylamino)quinoxalin-2-yl)sulfamoyl)-N-(piperidin-3-yl)benzamide 3-(N-(3-(2-chloro-5-methoxyphenylamino)quinoxalin-2-yl)sulfamoyl)-N-(piperidin-3-yl)benzamide: $^1$H NMR (400 MHz, d$_6$-DMSO): 12.82 (s, 1H), 9.12 (s, 1H), 9.04 (s, 1H); 8.85 (d, 1H), 8.65 (s, 1H), 8.55 (s, 1H), 8.18 (m, 1H), 7.98 (s, 1H), 7.69 (m, 2H), 7.43 (m, 2H), 6.69 (dd, 1H), 4.21 (s, 1H), 3.83 (s, 3H), 3.69 (m, 1H), 3.48 (m, 1H), 3.18 (s, 1H), 2.84 (q, 2H), 1.91 (s, 2H); MS (EI) for $C_{27}H_{27}ClN_6O_4S$: 567 (MH$^+$).

Example 513

3-(N-(3-(2-chloro-5-methoxyphenylamino)quinoxalin-2-yl)sulfamoyl)-N-(piperidin-2-ylmethyl)benzamide 3-(N-(3-(2-chloro-5-methoxyphenylamino)quinoxalin-2-yl)sulfamoyl)-N-(piperidin-2-ylmethyl)benzamide: NMR (400 MHz, d$_6$-DMSO): 12.78 (s, 1H), 9.16 (s, 1H), 9.09 (s, 1H), 8.79 (s, 1H), 8.59 (d, 2H), 8.22 (t, 2H), 7.99 (s, 1H), 7.74 (t, 1H), 7.66 (s, 1H), 7.42 (m, 2H), 6.69 (dd, 1H), 3.82 (s, 3H), 3.69 (dd, 1H), 3.57 (m, 1H), 3.50 (m, 3H), 3.22 (s, 2H), 2.82 (d, 1H), 1.68 (m, 5H); MS (EI) for $C_{28}H_{29}ClN_6O_4S$: 581 (MH$^+$).

Example 514

3-(3-aminopyrrolidine-1-carbonyl)-N-(3-(2-chloro-5-methoxyphenylamino)quinoxalin-2-yl)benzenesulfonamide MS (EI) $C_{26}H_{25}ClN_6O_4S$: 553 (MH$^+$).

Example 515

3-(3-aminoazetidine-1-carbonyl)-N-(3-(2-chloro-5-methoxyphenyl)amino)quinoxalin-2-yl)benzenesulfonamide MS (EI) $C_{25}H_{23}ClN_6O_4S$: 539 (MH$^+$).

Example 516

3-(3-aminopiperidine-1-carbonyl)-N-(3-(2-chloro-5-methoxyphenylamino)quinoxalin-2-yl)benzenesulfonamide MS (EI) $C_{27}H_{27}ClN_6O_4S$: 567 (MH$^+$).

Example 517

3-(N-(3-(2-chloro-5-methoxyphenylamino)quinoxalin-2-yl)sulfamoyl)-N-(pyrrolidin-3-yl)benzamide MS (EI) $C_{26}H_{25}ClN_6O_4S$: 553 (MH$^+$).

Example 518

N-(3-(2-chloro-5-methoxyphenylamino)quinoxalin-2-yl)-3-(3-(methylamino)pyrrolidine-1-carbonyl)benzenesulfonamide MS (EI) $C_{27}H_{27}ClN_6O_4S$: 567 (MH$^+$).

Example 519

N-(2-aminoethyl)-3-(N-(3-(2-chloro-5-methoxyphenylamino)quinoxalin-2-yl)sulfamoyl)benzamide MS (EI) $C_{24}H_{23}ClN_6O_4S$: 527 (MH$^+$).

Example 520

3-(4-amino-3-oxopyrazolidine-1-carbonyl)-N-(3-(2-chloro-5-methoxyphenylamino)quinoxalin-2-yl)benzenesulfonamide MS (EI) $C_{25}H_{22}ClN_7O_5S$: 568 (MH$^+$).

Example 521

3-(N-(3-(2-chloro-5-methoxyphenylamino)quinoxalin-2-yl)sulfamoyl)-N-((1-methylpiperidin-2-yl)methyl)benzamide A measured amount of 3-(N-(3-(2-chloro-5-methoxyphenylamino)quinoxalin-2-yl)sulfamoyl)-N-(piperidin-2-ylmethyl)benzamide (299 mg, 0.51 mmol, 1 eq) was dissolved in 2.3 mL of DMA. Formic acid (388 ul, 10.28 mmol, 20 eq) was added to solution with stirring followed by the addition of formaldehyde (508 ul of 37% aq. solution). The reaction was then stirred at room temperature overnight. Analysis of an aliquot of the reaction mixture by LCMS indicated the complete consumption of starting material. The reaction was diluted with methanol (2 mL). Preparative reverse-phase HPLC was used to isolate the desired product directly from the crude reaction mixture. A Waters Fractionlynx preparative reverse-phase HPLC; equipped with a Waters SunFire Prep C18, OCD 5 □M, 30×70 mm column and running a 5-100% gradient with a binary solvent system of 25 mM ammonium acetate in water/acetonitrile; was used to carry out the purification. $^1$H NMR (400 MHz, d$_6$-DMSO): 9.44 (s, 1H), 8.94 (s, 1H), 8.79 (t, 1H), 8.57 (s, 1H), 8.27 (d, 1H), 7.90 (d, 1H) 7.54 (t, 1H), 7.46 (d, 1H), 7.39 (d, 1H), 7.33 (d, 1H), 7.18 (m, 2H), 6.60 (dd, 1H), 3.82 (s, 3H), 3.59 (m, 2H), 3.00 (s, 1H), 2.90 (s, 3H), 1.62 (m, 7H); MS (EI) for $C_{29}H_{31}ClN_6O_4S$: 595 (MH$^+$).

Example 522

3-(N-(3-(2-chloro-5-methoxyphenylamino)quinoxalin-2-yl)sulfamoyl)-N-(1-methylpiperidin-3-yl)benzamide The title compound was prepared according to the above Examples. 1H NMR (400 MHz, d$_5$-DMSO): 9.43 (s, 1H), 8.93 (s, 1H), 8.59 (s, 1H), 8.24 (d, 1H), 7.87 (d, 1H), 7.47 (m, 2H), 7.40 (d, 1H), 7.33 (d, 1H), 7.19 (m, 2H), 6.60 (dd, 1H), 4.21 (s, 1H), 3.82 (s, 1H), 2.76 (s, 1H), 2.50 (m, 7H), 1.91 (m, 2H), 1.63 (m, 2H); MS (EI) for $C_{28}H_{29}ClN_6O_4S$: 581 (MH$^+$).

BIOLOGICAL ASSAYS

The compounds of the invention demonstrated the ability to bind to PI3K when tested in the assays described in Section II above. In another embodiment, the compounds in Section II and Section III bind to the PI3K with a binding affinity, for example, of about 50 µM or less, 20 µM or less, 10 µM or less, 5 µM or less, 2.5 µM or less or 1 µM or less. In an advantageous embodiment, the IC50 of the binding compounds is about 0.5 µM or less, about 0.3 µM or less, about 0.1 µM or less, about 0.08 μM or less, about 0.06 μM or less, about 0.05 μM or less, about 0.04 μM or less, 0.03 μM or less, in another embodiment, about 0.03 μM or less.

BIOLOGICAL MODELS

Several biological models were used to test the efficacy of a MEK compound of Formula I, Ia, Ic, Id, II, III, IV, or V in combination with a PI3K compound of Formula VI, VIa, VIb or VII or a PI3K compound of Formula VIII, VIIIa, VIIIb, or IX in inhibiting tumor cell proliferation. In brief, either A2058 or WM-266 melanoma cell lines (ATCC) were transplanted intradermally in the hindflank of athymic nude mice (Jackson Laboratories). Both cell lines contain the B-RAF V600E mutation (Solit et al., Nature 439: pages 358-362, February 2006) and the PTEN gene is deleted. The xenograft was allowed to grow and divide for 10 days. Starting on day 10, mice were treated daily with a vehicle control or with a selected compound from section I (MEK inhibitor of Formula I, Ia, Ic, Id, II, III, IV, or V) either alone or in combination with a compound from section II (PI3K inhibitor of Formulae Formula VI, VIa, VIb or VII) or a compound from section III (PI3K inhibitor of Formulae Formula VIII, VIIIa, VIIIb, or IX). The xenografts were allowed to grow for another 15 days and then the tumors were weighed.

Mice treated with the MEK inhibitor alone exhibited a 50-75% reduction in tumor growth over the 15 day treatment period. Mice carrying the A2058 xenograft and treated with a select MEK inhibitor at 10 mgs/kg showed a 60% reduction in tumor growth relative to mice treated with vehicle alone. Mice carrying the A2058 xenograft and treated with vehicle had a mean tumor weight of approximately 1100 mgs versus mice who were treated with the select MEK inhibitor who had a mean tumor weight of 450 mgs. Mice carrying the WM-266 xenograft and treated with vehicle had a mean tumor weight of 700 mgs while mice carrying the same xenograft and treated with the select MEK inhibitor had a mean tumor weight of 200 mgs. The MEK inhibitor inhibited the tumor growth of both tumors by 60-75% over the 15 day period of treatment.

Mice treated with a combination of MEK inhibitor and a selected Section II or Section III PI3K inhibitor also exhibited a reduction in tumor growth over the 15 day treatment period. Mice carrying the A2058 xenograft and treated with a select Section III PI3K inhibitor at 100 mgs/kg exhibited a 65% reduction in growth relative to animals treated with the vehicle alone (mean tumor size of 375 mgs for Section III PI3K inhibitor treated animals vs 1100 mgs for vehicle treated animals). Animals treated with a combination of a select MEK inhibitor (10 mgs/kg) and a selected Section III PI3K inhibitor (100 mgs/kg) exhibited an 80% reduction in tumor growth over the 15 day treatment period (mean tumor size of 200 mgs for the tumors treated with the combination of compounds vs 1100 mgs for the vehicle treated tumors).

Mice carrying the A2058 xenograft and treated with a select Section II PI3K inhibitor at 100 mgs/kg exhibited a 65% reduction in growth relative to animals treated with the vehicle alone (mean tumor size of 350 mgs for PI3K inhibitor treated animals vs 1100 mgs for vehicle treated animals). Animals treated with a combination of a select MEK inhibitor (10 mgs/kg) and a selected Section II PI3K inhibitor (100 mgs/kg) exhibited an 75% reduction in tumor growth over the 15 day treatment period (mean tumor size of 250 mgs for the tumors treated with the combination of compounds vs 1100 mgs for the vehicle treated tumors).

Similar results were observed in animals carrying the WM-266 xenograft and treated with the same combination of drugs. Mean tumor weights for the animals treated with the vehicle alone were 700 mgs after 15 days of treatment. Animals that had received the Section III PI3K or Section II PI3K inhibitors exhibited a 50% reduction in tumor growth (mean tumor size of 500 mgs for the tumors treated with each compound) and an 85% reduction in tumor growth for tumors treated with the combination of a select MEK and either the Section II PI3K or Section III PI3K inhibitors (mean tumor size of 100 mgs after 15 days of combination treatment).

Xenographs treated with the combination of a select MEK inhibitor and either a select Section III PI3K inhibitor or a select Section II PI3K inhibitor exhibited a greater reduction in tumor growth than tumors treated with either compound alone.

The foregoing invention has been described in some detail by way of illustration and example, for purposes of clarity and understanding. The invention has been described with reference to various specific and preferred embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

We claim:

1. A method of treating melanoma, comprising administering to a patient in need of such treatment a therapeutically effective amount of a first compound selected from:

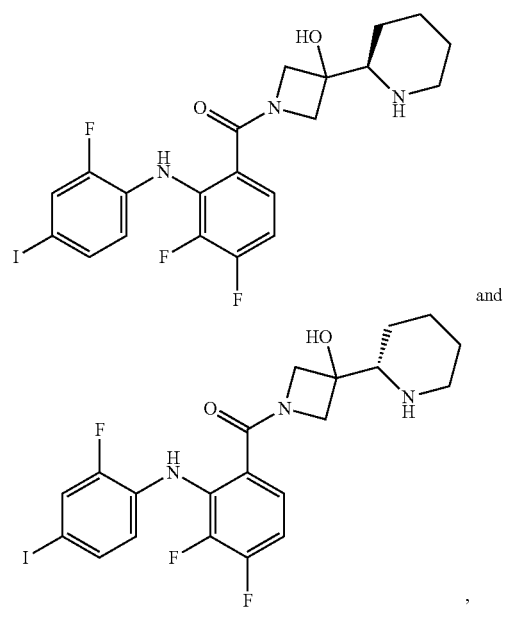

or a tautomer or pharmaceutically acceptable salt thereof;

and further comprising administering to the patient a therapeutically effective amount of a second compound:
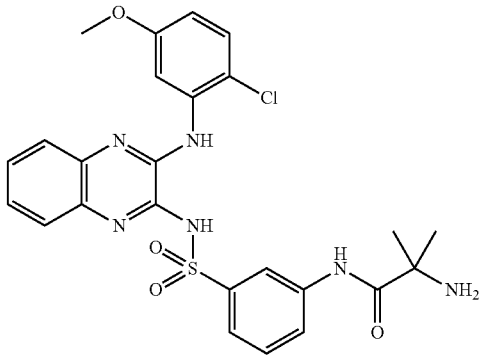 [SMILES: COc1ccc(Cl)c(Nc2nc3ccccc3nc2NS(=O)(=O)c2cccc(NC(=O)C(C)(C)N)c2)c1]
or a tautomer or pharmaceutically acceptable salt thereof.
2. The method of claim 1, wherein the first Compound is
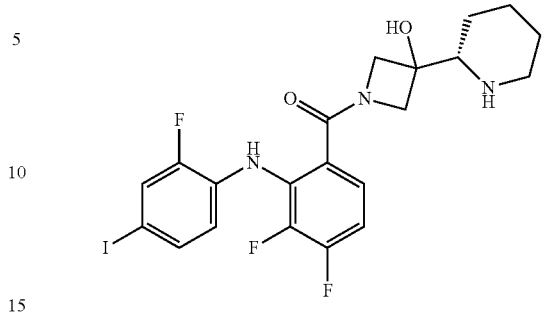
* * * * *